(12) United States Patent
Cotesta et al.

(10) Patent No.: US 11,702,409 B2
(45) Date of Patent: Jul. 18, 2023

(54) PYRAZOLYL DERIVATIVES USEFUL AS ANTI-CANCER AGENTS

(71) Applicant: NOVARTIS AG, Basel (CH)

(72) Inventors: Simona Cotesta, Basel (CH); Marc Gerspacher, Hägendorf (CH); Catherine Leblanc, Basel (CH); Edwige Liliane Jeanne Lorthiois, Niffer (FR); Bo Liu, Shanghai (CN); Rainer Machauer, Freiburg (DE); Robert Mah, Muenchenstein (CH); Christophe Mura, Rosenau (FR); Pascal Rigollier, Hagenthal-le-Bas (FR); Nadine Schneider, Basel (CH); Stefan Stutz, Basel (CH); Andrea Vaupel, Riehen (CH); Nicolas Warin, Basel (CH); Rainer Wilcken, Basel (CH)

(73) Assignee: NOVARTIS AG, Basel (CH)

( * ) Notice: Subject to any disclaimer, the term of this patent is extended or adjusted under 35 U.S.C. 154(b) by 167 days.

(21) Appl. No.: 17/125,335

(22) Filed: Dec. 17, 2020

(65) Prior Publication Data

US 2022/0363670 A1 Nov. 17, 2022

Related U.S. Application Data

(60) Provisional application No. 62/951,400, filed on Dec. 20, 2019.

(30) Foreign Application Priority Data

Oct. 30, 2020 (WO) ................ PCT/CN2020/125425

(51) Int. Cl.
| | | |
|---|---|---|
| *C07D 403/14* | (2006.01) | |
| *C07D 401/14* | (2006.01) | |
| *C07D 405/14* | (2006.01) | |
| *C07D 413/14* | (2006.01) | |
| *C07D 417/14* | (2006.01) | |
| *C07D 471/04* | (2006.01) | |
| *C07D 487/04* | (2006.01) | |

(52) U.S. Cl.
CPC ......... *C07D 403/14* (2013.01); *C07D 401/14* (2013.01); *C07D 405/14* (2013.01); *C07D 413/14* (2013.01); *C07D 417/14* (2013.01); *C07D 471/04* (2013.01); *C07D 487/04* (2013.01); *C07B 2200/13* (2013.01)

(58) Field of Classification Search
CPC .. C07D 403/14; C07D 401/14; C07D 405/14; C07D 413/14; C07D 417/14; C07D 471/04; C07D 487/04
USPC .................................................. 514/210.02
See application file for complete search history.

(56) References Cited

U.S. PATENT DOCUMENTS

| 2018/0334454 A1 | 11/2018 | Lanman et al. |
| 2019/0263821 A1 | 8/2019 | Kc et al. |

FOREIGN PATENT DOCUMENTS

| CN | 108069955 A | 5/2018 |
|---|---|---|
| EP | 3539957 A1 | 9/2019 |
| WO | WO 2000/019994 A1 | 4/2000 |
| WO | WO 2004/072033 A2 | 8/2004 |
| WO | WO 2006/026305 A1 | 3/2006 |
| WO | WO 2006/084015 A2 | 8/2006 |
| WO | WO 2007/002563 A1 | 1/2007 |
| WO | WO 2007/105058 A2 | 9/2007 |
| WO | WO 2009/005675 A1 | 1/2009 |
| WO | WO 2009/011880 A2 | 1/2009 |
| WO | WO 2009/016460 A2 | 2/2009 |
| WO | WO 2010/010154 A1 | 1/2010 |
| WO | WO 2010/108268 A1 | 9/2010 |
| WO | WO 2012/016993 A1 | 2/2012 |
| WO | WO 2013/155223 A1 | 10/2013 |
| WO | WO 2015/054572 A1 | 4/2015 |
| WO | WO 2016/164675 A1 | 10/2016 |
| WO | WO 2017/058805 A1 | 4/2017 |
| WO | WO 2017/058902 A1 | 4/2017 |

(Continued)

OTHER PUBLICATIONS

El-Tombary et al., "Synthesis of some substituted furan-2(5H)-ones and derived quinoxalinones as potential anti-microbial and anti-cancer agents", *Medicinal Chemistry Research* 20:865-876 (2011).

(Continued)

*Primary Examiner* — Kahsay Habte
(74) *Attorney, Agent, or Firm* — Lathrop GPM LLP; Brian C. Trinque; Nicole Sassu

(57) ABSTRACT

The present invention provides a compound of formula (I) or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof;

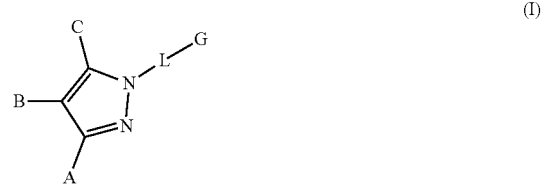

(I)

a method for manufacturing said compound, and its therapeutic uses. The present invention further provides a combination of pharmacologically active agents and a pharmaceutical composition comprising said compound.

34 Claims, 4 Drawing Sheets

Specification includes a Sequence Listing.

(56) References Cited

FOREIGN PATENT DOCUMENTS

| WO | WO 2017/201161 A1 | 11/2017 |
|---|---|---|
| WO | WO 2018/068017 A1 | 4/2018 |
| WO | WO 2018/140513 A1 | 8/2018 |
| WO | WO 2018/140514 A1 | 8/2018 |
| WO | WO 2018/140598 A1 | 8/2018 |
| WO | WO 2018/140599 A1 | 8/2018 |
| WO | WO 2018/140600 A1 | 8/2018 |
| WO | WO 2018/143315 A1 | 8/2018 |
| WO | WO 2018/217651 A1 | 11/2018 |
| WO | WO 2018/218070 A2 | 11/2018 |
| WO | WO 2019/099524 A1 | 5/2019 |
| WO | WO 2019/136147 A1 | 7/2019 |
| WO | WO 2019/213516 A1 | 11/2019 |
| WO | WO 2019/217691 A1 | 11/2019 |
| WO | WO 2019/232419 A1 | 12/2019 |

OTHER PUBLICATIONS

International Search Report and Written Opinion for International Application No. PCT/CN2020/125425, dated Feb. 1, 2021, 12 pages.

Lorthiois et al., "JDQ443, a Structurally Novel, Pyrazole-Based, Covalent Inhibitor of KRAS$^{G12C}$ for the Treatment of Solid Tumors", *Journal of Medicinal Chemistry*, https://doi.org/10.1021/acs.jmedchem.2c01438.

Newhouse et al., "Non-oxime pyrazole based inhibitors of B-Raf kinase", *Bioorganic & Medicinal Chemistry Letters* 21 (11):3488-3492 (2011).

Weiss et al., "Discovery, Preclinical Characterization, and Early Clinical Activity of JDQ443, a Structurally Novel, Potent, and Selective Covalent Oral Inhibitor of KRAS$^{G12C}$", *Cancer Discovery* 12:1500-1507 (2022).

SEQUENCE LISTING

<160> NUMBER OF SEQ ID NOS: 1

<210> SEQ ID NO 1
<211> LENGTH: 5128
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 1

```
atgcgtccgg cgtagaggat cgagatcgat ctcgatcccg cgaaattaat acgactcact      60 atagggggaat tgtgagcgga taacaattcc cctctagaaa taattttgtt taactttaag    120
aaggagatat acatatgaaa acacatcatc atcatcatca tggtggcggc agtggcggtg    180
gctcaggcgg tggttctctc gaggttctgt tccagggtcc gggtttgaac gacatcttcg    240
```

```
aagctcagaa gatcgaatgg cacgagggtg gcggtagtgg tggtggctct atgactgaat    300
acaagctggt tgttgttggt gcttgtggcg ttggtaagag cgcactgacc atccagctca    360
ttcagaatca cttcgtggac gagtacgacc cgaccatcga agattcttac cgtaaacagg    420
tggttattga tggcgaaacc tgtctgctgg atattctgga cactgctggt caggaagagt    480
actccgctat gcgtgatcag tacatgcgta ctggtgaagg ttttcctctgc gtgttcgcta    540
tcaacaacac caagtccttc gaagatatcc accattaccg tgaacagatc aaacgtgtga    600
aggacagcga agacgtgcca atggttctgg tgggcaacaa atgtgatctc ccgagccgta    660
ccgttgacac caaacaggca caagacctgg cacgttccta cggcatccca ttcattgaaa    720
ctagcgcgaa gactcgtcag ggtgtggacg acgcattcta cactctggtg cgtgaaattc    780
gcaagcacaa agagaaataa tggtaccgaa ttcgcggccg cctgcagcct aggctgctaa    840
acaaagcccg aaaggaagct gagttggctg ctgccaccgc tgagcaataa ctagcataac    900
cccttggggc ctctaaacgg gtcttgaggg gttttttgct gaaaggagga actatatccg    960
gattggcgaa tgggacgcgc cctgtagcgg cgcattaagt gcagcgtcaa aagggcgaca   1020
caaaatttat tctaaatgca taataaatac tgataacatc ttatagtttg tattatattt   1080
tgtattatcg ttgacatgta aattttgat atcaaaaact gattttccct ttattatttt   1140
cgagatttat tttcttaatt ctctttaaca aactagaaat attgtatata caaaaaatca   1200
taaataatag atgaatagtt taattatagg tgttcatcaa tcgaaaaagc aacgtatctt   1260
atttaaagtg cgttgctttt ttctcattta taaggttaaa taattctcat atatcaagca   1320
aagtgacagg cgcccttaaa tattctgaca atgctctttc cctaaactcc ccccataaa    1380
aaacccgcc gaagcgggtt tttacgttat ttgcggatta acgattactc gttatcagaa    1440
ccgcccaggg ggcccgagct taagactggc cgtcgtttta caacacagaa agagtttgta   1500
gaaacgcaaa aaggccatcc gtcaggggcc ttctgcttag tttgatgcct ggcagttccc   1560
tactctcgcc ttccgcttcc tcgctcactg actcgctgcg ctcggtcgtt cggctgcggc   1620
gagcggtatc agctcactca aaggcggtaa tacggttatc cacagaatca ggggataacg   1680
caggaaagaa catgtgagca aaaggccagc aaaaggccag gaaccgtaaa aaggccgcgt   1740
tgctggcgtt tttccatagg ctccgccccc ctgacgagca tcacaaaaat cgacgctcaa   1800
gtcagaggtg gcgaaacccg acaggactat aaagatacca ggcgtttccc cctggaagct   1860
ccctcgtgcg ctctcctgtt ccgaccctgc cgcttaccgg atacctgtcc gcctttctcc   1920
cttcgggaag cgtggcgctt tctcatagct cacgctgtag gtatctcagt tcggtgtagg   1980
tcgttcgctc caagctgggc tgtgtgcacg aaccccccgt tcagcccgac cgctgcgcct   2040
tatccggtaa ctatcgtctt gagtccaacc cggtaagaca cgacttatcg ccactggcag   2100
cagccactgg taacaggatt agcagagcga ggtatgtagg cggtgctaca gagttcttga   2160
agtggtgggc taactacggc tacactagaa gaacagtatt tggtatctgc gctctgctga   2220
agccagttac cttcggaaaa agagttggta gctcttgatc cggcaaacaa accaccgctg   2280
gtagcggtgg tttttttgtt tgcaagcagc agattacgcg cagaaaaaaa ggatctcaag   2340
aagatccttt gatcttttct acgggtctg acgctcagtg gaacgacgcg cgcgtaactc   2400
acgttaaggg attttggtca tgagcttgcg ccgtcccgtc aagtcagcgt aatgctctgc   2460
ttttagaaaa actcatcgag catcaaatga aactgcaatt tattcatatc aggattatca   2520
ataccatatt tttgaaaaag ccgtttctgt aatgaaggag aaaactcacc gaggcagttc   2580
cataggatgg caagatcctg gtatcggtct gcgattccga ctcgtccaac atcaatacaa   2640
```

```
cctattaatt tcccctcgtc aaaaataagg ttatcaagtg agaaatcacc atgagtgacg    2700
actgaatccg gtgagaatgg caaaagttta tgcatttctt tccagacttg ttcaacaggc    2760
cagccattac gctcgtcatc aaaatcactc gcatcaacca aaccgttatt cattcgtgat    2820
tgcgcctgag cgaggcgaaa tacgcgatcg ctgttaaaag gacaattaca aacaggaatc    2880
gagtgcaacc ggcgcaggaa cactgccagc gcatcaacaa tattttcacc tgaatcagga    2940
tattcttcta atacctggaa cgctgttttt ccggggatcg cagtggtgag taaccatgca    3000
tcatcaggag tacggataaa atgcttgatg gtcggaagtg gcataaattc cgtcagccag    3060
tttagtctga ccatctcatc tgtaacatca ttggcaacgc tacctttgcc atgtttcaga    3120
aacaactctg gcgcatcggg cttcccatac aagcgataga ttgtcgcacc tgattgcccg    3180
acattatcgc gagcccattt atacccatat aaatcagcat ccatgttgga atttaatcgc    3240
ggcctcgacg tttcccgttg aatatggctc atattcttcc ttttcaata ttattgaagc    3300 atttatcagg gttattgtct catgagcgga tacatatttg aatgtattta gaaaaataaa    3360
caaatagggg tcagtgttac aaccaattaa ccaattctga acattatcgc gagcccattt    3420
atacctgaat atggctcata caccccttg tttgcctggc ggcagtagcg cggtggtccc    3480
acctgacccc atgccgaact cagaagtgaa acgccgtagc gccgatggta gtgtggggac    3540
tccccatgcg agagtaggga actgccaggc atcaaataaa acgaaaggct cagtcgaaag    3600
actgggcctt tcgcccgggc taattagggg gtgtcgccct tcgctgaaga attgatcccg    3660
gtgcctaatg agtgagctaa cttacattaa ttgcgttgcg ctcactgccc gctttccagt    3720
cgggaaacct gtcgtgccag ctgcattaat gaatcggcca acgcgcgggg agaggcggtt    3780
tgcgtattgg gcgccagggt ggttttttctt ttcaccagtg acgggcaa cagctgattg    3840 cccttcaccg cctggccctg agagagttgc agcaagcggt ccacgctggt ttgccccagc    3900
aggcgaaaat cctgtttgat ggtggttaac ggcgggatat aacatgagct gtcttcggta    3960
tcgtcgtatc ccactaccga gatgtccgca ccaacgcgca gcccggactc ggtaatggcg    4020
cgcattgcgc ccagcgccat ctgatcgttg gcaaccagca tcgcagtggg aacgatgccc    4080
tcattcagca tttgcatggt ttgttgaaaa ccggacatgg cactccagtc gccttcccgt    4140
tccgctatcg gctgaatttg attgcgagtg agatatttat gccagccagc cagacgcaga    4200
cgcgccgaga cagaacttaa tgggcccgct aacagcgcga tttgctggtg acccaatgcg    4260
accagatgct ccacgcccag tcgcgtaccg tcttcatggg agaaaataat actgttgatg    4320
ggtgtctggt cagagacatc aagaaataac gccggaacat tagtgcaggc agcttccaca    4380
gcaatggcat cctggtcatc cagcggatag ttaatgatca gcccactgac gcgttgcgcg    4440
agaagattgt gcaccgccgc tttacaggct tcgacgccgc ttcgttctac catcgacacc    4500
accacgctgg cacccagttg atcggcgcga gatttaatcg ccgcgacaat tgcgacggc    4560 gcgtgcaggg ccagactgga ggtggcaacg ccaatcagca acgactgttt gcccgccagt    4620
tgttgtgcca cgcggttggg aatgtaattc agctccgcca tcgccgcttc cacttttccc    4680
cgcgttttcg cagaaacgtg gctggcctgg ttcaccacgc gggaaacggt ctgataagag    4740
acaccggcat actctgcgac atcgtataac gttactggtt tcacattcac caccctgaat    4800
tgactctctt ccgggcgcta tcatgccata ccgcgaaagg ttttgcgcca ttcgatggtg    4860
tccgggatct cgacgctctc ccttatgcga ctcctgcatt aggaagcagc ccagtagtag    4920
gttgaggccg ttgagcaccg ccgccgcaag gaatggtgca tgcaaggaga tggcgcccaa    4980
```

```
cagtccccg gccacggggc ctgccaccat acccacgccg aaacaagcgc tcatgagccc   5040
gaagtggcga gcccgatctt ccccatcggt gatgtcggcg ataggcgc cagcaaccgc   5100 acctgtggcg ccggtgatgc cggccacg                                     5128
```

PYRAZOLYL DERIVATIVES USEFUL AS ANTI-CANCER AGENTS

CLAIM OF PRIORITY

This application claims priority from U.S. Provisional Application Ser. No. 62/951,400 filed Dec. 20, 2019, and International Application Serial No. PCT/CN2020/125425 filed Oct. 30, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 1, 2020, is named PAT058632-US-NP_SL.txt and is 7,192 bytes in size.

FIELD OF THE INVENTION

The invention provides pyrazolyl derivative compounds; the use thereof for inhibiting KRAS G12C, HRAS G12C or NRAS G12C, and in particular KRAS G12C; methods of treating or preventing disease, in particular cancer, using said compounds; and processes and intermediates for making these compounds. The invention also provides these pyrazolyl derivative compounds for use in the treatment of cancer and specific cancers as defined herein.

BACKGROUND OF THE INVENTION

RAS are small GTPases acting as molecular ON/OFF switches which adopt an active/inactive state when bound to GTP/GDP, respectively. In response to growth factors, guanine exchange factors exchange GDP for GTP, turning Ras ON. RAS bound to GTP adopts conformations that recruit effector proteins to the plasma membrane, thereby activating signaling cascades causing cell growth, proliferation and survival. These cancer promoting signals are very transient and tightly controlled. They are turned off immediately by the GTPase activity of RAS itself, mainly due to the 100000 fold acceleration by GTPase activating proteins (GAPs) (Bos J L et al., Cell, Volume 129, Issue 5, 1 Jun. 2007, pp 865-877). In contrast, RAS mutants are insensitive to these GAPs, causing the RAS mutants to reside longer in the GTP bound state and shifting the GTP/GDP cycle in accordance to their intrinsic hydrolysis rate towards the ON state.

The three RAS genes constitute the most frequently mutated gene family in cancer, with RAS mutations found in ~25% of human tumors. Among the 3 paralogs, KRAS mutations are most frequent (85% of all RAS-driven cancers), whereas NRAS and HRAS mutations are less frequently reported (12% and 3%, respectively). The majority of KRAS mutations occurs at the hotspot residues G12, G13 and Q61. KRAS G12C mutations represent about 12% of all KRAS mutations and are prevalent in lung cancer patients (~13% lung adenoma carcinoma (LUAC)), ~3-5% colon adenocarcinomas, a smaller fractions of other cancer types and in about 20% of MYH polyposis colorectal adenomas (COSMIC v80 database; A. Aime' et al, Cancer genet. 2015, 208:390-5).

Patients with KRAS G12C positive solid tumors are only poorly treated with current therapies. There are currently no inhibitors of KRAS G12C, HRAS G12C or NRAS G12C approved for therapeutic use.

There thus remains a continued need to develop new options for the treatment of cancer, in particular, cancer tumors expressing G12C mutant Ras, in particular, for the treatment of KRAS, HRAS or NRAS G12C driven cancers. More particularly, there remains a need for the treatment of KRAS G12C-mutant cancers.

Irreversible RAS G12C inhibitors have been previously described (for example WO2014152588, WO2017201161, WO2018/217651 and WO2018119183).

SUMMARY OF THE INVENTION

The compounds described in this invention selectively react with, and inhibit, the G12C mutant KRAS, HRAS or NRAS proteins by forming an irreversible covalent bond with the cysteine at the position 12. This locks the RAS mutant protein in the inactive state. The irreversible binding of these compounds disrupts K-RAS downstream signaling. The compounds described in this invention may be used for the treatment of cancer, particularly the treatment of a cancer characterized by a KRAS, HRAS or NRAS G12C mutation, more particularly a cancer characterized by a KRAS G12C mutation.

The invention therefore provides compounds, pharmaceutically acceptable salts thereof, pharmaceutical compositions thereof and combinations thereof. The compounds are able to selectively bind to and inhibit the G12C mutant of either KRAS, HRAS or NRAS, and may be useful for the treatment of cancer, particularly the treatment of cancer characterized by a KRAS HRAS or NRAS G12C mutation. The invention also provides processes of making such compounds and intermediates useful in the synthesis of such compounds.

Various embodiments or aspects of the invention are described herein.

Provided herein is a compound of formula (I), as defined herein, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof,

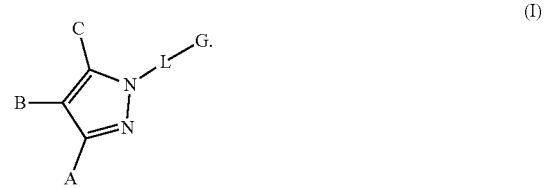

(I)

In another embodiment, the invention provides a compound of formula (I) as defined herein, or an atropisomer thereof, a pharmaceutically acceptable salt thereof, or a pharmaceutically acceptable salt of an atropisomer thereof.

In another embodiment, the invention provides a compound of formula (I) (or of subformulae (Ia), (Ib*), (Ic*), (Id*) or (Ie)), as defined herein, or an atropisomer thereof, a pharmaceutically acceptable salt thereof, or a pharmaceutically acceptable salt of an atropisomer thereof.

In another embodiment, the invention provides a compound of formula (I) as defined herein, or a pharmaceutically acceptable salt thereof.

In another embodiment, the invention provides a compound of formula (I) (or of subformulae (Ia), (Ib*), (Ic*), (Id*) or (Ie)), as defined herein, or a pharmaceutically acceptable salt thereof.

In another embodiment, the invention provides a pharmaceutical composition comprising a compound of formula (I) (or of subformulae thereof (Ia), (Ib*), (Ic*), (Id*) or (Ie)), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, and one or more pharmaceutically acceptable carriers.

In another embodiment, the invention provides a pharmaceutical composition comprising a compound of formula (I), (or of subformulae thereof (Ia), (Ib*), (Ic*), (Id*) or (Ie)), or a therapeutically effective amount of a compound of formula (I), (or of subformulae thereof (Ia), (Ib*), (Ic*), (Id*) or (Ie)), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, and optionally one or more pharmaceutically acceptable carriers.

In another embodiment, the invention provides a combination, in particular a pharmaceutical combination, comprising a compound of formula (I), (or of subformulae thereof (Ia), (Ib*), (Ic*), (Id*) or (Ie)), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, and one or more therapeutically active agents.

In another embodiment, the invention provides a pharmaceutical combination, comprising a compound of formula (I), (or of subformulae thereof (Ia), (Ib*), (Ic*), (Id*) or (Ie)), or an atropisomer thereof, or a pharmaceutically acceptable salt thereof, or a pharmaceutically acceptable salt of an atropisomer thereof, and one or more therapeutically active agents.

In a further embodiment, the invention relates to a method of inhibiting a G12C mutant KRAS, HRAS or NRAS protein (e.g., a G12C mutant KRAS protein) in a subject in need thereof, wherein the method comprises administering to the subject a therapeutically effective amount of a compound of formula (I) or subformulae thereof (Ia), (Ib*), (Ic*), (Id*) or (Ie) as defined herein, or or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

In yet another embodiment, the invention relates to a method of treating a disorder or disease in a subject in need thereof, wherein the disorder or disease is selected from cancer, e.g. lung cancer (including lung adenocarcinoma and non-small cell lung cancer), colorectal cancer (including colorectal adenocarcinoma), pancreatic cancer (including pancreatic adenocarcinoma), uterine cancer (including uterine endometrial cancer), rectal cancer (including rectal adenocarcinoma) and other solid tumors, and wherein the method comprises administering to the subject a therapeutically effective amount of a compound of formula (I) as defined herein or subformulae thereof (Ia), (Ib*), (Ic*), (Id*) or (Ie), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

In another embodiment, the invention provides intermediate compounds useful for making the compounds of the invention as well as methods of making a compound of formula (I) as defined herein or of subformulae thereof (Ia), (Ib*), (Ic*), (Id*) or (Ie), or a stereoisomer thereof, or an atropisomer thereof.

DETAILED DESCRIPTION

Figure 1:
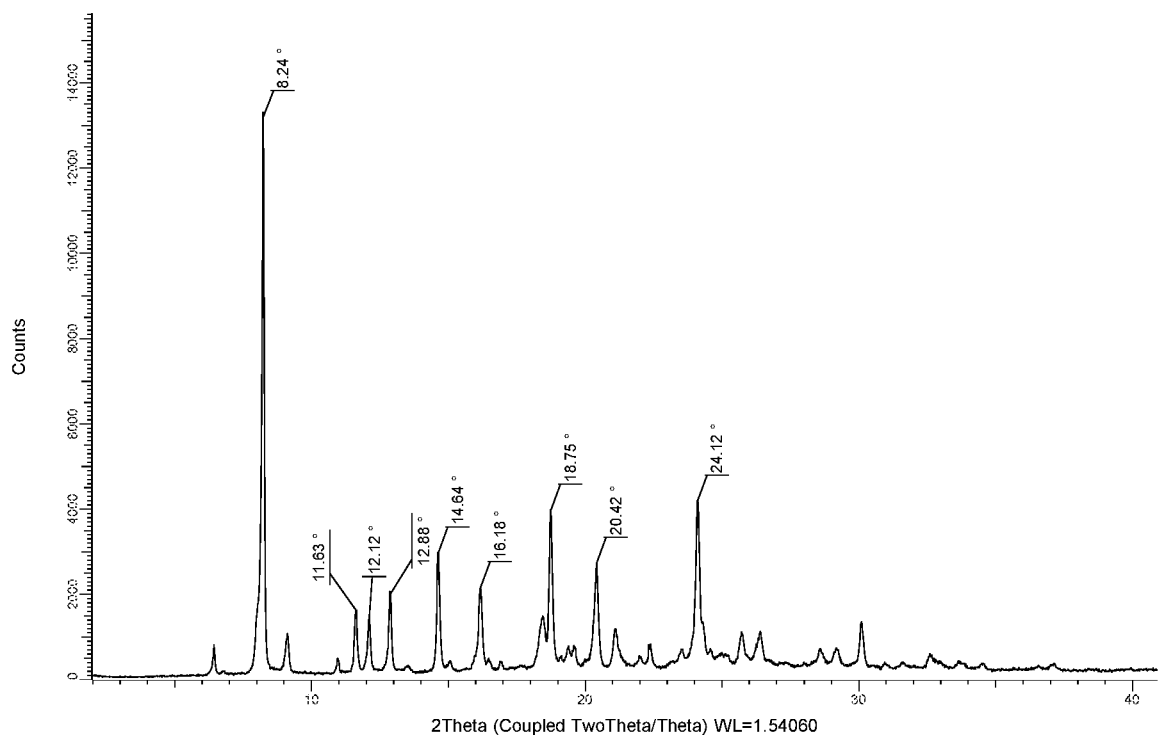
FIG. 1. illustrates the x-ray powder diffraction pattern of the hydrate (Modification HA) of a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Compound X).

The invention provides, in a first aspect, a compound of formula (I),

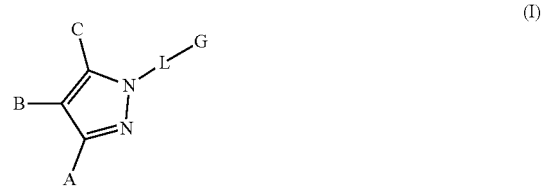

A is selected from the group consisting of
(a) $C_6$-$C_7$-cycloalkylene which is unsubstituted or substituted with one or more, preferably 1, 2 or 3, substituents independently selected from fluoro and $C_1$-$C_4$-alkyl;
(b) a 5-7 membered unsaturated heterocyclyl containing one carbon-carbon double bond and one oxygen atom as ring member, wherein said heterocyclyl is unsubstituted or substituted with one or more, preferably 1, 2 or 3, substituents, independently selected from fluoro and $C_1$-$C_4$-alkyl, preferably 1, 2 or 3, $C_1$-$C_4$-alkyl;
(c) $C_6$-$C_{10}$ aryl which is unsubstituted or substituted with 1, 2 or 3 $R^{42}$;
(d a) 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{43}$, and wherein a nitrogen atom, when present in the heteroaryl ring, is unsubstituted or substituted with a substituent selected from the group consisting of: $C_1$-$C_4$-alkyl, —$(CH_2)_{1-2}$—$C_{3-4}$-cycloalkyl, $C_3$-$C_6$-cycloalkyl, hydroxy-$C_1$-$C_4$-alkyl, fluoro-$C_1$-$C_4$-alkyl, $C_1$-$C_4$-alkoxy-$C_1$-$C_4$-alkyl, $N(R^9)(R^{10})$—$C_1$-$C_4$-alkyl, —$SO_2$—$C_1$-$C_4$-alkyl, —$SO_2$—$C_{3-4}$-cycloalkyl, —$(CH_2)_p$-Het$^{py}$, and —$(CH_2)_p$—$N(R^9)(R^{10})$, (preferably wherein said substituent is selected from the group consisting of fluoro-$C_1$-$C_4$-alkyl, N($R^9$)($R^{10}$)—$C_1$-$C_4$-alkyl, —$SO_2$—$C_{3-4}$-cycloalkyl, or —($CH_2$)$_{1-2}$—$C_{3-4}$-cycloalkyl);

(e) an 8-10 membered heteroaryl ring containing 1 to 3 heteroatoms independently selected from nitrogen, oxygen and sulfur or an 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 S(=O)$_2$ group in the hetero-bicyclic ring, wherein said heteroaryl ring or hetero-bicyclic ring is unsubstituted or substituted on a carbon atom with 1, 2, 3, 4 or 5 $R^{44}$, and wherein the hetero-bicyclic ring is further optionally substituted on a carbon atom by oxo and wherein a nitrogen atom, when present, is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, Het$^b$ and NR$^9$R$^{10}$; and wherein Het$^b$ is a 4- or 5- or 6-membered heterocyclic ring comprising 1 or 2 heteroatoms or groups independently selected from N, O, S, SO and SO$_2$ (preferably 1 oxygen atom, or 1 sulfur atom, or one S(=O) or one S(=O)$_2$ group, or 1 nitrogen atom and 1 oxygen atom, or 1-2 nitrogen atoms), wherein said heterocyclic ring Het$^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl, and wherein said heterocyclic ring Het$^b$ is further optionally substituted on a carbon atom by oxo, and wherein the nitrogen atom when present in Het$^b$ is optionally further substituted with $C_1$-$C_4$-alkyl which is optionally substituted with 1 to 3 substituents independently selected from fluoro, hydroxy and $C_1$-$C_4$-alkoxy;

wherein A is attached to the rest of the compound of Formula (I) by a carbon atom on A which is sp$^2$ hybridized;
wherein
B is selected from the group consisting of B$^1$ and B$^2$,
wherein B$^1$ is $C_{6-10}$ aryl which is unsubstituted or substituted with 1, 2, 3 or 4 R$^{Ba}$;
B$^2$ is a 6-13 membered heteroaryl which comprises 1, 2 or 3 nitrogen atoms, wherein B$^2$ is unsubstituted or substituted with 1, 2, 3 or 4 R$^{Bb}$;
C is selected from the group consisting of hydrogen, $C_1$-$C_3$ alkyl (preferably methyl), $C_3$-$C_5$ cycloalkyl (preferably cyclopropyl), fluoro-$C_1$-$C_3$ alkyl (preferably CHF$_2$ or CF$_3$), cyano, —CH$_2$—CN, —CH(CN)—CH$_3$, —CH$_2$—OH, —CH(OH)—CH$_3$ and halo;
L is selected from the group consisting of:

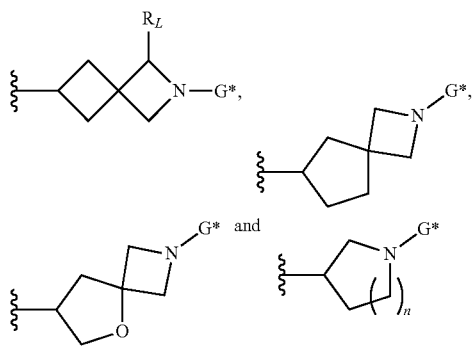

wherein n is 1, 2 or 3,
R$_L$ is selected from hydrogen, methyl, ethyl, —CH$_2$—CN and —CH$_2$—OH, where
G* represents the point of attachment to G;
G is selected from the group consisting of

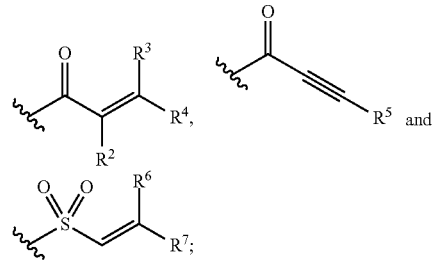

wherein
R$^2$ is selected from hydrogen, $C_1$-$C_3$ alkyl, —C(O)—$C_1$-$C_3$-alkyl, and fluoro;
R$^3$ is hydrogen;
R$^4$ is selected from hydrogen, methyl, —CH$_2$F, —CH$_2$—OCH$_3$ and —CH$_2$—N(CH$_3$)$_2$;
R$^5$ is selected from hydrogen and methyl;
R$^6$ is hydrogen;
R$^7$ is selected from hydrogen and methyl;
wherein R$^{42}$ is independently selected from the group consisting of: NR$^9$R$^{10}$, cyano, —(CH$_2$)$_p$—CN, halo, OH, hydroxy-$C_1$-$C_4$-alkyl, —(COOH), —(CH$_2$)$_p$—COOH, $C_1$-$C_4$-alkyl, fluoro-$C_1$-$C_4$-alkyl, $C_1$-$C_4$-alkoxy, $C_1$-$C_4$-alkoxy-$C_1$-$C_4$-alkyl, N(R$^9$)(R$^{10}$)—$C_1$-$C_4$-alkyl, N(R$^9$)(R$^{10}$)—$C_1$-$C_4$-alkyl-oxy, N(R$^9$)(R$^{10}$)—$C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, $C_1$-$C_4$-alkoxy-$C_1$-$C_4$-alkyl-oxy-$C_1$-$C_4$-alkyl, —SO$_2$—$C_1$-$C_4$-alkyl, —SO$_2$—$C_{3-4}$-cycloalkyl, —(CH$_2$)$_{1-2}$—$C_{3-4}$-cycloalkyl, Het$^{py}$, —(CH$_2$)$_p$-Het$^{py}$, —C(=O)—NR$^9$R$^{10}$, —(CH$_2$)$_p$—C(=O)NR$^9$R$^{10}$, (preferably from the group consisting of NR$^9$R$^{10}$, cyano, $C_1$-$C_4$-alkyl, fluoro, fluoro-$C_1$-$C_4$-alkyl, $C_1$-$C_4$-alkoxy, $C_1$-$C_4$-alkoxy-$C_1$-$C_4$-alkyl-oxy, hydroxy-$C_1$-$C_4$-alkyl, hydroxy-$C_1$-$C_4$-alkyl-oxy, Het$^{py}$, —(CH$_2$)$_p$-Het$^{py}$ and —C(=O)—NR$^9$R$^{10}$);

wherein R$^{43}$ is independently selected from the group consisting of oxo, NR$^9$R$^{10}$, cyano, —(CH$_2$)$_p$—CN, halo, OH, hydroxy-$C_1$-$C_4$-alkyl, —(COOH), —(CH$_2$)$_p$—COOH, $C_1$-$C_4$-alkyl, fluoro-$C_1$-$C_4$-alkyl, $C_1$-$C_4$-alkoxy, $C_1$-$C_4$-alkoxy-$C_1$-$C_4$-alkyl, N(R$^9$)(R$^{10}$)—$C_1$-$C_4$-alkyl, N(R$^9$)(R$^{10}$)—$C_1$-$C_4$-alkyl-oxy, N(R$^9$)(R$^{10}$)—$C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, $C_1$-$C_4$-alkoxy-$C_1$-$C_4$-alkyl-oxy-$C_1$-$C_4$-alkyl, —SO$_2$—$C_1$-$C_4$-alkyl, —SO$_2$—$C_{3-4}$-cycloalkyl, —(CH$_2$)$_{1-2}$—$C_{3-4}$-cycloalkyl, Het$^{py}$, —(CH$_2$)$_p$-Het$^{py}$, —C(=O)—NR$^9$R$^{10}$, —(CH$_2$)$_p$—C(=O)NR$^9$R$^{10}$, (CH$_2$)$_p$ NR$^9$R$^{10}$ (preferably from the group consisting of NR$^9$R$^{10}$, cyano, $C_1$-$C_4$-alkyl, fluoro, fluoro-$C_1$-$C_4$-alkyl, $C_1$-$C_4$-alkoxy, $C_1$-$C_4$-alkoxy-$C_1$-$C_4$-alkyl-oxy, Het and —(CH$_2$)$_p$—Het$^{py}$);

wherein R$^{44}$ is independently selected from the group consisting of cyano, CO$_2$H, halo, $C_1$-$C_4$-alkyl, fluoro-$C_1$-$C_4$-alkyl, hydroxy, hydroxy-$C_1$-$C_4$-alkyl, hydroxy-$C_1$-$C_4$-alkyl-oxy, $C_1$-$C_4$-alkoxy, $C_1$-$C_4$-alkoxy-$C_1$-$C_4$-alkyl, $C_1$-$C_4$-alkoxy-$C_1$-$C_4$-alkyl-oxy, NR$^9$R$^{10}$, (N(R$^9$)(R$^{10}$)—$C_1$-$C_4$-alkyl, (N(R$^9$)(R$^{10}$)—$C_1$-$C_4$-alkyl-oxy, —(CO)—$C_1$-$C_4$-alkyl, and R$^9$R$^{10}$N—$C_1$-$C_4$-alkyl-oxy-(CO)—$C_1$-$C_4$-alkyl;

wherein
p is 1 or 2 or 3;

$R^9$ is selected from hydrogen and $C_1$-$C_4$-alkyl;

$R^{10}$ is selected from the group consisting of hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl;

$Het^{py}$ is a 4-, 5-, 6- or 7-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, and wherein said heterocyclic ring is optionally substituted with oxo on one carbon atom, and wherein said heterocyclic ring is optionally further substituted on one or more carbon atoms with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl, and wherein the nitrogen atom, if present in said heterocycle, is optionally further substituted with $R^{10}$ (preferably $C_1$-$C_4$-alkyl (such as methyl));

or $Het^{py}$ is a 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one or more (e.g., 1, 2 or 3) substituents independently selected from $NR^9R^{10}$, —C(=O)—$NR^9R^{10}$, halo, $C_1$-$C_4$-alkyl, hydroxy-$C_1$-$C_4$-alkyl, fluoro-$C_1$-$C_4$-alkyl, cyano, OH, and $C_1$-$C_4$-alkoxy;

each $R^{Ba}$ is independently selected from the group consisting of hydroxy, $NH_2$, $C_1$-$C_4$-alkyl and halo;

each $R^{Bb}$ is independently selected from the group consisting of $C_1$-$C_4$-alkyl (preferably methyl), cyclopropyl, fluoro-$C_1$-$C_3$-alkyl (preferably $CHF_2$ or $CF_3$), cyano, halo (preferably fluoro or chloro), $NH_2$ and $C_1$-$C_3$-alkoxy (preferably methoxy), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

The invention provides, in a second aspect, a compound of formula (I),

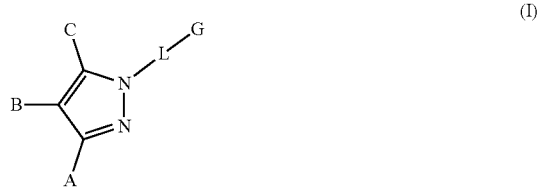

(I)

A is selected from the group consisting of (a) $C_5$-$C_7$-cycloalkylene which is unsubstituted or substituted with one or more, preferably 1, 2 or 3, substituents independently selected from fluoro and $C_1$-$C_4$-alkyl;

(b) 5-7 membered unsaturated heterocyclyl containing one carbon-carbon double bond and one oxygen atom as ring member, wherein said heterocyclyl is unsubstituted or substituted with one or more, preferably 1, 2 or 3, substituents, independently selected from fluoro and $C_1$-$C_4$-alkyl, preferably 1, 2 or 3, $C_1$-$C_4$-alkyl;

(c) $C_6$-$C_{10}$ aryl which is unsubstituted or substituted with 1, 2 or 3 $R^{A2}$;

(d) 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{A3}$, and wherein a nitrogen atom, when present in the heteroaryl ring, is unsubstituted or substituted with a substituent selected from the group consisting of: $C_1$-$C_4$-alkyl, —$(CH_2)_{1-2}$—$C_{3-4}$-cycloalkyl, $C_3$-$C_6$-cycloalkyl, hydroxy-$C_1$-$C_4$-alkyl, fluoro-$C_1$-$C_4$-alkyl, $C_1$-$C_4$-alkoxy-$C_1$-$C_4$-alkyl, $N(R^9)(R^{10})$—$C_1$-$C_4$-alkyl, —$SO_2$—$C_1$-$C_4$-alkyl, —$SO_2$—$C_{3-4}$-cycloalkyl, —$(CH_2)_p$-$Het^{py}$, and —$(CH_2)_p$—$N(R^9)(R^{10})$, (preferably wherein said substituent is selected from the group consisting of fluoro-$C_1$-$C_4$-alkyl, $N(R^9)(R^{10})$—$C_1$-$C_4$-alkyl, —$SO_2$—$C_{3-4}$-cycloalkyl, or —$(CH_2)_{1-2}$—$C_{3-4}$-cycloalkyl);

(e) 8-10 membered heteroaryl ring containing 1, 2 or 3 nitrogen atoms, or 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 $S(=O)_2$ group in the hetero-bicyclic ring, wherein said heteroaryl ring or hetero-bicyclic ring is unsubstituted or substituted on a carbon atom with 1, 2, 3, 4 or 5 $R^{A4}$, and wherein the hetero-bicyclic ring is further optionally substituted on a carbon atom by oxo and wherein a nitrogen atom, when present, is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$; and wherein $Het^b$ is a 4- or 5- or 6-membered heterocyclic ring comprising 1 or 2 heteroatoms or groups independently selected from N, O, S, SO and $SO_2$ (preferably 1 oxygen atom, or 1 sulfur atom, or one S(=O) or one $S(=O)_2$ group, or 1 nitrogen atom and 1 oxygen atom, or 1-2 nitrogen atoms), wherein said heterocyclic ring $Het^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is optionally further substituted with $C_1$-$C_4$-alkyl which is optionally substituted with 1 to 3 substituents independently selected from fluoro, hydroxy and $C_1$-$C_4$-alkoxy;

wherein A is attached to the rest of the compound of Formula (I) by a carbon atom on A which is $sp^2$ hybridized;

wherein

B is selected from the group consisting of $B^1$ and $B^2$, wherein $B^1$ is $C_{6-10}$ aryl which is unsubstituted or substituted with 1, 2, 3 or 4 $R^{Ba}$;

$B^2$ is a 6-13 membered heteroaryl which comprises 1, 2 or 3 nitrogen atoms, wherein $B^2$ is unsubstituted or substituted with 1, 2, 3 or 4 $R^{Bb}$;

C is selected from the group consisting of hydrogen, $C_1$-$C_3$ alkyl (preferably methyl), $C_3$-$C_5$ cycloalkyl (preferably cyclopropyl), fluoro-$C_1$-$C_3$ alkyl (preferably $CHF_2$ or $CF_3$), cyano, —$CH_2$—CN, —CH(CN)—$CH_3$, —$CH_2$—OH, —CH(OH)—$CH_3$ and halo;

L is selected from the group consisting of:

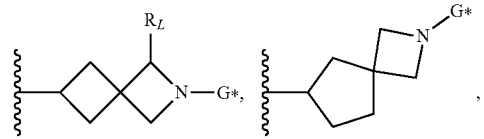

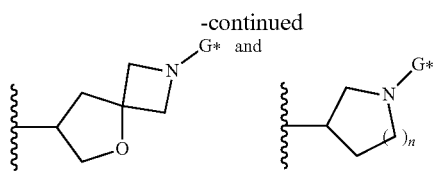

wherein n is 1, 2 or 3,
$R_L$ is selected from hydrogen, methyl, ethyl, —$CH_2$—CN and —$CH_2$—OH, where
G* represents the point of attachment to G;
G is selected from the group consisting of

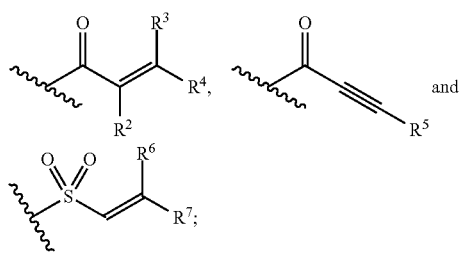

wherein
$R^2$ is selected from hydrogen, $C_1$-$C_3$ alkyl, —C(O)—$C_1$-$C_3$-alkyl, and fluoro;
$R^3$ is hydrogen;
$R^4$ is selected from hydrogen, methyl, —$CH_2F$, —$CH_2$—$OCH_3$ and —$CH_2$—$N(CH_3)_2$;
$R^5$ is selected from hydrogen and methyl;
$R^6$ is hydrogen;
$R^7$ is selected from hydrogen and methyl;
wherein $R^{42}$ is independently selected from the group consisting of: $NR^9R^{10}$, cyano, —$(CH_2)_p$—CN, halo, OH, hydroxy-$C_1$-$C_4$-alkyl, —(COOH), —$(CH_2)_p$—COOH, $C_1$-$C_4$-alkyl, fluoro-$C_1$-$C_4$-alkyl, $C_1$-$C_4$-alkoxy, $C_1$-$C_4$-alkoxy-$C_1$-$C_4$-alkyl, $N(R^9)(R^{10})$—$C_1$-$C_4$-alkyl, $N(R^9)(R^{10})$—$C_1$-$C_4$-alkyl-oxy, $N(R^9)(R^{10})$—$C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, $C_1$-$C_4$-alkoxy-$C_1$-$C_4$-alkyl-oxy-$C_1$-$C_4$-alkyl, —$SO_2$—$C_1$-$C_4$-alkyl, —$SO_2$—$C_{3-4}$-cycloalkyl, —$(CH_2)_{1-2}$—$C_{3-4}$-cycloalkyl, $Het^{py}$, —$(CH_2)_p$-$Het^{py}$, —C(=O)—$NR^9R^{10}$, —$(CH_2)_p$—C(=O)$NR^9R^{10}$, (preferably from the group consisting of $NR^9R^{10}$, cyano, $C_1$-$C_4$-alkyl, fluoro, fluoro-$C_1$-$C_4$-alkyl, $C_1$-$C_4$-alkoxy, $C_1$-$C_4$-alkoxy-$C_1$-$C_4$-alkyl-oxy, hydroxy-$C_1$-$C_4$-alkyl, hydroxy-$C_1$-$C_4$-alkyl-oxy, $Het^{py}$, —$(CH_2)_p$-$Het^{py}$ and —C(=O)—$NR^9R^{10}$);
wherein $R^{43}$ is independently selected from the group consisting of oxo, $NR^9R^{10}$, cyano, —$(CH_2)_p$—CN, halo, OH, hydroxy-$C_1$-$C_4$-alkyl, —(COOH), —$(CH_2)_p$—COOH, $C_1$-$C_4$-alkyl, fluoro-$C_1$-$C_4$-alkyl, $C_1$-$C_4$-alkoxy, $C_1$-$C_4$-alkoxy-$C_1$-$C_4$-alkyl, $N(R^9)(R^{10})$—$C_1$-$C_4$-alkyl, $N(R^9)(R^{10})$—$C_1$-$C_4$-alkyl-oxy, $N(R^9)(R^{10})$—$C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, $C_1$-$C_4$-alkoxy-$C_1$-$C_4$-alkyl-oxy-$C_1$-$C_4$-alkyl, —$SO_2$—$C_1$-$C_4$-alkyl, —$SO_2$—$C_{3-4}$-cycloalkyl, —$(CH_2)_{1-2}$—$C_{3-4}$-cycloalkyl, $Het^{py}$, —$(CH_2)_p$-$Het^{py}$, —C(=O)—$NR^9R^{10}$, —$(CH_2)_p$—C(=O)$NR^9R^{10}$, $(CH_2)_p$—$NR^9R^{10}$ (preferably from the group consisting of $NR^9R^{10}$, cyano, $C_1$-$C_4$-alkyl, fluoro, fluoro-$C_1$-$C_4$-alkyl, $C_1$-$C_4$-alkoxy, $C_1$-$C_4$-alkoxy-$C_1$-$C_4$-alkyl-oxy, $Het^{py}$ and —$(CH_2)_p$-$Het^{py}$);

wherein $R^{44}$ is independently selected from the group consisting of cyano, $CO_2H$, halo, $C_1$-$C_4$-alkyl, fluoro-$C_1$-$C_4$-alkyl, hydroxy, hydroxy-$C_1$-$C_4$-alkyl, hydroxy-$C_1$-$C_4$-alkyl-oxy, $C_1$-$C_4$-alkoxy, $C_1$-$C_4$-alkoxy-$C_1$-$C_4$-alkyl, $C_1$-$C_4$-alkoxy-$C_1$-$C_4$-alkyl-oxy, $NR^9R^{10}$, $(N(R^9)(R^{10})$—$C_1$-$C_4$-alkyl, $(N(R^9)(R^{10})$—$C_1$-$C_4$-alkyl-oxy, —(CO)—$C_1$-$C_4$-alkyl, and $R^9R^{10}N$—$C_1$-$C_4$-alkyl-oxy-(CO)—$C_1$-$C_4$-alkyl;
wherein
p is 1 or 2 or 3;
$R^9$ is selected from hydrogen and $C_1$-$C_4$-alkyl;
$R^{10}$ is selected from the group consisting of hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl;
$Het^{py}$ is a 4-, 5-, 6- or 7-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, and wherein said heterocyclic ring is optionally substituted with oxo on one carbon atom, and wherein said heterocyclic ring is optionally further substituted on one or more carbon atoms with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl, and wherein the nitrogen atom, if present in said heterocycle, is optionally further substituted with $R^{10}$ (preferably $C_1$-$C_4$-alkyl (such as methyl));
or $Het^{py}$ is a 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one or more (e.g., 1, 2 or 3) substituents independently selected from $NR^9R^{10}$, —C(=O)—$NR^9R^{10}$, halo, $C_1$-$C_4$-alkyl, hydroxy-$C_1$-$C_4$-alkyl, fluoro-$C_1$-$C_4$-alkyl, cyano, OH, and $C_1$-$C_4$-alkoxy;
each $R^{Ba}$ is independently selected from the group consisting of hydroxy, $NH_2$, $C_1$-$C_4$-alkyl and halo;
each $R^{Bb}$ is independently selected from the group consisting of $C_1$-$C_4$-alkyl (preferably methyl), cyclopropyl, fluoro-$C_1$-$C_3$-alkyl (preferably $CHF_2$ or $CF_3$), cyano, halo (preferably fluoro or chloro), $NH_2$ and $C_1$-$C_3$-alkoxy (preferably methoxy),
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Where the term "preferably" is mentioned in this specification, other invention embodiments especially relate to a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, wherein all the moieties or features specifically mentioned after the term "preferably" replace the more general term immediately preceding the one(s) that they specify.

In a further aspect, there is provided a compound of formula (I), or an atropisomer thereof, or a pharmaceutically acceptable salt thereof, or a pharmaceutically acceptable salt of an atropisomer thereof, for use as a medicament.

In a further aspect, there is provided a compound of formula (I), or an atropisomer thereof, or a pharmaceutically acceptable salt thereof, or a pharmaceutically acceptable salt of an atropisomer thereof, for use in the treatment of a disorder or a disease (for example a cancer) mediated by a KRAS, NRAS or HRAS G12C mutation, for example a KRAS G12C mutation.

In a further aspect, there is provided a compound of formula (I), or an atropisomer thereof, or a pharmaceutically acceptable salt thereof, or a pharmaceutically acceptable salt of a stereoisomer thereof, or a pharmaceutically acceptable salt of an atropisomer thereof for the manufacture of a medicament for the treatment of cancer, for example a cancer mediated by a KRAS, NRAS or HRAS G12C mutation.

In a further aspect, there is provided a method of treating a disorder or a cancer in a subject in need thereof, wherein the method comprises administrating to the subject a therapeutically effective amount of a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

In a further aspect, there is provided a method of treating a disorder or disease e.g., a cancer which is selected from lung cancer (including lung adenocarcinoma and non-small cell lung cancer), colorectal cancer (including colorectal adenocarcinoma), pancreatic cancer (including pancreatic adenocarcinoma), uterine cancer (including uterine endometrial cancer), rectal cancer (including rectal adenocarcinoma) and a solid tumor, in a subject in need thereof, wherein the method comprises administering to the subject a therapeutically effective amount of a compound of formula (I) as defined herein, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

In a further aspect, there is provided a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, for use in the treatment of cancer, e.g. lung cancer (including lung adenocarcinoma and non-small cell lung cancer), colorectal cancer (including colorectal adenocarcinoma), pancreatic cancer (including pancreatic adenocarcinoma), uterine cancer (including uterine endometrial cancer), rectal cancer (including rectal adenocarcinoma) and a solid tumor.

In a further aspect, there is provided a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, for use in the treatment of cancer, e.g. lung cancer (including lung adenocarcinoma and non-small cell lung cancer), colorectal cancer (including colorectal adenocarcinoma), pancreatic cancer (including pancreatic adenocarcinoma), uterine cancer (including uterine endometrial cancer), rectal cancer (including rectal adenocarcinoma) and a solid tumor, wherein the cancer is KRAS-, NRAS- or HRAS-G12C mutant, typically wherein the cancer is KRAS-G12C mutant.

In a further aspect, there is provided a pharmaceutical composition comprising a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, and a pharmaceutically acceptable carrier.

In a further aspect, there is provided a pharmaceutical composition comprising a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, for use as a medicament.

In a further aspect, there is provided a pharmaceutical composition comprising a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, for use in the treatment of cancer, e.g. lung cancer (including lung adenocarcinoma and non-small cell lung cancer), colorectal cancer (including colorectal adenocarcinoma), pancreatic cancer (including pancreatic adenocarcinoma), uterine cancer (including uterine endometrial cancer), rectal cancer (including rectal adenocarcinoma) and a solid tumor, optionally wherein the cancer is KRAS-, NRAS- or HRAS-G12C mutant.

In a further aspect, there is provided a combination comprising a compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, and one or more therapeutically active agents.

In a further aspect, there is provided a method for the manufacture of the compound of formula (I), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Unless specified otherwise, and unless context clearly indicates otherwise, the terms "a compound of the present invention" or "compounds of the invention" or "compounds of the formula (I)" or "a compound of formula (I)", include a compound or compounds of formula (I), (Ia), (Ib*), (Ic*), (Id*) and (Ie), and pharmaceutically acceptable salts thereof, as well as all stereoisomers (including diastereoisomers and enantiomers), atropisomers, rotamers, tautomers, and isotopically labeled compounds (including deuterium substitutions), as well as inherently formed moieties.

It will be understood that compounds prepared as intermediates may also be considered as compounds of the invention.

Compounds of formula 2(a), (2b*), (2c*) and (2d*), and salts thereof, are thus also considered as compounds of the invention.

Thus, unless specified otherwise, and unless context clearly indicates otherwise, the terms "a compound of formula (I)" or "a compound of" formula (I), or a pharmaceutically acceptable salt thereof, include a stereoisomer of a compound of formula (I), (Ia), (Ib*), (Ic*), (Id*) and (Ie), or an atropisomer thereof, or a pharmaceutically acceptable salt thereof, or a pharmaceutically acceptable salt of a stereoisomer of a compound of formula (I), (Ia), (Ib*), (Ic*), (Id*) and (Ie), or a pharmaceutically acceptable salt of a atropisomer a compound of formula (I), (Ia), (Ib*), (Ic*), (Id*) and (Ie).

The compounds of formula (I), (Ia), (Ib*), (Ic*), (Id*) and (Ie) include all stereoisomers, including diastereoisomers, atropisomers, enantiomers, mixtures thereof and racemic mixtures, including pharmaceutically acceptable salts thereof. The compounds of formula 2(a), (2b*), (2c*) and (2d*) also include all stereoisomers, including diastereoisomers, atropisomers, enantiomers, mixtures thereof and racemic mixtures, including salts thereof.

Where one isomer (e.g. enantiomer, diastereomer, atropisomer, or geometric isomer) has higher intrinsic activity as an inhibitor of RAS G12C mutant protein than its opposite isomer, the more active isomer is typically preferred.

The presence of diastereoisomers can be identified by a person of skill in the art with tools such as NMR. Separation of diastereoisomers can be carried out by a person of skill in the art using chromatographic methods, with tools such as HPLC (High Performance Liquid Chromatography), Thin Layer Chromatography, SFC (Supercritical Fluid Chromatography), GC (Gas Chromatography), or recrystallization techniques. Separation of enantiomers can be carried out by a person of skill in the art with tools such as chiral HPLC, chiral SFC, chiral GC.

Compounds of the present invention, in particular, ortho-substituted biaryl compounds may exhibit conformational, rotational isomerism, herein referred to as atropisomers (Eliel, E. and Wilen, S. (1994) Stereochemistry of Organic Compounds, John Wiley & Sons, Inc., pp. 1142-55). In some instances, depending upon the substituents on the bi-aryl ring moiety, such biaryl compounds of the present invention exhibit atropisomerism.

Thus, the compounds of formula (I), and subformulae (Ia), (Ib*), (Ic*), (Id*) and (Ie) and their isomeric mixtures (including diastereomeric mixtures, enantiomeric mixtures and racemic mixtures), also form part of the invention. Likewise, "diastereomerically enriched" or "enantiomerically enriched" mixtures of the compounds of formula (I), and subformulae (Ia), (Ib*), (Ic*), (Id*) and (Ie) also form part of the invention.

The present invention also provides a crystalline form of the Compound X, as defined herein, such as the hydrate (Modification HA) crystalline form, or the isopropyl alcohol (IPA) solvate crystalline form, or the ethanol (EtOH) solvate crystalline form or the propylene glycol solvate crystalline form of Compound X.

The present invention also provides a crystalline form of Compound X, as defined herein, having an X-ray powder diffraction spectrum substantially the same as the X-ray powder diffraction spectrum shown in FIG. 1, FIG. 2, FIG. 3 or FIG. 4.

The following definitions also apply unless otherwise provided or apparent from context:

As used herein, the term "halogen" (or halo) refers to fluorine, bromine, chlorine or iodine. Halogen-substituted groups and moieties, such as alkyl substituted with halogen (halo-alkyl) can be mono-, poly- or per-halogenated. Chloro and fluoro are preferred halo substituents on alkyl or cycloalkyl groups, with fluoro being most preferred, unless otherwise specified. Fluoro, chloro and bromo, are often preferred on aryl or heteroaryl groups, with fluoro being most preferred, unless otherwise specified.

As used herein, the term "hetero atoms" refers to nitrogen (N), oxygen (O) or sulfur (S) atoms, in particular nitrogen or oxygen, unless otherwise provided.

When multiple substituents are present, the substituents are selected independently unless otherwise indicated, so where 2 or 3 substituents are present, for example, those substituents may be the same or different.

As used herein, the term "$C_1$-$C_4$-alkyl" refers to a straight or branched hydrocarbon chain radical consisting solely of carbon and hydrogen atoms, containing no unsaturation, having from one to four carbon atoms, and which is attached to the rest of the molecule by a single bond. Examples of $C_1$-$C_4$-alkyl include, but are not limited to, methyl, ethyl, n-propyl, 1-methylethyl (iso-propyl) and n-butyl. A preferred example is methyl.

A $C_1$-$C_4$-alkyl radical when substituted by oxo includes a —C(O)—$C_1$-$C_3$-alkyl where the carbonyl portion of the substituent is attached to the rest of the molecule.

As used herein, the term "hydroxy-$C_1$-$C_4$-alkyl" refers to a $C_1$-$C_4$-alkyl radical as defined above, wherein one of the hydrogen atoms of the $C_1$-$C_4$-alkyl radical is replaced by OH. Examples of hydroxy-$C_1$-$C_4$-alkyl include, but are not limited to, hydroxy-methyl, 2-hydroxy-ethyl, 2-hydroxy-propyl, 3-hydroxy-propyl and 2-hydroxy-2-methyl-propyl.

As used herein, the term "$C_1$-$C_4$-alkoxy" refers to a radical of the formula —$OR_a$ where $R_a$ is a $C_1$-$C_4$ alkyl radical as generally defined above. Examples of $C_1$-$C_4$-alkoxy include, but are not limited to, methoxy, ethoxy, propoxy, isopropoxy and butoxy.

As used herein, the term "hydroxy$C_1$-$C_4$-alkoxy" refers to a $C_1$-$C_4$-alkoxy radical as defined above, wherein at least one of the hydrogen atoms of the $C_1$-$C_4$-alkoxy radical is replaced by OH. Examples of hydroxy$C_{1-4}$alkoxy include, but are not limited to, hydroxymethoxy, hydroxyethoxy, 2-hydroxypropoxy.

As used herein, the term "$C_1$-$C_4$-alkyl-oxy" refers to a "$C_1$-$C_4$-alkyl" radical as defined above, wherein said radical is attached by an oxygen atom to the rest of the molecule.

As used herein, a "hydroxy-$C_1$-$C_4$-alkyl-oxy" substituent refers to a hydroxy-$C_1$-$C_4$-alkyl radical as defined above, which is attached by an oxygen atom to the rest of the molecule. Examples of hydroxy-$C_1$-$C_4$-alkyl-oxy include, but are not limited to, hydroxymethoxy, hydroxyethoxy, 2-hydroxypropoxy.

As used herein, the term "$C_1$-$C_4$-alkoxy-$C_1$-$C_4$ alkyl" refers to a $C_1$-$C_4$-alkyl radical as defined above, wherein one of the hydrogen atoms of the $C_1$-$C_4$-alkyl radical is replaced by $C_1$-$C_4$-alkoxy.

As used herein, the term "$C_1$-$C_4$-alkoxy-hydroxy-$C_1$-$C_4$-alkyl" refers to a $C_1$-$C_4$-alkoxy-$C_1$-$C_4$-alkyl radical as defined above, wherein herein at least one of the hydrogen atoms of the $C_1$-$C_4$-alkyl radical is replaced by OH.

As used herein, the term "$C_1$-$C_4$-alkoxy-$C_1$-$C_4$-alkyl-oxy" refers to a "$C_1$-$C_4$-alkoxy-$C_1$-$C_4$-alkyl" as defined above, wherein said radical is attached by an oxygen atom to the rest of the molecule.

As used herein, the term "$C_1$-$C_4$-alkyl-carbonyl-oxy-$C_1$-$C_4$-alkyl-oxy" refers to a radical of formula $C_1$-$C_4$-alkyl-C(=O)—O—$C_1$-$C_4$-alkyl-O—, wherein said radical is attached by the last oxygen atom to the rest of the molecule.

As used herein, the term "halo-alkyl" refers to an alkyl as defined herein, which is substituted with one or more halo radicals as defined herein. The halo-alkyl can be monohalo-alkyl, dihalo-alkyl, trihalo-alkyl, or polyhalo-alkyl including perhalo-alkyl. A monohalo-alkyl can have one iodo, bromo, chloro or fluoro within the alkyl group. Chloro and fluoro are preferred on alkyl or cycloalkyl groups.

As used herein, the term "fluoro-alkyl" refers to an alkyl as defined herein, which is substituted with one or more fluoro. Non-limiting examples of fluoro-$C_1$-$C_4$-alkyl include trifluoromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl. Preferred fluoro-alkyl groups, unless specified otherwise, include monofluoro-, difluoro- and trifluoro-substituted methyl and ethyl groups, e.g. $CF_3$, $CF_2H$, $CFH_2$, and $CH_2CF_3$.

As used herein, the term "fluoro-alkoxy" refers to an alkoxy as defined herein, which is substituted with one or more fluoro.

As used herein, the term "$C_1$-$C_4$-alkylamino" refers to a radical of the formula —NH—$R_a$ where $R_a$ is a $C_1$-$C_4$ alkyl radical as defined above.

As used herein, the term "di-$C_1$-$C_4$ alkylamino" refers to a radical of the formula —N($R_a$)—$R_a$ where each $R_a$ is a $C_1$-$C_4$-alkyl radical, which may be the same or different, as defined above.

As used herein, a "$NR^9R^{10}$" or "N($R^9$)($R^{10}$)" substituent refers to a radical of the formula "—N($R^9$)($R^{10}$)" wherein said radical is attached to the rest of the molecule by the nitrogen atom to which an $R^9$ group and an $R^{10}$ group are also attached, and wherein $R^9$ and $R^{10}$ may be the same or different, and are as defined herein.

As used herein, the term "$R^9R^{10}$N—$C_1$-$C_4$-alkyl" or "N($R^9$)($R^{10}$)—$C_1$-$C_4$-alkyl" refers to a $C_1$-$C_4$ alkyl radical as defined above, wherein one of the hydrogen atoms of the $C_1$-$C_4$-alkyl radical is replaced by —N($R^9$)($R^{10}$).

As used herein, the term "$R^9R^{10}$N—$C_1$-$C_4$-alkyl-oxy" or "N($R^9$)($R^{10}$)—$C_1$-$C_4$-alkyl-oxy" refers to a $R^9R^{10}$N—$C_1$-$C_4$-alkyl radical (or N($R^9$)($R^{10}$)—$C_1$-$C_4$-alkyl radical) as defined above, which is connected by an oxygen atom to the rest of the molecule.

As used herein, the term "N($R^9$)($R^{10}$)—$C_1$-$C_4$-alkoxy" refers to a $C_1$-$C_4$ alkoxy radical as defined above, wherein one of the hydrogen atoms of the $C_1$-$C_4$-alkoxy radical is replaced by —N($R^9$)($R^{10}$).

As used herein, the term "—$SO_2$—$C_1$-$C_4$-alkyl" refers to a $C_1$-$C_4$-alkyl radical as defined above, which is attached to the rest of the molecule via an —S(=O)$_2$— linker.

As used herein, the term "—$SO_2$—$C_3$-$C_4$-cycloalkyl" refers to a $C_3$-$C_4$-cycloalkyl radical as defined below, which is attached to the rest of the molecule via an —S(=O)$_2$— linker.

As used herein, the term "hydroxy-$C_{1-4}$-alkoxy" refers to a $C_{1-4}$-alkoxy radical as defined above, wherein at least one of the hydrogen atoms of the $C_{1-4}$-alkoxy radical is replaced by OH. Examples of hydroxy$C_1$-$C_6$alkoxy include, but are not limited to, hydroxymethoxy, hydroxyethoxy, 2-hydroxypropoxy.

As used herein, the term "$C_1$-$C_4$ alkoxy-$C_1$-$C_4$ alkyl" refers to a $C_{1-4}$ alkyl radical as defined above, wherein one of the hydrogen atoms of the $C_{1-4}$ alkyl radical is replaced by $C_1$-$C_4$-alkoxy.

As used herein, the term "$C_1$-$C_4$-alkoxy-$C_1$-$C_4$-alkyl-oxy" refers to a "$C_1$-$C_4$ alkoxy-$C_1$-$C_4$ alkyl" as defined above, wherein said radical is attached to the rest of the molecule by an oxygen atom.

As used herein, the term "C(O)—$NR^9R^{10}$" refers to a radical of the formula —$R_{a1}$—$NR^9R^{10}$ where $R_{a1}$ is a carbonyl radical, "$NR^9R^{10}$" is as defined above and $R^9$ and $R^{10}$ may be the same or different, and are as defined herein.

As used herein, the term "C(O)$C_1$-$C_4$-alkyl" refers to a radical of the formula —$R_{a1}$—$C_1$-$C_4$-alkyl where $R_{a1}$ is a carbonyl radical and $C_1$-$C_4$-alkyl is as defined above.

As used herein, the term "cycloalkyl" refers to a saturated carbocyclic ring radical. $C_3$-$C_7$ cycloalkyl is any such ring radical containing 3 to 7 carbon atoms such as cyclopropyl, cyclobutyl, cyclopentyl, cyclohexyl and cycloheptyl.

As used herein, the term "cycloalkylene" refers to a non-aromatic carbocyclic ring radical containing at least one carbon-carbon double bond, preferably one carbon-carbon double bond. The term "monocyclic cycloalkylene" refers to a non-aromatic monocyclic carbocyclic ring radical containing at least one carbon-carbon double bond, preferably one carbon-carbon double bond. The term includes, but is not limited to "$C_5$-$C_7$-cycloalkylene" which is a non-aromatic carbocyclic ring radical containing 5 to 7 carbon atoms and one C—C double bond. Examples of suitable cycloalkylene groups are non-aromatic carbocyclic ring containing 5 to 7 carbon atoms and one or more C—C double bonds such as cyclopentenyl, cyclohexenyl (e.g., cyclohex-1-en-1-yl, cyclohex-2-en-1-yl, cyclohex-3-en-1-yl).

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Phenyl is sometimes preferred. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group.

The term "$C_6$-$C_{10}$ aryl" refers to a phenyl, 1,2,3,4-tetrahydronaphthyl, or naphthyl group. An example of a suitable $C_6$-$C_{10}$ aryl is a phenyl group. The term "phenyl" refers to a radical of the formula —$C_6H_5$. In substituted phenyl, one or more or the hydrogen atoms in —$C_6H_5$ are replaced with a substituent or with substituents, especially any one described herein.

As used herein, the term "heterocyclyl" or "heterocyclic ring" refers to a heterocyclic radical that is saturated or partially unsaturated but not aromatic, and can be a monocyclic or a polycyclic ring, including a fused or bridged bicyclic ring system. A heterocycle or heterocyclyl contains at least one non-carbon atom as a ring member, typically N, O or S unless otherwise specified. Unless otherwise specified, a heterocyclyl group has 3 to 10, and preferably 4 to 7 ring atoms; wherein one or more, preferably one to four, especially 1, 2 or 3 ring atoms are heteroatoms independently selected from O, S and N (the remaining ring atoms therefore being carbon). Where the heterocycle contains S or N as heteroatoms, the S may be present as SO or $SO_2$ groups and the N may be present as the N-oxide, where valency allows.

An unsaturated heterocyclyl can have one or two double bonds, but is not aromatic. Preferably, unless described as unsaturated, the heterocyclyl groups in the compounds of the invention are saturated single rings. Preferably, a heterocyclyl group has one or two heteroatoms as ring atoms, and preferably the heteroatoms are not directly connected to each other. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "5-7 membered unsaturated heterocyclyl" refers to a ring radical containing 5 to 7 ring atoms comprising 1, 2, or 3, heteroatoms individually selected from nitrogen, oxygen and sulfur, (optionally further comprising groups such as —S(=O)— and —S(=O)$_2$—) and containing one or more C—C double bonds, preferably one C—C double bond. The term includes a 5-, 6- or 7-membered non-aromatic monocyclic ring radical containing one or more C—C double bonds, preferably one C—C double bond, and 1, 2, or 3, heteroatoms individually selected from nitrogen, oxygen and sulfur, preferably one oxygen. Examples of 5-7 membered unsaturated heterocyclyls include, but are not limited to, 6-membered non-aromatic monocyclic radicals containing one oxygen and a C—C double bond such as 3,4-dihydro-2-H-pyranyl, 5,6-dihydro-2H-pyranyl and 2H-pyranyl.

The term "heteroaryl" is a 5-14 membered, typically 5-10 membered, monocyclic or bicyclic aromatic ring radical which comprises 1, 2, 3 or 4 heteroatoms individually selected from nitrogen, oxygen and sulfur in the ring radical. Typically, the heteroaryl is a 5-10 membered ring system, e.g., a 5-6 membered monocyclic or an 8-10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2, 3-triazolyl), 1- or 2- or 3-tetrazolyl, 2-, 3-, or 4-pyridyl, 3- or 4-pyridazinyl, 2-pyrazinyl, and 2-, 4-, or 5-pyrimidinyl.

A substituted heteroaryl is a heteroaryl group having one or more substituents, typically 1, 2 or 3 substituents, on the heteroaryl ring replacing a hydrogen atom that would be on the unsubstituted heteroaryl.

The term "5-6 membered heteroaryl" is an aromatic monocyclic ring radical which comprises 1, 2, 3 or 4 heteroatoms individually selected from nitrogen, oxygen and sulfur. The term includes a 5- or 6-membered aromatic ring radical containing 1, 2 or 3 heteroatoms selected from N, O and S as ring members, preferably 1-2 nitrogen atoms, or 1 nitrogen atom and one sulphur atom. The term includes 6-membered rings in which an aromatic tautomer exists, as for example in the case for the 1H-pyridin-2-one system. Examples of suitable 5-6 membered heteroaryl groups include, but are not limited to, 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2, 3-triazolyl), 1- or 2- or 3-tetrazolyl, 2-, 3-, or 4-pyridyl, 3- or 4-pyridazinyl, 2-pyrazinyl, and 2-, 4-, or 5-pyrimidinyl.

The term "8-10 membered heteroaryl" is an aromatic bicyclic ring radical which comprises 1, 2, 3 or 4 heteroatoms individually selected from nitrogen, oxygen and sulfur. Non limiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, and 2-, 3-, 4-, 5-, 6-, or 7-indazolyl. Examples of 8-10 membered heteroaryl include, but are not limited to: pyrrolo[2,3-b]pyridinyl, pyrrolo[2,3-c]pyridinyl, pyrrolo[3,2-c]pyridinyl, pyrrolo[3,2-b]pyridinyl, benzofuranyl, benzothiophenyl, indolyl, isoindolyl, indolininyl, benzimidazolyl, indazolyl.

The term "8-10 membered partially unsaturated heterobicyclyl" or "8-10 membered partially saturated hetero-bicyclic ring" includes (a) a 5-6 membered heteroaryl containing 1-3 or 1-2 nitrogen atoms fused to a second ring to form a 5,5-, 5,6-, 6,5-, or 6-6-ring system and (b) a phenyl ring fused to a second ring containing at least one heteroatom or heteroatom group to form a 6,5-, or 6-6-ring system.

The term "8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 $S(=O)_2$ group in the hetero-bicyclic ring" is an 8-10 membered bicyclic radical consisting of:

(i) a 5-6 membered heteroaryl ring containing 1, 2 or 3 nitrogen atoms wherein the heteroaryl ring is fused to a 5- or 6-membered saturated or partially saturated carbocyclic ring optionally incorporating one or two atoms or groups independently selected from 1-2 oxygen atoms, 1 sulfur atom and 0-1 $S(=O)_2$ group in the non-aromatic portion of the ring, or (ii) a phenyl ring wherein the phenyl ring is fused to a 5- or 6-membered saturated or partially saturated carbocyclic ring incorporating 1 to 3 heteroatoms or heteroatom groups independently selected from 0-3 nitrogen atoms, 0-2 oxygen atoms, 0-1 sulfur atom and 0-1 $S(=O)_2$ group (for example, 1 nitrogen atom and 1 oxygen atom; or 1, 2 or 3 nitrogen atoms; 1 oxygen atom; or 1 sulfur atom; or 1 —$S(=O)_2$ group) in the non-aromatic portion of the ring, provided that the point of attachment of the 8-10 membered partially saturated hetero-bicyclic ring to the rest of the molecule is on the 5-6 membered heteroaryl or on the phenyl ring.

The 8-10 membered partially saturated hetero-bicyclic radical is unsubstituted or substituted with one or more substituents as described herein and is further optionally substituted on a carbon atom by oxo (except on aromatic rings).

In one embodiment, the term "8-10 membered partially saturated hetero-bicyclic ring" is an 8-10 membered partially saturated hetero-bicyclic ring radical consisting of a 5-6 membered heteroaryl ring containing 1, 2 or 3 nitrogen atoms or consisting of a phenyl ring wherein the phenyl ring or the heteroaryl ring is fused to a 5- or 6-membered saturated or partially saturated carbocyclic ring optionally incorporating 1 nitrogen atom and 1 oxygen atom; or 1, 2 or 3 nitrogen atoms; 1 oxygen atom; or 1 sulfur atom; or 1 group selected from —$S(=O)$— and —$S(=O)_2$—, in the non-aromatic portion of the ring, provided that the point of attachment of the 8-10 membered partially saturated hetero-bicyclic ring to the rest of the molecule is on the 5-6 membered heteroaryl or on the phenyl ring. The bicyclic ring radical is unsubstituted or substituted with one or more substituents as described herein and is further optionally substituted on a carbon atom by oxo (except on aromatic rings). Thus, the term "8-10 membered partially unsaturated heterobicyclyl" includes (a) a 5-6 membered heteroaryl containing 1-2 nitrogen atoms fused to a second ring to form a 5,5-, 5,6-, 6,5-, or 6-6-ring system and (b) a phenyl ring fused to a second ring to form a 6,5-, or 6-6-ring system.

Examples of "8-10 membered partially saturated hetero-bicyclic ring" and "8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 $S(=O)_2$ group in the hetero-bicyclic ring" include, but are not limited to: indolinyl (e.g. indolin-5-yl), isoindolinyl (e.g. isoindolin-5-yl), dihydrobenzofuranyl (e.g. 2,3-dihydrobenzofuran-6-yl), dihydroisobenzofuranyl (e.g. 1,3-dihydroisobenzofuran-5-yl), tetrahydroindazolyl, tetrahydrobenzimidazolyl (e.g. 4,5,6,7-tetrahydro-1H-benzimidazol-5-yl), tetrahydroisoquinolinyl, tetrahydroquinoxalinyl, dihydrobenzimidazolyl (e.g. 2,3-dihydro-1H-benzo[c/]imidazol-5-yl), dihydrobenzothiophenyl (e.g. 1,3-dihydrobenzo[c]thiophen-5-yl), dihydrobenzothiophenyl dioxide (e.g. 1,3-dihydrobenzo[c]thiophen-5-yl 2,2-dioxide), dihydropyrrolopyrazolyl (e.g. 5,6-dihydro-4H-pyrrolo[1,2-b]pyrazol-3-yl), isoindolinonyl (e.g. isoindolin-1-one-5-yl), indolinonyl (e.g. indolin-2-one-5-yl), benzofuranonyl (e.g. benzofuran-2(3H)-one-6-yl), isobenzofuranonyl (e.g. isobenzofuran-1(3H)-one-6-yl), and the like. Preferably, the 8-10 membered partially saturated heterobicyclic ring or the "8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 $S(=O)_2$ group in the hetero-bicyclic ring" is selected from indolinyl (e.g. indolin-5-yl), isoindolinyl (e.g. isoindolin-5-yl), dihydrobenzofuranyl (e.g. 2,3-dihydrobenzofuran-6-yl), dihydroisobenzofuranyl (e.g. 1,3-dihydroisobenzofuran-5-yl), dihydrobenzimidazolyl (e.g. 2,3-dihydro-1H-benzo[c/]imidazol-5-yl), dihydrobenzothiophenyl (e.g. 1,3-dihydrobenzo[c]thiophen-5-yl, 2,3-dihydrobenzo[b]thiophen-6-yl), dihydrobenzothiophenyl dioxide (e.g. 1,3-dihydrobenzo[c]

thiophen-5-yl 2,2-dioxide), dihydropyrrolopyrazolyl (e.g. 5,6-dihydro-4H-pyrrolo[1,2-b]pyrazol-3-yl), isoindolinonyl (e.g. isoindolin-1-one-5-yl), indolinonyl (e.g. indolin-2-one-5-yl), benzofuranonyl (e.g. benzofuran-2(3H)-one-6-yl), isobenzofuranonyl (e.g. isobenzofuran-1(3H)-one-6-yl).

The term "cyano" refers to the radical —CN.
The term "amino" refers to the radical —$NH_2$.
The term "hydroxy" refers to the radical —OH.
The term "oxo" refers to the radical =O.

In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-.

For groups beginning with a hyphen (-) or (-), it is the group which immediately follows the hyphen which is the attachment point to the rest of the molecule. For example, —$(CH_2)_{1-2}$—$C_{3-4}$-cycloalkyl refers to a $C_{3-4}$-cycloalkyl radical which is attached to the rest of the molecule via a methylene or ethylene linker.

As used herein, the term "substituted with one or more substituents" includes substituted with 2, 3, 4, 5, or 6 substituents. Preferably, it includes 1 substituent or 2 or 3 substituents. For the avoidance of doubt, this term also includes instances where 2 or 3 substituents may be present on the same carbon atom where valency allows.

The use of any and all examples, or exemplary language (e.g. "such as") provided herein is intended merely to better illuminate the invention and does not pose a limitation on the scope of the invention otherwise claimed.

The term "substituted with 1, 2 or 3 substituents" is to be construed accordingly.

By the expression "A is attached to the rest of the compound of Formula (I) by a carbon atom on A which is $sp^2$ hybridized", this may be represented by the following diagram

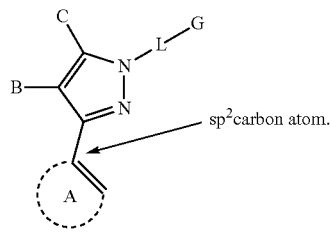

sp²carbon atom.

Where "heteroatom" or "heteroatoms" is mentioned for a ring, this refers to ring heteroatoms (where NH is also to be regarded as heteroatom which may be in place of "N").

As used herein, the term "nitrogen-protecting group" (PG) in a compound described herein, in a compound of formula (2a), (2b*), (2c*) and (2d*), or in the Schemes, refers to a group that should protect the functional groups concerned against unwanted secondary reactions, such as acylations, etherifications, esterifications, oxidations, solvolysis and similar reactions. It may be removed under deprotection conditions. Depending on the protecting group employed, the skilled person would know how to remove the protecting group to obtain the free amine $NH_2$ group by reference to known procedures. These include reference to organic chemistry textbooks and literature procedures such as J. F. W. McOmie, "Protective Groups in Organic Chemistry", T. W. Greene and P. G. M. Wuts, "Greene's Protective Groups in Organic Synthesis", and in "Methoden der organischen Chemie" (Methods of Organic Chemistry).

Preferred nitrogen-protecting groups include: $C_1$-$C_6$alkyl (e.g. tert-butyl), preferably $C_1$-$C_4$alkyl, more preferably $C_1$-$C_2$alkyl, most preferably $C_1$-alkyl which is mono-, di- or tri-substituted by trialkylsilyl-$C_1$-$C_7$alkoxy (eg. trimethylsilylethoxy), aryl, preferably phenyl, or a heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted by one or more, e.g. two or three, residues, e.g. selected from the group consisting of $C_1$-$C_7$alkyl, hydroxy, $C_1$-$C_7$alkoxy (e.g. para-methoxy benzyl (PMB)), $C_2$-$C_8$-alkanoyl-oxy, halogen, nitro, cyano, and $CF_3$, aryl-$C_1$-$C_2$-alkoxycarbonyl (preferably phenyl-$C_1$-$C_2$-alkoxycarbonyl (eg. benzyloxycarbonyl (Cbz), benzyloxymethyl (BOM), pivaloyloxymethyl (POM)), $C_1$-$C_{10}$-alkenyloxycarbonyl, C1-C6alkylcarbonyl (eg. acetyl orpivaloyl), $C_6$-$C_{10}$-arylcarbonyl; $C_1$-$C_6$-alkoxycarbonyl (eg. tertbutoxycarbonyl (Boc), methylcarbonyl, trichloroethoxycarbonyl (Troc), pivaloyl (Piv), allyloxycarbonyl), $C_6$-$C_{10}$-arylC1-C6-alkoxycarbonyl (e.g. 9-fluorenylmethyloxycarbonyl (Fmoc)), allyl or cinnamyl, sulfonyl or sulfenyl, succinimidyl group, silyl groups (e.g. triarylsilyl, trialkylsilyl, triethylsilyl (TES), trimethylsilylethoxymethyl (SEM), trimethylsilyl (TMS), triisopropylsilyl or tert-butyldimethylsilyl).

In embodiments of the invention, the nitrogen-protecting group is $C_1$-$C_6$-alkoxycarbonyl (eg. tertbutoxycarbonyl (Boc), methyloxycarbonyl, trichloroethoxycarbonyl (Troc), pivaloyl (Piv), allyloxycarbonyl). More preferably the nitrogen-protecting group is tertbutoxycarbonyl.

In embodiments of the invention, the nitrogen-protecting group is a $C_1$-$C_6$-alkoxycarbonyl (eg. tertbutoxycarbonyl or t-butyl carbamate (Boc), methyloxycarbonyl or methyl carbamate, ethyl carbamate, 9-fluorophenylmethyl carbamate (Fmoc) and analogs thereof, 2,2,2-trichloroethyl carbamate trichloroethoxycarbonyl (Troc), 2-trimethylsilylethyl carbamate (Teoc), pivaloyl (Piv), allyloxycarbonyl or allyl carbamate (Alloc), benzyl carbamate (Cbz)) or an amide protecting group e.g. $COCF_3$ (trifluoroacetamide), or N-allyl or N-benzyl and analogs thereof. More preferably the nitrogen-protecting group is tertbutoxycarbonyl.

The term "stereoisomer" or "stereoisomers" refer to compounds, which have identical chemical constitution, but differ with regard to the arrangement of the atoms or groups in space.

The term "diastereoisomer" or "diastereomer" refers to stereoisomers not related as mirror images. Diastereoisomers are characterized by differences in physical properties, and by some differences in chemical behaviour. Mixtures of diastereomers may separate under analytical procedures such as chromatography or crystallisation.

The term "enantiomer" refers to one of a pair of molecular entities which are mirror images of each other and non-superimposable.

The term "enantiomeric mixture" refers to an enantiomerically enriched mixture, a composition that comprises a greater proportion or percentage of one of the enantiomers of the compounds of the invention, in relation to the other enantiomer, or a racemate.

The term "diastereomeric mixture" refers to a diastereomerically enriched mixture or a mixture of diastereoisomers of equal proportion.

The term "diastereomerically enriched" refers to a composition that comprises a greater proportion or percentage of one of the diastereomers of the compounds of the invention, in relation to the other diastereoisomer(s).

The term "atropisomer" refers to a stereoisomer resulting from restricted rotation about single bonds where the rotation barrier is high enough to permit isolation of the isomeric species. Typically, rotation about the single bond in the molecule is prevented, or greatly slowed, as a result of steric interactions with other parts of the molecule and the substituents at both ends of the single bond are asymmetrical, resulting in a stereogenic unit termed a "chiral axis".

The absolute configuration of the chiral axes, for instance in exemplary compounds, is assigned using the Cahn-Ingold-Prelog (CIP) chirality rule, with stereodescriptors (aR) or (aS), or the CIP helicity rule, with stereodescriptors (P) or (M) (V. Prelog and G. Helmchen, *Angewandte Chemie International Edition*, 21(8): 567-583, 1982, https://doi.org/10.1002/anie_198205671; P. Mata, A. M. Lobo, C. Marshall, and A. P. Johnson, *Tetrahedron; Asymmetry*, 4(4): 657-688, 1993, https://doi.org/10.1016/S0957-4166(00)80173-1; both cited in H. A. Favre and W. H. Powell, *Nomenclature of Organic Chemistry; IUPAC Recommendations and Preferred Names* 2013 (the IUPAC "Blue Book"), Cambridge, UK: Royal Soc. of Chem., 2014, https://doi.org/10.1039/9781849733069, Chapter P-9, "Specification of Configuration and Conformation", https://doi.org/10.1039/9781849733069-01156).

This is shown below for Example 12a (the more active atropisomer), which has the a(R) or (M) configuration. Example 12b (the less active atropisomer) has the a(S) or (P) configuration. Their structures are depicted below for comparison.

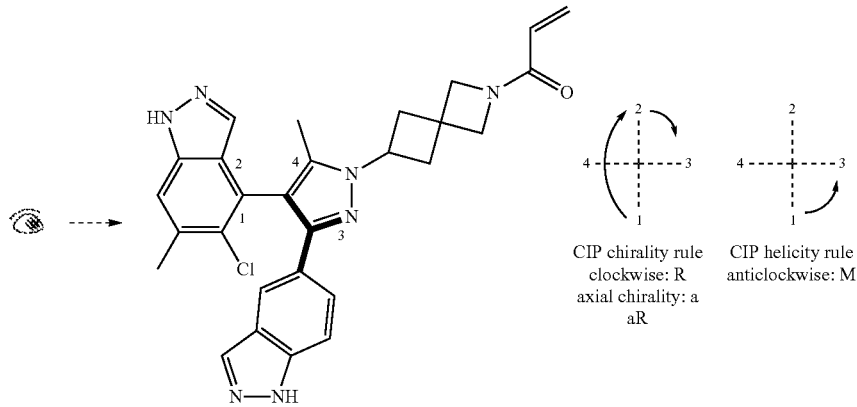

Example 12a: a(R)-1-(6-(4-(5-chloro-6-methyl-1H-indazol-4-yl)-3-(1H-indazol-5-yl)-5-methyl-1H-pyrazol-1-yl)-2-azaspiro[3.3]heptan-2-yl)prop-2-en-1-one 1-{6-[(4M)-(4-(5-chloro-6-methyl-1H-indazol-4-yl)-3-(1H-indazol-5-yl)-5-methyl-1H-pyrazol-1-yl)-2-azaspiro[3.3]heptan-2-yl}prop-2-en-1-one

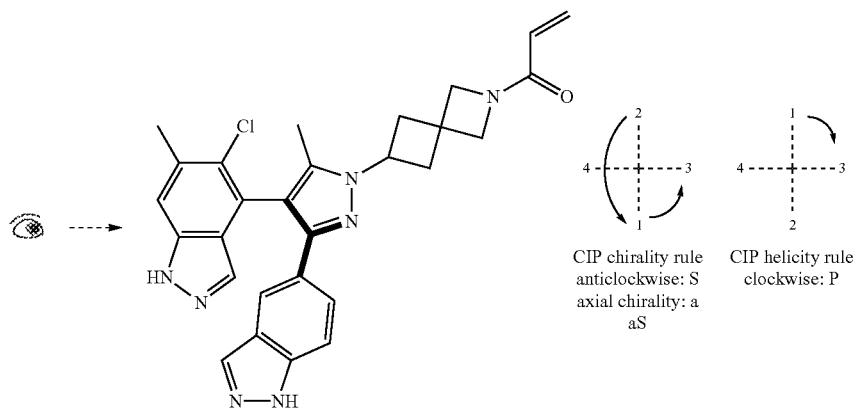

Example 12b: a(S)-1-(6-(4-(5-chloro-6-methyl-1H-indazol-4-yl)-3-(1H-indazol-5-yl)-5-methyl-1H-pyrazol-1-yl)-2-azaspiro[3.3]heptan-2-yl)prop-2-en-1-one 1-{6-[(4P)-(4-(5-chloro-6-methyl-1H-indazol-4-yl)-3-(1H-indazol-5-yl)-5-methyl-1H-pyrazol-1-yl)-2-azaspiro[3.3]heptan-2-yl}prop-2-en-1-one An alternative way of depicting the structures of Example 12a and 12b is as follows.

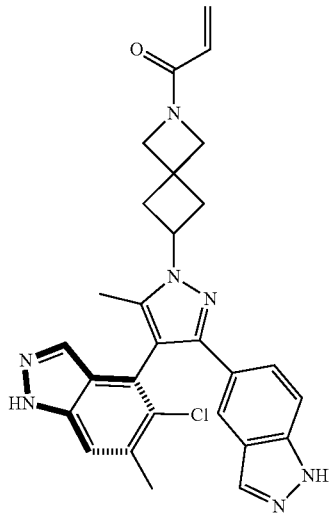

Example 12a

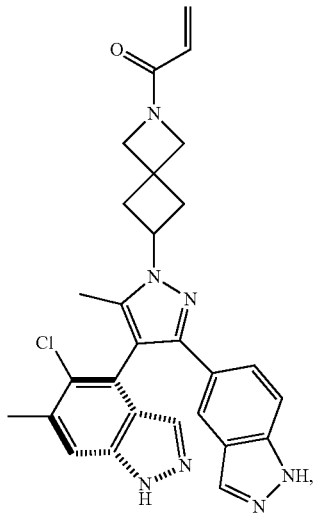

Example 12b

In embodiments of the invention, compounds of the invention adopt the same spatial orientation as shown in Example 12a.

Similarly, the compound of Example 1a can be described by the name "a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one". The compound of Example 1a can also be designated by the name "1-{6-[(4M)-4-(5-chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one".

The structure of the compound of Example 1a (also referred to herein as Compound X) is as follows.

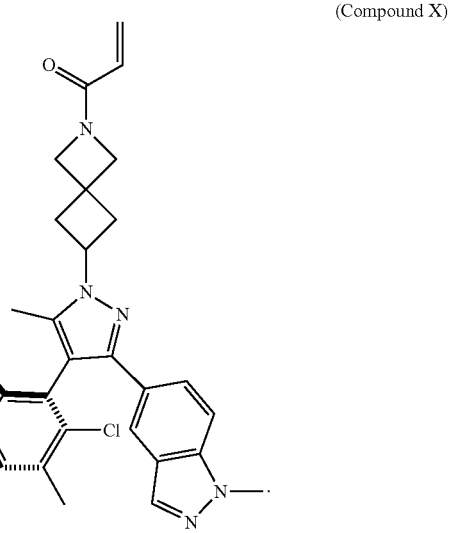

(Compound X)

An alternative way of depicting the structure of the compound of Example 1a (also referred to herein as Compound X) is as follows.

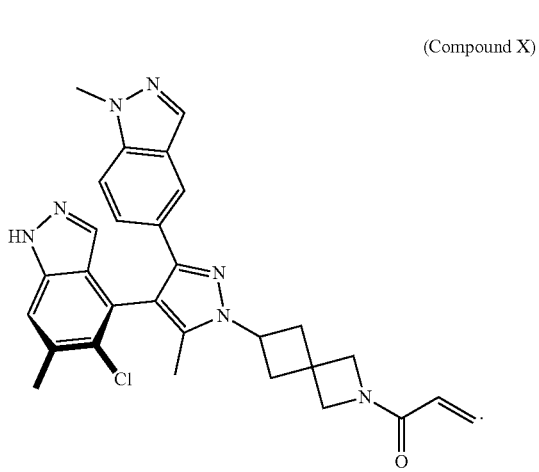

(Compound X)

The term "substantially the same" with reference to X-ray diffraction peak positions means that typical peak position and intensity variability are taken into account. For example, one skilled in the art will appreciate that the peak positions (2Θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

Various embodiments or aspects of the invention are described herein and in particular in the claims. It will be recognized that features specified in each embodiment may be combined with other specified features to provide further embodiments of the present invention. In particular, it will be recognized that features referred to in a particular embodiment or aspect are preferred aspects of the invention. The following enumerated embodiments are representative of the invention.

Embodiment 1. A compound of formula (I),

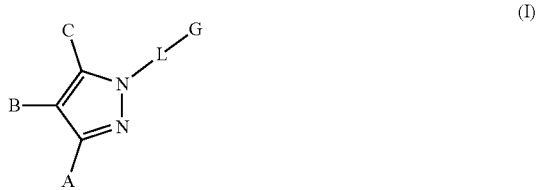

wherein
A is selected from the group consisting of
(a) $C_5$-$C_7$-cycloalkylene which is unsubstituted or substituted with one or more, preferably 1, 2 or 3, substituents independently selected from fluoro and $C_1$-$C_4$-alkyl;
(b) 5-7 membered unsaturated heterocyclyl containing one carbon-carbon double bond and one oxygen atom as ring member, wherein said heterocyclyl is unsubstituted or substituted with one or more, preferably 1, 2 or 3, substituents, independently selected from fluoro and $C_1$-$C_4$-alkyl, preferably 1, 2 or 3, $C_1$-$C_4$-alkyl;
(c) $C_6$-$C_{10}$ aryl which is unsubstituted or substituted with 1, 2 or 3 $R^{A2}$;
(d) 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{A3}$, and wherein a nitrogen atom, when present in the heteroaryl ring, is unsubstituted or substituted with a substituent selected from the group consisting of: $C_1$-$C_4$-alkyl, —$(CH_2)_{1-2}$—$C_{3-4}$-cycloalkyl, $C_3$-$C_6$-cycloalkyl, hydroxy-$C_1$-$C_4$-alkyl, fluoro-$C_1$-$C_4$-alkyl, $C_1$-$C_4$-alkoxy-$C_1$-$C_4$-alkyl, $N(R^9)(R^{10})$—$C_1$-$C_4$-alkyl, —$SO_2$—$C_1$-$C_4$-alkyl, —$SO_2$—$C_{3-4}$-cycloalkyl, —$(CH_2)_p$-Het$^{py}$, and —$(CH_2)_p$—$N(R^9)(R^{10})$, (preferably wherein said substituent is selected from the group consisting of fluoro-$C_1$-$C_4$-alkyl, $N(R^9)(R^{10})$—$C_1$-$C_4$-alkyl, —$SO_2$—$C_{3-4}$-cycloalkyl, or —$(CH_2)_{1-2}$—$C_{3-4}$-cycloalkyl);
(e) 8-10 membered heteroaryl ring containing 1, 2 or 3 nitrogen atoms, or 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 S($=$O)$_2$ group in the hetero-bicyclic ring, wherein said heteroaryl ring or hetero-bicyclic ring is unsubstituted or substituted on a carbon atom with 1, 2, 3, 4 or 5 $R^{A4}$, and wherein the hetero-bicyclic ring is further optionally substituted on a carbon atom by oxo and wherein a nitrogen atom, when present, is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, Het$^b$ and $NR^9R^{10}$; and
wherein Het$^b$ is a 4- or 5- or 6-membered heterocyclic ring comprising 1 or 2 heteroatoms or groups independently selected from N, O, S, SO and SO$_2$ (preferably 1 oxygen atom, or 1 sulfur atom, or one S($=$O) or one S($=$O)$_2$ group, or 1 nitrogen atom and 1 oxygen atom, or 1-2 nitrogen atoms), wherein said heterocyclic ring Het$^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl, and wherein said heterocyclic ring Het$^b$ is further optionally substituted on a carbon atom by oxo, and wherein the nitrogen atom when present in Het$^b$ is optionally further substituted with $C_1$-$C_4$-alkyl which is optionally substituted with 1 to 3 substituents independently selected from fluoro, hydroxy and $C_1$-$C_4$-alkoxy;
wherein A is attached to the rest of the compound of Formula (I) by a carbon atom on A which is sp$^2$ hybridized;
wherein
B is selected from the group consisting of B$^1$ and B$^2$,
wherein B$^1$ is $C_{6-10}$ aryl which is unsubstituted or substituted with 1, 2, 3 or 4 $R^{Ba}$;
B$^2$ is a 6-13 membered heteroaryl which comprises 1, 2 or 3 nitrogen atoms, wherein B$^2$ is unsubstituted or substituted with 1, 2, 3 or 4 $R^{Bb}$;
C is selected from the group consisting of hydrogen, $C_1$-$C_3$ alkyl (preferably methyl), $C_3$-$C_5$ cycloalkyl (preferably cyclopropyl), fluoro-$C_1$-$C_3$ alkyl (preferably $CHF_2$ or $CF_3$), cyano, —$CH_2$—CN, —CH(CN)—$CH_3$, —$CH_2$—OH, —CH(OH)—$CH_3$ and halo;
L is selected from the group consisting of:

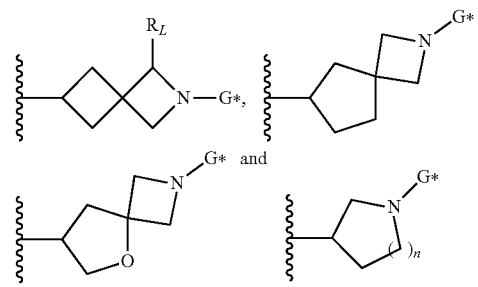

wherein n is 1, 2 or 3,
$R_L$ is selected from hydrogen, methyl, ethyl, —$CH_2$—CN and —$CH_2$—OH, where
G* represents the point of attachment to G;
G is selected from the group consisting of

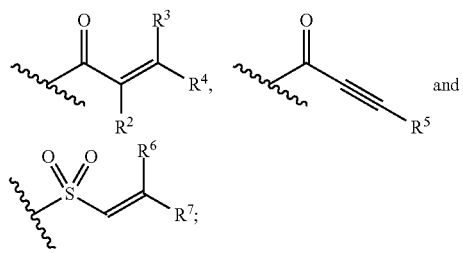

wherein
$R^2$ is selected from hydrogen, $C_1$-$C_3$ alkyl, —C(O)—$C_1$-$C_3$-alkyl, and fluoro;
$R^3$ is hydrogen;
$R^4$ is selected from hydrogen, methyl, —$CH_2F$, —$CH_2$—$OCH_3$ and —$CH_2$—$N(CH_3)_2$;
$R^5$ is selected from hydrogen and methyl;
$R^6$ is hydrogen;
$R^7$ is selected from hydrogen and methyl;
wherein $R^{A2}$ is independently selected from the group consisting of: $NR^9R^{10}$, cyano, —$(CH_2)_p$—CN, halo, OH, hydroxy-$C_1$-$C_4$-alkyl, —(COOH), —$(CH_2)_p$—COOH, $C_1$-$C_4$-alkyl, fluoro-$C_1$-$C_4$-alkyl, $C_1$-$C_4$-alkoxy, $C_1$-$C_4$-alkoxy-$C_1$-$C_4$-alkyl, $N(R^9)(R^{10})$—$C_1$-$C_4$-alkyl, $N(R^9)(R^{10})$—$C_1$-$C_4$-alkyl-oxy, $N(R^9)(R^{10})$—$C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, $C_1$-$C_4$- alkoxy-$C_1$-$C_4$-alkyl-oxy-$C_1$-$C_4$-alkyl, —$SO_2$—$C_1$-$C_4$-alkyl, —$SO_2$—$C_{3-4}$-cycloalkyl, —$(CH_2)_{1-2}$—$C_{3-4}$-cycloalkyl, $Het^{py}$, —$(CH_2)_p$-$Het^{py}$, —C(=O)—$NR^9R^{10}$, —$(CH_2)_p$—C(=O)$NR^9R^{10}$, (preferably from the group consisting of $NR^9R^{10}$, cyano, $C_1$-$C_4$-alkyl, fluoro, fluoro-$C_1$-$C_4$-alkyl, $C_1$-$C_4$-alkoxy, $C_1$-$C_4$-alkoxy-$C_1$-$C_4$-alkyl-oxy, hydroxy-$C_1$-$C_4$-alkyl, hydroxy-$C_1$-$C_4$-alkyl-oxy, $Het^{py}$, —$(CH_2)_p$-$Het^{py}$ and —C(=O)—$NR^9R^{10}$);

wherein $R^{43}$ is independently selected from the group consisting of oxo, $NR^9R^{10}$, cyano, —$(CH_2)_p$—CN, halo, OH, hydroxy-$C_1$-$C_4$-alkyl, —(COOH), —$(CH_2)_p$—COOH, $C_1$-$C_4$-alkyl, fluoro-$C_1$-$C_4$-alkyl, $C_1$-$C_4$-alkoxy, $C_1$-$C_4$-alkoxy-$C_1$-$C_4$-alkyl, $N(R^9)(R^{10})$—$C_1$-$C_4$-alkyl, $N(R^9)(R^{10})$—$C_1$-$C_4$-alkyl-oxy, $N(R^9)(R^{10})$—$C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, $C_1$-$C_4$-alkoxy-$C_1$-$C_4$-alkyl-oxy-$C_1$-$C_4$-alkyl, —$SO_2$—$C_1$-$C_4$-alkyl, —$SO_2$—$C_{3-4}$-cycloalkyl, —$(CH_2)_{1-2}$—$C_{3-4}$-cycloalkyl, $Het^{py}$, —$(CH_2)_p$-$Het^{py}$, —C(=O)—$NR^9R^{10}$, —$(CH_2)_p$—C(=O)$NR^9R^{10}$, $(CH_2)_p$—$NR^9R^{10}$ (preferably from the group consisting of $NR^9R^{10}$, cyano, $C_1$-$C_4$-alkyl, fluoro, fluoro-$C_1$-$C_4$-alkyl, $C_1$-$C_4$-alkoxy, $C_1$-$C_4$-alkoxy-$C_1$-$C_4$-alkyl-oxy, $Het^{py}$ and —$(CH_2)_p$—$Het^{py}$);

wherein $R^{44}$ is independently selected from the group consisting of cyano, $CO_2H$, halo, $C_1$-$C_4$-alkyl, fluoro-$C_1$-$C_4$-alkyl, hydroxy, hydroxy-$C_1$-$C_4$-alkyl, hydroxy-$C_1$-$C_4$-alkyl-oxy, $C_1$-$C_4$-alkoxy, $C_1$-$C_4$-alkoxy-$C_1$-$C_4$-alkyl, $C_1$-$C_4$-alkoxy-$C_1$-$C_4$-alkyl-oxy, $NR^9R^{10}$, $(N(R^9)(R^{10})$—$C_1$-$C_4$-alkyl, $(N(R^9)(R^{10})$—$C_1$-$C_4$-alkyl-oxy, —(CO)—$C_1$-$C_4$-alkyl, and $R^9R^{10}N$—$C_1$-$C_4$-alkyl-oxy-(CO)—$C_1$-$C_4$-alkyl; wherein p is 1 or 2 or 3;

$R^9$ is selected from hydrogen and $C_1$-$C_4$-alkyl;

$R^{10}$ is selected from the group consisting of hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl;

$Het^{py}$ is a 4-, 5-, 6- or 7-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, and wherein said heterocyclic ring is optionally substituted with oxo on one carbon atom, and wherein said heterocyclic ring is optionally further substituted on one or more carbon atoms with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl, and wherein the nitrogen atom, if present in said heterocycle, is optionally further substituted with $R^{10}$ (preferably $C_1$-$C_4$-alkyl (such as methyl));

or $Het^{py}$ is a 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one or more (e.g., 1, 2 or 3) substituents independently selected from $NR^9R^{10}$, —C(=O)—$NR^9R^{10}$, halo, $C_1$-$C_4$-alkyl, hydroxy-$C_1$-$C_4$-alkyl, fluoro-$C_1$-$C_4$-alkyl, cyano, OH, and $C_1$-$C_4$-alkoxy;

each $R^{Ba}$ is independently selected from the group consisting of hydroxy, $NH_2$, $C_1$-$C_4$-alkyl and halo;

each $R^{Bb}$ is independently selected from the group consisting of $C_1$-$C_4$-alkyl (preferably methyl), cyclopropyl, fluoro-$C_1$-$C_3$-alkyl (preferably $CHF_2$ or $CF_3$), cyano, halo (preferably fluoro or chloro), $NH_2$ and $C_1$-$C_3$-alkoxy (preferably methoxy), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 2. A compound according to Embodiment 1, wherein A is selected from the group consisting of (a) $C_5$-$C_7$-cycloalkylene which is unsubstituted or substituted with one or more, preferably 1, 2 or 3, substituents independently selected from fluoro and $C_1$-$C_4$-alkyl;

(b) 5-7 membered unsaturated heterocyclyl containing one carbon-carbon double bond and one oxygen atom as ring member, wherein said heterocyclyl is unsubstituted or substituted with one or more, preferably 1, 2 or 3, substituents, independently selected from fluoro and $C_1$-$C_4$-alkyl, preferably 1, 2 or 3, $C_1$-$C_4$-alkyl;

(c) $C_6$-$C_{10}$ aryl which is unsubstituted or substituted with 1, 2 or 3 $R^{42}$;

(d) 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{43}$, and wherein a nitrogen atom, when present in the heteroaryl ring, is unsubstituted or substituted with a substituent selected from the group consisting of: $C_1$-$C_4$-alkyl, —$(CH_2)_{1-2}$—$C_{3-4}$-cycloalkyl, $C_3$-$C_6$-cycloalkyl, hydroxy-$C_1$-$C_4$-alkyl, fluoro-$C_1$-$C_4$-alkyl, $C_1$-$C_4$-alkoxy-$C_1$-$C_4$-alkyl, $N(R^9)(R^{10})$—$C_1$-$C_4$-alkyl, —$SO_2$—$C_1$-$C_4$-alkyl, —$SO_2$—$C_{3-4}$-cycloalkyl, —$(CH_2)_p$-$Het^{py}$, and —$(CH_2)_p$—$N(R^9)(R^{10})$, (preferably wherein said substituent is selected from the group consisting of fluoro-$C_1$-$C_4$-alkyl, $N(R^9)(R^{10})$—$C_1$-$C_4$-alkyl, —$SO_2$—$C_{3-4}$-cycloalkyl, or —$(CH_2)_{1-2}$—$C_{3-4}$-cycloalkyl);

(e) 8-10 membered heteroaryl ring containing 1, 2 or 3 nitrogen atoms, wherein each nitrogen atom is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$, wherein said heteroaryl ring is unsubstituted or substituted on a carbon atom with 1, 2, 3, 4 or 5 $R^{44}$;

wherein $Het^b$ is a 4- or 5- or 6-membered heterocyclic ring comprising 1 or 2 heteroatoms or groups independently selected from N, O, S, SO and $SO_2$ (preferably 1 oxygen atom, or 1 sulfur atom, or one S(=O) or one S(=O)$_2$ group, or 1 nitrogen atom and 1 oxygen atom, or 1-2 nitrogen atoms), wherein said heterocyclic ring $Het^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is optionally further substituted with $C_1$-$C_4$-alkyl which is optionally substituted with 1 to 3 substituents independently selected from fluoro, hydroxy and $C_1$-$C_4$-alkoxy; and (f) 8-10 membered partially saturated hetero-bicyclic ring containing 1-3 nitrogen atoms, or 1-2 oxygen atoms, or 1 sulfur atom or 1 S(=O)$_2$ group in the hetero-bicyclic ring, wherein said hetero-bicyclic ring is unsubstituted or substituted on a carbon atom with 1, 2, 3, 4 or 5 $R^{44}$, and wherein the hetero-bicyclic ring is further optionally substituted on a carbon atom by oxo and wherein a nitrogen atom, when present, is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$; and wherein $Het^b$ is a 4- or 5- or 6-membered heterocyclic ring comprising 1 or 2 heteroatoms or groups independently selected from N, O, S, SO and $SO_2$ (preferably 1 oxygen atom, or 1 sulfur atom, or one S(=O) or one $S(=O)_2$ group, or 1 nitrogen atom and 1 oxygen atom, or 1-2 nitrogen atoms), wherein said heterocyclic ring $Het^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is optionally further substituted with $C_1$-$C_4$-alkyl which is optionally substituted with 1 to 3 substituents independently selected from fluoro, hydroxy and $C_1$-$C_4$-alkoxy, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 3. A compound according to Embodiment 1 or 2, wherein $Het^b$ is a 4- or 5- or 6-membered heterocyclic ring comprising 1 or 2 heteroatoms or groups independently selected from N, O, S, SO and $SO_2$ (preferably 1 oxygen atom, or 1 sulfur atom, or one S(=O) or one $S(=O)_2$ group, or 1 nitrogen atom and 1 oxygen atom, or 1-2 nitrogen atoms), wherein said heterocyclic ring $Het^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is optionally further substituted with $C_1$-$C_4$-alkyl wherein said $C_1$-$C_4$-alkyl is optionally substituted with 1 to 3 substituents independently selected from fluoro, hydroxy and $C_1$-$C_4$-alkoxy;

B is selected from the group consisting of $B^1$ and $B^2$;

$B^1$ is $C_{6-10}$ aryl which is unsubstituted or substituted with 1, 2, 3 or 4 $R^{Ba}$ and each $R^{Ba}$ is independently selected from the group consisting of hydroxy, $C_1$-$C_4$-alkyl and halo;

$B^2$ is a 6-10 (preferably 8-10) membered heteroaryl which comprises 1, 2 or 3 nitrogen atoms, wherein $B^2$ is unsubstituted or substituted with 1, 2, 3 or 4 $R^{Bb}$;

each $R^{Bb}$ is independently selected from the group consisting of $C_1$-$C_4$-alkyl (preferably methyl), fluoro-$C_1$-$C_3$-alkyl (preferably $CHF_2$ or $CF_3$), cyano, halo (preferably fluoro or chloro), $NH_2$ and $C_1$-$C_3$-alkoxy (preferably methoxy), $Het^{py}$ is a 4-, 5-, 6- or 7-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, and wherein said heterocyclic ring is optionally substituted with oxo on one carbon atom, and wherein said heterocyclic ring is further substituted on one or more carbon atoms with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl, and wherein the nitrogen atom, if present in said heterocycle, is optionally further substituted with $R^{10}$ (preferably $C_1$-$C_4$-alkyl (such as methyl));

or $Het^{py}$ is a 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one or more (e.g., 1, 2 or 3) substituents independently selected from $NR^9R^{10}$, halo, $C_1$-$C_4$-alkyl, cyano, OH, and $C_1$-$C_4$-alkoxy;

wherein $R^{A4}$ is independently selected from the group consisting of cyano, $CO_2H$, halo, $C_1$-$C_4$-alkyl, fluoro-$C_1$-$C_4$-alkyl, hydroxy, hydroxy-$C_1$-$C_4$-alkyl, hydroxy-$C_1$-$C_4$-alkyl-oxy, $C_1$-$C_4$-alkoxy, $C_1$-$C_4$-alkoxy-$C_1$-$C_4$-alkyl-oxy, —$NR^9R^{10}$, $R^9R^{10}N$—$C_1$-$C_4$-alkyl-oxy, —(CO)—$C_1$-$C_4$-alkyl;

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 4. A compound according to any one of the preceding Embodiments wherein $Het^b$ is a 4- or 5- or 6-membered heterocyclic ring comprising 1 or 2 heteroatoms or groups independently selected from N, O, S, SO and $SO_2$ (preferably 1 oxygen atom, or 1 sulfur atom, or one S(=O) or one $S(=O)_2$ group, or 1 nitrogen atom and 1 oxygen atom, or 1-2 nitrogen atoms), wherein said heterocyclic ring $Het^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is optionally further substituted with $C_1$-$C_4$-alkyl wherein said $C_1$-$C_4$-alkyl is optionally substituted with 1 to 3 substituents independently selected from fluoro, hydroxy and $C_1$-$C_4$-alkoxy;

$B^2$ is a 6-10 (preferably 8-10) membered heteroaryl which comprises 1, 2 or 3 nitrogen atoms, wherein $B^2$ is unsubstituted or substituted with 1, 2, 3 or 4 $R^{Bb}$;

$Het^{py}$ is a 4-, 5-, 6- or 7-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, and wherein said heterocyclic ring is optionally substituted with oxo on one carbon atom, and wherein said heterocyclic ring is further substituted on one or more carbon atoms with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl, and wherein the nitrogen atom, if present in said heterocycle, is optionally further substituted with $R^{10}$ (preferably $C_1$-$C_4$-alkyl (such as methyl));

or $Het^{py}$ is a 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one or more (e.g., 1, 2 or 3) substituents independently selected from $NR^9R^{10}$, halo, $C_1$-$C_4$-alkyl, cyano, OH, and $C_1$-$C_4$-alkoxy (preferably said heteroaryl ring is substituted by one or more amino groups);

$R^{A4}$ is independently selected from the group consisting of cyano, $CO_2H$, halo, $C_1$-$C_4$-alkyl, fluoro-$C_1$-$C_4$-alkyl, hydroxy, hydroxy-$C_1$-$C_4$-alkyl, hydroxy-$C_1$-$C_4$-alkyl-oxy, $C_1$-$C_4$-alkoxy, $C_1$-$C_4$-alkoxy-$C_1$-$C_4$-alkyl-oxy, —$NR^9R^{10}$ and $R^9R^{10}N$—$C_1$-$C_4$-alkyl-oxy, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 5. A compound according to any one of the preceding Embodiments wherein G is

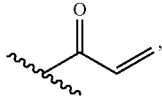

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 6. A compound according to any one of the preceding Embodiments, wherein L is

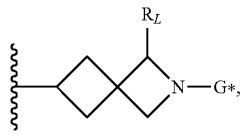

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 7. A compound according to Embodiment 6, wherein $R_L$ is hydrogen, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 8. A compound according to any one of the preceding Embodiments, wherein C is selected from $C_1$-$C_3$ alkyl (preferably methyl), fluoro-$C_1$-$C_3$ alkyl (preferably $CHF_2$ or $CF_3$), $CH_2$—CN, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 9. A compound according to any one of the preceding Embodiments, wherein B is

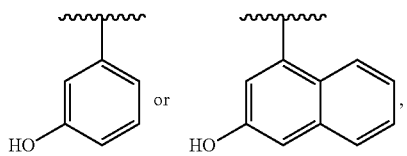

wherein B is unsubstituted or substituted with 1, 2 or 3 halo, or methyl groups or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 10. A compound according to any one of the preceding Embodiments, wherein B is

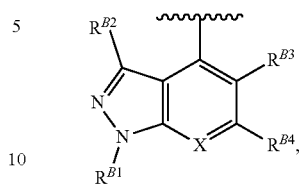

where X is N or C—$R^{B5}$;

where $R^{B1}$ is independently selected from hydrogen and $C_1$-$C_4$-alkyl (preferably methyl);

$R^{B2}$ is independently selected from hydrogen, halo (preferably chloro), $C_1$-$C_4$-alkyl (preferably methyl), cyclopropyl and $NH_2$;

$R^{B3}$ is independently selected from hydrogen, halo (preferably chloro), cyclopropyl and $C_1$-$C_4$-alkyl (preferably methyl);

$R^{B4}$ is independently selected from hydrogen, halo (preferably chloro or fluoro) and $C_1$-$C_4$-alkyl (preferably methyl), or $R^{B3}$ and $R^{B4}$ together with the atoms to which they are attached, form a 4-6 membered ring (preferably a 5-6 membered saturated or partially unsaturated carbocyclic ring) fused to the aromatic ring containing X;

$R^{B5}$ is independently selected from hydrogen, halo (preferably chloro) and $C_1$-$C_4$-alkyl (preferably methyl), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 11. A compound according to Embodiment 10, wherein $R^{B2}$ is independently selected from the group consisting of hydrogen, $NH_2$, and $CH_3$, or an atropisomer thereof, or a pharmaceutically acceptable salt thereof, or a pharmaceutically acceptable salt of an atropisomer thereof.

Embodiment 12. A compound according to Embodiment 10 or 11, wherein $R^{B4}$ is independently selected from hydrogen, halo (preferably chloro or fluoro) and $C_1$-$C_4$-alkyl (preferably methyl), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 13. A compound according to any one of Embodiments 10 to 12, wherein $R^{B1}$ is independently selected from hydrogen and methyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 14. A compound according to any one of Embodiments 10 to 13, wherein $R^{B1}$ is hydrogen, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 15. A compound according to any one of Embodiments 10 to 14, wherein $R^{B3}$ and $R^{B4}$ are each independently selected from halo (preferably chloro or fluoro) and $C_1$-$C_4$-alkyl (preferably methyl), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 16. A compound according to any one of Embodiments 10 to 15, wherein $R^{B3}$ is halo and $R^{B4}$ is $C_1$-$C_4$-alkyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 17. A compound according to any one of Embodiments 10 to 16, wherein $R^{B3}$ is chloro and $R^{B4}$ is methyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 18. A compound according to any one of Embodiments 10 to 16, wherein $R^{B3}$ is chloro and $R^{B4}$ is chloro, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 19. A compound according to any one of Embodiments 10 to 18, wherein X is CH or N, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 20. A compound according to any one of Embodiments 10 to 19, wherein X is CH, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 21. A compound of formula (Ia)

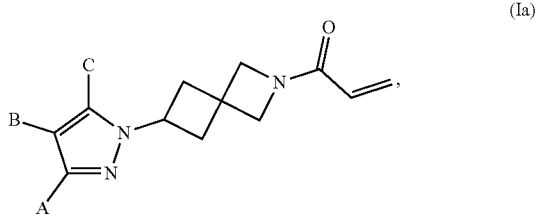

(Ia)

wherein A, B and C are as defined in any one of the preceding Embodiments, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 22. A compound of formula (I) or of formula (Ia) according to any one of the preceding Embodiments, wherein A is $C_5$-$C_7$-cycloalkylene which is unsubstituted or substituted with one or more, preferably 1, 2 or 3, substituents independently selected from fluoro and $C_1$-$C_4$-alkyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 23. A compound of formula (I) or of formula (Ia) according to any one of the preceding Embodiments, wherein A is

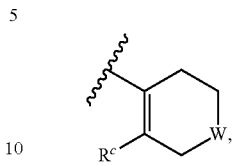

where W is O or $C(R^w)_2$, each $R^w$ is independently selected from hydrogen and fluorine, $R^c$ is hydrogen or $C_1$-$C_4$-alkyl and A is optionally further substituted with 1, 2 or 3 substituents independently selected from fluoro and $C_1$-$C_4$-alkyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 24. A compound of formula (I) or of formula (Ia) according to any one of Embodiments 1 to 21, wherein A is phenyl which is unsubstituted or substituted with 1, 2 or 3 $R^{A2'}$, preferably wherein $R^{A2}$ is independently selected from the group consisting of halo, OH, hydroxy-$C_1$-$C_4$-alkyl, —(COOH), $C_1$-$C_4$-alkyl, fluoro-$C_1$-$C_4$-alkyl, $C_1$-$C_4$-alkoxy, $C_1$-$C_4$-alkyl-carbonyl-oxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, —C(=O)—$NR^9R^{10}$, —$NR^9R^{10}$, $Het^{py}$ and —$(CH_2)_p$-$Het^{py}$, wherein p is 1 or 2;

$R^9$ is selected from hydrogen, $C_1$-$C_4$-alkyl and $C_1$-$C_4$-alkoxy-$C_1$-$C_4$-alkyl;

$R^{10}$ is selected from hydrogen, $C_1$-$C_4$-alkyl, hydroxy-$C_1$-$C_4$-alkyl and $C_1$-$C_4$-alkoxy-$C_1$-$C_4$-alkyl;

$Het^{py}$ is —$NR^{9a}R^{10a}$ and $R^{9a}$ and $R^{10a}$ together with the nitrogen form a 4- or 5- or 6-membered heterocyclic ring comprising one or two additional heteroatoms independently selected from O, N (such as pyrrolidin-1-yl, azetidin-1-yl or morpholin-1-yl) and S, or an N-oxide thereof, or an S-oxide (SO) or S-dioxide thereof, and wherein said heterocyclic ring is optionally substituted with oxo on one carbon atom, and wherein said heterocyclic ring is further substituted with one or two substituents independently selected from $C_1$-$C_4$-alkoxy (preferably methoxy), halo (preferably fluoro), $C_1$-$C_4$-alkyl, hydroxy-$C_1$-$C_4$-alkyl and fluoro-$C_1$-$C_4$-alkyl;

or $R^{9a}$ and $R^{10a}$ together with the nitrogen form a 4- or 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one amino group, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 25. A compound of formula (I) or of formula (Ia) according to any one of Embodiments 1 to 21, wherein A is a 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{A3}$, and wherein a nitrogen atom, when present in the heteroaryl ring, is unsubstituted or substituted with a substituent selected from the group consisting of: $C_1$-$C_4$-alkyl, —$(CH_2)_{1-2}$—$C_{3-4}$-cycloalkyl, hydroxy-$C_1$-$C_4$-alkyl, fluoro-$C_1$-$C_4$-alkyl, $C_1$-$C_4$-alkoxy-$C_1$-$C_4$-alkyl, $N(R^9)(R^{10})$—$C_1$-

C₄-alkyl, —SO₂—C₁-C₄-alkyl, —SO₂—C₃₋₄-cycloalkyl, —(CH₂)$_p$-Het$^{py}$, and —(CH₂)$_p$—N(R⁹)(R¹⁰), (preferably wherein said substituent is selected from the group consisting of fluoro-C₁-C₄-alkyl, N(R⁹)(R¹⁰)—C₁-C₄-alkyl, —SO₂—C₃₋₄-cycloalkyl, or —(CH₂)₁₋₂—C₃₋₄-cycloalkyl), or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 26. A compound of formula (I) or of formula (Ia) according to any one of Embodiments 1 to 21, wherein A is pyridin-1-yl, pyridin-2-yl or pyridin-3-yl, which is unsubstituted or substituted with 1, 2 or 3 substituents independently selected from NH₂, cyano, halo, OH, hydroxy-C₁-C₄-alkyl, —COOH, C₁-C₄-alkyl, fluoro-C₁-C₄-alkyl, C₁-C₄-alkoxy, di-C₁-C₄-alkylamino-C₁-C₄-alkyl-oxy, C₁-C₄-alkyl-carbonyl-oxy-C₁-C₄-alkyl-oxy, hydroxy-C₁-C₄-alkyl-oxy, C₁-C₄-alkoxy-C₁-C₄-alkyl-oxy, C₁-C₄-alkoxy-C₁-C₄-alkyl-oxy-C₁-C₄-alkyl, —C(═O)—NR⁹R¹⁰, NR⁹R¹⁰, Het$^{py}$ and —(CH₂)$_p$-Het$^{py}$, wherein
p is 1 or 2;
R⁹ is selected from hydrogen and C₁-C₄-alkyl,
R¹⁰ is selected from hydrogen, C₁-C₄-alkyl, hydroxy-C₁-C₄-alkyl, C₁-C₄-alkoxy-C₁-C₄-alkyl and di-C₁-C₄-alkyl-amino-C₁-C₄-alkyl,
Het$^{py}$ is NR$^{9a}$R$^{10a}$;
R$^{9a}$ and R$^{10a}$ together with the nitrogen form a 4- or 5- or 6-membered saturated or unsaturated heterocyclic ring comprising one or two heteroatoms independently selected from O, N (pyrrolidin-1-yl, azetidin-1-yl, morpholin-1-yl) and S, or an N-oxide thereof, or an S-oxide (SO) or S-dioxide thereof, and wherein said heterocyclic ring is optionally substituted with oxo on one carbon atom on said heterocyclic ring, and wherein said heterocyclic ring is further substituted with by 1, 2 or 3 substituents independently selected from C₁-C₄-alkoxy (preferably methoxy), halo (preferably fluoro), C₁-C₄-alkyl, hydroxy-C₁-C₄-alkyl and fluoro-C₁-C₄-alkyl;
or R$^{9a}$ and R$^{10a}$ together with the nitrogen form a 4- or 5- or 6-membered heteroaryl ring (preferably 1,2,4-triazol-1-yl or pyrazol-1-yl), comprising 1, 2 or 3 nitrogen atoms and wherein said heteroaryl ring is optionally substituted with one amino group,
a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 27. A compound of formula (I) or (Ia) according to any one of Embodiments 1 to 21, wherein A is pyridinyl substituted with 1, 2 or 3 substituents independently selected from NH₂, cyano, halo, C₁-C₄-alkyl, fluoro-C₁-C₄-alkyl, C₁-C₄-alkoxy, di-C₁-C₄-alkylamino-C₁-C₄-alkyl-oxy, —C(═O)—NR⁹R¹⁰, NR⁹R¹⁰,

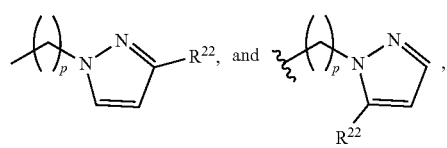

where p is 0, 1 or 2, preferably p is 0;
R²² is hydrogen or C₁-C₄-alkyl (preferably methyl), or amino;
R⁹ is selected from hydrogen and C₁-C₄-alkyl, R¹⁰ is selected from hydrogen, C₁-C₄-alkyl, hydroxy-C₁-C₄-alkyl, C₁-C₄-alkoxy-C₁-C₄-alkyl, and di-C₁-C₄-alkyl-amino-C₁-C₄-alkyl,
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 28. A compound of formula (I) or of formula (Ia) according to any one of Embodiments 1 to 21, wherein A is

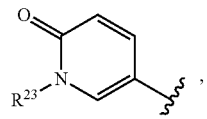

where R²³ is hydrogen, C₃-C₆-cycloalkyl, C₁-C₄-alkyl (preferably methyl), wherein A is unsubstituted or substituted with 1, 2 or 3 substituents independently selected from F, CH₃, CH₂F, CHF₂ and CF₃;
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 29. A compound of formula (I) or of formula (Ia) according to any one of Embodiments 1 to 21, wherein A is pyrimidin-5-yl which is unsubstituted or substituted with 1, 2 or 3 substituents independently selected from C₁-C₄-alkoxy (preferably methoxy) and CH₃, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 30. A compound of formula (I) or of formula (Ia) according to any one of Embodiments 1 to 21, wherein A is selected from the group consisting of

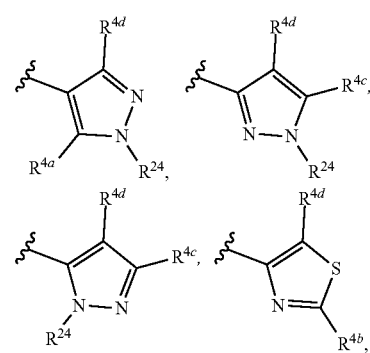

wherein R²⁴ is hydrogen, C₁-C₄-alkyl, hydroxy-C₁-C₄-alkyl, C₁-C₄-alkoxy-C₁-C₄-alkyl, —NR⁹R¹⁰C₁-C₄-alkyl, —SO₂—C₁-C₄-alkyl, —SO₂—C₃₋₄-cycloalkyl or —(CH₂)₁₋₂—C₃₋₄-cycloalkyl;
each of R$^{4a}$, R$^{4b}$, R$^{4c}$ and R$^{4d}$ is independently selected from hydrogen and C₁-C₄-alkyl (preferably methyl),
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 31. A compound of formula (I) or of formula (Ia) according to any one of the preceding Embodiments 1 to 21, wherein A is selected from the group consisting of:

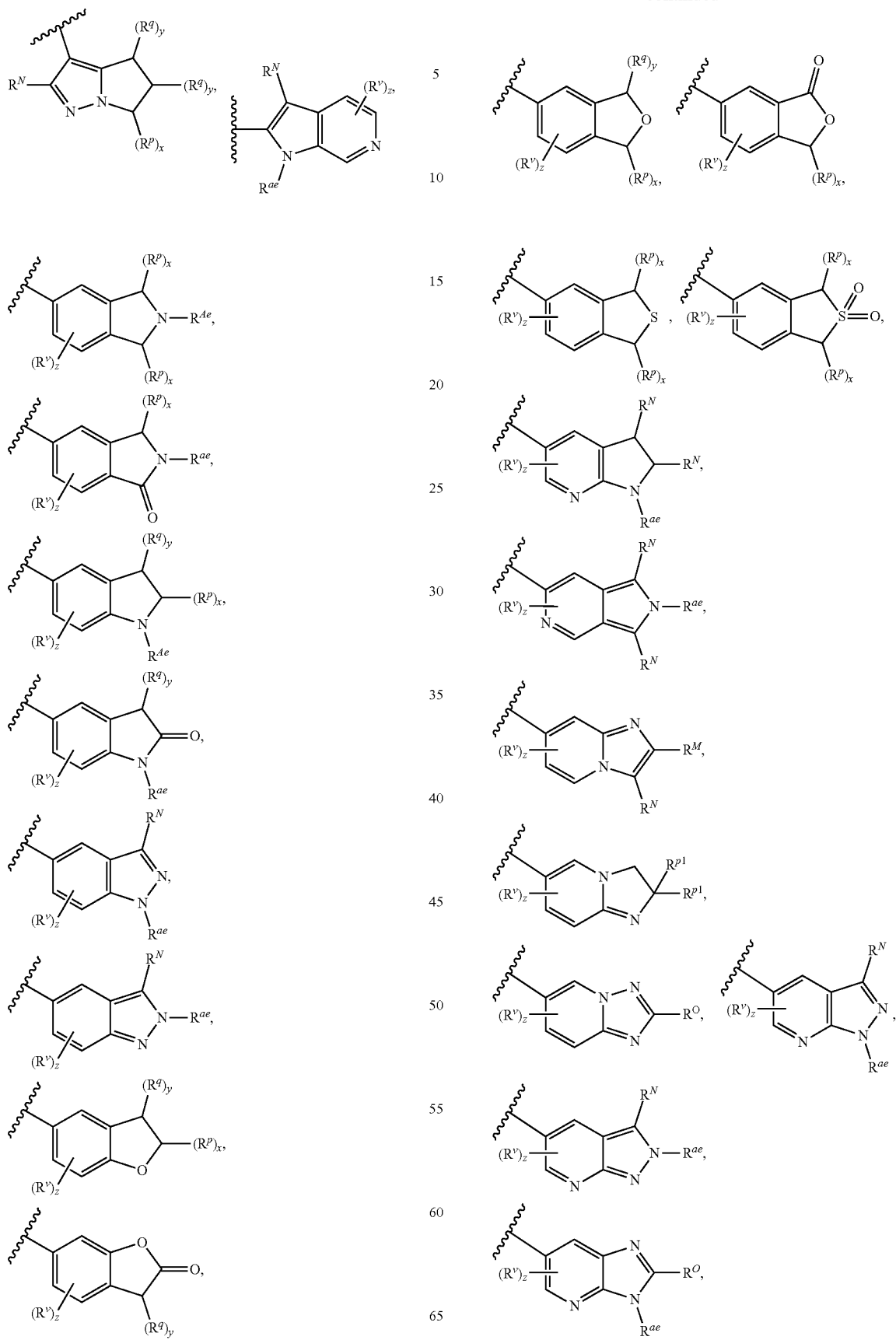

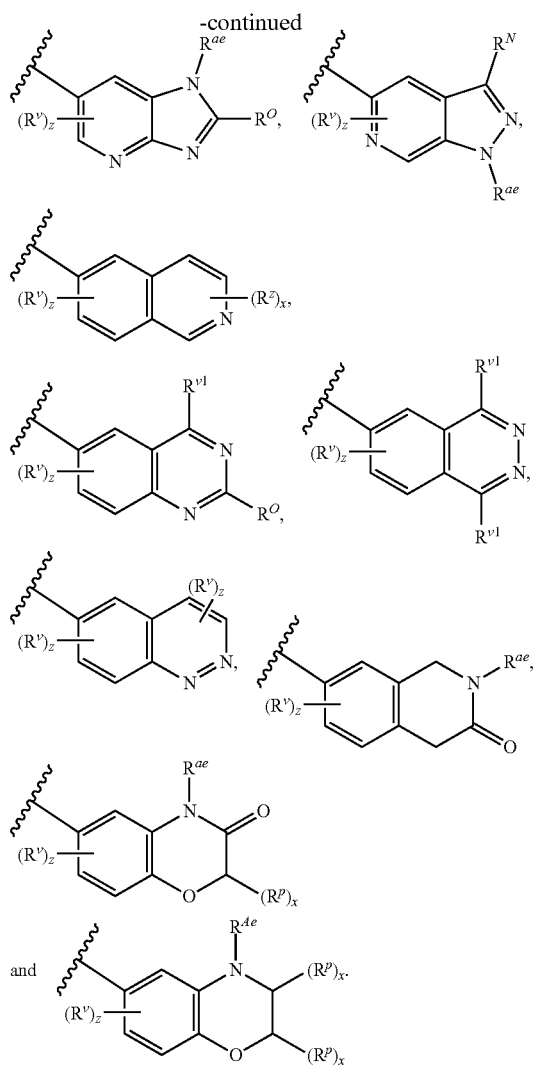

wherein
y is 0, 1 or 2 (preferably 0 or 1);
x is 0, 1 or 2 (preferably 0 or 1);
z is 0, 1 or 2;
$R^O$ is selected from the group consisting of hydrogen, $NR^9R^{10}$, $R^9R^{10}N-C_1-C_4$-alkyl-oxy, $C_1-C_4$-alkoxy-$C_1-C_4$-alkyl-oxy, hydroxy-$C_1-C_4$-alkyl-oxy and $C_1-C_4$-alkyl (preferably $R^O$ is hydrogen or $NR^9R^{10}$);

$R^M$ is hydrogen, halo or $C_1-C_4$-alkyl, wherein said alkyl is optionally substituted by OH, $C_1-C_4$-alkoxy or $NR^9R^{10}$ (preferably $R^M$ is hydrogen);

$R^N$ is hydrogen or $C_1-C_4$-alkyl, or halo or fluoro-$C_1-C_4$-alkyl (preferably hydrogen);

$R^q$ is independently selected from the group consisting of $C_1-C_4$-alkyl, hydroxy, $C_1-C_4$-alkoxy and $NR^9R^{10}$;

$R^p$ is $C_1-C_4$-alkyl;

each $R^{p1}$ is independently selected from hydrogen and $C_1-C_4$-alkyl;

$R^v$ is independently selected from halogen, $C_1-C_4$-alkyl and fluoro-$C_1-C_4$-alkyl;

$R^{ae}$ is selected from the group consisting of hydrogen and $C_1-C_4$-alkyl, wherein said alkyl is optionally substituted with 1 or 2 substituents selected from cyano, hydroxy, fluoro, $C_1-C_4$-alkoxy, $C_1-C_4$-alkoxy-$C_1-C_4$-alkyl-oxy, $Het^b$ and $NR^9R^{10}$;

$R^{Ae}$ is selected from the group consisting of hydrogen, —(CO)—$C_1-C_4$-alkyl and $C_1-C_4$-alkyl wherein the $C_1-C_4$alkyl in each instance is optionally substituted with 1 or 2 substituents selected from cyano, hydroxy, fluoro, $C_1-C_4$-alkoxy, $C_1-C_4$-alkoxy-$C_1-C_4$-alkyl-oxy, $Het^b$ and $NR^9R^{10}$;
wherein
$R^9$ is selected from hydrogen and $C_1-C_4$-alkyl;
$R^{10}$ is selected from hydrogen, $C_1-C_4$-alkyl, hydroxy-$C_1-C_4$-alkyl, $C_1-C_4$-alkoxy-$C_1-C_4$-alkyl and di-$C_1-C_4$-alkyl-amino-$C_1-C_4$-alkyl;

wherein $Het^b$ is a 4- or 5- or 6-membered heterocyclic ring comprising 1 or 2 heteroatoms or groups independently selected from N, O, S, SO and $SO_2$ (preferably comprising 1 oxygen atom, or 1 sulfur atom, or one S($=$O) or one S($=$O)$_2$ group, or 1 nitrogen atom and 1 oxygen atom, or 1-2 nitrogen atoms), wherein said heterocyclic ring $Het^b$ is unsubstituted or substituted on a carbon atom with one or two substituents independently selected from $C_1-C_4$-alkyl, hydroxy, cyano, fluoro, hydroxy-$C_1-C_4$-alkyl, $C_1-C_4$-alkoxy and fluoro-$C_1-C_4$-alkyl, and wherein said heterocyclic ring $Het^b$ is further optionally substituted on a carbon atom by oxo, and wherein the nitrogen atom when present in $Het^b$ is optionally further substituted with $C_1-C_4$-alkyl which is optionally substituted with 1 to 3 substituents independently selected from fluoro, hydroxy and $C_1-C_4$-alkoxy;

or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 32. A compound of formula (I) or of formula (Ia), according to any one of Embodiments 1 to 21, wherein A is selected from the group consisting of:

-continued

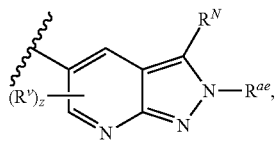

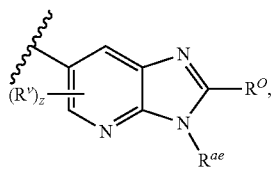

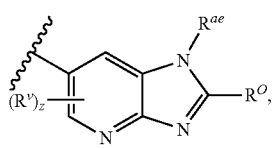

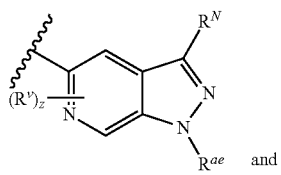

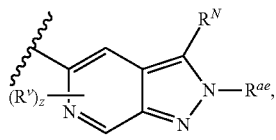

wherein z is 0, 1 or 2;

$R^v$ is independently selected from halogen, $C_1$-$C_4$-alkyl and fluoro-$C_1$-$C_4$-alkyl;

$R^N$ is hydrogen or $C_1$-$C_4$-alkyl, or halo or fluoro-$C_1$-$C_4$-alkyl (preferably hydrogen);

$R^O$ is selected from the group consisting of hydrogen, $NR^9R^{10}$, $N(R^9)(R^{10})$—$C_1$-$C_4$-alkyl-oxy, $C_1$-$C_4$-alkoxy-$C_1$-$C_4$-alkyl-oxy, hydroxy-$C_1$-$C_4$-alkyl-oxy and $C_1$-$C_4$-alkyl (preferably $R^O$ is hydrogen or $NR^9R^{10}$);

$R^{ae}$ is selected from the group consisting of hydrogen and $C_1$-$C_4$-alkyl, wherein said alkyl is optionally substituted with 1 or 2 substituents selected from cyano, hydroxy, fluoro, $C_1$-$C_4$-alkoxy, $C_1$-$C_4$-alkoxy-$C_1$-$C_4$-alkyl-oxy, Het$^b$ and $NR^9R^{10}$;

$R^9$ is selected from hydrogen and $C_1$-$C_4$-alkyl;

$R^{10}$ is selected from hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl;

wherein Het$^b$ is a 4- or 5- or 6-membered heterocyclic ring comprising 1 or 2 heteroatoms or groups independently selected from N, O, S, SO and SO$_2$ (preferably comprising 1 oxygen atom, or 1 sulfur atom, or one S(=O) or one S(=O)$_2$ group, or 1 nitrogen atom and 1 oxygen atom, or 1-2 nitrogen atoms), wherein said heterocyclic ring Het$^b$ is unsubstituted or substituted on a carbon atom with one or two substituents independently selected from $C_1$-$C_4$-alkyl, hydroxy, cyano, fluoro, hydroxy-$C_1$-$C_4$-alkyl, $C_1$-$C_4$-alkoxy and fluoro-$C_1$-$C_4$-alkyl, and wherein said heterocyclic ring Het$^b$ is further optionally substituted on a carbon atom by oxo, and wherein the nitrogen atom when present in Het$^b$ is further optionally substituted with $C_1$-$C_4$-alkyl which is optionally substituted with 1 to 3 substituents independently selected from fluoro, hydroxy and $C_1$-$C_4$-alkoxy;

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 33. A compound of formula (I) or of formula (Ia), according to any one of Embodiments 1 to 21, or Embodiment 31 or Embodiment 32, wherein A is selected from the group consisting of:

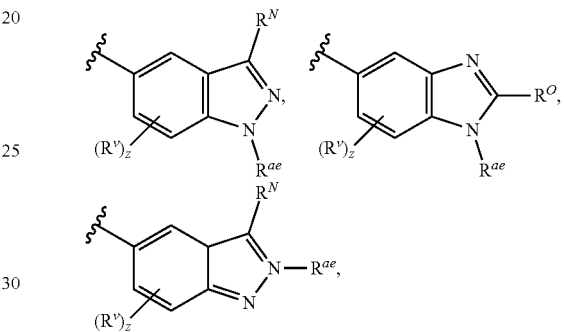

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 34. A compound of formula (I) or of formula (Ia) according to Embodiment 33, wherein $R^N$ is hydrogen or $C_1$-$C_4$-alkyl (preferably hydrogen);

$R^O$ is hydrogen or $NR^9R^{10}$;

$R^v$ is independently selected from fluoro, chloro and $C_1$-$C_4$-alkyl (e.g., methyl);

z is 0 or 1;

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 35. A compound of formula (I) or of formula (Ia) according to any one of Embodiments 31 to 34, wherein $R^{ae}$ is selected from the group consisting of hydrogen, $C_1$-$C_4$-alkyl, —(CH$_2$)$_2$-Het$^b$, —CH$_2$—CN, —(CH$_2$)$_2$—OH, —(CH$_2$)$_2$-O—$C_1$-$C_4$-alkyl, hydroxy-$C_1$-$C_4$-alkyl, —(CH$_2$)$_2$—O—(CH$_2$)$_2$—O—$C_1$-$C_4$-alkyl and —(CH$_2$)$_2$-di$C_1$-$C_4$-alkylamino, or wherein $R^{Ae}$ is selected from the group consisting of hydrogen, fluoro-$C_1$-$C_4$-alkyl and $C_1$-$C_4$-alkyl;

Het$^b$ is a 4-, 5- or 6-membered heterocyclic ring comprising 1 nitrogen atom and 1 oxygen atom, or 1-2 nitrogen atoms, wherein said heterocyclic ring is unsubstituted or substituted on a carbon atom by one or two substituents independently selected from $C_1$-$C_4$-alkyl, hydroxy-$C_1$-$C_4$-alkyl, $C_1$-$C_4$-alkoxy and fluoro, and wherein the nitrogen atom when present in the heterocycle is optionally further substituted with $C_1$-$C_4$-alkyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 36. A compound of formula (I) or of formula (Ia) according to any one of Embodiments 31 to 35, wherein $R^{ae}$ is selected from the group consisting of hydrogen, methyl, —$CH_2$—CN, —$(CH_2)_2$—OH, —$(CH_2)_2$—$OCH_3$, —$(CH_2)$—$C(CH_3)_2$—OH, —$(CH_2)_2$—O—$(CH_2)_2$—$OCH_3$, —$(CH_2)_2$—$N(CH_3)_2$ and —$(CH_2)_2$-$Het^b$;

wherein said $Het^b$ is a 4-, 5- or 6-membered heterocyclic ring comprising 1 nitrogen atom and 1 oxygen atom, or 1-2 nitrogen atoms, wherein said heterocyclic ring is unsubstituted or substituted on a carbon atom by one or two substituents independently selected from $C_1$-$C_4$-alkyl, hydroxy-$C_1$-$C_4$-alkyl $C_1$-$C_4$-alkoxy and fluoro, and wherein the nitrogen atom when present in the heterocycle is optionally further substituted with $C_1$-$C_4$-alkyl, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 37. A compound of formula (I) or of formula (Ia) according to any one of Embodiments 31 to 36, wherein $R^{ae}$ is selected from the group consisting of hydrogen, methyl, —$CH_2$—CN, —$(CH_2)_2$—OH, —$(CH_2)_2$—$OCH_3$, —$(CH_2)$—$C(CH_3)_2$—OH, —$(CH_2)_2$—O—$(CH_2)_2$—$OCH_3$, —$(CH_2)_2$—$N(CH_3)_2$, and —$(CH_2)_2$-$Het^b$, wherein $Het^b$ is selected from the group consisting of azetidin-1-yl, pyrrolidin-1-yl, pyrrolidin-3-yl and morpholin-1-yl, and wherein said heterocyclic ring is optionally further substituted with one or two substituents independently selected from methyl, hydroxy-methyl, methoxy and fluoro, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 38. A compound of formula (I) or of formula (Ia) according to any one of Embodiments 31 to 36, wherein $R^{ae}$ is selected from the group consisting of hydrogen, fluoro-$C_1$-$C_4$-alkyl, $C_1$-$C_4$-alkyl, —$(CH_2)_2$-$Het^b$, —$(CH_2)_2$-OH, —$(CH_2)_2$—O—$C_1$-$C_4$-alkyl, hydroxy-$C_1$- $C_4$-alkyl, —$(CH_2)_2$—O—$(CH_2)_2$—O—$C_1$-$C_4$-alkyl and —$(CH_2)_2$-di$C_1$-$C_4$-alkylamino, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

Embodiment 39. A compound of formula (Ib*),

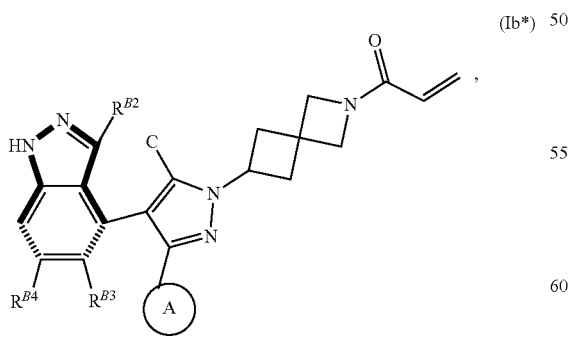

(Ib*)

wherein A, C, $R^{B2}$, $R^{B3}$ and $R^{B4}$ are as defined in any one of the preceding Embodiments, wherein A is unsubstituted or substituted as defined in any one of the preceding Embodiments, or a pharmaceutically acceptable salt thereof.

Embodiment 40. A compound of formula (Ic*),

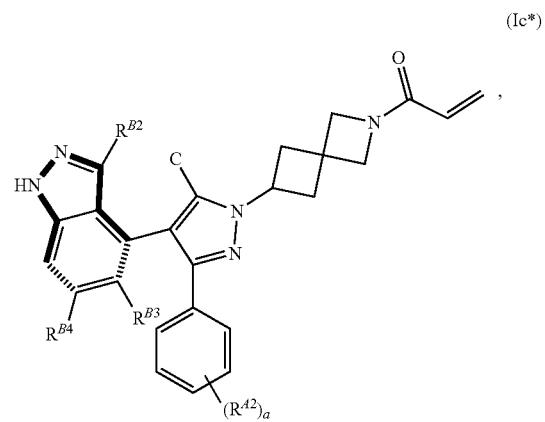

(Ic*)

wherein C, $R^{A2}$, $R^{B2}$, $R^{B3}$ and $R^{B4}$ are as defined in any one of the preceding Embodiments, wherein a is 0, 1, 2 or 3 (preferably a is 0 or 1 or 2), or a pharmaceutically acceptable salt thereof.

Embodiment 41. A compound of formula (Id*),

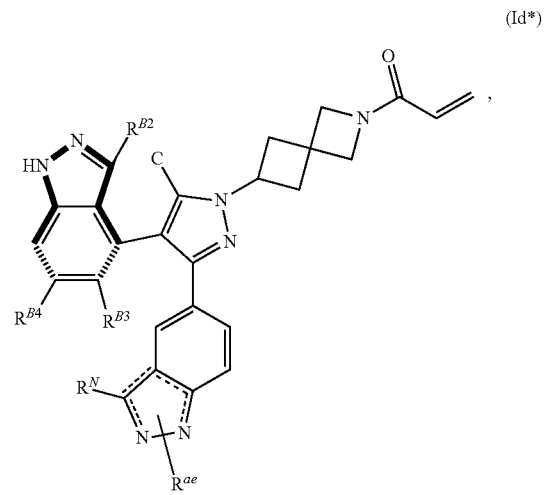

(Id*)

wherein C, $R^{B2}$, $R^N$, $R^{B3}$ and $R^{B4}$ are as defined in any one of the preceding Embodiments, wherein the ---- lines indicate a single bond or a double bond;

and $R^{ae}$ is as defined above.

Embodiment 42. A compound according to any one of the preceding Embodiments, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, selected from the compound of any one of Examples.

Embodiment 43. A compound which is selected from:

a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one, a(R)(S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl)prop-2-en-1-one, a(R)1-(6-(4-(5-chloro-6-methyl-1H-indazol-4-yl)-5-methyl-3-phenyl-1H-pyrazol-1-yl)-2-azaspiro[3.3]heptan-2-yl)prop-2-en-1-one, a(R)1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one, a(R)1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one, a(R)1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one, a(R)1-(6-(4-(5-chloro-6-methyl-1H-indazol-4-yl)-3-(4-(hydroxymethyl)phenyl)-5-methyl-1H-pyrazol-1-yl)-2-azaspiro[3.3]heptan-2-yl)prop-2-en-1-one, a(R)1-(6-(4-(5-chloro-6-methyl-1H-indazol-4-yl)-3-(2-fluoro-4-(2-methoxyethoxy)phenyl)-5-methyl-1H-pyrazol-1-yl)-2-azaspiro[3.3]heptan-2-yl)prop-2-en-1-one, a(R)1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one and a(R)1-(6-(4-(3-amino-5-chloro-6-methyl-1H-indazol-4-yl)-5-methyl-3-phenyl-1H-pyrazol-1-yl)-2-azaspiro[3.3]heptan-2-yl)prop-2-en-1-one, or a pharmaceutically acceptable salt thereof.

Embodiment 44. A compound which is selected from:

1-{6-[(4M)-4-(5-Chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one, 1-{6-[(4M)-4-(5-Chloro-6-methyl-1H-indazol-4-yl)-3-(1-{2-[(3S)-3-fluoropyrrolidin-1-yl]ethyl}-1H-indazol-5-yl)-5-methyl-1H-pyrazol-1-yl]-2-azaspiro[3.3]heptan-2-yl}prop-2-en-1-one, 1-{6-[(4M)-4-(5-Chloro-6-methyl-1H-indazol-4-yl)-5-methyl-3-phenyl-1H-pyrazol-1-yl]-2-azaspiro[3.3]heptan-2-yl}prop-2-en-1-one, 1-{6-[(4M)-4-(5-Chloro-6-methyl-1H-indazol-4-yl)-3-[2-(2-methoxyethyl)-2H-indazol-5-yl]-5-methyl-1H-pyrazol-1-yl}-2-azaspiro[3.3]heptan-2-yl)prop-2-en-1-one, 1-(6-{(4M)-4-(5-Chloro-6-methyl-1H-indazol-4-yl)-3-[2-(2-hydroxy-2-methylpropyl)-2H-indazol-5-yl]-5-methyl-1H-pyrazol-1-yl}-2-azaspiro[3.3]heptan-2-yl)prop-2-en-1-one, 1-{6-[(4M)-4-(5-Chloro-6-methyl-1H-indazol-4-yl)-3-{2-[2-(2-methoxyethoxy)ethyl]-2H-indazol-5-yl}-5-methyl-1H-pyrazol-1-yl]-2-azaspiro[3.3]heptan-2-yl}prop-2-en-1-one, 1-(6-{(4M)-4-(5-Chloro-6-methyl-1H-indazol-4-yl)-3-[4-(hydroxymethyl)phenyl]-5-methyl-1H-pyrazol-1-yl}-2-azaspiro[3.3]heptan-2-yl)prop-2-en-1-one, 1-(6-{(4M)-4-(5-Chloro-6-methyl-1H-indazol-4-yl)-3-[2-fluoro-4-(2-methoxyethoxy)phenyl]-5-methyl-1H-pyrazol-1-yl}-2-azaspiro[3.3]heptan-2-yl)prop-2-en-1-one, 1-(6-{(4M)-4-(3-Amino-5-chloro-6-methyl-1H-indazol-4-yl)-3-[2-(2-methoxyethyl)-2H-indazol-5-yl]-5-methyl-1H-pyrazol-1-yl}-2-azaspiro[3.3]heptan-2-yl)prop-2-en-1-one, 1-{6-[(4M)-4-(3-Amino-5-chloro-6-methyl-1H-indazol-4-yl)-5-methyl-3-phenyl-1H-pyrazol-1-yl]-2-azaspiro[3.3]heptan-2-yl}prop-2-en-1-one, or a pharmaceutically acceptable salt thereof.

Embodiment 45: A compound which is selected from the group of compounds with the following structure and name:

| Structure | Name | |
|---|---|---|
| 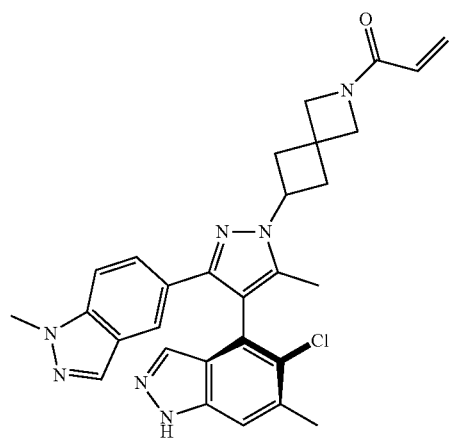 | 1-{6-[(4M)-4-(5-Chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one | (Example 1a); |

-continued

| Structure | Name | |
|---|---|---|
| 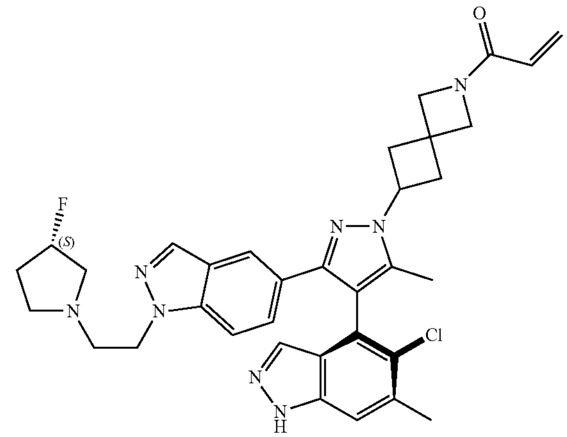 | 1-{6-[(4M)-4-(5-Chloro-6-methyl-1H-indazol-4-yl)-3-(1-{2-[(3S)-3-fluoropyrrolidin-1-yl]ethyl}-1H-indazol-5-yl)-5-methyl-1H-pyrazol-1-yl]-2-azaspiro[3.3]heptan-2-yl}prop-2-en-1-one | (Example 18a); |
| 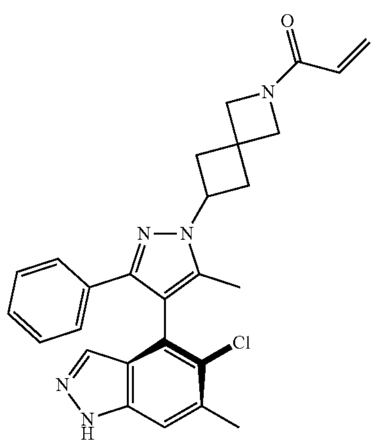 | 1-{6-[(4M)-4-(5-Chloro-6-methyl-1H-indazol-4-yl)-5-methyl-3-phenyl-1H-pyrazol-1-yl]-2-azaspiro[3.3]heptan-2-yl}prop-2-en-1-one | (Example 26a); |
| 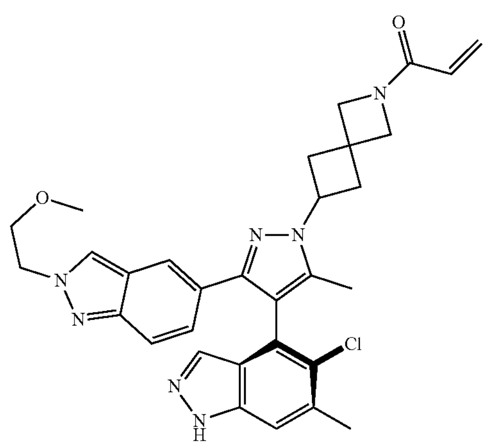 | 1-(6-{(4M)-4-(5-Chloro-6-methyl-1H-indazol-4-yl)-3-[2-(2-methoxyethyl)-2H-indazol-5-yl]-5-methyl-1H-pyrazol-1-yl}-2-azaspiro[3.3]heptan-2-yl)prop-2-en-1-one | (Example 41a); |

-continued

| Structure | Name | |
|---|---|---|
| 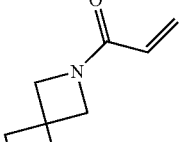 | 1-(6-{(4M)-4-(5-Chloro-6-methyl-1H-indazol-4-yl)-3-[2-(2-hydroxy-2-methylpropyl)-2H-indazol-5-yl]-5-methyl-1H-pyrazol-1-yl}-2-azaspiro[3.3]heptan-2-yl)prop-2-en-1-one | (Example 42a), | or a pharmaceutically acceptable salt thereof.

Embodiment 46. A compound which is selected from a compound with the following structure and name:

| Structure | Name | |
|---|---|---|
| 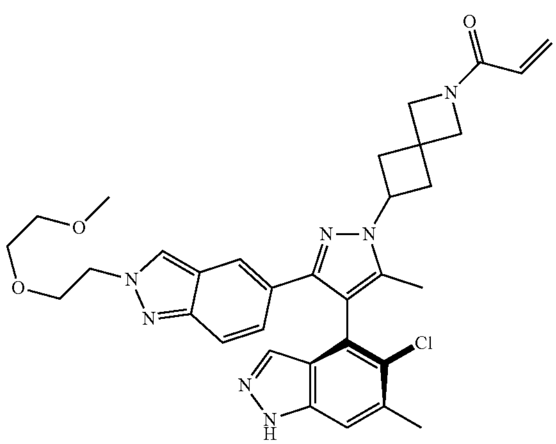 | 1-{6-[(4M)-4-(5-Chloro-6-methyl-1H-indazol-4-yl)-3-{2-[2-(2-methoxyethoxy)ethyl]-2H-indazol-5-yl}-5-methyl-1H-pyrazol-1-yl]-2-azaspiro[3.3]heptan-2-yl}prop-2-en-1-one | (Example 43a); |
| 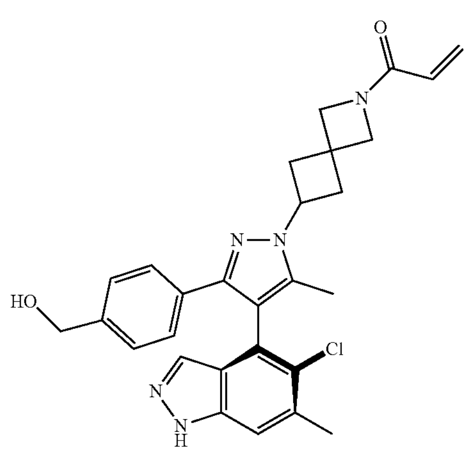 | 1-(6-{(4M)-4-(5-Chloro-6-methyl-1H-indazol-4-yl)-3-[4-(hydroxymethyl)phenyl]-5-methyl-1H-pyrazol-1-yl}-2-azaspiro[3.3]heptan-2-yl)prop-2-en-1-one | (Example 47a); |

-continued

| Structure | Name | |
|---|---|---|
| 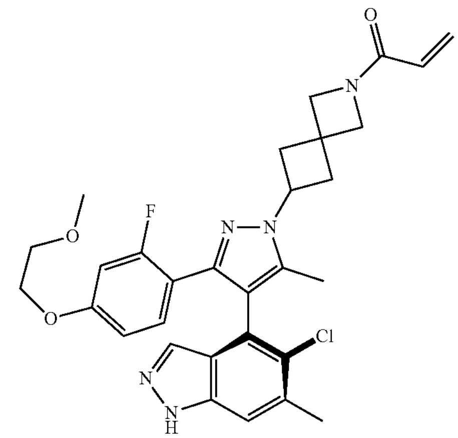 | 1-(6-{(4M)-4-(5-Chloro-6-methyl-1H-indazol-4-yl)-3-[2-fluoro-4-(2-methoxyethoxy)phenyl]-5-methyl-1H-pryazol-1-yl}-2-azaspiro[3.3]heptan-2-yl)prop2-en-1-one | (Example 60a); |
| 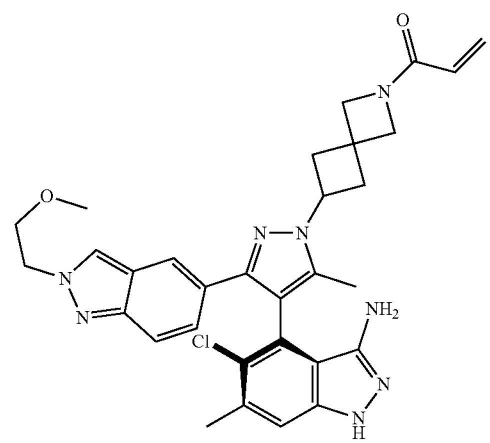 | 1-(6-{(4M)-4-(3-Amino-5-chloro-6-methyl-1H-indazol-4-yl)-3-[2-(2-methoxyethyl)-2H-indazol-5-yl]-5-methyl-1H-pyrazol-1-yl}-2-azaspiro[3.3]heptan-2-yl)prop-2-en-1-one | (Example 69a); |
| | 1-{6-[(4M)-4-(3-Amino-5-chloro-6-methyl-1H-indazol-4-yl)-5-methyl-3-phenyl-1H-pyrazol-1-yl]-2-azaspiro[3.3]heptan-2-yl}prop-2-en-1-one | (Example 70a), | or a pharmaceutically acceptable salt thereof.

Embodiment 47. A crystalline form of a compound according to any one of the preceding Embodiments.

Embodiment 48. A compound according to any one of the preceding Embodiments, or a stereoisomer thereof, or an atropisomer thereof, or a pharmaceutically acceptable salt thereof, or a crystalline form thereof, or a pharmaceutically acceptable salt of a stereoisomer thereof, or a pharmaceutically acceptable salt of an atropisomer thereof, for use as a medicament.

Embodiment 49. A compound according to any one of the preceding Embodiments, or a stereoisomer thereof, or an atropisomer thereof, or a pharmaceutically acceptable salt thereof, or a crystalline form thereof, or a pharmaceutically acceptable salt of a stereoisomer thereof, or a pharmaceutically acceptable salt of an atropisomer thereof, for use in treating cancer.

Embodiment 50. A pharmaceutical composition comprising a compound according to any one of the preceding Embodiments, or a stereoisomer thereof, or an atropisomer thereof, or a pharmaceutically acceptable salt thereof, or a crystalline form thereof, or a pharmaceutically acceptable salt of a stereoisomer thereof, or a pharmaceutically acceptable salt of an atropisomer thereof, and at least one pharmaceutically acceptable excipient.

Embodiment 51. A compound of formula (2a),

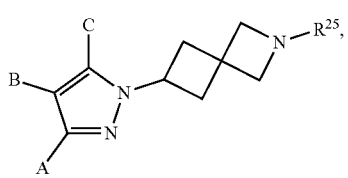

(2a)

wherein A, B and C are as defined in any one of the preceding Embodiments and $R^{25}$ is hydrogen or a nitrogen-protecting group, or a salt thereof.

Embodiment 52. A compound of formula (2b*),

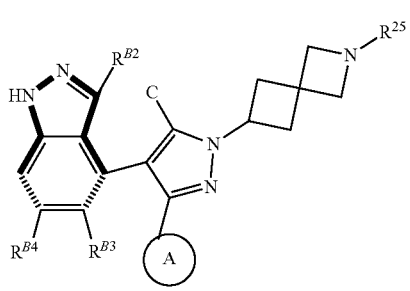

(2b*)

wherein A, C, $R^{B2}$, $R^{B3}$ and $R^{B4}$ are as defined in any one of the preceding Embodiments, $R^{25}$ is hydrogen or a nitrogen-protecting group, wherein A is unsubstituted or substituted as defined in any one of the preceding Embodiments, or a salt thereof.

Embodiment 53. A compound of formula (2c*),

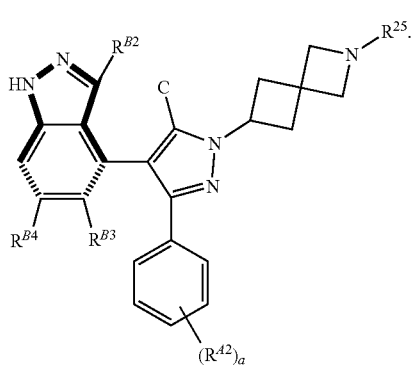

(2c*)

wherein C, $R^{42}$, $R^{B2}$, $R^{B3}$ and $R^{B4}$ are as defined in any one of the preceding Embodiments, $R^{25}$ is hydrogen or a nitrogen-protecting group, wherein a is 0, 1, 2 or 3 (preferably a is 0 or 1 or 2), or a pharmaceutically acceptable salt thereof.

Embodiment 54. A compound of formula (2d*),

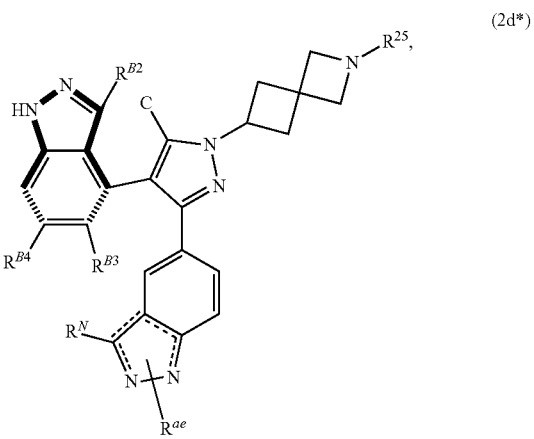

(2d*)

wherein C, $R^{ae}$, $R^{B2}$, $R^{N}$, $R^{B3}$ and $R^{B4}$ are as defined in any one of the preceding Embodiments, $R^{25}$ is hydrogen or a nitrogen-protecting group, wherein the ---- lines indicate a single bond or a double bond, or a salt thereof.

Embodiment 55. A crystalline form of Compound X such as the hydrate (Modification HA) crystalline form, or the isopropyl alcohol (IPA) solvate crystalline form, or the ethanol (EtOH) solvate crystalline form or the propylene glycol solvate crystalline form of Compound X.

Embodiment 56. A crystalline form of Compound X having an X-ray powder diffraction spectrum substantially the same as the X-ray powder diffraction spectrum shown in FIG. 1, FIG. 2, FIG. 3 or FIG. 4.

In embodiments of the invention, $Het^{py}$ is a 4-, 5-, 6- or 7-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, and wherein said heterocyclic ring is unsubstituted or substituted with oxo on one carbon atom, and wherein said heterocyclic ring is optionally further substituted on one or more carbon atoms with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl, and wherein the nitrogen atom, if present in said heterocycle, is optionally further substituted with $R^{10}$ (preferably $C_1$-$C_4$-alkyl (such as methyl)).

In embodiments of the invention, $Het^{py}$ is a 5- or 6-membered heteroaryl ring (preferably 1,2,4-triazol-1-yl or pyrazol-1-yl), comprising 1, 2 or 3 nitrogen atoms and wherein said heteroaryl ring is unsubstituted or substituted with one or more (e.g., 1, 2 or 3) substituents independently selected from $NR^9R^{10}$, —C(=O)—$NR^9R^{10}$, halo, $C_1$-$C_4$-alkyl, hydroxy-$C_1$-$C_4$-alkyl, fluoro-$C_1$-$C_4$-alkyl, cyano, OH, and $C_1$-$C_4$-alkoxy, or wherein said heteroaryl ring is unsubstituted or substituted with one or more (e.g., 1, 2 or 3) substituents independently selected from $NR^9R^{10}$, halo, $C_1$-$C_4$-alkyl, cyano, OH, and $C_1$-$C_4$-alkoxy, In embodiments of the invention, said heteroaryl ring is substituted by one or more amino groups.

In embodiments of the invention, A is $C_5$-$C_7$-cycloalkylene which is unsubstituted or substituted with one or more, preferably 1, 2 or 3, substituents independently selected from fluoro and $C_1$-$C_4$-alky. For example A is

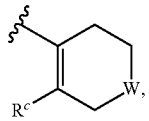

where W is O or $C(R^w)_2$, wherein each $R^w$ is independently selected from H and fluorine, $R^c$ is hydrogen or $C_1$-$C_4$-alkyl, and A is optionally further substituted with 1, 2 or 3 substituents independently selected from fluoro and $C_1$-$C_4$-alkyl.

Representative examples of A include, but are not limited to:

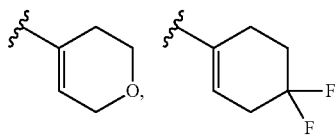

In embodiments of the invention, A is a $C_6$-$C_{10}$ aryl, e.g., a phenyl group, which may be unsubstituted or substituted with one or more $R^{42}$ substituents (for example, by 1, 2 or 3 substituents).

When A is phenyl, a substituent on A, when present, is preferably on the position para to the point of attachment of the phenyl to the pyrazolyl moiety of the compound of Formula (I) and (Ia).

When A is phenyl is substituted by a $R^{42}$ which is fluoro, $R^{42}$ may be on the position, ortho, para or meta to the point of attachment of the phenyl to the pyrazolyl moiety of the compound of Formula (I) and (Ia).

When A is phenyl, $R^{42}$, when present, is preferably selected from the group consisting of halo, OH, hydroxy-$C_1$-$C_4$-alkyl, —(COOH), $C_1$-$C_4$-alkyl, fluoro-$C_1$-$C_4$-alkyl, $C_1$-$C_4$-alkoxy, fluoro-$C_1$-$C_4$-alkoxy, $C_1$-$C_4$-alkyl-carbonyloxy-$C_1$-$C_4$-alkyl-oxy, hydroxy-$C_1$-$C_4$-alkyl-oxy, $C_1$-$C_4$-alkoxy-$C_1$-$C_4$-alkyl-oxy, —$SO_2$—$C_1$-$C_4$-alkyl, —C(O)—$NR^9R^{10}$, $NR^9R^{10}$, $NR^{9a}R^{10a}$, $Het^{py}$, —$(CH_2)_p$-$Het^{py}$ and —$NR^{9a}R^{10a}$ and —$(CH_2)_pNR^{9a}R^{10a}$, wherein p is 1 or 2;

$Het^{py}$ is a 4- or 5- or 6-membered heterocyclic ring comprising 1 oxygen atom, or 1 sulfur atom, or one S(=O) or one $S(=O)_2$ group, or 1 nitrogen atom and 1 oxygen atom, or 1-2 nitrogen atoms, wherein said heterocyclic ring is unsubstituted or substituted on a carbon atom by one or two substituents independently selected from $C_1$-$C_4$-alkyl, hydroxy-$C_1$-$C_4$-alkyl, $C_1$-$C_4$-alkoxy, halo and fluoro-$C_1$-$C_4$-alkyl, and wherein said heterocyclic ring is further optionally substituted on a carbon atom by oxo and wherein the nitrogen atom when present in the heterocycle is optionally further substituted with $C_1$-$C_4$-alkyl;

$R^9$ is selected from hydrogen and $C_1$-$C_4$-alkyl;

$R^{10}$ is selected from hydrogen, $C_1$-$C_4$-alkyl, hydroxy-$C_1$-$C_4$-alkyl, and $C_1$-$C_4$-alkoxy-$C_1$-$C_4$-alkyl;

$R^{9a}$ and $R^{10a}$ together with the nitrogen form a 4- or 5- or 6-membered (saturated or unsaturated) heterocyclic ring comprising one or two additional heteroatoms independently selected from O, N (preferably wherein said heterocyclic ring is pyrrolidin-1-yl, azetidin-1-yl or morpholin-1-yl) and S, or an N-oxide thereof, or an S-oxide (SO) or S-dioxide thereof, and wherein said heterocyclic ring is optionally substituted with oxo on one carbon atom on said heterocyclic ring, and wherein said heterocyclic ring is optionally further substituted by one or two substituents independently selected from $C_1$-$C_4$-alkoxy (methoxy), halo (fluoro), $C_1$-$C_4$-alkyl, hydroxy-$C_1$-$C_4$-alkyl, and fluoro-$C_1$-$C_4$-alkyl;

or $R^{9a}$ and $R^{10a}$ together with the nitrogen form a 5- or 6-membered heteroaryl ring (preferably wherein said heteroaryl ring is 1,2,4-triazol-1-yl and pyrazol-1-yl), comprising 1, 2 or 3 nitrogen atoms, and wherein said heteroaryl ring is optionally substituted with one or two amino groups;

When there are two $R^{42}$ substituents on the phenyl ring, they are preferably on the positions (a) ortho and para, or (b) meta and para or (c) ortho and meta relative to the point of attachment of the phenyl to the pyrazolyl moiety of the compound of Formula (I) and (Ia).

Representative $R^{42}$ substituents on the phenyl include, but are not limited to, $NH_2$, CN, F, OH, —$CH_2$—OH, (COOH), —$CH_3$, —O—$CH_2$—$CH_2$—OH, —O—$CH_2$—$CH_3$, —O—$CH_2$—$CH_2$—O—$(C_0)$—$CH_3$, —$N(CH_3)(CH_2$—$CH_2$—$OCH_3)$, —$N(H)(CH_2$—$CH_2$—$OCH_3)$, —$CH_2$—O—$CH_2$—$CH_2$—O—$CH_3$, —$SO_2$—$CH_3$, —C(O)—NH—$(CH_2$—$CH_2$—$OCH_3)$, —$C(O)$—$N(CH_3)$—$(CH_2$—$CH_2$—$OCH_3)$, —$C(O)$—NH—$CH_2$—$C(CH_3)_2OH$, —C(O)—N$(CH_3)$—$CH_2$—$C(CH_3)_2$—OH, —C(O)—N(H)—$C(CH_3)_2$—$CH_2$—$OCH_3$—C(O)—N(H)—$CH_2$—$CH_2$—$N(CH_3)_2$, —$(CH_2)_p$-$Het^{py}$ wherein $Het^{py}$ is a 4-, 5- or 6-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group or $Het^{py}$ is a 5- or 6-membered heteroaryl ring comprising 1, 2 or 3 nitrogen atoms;

wherein said 5- or 6-membered heterocyclic ring may be further substituted with one or two substituents independently selected from oxo, $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl; or wherein said wherein said 5- or 6-membered heterocyclic ring may be further substituted with one or two substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl;

wherein said 5- or 6-membered heteroaryl ring comprising 1, 2 or 3 nitrogen atoms may be further substituted with 1, 2 or 3 substituents independently selected from amino, $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl; or wherein said 5- or 6-membered heteroaryl ring may be further substituted with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, and fluoro-$C_1$-$C_4$-alkyl; and p is 0, 1 or 2, (preferably 0 or 1).

For example, representative examples of $R^{42}$ include:

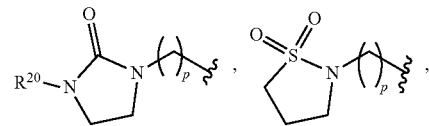

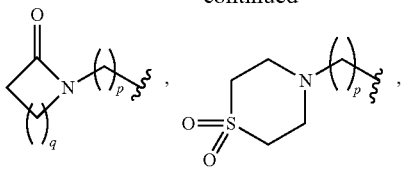

wherein $R^{20}$ is hydrogen or $C_1$-$C_4$-alkyl (preferably methyl);

wherein p is 0, 1 or 2, (preferably 0 or 1);

q is 1, 2 or 3, (preferably 1 or 2).

For example, representative examples of $R^{42}$ include

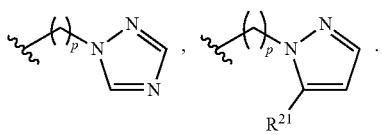

where $R^{21}$ is hydrogen or $C_1$-$C_4$-alkyl (preferably methyl), or amino, where p is 0, 1 or 2, preferably p is 0 or 1.

In embodiments of the invention, A is a 5-6 membered heteroaryl ring containing 1, 2 or 3 heteroatoms independently selected from N, O and S as ring members, wherein said heteroaryl ring is unsubstituted or substituted on one or more (e.g., 1, 2 or 3) carbon atoms with $R^{43}$, and wherein a nitrogen atom, when present in the heteroaryl ring, is unsubstituted or substituted with a substituent selected from the group consisting of: $C_1$-$C_4$-alkyl, —$(CH_2)_{1-2}$—$C_{3-4}$-cycloalkyl, hydroxy-$C_1$-$C_4$-alkyl, fluoro-$C_1$-$C_4$-alkyl, $C_1$-$C_4$-alkoxy-$C_1$-$C_4$-alkyl, $N(R^9)(R^{10})$—$C_1$-$C_4$-alkyl, —$SO_2$—$C_1$-$C_4$-alkyl, —$SO_2$—$C_{3-4}$-cycloalkyl, —$(CH_2)_p$-$Het^{py}$, and —$(CH_2)_p$—$N(R^9)(R^{10})$, (preferably wherein said substituent is selected from the group consisting of fluoro-$C_1$-$C_4$-alkyl, $N(R^9)(R^{10})$—$C_1$-$C_4$-alkyl, —$SO_2$—$C_{3-4}$-cycloalkyl, or —$(CH_2)_{1-2}$—$C_{3-4}$-cycloalkyl).

For example, A may be a pyridin-2-yl or pyridin-3-yl or pyridin-4-yl group, which may be unsubstituted or substituted with one or more substituents $R^{43}$. A is preferably a pyridin-3-yl or pyridin-4-yl group.

When A is pyridin-3-yl, an $R^{43}$ substituent on A, e.g. a $C_1$-$C_4$-alkyl, when present, is preferably on the 2- or 6-positions on the pyridinyl ring of the compound of Formula (I) and (Ia).

When there are two substituents (e.g., fluoro and amino) on the pyridin-3-yl ring, they are preferably on the 5- and 6-positions of the pyridin-3-yl ring of the compound of Formula (I) and (Ia).

When A is pyridin-4-yl, an $R^{43}$ substituent on A, e.g. a $C_1$-$C_4$-alkyl, when present, is preferably on the 2- or 3-position (preferably 3-position) on the pyridinyl ring of the compound of Formula (I) and (Ia).

When A is pyridin-4-yl, two $R^{43}$ substituents on A, which are preferably independently selected from $C_1$-$C_4$-alkyl, fluoro and amino (more preferably $C_1$-$C_4$-alkyl) when present, is preferably on the 2- and 6-positions on the pyridinyl ring of the compound of Formula (I) and (Ia).

Representative substituents on the pyridinyl include, but are not limited to, $NH_2$, F, CN, OH, —$CH_2$—OH, —COOH, —$CH_3$, —O—$CH_2$—$CH_2$—OH, —O—$(CH_2)_3$—$N(CH_3)_2$, —O—$CH_2$—$CH_3$, —O—$CH_2$—$CH_2$—O—$(CO)$—$CH_3$, —$N(CH_3)(CH_2$—$CH_2$—$OCH_3)$, —$N(H)$ $(CH_2$—$CH_2$—$OCH_3)$—$CH_2$—O—$CH_2$—$CH_2$—O— $CH_3$—$SO_2$—$CH_3$, —$C(O)$—$NH$—$(CH_2$—$CH_2$—$OCH_3)$, —$C(O)$—$N(CH_3)$—$(CH_2$—$CH_2$—$OCH_3)$, —$C(O)$—$NH$— $CH_2$—$C(CH_3)_2OH$, —$C(O)$—$N(CH_3)_2$, —$C(O)$—$N(CH_3)$—$CH_2$—$C(CH_3)_2$—$OH$, —$C(O)$—$N(H)$—$C(CH_3)_2$—$CH_2$—$OCH_3$, —$C(O)$—$N(H)$—$CH_2$—$CH_2$—$N(CH_3)_2$, —$(CH_2)_p$-$Het^{py}$, wherein $Het^{py}$ is a 4-, 5- or 6-membered saturated heterocyclic ring comprising one or two heteroatoms independently selected from O, N (such as pyrrolidin-1-yl, azetidin-1-yl, morpholin-1-yl) and S, or comprising an S-oxide (SO) or S-dioxide ($SO_2$) group, wherein said heterocyclic ring may be further substituted with 1, 2 or 3 substituents independently selected from $C_1$-$C_4$-alkoxy (preferably methoxy), halo (preferably fluoro), $C_1$-$C_4$-alkyl, hydroxy-$C_1$-$C_4$-alkyl, fluoro-$C_1$-$C_4$-alkyl, and —$C(O)$—$N(CH_3)$—$(CH_2$—$CH_2$—$OCH_3)$, or $Het^{py}$ is a 5- or 6-membered heteroaryl ring comprising 1, 2 or 3 nitrogen atoms, wherein said heteroaryl ring may be further substituted with 1, 2 or 3 substituents independently selected from $C_1$-$C_4$-alkoxy (methoxy), halo (fluoro), $C_1$-$C_4$-alkyl, hydroxy-$C_1$-$C_4$-alkyl, and fluoro-$C_1$-$C_4$-alkyl.

For example, representative examples of $R^{43}$ when A is pyridinyl may be selected from

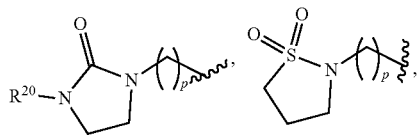

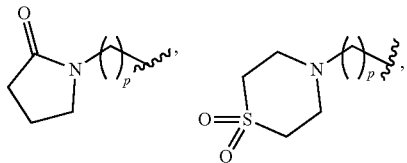

wherein $R^{20}$ is hydrogen or $C_1$-$C_4$-alkyl (preferably methyl), wherein p is 0. 1 or 2, preferably p is 0 or 1.

For example, representative examples of $R^{43}$ when A is pyridinyl, e.g., pyridin-3-yl, may be selected from

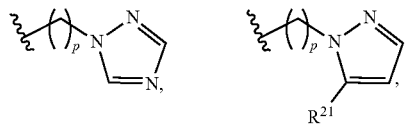

wherein $R^{21}$ is hydrogen or $C_1$-$C_4$-alkyl (preferably methyl), or amino, wherein p is 0, 1 or 2. Preferably p is 0 or 1.

In embodiments of the compounds of Formula (I) and (Ia), representative substituents $R^{43}$ when A is a pyridinyl ring, are $NH_2$, F, —$CH_3$, —$CF_3$, —$CH_2OH$, CN, —$C(O)$—$N(H)$—$C(CH_3)_2$—$CH_2$—O—$CH_3$, —$C(O)$—$N(CH_3)$—$(CH_2$—$CH_2$—$OCH_3)$, —O—$(CH_2)_3$—$N(CH_3)_2$,

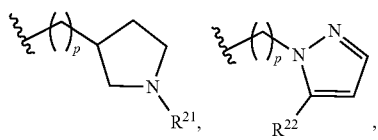

wherein p is 0, 1 or 2, preferably p is 1 or 2;
R$^{21}$ is hydrogen or C$_1$-C$_4$-alkyl (preferably methyl),
R$^{22}$ is hydrogen or C$_1$-C$_4$-alkyl (preferably methyl), or amino,
Preferably, p is 0, and R$^{22}$ is amino.

In embodiments of the invention, A is a pyrimidin-3-yl group or a pyrimidin-5-yl group, which may be unsubstituted or substituted with one or more substituents R$^{43}$. Representative substituents on the pyrimidinyl group include —O—CH$_3$, In embodiments of the invention, A is selected from the group consisting of

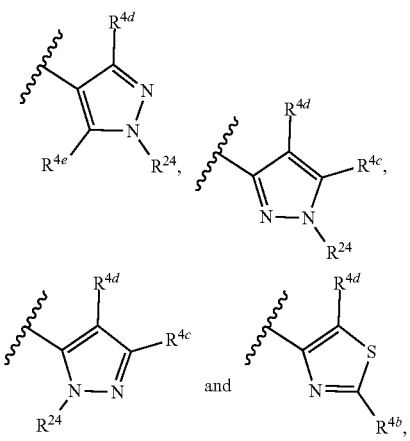

wherein R$^{24}$ is hydrogen, C$_1$-C$_4$-alkyl, hydroxy-C$_1$-C$_4$-alkyl, C$_1$-C$_4$-alkoxy-C$_1$-C$_4$-alkyl, —NR$^9$R$^{10}$C$_1$-C$_4$-alkyl, —SO$_2$—C$_1$-C$_4$-alkyl, —SO$_2$—C$_{3-4}$-cycloalkyl or —(CH$_2$)$_{1-2}$—C$_{3-4}$-cycloalkyl; or wherein R$^{24}$ is hydrogen, C$_1$-C$_4$-alkyl, hydroxy-C$_1$-C$_4$-alkyl, C$_1$-C$_4$-alkoxy-C$_1$-C$_4$-alkyl, amino-C$_1$-C$_4$-alkyl, C$_1$-C$_4$-alkylamino-C$_1$-C$_4$-alkyl, di-C$_1$-C$_4$-alkylamino-C$_1$-C$_4$-alkyl, —SO$_2$—C$_1$-C$_4$-alkyl, —SO$_2$—C$_{3-4}$-cycloalkyl or —CH$_2$)$_{1-2}$—C$_{3-4}$-cycloalkyl;
each of R$^{4a}$, R$^{4b}$, R$^{4c}$ and R$^{4d}$ is independently selected from hydrogen and C$_1$-C$_4$-alkyl (preferably methyl).

R$^{24}$ is preferably di-C$_1$-C$_4$-alkylamino-C$_1$-C$_4$-alkyl (e.g., —CH$_2$—CH$_2$—N(CH$_3$)$_2$) or —SO$_2$—C$_{3-4}$-cycloalkyl (e.g., —SO$_2$-cyclopropyl).

R$^{4c}$ is preferably C$_1$-C$_4$-alkyl (e.g., methyl) and each of R$^{4a}$, R$^{4b}$ and R$^{4d}$ is preferably hydrogen.

When R$^{24}$ is di-C$_1$-C$_4$-alkylamino-C$_1$-C$_4$-alkyl, R$^{4c}$ is preferably C$_1$-C$_4$-alkyl (e.g., methyl) and each of R$^{4a}$ and R$^{4d}$ is hydrogen.

In embodiments of the invention, A is (i) an 8-10 membered heteroaryl ring containing 1 to 3 heteroatoms independently selected from nitrogen, oxygen and sulfur (e.g., 1 to 3 heteroatoms independently selected from 0-3 nitrogen atoms, 0-1 oxygen atom, and 0-1 sulfur atom), or (ii) 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 S(=O)$_2$ group in the hetero-bicyclic ring, wherein said heteroaryl ring or hetero-bicyclic ring is unsubstituted or substituted on a carbon atom with 1, 2, 3, 4 or 5 R$^{44}$, and wherein the hetero-bicyclic ring is further optionally substituted on a carbon atom by oxo and wherein a nitrogen atom, when present, is unsubstituted or substituted with a substituent which is —(CO)—C$_1$-C$_4$-alkyl or C$_1$-C$_4$-alkyl, and wherein said C$_1$-C$_4$-alkyl is optionally substituted with 1 or 2 substituents independently selected from cyano, hydroxy, oxo, fluoro, C$_1$-C$_4$-alkoxy, C$_1$-C$_4$-alkoxy-C$_1$-C$_4$-alkyl-oxy, Het$^b$ and NR$^9$R$^{10}$.

In embodiments of the invention, A is an 8-10 membered heteroaryl ring containing 1 to 3 heteroatoms independently selected from nitrogen, oxygen and sulfur. For example, A is an 8-membered heteroaryl containing 1-3 heteroatoms independently selected from 0-3 nitrogen atoms, 0-1 oxygen atom, and 0-1 sulfur atoms. The heteroaryl ring is unsubstituted or substituted on a carbon atom with 1, 2, 3, 4 or 5 R$^{44}$, and a nitrogen atom, when present, is unsubstituted or substituted with a substituent which is —(CO)—C$_1$-C$_4$-alkyl or C$_1$-C$_4$-alkyl, and wherein said C$_1$-C$_4$-alkyl is optionally substituted with 1 or 2 substituents independently selected from cyano, hydroxy, oxo, fluoro, C$_1$-C$_4$-alkoxy, C$_1$-C$_4$-alkoxy-C$_1$-C$_4$-alkyl-oxy, Het$^b$ and NR$^9$R$^{10}$.

Representative examples of A thus also include

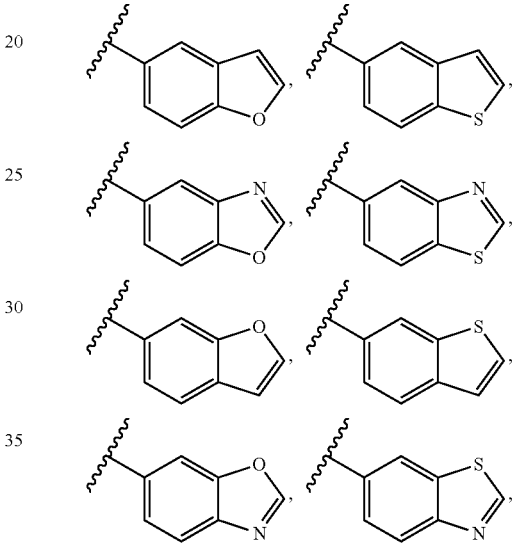

where the squiggly line denotes the point of attachment of A to the rest of the molecule.

In embodiments of the invention, A is an 8-10 membered heteroaryl ring containing 1, 2 or 3 nitrogen atoms, or 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 S(=O)$_2$ group in the hetero-bicyclic ring, wherein said heteroaryl ring or hetero-bicyclic ring is unsubstituted or substituted on a carbon atom with 1, 2, 3, 4 or 5 R$^{44}$, and wherein the hetero-bicyclic ring is further optionally substituted on a carbon atom by oxo and wherein a nitrogen atom, when present, is unsubstituted or substituted with a substituent which is —(CO)—C$_1$-C$_4$-alkyl or C$_1$-C$_4$-alkyl, and wherein said C$_1$-C$_4$-alkyl is optionally substituted with 1 or 2 substituents independently selected from cyano, hydroxy, oxo, fluoro, C$_1$-C$_4$-alkoxy, C$_1$-C$_4$-alkoxy-C$_1$-C$_4$-alkyl-oxy, Het$^b$ and NR$^9$R$^{10}$.

In embodiments of the invention, A is an 8-10 membered heteroaryl ring containing 1, 2 or 3 nitrogen atoms, or 8-10 membered partially saturated hetero-bicyclic ring containing 1-3 nitrogen atoms or 1-2 oxygen atoms or 1 sulfur atom or 1 S(=O)$_2$ group in the hetero-bicyclic ring, wherein said heteroaryl ring or hetero-bicyclic ring is unsubstituted or substituted on a carbon atom with 1, 2, 3, 4 or 5 R$^{44}$, and wherein the hetero-bicyclic ring is further optionally substituted on a carbon atom by oxo and wherein a nitrogen atom, when present, is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$.

In embodiments of the invention, the nitrogen atom, when present in the above mentioned 8-10 membered heteroaryl ring or above mentioned 8-10 membered partially saturated hetero-bicyclic ring, is unsubstituted or substituted with $C_1$-$C_4$-alkyl which is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$.

In embodiments of the invention, $Het^b$ is a 4- or 5- or 6-membered heterocyclic ring or heteroaryl ring comprising 1 or 2 heteroatoms or groups independently selected from N, O, S, SO and $SO_2$ (preferably comprising 1 oxygen atom, or 1 sulfur atom, or one S(=O) or one S(=O)$_2$ group, or 1 nitrogen atom and 1 oxygen atom, or 1-2 nitrogen atoms; more preferably comprising 1 nitrogen atom and 1 oxygen atom, or 1-2 nitrogen atoms), wherein said heterocyclic ring $Het^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl (preferably selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, and fluoro-$C_1$-$C_4$-alkyl), and wherein said heterocyclic ring $Het^b$ is further optionally substituted on a carbon atom by oxo, and wherein the nitrogen atom when present in $Het^b$ is optionally further substituted with $C_1$-$C_4$-alkyl wherein said $C_1$-$C_4$-alkyl is optionally substituted with 1 to 3 substituents independently selected from fluoro, hydroxy and $C_1$-$C_4$-alkoxy.

In embodiments of the invention, $Het^b$ is azetidin-1-yl, pyrrolidin-1-yl, pyrrolidin-3-yl or morpholin-1-yl, and is optionally substituted with fluoro, hydroxy and $C_1$-$C_4$-alkoxy (e.g. by methyl, hydroxy-methyl, methoxy and fluoro).

In embodiments of the invention, A is an 8-10 membered heteroaryl ring containing 1, 2 or 3 nitrogen atoms, or an 8-10 membered partially saturated hetero-bicyclic ring containing containing 1 to 3 heteroatoms or heteroatom groups independently selected from 0-3 nitrogen atoms, 0-2 oxygen atoms, 0-1 sulfur atom and 0-1 S(=O)$_2$ group in the hetero-bicyclic ring wherein when A contains a nitrogen, that nitrogen is substituted by $R^{ae}$ or $R^{Ae}$.

In embodiments of the invention, A is an 8-10 membered heteroaryl ring containing 1, 2 or 3 nitrogen atoms, or an 8-10 membered partially saturated hetero-bicyclic ring containing containing 1-3 nitrogen atoms or 1-2 oxygen atoms or 1 sulfur atom or 0-1 S(=O)$_2$ group in the hetero-bicyclic ring wherein when A contains a nitrogen, that nitrogen is substituted by $R^{ae}$ or $R^{Ae}$.

In embodiments of the invention, A is an 8-10 membered heteroaryl ring containing 1, 2 or 3 nitrogen atoms, wherein at least one of the nitrogen atoms is substituted by $R^{ae}$ or $R^{Ae}$.

In embodiments of the invention, A is an 8-10 membered heteroaryl ring containing 1, 2 or 3 nitrogen atoms, wherein one of the nitrogen atoms is substituted by $R^{ae}$ or $R^{Ae}$.

In embodiments of the invention, $R^{Ae}$ is selected from the group consisting of hydrogen, —(CO)—$C_1$-$C_4$-alkyl and $C_1$-$C_4$-alkyl wherein the $C_1$-$C_4$alkyl in each instance is optionally substituted with 1 or 2 substituents selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$.

In embodiments of the invention, $R^{Ae}$ is selected from the group consisting of hydrogen, fluoro-$C_1$-$C_4$-alkyl and $C_1$-$C_4$-alkyl (e.g. methyl).

In embodiments of the invention, $R^{ae}$ is selected from the group consisting of hydrogen and $C_1$-$C_4$-alkyl, wherein said alkyl is optionally substituted with 1 or 2 substituents independently selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$.

In embodiments of the invention, $R^{ae}$ is selected from the group consisting of hydrogen, $C_1$-$C_4$-alkyl, —(CH$_2$)$_2$-$Het^b$, —CH$_2$—CN, —(CH$_2$)$_2$.OH, —(CH$_2$)$_2$.O—$C_1$-$C_4$-alkyl, hydroxy-$C_1$-$C_4$-alkyl, —(CH$_2$)$_2$—O—(CH$_2$)$_2$—O—$C_1$-$C_4$-alkyl and —(CH$_2$)$_2$-di$C_1$-$C_4$-alkylamino, (for example when $Het^b$ is selected from the group consisting of azetidin-1-yl, pyrrolidin-1-yl, pyrrolidin-3-yl and morpholin-1-yl) Preferably $R^{ae}$ is selected from the group consisting of hydrogen, $C_1$-$C_4$-alkyl and —CH$_2$—CN. Preferably $R^{ae}$ is selected from the group consisting of hydrogen and $C_1$-$C_4$-alkyl.

In embodiments of the invention, y is 0, 1 or 2 (preferably 0 or 1).

In embodiments of the invention, x is 0, 1 or 2 (preferably 0 or 1).

In embodiments of the invention, z is 0, 1 or 2 (preferably 0 or 1).

In embodiments of the invention, $R^q$ is selected from the group consisting of $C_1$-$C_4$-alkyl, hydroxy, $C_1$-$C_4$-alkoxy and $NR^9R^{10}$ and y is 0 or 1.

Preferably $R^q$ is selected from the group consisting of $C_1$-$C_4$-alkyl and hydroxy.

Typical examples of A as an 8-10 membered heteroaryl ring or hetero-bicyclic ring include

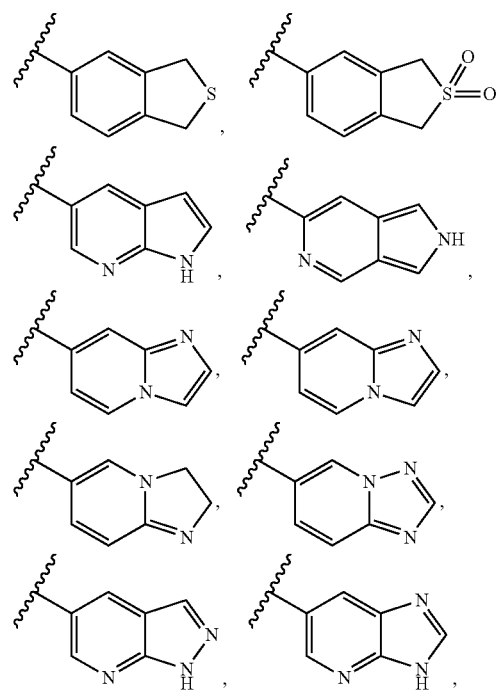

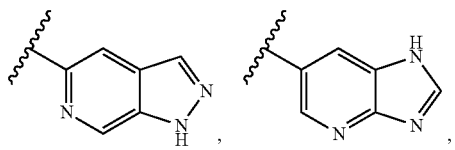

where the squiggly line 〜 denotes the point of attachment of A to the rest of the molecule, wherein A is unsubstituted or substituted with 1, 2, 3, 4 or 5 $R^{44}$ (preferably by 1 or 2 $R^{44}$), where the nitrogen atom in the NH moiety in the structures above may also be replaced with a N—$R^{ae}$, wherein $R^{ae}$ is $C_1$-$C_4$-alkyl which is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$. Preferably, $R^{ae}$ is hydrogen or $C_1$-$C_4$-alkyl such as methyl.

For example, typical examples of A include

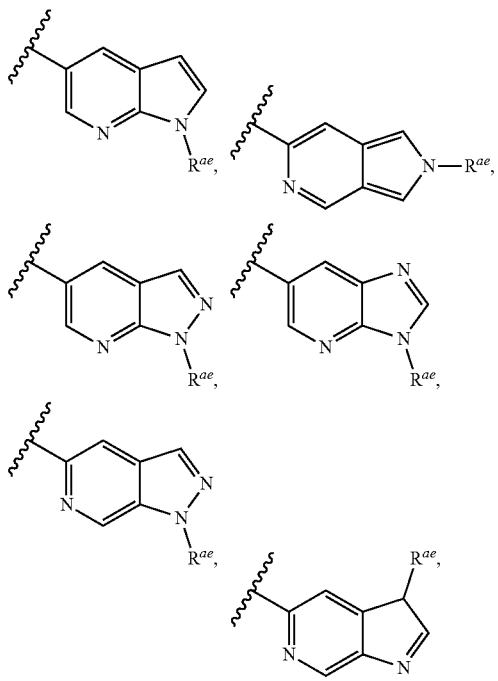

where the squiggly line denotes the point of attachment of A to the rest of the molecule, wherein A is unsubstituted or substituted with 1, 2, 3, 4 or 5 $R^{44}$ (preferably by 1 or 2 $R^{44}$), wherein $R^{ae}$ is hydrogen or $C_1$-$C_4$-alkyl which is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$. Preferably, $R^{ae}$ is hydrogen or $C_1$-$C_4$-alkyl such as methyl.

Representative examples of A also include:

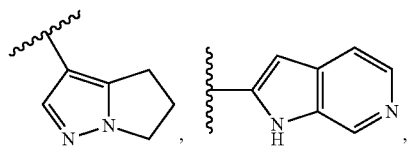

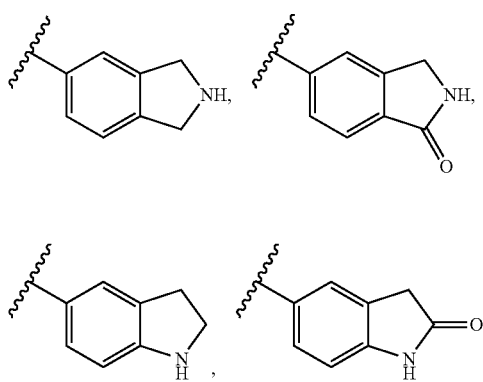

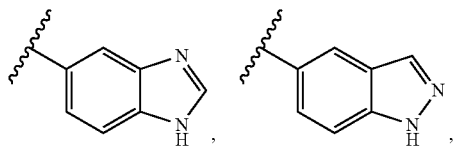

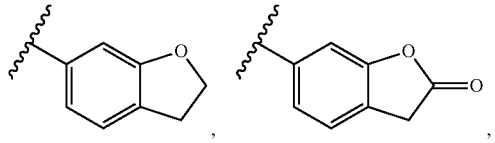

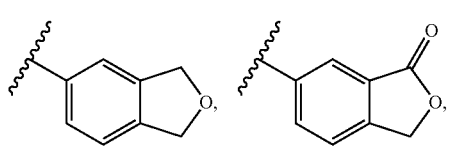

where the squiggly line denotes the point of attachment of A to the rest of the molecule, wherein A is unsubstituted or substituted with 1, 2, 3, 4 or 5 $R^{44}$ (preferably by 1 or 2 $R^{44}$), where the nitrogen atom in the NH moiety in the structures above may also be replaced with a N—$R^{Ae}$ or N—$R^{ae}$, wherein $R^{Ae}$ is selected from the group consisting of hydrogen, —(CO)—$C_1$-$C_4$-alkyl and $C_1$-$C_4$-alkyl wherein the $C_1$-$C_4$alkyl in each instance is optionally substituted with 1 or 2 substituents independently selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$ and $R^{ae}$ is $C_1$-$C_4$-alkyl which is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$. Preferably, Preferably, $R^{Ae}$ is hydrogen or $C_1$-$C_4$-alkyl such as methyl. Preferably $R^{ae}$ is hydrogen or $C_1$-$C_4$-alkyl such as methyl.

Thus, typical examples of A include:

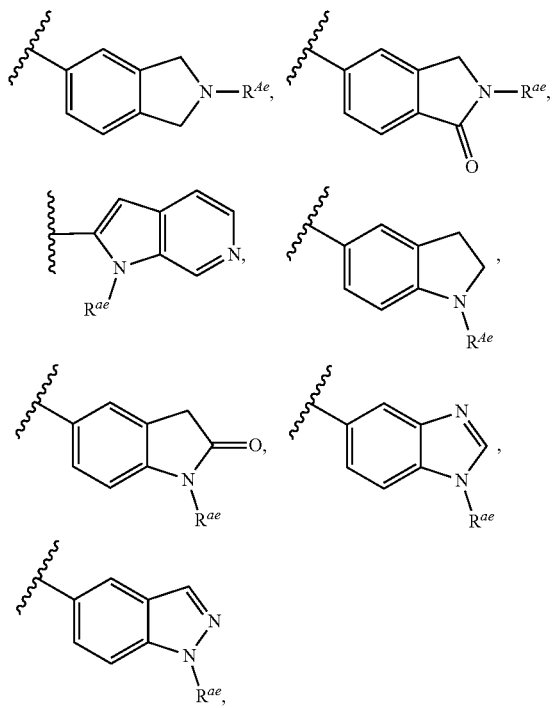

where the squiggly line denotes the point of attachment of A to the rest of the molecule, wherein A is unsubstituted or substituted with 1, 2, 3, 4 or 5 $R^{A4}$ (preferably by 1 or 2 $R^{A4}$), wherein $R^{Ae}$ is selected from the group consisting of hydrogen, —(CO)—$C_1$-$C_4$-alkyl and $C_1$-$C_4$-alkyl wherein the $C_1$-$C_4$alkyl in each instance is optionally substituted with 1 or 2 substituents independently selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$ and $R^{ae}$ is $C_1$-$C_4$-alkyl which is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$. Preferably, $R^{Ae}$ is hydrogen or $C_1$-$C_4$-alkyl such as methyl. Preferably $R^{ae}$ is hydrogen or $C_1$-$C_4$-alkyl such as methyl.

Other representative examples of A include,

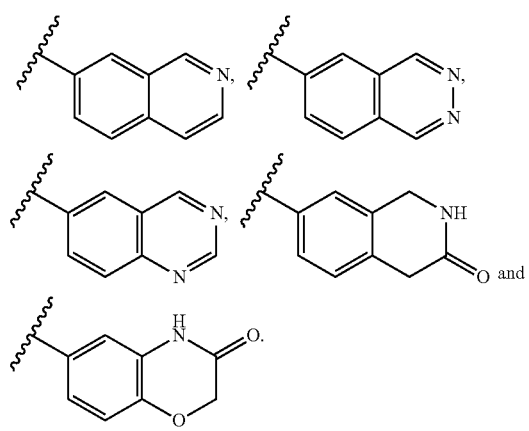

where the squiggly line denotes the point of attachment of A to the rest of the molecule, wherein A is unsubstituted or substituted with 1, 2, 3, 4 or 5 $R^{A4}$ (preferably by 1 or 2 $R^{A4}$), where the nitrogen atom in the NH moiety in the structures above may also be replaced with a N—$R^{ae}$ or N—$R^{Ae}$, wherein $R^{Ae}$ is selected from the group consisting of hydrogen, —(CO)—$C_1$-$C_4$-alkyl and $C_1$-$C_4$-alkyl wherein the $C_1$-$C_4$alkyl in each instance is optionally substituted with 1 or 2 substituents independently selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$ and $R^{ae}$ is $C_1$-$C_4$-alkyl which is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, $Het^b$ and $NR^9R^{10}$. Preferably, Preferably, $R^{Ae}$ is hydrogen or $C_1$-$C_4$-alkyl such as methyl. Preferably $R^{ae}$ is hydrogen or $C_1$-$C_4$-alkyl such as methyl. The term "$C_{6-10}$ aryl", as used herein and also with reference to substituent B, refers to a phenyl or naphthyl group, wherein the phenyl or naphthyl is unsubstituted or substituted with 1, 2, 3 or 4 (preferably 1 or 2) $R^{Ba}$.

In embodiments of the invention, $R^{Ba}$ is independently selected from the group consisting of hydroxy, $NH_2$, $C_1$-$C_4$-alkyl and halo, or preferably selected from the group consisting of hydroxy, $C_1$-$C_4$-alkyl and halo.

In embodiments of the invention, B is 3-hydroxy-phenyl or 3-hydroxy-naphthyl, wherein B is unsubstituted or substituted with 1, 2 or 3 halo (preferably chloro) atoms. In further embodiments of the invention, B is

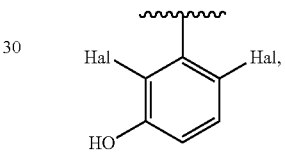

wherein Hal represents a halogen atom.
In embodiments of the invention, B is

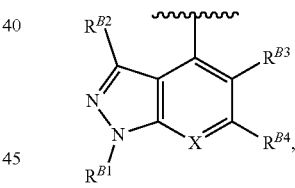

wherein X is N or C—$R^{B5}$;
$R^{B1}$ is independently selected from hydrogen and $C_1$-$C_4$-alkyl (preferably methyl);
$R^{B2}$ is independently selected from hydrogen, halo (preferably chloro), $C_1$-$C_4$-alkyl (preferably methyl), cyclopropyl and $NH_2$;
$R^{B3}$ is independently selected from hydrogen, halo (preferably chloro), cyclopropyl and $C_1$-$C_4$-alkyl (preferably methyl);
$R^{B4}$ is independently selected from hydrogen, halo (preferably chloro or fluoro) and $C_1$-$C_4$-alkyl (preferably methyl), or $R^{B3}$ and $R^{B4}$ together with the atoms to which they are attached, form a 4-6 membered ring (preferably a 5-6 membered saturated or partially unsaturated carbocyclic ring) fused to the aromatic ring containing X;
$R^{B5}$ is independently selected from hydrogen, halo (preferably chloro) and $C_1$-$C_4$-alkyl (preferably methyl).

In embodiments of the invention, X is N or C—$R^{B5}$, $R^{B1}$ is independently selected from hydrogen and $C_1$-$C_4$-alkyl, $R^{B2}$ is independently selected from hydrogen and $NH_2$, $R^{B3}$ and $R^{B4}$ are each independently selected from hydrogen, halo (preferably chloro) and $C_1$-$C_4$-alkyl (preferably methyl), or $R^{B3}$ and $R^{B4}$ together with the atoms to which they are attached, form a 4-6 membered ring (preferably a 5-6 membered saturated or partially unsaturated carbocyclic ring) used to the aromatic ring containing X.

$R^{B5}$ is independently selected from hydrogen, halo (preferably chloro) and $C_1$-$C_4$-alkyl (preferably methyl).

In embodiments of the invention, B is

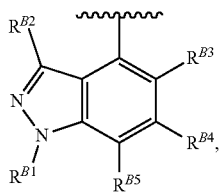

wherein $R^{B1}$ is independently selected from hydrogen and $C_1$-$C_4$-alkyl, $R^{B2}$ is independently selected from hydrogen, $C_1$-$C_4$-alkyl and $NH_2$, $R^{B3}$ and $R^{B4}$ are each independently selected from hydrogen, halo (preferably fluoro or chloro, more preferably chloro) and $C_1$-$C_4$-alkyl (preferably methyl), $R^{B5}$ is independently selected from hydrogen, halo (preferably chloro) and $C_1$-$C_4$-alkyl (preferably methyl).

In embodiments of the invention, X is N or C—$R^{B5}$, wherein $R^{B1}$ is independently selected from hydrogen and $C_1$-$C_4$-alkyl, $R^{B2}$ is independently selected from hydrogen and $NH_2$, $R^{B3}$ and $R^{B4}$ are each independently selected from hydrogen, halo (preferably chloro) and $C_1$-$C_4$-alkyl (preferably methyl).

$R^{B5}$ is independently selected from hydrogen, halo (preferably chloro) and $C_1$-$C_4$-alkyl (preferably methyl).

In embodiments of the invention, X is N or CH, preferably X is CH.

In embodiments of the invention, X is CH and $R^{B1}$ is hydrogen or $C_1$-$C_4$-alkyl (such as methyl).

In embodiments of the invention, $R^{B1}$ is hydrogen or $C_1$-$C_4$-alkyl (such as methyl), preferably $R^{B1}$ is hydrogen.

In embodiments of the invention, $R^{B2}$ is hydrogen or amino, preferably $R^{B2}$ is hydrogen.

In embodiments of the invention, $R^{B3}$ and $R^{B4}$ are each independently selected from halo (preferably chloro) and $C_1$-$C_4$-alkyl (preferably methyl).

The present invention provides compounds of Formula (I) and (Ia), wherein $R^{B1}$ is independently selected from hydrogen and $C_1$-$C_4$-alkyl, $R^{B2}$ is amino, $R^{B3}$ is halo (preferably chloro) and $R^{B4}$ is methyl, and X is CH, or $R^{B2}$ is amino, $R^{B3}$ is halo (preferably chloro) or methyl, $R^{B4}$ is hydrogen, X is CH, or $R^{B2}$ is hydrogen, $R^{B3}$ is halo (preferably chloro) or methyl and $R^{B4}$ is hydrogen, X is CH, In embodiments of the invention, $R^{B2}$ is amino, $R^{B3}$ and $R^{B4}$ are both halo (preferably chloro), and X is CH.

In embodiments of the invention, $R^{B1}$ is $C_1$-$C_4$-alkyl (preferably methyl), $R^{B2}$, $R^{B3}$, $R^{B4}$ and $R^{B5}$ are all hydrogen.

In embodiments of the invention, X is N, $R^{B1}$ and $R^{B2}$ are hydrogen, $R^{B3}$ is independently selected from halo (preferably chloro) and $C_1$-$C_4$-alkyl (preferably methyl), $R^{B4}$ is halo (preferably chloro).

In a further aspect of the invention there is provided a compound which is selected from any one depicted in the Examples, or a pharmaceutically acceptable salt thereof.

In a further aspect of the invention, there is provided a compound which is selected from the group consisting of:

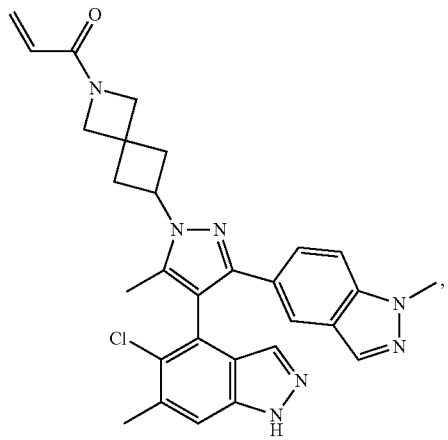

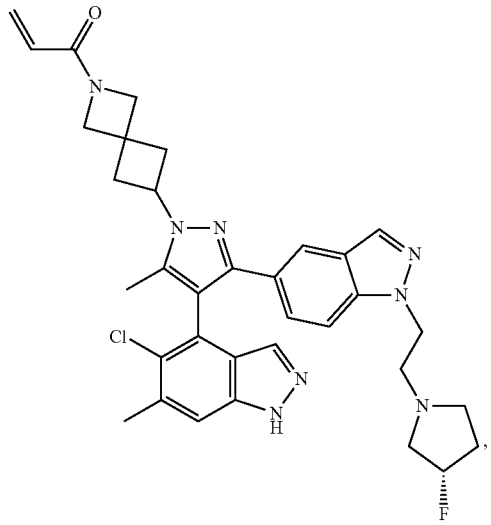

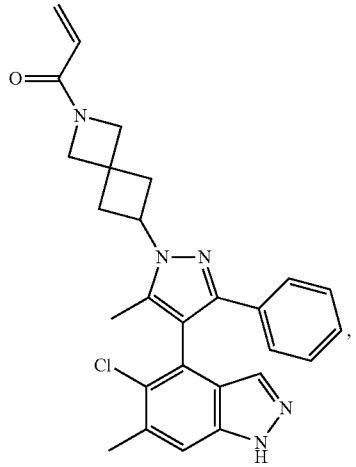

69
-continued
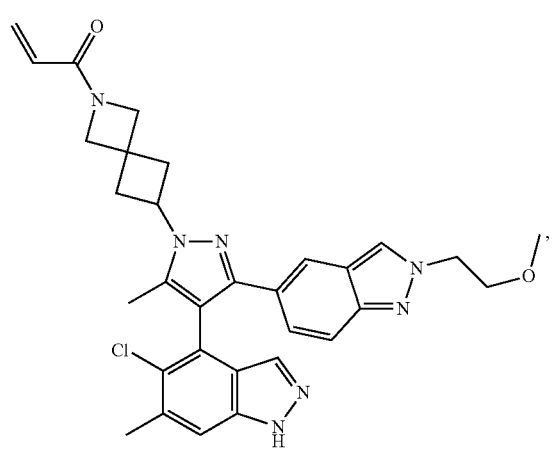
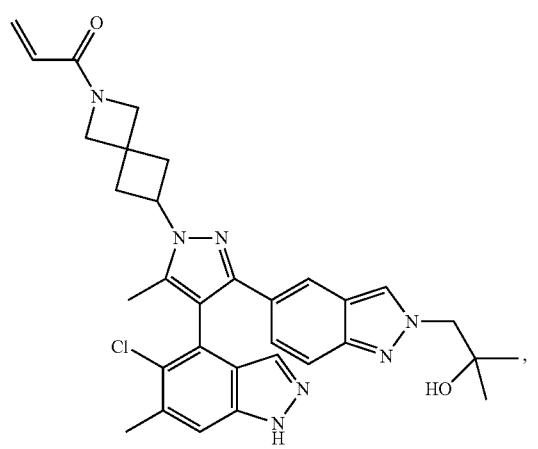
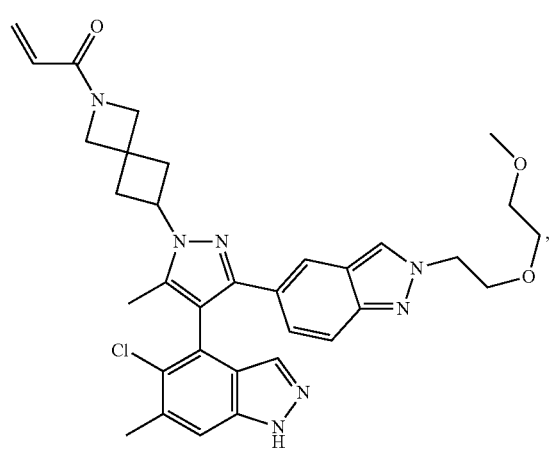
70
-continued
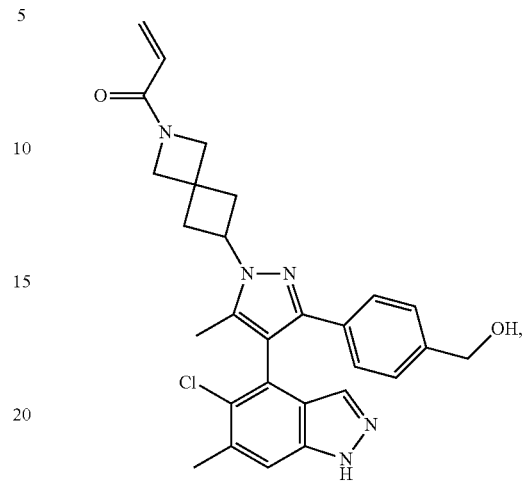
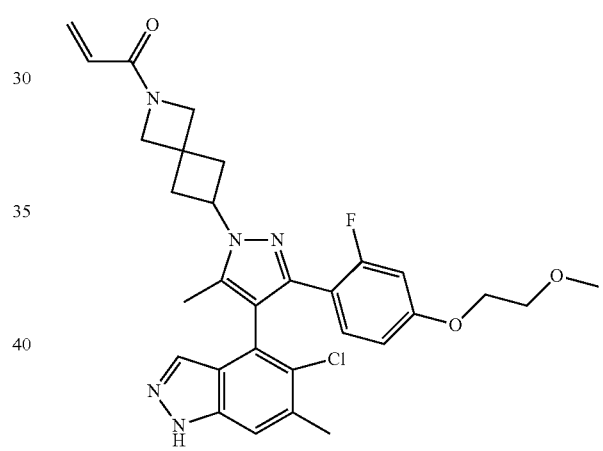
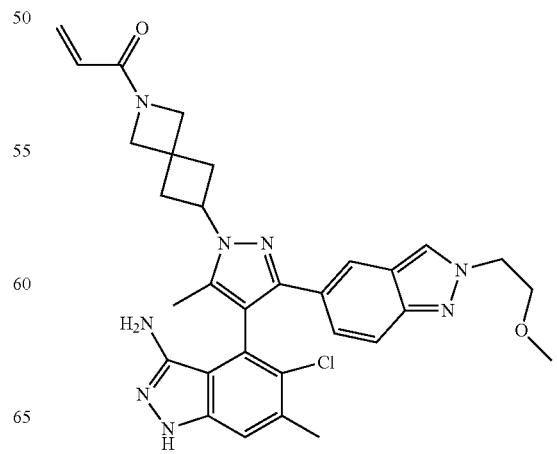
and -continued

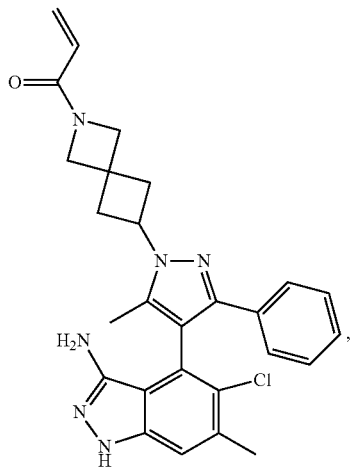

or a pharmaceutically acceptable salt thereof.

In a further aspect of the invention, there is provided a compound which is selected from the group consisting of:

a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Example 1a), a(R)(S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl)prop-2-en-1-one (Example 18a),

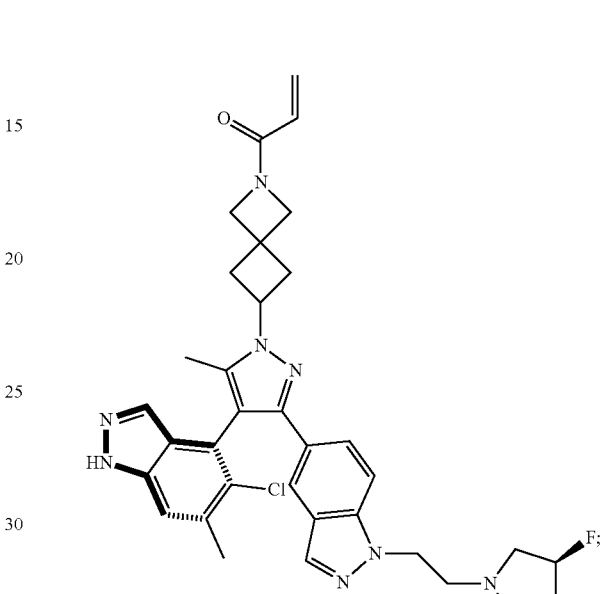

a(R)1-(6-(4-(5-chloro-6-methyl-1H-indazol-4-yl)-5-methyl-3-phenyl-1H-pyrazol-1-yl)-2-azaspiro[3.3]heptan-2-yl)prop-2-en-1-one (Example 26a),

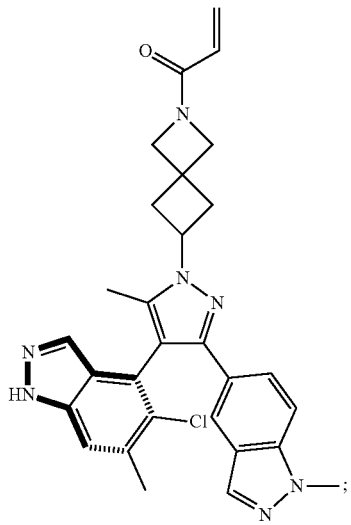

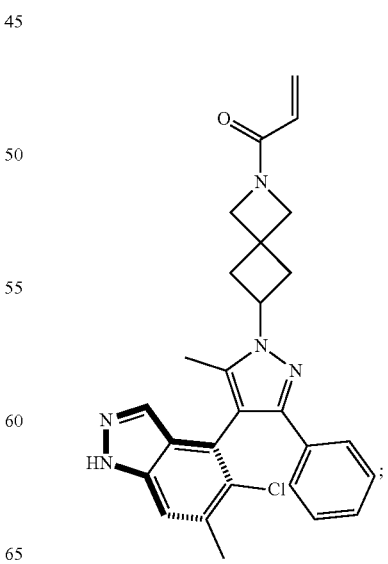

a(R)1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one (Example 41a),

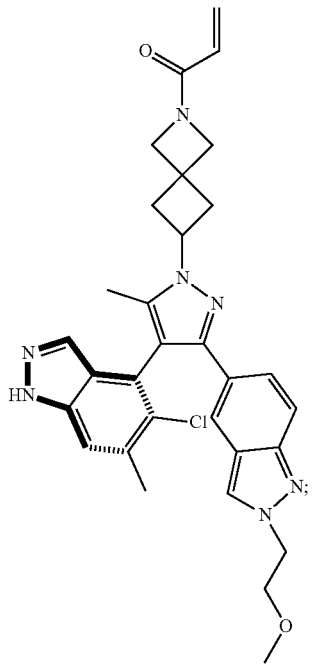

a(R)1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one (Example 42a),

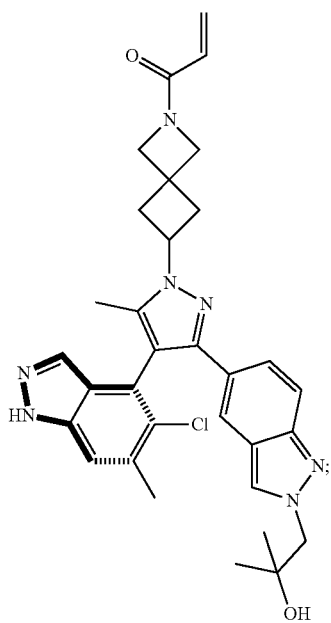

a(R)1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one (Example 43a),

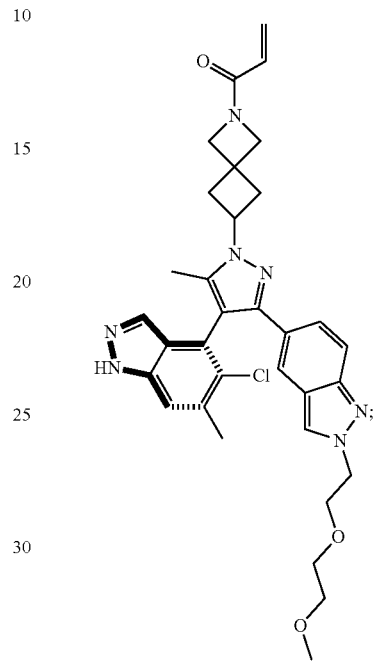

a(R)1-(6-(4-(5-chloro-6-methyl-1H-indazol-4-yl)-3-(4-(hydroxymethyl)phenyl)-5-methyl-1H-pyrazol-1-yl)-2-azaspiro[3.3]heptan-2-yl)prop-2-en-1-one (Example 47a),

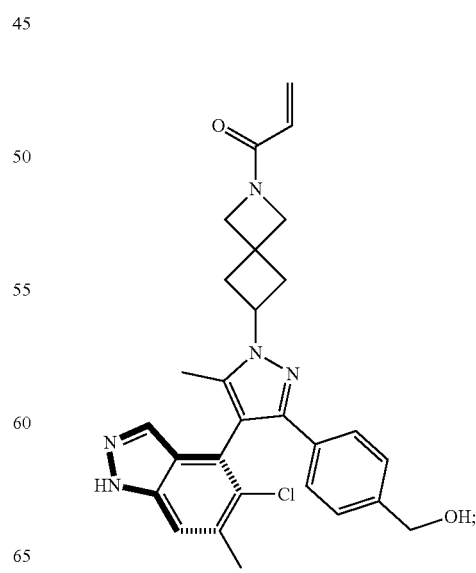

a(R)1-(6-(4-(5-chloro-6-methyl-1H-indazol-4-yl)-3-(2-fluoro-4-(2-methoxyethoxy)phenyl)-5-methyl-1H-pyrazol-1-yl)-2-azaspiro[3.3]heptan-2-yl)prop-2-en-1-one (Example 60a),

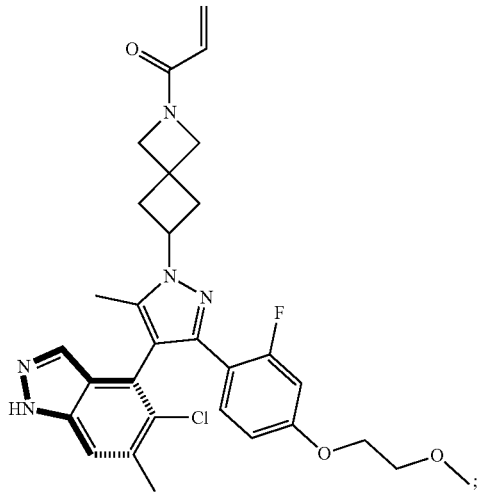

a(R)1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one (Example 69a),

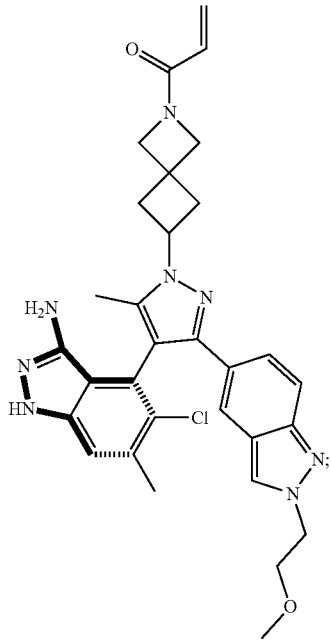

and a(R)1-(6-(4-(3-amino-5-chloro-6-methyl-1H-indazol-4-yl)-5-methyl-3-phenyl-1H-pyrazol-1-yl)-2-azaspiro[3.3]heptan-2-yl)prop-2-en-1-one (Example 70a),

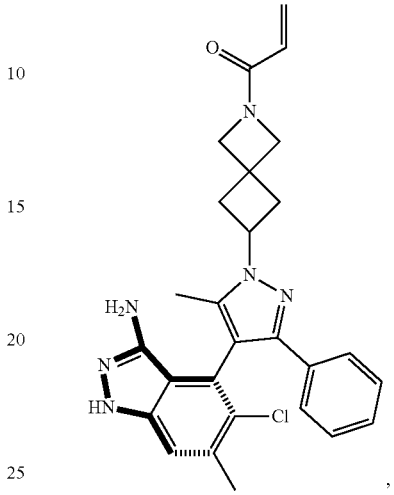

or a pharmaceutically acceptable salt thereof.

The present invention provides a compound which is selected from the group consisting of:

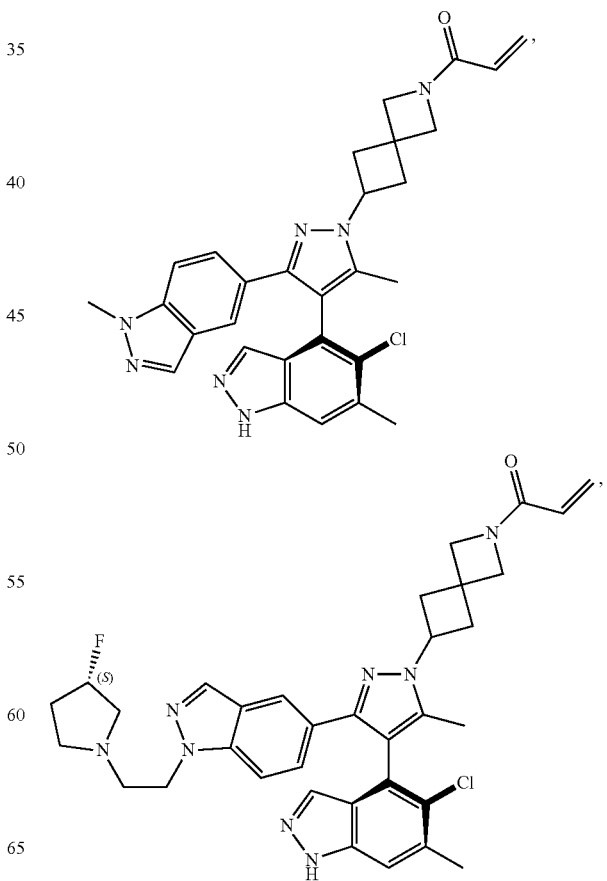

77
-continued
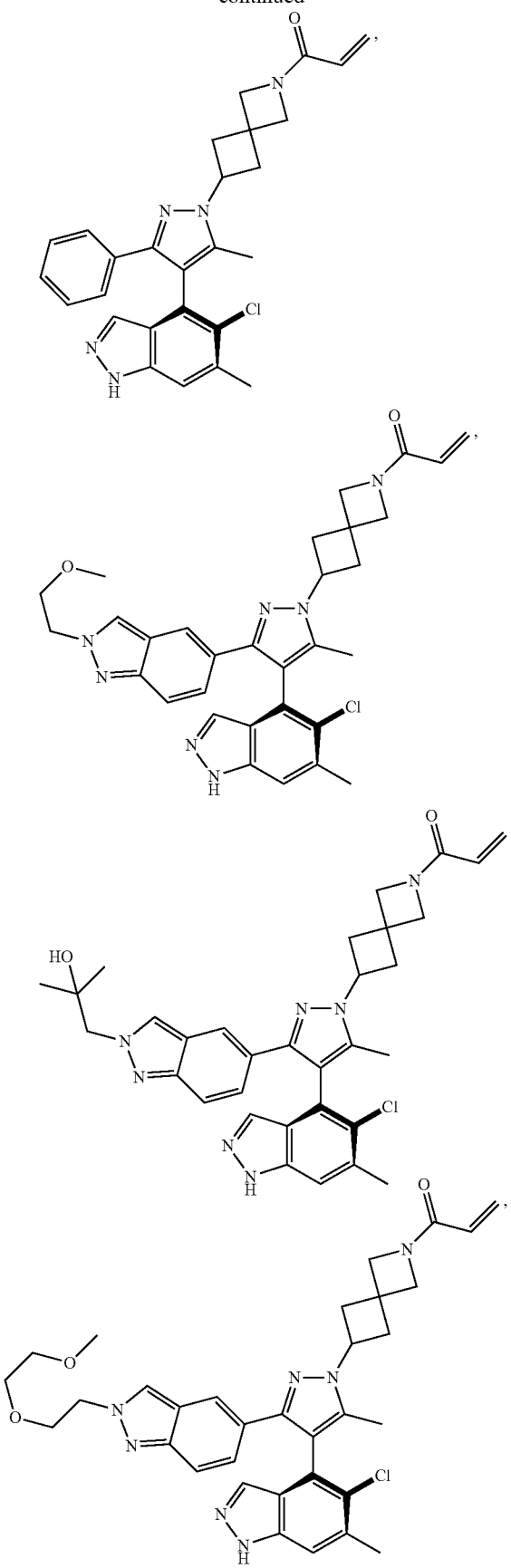
78
-continued
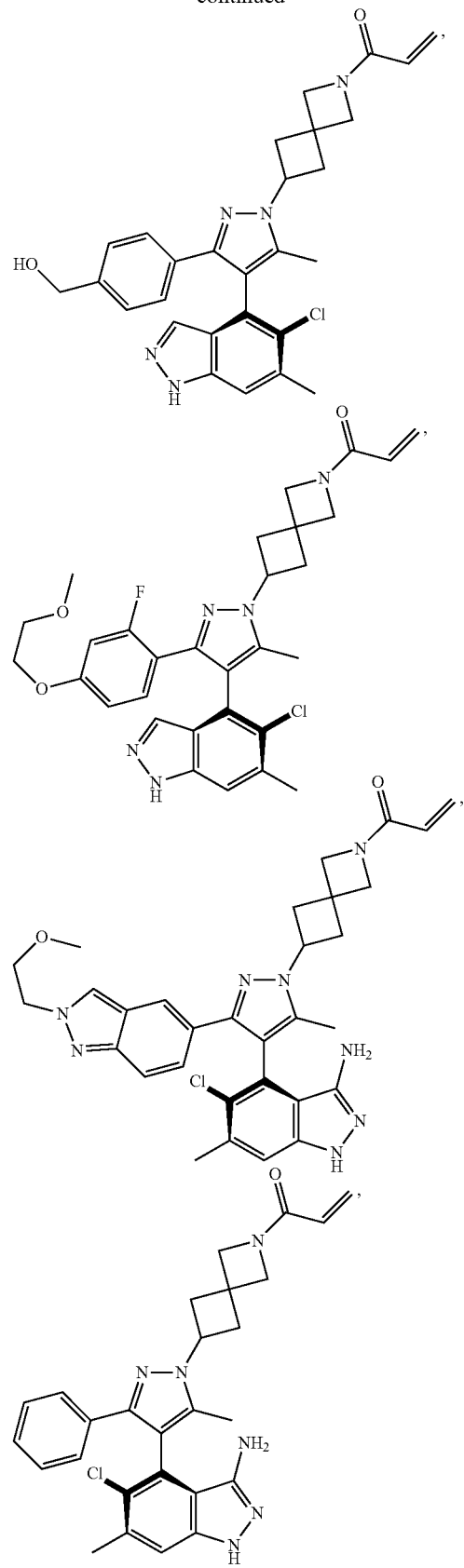
or a pharmaceutically acceptable salt thereof.

Depending on the choice of the starting materials and procedures, the compounds can be present in the form of one of the possible isomers or as mixtures thereof, for example as pure optical isomers, or as isomer mixtures, such as racemates and diastereomeric mixtures, depending on the number of asymmetric centers. The present invention is meant to include all such possible isomers, including racemic mixtures, enantiomerically enriched mixtures, diastereomeric mixtures and optically pure forms. Optically active (R)- and (S)-isomers may be prepared using chiral synthons or chiral reagents, or resolved using conventional techniques. If the compound contains a disubstituted or trisubstituted cycloalkyl, the cycloalkyl substituent(s) may have a cis- or trans-configuration. The present invention includes cis and trans configurations of substituted cycloalkyl groups as well as mixtures thereof. All tautomeric forms are also intended to be included. In particular, where a heteroaryl ring containing N as a ring atom is 2-pyridone, for example, tautomers where the carbonyl is depicted as a hydroxy (e.g., 2-hydroxypyridine) are included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, trifluoroacetic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Pharmaceutically acceptable salts are preferred.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{17}$O, $^{18}$O, $^{18}$F, $^{35}$S, $^{36}$Cl, respectively. The invention includes various isotopically labeled compounds as defined herein, for example those into which radioactive isotopes, such as $^3$H and $^{14}$C, or those into which non-radioactive isotopes, such as $^3$H and $^{14}$C are present. Such isotopically labelled compounds are useful in metabolic studies (with $^{14}$C), reaction kinetic studies (with, for example $^2$H and $^{13}$C), detection or imaging techniques, such as positron emission tomography (PET) or single-photon emission computed tomography (SPECT) including drug or substrate tissue distribution assays, or in radioactive treatment of patients. In particular, an $^{18}$F compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Further, substitution with heavier isotopes, particularly deuterium (i.e., $^2$H or D), may afford certain therapeutic advantages resulting from greater metabolic stability, for example increased in vivo half-life or reduced dosage requirements or an improvement in therapeutic index. It is understood that deuterium in this context is regarded as a substituent of a compound of formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The invention also relates to the compounds of any of the embodiments mentioned wherein one or more hydrogen atoms in one or more substituents are replaced with deuterium, e.g. all hydrogens in one or more alkyl substituents are replaced with deuterium (the respective moiety/moieties are then perdeuterated).

In embodiments of the invention, $C_1$-$C_3$-alkyl (or methyl) may be deuterated or perdeuterated, in particular, when the $C_1$-$C_3$-alkyl (or methyl) is present as substituent C in the compounds of the invention and/or when the $C_1$-$C_3$-alkyl (or methyl) is present as a substituent on A and/or B, when A or B is an indazolyl ring.

The invention also relates to crystalline forms of the compounds of formula (I).

The hydrate (Modification HA) crystalline form of Compound X can be obtained from the isopropyl (IPA) solvate, ethanol (EtOH) solvate, methanol solvate, and propylene glycolate solvate of Compound X. The hydrate (Modification HA) crystalline form of Compound X may be characterized by an x-ray powder diffraction pattern (XRPD) comprising at least one, two, three or four peaks having an angle of refraction 2θ values (CuKα λ=1.5418 Å) selected from the group consisting of 8.2°, 11.6°, 12.9° and 18.8°, measured at a temperature of about 25° C. and an x-ray wavelength, λ, of 1.5418 Å. The hydrate (Modification HA) crystalline form may also be characterized by an x-ray powder diffraction pattern (XRPD) comprising at least one, two, three or four or all peaks having an angle of refraction 2θ values (CuKα λ=1.5418 Å) selected from the group consisting of 8.2°, 11.6°, 12.1°, 12.9°, 14.6°, 16.2°, 18.8°, 20.4° and 24.1°, measured at a temperature of about 25° C. and an x-ray wavelength, λ, of 1.5418 Å.

The isopropyl alcohol (IPA) solvate of Compound X may be characterized by an x-ray powder diffraction pattern (XRPD) comprising at least one, two, or three peaks having an angle of refraction 2θ values (CuKα λ=1.5418 Å) selected from the group consisting of 7.5°, 12.5° and 17.6° measured at a temperature of about 25° C. and an x-ray wavelength, λ, of 1.5418 Å. The isopropyl alcohol solvate of Compound X may be characterized by an x-ray powder diffraction pattern (XRPD) comprising at least one, two, three or four or more, or all peaks having an angle of refraction 2θ values (CuKα λ=1.5418 Å) selected from the group consisting of 7.5°, 12.5°, 15.5°, 16.4°, 17.6°, 21.4° and 24.4°, measured at a temperature of about 25° C. and an x-ray wavelength, λ, of 1.5418 Å.

The ethanol (EtOH) solvate of Compound X may be characterized by an x-ray powder diffraction pattern (XRPD) comprising at least one, two, or three or four peaks having an angle of refraction 2θ values (CuKα λ=1.5418 Å) selected from the group consisting of 7.9°, 12.7°, 18.2° and 23.1°, measured at a temperature of about 25° C. and an x-ray wavelength, λ, of 1.5418 Å. The ethanol solvate of Compound X may be characterized by an x-ray powder diffraction pattern (XRPD) comprising at least one, two, three or four or more, or all peaks having an angle of refraction 2θ values (CuKα λ=1.5418 Å) selected from the group consisting of 7.9°, 12.7°, 13.1°, 15.5°, 15.9°, 16.9°, 18.2°, 18.6°, and 23.1°, measured at a temperature of about 25° C. and an x-ray wavelength, λ, of 1.5418 Å.

The propylene glycol solvate of Compound X may be characterized by an x-ray powder diffraction pattern (XRPD) comprising at least one, two, or three or four peaks having an angle of refraction 2θ values (CuKα λ=1.5418 Å) selected from the group consisting of 7.3°, 13.2°, 18.0° and 22.5°, measured at a temperature of about 25° C. and an x-ray wavelength, λ, of 1.5418 Å. The propylene glycol solvate of Compound X may be characterized by an x-ray powder diffraction pattern (XRPD) comprising at least one, two, three or four or more, or all peaks having an angle of refraction 2θ values (CuKα λ=1.5418 Å) selected from the group consisting of 7.3°, 13.2°, 15.6°, 16.2°, 18.0°, 22.5°, 22.8°, 23.2° and 25.1°, measured at a temperature of about 25° C. and an x-ray wavelength, λ, of 1.5418 Å.

As used herein, the term "pharmaceutically acceptable carrier" includes any one or more selected from all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease such as a cancer driven by a KRAS, HRAS or NRAS G12C mutation.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of KRAS, HRAS or NRAS G12C mutant protein.

As used herein, the term "subject" refers to an animal. Typically the animal is a mammal. A subject also refers to, for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric centre in the compounds of the present invention can be present in a racemic mixture or in a mixture of enantiomers or in enantiomerically enriched form. In certain embodiments, for example, as a mixture of enantiomers, each asymmetric centre is present in at least 10% enantiomeric excess, at least 20% enantiomeric excess, at least 30% enantiomeric excess, at least 40% enantiomeric excess, at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. In certain embodiments, for example, in enantiomerically enriched form, each asymmetric centre is present in at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess.

Accordingly, as used herein, a compound of the present invention can be in the form of one of the possible isomers, enantiomers, atropisomers, diastereoisomers, tautomers or mixtures thereof, for example, as substantially pure, diastereoisomers, optical isomers (enantiomers), racemates or mixtures thereof.

Any resulting mixtures of isomers can be separated on the basis of the physicochemical differences of the constituents, into the pure or substantially pure optical isomers, diastereoisomers, atropisomers, racemates, for example, by chromatography and/or fractional crystallization.

Any resulting racemates of final products or intermediates can be resolved into the optical enantiomers by known methods, e.g., by separation of the diastereomeric salts thereof, obtained with an optically active acid or base, and liberating the optically active acidic or basic compound. In particular, a basic moiety may thus be employed to resolve the compounds of the present invention into their optical enantiomers, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Typically, the compounds of formula (I) can be prepared according to the Schemes provided infra. The examples which outline specific synthetic routes, and the generic schemes below provide guidance to the synthetic chemist of ordinary skill in the art, who will readily appreciate that the solvent, concentration, reagent, protecting group, order of synthetic steps, time, temperature, and the like can be modified as necessary.

The schemes provided infra are intended to represent single diastereomers/enantiomers as well as their isomeric mixtures. Separation of diastereomers/enantiomers may be performed according to techniques described herein. If not defined otherwise, in the general schemes described below, the substituents Z, $X_1$, $X_2$, $Ar^1$ and $Ar^2$ are as defined herein. In the general schemes below, $Ar^1$ corresponds to a substituent A, as defined for a compound of formula (I) and $Ar^2$ corresponds to a substituent B, as defined for a compound of formula (I). In particular, the substituents C, $R^2$, $R^3$, $R^4$ and $R^5$ are as defined herein and in particular in the claims. The amine protecting group (also referred to herein as nitrogen-protecting group) is referred to as "PG" in the Schemes below. In the Schemes below, the compound of formula (Iy) is a compound of formula RC(O)—X and the R—C(O) substituent attached to the nitrogen atom of the spiro linker on the compound of formula (Ie) is to be construed accordingly. In the Schemes below, $Ar^1$ corresponds to substituent A of the compound of formula (I), as appropriate, and $Ar^2$ corresponds to substituent B of the compound of formula (I), as appropriate.

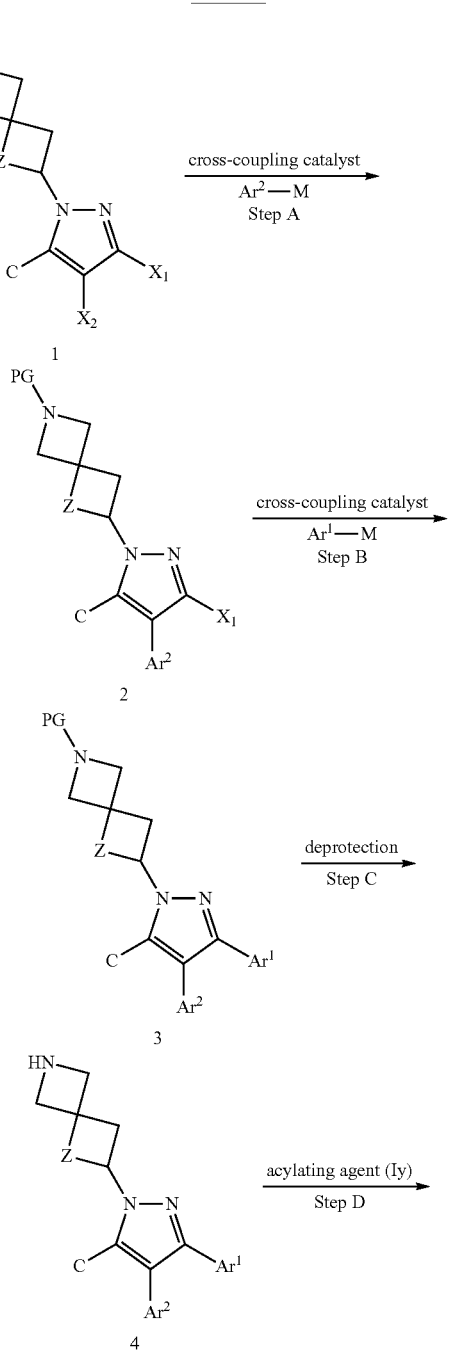

Scheme-1

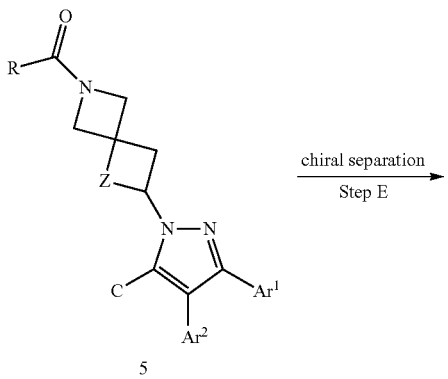

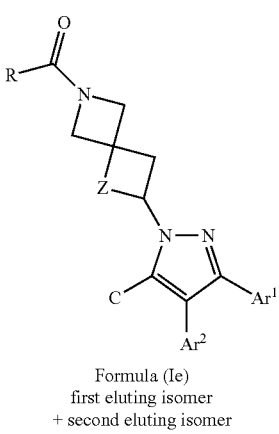

Formula (Ie)
first eluting isomer
+ second eluting isomer

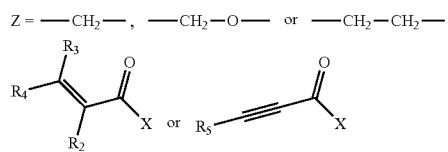

Formula (Iy)

Scheme-1 synthesis: A compound of Formula (Ie) as disclosed herein can be synthesised as outlined in Scheme-1. An appropriate di-halogenated heteroaromatic (1) is reacted with an aryl or heteroaryl ($Ar^2$) coupling partner such as a boronic acid/ester in a Suzuki (or Stille) type cross-coupling reaction in the presence of a palladium catalyst such as RuPhos-Pd-G3/RuPhos in a solvent such as 1,4-dioxane (or toluene) with a base such as $K_3PO_4$ (or $Na_2CO_3$) to provide compound (2). In step B, the substituent $Ar^1$ is introduced with a palladium cross-coupling reaction, using a suitably functionalized aryl or heteroaryl system, for example an aryl boronic acid in the presence of a palladium catalyst such as RuPhos-Pd-G3/RuPhos in a solvent such as toluene with a base such as $K_3PO_4$ to provide compound (3). In step C, the protecting groups (PG) are removed under appropriate conditions depending upon the protecting group used. For example the Boc group of compound (3) is removed using conditions known in the art, with an organic acid such as trifluoroacetic acid in a solvent such as dichloromethane or with a mineral acid such as sulfuric acid in a solvent such as 1,4-dioxane to provide compound (4). $Ar^2$ may also contain a protecting group (for example, THP) which is removed in the same reaction under the aforementioned conditions for cleaving the Boc group. In step D, compound (5) may be made by reaction of compound (4) with a compound of formula (Iy) where X is a leaving group, for example halo (such as chloro) in the presence of a suitable base (such as Hunig's base); or where X is OH and the reaction is carried out under standard amide bond forming conditions (for example in the presence of an amide coupling reagent such as HATU and a suitable base such DIPEA). For example, the acrylamide is introduced by treating compound (4) with acrylic acid in presence of a coupling agent such as propylphosphonic anhydride and a base such as Hunig's base in a solvent such as methylene chloride to provide compound (5). Alternatively compound (4) can be treated with acryloyl chloride in the presence of a base such as aqueous sodium bicarbonate in a solvent such as THF. In step E, the mixture of atropisomers is separated using SFC or HPLC conditions with the appropriate column and eluent.

Compounds (1), (2), (3) and (4) as shown and described above for Scheme-1 are useful intermediates for preparing compounds of Formula (Ie)

Scheme-2

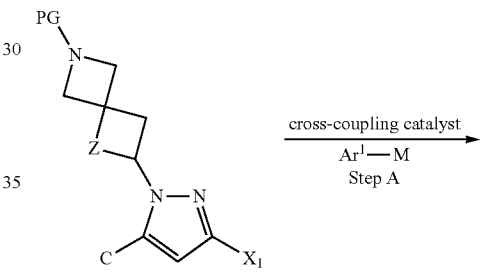

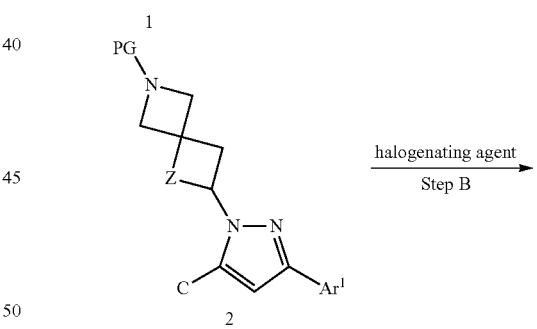

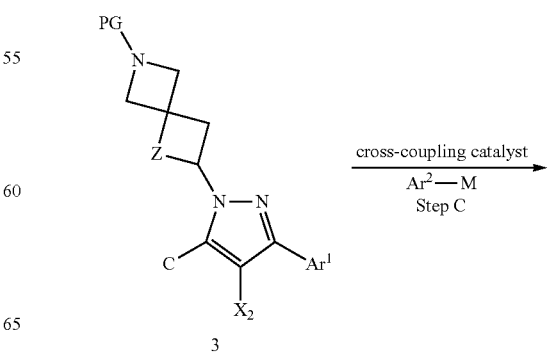

-continued

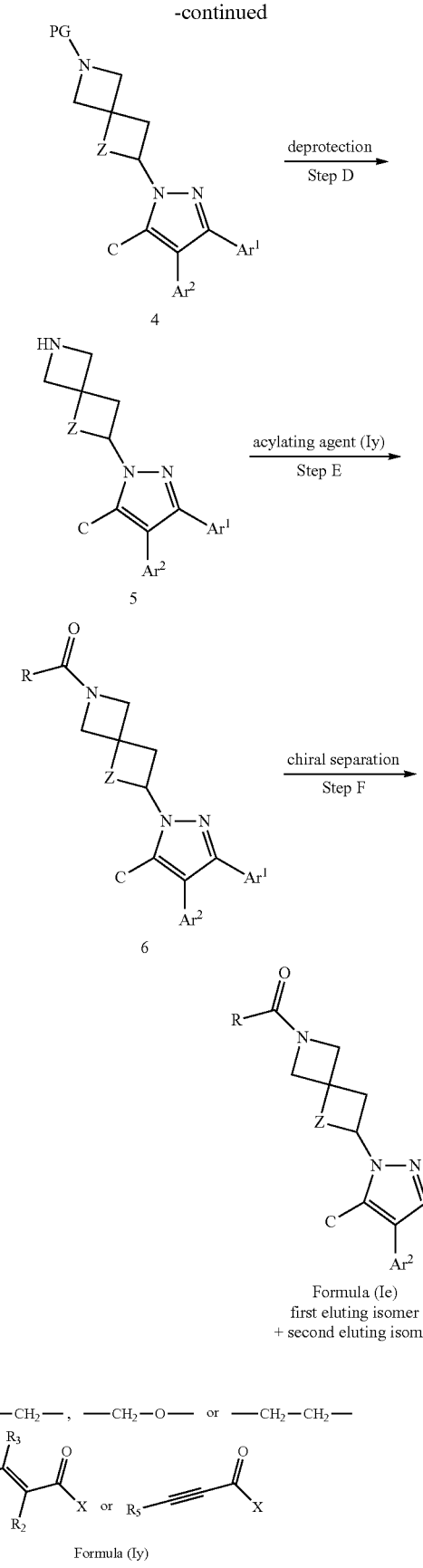

Scheme-2 synthesis: Scheme-2 provides an alternative method for preparation of compounds of Formula (Ie) as disclosed herein. After a cross-coupling reaction such as a Suzuki reaction of a halogenated heteroaromatic (1) with an aryl or heteroaryl coupling partner such as a boronic acid/ester in the presence of a palladium catalyst such as RuPhos-Pd-G3/RuPhos in a solvent such as 1,4-dioxane (or toluene) with a base such as $K_3PO_4$ (or $Na_2CO_3$), compound (2) is treated with an halogenating agent such as N-iodosuccinimide or N-bromosuccinimide in a solvent such as THF or $CH_3CN$. In step C the substituent $Ar^2$ is introduced with a palladium-catalyzed coupling reaction, using a suitably functionalized aryl or heteroaryl system for example an aryl boronic ester in the presence of a palladium catalyst such as RuPhos-Pd-G3/RuPhos in a solvent such as 1,4-dioxane with a base such as $K_3PO_4$ to provide compound (4). The remaining steps D-F are analogous to steps C-E in Scheme-1 described above.

Compounds (1), (2), (3), (4) and (5) as shown and described above for Scheme-2 are useful intermediates for preparing compounds of Formula (Ie)

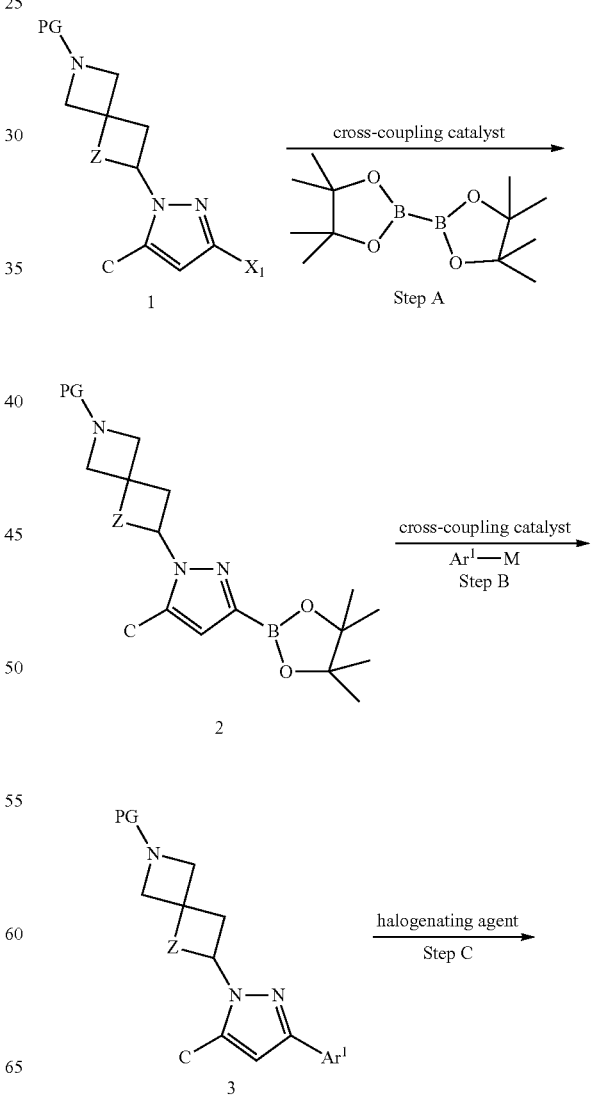

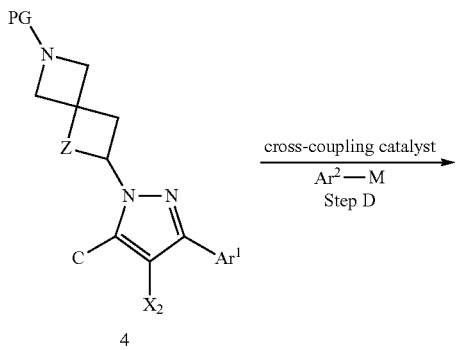
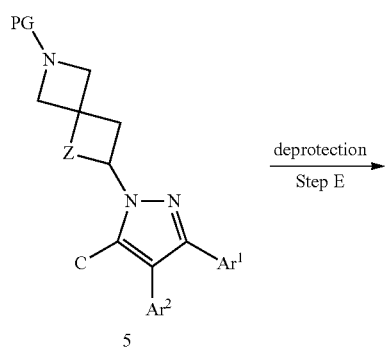
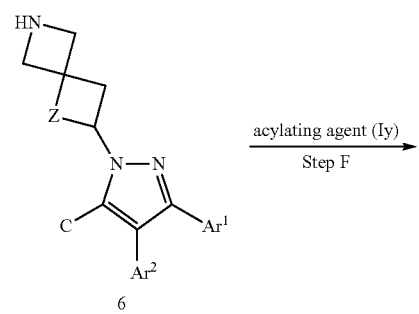
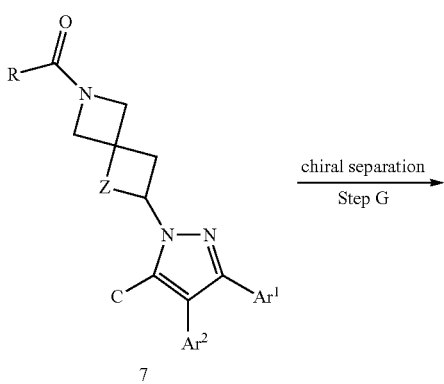
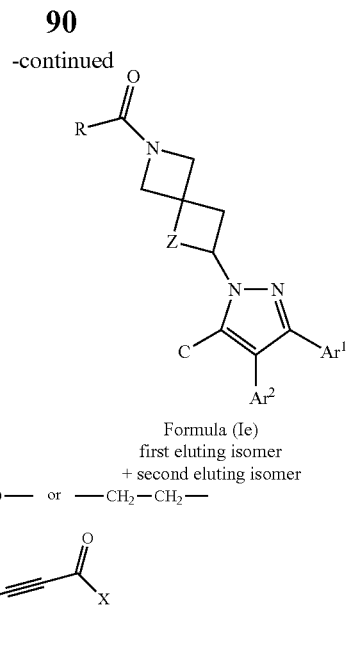

Formula (Ie)
first eluting isomer
+ second eluting isomer $Z = -CH_2-$, $-CH_2-O-$ or $-CH_2-CH_2-$ Formula (Iy)

Scheme-3 synthesis: Scheme-3 provides an alternative method for preparation of compounds of Formula (Ie) as disclosed herein. The halogenated heteroaromatic (1) is converted into heteroaromatic boronic ester (2) with bis-(pinacolato)-diboron in the presence of a palladium catalyst such as $PdCl_2$(dppf).$CF_2Cl_2$ adduct in a solvent such as 1,4-dioxane with a base such as potassium acetate. In step B, the substituent $Ar^1$ is introduced with a palladium coupling reaction, using a suitably functionalized aryl or heteroaryl system for example heteroaryl halide in the presence of a palladium catalyst such as RuPhos-Pd-G3/RuPhos in a solvent such as toluene with a base such as $K_3PO_4$ to provide compound (3). The remaining steps C-G are analogous to steps B-F in Scheme-2 described above.

Compounds (1), (2), (3), (4), (5) and (6) as shown and described above for Scheme-3 are useful intermediates for preparing compounds of Formula (Ie)

Scheme-4

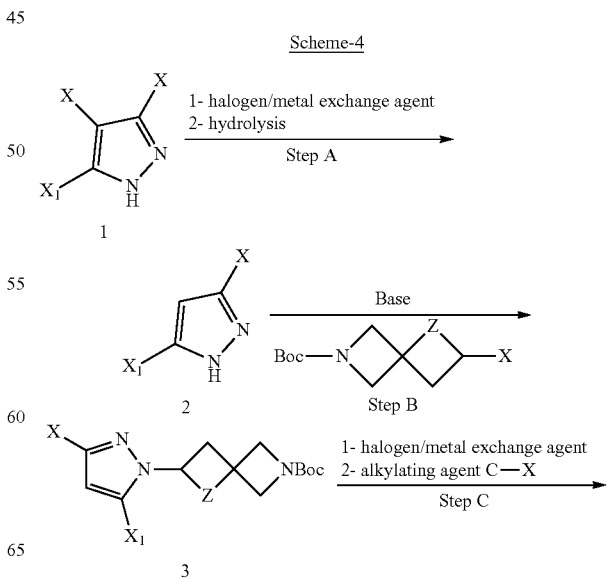

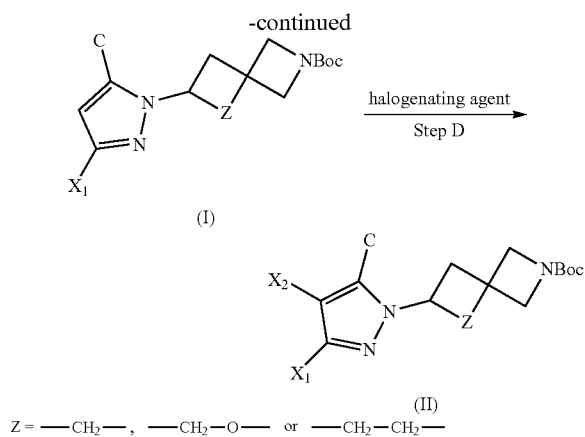

Z = —CH₂—, —CH₂—O— or —CH₂—CH₂—

Scheme-4 synthesis: A halogenated heteroaromatic compound of formula (I) or a di-halogenated heteroaromatic compound of formula (II) can be obtained as outlined in Scheme-4. An appropriate tri-halogenated heteroaromatic (1) such as 3,4,5-dibromo-1H-pyrazole is reacted with a metal-halogen exchange agent, such as an alkyl lithium agent, for example, n-Butyl lithium, in a solvent such as THF, to provide, after hydrolysis with, for example, methanol, compound (2). In step B, a N-protected linker is introduced by reaction with a suitably functionalized N-protected linker for example functionalized with a tosylate in the presence of a base such as cesium carbonate in a solvent such as DMF to provide compound (3). In step C, a halogen/metal exchange is performed using the appropriate reagent such as n-Butyl lithium, in a solvent such as THF to provide, after reaction with the appropriate alkylating agent such as methyl iodide, the halogenated heteroaromatic compound of formula (I). The compound of formula (I) is treated with a halogenating agent such as N-iodosuccinimide in a solvent such as CH₃CN, to provide a di-halogenated heteroaromatic ring of formula (II).

Scheme-5

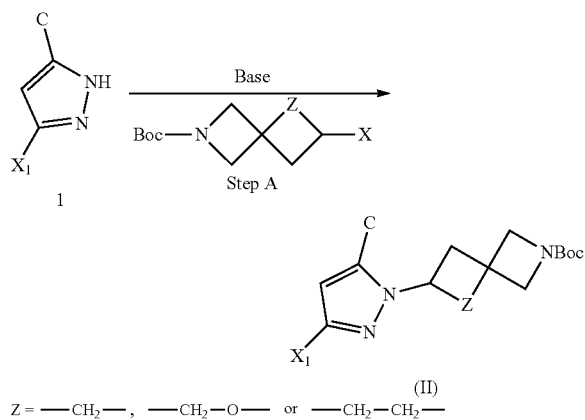

Z = —CH₂—, —CH₂—O— or —CH₂—CH₂—

Scheme-5 synthesis: Scheme-5 provides an alternative method for preparation of a halogenated heteroaromatic compound of formula (I). An appropriate halogenated heteroaromatic (1) such as 3-iodo-5-methyl-1H-pyrazole is alkylated with a suitably functionalized N-protected linker for example functionalized with a tosylate in the presence of a base such as cesium carbonate in a solvent such as DMF to provide the halogenated heteroaromatic compound of formula (I).

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol;

c) binders, e.g., magnesium aluminum silicate, starch paste, gelatin, tragacanth, methylcellulose, sodium carboxymethylcellulose and/or polyvinylpyrrolidone;

d) disintegrants, e.g., starches, agar, alginic acid or its sodium salt, or effervescent mixtures; and e) absorbents, colorants, flavors and sweeteners.

In an embodiment, the pharmaceutical compositions are capsules comprising the active ingredient only.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, for-mulations well-known in the art. Such may contain solubilizers, stabilizers, tonicity enhancing agents, buffers and preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula (I) in free form or in pharmaceutically acceptable salt form, exhibit valuable pharmacological properties, e.g. RAS-mutant inhibiting properties, e.g. as indicated in the in vitro tests as provided in the examples, and are therefore indicated for therapy or for use as research chemicals, e.g. as tool compounds.

Particularly interesting compounds of the invention have good potency in the biological assays described herein, in particular in the covalent competition assay as described herein. In another aspect, they should have a favourable safety profile. In another aspect, they should possess favourable pharmacokinetic properties.

Compounds of the present invention preferably have an IC 50 of less than 0.5 µM, more preferably of less than 0.1 µM.

Having regard to their activity as RAS mutant inhibitors, in particular, KRAS, HRAS or NRAS G12C mutant inhibitors, compounds of the formula (I) in free or pharmaceutically acceptable salt form, are useful in the treatment of conditions which are driven by KRAS, HRAS or NRAS G12C mutations, such as a cancer that is responsive (meaning especially in a therapeutically beneficial way) to inhibition of RAS mutant proteins, in particular, KRAS, HRAS or NRAS G12C mutant proteins, most especially a disease or disorder as mentioned herein below.

Compounds of the invention may be useful in the treatment of cancer. In particular, the compounds of the invention may be useful in the treatment of an indication which is selected from the group consisting of lung cancer (such as lung adenocarcinoma and non-small cell lung cancer), colorectal cancer (including colorectal adenocarcinoma), pancreatic cancer (including pancreatic adenocarcinoma), uterine cancer (including uterine endometrial cancer), rectal cancer (including rectal adenocarcinoma) and a solid tumor.

The compounds of the invention may also be useful in the treatment of solid malignancies characterized by mutations of RAS.

The compounds of the invention may also be useful in the treatment of solid malignancies characterized by one or more mutations of KRAS, in particular G12C mutations in KRAS.

Thus, as a further embodiment, the present invention provides the use of a compound of formula (I) or a pharmaceutically acceptable salt thereof, in therapy. As a further embodiment, the present invention provides a compound of formula (I) or a pharmaceutically acceptable salt thereof for use in therapy. Thus, as a further embodiment, the present invention provides the use of a compound of formula (I) or a pharmaceutically acceptable salt thereof, for the manufacture of a medicament. In a preferred embodiment, the therapy or the therapy which the medicament is useful for is selected from a disease which may be treated by inhibition of RAS mutant proteins, in particular, KRAS, HRAS or NRAS G12C mutant proteins. In another embodiment, the invention provides a method of treating a disease, which is treated by inhibition of a RAS mutant protein, in particular, a G12C mutant of either KRAS, HRAS or NRAS protein, in a subject in need thereof, wherein the method comprises the administration of a therapeutically effective amount of a compound of formula (I) or a pharmaceutically acceptable salt thereof, to the subject.

In a more preferred embodiment, the disease is selected from the afore-mentioned list, suitably non-small cell lung cancer, colorectal cancer and pancreatic cancer.

In a preferred embodiment, the therapy is for a disease, which may be treated by inhibition of a RAS mutant protein, in particular, a G12C mutant of either KRAS, HRAS or NRAS protein. In a more preferred embodiment, the disease is selected from the afore-mentioned list, suitably non-small cell lung cancer, colorectal cancer and pancreatic cancer, which is characterized by a G12C mutation in either KRAS, HRAS or NRAS.

In one embodiment of the present invention, there is provided a compound which is selected from the group consisting of:
a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one,
a(R)—(S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl)prop-2-en-1-one,
a(R)-1-(6-(4-(5-chloro-6-methyl-1H-indazol-4-yl)-5-methyl-3-phenyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(4-(hydroxymethyl)phenyl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-fluoro-4-(2-methoxyethoxy)phenyl)-5-methyl-1H-pyrazol-1-yl)-2-azaspiro[3.3]heptan-2-yl)prop-2-en-1-one, a(R)-1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one and a(R)-1-(6-(4-(3-amino-5-chloro-6-methyl-1H-indazol-4-yl)-5-methyl-3-phenyl-1H-pyrazol-1-yl)-2-azaspiro[3.3]heptan-2-yl)prop-2-en-1-one, or a pharmaceutically acceptable salt thereof for use in the treatment of a cancer or a solid malignancy, optionally characterized by a KRAS, HRAS or NRAS G12C mutation.

In one embodiment of the present invention, there is provided a compound which is selected from the group consisting of:

a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one, a(R)—(S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-5-methyl-3-phenyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one, a(R)1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one and a(R)-1-(6-(4-(3-amino-5-chloro-6-methyl-1H-indazol-4-yl)-5-methyl-3-phenyl-1H-pyrazol-1-yl)-2-azaspiro[3.3]heptan-2-yl)prop-2-en-1-one, or a pharmaceutically acceptable salt thereof, for use in the treatment of a cancer which is selected from lung cancer (such as lung adenocarcinoma and non-small cell lung cancer), colorectal cancer (including colorectal adenocarcinoma), pancreatic cancer (including pancreatic adenocarcinoma), uterine cancer (including uterine endometrial cancer) and rectal cancer (including rectal adenocarcinoma); more suitably, lung cancer, colorectal cancer or pancreatic cancer or a solid tumor.

In one embodiment of the present invention, there is provided a compound which is selected from the group consisting of:

a-(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one, a(R)—(S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl) prop-2-en-1-one, a(R)-1-(6-(4-(5-chloro-6-methyl-1H-indazol-4-yl)-5-methyl-3-phenyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(4-(hydroxymethyl)phenyl)-5-methyl-1H-pyrazol-1-yl)-2-azaspiro[3.3]heptan-2-yl)prop-2-en-1-one, a(R)-1-(6-(4-(5-chloro-6-methyl-1H-indazol-4-yl)-3-(2-fluoro-4-(2-methoxyethoxy)phenyl)-5-methyl-1H-pyrazol-1-yl)-2-azaspiro[3.3]heptan-2-yl)prop-2-en-1-one, a(R)-1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one and a(R)-1-(6-(4-(3-amino-5-chloro-6-methyl-1H-indazol-4-yl)-5-methyl-3-phenyl-1H-pyrazol-1-yl)-2-azaspiro[3.3]heptan-2-yl)prop-2-en-1-one, or a pharmaceutically acceptable salt thereof, for use in the treatment of a cancer which is selected from lung cancer (such as lung adenocarcinoma and non-small cell lung cancer), colorectal cancer (including colorectal adenocarcinoma), pancreatic cancer (including pancreatic adenocarcinoma), uterine cancer (including uterine endometrial cancer) and rectal cancer (including rectal adenocarcinoma); more suitably, lung cancer, colorectal cancer or pancreatic cancer or a solid tumor, wherein the cancer is KRAS G12C-mutant. More suitably, the cancer to be treated by the compound of the invention is KRAS G12C-mutant lung cancer, including KRAS G12C-mutant non-small cell lung cancer.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the present invention. In embodiments of the invention, the other therapeutic agent may be an anti-cancer agent.

In one embodiment, the invention provides a product comprising a compound of the present invention and at least one other therapeutic agent as a combined preparation for simultaneous, separate or sequential use in therapy. In one embodiment, the therapy is the treatment of a disease or condition characterized by a KRAS, HRAS or NRAS G12C mutation. Products provided as a combined preparation include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a compound of the present invention and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Preparation of Compounds

Compounds of the present invention can be prepared as described in the following Examples. The Examples are intended to illustrate the invention and are not to be construed as being limitations thereof.

General Methods and Conditions:

Temperatures are given in degrees Celsius. If not mentioned otherwise, all evaporations are performed under reduced pressure, typically between about 15 mm Hg and 100 mm Hg (=20-133 mbar).

Mass spectra were acquired on LC-MS, SFC-MS, or GC-MS systems using electrospray, chemical and electron impact ionization methods with a range of instruments of the following configurations: Waters Acquity UPLC with Waters SQ detector or Mass spectra were acquired on LCMS systems using ESI method with a range of instruments of the following configurations: Waters Acquity LCMS with PDA detector. $[M+H]^+$ refers to the protonated molecular ion of the chemical species.

NMR spectra were run with Bruker Ultrashield™ 400 (400 MHz), Bruker Ultrashield™ 600 (600 MHz) and Bruker Ascend™ 400 (400 MHz) spectrometers, both with and without tetramethylsilane as an internal standard.

Chemical shifts (δ-values) are reported in ppm downfield from tetramethylsilane, spectra splitting pattern are designated as singlet (s), doublet (d), triplet (t), quartet (q), multiplet, unresolved or more overlapping signals (m), broad signal (br). Solvents are given in parentheses. Only signals of protons that are observed and not overlapping with solvent peaks are reported.

Celite: Celite® (the Celite corporation)=filtering aid based on diatomaceous earth Phase separator: Biotage—Isolute phase separator—(Part number: 120-1908-F for 70 mL and part number: 120-1909-J for 150 mL)

SiliaMetS® Thiol: SiliCYCLE thiol metal scavenger—(R51030B, Particle Size: 40-63 μm).

X-ray powder diffraction (XRPD) patterns described herein were obtained using a Bruker Advance D8 in reflection geometry. Powder samples were analyzed using a zero background Si flat sample holder. The radiation was Cu Kα (λ=1.5418 Å). Patterns were measured between 2° and 40° 2theta.

Sample amount: 5-10 mg
Sample holder: zero background Si flat sample holder
XRPD Parameters:

| | |
|---|---|
| Instrument | Bruker D8 Advance |
| Detector | LYNXEYE (1D mode), open angle: 2.948°, scan mode: continuous scan |
| Radiation | CuKα (0.15418 nm) |
| Monochromator | Nickel filter |
| X-ray generator power | 40 kV, 40 mA |
| Goniometer radius | 280 mm |
| Step size | 0.0164° (2-theta value) |
| Time per step | 0.3 second per step |
| Scan range | 2° to 40° (2-theta value) |
| Scan time | About 768 seconds |
| Slits | Primary: fixed illuminated sample size 10 mm; secondary: open angle 2.2°, axial soller: 2.5° |

Instrumentation

Microwave: All microwave reactions were conducted in a Biotage Initiator, irradiating at 0-400 W from a magnetron at 2.45 GHz with Robot Eight/Robot Sixty processing capacity, unless otherwise stated.

UPLC-MS and MS analytical Methods: Using Waters Acquity UPLC with Waters SQ detector.

UPLC-MS-1: Acquity HSS T3; particle size: 1.8 μm; column size: 2.1×50 mm; eluent A: $H_2O$+0.05% HCOOH+3.75 mM ammonium acetate; eluent B: $CH_3CN$+0.04% HCOOH; gradient: 5 to 98% B in 1.40 min then 98% B for 0.40 min; flow rate: 1 mL/min; column temperature: 60° C.

UPLC-MS-2: Acquity HSS T3; particle size: 1.8 μm; column size: 2.1×100 mm; eluent A: $H_2O$+0.05% HCOOH+3.75 mM ammonium acetate; eluent B: $CH_3CN$+0.04% HCOOH; gradient: 5 to 98% B in 9.4 min then 98% B for 0.40 min; flow rate: 1.0 mL/min; column temperature: 60° C.

UPLC-MS-3: Acquity BEH C18; particle size: 1.7 μm; column size: 2.1×50 mm; eluent A: $H_2O$+4.76% isopropanol+0.05% HCOOH+3.75 mM ammonium acetate; eluent B: isopropanol+0.05% HCOOH; gradient: 1 to 98% B in 1.7 min then 98% B for 0.1 min min; flow rate: 0.6 mL/min; column temperature: 80° C.

UPLC-MS-4: Acquity BEH C18; particle size: 1.7 μm; column size: 2.1×100 mm; eluent A: $H_2O$+4.76% isopropanol+0.05% HCOOH+3.75 mM ammonium acetate; eluent B: isopropanol+0.05% HCOOH; gradient: 1 to 60% B in 8.4 min then 60 to 98% B in 1 min; flow rate: 0.4 mL/min; column temperature: 80° C.

UPLC-MS-5: Ascentis Express C18; particle size: 2.7 μm; column size: 2.1×50 mm; eluent A: $H_2O$+4.76% isopropanol+0.05% HCOOH+3.75 mM ammonium acetate; eluent B: isopropanol+0.05% HCOOH; gradient: 1 to 50% B in 1.4 min, 50 to 98% B in 0.30 min, then 98% for 0.10 min; flow rate: 1 mL/min; column temperature: 80° C.

UPLC-MS-6: Acquity BEH C18; particle size: 1.7 μm; column size: 2.1×50 mm; eluent A: $H_2O$+0.05% HCOOH+3.75 mM ammonium acetate; eluent B: isopropanol+0.05% HCOOH; gradient: 5 to 98% B in 1.7 min then 98% B for 0.1 min; flow rate: 0.6 mL/min; column temperature: 80° C.

UPLC-MS-7: Acquity BEH C18; particle size: 1.7 μm; column size: 2.1×50 mm; eluent A: $H_2O$+0.05% HCOOH+3.75 mM ammonium acetate; eluent B: isopropanol+0.05% HCOOH; gradient: 5 to 98% B in 1.7 min then 98% B for 0.1 min; flow rate: 0.7 mL/min; column temperature: 80° C.

UPLC-MS-8: Acquity HSS T3; particle size: 1.8 μm; column size: 2.1×100 mm; eluent A: $H_2O$+0.05% HCOOH+3.75 mM ammonium acetate; eluent B: $CH_3CN$+0.04% HCOOH; gradient: 5 to 98% B in 9.4 min then 98% B for 0.40 min; flow rate: 0.8 mL/min; column temperature: 60° C.

UPLC-MS-9: CORTECS C18+; particle size: 2.7 μm; column size: 2.1×50 mm; eluent A: $H_2O$+4.76% isopropanol+0.05% HCOOH+3.75 mM ammonium acetate; eluent B: isopropanol+0.05% HCOOH; gradient: 1 to 50% B in 1.4 min, 50 to 98% B in 0.30 min, then 98% for 0.10 min; flow rate: 1 mL/min; column temperature: 80° C.

UPLC-MS-10: Acquity HSS T3; particle size: 1.8 μm; column size: 2.1×50 mm; eluent A: $H_2O$+0.05% HCOOH+3.75 mM ammonium acetate; eluent B: isopropanol+0.05% HCOOH; gradient: 5 to 98% B in 1.7 min then 98% B for 0.10 min; flow rate: 0.6 mL/min; column temperature: 80° C.

UPLC-MS-11: Acquity BEH C18; particle size: 1.7 μm; column size: 2.1×50 mm; eluent A: $H_2O$+0.2% HCOOH; eluent B: $CH_3CN$; gradient: 5 to 98% B in 1.4 min then 98% B for 0.4 min; flow rate: 1.0 mL/min; column temperature: 80° C.

UPLC-MS-12: Acquity BEH C18; particle size: 1.7 μm; column size: 2.1×100 mm; eluent A: $H_2O$+0.05% HCOOH+3.75 mM ammonium acetate; eluent B: isopropanol+0.05% HCOOH; gradient: 5 to 60% B in 8.4 min then 60 to 98% B in 1 min; flow rate: 0.4 mL/min; column temperature: 80° C.

UPLC-MS-13: Acquity HSS T3; particle size: 1.8 μm; column size: 2.1×100 mm; eluent A: $H_2O$+0.05% HCOOH+3.75 mM ammonium acetate; eluent B: isopropanol+0.05% HCOOH; gradient: 5 to 60% B in 8.4 min then 60 to 98% B in 1 min; flow rate: 0.4 mL/min; column temperature: 80° C.

LCMS-1: Acquity BEH C18; particle size: 1.7 μm; column size: 2.1×50 mm; eluent A: $H_2O$+0.10% HCOOH+2.0 mM ammonium acetate; eluent B: $CH_3CN$+0.10% HCOOH; gradient: 98:2 at 0.01 min up to 0.3 min, 50:50 at 0.6 min, 25:75 at 1.1 min, 0:100 at 2.0 min up to 2.70 min at flow rate: 0.60 mL/min, 98:2 at 2.71 min up to 3.0 min at flow rate: 0.55 mL/min; column temperature: RT.

LCMS-2: Acquity BEH C18; particle size: 1.7 μm; column size: 2.1×50 mm; eluent A: $H_2O$+0.10% HCOOH+2.0 mM ammonium acetate; eluent B: $CH_3CN$+0.10% HCOOH; gradient 50:50 at 0.01 min, 10:90 at 1.0 min, 0:100 at 1.5 min up to 4.50 min, 50:50 at 4.6 min up to 5.0 min; flow rate: 0.40 mL/min; column temperature: RT.

LCMS-3: X-Bridge C18; particle size: 3.5 μm; column size: 50×4.6 mm; Eluent A: 5.0 mM ammonium bicarbonate; eluent B: $CH_3CN$; Gradient: 95:5 at 0.01 min, 10:90 at 5.0 min, 5:95 at 5.80 min till 7.20 min, 95:5 at 7.21 min up to 10.0 min at flow rate: 1 mL/min; Column temperature: RT.

LCMS-4: Acquity BEH C18; particle size: 1.7 μm; column size: 2.1×50 mm; eluent A: $H_2O$+0.10% HCOOH+2.0 mM ammonium acetate; eluent B: $CH_3CN$+0.10% HCOOH; gradient 98:2 at 0.01 min up to 0.5 min, 10:90 at 5.0 min, 5:95 at 6.0 min up to 7.0 min, 98:2 at 7.01 min up to 8.0 min; flow rate: 0.45 mL/min; column temperature: RT.

LCMS-5: YMC-Pack ODS-AQ; particle size: 5.0 μm; column size: 4.6×250 mm; Eluent A: 10 mM ammonium acetate+0.10% HCOOH; Eluent B: $CH_3CN$+0.10% HCOOH; gradient 90:10 at 0.01 min, 70:30 at 10 min, 60:40 at 20 min, 0:100 at 30 min up to 33 min, 90:10 at 33.01 min up to 35.0 min; flow rate: 1.0 mL/min; column temperature: RT.

MS-1: MS flow injection; eluent A: $H_2O$+4.76% isopropanol+0.05% HCOOH+3.75 mM ammonium acetate; eluent B: isopropanol+0.04% HCOOH; gradient: isocratic 70% B for 0.8 min; flow rate: 0.4 mL/min.

Preparative Methods:

Normal Phase Chromatography: Normal phase chromatography was run on silica gel using prepacked columns, as detailed below, or using glass columns following standard flash chromatography methodology, unless otherwise stated.

| | |
|---|---|
| System 1 | Teledyne ISCO, CombiFlash Rf |
| System 2 | Biotage Isolera |
| Column | pre-packed RediSep Rf cartridges, or SNAP cartridges |
| Sample adsorbtion | onto Isolute, or on silica gel, or applied as solutions |

Reversed Phase HPLC and SFC:

RP-HPLC-1: Gilson PLC 2020, column: Maisch Reprosil C18 5 μm, 250×30 mm, detection UV 215 & 254 nM, mobile phase: A: water+0.1% TFA, B: acetonitrile; gradient: 30 to 95% B in 25 min.

RP-HPLC-5: Agela-H1000GC500, column: Welch Ultimate XB C18 40 μm, 100×400 mm, detection UV, mobile phase: A: water+0.1% $NH_4HCO_3$, B: acetonitrile; gradient: 60 to 100% B in 50 min.

SFC-1: column: Reprosphere PEI 100 A 5 μm; 250×30 mm; mobile phase; flow rate: 30 mL/min; column temperature: 40° C.; back pressure: 120 bar.

Chiral HPLC/SFC Methods:

C-SFC-1: column: Amylose-C NEO 5 μm; 250×30 mm; mobile phase; flow rate: 80 mL/min; column temperature: 40° C.; back pressure: 120 bar.

C-SFC-2: column: LuxAmylose-1 5 μm; 250×30 mm; mobile phase; flow rate: 80 mL/min; column temperature: 40° C.; back pressure: 120 bar.

C-SFC-3: column: Chiralpak AD-H 5 μm; 100×4.6 mm; mobile phase; flow rate: 3 mL/min; column temperature: 40° C.; back pressure: 1800 psi.

C-SFC-4: column: Chiralpak AD-H 5 μm; 250×30 mm; mobile phase; flow rate: 80 mL/min; column temperature: 40° C.; back pressure: 120 bar.

C-SFC-5: column: Chiralpak IB-N 5 μm; 250×30 mm; mobile phase; flow rate: 80 mL/min; column temperature: 40° C.; back pressure: 120 bar.

C-SFC-6: column: Chiralpak IB-N 5 μm; 100×4.6 mm; mobile phase; flow rate: 3 mL/min; column temperature: 40° C.; back pressure: 1800 psi.

C-SFC-7: column: Chiralpak IG 5 μm; 250×30 mm; mobile phase; flow rate: 80 mL/min; column temperature: 40° C.; back pressure: 120 bar.

C-SFC-8: column: Chiralpak IG 5 µm; 100×4.6 mm; mobile phase; flow rate: 3 mL/min; column temperature: 40° C.; back pressure: 1800 psi.

C-SFC-9: column: Chiralpak AD-YMC 5 µm; 250×30 mm; mobile phase; flow rate: 80 mL/min; column temperature: 40° C.; back pressure: 120 bar.

C-SFC-10: column: Chiralpak IG 5 µm; 250×30 mm; mobile phase; flow rate: 100 mL/min; column temperature: 40° C.; back pressure: 120 bar.

C-SFC-11: column: Lux Cellulose 5 µm; 100×4.6 mm; mobile phase; flow rate: 3 mL/min; column temperature: 20° C.; back pressure: 120 bar.

C-SFC-12: column: Chiralpak OD-H 5 µm; 250×30 mm; mobile phase; flow rate: 80 mL/min; column temperature: 40° C.; back pressure: 110 bar.

C-SFC-13: column: Chiralpak OD-H 5 µm; 100×4.6 mm; mobile phase; flow rate: 3 mL/min; column temperature: 40° C.; back pressure: 120 bar.

C-SFC-14: Waters SFC 200 with UV detector; column: Chiralpak AD-H 5 µm; 250×30 mm; mobile phase; flow rate: 80 mL/min; column temperature: 40° C.; back pressure: 100 bar.

C-SFC-15: Waters SFC investigator with PDA detector; column: Chiralpak AD-H 5 µm; 250×4.6 mm; mobile phase; flow rate: 4 mL/min; column temperature: 40° C.; back pressure: 100 bar.

C-SFC-16: Waters SFC 200 with UV detector; column: Chiralpak IG 5 µm; 250×30 mm; mobile phase; flow rate: 80 mL/min; column temperature: 40° C.; back pressure: 100 bar.

C-SFC-17: Waters SFC 200 with UV detector; column: Chiralpak IG 5 µm; 250×21 mm; mobile phase; flow rate: 80 mL/min; column temperature: 40° C.; back pressure: 100 bar.

C-SFC-18: Waters SFC investigator with PDA detector; column: Chiralpak IG 5 µm; 250×4.6 mm; mobile phase; flow rate: 4 mL/min; column temperature: 40° C.; back pressure: 100 bar.

C-SFC-19: Waters SFC investigator with PDA detector; column: Chiralpak IC 5 µm; 250×4.6 mm; mobile phase; flow rate: 4 mL/min; column temperature: 40° C.; back pressure: 100 bar.

C-SFC-20: column: Lux Cellulose 5 µm; 250×30 mm; mobile phase; flow rate: 80 mL/min; column temperature: 40° C.; back pressure: 120 bar.

C-HPLC-1: column: Chiralpak IC 5 µm; 250×20 mm; mobile phase; flow rate: 10 mL/min; column temperature: RT.

C-HPLC-2: column: ChiralPak ID 5 µm; 250×25 mm; mobile phase; flow rate: 15 mL/min; column temperature: RT.

C-HPLC-3: column: Chiralpak IC 3 µm; 100×4.6 mm; mobile phase; flow rate: 0.42 mL/min; column temperature: RT; back pressure: 1800 psi.

C-HPLC-4: column: Chiralpak IC-3 3 µm; 100×3 mm; mobile phase; flow rate: 0.42 mL/min; column temperature: RT.

C-HPLC-5: column: Chiralpak IA 5 µm; 250×4.6 mm; mobile phase; flow rate: 1 mL/min; column temperature: RT; back pressure: 49 bar.

C-HPLC-6: column: Chiralpak IA 5 µm; 250×30 mm; mobile phase; flow rate: 20 mL/min; column temperature: RT.

C-HPLC-7: column: ChiralPak ID 5 µm; 250×4.6 mm; mobile phase; flow rate: 1 mL/min; column temperature: RT.

C-HPLC-8: column: ChiralPak AD 5 µm; 250×30 mm; mobile phase; flow rate: 20 mL/min; column temperature: RT.

C-HPLC-9: column: ChiralPak AD 3 µm; 100×3.0 mm; mobile phase; flow rate: 0.42 mL/min; column temperature: RT.

C-HPLC-10: column: Chiralpak IG-3; 3 µm; 100×3.0 mm; mobile phase; flow rate: 0.42 mL/min; column temperature: 25° C.

C-HPLC-11: column: Chiralpak IG 5 µm; 250×20 mm; mobile phase; flow rate: 10 mL/min; column temperature: 25° C.

C-HPLC-12: column: Chiralpak IA-5; 5 µm; 250×3.0 mm; mobile phase; flow rate: 1 mL/min; column temperature: 25° C.

C-HPLC-13: column: Chiralpak IG-3; 3 µm; 100×3.0 mm; mobile phase; flow rate: 0.42 mL/min; column temperature: 25° C.

C-HPLC-14: column: Chiralcel OZ; 3 µm; 250×25 mm; mobile phase; flow rate: 15 mL/min; column temperature: 25° C.

C-HPLC-15: column: Chiralcel OZ; 3 µm; 100×3.0 mm; mobile phase; flow rate: 0.42 mL/min; column temperature: 25° C.

C-HPLC-16: column: Chiralcel OZ; 5 µm; 250×4.6 mm; mobile phase; flow rate: 1.0 mL/min; column temperature: 25° C.

C-HPLC-17: column: Chiralpak IG 5 µm; 250×20 mm; mobile phase; flow rate: 12 mL/min; column temperature: 25° C.

C-HPLC-18: column: Lux Amylose-1 5 µm; 250×20 mm; mobile phase; flow rate: 10 mL/min; column temperature: 40° C.; back pressure: 120 bar.

C-HPLC-19: column: ChiralPak AD 5 µm; 250×25 mm; mobile phase; flow rate: 15 mL/min; column temperature: RT.

C-HPLC-20: column: Chiralpak IC 5 µm; 250×4.6 mm; mobile phase; flow rate: 1 mL/min; column temperature: RT.

C-HPLC-21: column: Chiralpak AD-H 5 µm; 250×21 mm; mobile phase; flow rate: 18 mL/min; column temperature: 40° C.

C-HPLC-22: column: Chiralpak AD-H 5 µm; 250×4.6 mm; mobile phase; flow rate: 1 mL/min; column temperature: 25° C.

C-HPLC-23: column: Chiralcel OX-H 5 µm; 250×21 mm; mobile phase; flow rate: 18 mL/min; column temperature: 40° C.

C-HPLC-24: column: Chiralpak OX-H 5 µm; 250×4.6 mm; mobile phase; flow rate: 1 mL/min; column temperature: 25° C.

C-HPLC-25: column: Chiralpak IBN 5 µm; 250×21 mm; mobile phase; flow rate: 18 mL/min; column temperature: 40° C.

C-HPLC-26: column: Chiralpak IBN 5 µm; 250×4.6 mm; mobile phase; flow rate: 1 mL/min; column temperature: 25° C.

C-HPLC-27: column: Chiralpak IC 5 µm; 250×21 mm; mobile phase; flow rate: 18 mL/min; column temperature: 40° C.

C-HPLC-28: column: Chiralpak IG, 5 µm; 250×21 mm; mobile phase; flow rate: 18 mL/min; column temperature: 40° C.

C-HPLC-29: column: ChiralPak IG 5 µm; 250×4.6 mm; mobile phase; flow rate: 1 mL/min; column temperature: 25° C.

C-HPLC-30: column: Chiralpak IC 5 μm; 250×30 mm; mobile phase; flow rate: 20 mL/min; column temperature: RT.

Abbreviations used are those conventional in the art.

Abbreviations

| Abbreviation | Description |
|---|---|
| AcCN, ACN | acetonitrile |
| Ac₂O | acetic anhydride |
| AcOH | acetic acid |
| AIBN | 2,2'-azobis(2-methylpropionitrile) |
| aq. | aqueous |
| Ar | argon |
| B₂Pin₂ | 4,4,4',4',5,5,5',5'-Octamethyl-2,2'-bi(1,3,2-dioxaborolane) |
| BPR | back pressure |
| brine | saturated aqueous sodium chloride |
| n-BuLi | n-butyl lithium |
| conc. | concentrated |
| DAST | N,N-dethyl-1,1,1-trifluoro-λ⁴-sulfanamine |
| DCE | dichloroethane |
| DCM | dichloromethane |
| DEA | diethylamine |
| DHP | 3,4-dihydropyran |
| DIPEA | N,N-diisopropylethylamine, N-ethyl-N-isopropylpropan-2-amine |
| DMA | N,N-dimethylacetamide |
| DMAP | N,N-dimethylpyridin-4-amine |
| DMF | N,N-Dimethylformamide |
| DMSO | dimethylsulfoxide |
| DMSO-d₆ | hexadeuterodimethyl sulfoxide |
| dppf | 1,1'-bis(diphenylphosphanyl) ferrocene |
| ee | enantiomeric excess |
| ESI | electrospray ionization |
| ESI-MS | electrospray ionization mass spectroscopy |
| EtOAc | ethyl acetate |
| GBq | gigabecquerel |
| h | Hour (s) |
| HPLC | high-performance liquid chromatography |
| IPA | 2-propanol |
| KOAc | potassium acetate |
| L/mL/μL | litre/millilitre/microlitre |
| LC-MS or LCMS | liquid chromatography and mass spectroscopy |
| M | molar |
| MeOH | methanol |
| min | minutes |
| MTBE | methyl tert-butyl ether |
| MS | mass spectroscopy |
| MW, mw | microwave |
| m/z | mass to charge ratio |
| N | normality |
| N₂ | nitrogen |
| NaOtBu | Sodium tert-butoxide |
| NBS | N-bromosuccinimide |
| NCS | N-chlorosuccinimide |
| NIS | N-iodosuccinimide |
| NEt₃, Et₃N, TEA | triethylamine |
| PDA | Photodiode array detector |
| NMR | nuclear magnetic resonance |
| Pd(PPh₃)₄ | tetrakis(triphenylphosphane)palladium(0) |
| iPrMgCl | Isopropylmagnesium chloride |
| PTSA | p-toluenesulfonic acid |
| RM | reaction mixture |
| RP | reversed phase |
| Rt | retention time |
| RT | room temperature |
| RuPhos | 2-dicyclohexylphosphino-2',6'-diisopropoxybiphenyl |
| RuPhos-Pd-G3 | (2-dicyclohexylphosphino-2',6'-diisopropoxy-1,1'-biphenyl)[2-(2'-amino-1,1'-biphenyl)]palladium(II) methanesulfonate |
| Sat. | saturated |
| SFC | supercritical fluid chromatography |
| SQ | Single-quadrupole |
| TBAF | Tetrabutylammonium fluoride |
| tBME, TBME, TBMe | tert-butyl methyl ether |
| TBq | terabecquerel |
| t-BuOH | tert-butanol |
| tBuXPhos-Pd-G3 | tBuXPhos-Pd-G3, [(2-Di-tert-butylphosphino-2',4',6'-triisopropyl-1,1'-biphenyl)-2-(2'-amino-1,1'-biphenyl)] palladium(II) methanesulfonate |
| TFA | trifluoroacetic acid |
| THF | tetrahydrofuran |
| TLC | thin-layer chromatography |
| T₃P | propylphosphonic anhydride |
| TsCl | tosyl chloride, 4-Methylbenzene-1-sulfonyl chloride |
| UPLC | ultra-performance liquid chromatography |
| XPhos | 2-dicyclohexylphosphino-2',4',6'-triisopropylbiphenyl |
| XPhos-Pd-G3 | (2-dicyclohexylphosphino-2',4',6'-triisopropyl-1,1'-biphenyl)[2-(2'-amino-1,1'-biphenyl)]palladium(II) methanesulfonate |

All starting materials, building blocks, reagents, acids, bases, dehydrating agents, solvents, and catalysts utilized to prepare the compounds of the present invention are either commercially available or can be produced by organic synthesis methods known to one of ordinary skill in the art. Furthermore, the compounds of the present invention can be produced by organic synthesis methods known to one of ordinary skill in the art as shown in the following examples.

The structures of all final products, intermediates and starting materials are confirmed by standard analytical spectroscopic characteristics, e.g., MS, IR, NMR. The absolute stereochemistry of representative examples of the preferred (most active) atropisomers has been determined by analyses of X-ray crystal structures of complexes in which the respective compounds are bound to the KRASG12C mutant or by analyses of small molecule X-ray crystal structures. In all other cases where X-ray structures are not available, the stereochemistry has been assigned by analogy, assuming that, for each pair, the atropoisomer exhibiting the highest activity in the covalent competition assay has the same configuration as observed by X-ray crystallography for the representative examples mentioned above. The absolute stereochemistry is assigned according to the Cahn-Ingold-Prelog rule, as depicted above for Example 12a (the more active atropisomer), which is representative for other examples, and which has the a(R) configuration.

Preparation of Final Compounds
Method-1: Synthetic Scheme

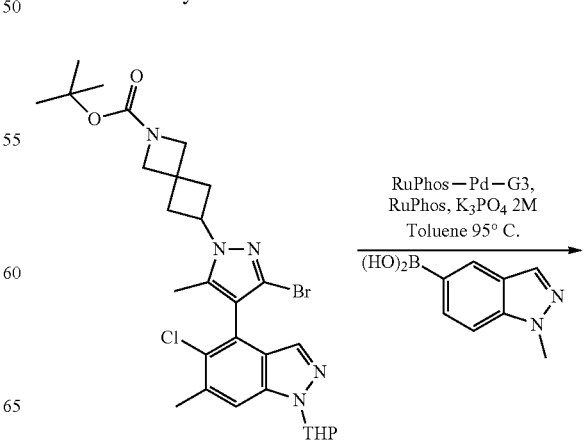

-continued

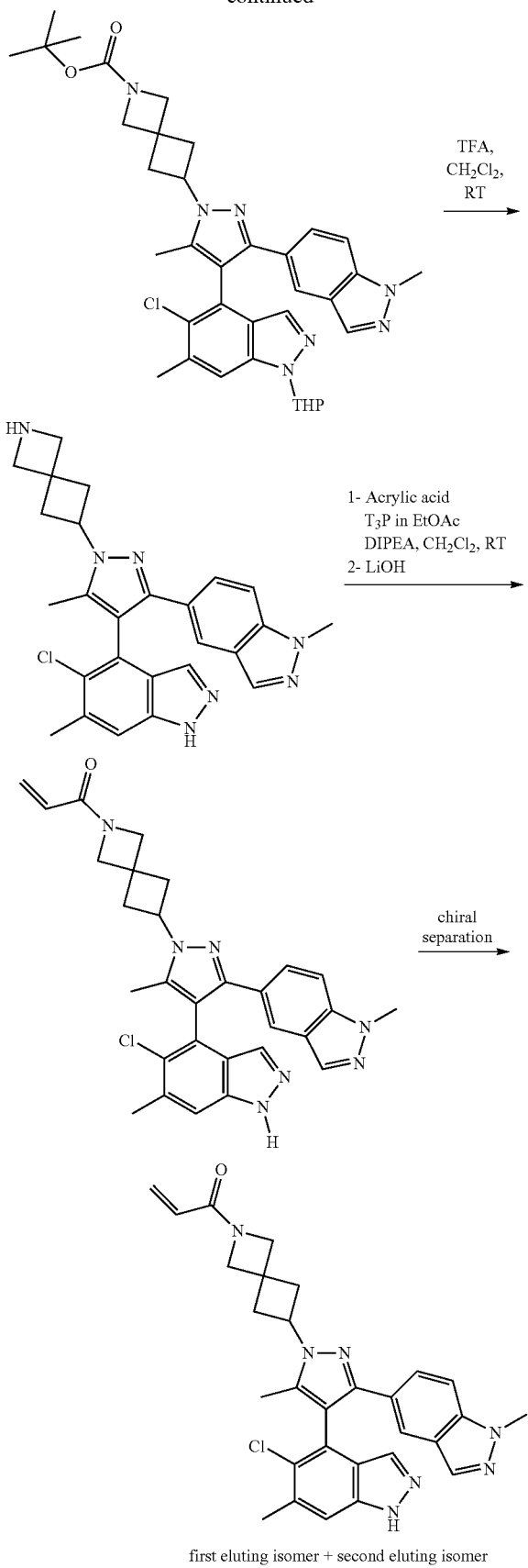

first eluting isomer + second eluting isomer

Example 1a: a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one or 1-{6-[(4M)-4-(5-chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one and Example 1b: a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one or 1-{6-[(4P)-4-(5-chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one Step 1: Tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate In a 500 mL flask, tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 10 g, 16.5 mmol), (1-methyl-1H-indazol-5-yl)boronic acid (6.12 g, 33.1 mmol), RuPhos (1.16 g, 2.48 mmol) and RuPhos-Pd-G3 (1.66 g, 1.98 mmol) were suspended in toluene (165 mL) under argon. $K_3PO_4$ (2M, 24.8 mL, 49.6 mmol) was added and the reaction mixture was placed in a preheated oil bath (95° C.) and stirred for 45 min. The reaction mixture was poured into a sat. aq. $NH_4Cl$ solution and was extracted with EtOAc (×3). The combined organic layers were washed with a sat. aq. $NaHCO_3$ solution, dried (phase separator) and concentrated under reduced pressure. The crude residue was diluted with THF (50 mL), SiliaMetS® Thiol (15.9 mmol) was added and the mixture swirled for 1 h at 40° C. The mixture was filtered, the filtrate was concentrated and the crude residue was purified by normal phase chromatography (eluent: MeOH in $CH_2Cl_2$ from 0 to 2%), the purified fractions were again purified by normal phase chromatography (eluent: MeOH in $CH_2Cl_2$ from 0 to 2%) to give the title compound as a beige foam. UPLC-MS-3: Rt=1.23 min; MS m/z [M+H]⁺; 656.3/658.3.

Step 2: 5-Chloro-6-methyl-4-(5-methyl-3-(1-methyl-1H-indazol-5-yl)-1-(2-azaspiro[3.3]heptan-6-yl)-1H-pyrazol-4-yl)-1H-indazole TFA (19.4 mL, 251 mmol) was added to a solution of tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate (Step 1, 7.17 g, 10.0 mmol) in $CH_2Cl_2$ (33 mL). The reaction mixture was stirred at RT under nitrogen for 1.5 h. The RM was concentrated under reduced pressure to give the title compound as a trifluoroacetate salt, which was used without purification in the next step. UPLC-MS-3: Rt=0.74 min; MS m/z [M+H]⁺; 472.3/474.3.

Step 3: 1-(6-(4-(5-Chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one A mixture of acrylic acid (0.69 mL, 10.1 mmol), propylphosphonic anhydride (50% in EtOAc, 5.94 mL, 7.53 mmol) and DIPEA (21.6 mL, 126 mmol) in $CH_2Cl_2$ (80 mL) was stirred for 20 min at RT and then added (dropping funnel) to an ice-cooled solution of 5-chloro-6-methyl-4-(5-methyl-3-(1-methyl-1H-indazol-5-yl)-1-(2-azaspiro[3.3]heptan-6-yl)-1H-pyrazol-4-yl)-1H-indazole trifluoroacetate (Step 2, 6.30 mmol) in $CH_2Cl_2$ (40 mL). The reaction mixture was stirred at RT under nitrogen for 15 min. The RM was poured into a sat. aq. $NaHCO_3$ solution and extracted with $CH_2Cl_2$ (×3). The combined organic layers were dried (phase separator) and concentrated. The crude residue was diluted with THF (60 mL) and LiOH (2N, 15.7 mL, 31.5 mmol) was added. The mixture was stirred at RT for 30 min until disappearance (UPLC) of the side product resulting from the reaction of the acryloyl chloride with the free NH group of the indazole then was poured into a sat. aq. $NaHCO_3$ solution and extracted with $CH_2Cl_2$ (3×). The combined organic layers were dried (phase separator) and concentrated. The crude residue was purified by normal phase chromatography (eluent: MeOH in $CH_2Cl_2$ from 0 to 5%) to give the title compound. The isomers were separated by chiral SFC (C-SFC-1; mobile phase: $CO_2$/[IPA+0.1% $Et_3N$]: 69/31) to give Example 1a: a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one as the second eluting peak (white powder): $^1$H NMR (600 MHz, DMSO-$d_6$) δ 13.1 (s, 1H), 7.89 (s, 1H), 7.59 (s, 1H), 7.55 (s, 1H), 7.42 (m, 2H), 7.30 (d, 1H), 6.33 (m, 1H), 6.12 (m, 1H), 5.68 (m, 1H), 4.91 (m, 1H), 4.40 (s, 1H), 4.33 (s, 1H), 4.11 (s, 1H), 4.04 (s, 1H), 3.95 (s, 3H), 2.96-2.86 (m, 2H), 2.83-2.78 (m, 2H), 2.49 (s, 3H), 2.04 (s, 3H); UPLC-MS-4: Rt=4.22 min; MS m/z [M+H]$^+$ 526.3/528.3; C-SFC-3 (mobile phase: $CO_2$/[IPA+0.1% $Et_3N$]: 67/33): Rt=2.23 min. Throughout this description, the compound of Example 1a is also referred to as "Compound X".

The other isomer Example 1b; a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one was obtained as the first eluting peak: C-SFC-3 (mobile phase: $CO_2$/[IPA+0.1% $Et_3N$]: 67/33): Rt=1.55 min.

Method-1a: similar to Method-1 except that Step 2 was performed as described below:

To a stirred solution of tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate (Step 1, 1.66 g, 2.10 mmol) in dioxane (40 mL) was added sulfuric acid (3.30 mL, 42.0 mmol) and the mixture was stirred at RT overnight. The mixture was diluted with water, neutralized with a sat. aq. $NaHCO_3$ solution (to pH 8-9), extracted with n-butanol (×2) and the combined organic extracts were washed with water (×2), dried (phase separator) and evaporated. The crude material 5-chloro-6-methyl-4-(5-methyl-3-(1-methyl-1H-indazol-5-yl)-1-(2-azaspiro[3.3]heptan-6-yl)-1H-pyrazol-4-yl)-1H-indazole was dried overnight under high vacuum and used without purification in the next step.

Note: for some of the examples in table 1 and in table 2, $CH_2Cl_2$ can be used for the extraction instead of n-butanol.

Method-1b: similar to Method-1 except that Step 3 was performed as described below:

To an ice-cooled solution of 5-chloro-6-methyl-4-(5-methyl-3-(1-methyl-1H-indazol-5-yl)-1-(2-azaspiro[3.3]heptan-6-yl)-1H-pyrazol-4-yl)-1H-indazole (trifluoroacetate (Step 2) or free base (Step 2 method-1a), 0.25 mmol) in THF (4 mL) was added under Argon $NaHCO_3$ (516 mg, 6.14 mmol), $H_2O$ (0.20 mL) and acryloyl chloride (0.026 mL, 0.32 mmol). The reaction mixture was stirred for 60 min at 0° C. Then, LiOH (2 M in water, 4.91 mL, 9.83 mmol) was added and the mixture was stirred for 1 h at 0° C. until disappearance (UPLC) of the side product resulting from the reaction of the acryloyl chloride with the indazole NH. A sat. aq. $NaHCO_3$ solution was added, the layers were separated and the aqueous layer was extracted with $CH_2Cl_2$ (2×). The combined organic extracts were washed with a sat. aq. $NaHCO_3$ solution, dried ($Na_2SO_4$), filtered and evaporated. The crude residue was purified by normal phase chromatography (eluent: MeOH in $CH_2Cl_2$ from 0 to 9%) to give 1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one.

Method-1c: similar to Method-1 except that in Step 1 XPhos and XPhos-Pd-G2 were used instead of Ruphos and RuPhos-Pd-G3.

Method-1d: similar to Method-1 except that in Step 1 dioxane was used instead of toluene.

Method-1e: similar to Method-1 except that in Step 1 $Na_2CO_3$ (2 M, 3 eq), $Pd(PPh_3)_4$ (0.1 eq) and dioxane were used instead of $K_3PO_4$, RuPhos, RuPhos-Pd-G3 and toluene.

Method-1f: similar to Method-1 except that in Step 1 solid $Na_2CO_3$ (3 eq) was used instead of $K_3PO_4$ and $H_2O$ (10% v/v toluene) was also added.

Method-1j: similar to Method-1 except that Step 3 was performed using $Et_3N$ and acryloyl chloride in $CH_2Cl_2$ similarly as described in Method-9 Step 3.

Method-1k: similar to Method-1 except that Step 3 was performed using $iPr_2NEt$ and acryloyl chloride in $CH_2Cl_2$ as described in Method-9 Step 3.

The following examples 2 to 44 in Table 1 below were prepared using analogous methods to Method 1 from intermediates (in Step 1) described in the intermediates synthesis section or commercially available.

TABLE 1

| Example | Structure | Method, intermediates (in Step 1) and chiral separation conditions used and order of elution | Characterizing data |
|---|---|---|---|
| 2a/2b | 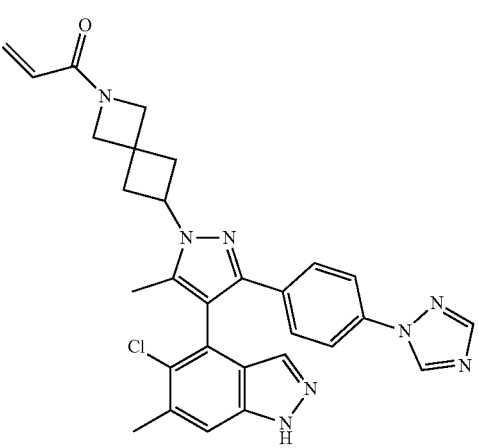<br>1-(6-(3-(4-(1H-1,2,4-triazol-1-yl)phenyl)-4-(5-chloro-6-methyl-1H-indazol-4-yl)-5-methyl-1H-pyrazol-1-yl)-2-azaspiro[3.3]heptan-2-yl)prop-2-en-1-one | Using Method-1b from 1-(4-(4,4,5,5-tetramethyl-1,3,2-dioxaborolan-2-yl)phenyl)-1H-1,2,4-triazole (Step 1) and C-SFC-2 (mobile phase: $CO_2$/IPA 65/35): Example 2a = $2^{nd}$ eluting isomer, Example 2b = $1^{st}$ eluting isomer | Example 2a: $^1$H NMR (600 MHz, DMSO-$d_6$) δ 13.1 (s, 1H), 9.17 (s, 1H), 8.19 (s, 1H), 7.67 (d, 2H), 7.58 (s, 1H), 7.47 (s, 1H), 7.40 (d, 2H), 6.33 (m, 1H), 6.11 (m, 1H), 5.68 (m, 1H), 4.92 (m, 1H), 4.39 (s, 1H), 4.33 (s, 1H), 4.10 (s, 1H), 4.04 (s, 1H), 2.94-2.86 (m, 2H), 2.83-2.78 (m, 2H), 2.50 (s, 3H), 2.03 (s, 3H); UPLC-MS-12: Rt = 4.07 min; MS m/z [M + H]$^+$: 539.2/541.2; C-SFC-3 (mobile phase: $CO_2$/IPA 65/35): Rt = 3.13 min, Example 2b: C-SFC-3 (mobile phase: $CO_2$/IPA 65/35): Rt = 1.68 min. |
| 3a/3b | 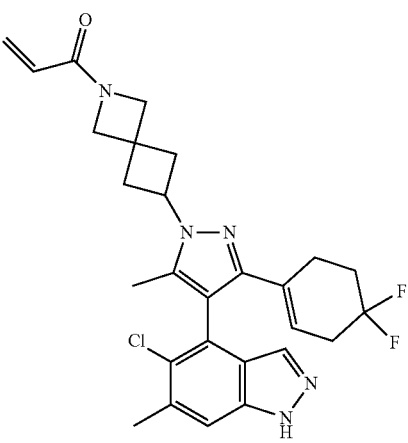<br>1-(6-(4-(5-chloro-6-methyl-1H-indazol-4-yl)-3-(4,4-difluorocyclohex-1-en-1-yl)-5-methyl-1H-pyrazol-1-yl)-2-azaspiro[3.3]heptan-2-yl)prop-2-en-1-one | Using Method-1b,c from [1227068-84-9] (Step 1) and C-HPLC-21 (mobile phase: Hexane/IPA 88/12; flow rate: 18 mL/min; UV: 220 nM): Example 3a = $2^{nd}$ eluting isomer, Example 3b = $1^{st}$ eluting isomer | Example 3a: $^1$H NMR (400 MHz, DMSO-$d_6$) δ 13.14 (s, 1H), 7.53 (s, 1H), 7.50 (s, 1H), 6.36 (m, 1H), 6.14 (m, 1H), 5.70 (m, 1H), 5.23 (m, 1H), 4.87-4.81 (m, 1H), 4.37 (s, 1H), 4.30 (s, 1H), 4.09 (s, 1H), 4.02 (s, 1H), 2.82-2.76 (m, 4H), 2.56 (m, 2H), 2.48 (s, 3H), 2.38-2.25 (m, 2H), 2.09-1.98 (m, 2H), 1.95 (s, 3H); LCMS-2: Rt = 1.69 min; MS m/z [M + H]$^+$: 512.3/514.3; C-HPLC-22 (mobile phase: Hexane/IPA 80/20; UV 220 nM): Rt = 10.7 min, Example 3b: C-HPLC-22 (mobile phase: Hexane/IPA 80/20; UV 220 nM): Rt = 8.94 min. |

TABLE 1-continued

| Example | Structure | Method, intermediates (in Step 1) and chiral separation conditions used and order of elution | Characterizing data |
|---|---|---|---|
| 4a/4b | 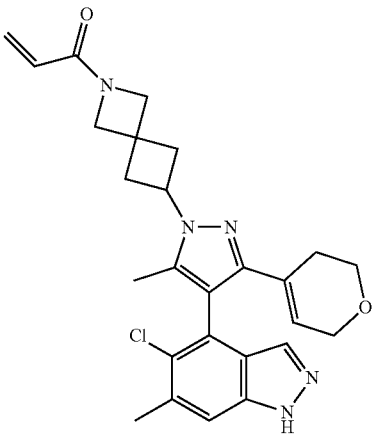<br>1-(6-(4-(5-chloro-6-methyl-1H-indazol-4-yl)-3-(3,6-dihydro-2H-pyran-4-yl)-5-methyl-1H-pyrazol-1-yl)-2-azaspiro[3.3]heptan-2-yl)prop-2-en-1-one | Using Method-1b from [287944-16-5] (Step 1) and C-SFC-14 (mobile phase: $CO_2$/MeOH 80/20; UV: 240 nM): Example 4a = $2^{nd}$ eluting isomer, Example 4b = $1^{st}$ eluting isomer | Example 4a: $^1$H NMR (400 MHz, DMSO-$d_6$) δ 13.15 (s, 1H), 7.53 (s, 1H), 7.52 (s, 1H), 6.36 (m, 1H), 6.14 (m, 1H), 5.70 (m, 1H), 5.33 (m, 1H), 4.86-4.80 (m, 1H), 4.37 (s, 1H), 4.30 (s, 1H), 4.08 (s, 1H), 4.01 (s, 1H), 3.91-3.77 (m, 2H), 3.65 (m, 2H), 2.81-2.76 (m, 4H), 2.52 (s, 3H), 2.34 (m, 2H), 1.95 (s, 3H); LCMS-4: Rt = 4.29 min; MS m/z [M + H]$^+$: 477.2/479.2: C-SFC-15 (mobile phase: $CO_2$/MeOH 65/35; UV: 240 nM): Rt = 3.32 min, Example 4b: C-SFC-15 (mobile phase: $CO_2$/MeOH 65/35; UV: 240 nM): Rt = 2.11 min. |
| 5a/5b | 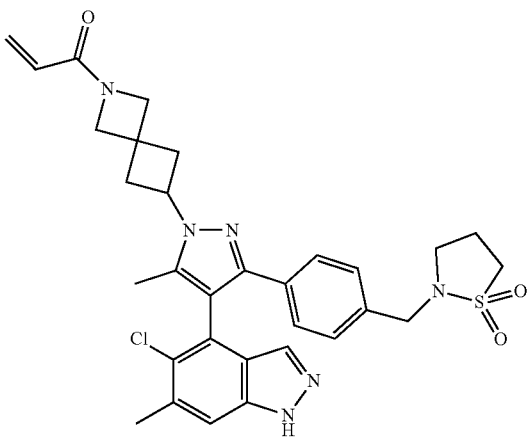<br>1-(6-(4-(5-chloro-6-methyl-1H-indazol-4-yl)-3-(4-((1,1-dioxidoisothiazolidin-2-yl)methyl)phenyl)-5-methyl-1H-pyrazol-1-yl)-2-azaspiro[3.3]heptan-2-yl)prop-2-en-1-one | Using Method-1b from 2-(4-(4,4,5,5-tetramethyl-1,3,2-dioxaborolan-2-yl)benzyl)isothiazolidine 1,1-dioxide (Intermediate B1) (Step 1) and C-SFC-17 (mobile phase: $CO_2$/MeOH 70/30; UV: 257 nM); Example 5a = $2^{nd}$ eluting isomer, Example 5b = $1^{st}$ eluting isomer, | Example 5a: $^1$H NMR (400 MHHz, DMSO-$d_6$) δ 13.14 (s, 1H), 7.55 9s, 1H), 7.42 (s, 1H), 7.25 (m, 2H), 7.13 (m, 2H), 6.32 (m, 1H), 6.13 (m, 1H), 5.67 (m, 1H), 4.91 (m, 1H), 4.39 (s, 1H), 4.32 (s, 1H), 4.09 (s, 1H), 4.03 (s, 1H), 3.97 (s, 2H), 3.22 (t, 2H), 2.97 (t, 2H), 2.9-2.8 (m, 4H), 2.15 (m, 2H), 2.00 (s, 3H); LCMS-2: Rt = 1.52 min; MS m/z [M + H]$^+$: 605.5/607.5; C-SFC-18 (mobile phase: $CO_2$/MeOH 55/45; UV: 257 nM): Rt = 8.08 min, Example 5b: C-SFC-18 (mobile phase: $CO_2$/MeOH 55/45; UV: 257 nM): Rt = 6.32 min. |

TABLE 1-continued

| Example | Structure | Method, intermediates (in Step 1) and chiral separation conditions used and order of elution | Characterizing data |
|---|---|---|---|
| 6a/6b | 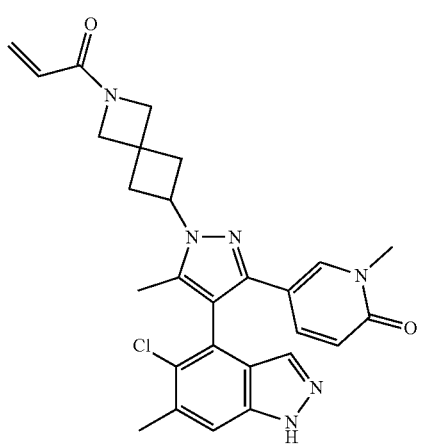<br>5-(1-(2-acryloyl-2-azaspiro[3.3]heptan-6-yl)-4-(5-chloro-6-methyl-1H-indazol-4-yl)-5-methyl-1H-pyrazol-3-yl)-1-methylpyridin-2(1H)-one | Using Method-1b,c from [1002309-52-5] (Step 1) and C-SFC-16 (mobile phase: $CO_2$/MeOH 75/25; UV: 260 nM); Example 6a = $2^{nd}$ eluting isomer, Example 6b = $1^{st}$ eluting isomer | Example 6a: $^1$H NMR (400 MHz, DMSO-$d_6$) δ 13.21 (s, 1H), 7.64 (s, 1H), 7.58 (s, 1H), 7.52 (s, 1H), 7.02 (d, 1H), 6.38 (m, 1H), 6.18-6.10 (m, 2H), 5.71 (m, 1H), 4.92 (m, 1H), 4.40 (s, 1H), 4.32 (s, 1H), 4.11 (s, 1H), 4.03 (s, 1H), 3.32 (s, 3H), 2.86-2.78 (m, 4H), 2.48 (s, 3H), 2.01 (s, 3H); LCMS-2: Rt = 1.44 min; MS m/z [M + H]$^+$: 503.4/505.4; C-SFC-18 (mobile phase: $CO_2$/MeOH 65/35; UV: 260 nM): Rt = 8.63 min, Example 6b: SFC-18 (mobile phase: $CO_2$/MeOH 65/35, UV: 260 nM): Rt = 6.99 min. |
| 7a/7b | 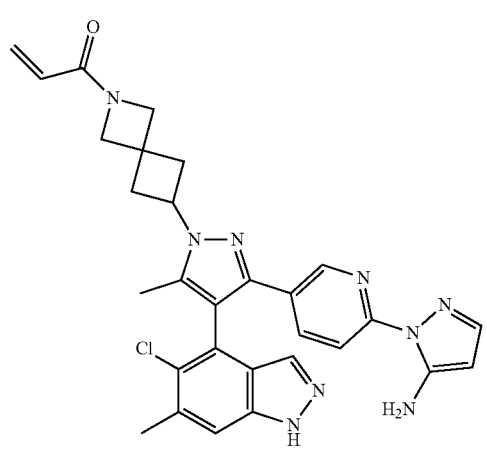<br>1-(6-(3-(6-(5-amino-1H-pyrazol-1-yl)pyridin-3-yl)-4-(5-chloro-6-methyl-1H-indazol-4-yl)-5-methyl-1H-pyrazol-1-yl)-2-azaspiro[3.3]heptan-2-yl)prop-2-en-1-one | Using Method-1b from tert-butyl (1-(5-(4,4,5,5-tetramethyl-1,3,2-dioxaborolan-2-yl)pyridin-2-yl)-1H-pyrazol-5-yl)carbamate (Intermediate B3) (Step 1) and C-HPLC-23 (mobile phase: Hexane/IPA/ACN 60/28/12; flow rate: 18 mL/min; UV: 272 nM): Example 7a = $1^{st}$ eluting isomer, Example 7b = $2^{nd}$ eluting isomer | Example 7a: $^1$H NMR (400 MHz, DMSO-$d_6$) δ 13.19 (s, 1H), 8.01 (s, 1H), 7.82 (m, 1H), 7.72 (m, 1H), 7.58 (s, 1H), 7.50 (s, 1H), 7.30 (s, 1H), 6.62 (s, 2H), 6.36 (m, 1H), 6.13 (m, 1H), 5.69 (m, 1H), 5.34 (s, 1H), 4.94 (m, 1H), 4.39 (s, 1H), 4.32 (s, 1H), 4.11 (s, 1H), 4.03 (s, 1H), 2.88-2.80 (m, 4H), 2.05 (s, 3H); LCMS-2: Rt = 1.57 min; MS m/z [M + H]$^+$: 554.5/556.5; C-HPLC-24 (mobile phase: Hexane/IPA/ACN 70/15/15 gradient; UV: 272 nM): Rt = 9.03 min, Example 7b: HPLC-24 (mobile phase: Hexane/IPA/ACN 70/15/15 gradient; UV: 272 nM): Rt = 11.01 min. |

TABLE 1-continued

| Example | Structure | Method, intermediates (in Step 1) and chiral separation conditions used and order of elution | Characterizing data |
|---|---|---|---|
| 8a/8b | 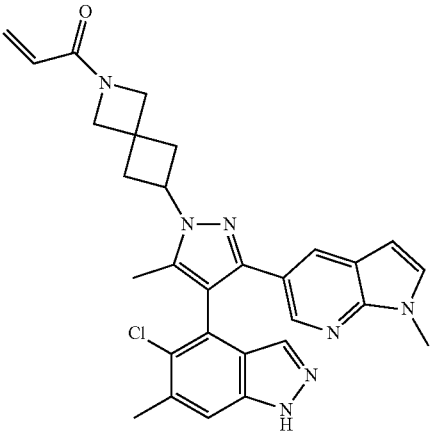<br>1-(6-(4-(5-chloro-6-methyl-1H-indazol-4-yl)-5-methyl-3-(1-methyl-1H-pyrrolo[2,3-b]pyridin-5-yl)-1H-pyrazol-1-yl)-2-azaspiro[3.3]heptan-2-yl)prop-2-en-1-one | Using Method-1b from [1220696-34-3] (Step 1) and C-HPLC-25 (mobile phase: Hexane/IPA/ACN 60/28/12; UV: 248 nM): Example 8a = 1$^{st}$ eluting isomer, Example 8b = 2$^{nd}$ eluting isomer | Example 8a: $^1$H NMR (400 MHz, DMSO-$d_6$) δ 13.12 (s, 1H), 7.97 (s, 1H), 7.89 (s, 1H), 7.55 (s, 1H), 7.43 (m, 2H), 6.36-6.29 (m, 2H), 6.13 (m, 1H), 5.69 (m, 1H), 4.92 (m, 1H), 4.39 (s, 1H), 4.32 (s, 1H), 4.11 (s, 1H), 4.04 (s, 1H), 3.71 (s, 3H), 2.91-2.80 (m, 4H), 2.04 (s, 3H); LCMS-2: Rt = 1.54 min; MS m/z [M + H]$^+$: 526.5/528.5; C-HPLC-26 (mobile phase: Hexane/IPA gradient; UV: 248 nM): Rt = 12.6 min, Example 8b: HPLC-26 (mobile phase: Hexane/IPA gradient; UV: 248 nM): Rt = 13.8 min. |
| 9a/9b | 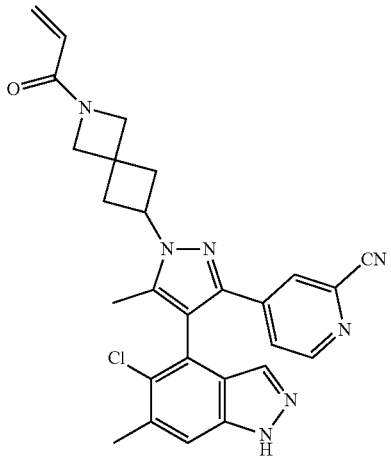<br>4-(1-(2-acryloyl-2-azaspiro[3.3]heptan-6-yl)-4-(5-chloro-6-methyl-1H-indazol-4-yl)-5-methyl-1H-pyrazol-3-yl)picolinonitrile | Using Method-1b from 2-cyanopyridine-4-boronic acid pinacol ester (Step 1) and C-SFC-17 (mobile phase: CO$_2$/MeOH 70/30; UV: 212 nM): Example 9a = 1$^{st}$ eluting isomer, Example 9b = 2$^{nd}$ eluting isomer | Example 9a: $^1$H NMR (400 MHz, DMSO-$d_6$) δ 13.27 (s, 1H), 8.50 (d, 1H), 7.85 (s, 1H), 7.64 (s, 1H), 7.53 (s, 1H), 7.24 (d, 1H), 6.35 (m, 1H), 6.13 (m, 1H), 5.69 (m, 1H), 5.00 (m, 1H), 4.39 (s, 1H), 4.33 (s, 1H), 4.10 (s, 1H), 4.03 (s, 1H), 2.91-2.80 (m, 4H), 2.05 (s, 3H); LCMS-2: Rt = 1.66 min; MS m/z [M + H]$^+$: 498.5/500.5; C-SFC-18 (mobile phase: CO$_2$/MeOH 60/40; UV: 212 nM): Rt = 3.22 min. Example 9b: C-SFC-18 (mobile phase: CO$_2$/MeOH 60/40; UV: 212 nM): Rt = 3.95 min. |

TABLE 1-continued

| Example | Structure | Method, intermediates (in Step 1) and chiral separation conditions used and order of elution | Characterizing data |
|---|---|---|---|
| 10a/10b | 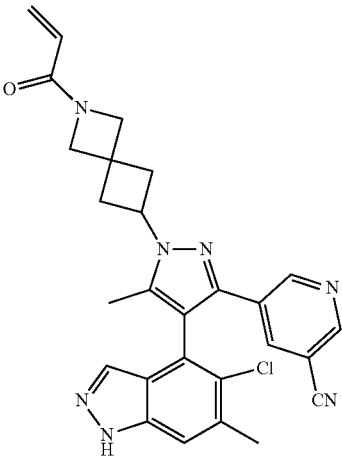<br>5-(1-(2-acryloyl-2-azaspiro[3.3]heptan-6-yl)-4-(5-chloro-6-methyl-1H-indazol-4-yl)-5-methyl-1H-pyrazol-3-yl)nicotinonitrile | Using Method-1b,d from 2-cyanopyridine-5-boronic acid pinacol ester (Step 1) and C-HPLC-27 (mobile phase: Hexane/IPA/MeOH 60/12/28; UV 265 nM): Example 10a = $2^{nd}$ eluting isomer, Example 10b = $1^{st}$ eluting isomer | Example 10a: $^1$H NMR (400 MHz, DMSO-$d_6$) δ 13.27 (s, 1H), 8.82 (m, 1H), 8.41 (s, 1H), 8.14 (s, 1H), 7.62 (s, 1H), 7.53 (s, 1H), 6.32 (m, 1H), 6.13 (m, 1H), 5.69 (m, 1H), 4.95 (m, 1H), 4.39 (s, 1H), 4.32 (s, 1H), 4.10 (s, 1H), 4.03 (s, 1H), 2.88-2.80 (m, 4H), 2.03 (s, 3H); LCMS-2: Rt = 1.57 min; MS m/z [M + H]$^+$: 498.7/500.7; C-SFC-19 (mobile phase: CO$_2$/MeOH 55/45; UV: 260 nM): Rt = 9.79 min, Example 10b: C-SFC-19 (mobile phase: CO$_2$/MeOH 55/45; UV: 260 nM): Rt = 8.37 min. |
| 11a/11b | 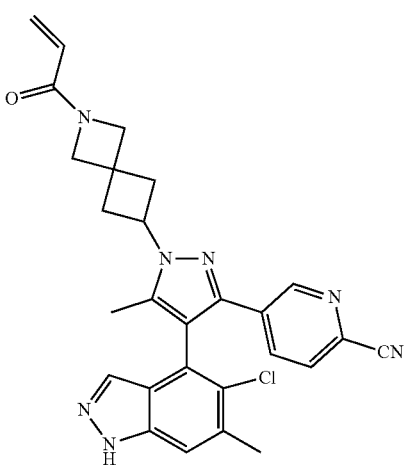<br>5-(1-(2-acryloyl-2-azaspiro[3.3]heptan-6-yl)-4-(5-chloro-6-methyl-1H-indazol-4-yl)-5-methyl-1H-pyrazol-3-yl)picolinonitrile | Using Method-1,b,e from 5-(4,4,5,5-tetramethyl-1,3,2-dioxaborolan-2-yl)picolinonitrile (Step 1) and C-HPLC-27 (mobile phase: Hexane/IPA/MeOH 50/25/25; UV: 298 nM): Example 11a = $2^{nd}$ eluting isomer, Example 11b = $1^{st}$ eluting isomer | Example 11a: $^1$H NMR (400 MHz, DMSO-$d_6$) δ 13.27 (s, 1H), 8.57 (s, 1H), 7.90 (d, 1H), 7.78 (d, 1H), 7.63 (s, 1H), 7.54 (s, 1H), 6.35 (m, 1H), 6.14 (m, 1H), 5.71 (m, 1H), 5.02 (m, 1H), 4.40 (s, 1H), 4.34 (s, 1H), 4.12 (s, 1H), 4.05 (s, 1H), 2.92-2.84 (m, 4H), 2.07 (s, 3H); LCMS-2: Rt = 1.59 min; MS m/z [M + H]$^+$: 498.7/500.7; C-HPLC-20 (mobile phase: Hexane/IPA/MeOH 50/25/25; UV 298 nM): Rt = 17.7 min, Example 11b: C-HPLC-20 (mobile phase: Hexane/IPA/MeOH 50/25/25; UV 296 nM): Rt = 15.6 min. |

TABLE 1-continued

| Example | Structure | Method, intermediates (in Step 1) and chiral separation conditions used and order of elution | Characterizing data |
|---|---|---|---|
| 12a/12b | 1-(6-(4-(5-chloro-6-methyl-1H-indazol-4-yl)-3-(1H-indazol-5-yl)-5-methyl-1H-pyrazol-1-yl)-2-azaspiro[3.3]heptan-2-yl)prop-2-en-1-one | Using Method-1b from 5-(4,4,5,5-tetramethyl-1,3,2-dioxaborolan-2-yl)-1H-indazole (Step 1) and C-HPLC-30 (mobile phase: heptane/CH$_2$Cl$_2$/EtOH 55/30/15 + 0.05% Et$_3$N); Example 12a = 2$^{nd}$ eluting isomer, Example 12b = 1$^{st}$ eluting isomer | Example 12a: $^1$H NMR (600 MHz, DMSO-d$_6$) δ 13.1 (s, 1H), 12.9 (s, 1H), 7.89 (s, 1H), 7.55 (m, 2H), 7.41 (s, 1H), 7.34-7.29 (m, 2H), 6.32 (m, 1H), 6.10 (m, 1H), 5.68 (m, 1H), 4.91 (m, 1H), 4.39 (s, 1H), 4.32 (s, 1H), 4.11 (s, 1H), 4.03 (s, 1H), 2.95-2.86 (m, 2H), 2.82-2.76 (m, 2H), 2.54 (s, 3H), 2.02 (s, 3H); UPLC-MS-4: Rt = 3.98 min; MS m/z [M + H]$^+$: 512.2/514.2; C-HPLC-20 (mobile phase: heptane/CH$_2$Cl$_2$/EtOH 55/30/15 + 0.1% Et$_3$N): Rt = 18.7 min, Example 12b: C-HPLC-20 (mobile phase: heptane/CH$_2$Cl$_2$/EtOH 55/30/15 + 0.1% Et$_3$N): Rt = 14.5 min. |
| 13a/13b | 1-(4-(1-(2-acryloyl-2-azaspiro[3.3]heptan-6-yl)-4-(5-chloro-6-methyl-1H-indazol-4-yl)-5-methyl-1H-pyrazol-3-yl)phenyl)-3-methylimidazolidin-2-one | Using Method-1a,b from 1-methyl-3-(4-(4,4,5,5-tetramethyl-1,3,2-dioxaborolan-2-yl)phenyl)imidazolidin-2-one (Intermediate B4) (Step 1) and C-SFC-2 (mobile phase: CO$_2$/IPA 55/45): Example 13a = 2$^{nd}$ eluting isomer, Example 13b = 1$^{st}$ eluting isomer | Example 13a: $^1$H NMR (600 MHz, DMSO-d$_6$) δ 13.1 (s, 1H), 7.55 (s, 1H), 7.42 (s, 1H), 7.35 (d, 2H), 7.18 (d, 2H), 6.33 (m, 1H), 6.11 (m, 1H), 5.68 (m, 1H), 4.89 (m, 1H), 4.39 (s, 1H), 4.33 (s, 1H), 4.10 (s, 1H), 4.03 (s, 1H), 3.67 (t, 2H), 3.37 (t, 2H), 2.92-2.83 (m, 2H), 2.82-2.77 (m, 2H), 2.72 (s, 3H), 2.52 (s, 3H), 2.00 (s, 3H); UPLC-MS-6: Rt = 0.90 min; MS m/z [M + H]$^+$: 570.2/572.2; C-SFC-3 (mobile phase: CO$_2$/IPA 55/45): Rt = 2.01 min, Example 13b: C-SFC-3 (mobile phase: CO$_2$/IPA 55/45): Rt = 0.98 min. |

TABLE 1-continued

| Example | Structure | Method, intermediates (in Step 1) and chiral separation conditions used and order of elution | Characterizing data |
|---|---|---|---|
| 14 | 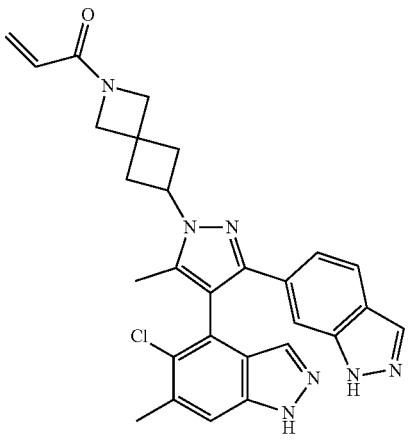<br>1-(6-(4-(5-chloro-6-methyl-1H-indazol-4-yl)-3-(1H-indazol-6-yl)-5-methyl-1H-pyrazol-1-yl)-2-azaspiro[3.3]heptan-2-yl)prop-2-en-1-one | Using Method-1e,j from (1-(tetrahydro-2H-pyran-2-yl)-1H-indazol-6-yl)boronic acid (Intermediate B21) (Step 1) | Example 14a: $^1$H NMR (600 MHz, MeOH-$d_4$) δ 7.93 (s, 1H), 7.59 (m, 1H), 7.53 (s, 1H), 7.45 (m, 1H), 7.38 (m, 1H), 7.29 (m, 1H), 6.39 (m, 1H), 6.28 (m, 1H), 5.77 (m, 1H), 4.99 (m, 1H), 4.51 (s, 1H), 4.46 (s, 1H), 4.27 (s, 1H), 4.24 (s, 1H), 3.12-3.05 (m, 2H), 2.93-2.89 (m, 2H), 2.56 (s, 3H), 2.11 (s, 1.5H), 2.13 (s, 1.5H); UPLC-MS-1: Rt = 0.91 min; MS m/z [M + H]$^+$: 512.3/514.3. |
| 15a/15b | 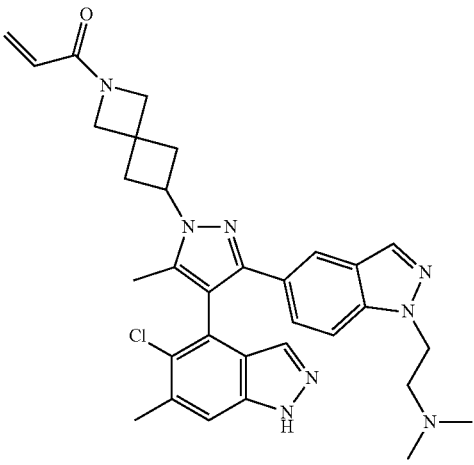<br>1-(6-(4-(5-chloro-6-methyl-1H-indazol-4-yl)-3-(1-(2-(dimethylamino)ethyl)-1H-indazol-5-yl)-5-methyl-1H-pyrazol-1-yl)-2-azaspiro[3.3]heptan-2-yl)prop-2-en-1-one | Using Method-1e,k from N,N-dimethyl-2-(5-(4,4,5,5-tetramethyl-1,3,2-dioxaborolan-2-yl)-1H-indazol-1-yl)ethan-1-amine (Intermediate B5) (Step 1) and C-HPLC-1 (mobile phase: Hepane/CH$_2$Cl$_2$/EtOH/Et$_3$N 60/30/10/0.05): Example 15a = 2$^{nd}$ eluting isomer, Example 15b = 1$^{st}$ eluting isomer | Example 15a: $^1$H NMR (600 MHz, DMSO-$d_6$) δ 13.13 (s, 1H), 7.90 (s, 1H), 7.56 (m, 2H), 7.47 (m, 1H), 7.43 (s, 1H), 7.30 (m, 1H), 6.33 (m, 1H), 6.12 (m, 1H), 5.69 (m, 1H), 4.92 (m, 1H), 4.40 (s, 1H), 4.38 (t, 2H), 4.33 (s, 1H), 4.11 (s, 1H), 4.04 (s, 1H), 2.95-2.87 (m, 2H), 2.82-2.78 (m, 2H), 2.64 (t, 2H), 2.49 (s, 3H), 2.12 (s, 6H), 2.03 (s, 3H); UPLC-MS-1: Rt = 0.77 min; MS m/z [M + H]$^+$: 583.4/585.4; C-HPLC-20 (mobile phase: Hepane/CH$_2$Cl$_2$/EtOH/Et$_3$N 60/30/10/0.05): Rt = 23.8 min, Example 15b: C-HPLC-20 (mobile phase: Hepane/CH$_2$Cl$_2$/EtOH/Et$_3$N 60/30/10/0.05): Rt = 19.2 min. |

| Example | Structure | Method, intermediates (in Step 1) and chiral separation conditions used and order of elution | Characterizing data |
| --- | --- | --- | --- |
| 16a/16b | 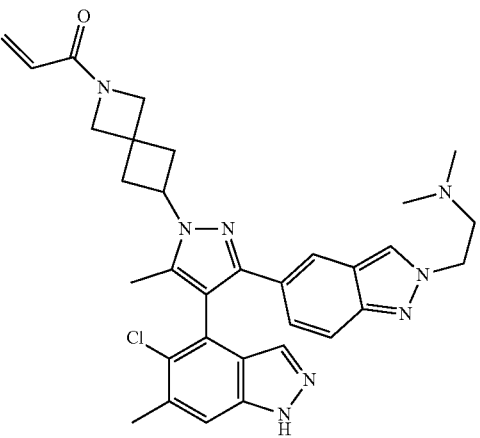<br>1-(6-(4-(5-chloro-6-methyl-1H-indazol-4-yl)-3-(2-(2-(dimethylamino)ethyl)-2H-indazol-5-yl)-5-methyl-1H-pyrazol-1-yl)-2-azaspiro[3.3]heptan-2-yl)prop-2-en-1-one | Using Method-1e,j from N,N-dimethyl-2-(5-(4,4,5,5-tetramethyl-1,3,2-dioxaborolan-2-yl)-2H-indazol-2-yl)ethan-1-amine (Intermediate B6) (Step 1) and C-SFC-7 (mobile phase: CO$_2$/[MeOH + 0.1% Et$_3$N] 55/45): Example 16a = 2$^{nd}$ eluting isomer, Example 16b = 1$^{st}$ eluting isomer | Example 16a: $^1$H NMR (600 MHz, DMSO-d$_6$) δ 13.12 (s, 1H), 8.12 (s, 1H), 7.55 (s, 1H), 7.43 (s, 1H), 7.40-7.39 (m, 2H), 7.30 (m, 1H), 6.33 (m, 1H), 6.12 (m, 1H), 5.69 (m, 1H), 4.90 (m, 1H), 4.40-4.38 (m, 3H), 4.33 (s, 1H), 4.11 (s, 1H), 4.04 (s, 1H), 2.95-2.87 (m, 2H), 2.81-2.77 (m, 2H), 2.72 (t, 2H), 2.49 (s, 3H), 2.13 (s, 6H), 2.02 (s, 3H); UPLC-MS-1: Rt = 0.78 min; MS m/z [M + H]$^+$: 583.5/585.5; C-SFC-8 (mobile phase: CO$_2$/[MeOH + 0.1% Et$_3$N] 55/45): Rt = 3.53 min, Example 16b: C-SFC-8 (mobile phase: CO$_2$/[MeOH + 0.1% Et$_3$N] 55/45): Rt = 2.20 min. |
| 17a/17b | 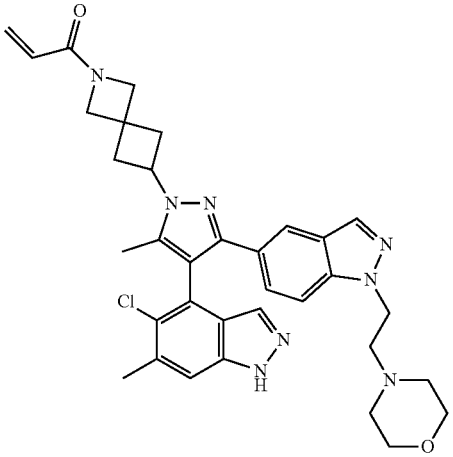<br>1-(6-(4-(5-chloro-6-methyl-1H-indazol-4-yl)-5-methyl-3-(1-(2-morpholinoethyl)-1H-indazol-5-yl)-1H-pyrazol-1-yl)-2-azaspiro[3.3]heptan-2-yl)prop-2-en-1-one | Using Method-1b from 4-(2-(5-(4,4,5,5-tetramethyl-1,3,2-dioxaborolan-2-yl)-1H-indazol-1-yl)ethyl)morpholine (Intermediate B7) (Step 1) and C-SFC-1 (mobile phase: CO$_2$/[EtOH + 0.1% Et$_3$N] 72/28): Example 17a = 2$^{nd}$ eluting isomer, Example 17b = 1$^{st}$ eluting isomer | Example 17a: $^1$H NMR (600 MHz, DMSO-d$_6$) δ 13.12 (s, 1H), 7.91 (s, 1H), 7.59 (d, 1H), 7.55 (s, 1H), 7.46 (dd, 1H), 7.43 (s, 1H), 7.27 (dd, 1H), 6.33 (m, 1H), 6.12 (m, 1H), 5.69 (m, 1H), 4.91 (m, 1H), 4.41 (t, 2H), 4.40 (s, 1H), 4.33 (s, 1H), 4.11 (s, 1H), 4.04 (s, 1H), 3.45-3.42 (m, 4H), 2.95-2.87 (m, 2H), 2.83-2.77 (m, 2H), 2.69 (t, 2H), 2.49 (s, 3H), 2.36 (m, 4H), 2.12 (s, 3H); UPLC-MS-10: Rt = 0.79 min; MS m/z [M + H]$^+$: 625.2/627.2; C-SFC-3 (mobile phase: CO$_2$/[EtOH + 0.1% Et$_3$N] 70/30): Rt = 4.20 min, Example 17b: C-SFC-3 (mobile phase: CO$_2$/[EtOH + 0.1% Et$_3$N] 70/30): Rt = 2.96 min. |

TABLE 1-continued

| Example | Structure | Method, intermediates (in Step 1) and chiral separation conditions used and order of elution | Characterizing data |
| --- | --- | --- | --- |
| 18a/18b | (S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl)prop-2-en-1-one | Using Method-1b from (S)-1-(2-(3-fluoropyrrolidin-1-yl)ethyl)-5-(4,4,5,5-tetramethyl-1,3,2-dioxaborolan-2-yl)-1H-indazole (Intermediate B8) (Step 1) and C-SFC-1 (mobile phase: CO$_2$/[IPA + 0.1% Et$_3$N] 72/28); Example 18a 2$^{nd}$ eluting isomer, Example 18b = 1$^{st}$ eluting isomer | Example 18a: $^1$H NMR (600 MHz, DMSO-d$_6$) δ 13.12 (s, 1H), 7.91 (s, 1H), 7.58 (d, 1H), 7.56 (s, 1H), 7.48 (dd, 1H), 7.43 (s, 1H), 7.30 (dd, 1H), 6.33 (m, 1H), 6.12 (m, 1H), 5.69 (m, 1H), 5.17-5.05 (m, 1H), 4.91 (m, 1H), 4.41 (t, 2H), 4.40 (s, 1H), 4.33 (s, 1H), 4.11 (s, 1H), 4.04 (s, 1H), 2.95-2.72 (m, 8H), 2.61-2.53 (m, 1H), 2.49 (s, 3H), 2.29 (m, 1H), 2.07-1.96 (m, 1H), 2.03 (s, 3H), 1.82-1.72 (m, 1H); UPLC-MS-3: Rt = 0.77 min; MS m/z [M + H]$^+$: 627.4/629.4; C-SFC-3 (mobile phase: CO$_2$/[IPA + 0.1% Et$_3$N] 70/30): Rt = 4.26 min, Example 18b: C-SFC-3 (mobile phase: CO$_2$/[IPA + 0.1% Et$_3$N] 70/30): Rt = 3.41 min. |
| 19a/19b | 1-(6-(4-(5-chloro-1H-indazol-4-yl)-5-methyl-3-(pyridin-3-yl)-1H-pyrazol-1-yl)-2-azaspiro[3.3]heptan-2-yl)prop-2-en-1-one | Using Method-1b,e from 3-pyridine boronic acid pinacol ester and Intermediate C5 (Step 1) and C-SFC-2 (mobile phase: IPA/CO$_2$ 30:70): Example 19a = 1$^{st}$ eluting isomer, Example 19b = 2$^{nd}$ eluting isomer | Example 19a: $^1$H NMR (600 MHz, DMSO-d$_6$) δ 13.35 (s, 1H), 8.35 (s, 2H), 7.53-7.63 (m, 3H), 7.48 (m, 1H), 7.24 (m, 1H), 6.31 (m, 1H), 6.11 (m, 1H), 5.68 (m, 1H), 4.94 (m, 1H), 4.39 (s, 1H), 4.32 (s, 1H), 4.10 (s, 1H), 4.03 (s, 1H), 2.76-2.94 (m, 4H), 2.06 (s, 3H); UPLC-MS-1: Rt = 0.83 min, MS m/z [M + H]$^+$: 459.1/461.1; C-SFC-3 (mobile phase: IPA/CO$_2$ 30:70): Rt = 2.05 min, Example 19b: C-SFC-3 (mobile phase: IPA/CO$_2$ 30:70): Rt = 2.92 min. |

TABLE 1-continued

| Example | Structure | Method, intermediates (in Step 1) and chiral separation conditions used and order of elution | Characterizing data |
|---|---|---|---|
| 20a/20b | 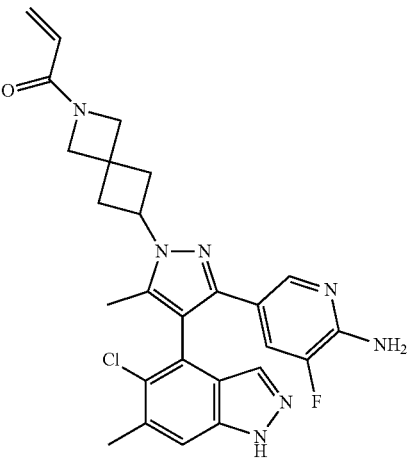<br>1-(6-(3-(6-amino-5-fluoropyridin-3-yl)-4-(5-chloro-6-methyl-1H-indazol-4-yl)-5-methyl-1H-pyrazol-1-yl)-2-azaspiro[3.3]heptan-2-yl)prop-2-en-1-one | Using Method-1b,e from [944401-75-6] (Step 1) and C-SFC-2 (mobile phase: IPA/CO$_2$ 35:65): Example 20a = 1$^{st}$ eluting isomer, Example 20b = 2$^{nd}$ eluting isomer | Example 20a: $^1$H NMR (600 MHz, DMSO-d$_6$) δ 13.35 (s, 1H), 7.56 (s, 1H), 7.46 (s, 1H), 7.41 (s, 1H), 7.20 (m, 1H), 6.32 (m, 1H), 6.18 (s, 2H), 6.10 (m, 1H), 5.68 (m, 1H), 4.87 (m, 1H), 4.38 (s, 1H), 4.31 (s, 1H), 4.09 (s, 1H), 4.02 (s, 1H), 2.81-2.91 (m, 2H), 2.77 (m, 2H), 2.50 (s, 3H), 2.00 (s, 3H); UPLC-MS-1: Rt = 0.87 min, MS m/z [M + H]$^+$: 506.3/508.3; C-SFC-3 (mobile phase: IPA/CO$_2$ 35:65): Rt = 1.46 min, Example 20b: C-SFC-3 (mobile phase: IPA/CO$_2$ 35:65): Rt = 2.07 min. |
| 21a/21b | 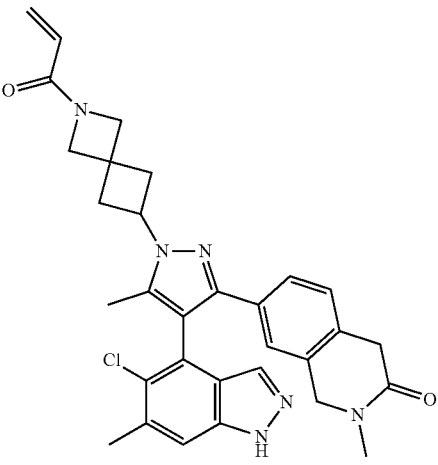<br>7-(1-(2-acryloyl-2-azaspiro[3.3]heptan-6-yl)-4-(5-chloro-6-methyl-1H-indazol-4-yl)-5-methyl-1H-pyrazol-3-yl)-2-methyl-1,4-dihydroisoquinolin-3(2H)-one | Using Method-1b,e from Intermediate B9 (Step 1) and C-SFC-4 (mobile phase: IPA/CO$_2$ 35:65): Example 21a 2$^{nd}$ eluting isomer, Example 21b = 1$^{st}$ eluting isomer | Example 21a: $^1$H NMR (400 MHz, DMSO-d$_6$) δ 13.11 (s, 1H), 7.54 (s, 1H), 7.42 (s, 1H), 7.37 (s, 1H), 6.87 (m, 2H), 6.32 (m, 1H), 6.11 (m, 1H), 5.68 (m, 1H), 4.90 (m, 1H), 4.39 (s, 2.6H), 4.31 (s, 1H), 4.16 (s, 0.4H), 4.10 (s, 1H), 4.02 (s, 1H), 3.40 (s, 2H), 2.91 (s, 3H), 2.73-2.94 (m, 4H), 2.01 (s, 3H); UPLC-MS-7: Rt = 0.81 min, MS m/z [M + H]$^+$: 555.2/557.2; C-SFC-3 (mobile phase: IPA/CO$_2$ 33:67): Rt = 3.16 min, Example 21b: C-SFC-3 (mobile phase: IPA/CO$_2$ 33:67): Rt = 2.24 min. |

TABLE 1-continued

| Example | Structure | Method, intermediates (in Step 1) and chiral separation conditions used and order of elution | Characterizing data |
|---|---|---|---|
| 22a/22b | 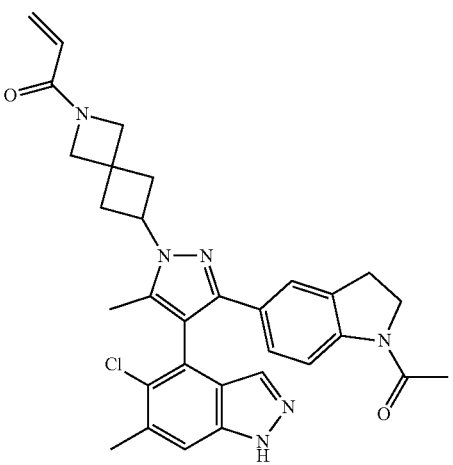<br>1-(6-(3-(1-acetylindolin-5-yl)-4-(5-chloro-6-methyl-1H-indazol-4-yl)-5-methyl-1H-pyrazol-1-yl)-2-azaspiro[3.3]heptan-2-yl)prop-2-en-1-one | Using Method-1e,k from 1-(5-(4,4,5,5-tetramethyl-1,3,2-dioxaborolan-2-yl)indolin-1-yl)ethan-1-one (Step 1) and C-SFC-2 (mobile phase: IPA/$CO_2$ 35:65): Example 22a = $2^{nd}$ eluting isomer, Example 22b = $1^{st}$ eluting isomer | Example 22a: $^1$H NMR (600 MHz, DMSO-$d_6$) δ 13.11 (s, 1H), 7.69 (m, 1H), 7.53 (s, 1H), 7.40 (s, 1H), 7.27 (m, 1H), 6.80 (m, 1H), 6.31 (m, 1H), 6.11 (m, 1H), 5.68 (m, 1H), 4.88 (m, 1H), 4.39 (s, 1H), 4.31 (s, 1H), 4.09 (s, 1H), 3.97-4.05 (m, 3H), 2.95-3.07 (m, 2H), 2.81-2.93 (m, 2H), 2.77 (m, 2H), 2.48 (s, 3H), 2.08 (s, 3H), 2.00 (s, 3H); UPLC-MS-2: Rt = 4.56 min, MS m/z [M + H]$^+$: 555.4/557.4; C-SFC-3 (mobile phase: IPA/$CO_2$ 35:65): Rt = 3.26 min,<br>Example 22b: C-SFC-3 (mobile phase: IPA/$CO_2$ 35:65): Rt = 2.03 min. |
| 23a/23b | 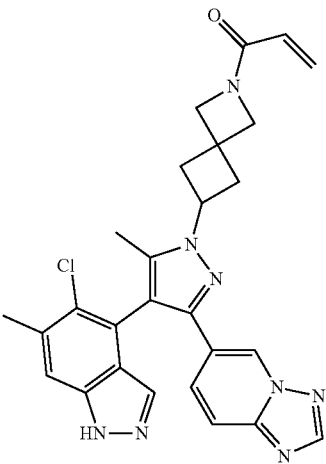<br>1-(6-(3-([1,2,4]triazolo[1,5-a]pyridin-6-yl)-4-(5-chloro-6-methyl-1H-indazol-4-yl)-5-methyl-1H-pyrazol-1-yl)-2-azaspiro[3.3]heptan-2-yl)prop-2-en-1-one | Using Method-1b,f from [1,2,4]triazolo[1,5-a]pyridin-6-ylboronic acid (Step 1) and C-SFC-12 (mobile phase: MeOH/$CO_2$ 30:70): Example 23a = $1^{st}$ eluting isomer, Example 23b = $2^{nd}$ eluting isomer | Example 23a: $^1$H NMR (600 MHz, DMSO-$d_6$) δ 13.19 (s, 1H), 9.19 (s, 1H), 8.43 (s, 1H), 7.58 (m, 2H), 7.52 (s, 1H), 7.08 (m, 1H), 6.33 (m, 1H), 6.11 (m, 1H), 5.68 (m, 1H), 4.95 (m, 1H), 4.40 (s, 1H), 4.31 (s, 1H), 4.11 (s, 1H), 4.02 (s, 1H), 2.76-2.94 (m, 4H), 2.48 (s, 3H), 2.06 (s, 3H); UPLC-MS-2: Rt = 3.82 min, MS m/z [M + H]$^+$: 513.3/515.3; C-SFC-13 (mobile phase: MeOH/$CO_2$ 40:60): Rt = 6.62 min,<br>Example 23b: C-SFC-13 (mobile phase: MeOH/$CO_2$ 40:60): Rt = 7.84 min. |

TABLE 1-continued

| Example | Structure | Method, intermediates (in Step 1) and chiral separation conditions used and order of elution | Characterizing data |
|---|---|---|---|
| 24a/24b | 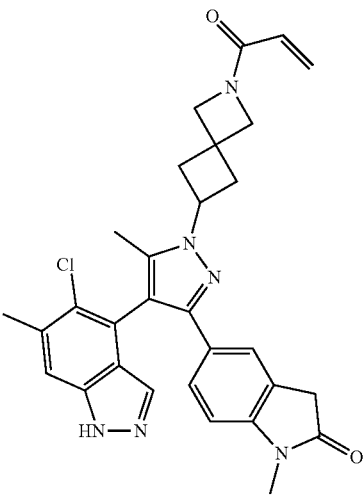<br>5-(1-(2-acryloyl-2-azaspiro[3.3]heptan-6-yl)-4-(5-chloro-6-methyl-1H-indazol-4-yl)-5-methyl-1H-pyrazol-3-yl)-1-methylindolin-2-one | Using Method-1b,f from Intermediate B10 and C-SFC-2 (IPA/CO$_2$ 35:65):<br>Example 24a = 2$^{nd}$ eluting isomer,<br>Example 24b = 1$^{st}$ eluting isomer | Example 24a: $^1$H NMR (600 MHz, DMSO-d$_6$) δ 13.12 (s, 1H), 7.54 (s, 1H), 7.44 (s, 1H), 7.42 (s, 1H), 6.84 (m, 1H), 6.67 (m, 1H), 6.32 (m, 1H), 6.11 (m, 1H), 5.68 (m, 1H), 4.88 (m, 1H), 4.39 (s, 1H), 4.31 (s, 1H), 4.10 (s, 1H), 4.01 (s, 1H), 3.48 (s, 2H), 3.01 (s, 3H), 2.81-2.93 (m, 2H), 2.72-2.81 (m, 2H), 2.48 (s, 3H), 2.00 (s, 3H); UPLC-MS-2: Rt = 4.43 min, MS m/z [M + H]$^+$ 541.4/543.3; C-SFC-3 (mobile phase: IPA/CO$_2$ 35:65): Rt = 2.11 min, Example 24b: C-SFC-3 (mobile phase: IPA/CO$_2$ 35:65): Rt = 1.49 min. |
| 25a/25b | 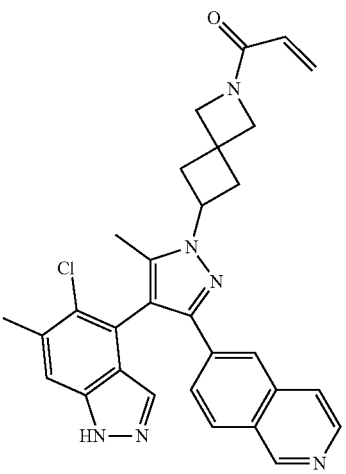<br>1-(6-(4-(5-chloro-6-methyl-1H-indazol-4-yl)-3-(isoquinolin-6-yl)-5-methyl-1H-pyrazol-1-yl)-2-azaspiro[3.3]heptan-2-yl)prop-2-en-1-one | Using Method-1a,b,e from 6-(4,4,5,5-tetramethyl-1,3,2-dioxaborolan-2-yl)isoquinoline [675576-26-8] (Step 1) and C-HPLC-1 (mobile phase: n-heptane/DCM/MeOH/Et$_3$N 50:30:20:0.05):<br>Example 25a = 2$^{nd}$ eluting isomer,<br>Example 25b = 1$^{st}$ eluting isomer | Example 25a: $^1$H NMR (400 MHz, DMSO-d$_6$) δ 13.15 (s, 1H), 9.15 (s, 1H), 8.38 (m, 1H), 7.89 (m, 1H), 7.76 (s, 1H), 7.59 (s, 1H), 7.54 (m, 1H), 7.52 (m, 1H), 7.46 (s, 1H), 6.33 (m, 1H), 6.11 (m, 1H), 5.68 (m, 1H), 4.96 (m, 1H), 4.41 (s, 1H), 4.34 (s, 1H), 4.12 (s, 1H), 4.05 (s, 1H), 2.77-3.00 (m, 4H), 2.07 (s, 3H); UPLC-MS-1: Rt = 0.87 min, MS m/z [M + H]$^+$ : 522.9/524.8; C-HPLC-20 (mobile phase: nheptane/DCM/MeOH/DEA 50:25:25:0.05): Rt = 11.70 min, Example 25b: C-HPLC-20 (mobile phase: nheptane/DCM/MeOH/DEA 50:25:25:0.05): Rt = 10.06 min. |

TABLE 1-continued

| Example | Structure | Method, intermediates (in Step 1) and chiral separation conditions used and order of elution | Characterizing data |
|---|---|---|---|
| 26a/26b | 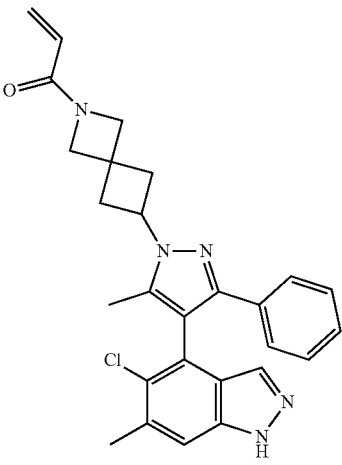<br>1-(6-(4-(5-chloro-6-methyl-1H-indazol-4-yl)-5-methyl-3-phenyl-1H-pyrazol-1-yl)-2-azaspiro[3.3]heptan-2-yl)prop-2-en-1-one | Using Method-1a,b from phenyl-boronic acid (Step 1) and C-SFC-4 (mobile phase: $CO_2$/IPA: 70/30): Example 26a $2^{nd}$ eluting isomer, Example 26b = $1^{st}$ eluting isomer | Example 26a: $^1$H NMR (600 MHz, DMSO-$d_6$) δ 13.13 (s, 1H), 7.55 (s, 1H), 7.43 (s, 1H), 7.28-7.22 (m, 2H), 7.16 (m, 3H), 6.45-6.23 (m, 1H), 6.18-6.08 (m, 1H), 5.75-5.63 (m, 1H), 5.02-4.83 (m, 1H), 4.40 (s, 1H), 4.34 (s, 1H), 4.11 (s, 1H), 4.04 (s, 1H), 2.96-2.73 (m, 4H), 2.02 (s, 3H); UPLC-MS 6: Rt = 1.02 min; MS m/z [M + H]$^+$: 472.2/474.1; C-SFC-3 (mobile phase: $CO_2$/IPA 70/30): Rt = 2.10 min, Example 26b: C-SFC-3 (mobile phase: $CO_2$/IPA 70/30): Rt = 1.64 min. |
| 27a/27b | 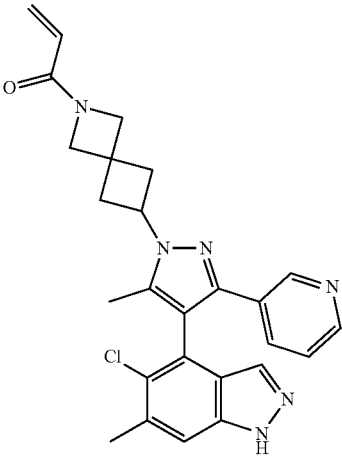<br>1-(6-(4-(5-chloro-6-methyl-1H-indazol-4-yl)-5-methyl-3-(pyridin-3-yl)-1H-pyrazol-1-yl)-2-azaspiro[3.3]heptan-2-yl)prop-2-en-1-one | Using Method-1a,b from (pyridin-3-yl)-boronic acid (Step 1) and C-HPLC-17 (mobile phase: heptane/TBME/[EtOH + 0.05% Et$_3$N]: 60/20/20): Example 27a = $1^{st}$ eluting isomer, Example 27b = $2^{nd}$ eluting isomer | Example 27a: $^1$H NMR (600 MHz, DMSO-$d_6$) δ 13.20 (s, 1H), 8.45-8.20 (m, 2H), 7.65-7.60 (m, 1H), 7.58 (s, 1H), 7.48 (s, 1H), 7.27-7.21 (m, 1H), 6.38-6.24 (m, 1H), 6.16-6.05 (m, 1H), 5.72-5.60 (m, 1H), 5.01-4.85 (m, 1H), 4.39 (s, 1H), 4.33 (s, 1H), 4.10 (s, 1H), 4.04 (s, 1H), 3.00-2.76 (m, 4H), 2.04 (s, 3H); UPLC-MS 1: Rt = 0.89 min; MS m/z [M + H]$^+$: 473.2/475.2; C-HPLC-7 (mobile phase: heptane/DCM/[EtOH + 0.05% Et$_3$N]: 70/20/10): Rt = 21.6 min, Example 27b: C-HPLC-7 (mobile phase: heptane/DCM/[EtOH + 0.05% Et$_3$N] 70/20/10): Rt = 31.6 min. |

TABLE 1-continued

| Example | Structure | Method, intermediates (in Step 1) and chiral separation conditions used and order of elution | Characterizing data |
|---|---|---|---|
| 28a/28b | 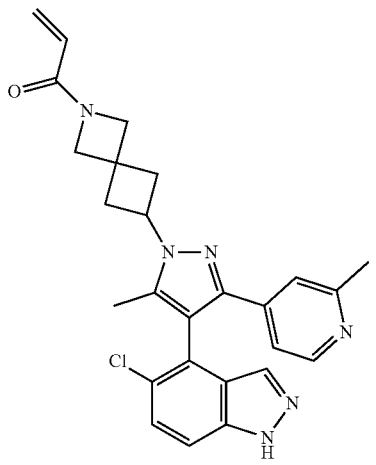<br>1-(6-(4-(5-chloro-1H-indazol-4-yl)-5-methyl-3-(2-methylpyridin-4-yl)-1H-pyrazol-1-yl)-2-azaspiro[3.3]heptan-2-yl)prop-2-en-1-one | Using Method-1a,b from (2-methylpyridin-4-yl)boronic acid and Intermediate C5 (Step 1) and C-HPLC-1 (mobile phase: heptane/EtOH 1:1): Example 28a = $2^{nd}$ eluting isomer, Example 28b = $1^{st}$ eluting isomer | Example 28a: $^1$H NMR (600 MHz, DMSO-$d_6$) δ 13.36 (s, 1H), 8.16 (d, 1H), 7.62 (d, 1H), 7.56 (s, 1H), 7.50 (d, 1H), 7.21 (s, 1H), 6.78 (m, 1H), 6.32 (m, 1H), 6.11 (m, 1H), 5.8 (m, 1H), 4.94 (m, 1H), 4.39 (s, 1H), 4.32 (s, 1H), 4.10 (s, 1H), 4.03 (s, 1H), 2.92-2.77 (m, 4H), 2.31 (s, 3H), 2.04 (s, 3H); UPLC-MS 1: Rt = 0.73 min; MS m/z [M + H]$^+$: 473.5/475.5; C-HPLC-3 (mobile phase: heptane/EtOH 1:1): Rt = 7.53 min, Example 28b: C-HPLC-3 (mobile phase: heptane/EtOH 1:1): Rt = 5.11 min. |
| 29a/29b | 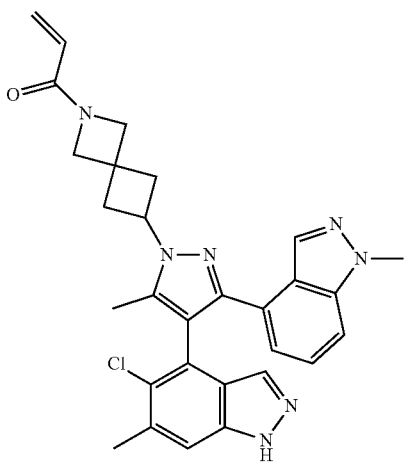<br>1-(6-(4-(5-chloro-6-methyl-1H-indazol-4-yl)-5-methyl-3-(1-methyl-1H-indazol-4-yl)-1H-pyrazol-1-yl)-2-azaspiro[3.3]heptan-2-yl)prop-2-en-1-one | Using Method-1a,b from (1-methyl-1H-indazol-4-yl)boronic acid (Step 1) and C-SFC-2 (mobile phase: CO$_2$/EtOH + 0.25% Et$_3$N] 65/35): Example 29a = $1^{st}$ eluting isomer, Example 29b = $2^{nd}$ eluting isomer | Example 29a: $^1$H NMR (600 MHz, DMSO-$d_6$) δ 13.11 (s, 1H), 8.30 (s, 1H), 7.53 (s, 1H), 7.42 (d, 1H), 7.38 (s, 1H), 7.04 (t, 1H), 6.56 (d, 1H), 6.33 (m, 1H), 6.11 (m, 1H), 5.68 (m, 1H), 4.97 (m, 1H), 4.41 (s, 1H), 4.34 (s, 1H), 4.13 (s, 1H), 4.05 (s, 1H), 4.01 (s, 3H), 2.99-2.81 (m, 4H), 2.48 (s, 3H), 2.07 (s, 3H); UPLC-MS-1: Rt = 1.01 min; MS m/z [M + H]$^+$: 526.2/528.1; C-SFC-3 (mobile phase: CO$_2$/[EtOH + 0.10% Et$_3$N] 68/32): Rt = 2.29 min, Example 29b: C-SFC-3 (mobile phase: CO$_2$/[EtOH + 0.10% Et$_3$N] 68/32): Rt = 2.76 min. |

TABLE 1-continued

| Example | Structure | Method, intermediates (in Step 1) and chiral separation conditions used and order of elution | Characterizing data |
|---|---|---|---|
| 30a/30b | 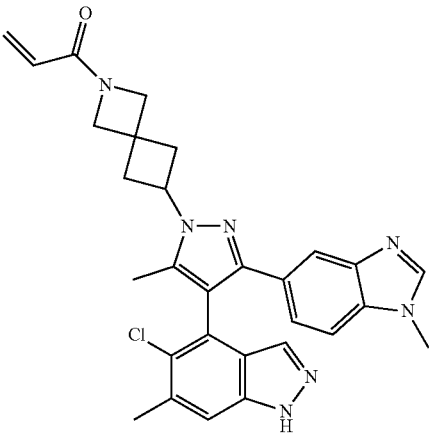<br>1-(6-(4-(5-chloro-6-methyl-1H-indazol-4-yl)-5-methyl-3-(1-methyl-1H-benzo[d]imidazol-5-yl)-1H-pyrazol-1-yl)-2-azaspiro[3.3]heptan-2-yl)prop-2-en-1-one | Using Method-1a,b from (1-methyl-1H-benzo[d]imidazol-5-yl)boronic acid (Step 1) and C-SFC-2 (mobile phase: $CO_2$/IPA 65/35): Example 30a = $2^{nd}$ eluting isomer, Example 30b = $1^{st}$ eluting isomer | Example 30a: $^1$H NMR (600 MHz, DMSO-$d_6$) δ 13.12 (s, 1H), 8.09-8.01 (m, 1H), 7.55 (s, 1H), 7.44-7.28 (m, 4H), 6.40-6.26 (m, 1H), 6.17-6.06 (m, 1H), 5.77-5.57 (m, 1H), 4.97-4.80 (m, 1H), 4.40 (s, 1H), 4.34 (s, 1H), 4.11 (s, 1H), 4.05 (s, 1H), 3.75 (d, 3H), 3.01-2.74 (m, 4H), 2.03 (s, 3H); UPLC-MS-4; Rt = 3.73 min; MS m/z [M + H]$^+$: 526.3/528.3; C-SFC-3 (mobile phase: $CO_2$/IPA 65/35): Rt = 2.48 min, Example 30b: C-SFC-3; (mobile phase: $CO_2$/IPA 65/35): Rt = 1.58 min. |
| 31a/31b | 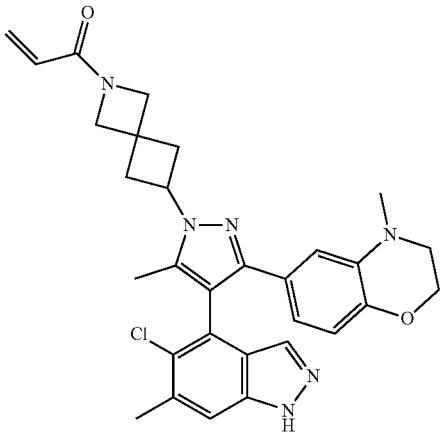<br>1-(6-(4-(5-chloro-6-methyl-1H-indazol-4-yl)-5-methyl-3-(4-methyl-3,4-dihydro-2H-benzo[b][1,4]oxazin-6-yl)-1H-pyrazol-1-yl)-1H-pyrazol-1-yl)-2-azaspiro[3.3]heptan-2-yl)prop-2-en-1-one | Using Method-1a,b from 4-methyl-6-(4,4,5,5-tetramethyl-1,3,2-dioxaborolan-2-yl)-3,4-dihydro-2H-benzo[b][1,4]oxazine (Intermediate B11) (Step 1) and C-SFC-2 (mobile phase: $CO_2$/IPA 65/35): Example 31a = $2^{nd}$ eluting isomer, Example 31b = $1^{st}$ eluting isomer | Example 31a: $^1$H NMR (600 MHz, DMSO-$d_6$) δ 13.13 (s, 1H), 7.55 (s, 1H), 7.43 (s, 1H), 6.68 (m, 1H), 6.52-6.42 (m, 2H), 6.32 (m, 1H), 6.11 (m, 1H), 5.68 (m, 1H), 4.86 (m, 1H), 4.38 (s, 1H), 4.33 (s, 1H), 4.16-4.11 (m, 2H), 4.09 (s, 1H), 4.04 (s, 1H), 3.14-3.02 (m, 2H), 2.92-2.73 (m, 4H), 2.49 (s, 3H), 2.30 (s, 1.5H), 2.29 (s, 1.5H), 1.99 (s, 3H); UPLC-MS-4; Rt = 5.00 min; MS m/z [M + H]$^+$: 543.3/545.3; C-SFC-3 mobile phase: $CO_2$/IPA 65/35): Rt = 2.03 min, Example 31b: C-SFC-3 (mobile phase: $CO_2$/IPA 65/35): Rt = 1.46 min. |

TABLE 1-continued

| Example | Structure | Method, intermediates (in Step 1) and chiral separation conditions used and order of elution | Characterizing data |
|---|---|---|---|
| 32a/32b | 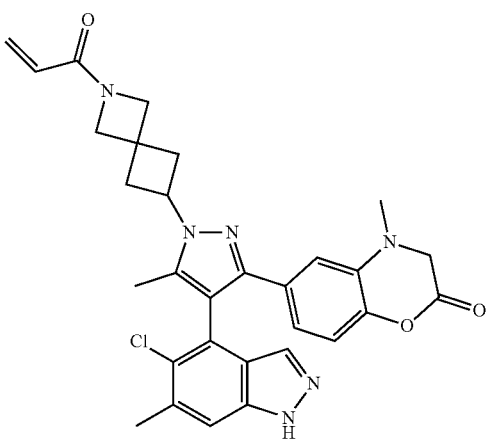<br>6-(1-(2-acryloyl-2-azaspiro[3.3]heptan-6-yl)-4-(5-chloro-6-methyl-1H-indazol-4-yl)-5-methyl-1H-pyrazol-3-yl)-4-methyl-3,4-dihydro-2H-benzo[b][1,4]oxazin-2-one | Using Method-1a,b from 4-methyl-6-(4,4,5,5-tetramethyl-1,3,2-dioxaborolan-2-yl)-3,4-dihydro-2H-benzo[b][1,4]oxazin-2-one (Intermediate B12) (Step 1) and C-SFC-4 (mobile phase: $CO_2$/IPA 72/28): Example 32a = $2^{nd}$ eluting isomer, Example 32b = $1^{st}$ eluting isomer | Example 32a: $^1$H NMR (600 MHz, DMSO-d$_6$) δ 13.21 (s, 1H), 7.58 (s, 1H), 7.48 (s, 1H), 7.01-6.94 (m, 1H), 6.94-6.90 (m, 1H), 6.82-6.77 (m, 1H), 6.33 (m, 1H), 6.11 (m, 1H), 5.69 (m, 1H), 4.91 (m, 1H), 4.58 (s, 2H), 4.39 (s, 1H), 4.34 (s, 1H), 4.10 (s, 1H), 4.05 (s, 1H), 3.08-3.00 (m, 1H), 2.93-2.72 (m, 6H), 2.02 (s, 3H); UPLC-MS-1; Rt = 0.96 min; MS m/z [M + H]$^+$: 557.3/559.3; C-SFC-3; (mobile phase: $CO_2$/[IPA + 0.1% Et$_3$N] 70/30): Rt = 2.56 min, Example 32b: C-SFC-3; (mobile phase: $CO_2$/[IPA + 0.1% Et$_3$N] 70/30): Rt = 2.01 min. |
| 33a/33b | 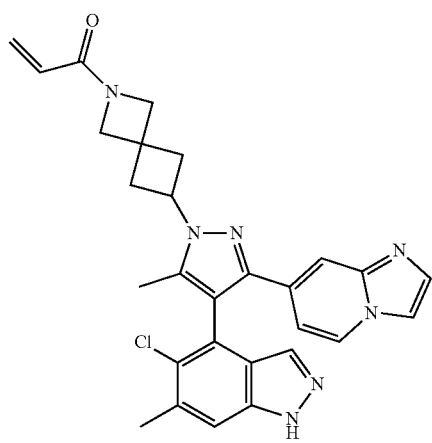<br>1-(6-(4-(5-chloro-6-methyl-1H-indazol-4-yl)-3-(imidazo[1,2-a]pyridin-7-yl)-5-methyl-1H-pyrazol-1-yl)-2-azaspiro[3.3]heptan-2-yl)prop-2-en-1-one | Using Method-1k from 7-(4,4,5,5-tetramethyl-1,3,2-dioxaborolan-2-yl)imidazo[1,2-a]pyridine (Step 1) and C-HPLC-1 (mobile phase: heptane/DCM/[MeOH + 0.05% Et$_3$N] 60/20/20): Example 33a = $2^{nd}$ eluting isomer, Example 33b = $1^{st}$ eluting isomer | Example 33a: $^1$H NMR (600 MHz, DMSO-d$_6$) 13.23 (s, 1H), 8.41 (m, 1H), 7.83 (s, 1H), 7.63 (s, 1H), 7.52 (s, 1H), 7.42 (s, 1H), 7.15 (m, 1H), 6.94 (s, 1H), 6.33 (m, 1H), 6.12 (m, 1H), 5.69 (m, 1H), 4.92 (m, 1H), 4.40 (s, 1H), 4.34 (s, 1H), 4.11 (s, 1H), 4.05 (s, 1H), 2.95-2.80 (m, 4H), 2.03 (s, 3H); UPLC-MS-8; Rt = 3.44 min; MS m/z [M + H]$^+$: 512.3/514.3; C-HPLC-3 (mobile phase: heptane/DCM/[MeOH + 0.05% DEA] 60/20/20): Rt = 17.67 min, Example 33b: C-HPLC-3 (mobile phase: heptane/DCM/[MeOH + 0.05% DEA] 60/20/20): Rt = 16.43 min. |

TABLE 1-continued

| Example | Structure | Method, intermediates (in Step 1) and chiral separation conditions used and order of elution | Characterizing data |
|---|---|---|---|
| 34a/34b | 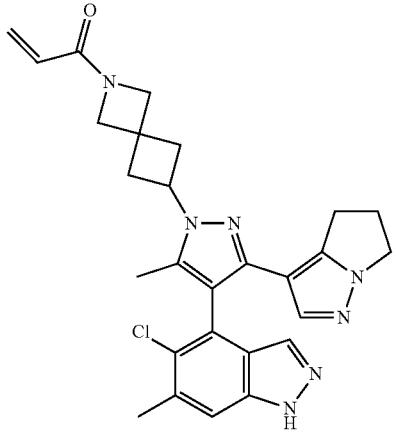<br>1-(6-(4-(5-chloro-6-methyl-1H-indazol-4-yl)-3-(5,6-dihydro-4H-pyrrolo[1,2-b]pyrazol-3-yl)-5-methyl-1H-pyrazol-1-yl)-2-azaspiro[3.3]heptan-2-yl)prop-2-en-1-one | Using Method-1a,b from 3-(4,4,5,5-tetramethyl-1,3,2-dioxaborolan-2-yl)-5,6-dihydro-4H-pyrrolo[1,2-b]pyrazole (Step 1) and C-SFC-4 (mobile phase: $CO_2$/IPA 65/35): Example 34a = $2^{nd}$ eluting isomer, Example 34b = $1^{st}$ eluting isomer | Example 34a: $^1$H NMR (600 MHz, DMSO-$d_6$) 13.15 (s, 1H), 7.57 (s, 1H), 7.43 (s, 1H), 6.84 (s, 1H), 6.32 (m, 1H), 6.11 (m, 1H), 5.68 (m, 1H), 4.84 (m, 1H), 4.37 (s, 1H), 4.32 (s, 1H), 4.08 (s, 1H), 4.03 (s, 1H), 3.96-3.87 (m, 2H), 2.87-2.74 (m, 4H), 2.37-2.26 (m, 2H), 2.00 (s, 3H); UPLC-MS-1; Rt = 0.90 min; MS m/z [M + H]$^+$: 502.2/504.2; C-SFC-3 (mobile phase: $CO_2$/IPA 65/35): Rt = 2.58 min, Example 34B: C-SFC-3 (mobile phase: $CO_2$/IPA 65/35): Rt = 1.56 min. |
| 35a/35b | 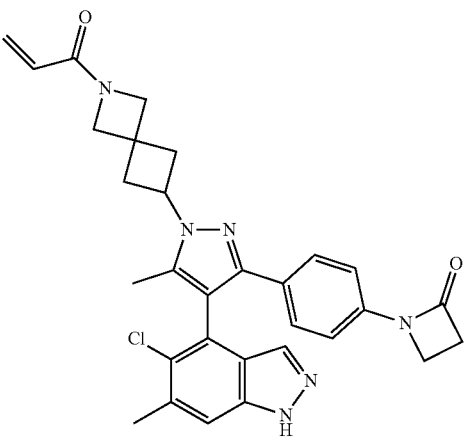<br>1-(4-(1-(2-acryloyl-2-azaspiro[3.3]heptan-6-yl)-4-(5-chloro-6-methyl-1H-indazol-4-yl)-5-methyl-1H-pyrazol-3-yl)phenyl)azetidin-2-one | Using Method-1a,b from 1-(4-(4,4,5,5-tetramethyl-1,3,2-dioxaborolan-2-yl)phenyl)azetidin-2-one (Intermediate B13) (Step 1) and C-SFC-1 (mobile phase: $CO_2$/IPA 65/35): Example 35a = $2^{nd}$ eluting isomer, Example 35b = $1^{st}$ eluting isomer | Example 35a: $^1$H NMR (600 MHz, DMSO-$d_6$) 13.13 (s, 1H), 7.55 (s, 1H), 7.42 (s, 1H), 7.23 (d, 2H), 7.14 (d, 2H), 6.41-6.23 (m, 1H), 6.20-6.06 (m, 1H), 5.79-5.60 (m, 1H), 5.02-4.77 (m, 1H), 4.40 (s, 1H), 4.33 (s, 1H), 4.11 (s, 1H), 4.04 (s, 1H), 3.56-3.51 (m, 2H), 3.07-2.96 (m, 2H), 2.96-2.74 (m, 4H), 2.02 (s, 3H); UPLC-MS-12: Rt = 4.16 min; MS m/z [M + H]$^+$: 541.2/543.3; C-SFC-3 (mobile phase: $CO_2$/IPA 65/35): Rt = 2.95 min, Example 35b: C-SFC-3 (mobile phase: $CO_2$/IPA 65/35): Rt = 1.65 min. |

TABLE 1-continued

| Example | Structure | Method, intermediates (in Step 1) and chiral separation conditions used and order of elution | Characterizing data |
|---|---|---|---|
| 36a/36b | 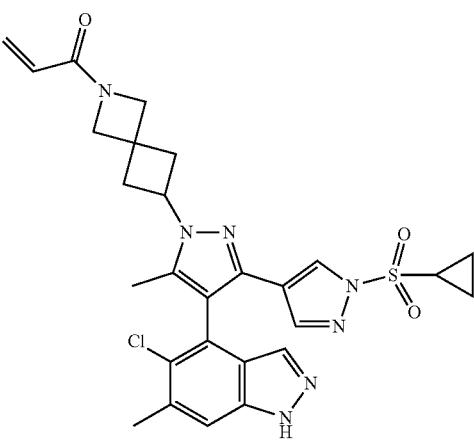<br>1-(6-(4-(5-chloro-6-methyl-1H-indazol-4-yl)-1'-(cyclopropylsulfonyl)-5-methyl-1H,1'H-[3,4'-bipyrazol]-1-yl)-2-azaspiro[3.3]heptan-2-yl)prop-2-en-1-one | Using Method-1a,b from 1-(cyclopropylsulfonyl)-4-(4,4,5,5-tetramethyl-1,3,2-dioxaborolan-2-yl)-1H-pyrazole (Step 1) and C-HPLC-11; (mobile phase: heptane/IPA 1:1): Example 36a = $2^{nd}$ eluting isomer, Example 36b = $1^{st}$ eluting isomer | Example 36a: $^1$H NMR (600 MHz, DMSO-$d_6$) δ 13.24 (s, 1H), 7.76 (s, 0.5H), 7.74 (s, 0.5H), 7.63 (s, 1H), 7.51 (s, 1H), 7.46 (d, 0.5H), 7.44 (s, 0.5H), 6.33 (m, 1H), 6.11 (m, 1H), 5.69 (m, 1H), 4.91 (m, 1H), 4.39 (s, 1H), 4.33 (s, 1H), 4.10 (s, 1H), 4.03 (s, 1H), 3.02 (m, 1H), 2.94-2.74 (m, 4H), 2.05 (s, 3H), 1.15-1.00 (m, 4H); UPLC-MS-1: Rt = 0.98 min; MS m/z [M + H]$^+$: 566.2/568.0; C-HPLC-10 (mobile phase: heptane/IPA 1:1): Rt = 8.69 min, Example 36b: C-HPLC-10 (mobile phase: heptane/IPA 1:1): Rt = 6.05 min. |
| 37a/37b | 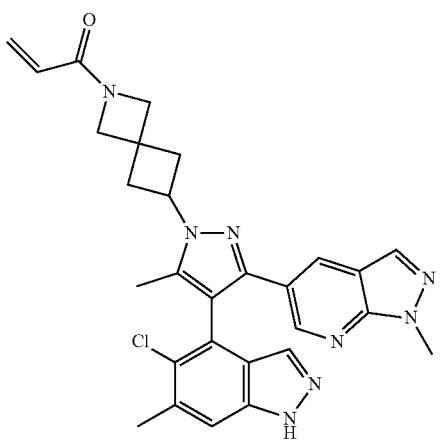<br>1-(6-(4-(5-chloro-6-methyl-1H-indazol-4-yl)-5-methyl-3-(1-methyl-1H-pyrazolo[3,4-b]pyridin-5-yl)-1H-pyrazol-1-yl)-2-azaspiro[3.3]heptan-2-yl)prop-2-en-1-one | Using Method-1a,b from 1-methyl-5-(4,4,5,5-tetramethyl-1,3,2-dioxaborolan-2-yl)-1H-pyrazolo[3,4-b]pyridine (Intermediate B14) (Step 1) and C-HPLC-1 (mobile phase: heptane/DCM/[MeOH + 0.05% Et$_3$N] 70/20/10): Example 37a = $2^{nd}$ eluting isomer, Example 37b = $1^{st}$ eluting isomer | Example 37a: $^1$H NMR (600 MHz, DMSO-$d_6$) δ 13.17 (s, 1H), 8.32 (s, 1H), 8.06 (s, 2H), 7.58 (s, 1H), 7.47 (s, 1H), 6.33 (m, 1H), 6.13 (m, 1H), 5.69 (m, 1H), 4.95 (m, 1H), 4.40 (s, 1H), 4.33 (s, 1H), 4.11 (s, 1H), 4.04 (s, 1H), 3.97 (s, 3H), 2.97-2.85 (m, 2H), 2.85-2.77 (m, 2H), 2.48 (s, 3H), 2.07 (s, 3H); UPLC-MS-1: Rt = 0.92 min; MS m/z [M + H]$^+$: 527.3/529.3; C-HPLC-12 (mobile phase: heptane/DCM/[EtOH + 0.05% Et$_3$N] 70/20/10): Rt = 7.60 min, Example 73b: C-HPLC-12 (mobile phase: heptane/DCM/[EtOH + 0.05% Et$_3$N] 70/20/10): Rt = 6.60 min. |

TABLE 1-continued

| Example | Structure | Method, intermediates (in Step 1) and chiral separation conditions used and order of elution | Characterizing data |
|---|---|---|---|
| 38a/38b | 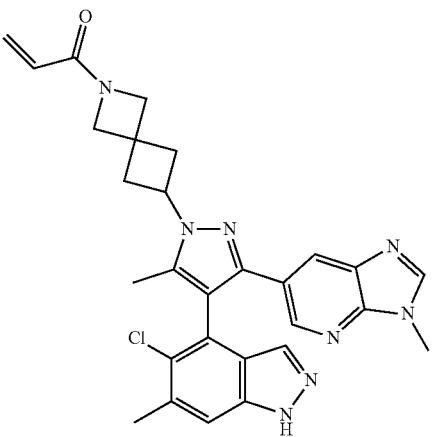<br>1-(6-(4-(5-chloro-6-methyl-1H-indazol-4-yl)-5-methyl-3-(3-methyl-3H-imidazo[4,5-b]pyridin-6-yl)-1H-pyrazol-1-yl)-2-azaspiro[3.3]heptan-2-yl)prop-2-en-1-one | Using Method-1a,b from 3-methyl-6-(4,4,5,5-tetramethyl-1,3,2-dioxaborolan-2-yl)-3H-imidazo[4,5-b]pyridine (Step 1) and C-HPLC-18 (mobile phase: n-heptane/DCM/[EtOH + 0.05% NEt$_3$] 70:20:10): Example 38a = 2$^{nd}$ eluting isomer, Example 38b = 1$^{st}$ eluting isomer | Example38a: $^1$H NMR (600 MHz, DMSO-d$_6$) δ 13.17 (s, 1H), 8.34 (s, 1H), 8.27 (s, 1H), 7.74 (s, 1H), 7.59 (s, 1H), 7.47 (s, 1H), 6.33 (m, 1H), 6.12 (m, 1H), 5.69 (m, 1H), 4.94 (m, 1H), 4.40 (s, 1H), 4.34 (s, 1H), 4.11 (s, 1H), 4.05 (s, 1H), 3.75 (s, 3H), 2.99-2.80 (m, 4H), 2.06 (s, 3H); UPLC-MS-1; Rt = 0.84 min; MS m/z [M + H]$^+$: 527.3/529.3; C-HPLC-5 (mobile phase: n-heptane/DCM/[EtOH + 0.05% NEt$_3$] 75:15:10): Rt = 13.39 min, Example 38b: C-HPLC-5 (mobile phase: n-heptane/DCM/[EtOH + 0.05% NEt$_3$] 75:15:10): Rt = 11.88 min. |
| 39a/39b | 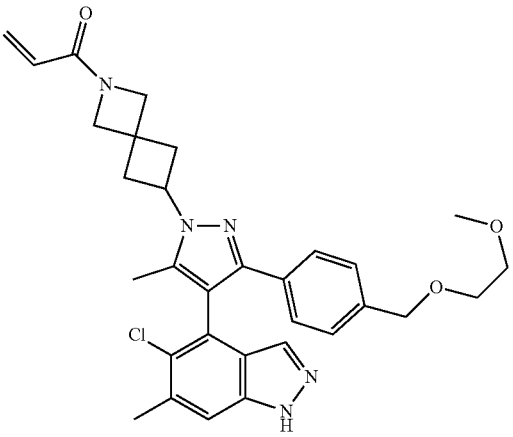<br>1-(6-(4-(5-chloro-6-methyl-1H-indazol-4-yl)-3-(4-((2-methoxyethoxy)methyl)phenyl)-5-methyl-1H-pyrazol-1-yl)-2-azaspiro[3.3]heptan-2-yl)prop-2-en-1-one | Using Method-1d from 2-(4-((2-methoxyethoxy)methyl)phenyl)-4,4,5,5-tetramethyl-1,3,2-dioxaborolane (Step 1) and C-SFC-1 (mobile phase: CO$_2$/[IPA + 0.1% TEA] 72/28): Example 39a = 2$^{nd}$ eluting isomer, Example 39b = 1$^{st}$ eluting isomer | Example 39a: $^1$H NMR (400 MHz, DMSO-d$_6$) δ 13.11 (s, 1H), 7.54 (s, 1H), 7.41 (s, 1H), 7.22 (d, 2H), 7.09 (d, 2H), 6.36-6.28 (m, 1H), 6.13-6.08 (m, 1H), 5.70-5.65 (m, 1H), 4.94-4.85 (m, 1H), 4.38 (s, 1H), 4.36 (s, 2H), 4.32 (s, 1H), 4.09 (s, 1H), 4.02 (s, 1H), 3.49-3.41 (m, 4H), 3.21 (s, 3H), 2.92-2.76 (m, 4H), 2.49 (s, 3H), 2.01 (s, 3H); UPLC-MS-3: Rt = 0.97 min; MS m/z [M + H]$^+$: 560.5/562.5; C-SFC-3 (mobile phase: CO$_2$/[IPA + 0.1% NH$_3$] 72.28): Rt = 2.69 min, Example 39b: C-SFC-3 (mobile phase: CO$_2$/[IPA + 0.1% NH3] 72/28): Rt = 2.00 min. |

TABLE 1-continued

| Example | Structure | Method, intermediates (in Step 1) and chiral separation conditions used and order of elution | Characterizing data |
|---|---|---|---|
| 40a/40b | 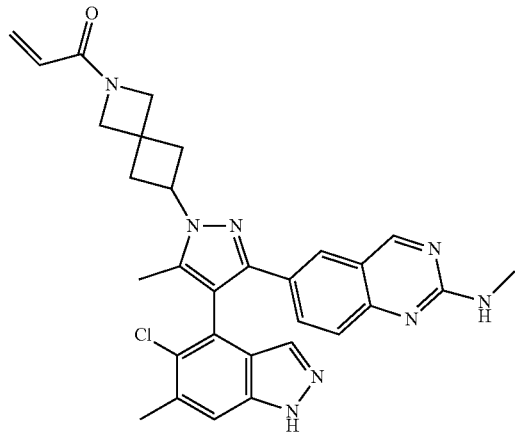<br>1-(6-(4-(5-chloro-6-methyl-1H-indazol-4-yl)-5-methyl-3-(2-(methylamino)quinazolin-6-yl)-1H-pyrazol-1-yl)-2-azaspiro[3.3]heptan-2-yl)prop-2-en-1-one | Using Method-1d from N-methyl-6-(4,4,5,5-tetramethyl-1,3,2-dioxaborolan-2-yl)quinazolin-2-amine (Step 1) and C-SFC-9 (mobile phase: $CO_2$/IPA 67/33): Example 40a = $2^{nd}$ eluting isomer, Example 40b = $1^{st}$ eluting isomer | Example 40a: $^1$H NMR (400 MHz, DMSO-$d_6$) δ 13.13 (s, 1H), 8.88 (br s, 1H), 7.69 (s, 1H), 7.58 (s, 1H), 7.48-7.45 (m, 2H), 7.33-7.24 (m, 2H), 6.38-6.31 (m, 1H), 6.15-6.09 (m, 1H), 5.71-5.67 (m, 1H), 4.99-4.89 (m, 1H), 4.41 (s, 1H), 4.34 (s, 1H), 4.12 (s, 1H), 4.04 (s, 1H), 2.97-2.79 (m, 7H), 2.06 (s, 3H); UPLC-MS-3: Rt = 0.87 min; MS m/z [M + H]$^+$: 553.2/555.2; C-SFC-3 (mobile phase: $CO_2$/IPA 67/33): Rt = 3.72 min, Example 40b: C-SFC-3 (mobile phase: $CO_2$/IPA 67/33): Rt = 2.74 min. |
| 41a/41b | 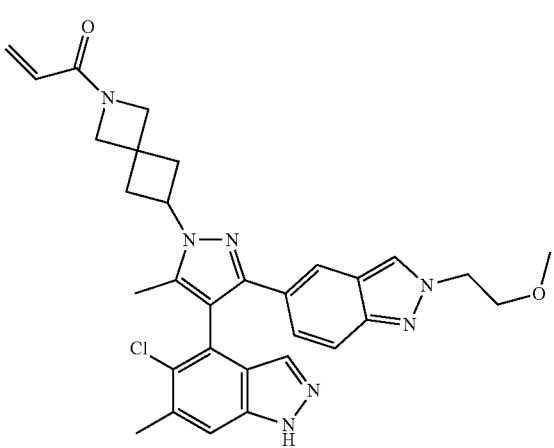<br>1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one | Using Method-1d from 2-(2-methoxyethyl)-5-(4,4,5,5-tetramethyl-1,3,2-dioxaborolan-2-yl)-2H-indazole (Intermediate B11) (Step 1) and C-SFC-7 (mobile phase: $CO_2$/MeOH 55/45): Example 41a = $2^{nd}$ eluting isomer, Example 41b = $1^{st}$ eluting isomer | Example 41a: $^1$H NMR (400 MHz, DMSO-$d_6$) δ 13.09 (br s, 1H), 8.16 (s, 1H), 7.54 (s, 1H), 7.43-7.39 (m, 3H), 7.30 (d, 1H), 6.36-6.29 (m, 1H), 6.14-6.08 (m, 1H), 5.70-5.66 (m, 1H), 4.95-4.85 (m, 1H), 4.46 (t, 2H), 4.39 (s, 1H), 4.32 (s, 1H), 4.10 (s, 1H), 4.03 (s, 1H), 3.76 (t, 2H), 3.19 (s, 3H), 2.95-2.76 (m, 4H), 2.02 (s, 3H); UPLC-MS-3: Rt = 0.91 min; MS m/z [M + H]$^+$: 570.5/572.5; C-SFC-8 (mobile phase: $CO_2$/MeOH 55/45): Rt = 3.18 min, Example 41b: C-SFC-8 (mobile phase: $CO_2$/MeOH 55/45): Rt = 2.18 min. |

TABLE 1-continued

| Example | Structure | Method, intermediates (in Step 1) and chiral separation conditions used and order of elution | Characterizing data |
|---|---|---|---|
| 42a/42b | 1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one | Using Method-1d from 2-methyl-1-(5-(4,4,5,5-tetramethyl-1,3,2-dioxaborolan-2-yl)-2H-indazol-2-yl)propan-2-ol (Intermediate B23) (Step 1) and C-SFC-7 (mobile phase: $CO_2$/MeOH 57/43): Example 42a = $2^{nd}$ eluting isomer, Example 42b = $1^{st}$ eluting isomer | Example 42a: $^1$H NMR (400 MHz, DMSO-$d_6$) δ 13.09 (s, 1H), 8.11 (s, 1H), 7.54 (s, 1H), 7.47 (s, 1H), 7.43-7.38 (m, 2H), 7.28-7.24 (m, 1H), 6.37-6.29 (m, 1H), 6.14-6.08 (m, 1H), 5.70-5.66 (m, 1H), 4.95-4.85 (m, 1H), 4.78 (s, 1H), 4.39 (s, 1H), 4.32 (s, 1H), 4.22 (s, 2H), 4.11 (s, 1H), 4.04 (s, 1H), 2.95-2.76 (m, 4H), 2.02 (s, 3H), 1.06 (s, 6H); UPLC-MS-5: Rt = 0.87 min; MS m/z [M + H]$^+$: 584.5/586.5; C-SFC-8 (mobile phase: $CO_2$/[MeOH + 0.025% NH$_3$] 55/45): Rt = 3.03 min, Example 42b: C-SFC-8 (mobile phase: $CO_2$/[MeOH + 0.025% NH$_3$] 55/45): Rt = 1.49 min. |
| 43a/43b | 1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one | Using Method-1d from 2-(2-(2-methoxyethoxy)ethyl)-5-(4,4,5,5-tetramethyl-1,3,2-dioxaborolan-2-yl)-2H-indazole (Intermediate B24) (Step 1) and C-SFC-10 (mobile phase: $CO_2$/MeOH 55/45): Example 43a = $2^{nd}$ eluting isomer, Example 43b = $1^{st}$ eluting isomer | Example 43a: $^1$H NMR (400 MHz, DMSO-$d_6$) δ 13.09 (s, 1H), 8.17 (s, 1H), 7.54 (s, 1H), 7.43-7.39 (m, 3H), 7.32-7.29 (m, 1H), 6.37-6.29 (m, 1H), 6.14-6.08 (m, 1H), 5.70-5.66 (m, 1H), 4.95-4.85 (m, 1H), 4.46 (t, 2H), 4.39 (s, 1H), 4.33 (s, 1H), 4.11 (s, 1H), 4.04 (s, 1H), 3.85 (t, 2H), 3.51-3.46 (m, 2H), 3.27-3.34 (m, 2H), 3.13 (s, 3H), 2.95-2.76 (m, 4H), 2.02 (s, 3H); UPLC-MS-5: Rt = 0.87 min; MS m/z [M + H]$^+$ 614.5/616.5; C-SFC-8 (mobile phase: $CO_2$/MeOH 55/45): Rt = 3.47 min, Example 43b: C-SFC-8 (mobile phase: $CO_2$/MeOH 55/45): Rt = 2.59 min. |

TABLE 1-continued

| Example | Structure | Method, intermediates (in Step 1) and chiral separation conditions used and order of elution | Characterizing data |
|---|---|---|---|
| 44a/44b | 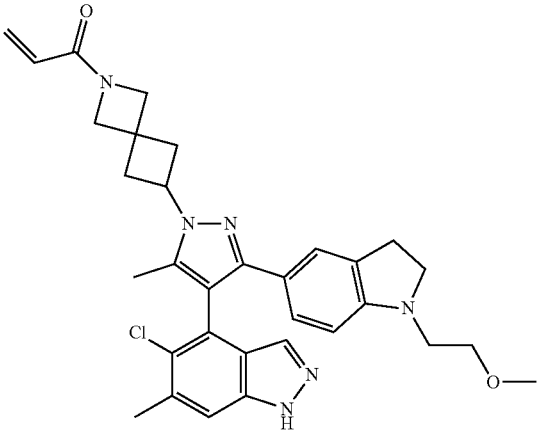<br>1-(6-(4-(5-chloro-6-methyl-1H-indazol-4-yl)-3-(1-(2-methoxyethyl)indolin-5-yl)-5-methyl-1H-pyrazol-1-yl)-2-azaspiro[3.3]heptan-2-yl)prop-2-en-1-one | Using Method-1d from 1-(2-methoxyethyl)-5-(4,4,5,5-tetramethyl-1,3,2-dioxaborolan-2-yl)indoline (Intermediate B25) (Step 1) and C-SFC-1 (mobile phase: $CO_2$/[IPA + 0.1 $NEt_3$] 67/33): Example 44a = $2^{nd}$ eluting isomer, Example 44b = $1^{st}$ eluting isomer | Example 44a: $^1$H NMR (400 MHz, DMSO-$d_6$) δ 13.07 (s, 1H), 7.51 (s, 1H), 7.39 (s, 1H), 7.17 (s, 1H), 6.65 (d, 1H), 6.36-6.28 (m, 1H), 6.16 (d, 1H), 6.10 (m, 1H), 5.70-5.66 (m, 1H), 4.89-4.79 (m, 1H), 4.38 (s, 1H), 4.31 (s, 1H), 4.09 (s, 1H), 4.02 (s, 1H), 3.45 (t, 2H), 3.22 (s, 3H), 3.11 (t, 2H), 2.90-2.73 (m, 6H), 1.97 (s, 3H); UPLC-MS-5: Rt = 1.02 min; MS m/z [M + H]$^+$ 571.5/573.5; C-SFC-3 (mobile phase: $CO_2$/[IPA + 0.1% $NEt_3$] 67/33): Rt = 2.69 min, Example 44b: C-SFC-3 (mobile phase: $CO_2$/[IPA + 0.1% $NEt_3$] 67/33): Rt = 1.63 min. |

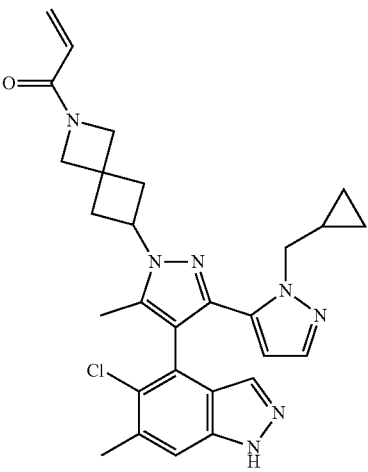 [SMILES: C=CC(=O)N1CC2(CC(n3nc(-c4ccnn4CC4CC4)c(-c4c(Cl)c(C)cc5[nH]ncc45)c3C)C2)C1]

Examples 45a/45b: 1-(6-(4-(5-chloro-6-methyl-1H-indazol-4-yl)-2'-(cyclopropylmethyl)-5-methyl-1H,2'H-[3,3'-bipyrazol]-1-yl)-2-azaspiro[3.3]heptan-2-yl)prop-2-en-1-one The title examples were prepared using similar method to Method-1 b step 2 and 3 from tert-butyl 6-(4-(5-chloro-6-methyl-1-(tetrahydro-2H-pyran-2-yl)-1H-indazol-4-yl)-2'-(cyclopropylmethyl)-5-methyl-1H,2'H-[3,3'-bipyrazol]-1-yl)-2-azaspiro[3.3]heptane-2-carboxylate (prepared as described below). The isomers were separated by chiral SFC (C-SFC-2; mobile phase: $CO_2$/MeOH: 72/28) to give the title compound Example 45a as the second eluting peak: $^1$H NMR (400 MHz, DMSO-$d_6$) δ 13.12 (s, 1H), 7.54 (s, 1H), 7.46 (s, 1H), 7.15 (d, 1H), 6.32 (m, 1H), 6.10 (m, 1H), 5.67 (m, 1H), 5.45 (d, 1H), 4.96 (m, 1H), 4.38 (s, 1H), 4.36-4.21 (m, 3H), 4.09 (s, 1H), 4.00 (s, 1H), 2.90-2.78 (m, 4H), 2.47 (s, 3H), 2.04 (s, 3H), 1.32-1.22 (m, 1H), 0.49-0.29 (m, 4H); UPLC-MS-3: Rt=0.97 min; MS m/z [M+H]$^+$ 516.3/518.3; C-SFC-3 (mobile phase: $CO_2$/MeOH: 72/28): Rt=2.27 min. The other isomer Example 45b was obtained as the first eluting peak: C-SFC-3 (mobile phase: mobile phase: $CO_2$/MeOH: 72/28): Rt=1.19 min.

Tert-butyl 6-(4-(5-chloro-6-methyl-1-(tetrahydro-2H-pyran-2-yl)-1H-indazol-4-yl)-2'-(cyclopropylmethyl)-5-methyl-1H,2'H-[3,3'-bipyrazol]-1-yl)-2-azaspiro[3.3]heptane-2-carboxylate. Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 300 mg, 0.47 mmol), 1-(cyclopropylmethyl)-5-(4,4,5,5-tetramethyl-1,3,2-dioxaborolan-2-yl)-1H-pyrazole (175 mg, 0.71 mmol) and $PdCl_2$ (dppf).$CH_2Cl_2$ adduct (38.5 mg, 0.047 mmol) were suspended in acetonitrile (2.25 mL). Aqueous $Na_2CO_3$ (2M, 0.48 mL, 0.97 mmol) was added and the suspension was flushed with argon and submitted to microwave irradiations at 120° C. for 20 min. The reaction mixture was allowed to reach RT, diluted with EtOAc, a sat. aq. $NaHCO_3$ solution was added and the layers were separated. The aqueous layer was extracted with EtOAc (×2) and the combined organic extracts were washed with brine and dried ($MgSO_4$), filtered and concentrated to half of the volume. SiliaMetS® Thiol (100 mg) was added and the mixture was stirred at RT for 15 min, filtered and concentrated. The crude residue was purified by normal flash column chromatography (eluent: EtOAc in c-hexane from 20 to 70%) to give the title compound. UPLC-MS-3: Rt=1.28 min; MS m/z [M+H]$^+$; 646.3/648.2.

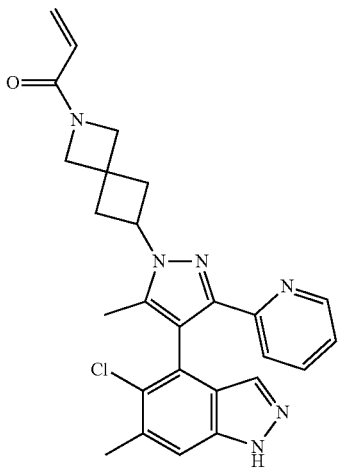 [SMILES: C=CC(=O)N1CC2(CC(n3nc(-c4ccccn4)c(-c4c(Cl)c(C)cc5[nH]ncc45)c3C)C2)C1]
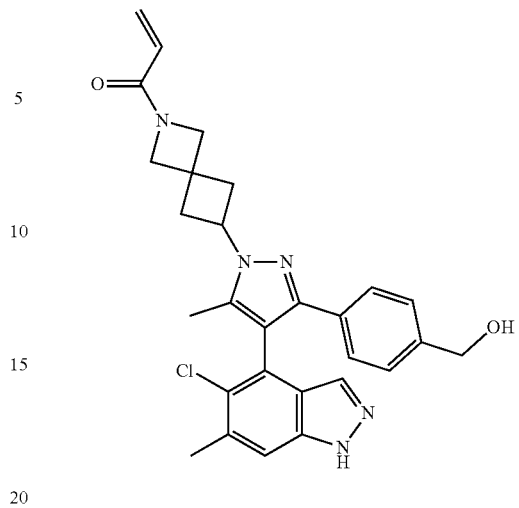

Examples 46a/46b: 1-(6-(4-(5-chloro-6-methyl-1H-indazol-4-yl)-5-methyl-3-(pyridin-2-yl)-1H-pyrazol-1-yl)-2-azaspiro[3.3]heptan-2-yl)prop-2-en-1-one The title examples were prepared using similar method to Method-1 b step 2 and 3 from tert-butyl 6-(4-(5-chloro-6-methyl-1H-indazol-4-yl)-5-methyl-3-(pyridin-2-yl)-1H-pyrazol-1-yl)-2-azaspiro[3.3]heptane-2-carboxylate (prepared as described below). The isomers were separated by chiral SFC (C-SFC-2; mobile phase: $CO_2$/MeOH: 63/37) to give the title compound Example 46a as the first eluting peak: $^1$H NMR (400 MHz, DMSO-$d_6$) δ 13.0 (s, 1H), 8.16 (d, 1H), 7.69 (t, 1H), 7.66 (d, 1H), 7.47 (s, 1H), 7.40 (s, 1H), 7.12 (t, 1H), 6.33 (m, 1H), 6.12 (m, 1H), 5.69 (m, 1H), 4.94 (m, 1H), 4.40 (s, 1H), 4.33 (s, 1H), 4.11 (s, 1H), 4.04 (s, 1H), 2.92-2.79 (m, 4H), 2.46 (s, 3H), 2.03 (s, 3H); UPLC-MS-3: Rt=0.84 min; MS m/z [M+H]$^+$ 473.2/475.2; C-SFC-3 (mobile phase: $CO_2$/MeOH: 65/35): Rt=0.97 min. The other isomer Example 46b was obtained as the second eluting peak: C-SFC-3 (mobile phase: $CO_2$/MeOH: 65/35): Rt=3.28 min.

Tert-butyl 6-(4-(5-chloro-6-methyl-1H-indazol-4-yl)-5-methyl-3-(pyridin-2-yl)-1H-pyrazol-1-yl)-2-azaspiro[3.3]heptane-2-carboxylate To a solution of tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 1.35 g, 2.23 mmol) and bis(tri-t-butylphosphine)palladium (68 mg, 0.13 mmol) in THF (3 mL) placed under an argon atmosphere was added 2-pyridylzinc bromide (0.5 M in THF, 14.0 mL, 7.00 mmol). The reaction mixture was heated at 70° C. for 3 h. The RM was poured into a sat. aq. solution of NaHCO$_3$ and extracted with EtOAc (×2). The combined organic extracts were washed with brine, dried (Na$_2$SO$_4$), filtered and concentrated. The crude residue was dissolved in THF (20 mL), SiliaMetS® Thiol (1.3 mmol) was added and the mixture was stirred at RT for 1 h, filtered and concentrated. The crude residue was purified by normal phase chromatography (eluent: MeOH in CH$_2$Cl$_2$ from 0 to 5%) to give a mixture containing the desired material which was purified again by normal phase chromatography (eluent: EtOAc) to give the title compound. UPLC-MS-3: Rt=1.22 min; MS m/z [M+H]$^+$; 603.3/605.2.

Examples 47a/47b: 1-(6-(4-(5-chloro-6-methyl-1H-indazol-4-yl)-3-(4-(hydroxymethyl)phenyl)-5-methyl-1H-pyrazol-1-yl)-2-azaspiro[3.3]heptan-6-yl) prop-2-en-1-one To a solution of 4-(4-(5-chloro-6-methyl-1H-indazol-4-yl)-5-methyl-1-(2-azaspiro[3.3]heptan-6-yl)-1H-pyrazol-3-yl)benzyl acetate trifluoroacetate (prepared as described below, 0.7 mmol) in THF (12 mL) and water (0.3 mL) were successively added NaHCO$_3$ (588 mg, 7.0 mmol) and acryloyl chloride (70 μL, 0.84 mmol) and the reaction mixture was stirred at RT for 2.5 h. LiOH was added (2M, 3.50 mL, 7.00 mmol) and the RM was stirred at RT for 45 min until disappearance (UPLC) of the side product resulting from reaction of acryloyl chloride with the indazole NH. The RM was diluted with water and extracted with EtOAc (×2). The combined organic extracts were washed with brine, dried (Na$_2$SO$_4$), filtered and evaporated. The crude residue was dissolved in THF (12 mL), LiOH (2M, 3.50 mL, 7 mmol) was added and the reaction mixture was stirred at RT for 2 h. The RM was diluted with water and extracted with EtOAc (×2). The combined organic extracts were washed with brine, dried (Na$_2$SO$_4$), filtered and evaporated. The crude residue was purified by reverse phase HPLC (RP-HPLC-1), the purified fractions were neutralized with a sat. aq. solution of NaHCO$_3$ and extracted with EtOAc. The organic extract was washed with brine, dried (Na$_2$SO$_4$), filtered and evaporated. The isomers were separated by chiral SFC (C-SFC-2; mobile phase: $CO_2$/IPA: 70/30) to give the title compound Example 47a as the second eluting peak: $^1$H NMR (400 MHz, DMSO-$d_6$) δ 13.12 (s, 1H), 7.54 (s, 1H), 7.40 (s, 1H), 7.19 (d, 2H), 7.08 (d, 2H), 6.32 (m, 1H), 6.11 (m, 1H), 5.68 (m, 1H), 5.08 (t, 1H), 4.89 (m, 1H), 4.39-4.37 (m, 3H), 4.32 (s, 1H), 4.10 (s, 1H), 4.02 (s, 1H), 2.91-2.76 (m, 4H), 2.48 (s, 3H), 2.01 (s, 3H); UPLC-MS-3: Rt=0.88 min; MS m/z [M+H]$^+$ 502.1/504.1; C-SFC-3 (mobile phase: $CO_2$/IPA: 70/30): Rt=3.78 min. The other isomer Example 47b was obtained as the first eluting peak: C-SFC-3 (mobile phase: mobile phase: $CO_2$/IPA: 70/30): Rt=2.85 min.

4-(4-(5-Chloro-6-methyl-1H-indazol-4-yl)-5-methyl-1-(2-azaspiro[3.3]heptan-6-yl)-1H-pyrazol-3-yl) benzyl acetate trifluoroacetate The title compound was prepared using similar method to Method-1 step 1 and 2 from tert-butyl 6-(3-bromo-4-(5- chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1) and 4-(4,4,5,5-tetramethyl-1,3,2-dioxaborolan-2-yl)benzyl acetate [562098-08-2]; UPLC-MS-6: Rt=0.80 min; MS m/z [M+H]+ 490.2/492.2.

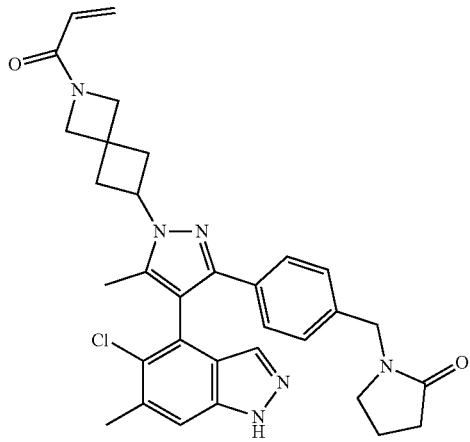 [SMILES: C=CC(=O)N1CC2(CC(n3nc(-c4ccc(CN5CCCC5=O)cc4)c(-c4c(Cl)c(C)cc5[nH]ncc45)c3C)C2)C1]

Example 48: 1-(4-(1-(2-acryloyl-2-azaspiro[3.3]heptan-6-yl)-4-(5-chloro-6-methyl-1H-indazol-4-yl)-5-methyl-1H-pyrazol-3-yl)benzyl)pyrrolidin-2-one The title example was prepared using similar method to Method-1 b step 2 and 3 from tert-butyl 6-(4-(5-chloro-6-methyl-1-(tetrahydro-2H-pyran-2-yl)-1H-indazol-4-yl)-5-methyl-3-(4-((2-oxopyrrolidin-1-yl)methyl)phenyl)-1H-pyrazol-1-yl)-2-azaspiro[3.3]heptane-2-carboxylate (prepared as described below). $^1$H NMR (400 MHz, DMSO-$d_6$) δ 13.12 (s, 1H), 7.54 (s, 1H), 7.41 (s, 1H), 7.23 (d, 2H), 6.99 (d, 2H), 6.32 (m, 1H), 6.10 (m, 1H), 5.67 (m, 1H), 4.89 (m, 1H), 4.37 (s, 1H), 4.31 (s, 1H), 4.25 (s, 2H), 4.09 (s, 1H), 4.02 (s, 1H), 3.14 (t, 2H), 2.93-2.73 (m, 4H), 2.47 (s, 3H), 2.24 (t, 2H), 2.00 (s, 3H), 1.87 (p, 2H); UPLC-MS-3: Rt=0.92 min; MS m/z [M+H]+ 569.3/571.3.

Tert-butyl 6-(4-(5-chloro-6-methyl-1-(tetrahydro-2H-pyran-2-yl)-1H-indazol-4-yl)-5-methyl-3-(4-((2-oxopyrrolidin-1-yl)methyl)phenyl)-1H-pyrazol-1-yl)-2-azaspiro[3.3]heptane-2-carboxylate Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 300 mg, 0.47 mmol) and 1-(4-(4,4,5,5-tetramethyl-1,3,2-dioxaborolan-2-yl)benzyl)pyrrolidin-2-one (Intermediate B2, 473 mg, 0.94 mmol) were suspended in DMF (3.95 mL). Aqueous K$_3$PO$_4$ (1M, 0.94 mL, 0.942 mmol) and Pd(Ph$_3$P)$_4$ (27.2 mg, 0.024 mmol) were added and the suspension was flushed with argon and submitted to microwave irradiations at 120° C. for 45 min. The reaction mixture was allowed to reach RT, diluted with EtOAc, a sat. aq. NaHCO$_3$ solution was added and the layers were separated. The aqueous layer was extracted with EtOAc (×2) and the combined organic extracts were washed with brine and dried (MgSO$_4$), filtered and concentrated. The crude residue was purified by normal flash column chromatography (eluent: (MeOH/CH$_2$Cl$_2$ 9/1) in CH$_2$Cl$_2$ from 0 to 50%) to give the title compound. UPLC-MS-3: Rt=1.22 min; MS m/z [M+H]+; 699.4/701.4.

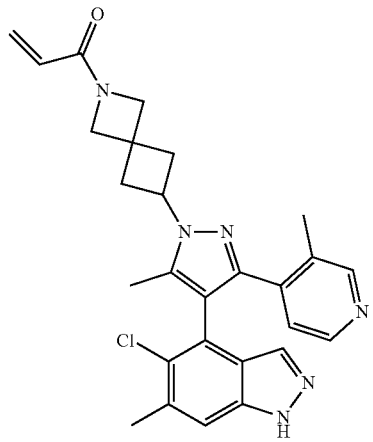 [SMILES: C=CC(=O)N1CC2(CC(n3nc(-c4ccncc4C)c(-c4c(Cl)c(C)cc5[nH]ncc45)c3C)C2)C1]

Examples 49a/49b: 1-(6-(4-(5-chloro-6-methyl-1H-indazol-4-yl)-5-methyl-3-(3-methylpyridin-4-yl)-1H-pyrazol-1-yl)-2-azaspiro[3.3]heptan-2-yl)prop-2-en-1-one The title examples were prepared using similar method to Method-1 b step 2 and 3 from tert-butyl 6-(4-(5-chloro-6-methyl-1-(tetrahydro-2H-pyran-2-yl)-1H-indazol-4-yl)-5-methyl-3-(3-methylpyridin-4-yl)-1H-pyrazol-1-yl)-2-azaspiro[3.3]heptane-2-carboxylate (prepared as described below). The isomers were separated by chiral HPLC C-HPLC-23 (mobile phase: Hexane/IPA/ACN 60/28/12; flow rate: 20 mL/min; UV: 227 nM) to give the title compound Example 49a as the second eluting peak: $^1$H NMR (400 MHz, DMSO-$d_6$) δ 13.11 (s, 1H), 8.35 (s, 1H), 8.13 (d, 1H), 7.50 (s, 1H), 7.45 (s, 1H), 6.79 (d, 1H), 6.34 (m, 1H), 6.13 (m, 1H), 5.70 (m, 1H), 4.97 (m, 1H), 4.39 (s, 1H), 4.30 (s, 1H), 4.11 (s, 1H), 4.00 (s, 1H), 2.89 (m, 4H), 2.44 (s, 3H), 2.13 (s, 3H), 2.03 (s, 3H); LCMS-2: Rt=1.39 min; MS m/z [M+H]+=487.9/490.0; C-HPLC-24 (mobile phase: 0.1% DEA in Hexane/IPA/ACN gradient; UV: 262 nM): Rt=10.3 min. The other isomer Example 49b was obtained as the first eluting peak: C-HPLC-24 (mobile phase: 0.1% DEA in Hexane/IPA/ACN gradient, UV: 262 nM): Rt=8.98 min.

Tert-butyl 6-(4-(5-chloro-6-methyl-1-(tetrahydro-2H-pyran-2-yl)-1H-indazol-4-yl)-5-methyl-3-(3-methylpyridin-4-yl)-1H-pyrazol-1-yl)-2-azaspiro[3.3]heptane-2-carboxylate Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 0.40 g, 0.66 mmol), 3-picoline-4-boronic acid (0.27 g, 1.98 mmol) and K$_3$PO$_4$ (0.42 g, 1.98 mmol) were dissolved in t-BuOH:H$_2$O (5:1) (24 mL) and the mixture was degassed with argon for 15 min. XPhos (0.094 g, 0.19 mmol) and Pd$_2$dba$_3$ (0.06 g, 0.07 mmol) were added and and the reaction mixture was stirred at 120° C. for 4 h in sealed conditions. The reaction mixture was quenched with water and extracted with EtOAc (×3). The combined organic layers were washed with brine, dried (sodium sulfate), filtered and concentrated under vacuum. The crude residue was purified by C18 (15 micron) reverse phase chromatography (eluent: 0-68% CH$_3$CN in H$_2$O containing 0.1%

HCOOH) to obtain the desired product. LCMS-1: Rt=1.82 min; MS m/z [M+H]+; 617.7/620.6.

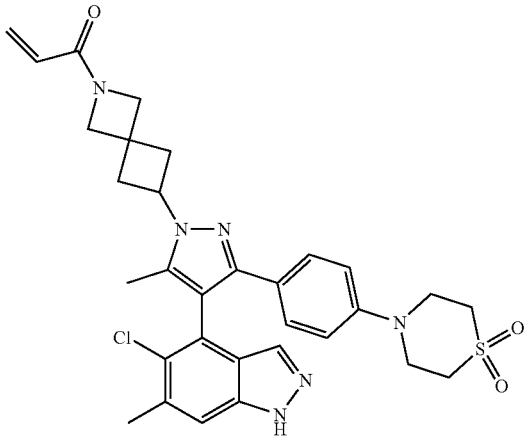 [SMILES: C=CC(=O)N1CC2(CC(n3nc(-c4ccc(N5CCS(=O)(=O)CC5)cc4)c(-c4c(Cl)c(C)cc5[nH]ncc45)c3C)C2)C1]

Examples 50a/50b: 1-(6-(4-(5-chloro-6-methyl-1H-indazol-4-yl)-3-(4-(1,1-dioxidothiomorpholino)phenyl)-5-methyl-1H-pyrazol-1-yl)-2-azaspiro[3.3]heptan-2-yl)prop-2-en-1-one The title examples were prepared using similar protocols as described for Examples 49a and 49b starting form Intermediate C1 and 4-(4-(4,4,5,5-tetramethyl-1,3,2-dioxaborolan-2-yl)phenyl)thiomorpholine 1,1-dioxide (Intermediate B15). The isomers were separated by chiral HPLC C-HPLC-23 (mobile phase: MeOH:ACN (80:20); flow rate: 15 mL/min; UV: 270 nM) to give the title compound Example 50a as the first eluting: $^1$H NMR (400 MHz, CDCl$_3$) δ 10.12 (s, 1H), 7.55 (s, 1H), 7.42 (s, 1H), 7.34 (d, 2H), 6.73 (d, 2H), 6.42 (m, 1H), 6.29 (m, 1H), 5.75 (m, 1H), 4.79 (m, 1H), 4.41 (s, 1H), 4.38 (s, 1H), 4.27 (s, 2H), 3.80 (m, 4H), 3.15 (m, 2H), 3.05 (m, 4H), 2.86 (m, 2H), 2.60 (s, 3H), 2.09 (s, 3H); LCMS-2: Rt=1.53 min; MS m/z [M+H]+: 605.5/607.5; C-SFC-19 (mobile phase: CO$_2$/MeOH/ACN 55/22.5/22.5; UV: 270 nM): Rt=6.77 min. The other isomer Example 50b was obtained as the second eluting peak: C-SFC-19 (mobile phase: CO$_2$/MeOH/ACN 55/22.5/22.5; UV: 270 nM): Rt=10.8 min.

Examples 51a/51b: 1-(6-(4-(5-chloro-6-methyl-1H-indazol-4-yl)-5-methyl-3-(thiazol-4-yl)-1H-pyrazol-1-yl)-2-azaspiro[3.3]heptan-2-yl)prop-2-en-1-one The title examples were prepared using similar method to Method-1 b step 2 and 3 from tert-butyl 6-(4-(5-chloro-6-methyl-1-(tetrahydro-2H-pyran-2-yl)-1H-indazol-4-yl)-5-methyl-3-(thiazol-4-yl)-1H-pyrazol-1-yl)-2-azaspiro[3.3]heptane-2-carboxylate (prepared as described below). The isomers were separated by chiral HPLC C-HPLC-23 (mobile phase: [Hexane+0.1% Et$_2$NH]/[IPA+0.1% Et$_2$NH]/CH$_3$CN (60/28/12); flow rate: 20 mL/min; UV: 216 nM) to give the title compound Example 51a as the first eluting peak: $^1$H NMR (400 MHz, DMSO-d6) δ 13.07 (s, 1H), 8.84 (s, 1H), 7.49 (s, 1H), 7.39 (s, 1H), 7.34 (s, 1H), 6.32 (m, 1H), 6.12 (m, 1H), 5.67 (m, 1H), 4.92 (m, 1H), 4.38 (s, 1H), 4.30 (s, 1H), 4.09 (s, 1H), 4.00 (s, 1H), 2.84-2.78 (m, 4H), 2.46 (s, 3H), 2.02 (s, 3H); LCMS-1: Rt=1.49 min; MS m/z [M+H]+: 479.3/481.3; C-HPLC-24 (mobile phase: 0.1% DEA in Hexane/IPA/CH$_3$CN gradient): Rt=10.0 min. The other isomer Example 51 b was obtained as the second eluting peak: C-HPLC-24 (mobile phase: 0.1% DEA in Hexane/IPA/CH$_3$CN gradient): Rt=12.3 min.

Tert-butyl 6-(4-(5-chloro-6-methyl-1-(tetrahydro-2H-pyran-2-yl)-1H-indazol-4-yl)-5-methyl-3-(thiazol-4-yl)-1H-pyrazol-1-yl)-2-azaspiro[3.3]heptane-2-carboxylate Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 0.30 g, 0.49 mmol), 4-(tributylstannyl)thiazole (0.28 g, 0.74 mmol) and anhydrous LiCl (0.03 g, 0.74 mmol) were suspended in dry toluene and the mixture was degassed with nitrogen for 10 min. The reaction mixture was then heated to 100° C. for 16 h in sealed tube conditions. The RM was filtered through a pad of celite and washed with ethyl acetate. The filtrate was concentrated under vacuum and the crude residue was purified by C18 (15 micron) reverse phase chromatography (eluent: 0-100% CH$_3$CN in H$_2$O containing 0.1% HCOOH) to obtain the title product. LCMS-1: Rt=2.06; 2.08 min; MS m/z [M+H]+: 609.8/611.8.

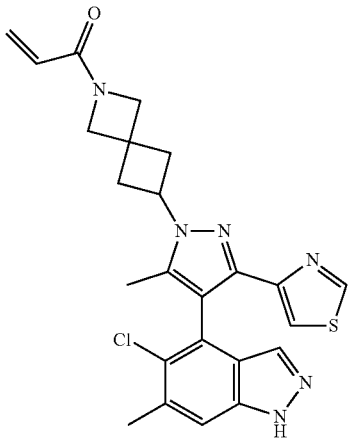 [SMILES: C=CC(=O)N1CC2(CC(n3nc(-c4cscn4)c(-c4c(Cl)c(C)cc5[nH]ncc45)c3C)C2)C1]

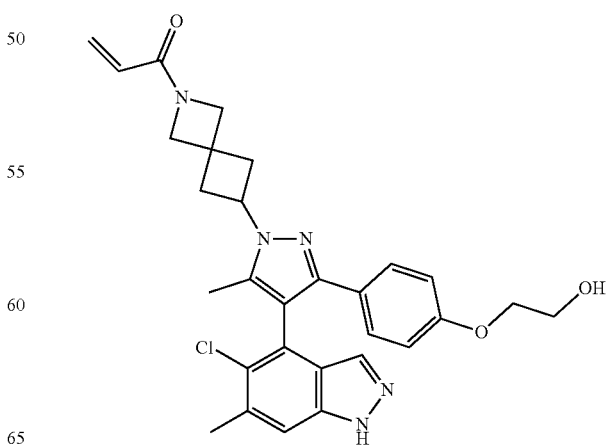

Examples 52a/52b: 1-(6-(4-(5-chloro-6-methyl-1H-indazol-4-yl)-3-(4-(2-hydroxyethoxy)phenyl)-5-methyl-1H-pyrazol-1-yl)-2-azaspiro[3.3]heptan-2-yl)prop-2-en-1-one

Step 1: Tert-butyl 6-(4-(5-chloro-6-methyl-1-(tetrahydro-2H-pyran-2-yl)-1H-indazol-4-yl)-3-(4-(2-hydroxyethoxy)phenyl)-5-methyl-1H-pyrazol-1-yl)-2-azaspiro[3.3]heptane-2-carboxylate Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 0.50 g, 0.83 mmol), 2-(4-(4,4,5,5-tetramethyl-1,3,2-dioxaborolan-2-yl)phenoxy)ethan-1-ol (0.22 g, 0.83 mmol) and $K_3PO_4$ (0.52 g, 2.48 mmol) were added in 1,4-dioxane:$H_2O$ (2:1) (12 mL) and the mixture was degassed with nitrogen for 10 min. RuPhos (0.038 g, 0.08 mmol) and RuPhos-Pd-G3 (0.034 g, 0.08 mmol) were added and the reaction mixture was stirred at 100° C. for 2 h. After completion of the reaction, the RM was poured into water and extracted with EtOAc (×2). The combined organic layers were washed with brine, dried ($Na_2SO_4$), filtered and concentrated under vacuum. The crude residue was purified by normal phase chromatography (eluent: 0-60% EtOAc in Hexane) to obtain the title product. LCMS-1: Rt=2.05, 2.09 min; MS m/z [M+H]$^+$: 662.7.3/664.7.

Step 2: Tert-butyl 6-(3-(4-(2-acetoxyethoxy)phenyl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate Tert-butyl 6-(4-(5-chloro-6-methyl-1-(tetrahydro-2H-pyran-2-yl)-1H-indazol-4-yl)-3-(4-(2-hydroxyethoxy)phenyl)-5-methyl-1H-pyrazol-1-yl)-2-azaspiro[3.3]heptane-2-carboxylate (0.45 g, 0.68 mmol) was dissolved in $CH_2Cl_2$ (5 mL). $Et_3N$ (0.21 g, 2.03 mmol) was added and the reaction mixture was cooled to 0° C. under nitrogen atmosphere and stirred for 10 min. Acetyl chloride (0.08 g, 1.02 mmol) in $CH_2Cl_2$ (0.5 mL) was added dropwise and the reaction mixture was stirred at RT for 2 h. After completion of the reaction, the RM was diluted with $CH_2Cl_2$, washed with water, brine, dried ($Na_2SO_4$), filtered and concentrated under vacuum to afford the title product which was directly used in the next step without further purification. LCMS-1: Rt=2.14, 2.16 min; MS m/z [M+H]$^+$: 704.6/706.6.

Step-3: 2-(4-(4-(5-Chloro-6-methyl-1H-indazol-4-yl)-5-methyl-1-(2-azaspiro[3.3]heptan-6-yl)-1H-pyrazol-3-yl)phenoxy)ethyl acetate Tert-butyl 6-(3-(4-(2-acetoxyethoxy)phenyl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (0.68 mmol) was dissolved in dry $CH_2Cl_2$ (5 mL) and cooled to 0° C. TFA (6 mL) was added and reaction mixture was stirred at room temperature for 5 h. After completion of the reaction, the RM was concentrated under vacuum, co-distilled with $CH_2Cl_2$ several times to afford a crude residue which was purified by trituration with diethylether and filtration to obtain the desired product which was directly used in the next step without further purification. LCMS-1: Rt=1.49 min; MS m/z [M+H]$^+$: 520.4.

Step-4: 2-(4-(1-(2-Acryloyl-2-azaspiro[3.3]heptan-6-yl)-4-(5-chloro-6-methyl-1H-indazol-4-yl)-5-methyl-1H-pyrazol-3-yl)phenoxy)ethyl acetate 2-(4-(4-(5-Chloro-6-methyl-1H-indazol-4-yl)-5-methyl-1-(2-azaspiro[3.3]heptan-6-yl)-1H-pyrazol-3-yl)phenoxy)ethyl acetate (0.22 g, 0.42 mmol) was dissolved in THF (2 mL). $NaHCO_3$ (0.35 g, 4.15 mmol) in water (2.5 mL) was added and the reaction mixture was stirred at RT for 10 min. The reaction mixture was cooled to 0° C. and a solution of acrolyl chloride (0.04 g, 0.46 mmol) in THF (0.5 mL) was added dropwise and stirred for 40 min. After completion of the reaction, the RM was diluted with water and extracted with EtOAc (×2). The combined organic layers were washed with water, brine, dried ($Na_2SO_4$), filtered and concentrated under vacuum. The crude residue was purified by C18 silica gel (15 micron) reverse phase chromatography (eluent: 0-43% $CH_3CN$ in $H_2O$ containing 0.1% $NH_3$) to afford the desired product. The isomers were separated by chiral HPLC C-HPLC-23 (mobile phase: Hexane/IPA/ACN 70/21/9; flow rate: 18 mL/min; UV: 264 nM) to give the title compound Isomer-I as the first eluting peak: LCMS-1: Rt=1.63 min; MS m/z [M+H]$^+$ 574.8; C-HPLC-29 (mobile phase: Hexane/IPA gradient): Rt=11.8 min. The other isomer-II was obtained as the second eluting peak: LCMS-1: Rt=1.63 min; MS m/z [M+H]$^+$: 574.8; C-HPLC-29 (mobile phase: Hexane/IPA gradient): Rt=13.8 min.

Step-5: Example 52a: 1-(6-(4-(5-chloro-6-methyl-1H-indazol-4-yl)-3-(4-(2-hydroxyethoxy)phenyl)-5-methyl-1H-pyrazol-1-yl)-2-azaspiro[3.3]heptan-2-yl)prop-2-en-1-one The title example was prepared using similar method as described for the preparation of Example 52b 1-(6-(4-(5-chloro-6-methyl-1H-indazol-4-yl)-3-(4-(2-hydroxyethoxy)phenyl)-5-methyl-1H-pyrazol-1-yl)-2-azaspiro[3.3]heptan-2-yl)prop-2-en-1-one (Step 6) starting from 2-(4-(1-(2-acryloyl-2-azaspiro[3.3]heptan-6-yl)-4-(5-chloro-6-methyl-1H-indazol-4-yl)-5-methyl-1H-pyrazol-3-yl)phenoxy)ethyl acetate Isomer-II instead of Isomer-I; LCMS-3: Rt=3.30 min; MS m/z [M+H]$^+$: 532/534; $^1$H NMR (400 MHz, $CD_3OD$) δ 7.49 (s, 1H), 7.39 (s, 1H), 7.23 (d, 2H), 6.75 (d, 2H), 6.39 (m, 1H), 6.28 (m, 1H), 5.77 (m, 1H), 5.01 (m, 1H), 4.48 (s, 1H), 4.42 (s, 1H), 4.24 (s, 1H), 4.19 (s, 1H), 3.96 (m, 2H), 3.82 (m, 2H), 3.05 (m, 2H), 2.88 (m, 2H), 2.55 (s, 3H), 2.09 (s, 3H); C-HPLC-29 (mobile phase: [Hexane+0.1% $Et_2NH$]/[IPA+0.1% $Et_2NH$] gradient): Rt=11.2 min.

Step-6: Example 52b: 1-(6-(4-(5-chloro-6-methyl-1H-indazol-4-yl)-3-(4-(2-hydroxyethoxy)phenyl)-5-methyl-1H-pyrazol-1-yl)-2-azaspiro[3.3]heptan-2-yl)prop-2-en-1-one 2-(4-(1-(2-Acryloyl-2-azaspiro[3.3]heptan-6-yl)-4-(5-chloro-6-methyl-1H-indazol-4-yl)-5-methyl-1H-pyrazol-3-yl)phenoxy)ethyl acetate (0.05 g, 0.08 mmol) Isomer-I was dissolved in MeOH (2.5 mL) and cooled to 0° C. $LiOH.H_2O$ (1M in water, 0.08 mL, 0.08 mmol) was added dropwise and the reaction mixture was stirred at RT for 1 h. After completion of the reaction, the RM was diluted with water and extracted with EtOAc (×2). The combined organic layers were washed with water, brine, dried ($Na_2SO_4$), filtered and concentrated under vacuum. The crude residue was purified by C18 silica gel (15 micron) reverse phase chromatography (eluent: 0-40% $CH_3CN$ in $H_2O$ containing 0.025% $NH_3$) to afford the title product: C-HPLC-29 (mobile phase: [Hexane+0.1% $Et_2NH$]/[IPA+0.1% $Et_2NH$] gradient): Rt=9.37 min.

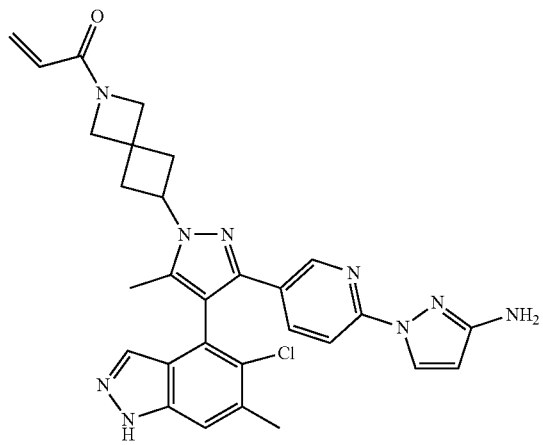 [SMILES: C=CC(=O)N1CC2(CC(n3nc(-c4ccc(-n5ccc(N)n5)nc4)c(-c4c(Cl)c(C)cc5[nH]ncc45)c3C)C2)C1]

Example 53: 1-(6-(3-(6-(3-amino-1H-pyrazol-1-yl)pyridin-3-yl)-4-(5-chloro-6-methyl-1H-indazol-4-yl)-5-methyl-1H-pyrazol-1-yl)-2-azaspiro[3.3]heptan-2-yl)prop-2-en-1-one The title example was prepared using similar method to Method-1 b step 2 and 3 from tert-butyl 6-(3-(6-(3-amino-1H-pyrazol-1-yl)pyridin-3-yl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (prepared in 2 steps as described below). $^1$H NMR (400 MHz, DMSO-$d_6$) δ 13.23 (s, 1H), 8.12 (s, 1H), 7.90-7.86 (m, 2H), 7.59 (s, 1H), 7.49 (m, 2H), 6.36 (m, 1H), 6.13 (m, 1H), 5.73 (s, 1H), 5.69 (m 2H), 5.26 (s, 2H), 4.93 (m, 1H), 4.39 (s, 1H), 4.32 (s, 1H), 4.1 (s, 1H), 4.03 (s, 1H), 2.89-2.79 (m, 4H), 2.03 (s, 3H); LCMS-1: Rt=1.53 min; MS m/z [M+H]$^+$: 554.8/556.8.

Tert-butyl 6-(3-(6-(3-amino-1H-pyrazol-1-yl)pyridin-3-yl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate Step 1: Tert-butyl 6-(4-(5-chloro-6-methyl-1-(tetrahydro-2H-pyran-2-yl)-1H-indazol-4-yl)-5-methyl-3-(6-(3-nitro-1H-pyrazol-1-yl)pyridin-3-yl)-1H-pyrazol-1-yl)-2-azaspiro[3.3]heptane-2-carboxylate Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 0.50 g, 0.83 mmol), 2-(3-nitro-1H-pyrazol-1-yl)-5-(4,4,5,5-tetramethyl-1,3,2-dioxaborolan-2-yl)pyridine (Intermediate B16) (0.52 g, 1.65 mmol) and $K_3PO_4$ (0.53 g, 2.48 mmol) were dissolved in 1,4-dioxane (4 mL) and $H_2O$ (2 mL). The reaction mixture was degassed with $N_2$ for 5 min. Ruphos (0.04 g, 0.08 mmol) and Ruphos-Pd-G3 (0.035 g, 0.04 mmol) were added and the reaction mixture was stirred at 120° C. for 1 h. After completion of the reaction, the RM was diluted with water and extracted with ethyl acetate (×2). The combined organic layers were washed with brine, dried ($Na_2SO_4$), filtered and concentrated under vacuum. The crude residue was purified by normal phase chromatography (eluent: 30-40% EtOAc in Hexane) to obtain the desired product. LCMS-1: Rt=2.24 min; MS m/z [M+H]$^+$: 714.6/716.5.

Step 2: Tert-butyl 6-(3-(6-(3-amino-1H-pyrazol-1-yl)pyridin-3-yl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate Tert-butyl 6-(4-(5-chloro-6-methyl-1-(tetrahydro-2H-pyran-2-yl)-1H-indazol-4-yl)-5-methyl-3-(6-(3-nitro-1H-pyrazol-1-yl)pyridin-3-yl)-1H-pyrazol-1-yl)-2-azaspiro[3.3]heptane-2-carboxylate (0.53 g, 0.7 mmol) was dissolved in dry IPA under nitrogen atmosphere. 10% Dry Pd/C (0.25 g) was added and the reaction mixture was stirred under an atmosphere of $H_2$ (1 atm) at RT for 1 h. The RM was filtered through a pad of celite, filtrated and was concentrated in vacuo to afford the desired product which was directly used in the next step without further purification. LCMS-1: Rt=2.06, 2.09 min; MS m/z [M+H]$^+$: 684.5/686.5.

Method-2: Synthetic Scheme

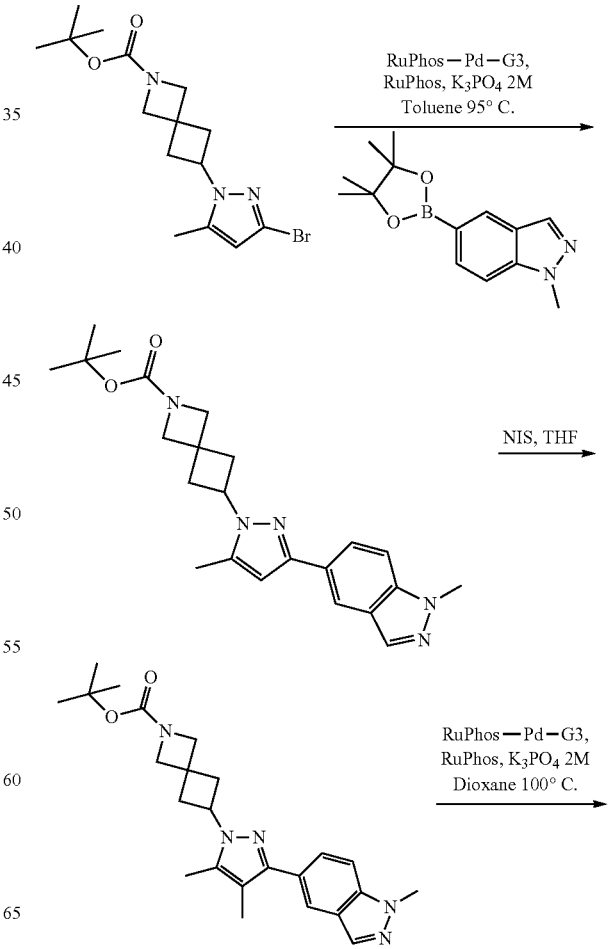

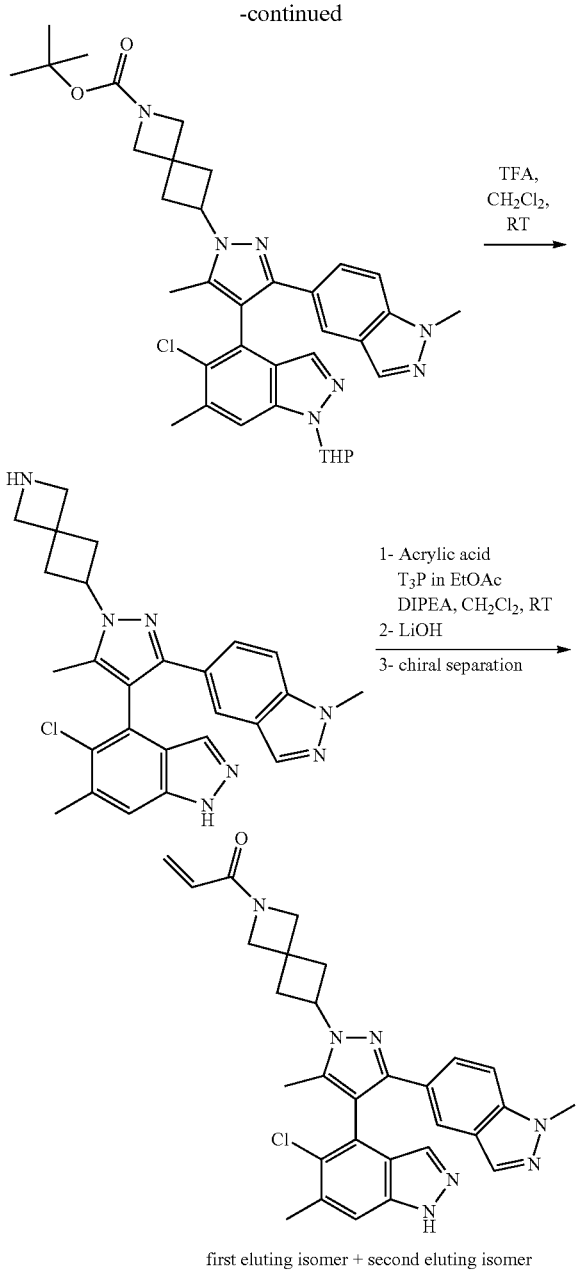

Examples 1a: a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one and 1b: a(S)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one Alternatively, examples 1a and 1b can be prepared following the method described below:

Step 1: Tert-butyl 6-(5-methyl-3-(1-methyl-1H-indazol-5-yl)-1H-pyrazol-1-yl)-2azaspiro[3.3]heptane-2-carboxylate To a stirred solution of tert-butyl 6-(3-bromo-5-methyl-1H-pyrazol-1-yl)-2-azaspiro[3.3]heptane-2-carboxylate (Intermediate C3, 2.00 g, 5.61 mmol), 1-methyl-5-(4,4,5,5-tetramethyl-1,3,2-dioxaborolan-2-yl)-1H-indazole (1.59 g, 6.18 mmol) and $K_3PO_4$ (3.57 g, 16.8 mmol) in dioxane (20 mL) and $H_2O$ (4 mL) was added under argon atmosphere RuPhos (0.26 g, 0.56 mmol) and RuPhos-Pd-G3 (0.47 g, 0.56 mmol). The reaction mixture was stirred for 1 h at 100° C. The reaction mixture was quenched by addition of a sat. aq. $NaHCO_3$ solution, extracted with EtOAc (2×) and the combined organic extracts were washed with a sat. aq. $NaHCO_3$ solution, dried ($Na_2SO_4$) and evaporated. The crude residue was purified by normal phase chromatography (eluent: EtOAc in c-hexane from 0 to 90%) to give the title compound as a brown solid. UPLC-MS-3: Rt=1.14 min; MS m/z [M+H]⁺: 408.2.

Step 2: Tert-butyl 6-(4-iodo-5-methyl-3-(1-methyl-1H-indazol-5-yl)-1H-pyrazol-1-yl)-2-azaspiro[3.3]heptane-2-carboxylate To a stirred solution of tert-butyl 6-(5-methyl-3-(1-methyl-1H-indazol-5-yl)-1H-pyrazol-1-yl)-2-azaspiro[3.3]heptane-2-carboxylate (2.13 g, 5.23 mmol) in THF (50 mL) was added under argon atmosphere, NIS (1.53 g, 6.80 mmol) and the reaction mixture was stirred for 1 h at RT. The reaction mixture was quenched by addition of a sat. aq. $NaHCO_3$ solution, extracted with EtOAc (2×) and the combined organic extracts were washed with a sat. aq. $NaHCO_3$ solution, dried ($Na_2SO_4$), filtered and evaporated. The crude residue was purified by normal phase chromatography (eluent: EtOAc in c-hexane from 0 to 80%) to give the title compound as a brown solid. UPLC-MS-3: Rt=1.22 min; MS m/z [M+H]⁺: 534.1.

Step 3: Tert-butyl 6-(4-(5-chloro-6-methyl-1-(tetrahydro-2H-pyran-2-yl)-1H-indazol-4-yl)-5-methyl-3-(1-methyl-1H-indazol-5-yl)-1H-pyrazol-1-yl)-2-azaspiro[3.3]heptane-2-carboxylate To a stirred solution of tert-butyl 6-(4-iodo-5-methyl-3-(1-methyl-1H-indazol-5-yl)-1H-pyrazol-1-yl)-2-azaspiro[3.3]heptane-2-carboxylate (100 mg, 0.187 mmol), 5-chloro-6-methyl-1-(tetrahydro-2H-pyran-2-yl)-4-(4,4,5,5-tetramethyl-1,3,2-dioxaborolan-2-yl)-1H-indazole (Intermediate D1, 85 mg, 0.225 mmol) and $K_3PO_4$ (119 mg, 0.56 mmol) in dioxane (2 mL) and $H_2O$ (0.50 mL) was added under argon atmosphere RuPhos (8.75 mg, 0.019 mmol) and RuPhos-Pd-G3 (15.7 mg, 0.019 mmol). The reaction mixture was degassed with $N_2$ and stirred for 1 h at 100° C. The reaction mixture was quenched by addition of a sat. aq. $NaHCO_3$ solution, extracted with EtOAc (2×) and the combined organic extracts were washed with a sat. aq. $NaHCO_3$ solution, dried ($Na_2SO_4$), filtered and evaporated. The crude residue was diluted in THF (3 mL), SiliaMetS® Thiol (0.076 mmol) (i.e. functionalized silica gel designed to remove metals from a reaction mixture) was added and the mixture swirled for 1 h at 40° C. The mixture was filtered, the filtrate was concentrated and the crude residue was purified by normal phase chromatography (eluent: EtOAc in c-hexane 0 to 100%) to give the title compound as a yellow solid. UPLC-MS-3: Rt=1.25 min; MS m/z [M+H]⁺: 656.3/658.3.

Steps 4, 5 and Chiral Separation of the Isomers were Performed as Described in Method-1

Method-2a: similar to Method-2 except that Step 4 was performed using sulfuric acid in dioxane as described in Step 2 of Method-1a.

Method-2b: similar to Method-2 except that Step 5 was performed using acryloyl chloride and $NaHCO_3$ in THF/water as described in Step 3 of Method-1b.

Method-2c: similar to Method-2 except that NBS was used instead of NIS in Step 2.

Method-2d: similar to Method-2 except that Step 3 was performed using $Et_3N$ and acryloyl chloride in $CH_2Cl_2$ as described in Method-9 Step 3.

The following examples 54 to 58 in Table 2 below were prepared using analogous methods to Method-2 from intermediates (in Step 1 or 3) described in the intermediates synthesis section or commercially available.

| Example | Structure | Method, intermediates (in Step 1 or 3) and chiral separation conditions used and order of elution | Characterizing data |
|---|---|---|---|
| 54a/54b | 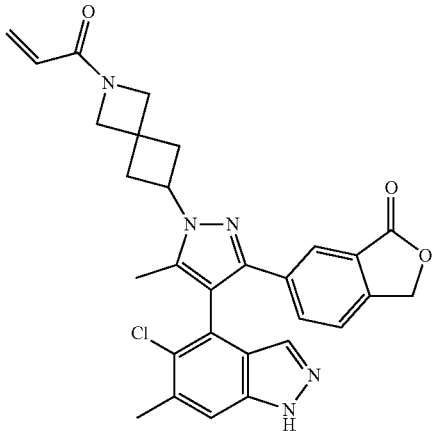<br>6-(1-(2-acryloyl-2-azaspiro[3.3]heptan-6-yl)-4-(5-chloro-6-mehtyl-1H-indazol-4-yl)-5-methyl-1H-pyrazol-3-yl)isobenzofuran-1(3H)-one | Using Method-2c,d from 6-(4,4,5,5-tetramethyl-1,3,2-dioxaborolan-2-yl)isobenzofuran-1-(3H)-one (Intermediate B17)(Step 1) and C-SFC-2 (mobile phase: $CO_2$/IPA 65/35): Example 54a = $2^{nd}$ eluting isomer, Example 54b = $1^{st}$ eluting isomer | Example 54a: $^1$H NMR (600 MHz, DMSO-$d_6$) δ 13.1 (s, 1H), 7.64-7.59 (m, 3H), 7.50-7.48 (m, 2H), 6.33 (M, 1H), 6.12 (m, 1H), 5.68 (M, 1H), 5.34 (s, 2H), 4.94 (m, 1H), 4.40 (s, 1H), 4.34 (s, 1H), 4.11 (s, 1H), 4.04 (s, 1H), 2.95-2.88 (m, 2H), 2.83-2.79 (m, 2H), 2.49 (s, 3H), 2.05 (s, 3H). UPLC-MS-14: Rt= 0.82 min; MS m/z [M + H]$^+$: 528.1/530.1; C-SFC-3 (mobile phase: $CO_2$/IPA 65/35): Rt = 2.26 min, Example 54b: C-SFC-3 (mobile phase: $CO_2$/IPA 65/35): Rt= 1.55 min |
| 55a/55b | 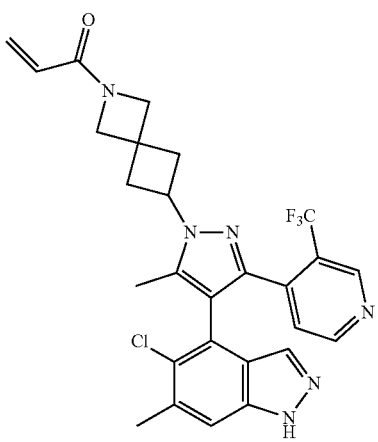<br>1-(6-(4-(5-chloro-6-methyl-1H-indazol-4-yl)-5-methyl-3-(3-(trifluoromethyl)pyridin-4-yl)-1H-pyrazol-1-yl)-2-azaspiro[3.3]heptan-2-yl)prop-2-en-1-one | Using Method-2a,b,c from [1204334-17-7] (Step 1) and C-SFC-2 (mobile phase: $CO_2$/IPA 78/22): Example 55a = $2_{nd}$ eluting isomer, Example 55b = $1^{st}$ eluting isomer | Example 55a: $^1$H NMR (600 MHz, DMSO-$d_6$) δ 13.2 (s, 1H), 8.96 (s, 1H), 8.55 (d, 1H), 7.52 (s, 1H), 7.45 (s, 1H), 6.86 (t, 1H), 6.31 (m, 1H), 6.10 (m, 1H), 5.67 (m, 1H), 4..98 (m, 1H), 4.38 (s, 1H), 4.27 (s, 1H), 4.09 (s, 1H), 3.97 (s, 1H), 2.84-2.78 (m, 4H), 2.44 (s, 3H), 2.11 (s, 3H). UPLC-MS-10: Rt = 0.96 min; MS m/z [M + H]$^+$: 541.1/543.1; C-SFC-3 (mobile phase: $CO_2$/IPA 78/22): Rt= 3.10 min, Example 55b: C-SFC-3 (mobile phase: $CO_2$/IPA 78/22): Rt = 2.27 min. |

| Example | Structure | Method, intermediates (in Step 1 or 3) and chiral separation conditions used and order of elution | Characterizing data |
|---|---|---|---|
| 56a/56b | 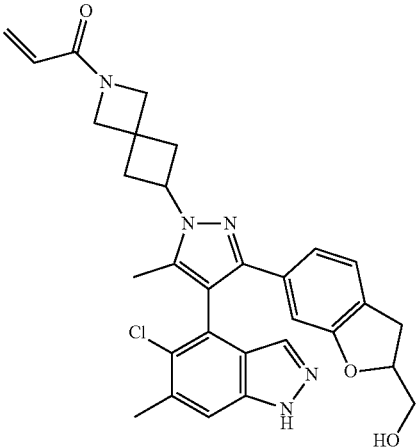<br>1-(6-(4-(5-chloro-6-methyl-1H-indazol-4-yl)-3-(2-(hydroxymethyl)-2,3-dihydrobenzofuran-6-yl)-5-methyl-1H-pyrazol-1-yl)-2-azaspiro[3.3]heptan-2-yl)prop-2-en-1-one | Using Method-2b for steps 3-5 from Intermediate C8 second eluting isomer and C-SFC-2 (mobile phase: $CO_2$/IPA 67/33): Example 56a = $2^{nd}$ eluting isomer, Example 56b = $1^{st}$ eluting isomer | Example 56a: $^1$H NMR (400 MHz, DMSO-$d_6$) δ 13.09 (s, 1H), 7.52 (s, 1H), 7.40 (s, 1H), 7.31 (s, 1H), 6.71 (d, 1H), 6.41 (d, 1H), 6.37-6.25 (m, 1H), 6.17-6.02 (m, 1H), 5.73-5.59 (m, 1H), 4.92 (t, 1H), 4.90-4.81 (m, 1H), 4.76-4.65 (m, 1H), 4.38 (s, 1H), 4.31 (s, 1H), 4.09 (s, 1H), 4.02 (s, 1H), 3.52-3.48 (m, 2H), 3.09 (dd, 1H), 2.90-2.81 (m, 3H), 2.80-2.72 (m, 2H), 2.47 (s, 3H), 1.98 (s, 3H); UPLC-MS-3: Rt = 0.89 min; MS m/z [M + H]$^+$: 544.4/546.4; C-SFC-3 (mobile phase: $CO_2$/IPA 67/33): Rt = 2.77 min, Example 56b: C-SFC-3 (mobile phase: $CO_2$/IPA 67/33): Rt = 1.96 min. |
| 57a/57b | 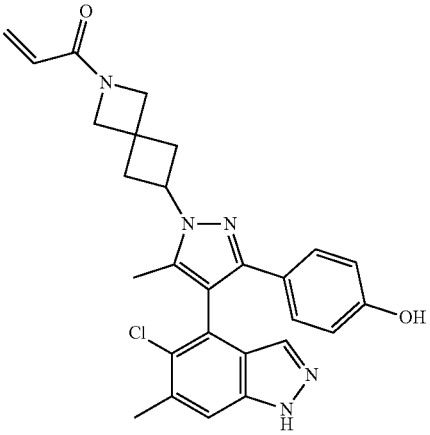<br>1-(6-(4-(5-chloro-6-methyl-1H-indazol-4-yl)-3-(4-hydroxyphenyl)-5-methyl-1H-pyrazol-1-yl)-2-azaspiro[3.3]heptan-2-yl)prop-2-en-1-one | Using Method-2c from 4-(4,4,5,5-tetramethyl-1,3,2-dioxaborolan-2-yl)phenol (Step 1) and C-SFC-7 (mobile phase: $CO_2$/IPA 60/40): Example 57a = $2^{nd}$ eluting isomer, Example 57b = $1^{st}$ eluting isomer | Example 57a: $^1$H NMR (400 MHz, DMSO-$d_6$) δ 13.08 (s, 1H), 9.30 (s, 1H), 7.52 (s, 1H), 7.38 (s, 1H), 7.05 (d, 2H), 6.52 (d, 2H), 6.35-6.28 (m, 1H), 6.12-6.08 (m, 1H), 5.69-5.65 (m, 1H), 4.90-4.81 (m, 1H), 4.38 (s, 1H), 4.30 (s, 1H), 4.09 (s, 1H), 4.02 (s, 1H), 2.90-2.73 (m, 4H), 1.98 (s, 3H); UPLC-MS-3: Rt = 0.88 min; MS m/z [M + H]$^+$: 488.2/490.2; C-SFC-8 (mobile phase: $CO_2$/IPA 60/40): Rt = 2.07 min, Example 57b: C-SFC-8 (mobile phase: $CO_2$/IPA 60/40): Rt = 1.52 min. |

| Example | Structure | Method, intermediates (in Step 1 or 3) and chiral separation conditions used and order of elution | Characterizing data |
|---------|-----------|---------------------------------------------------------------------------------------------------|---------------------|
| 58a/58b | 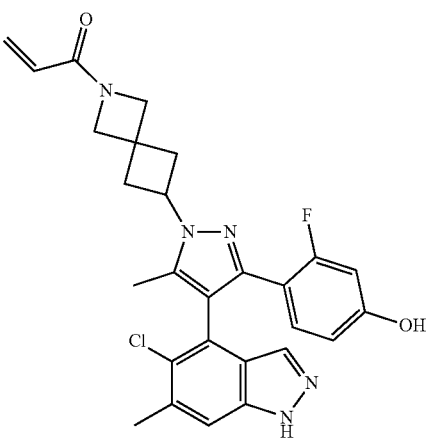  1-(6-(4-(5-chloro-6-methyl-1H-indazol-4-yl)-3-(2-fluoro-4-hydroxyphenyl)-5-methyl-1H-pyrazol-1-yl)-2-azaspiro[3.3]heptan-2-yl)prop-2-en-1-one | Using Method-2c from 3-fluoro-4-(4,4,5,5-tetramethyl-1,3,2-dioxaborolan-2-yl)phenol (Step 1) and C-SFC-1 (mobile phase: $CO_2$/[IPA + 0.1% $NEt_3$] 72/28): Example 58a = $2^{nd}$ eluting isomer, Example 58b = $1^{st}$ eluting isomer | Example 58a: $^1$H NMR (400 MHz, DMSO-$d_6$) δ 12.98 (s, 1H), 9.79 (s, 1H), 7.43 (s, 1H), 7.34 (s, 1H), 7.07 (t, 1H), 6.47 (dd, 1H), 6.35-6.27 (m, 2H), 6.13-6.07 (m, 1H), 5.69-5.65 (m, 1H), 4.93-4.84 (m, 1H), 4.38 (s, 1H), 4.28 (s, 1H), 4.09 (s, 1H), 3.99 (s, 1H), 2.89-2.74 (m, 4H), 2.44 (s, 3H), 2.05 (s, 3H). UPLC-MS-3: Rt = 0.92 min; MS m/z [M + H]$^+$: 506.3/608.3; C-SFC-3 (mobile phase: $CO_2$/[IPA + 0.025% $NH_3$] 70/30): Rt = 2.49 min, Example 58b: C-SFC-3 (mobile phase: $CO_2$/[IPA + 0.025% $NH_3$] 70/30): Rt = 1.78 min. |

Examples 59a/59b: 1-(6-(4-(5-chloro-6-methyl-1H-indazol-4-yl)-5-methyl-3-(1H-pyrrolo[2,3-c]pyridin-2-yl)-1H-pyrazol-1-yl)-2-azaspiro[3.3]heptan-2-yl)prop-2-en-1-one

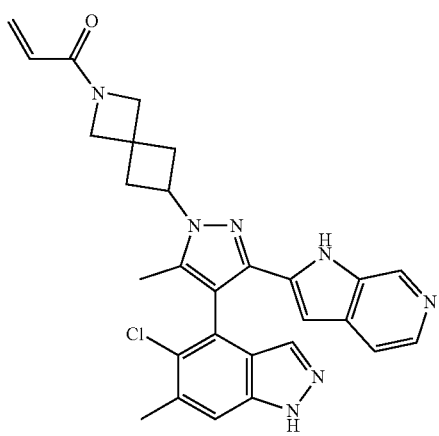 [SMILES: C=CC(=O)N1CC2(CC(n3nc(-c4cc5ccncc5[nH]4)c(-c4c(Cl)c(C)cc5[nH]ncc45)c3C)C2)C1]

The title example was prepared using a similar method to Method-2a,b Steps 3 to 5 from tert-butyl 6-(4-bromo-5-methyl-3-(1H-pyrrolo[2,3-c]pyridin-2-yl)-1H-pyrazol-1-yl)-2-azaspiro[3.3]heptane-2-carboxylate (prepared as described below). The isomers were separated by chiral SFC (C-SFC-7; mobile phase: $CO_2$/[MeOH+0.1% $NEt_3$]: 50/50) to give the title compound Example 59a as the second eluting peak: $^1$H NMR (600 MHz, DMSO-$d_6$) δ 13.20 (d, 1H), 11.68 (s, 1H), 8.71 (s, 1H), 7.92 (d, 1H), 7.63 (s, 1H), 7.50 (s, 1H), 7.20 (d, 1H), 6.52 (s, 1H), 6.41-6.28 (m, 1H), 6.17-6.02 (m, 1H), 5.74-5.61 (m, 1H), 5.06-4.87 (m, 1H), 4.42 (s, 1H), 4.34 (s, 1H), 4.13 (s, 1H), 4.05 (s, 1H), 3.04-2.91 (m, 2H), 2.84 (s, 2H), 2.53 (s, 3H), 2.04 (s, 3H); UPLC-MS-3: Rt=0.77 min; MS m/z [M+H]$^+$ 512.2/514.2; C-SFC-8 (mobile phase: $CO_2$/[MeOH+0.1% $NEt_3$]: 50/50): Rt=2.43 min. The other isomer Example 59b was obtained as the first eluting peak: C-SFC-8 (mobile phase: mobile phase: $CO_2$/[MeOH+0.1% $NEt_3$]: 50/50): Rt=1.28 min.

Tert-butyl 6-(4-bromo-5-methyl-3-(1H-pyrrolo[2,3-c]pyridin-2-yl)-1H-pyrazol-1-yl)-2-azaspiro[3.3]heptane-2-carboxylate To a stirred solution of tert-butyl 6-(4-bromo-3-iodo-5-methyl-1H-pyrazol-1-yl)-2-azaspiro[3.3]heptane-2-carboxylate (Intermediate C7, 400 mg, 0.83 mmol), (1H-pyrrolo[2,3-c]pyridin-2-yl)boronic acid (202 mg, 1.24 mmol) and potassium phosphate (2M aq. solution, 1.24 mL, 2.48 mmol) in 1,4-dioxane (10 mL) was added tetrakis (triphenylphosphine)palladium (96 mg, 0.08 mmol). The reaction mixture was stirred at 90° C. for 1 h. Then, It was allowed to cool to RT, diluted with water (10 mL) and extracted twice with EtOAc. The combined organic layers were concentrated and the remaining crude material purified by normal flash column chromatography (eluent: MeOH in $CH_2Cl_2$ from 0 to 5%) to give the title compound. UPLC-MS-4: Rt=4.19 min; MS m/z [M+H]$^+$: 472.0/474.0.

Examples 60a/60b: 1-(6-(4-(5-chloro-6-methyl-1H-indazol-4-yl)-3-(2-fluoro-4-(2-methoxyethoxy)phenyl)-5-methyl-1H-pyrazol-1-yl)-2-azaspiro[3.3]heptan-2-yl)prop-2-en-1-one

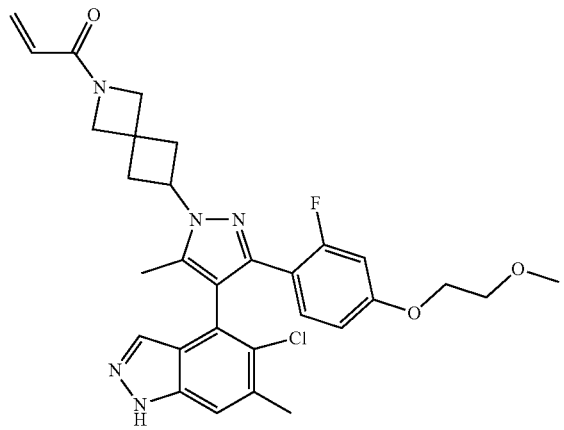 [SMILES: C=CC(=O)N1CC2(CC(n3nc(-c4ccc(OCCOC)cc4F)c(-c4c(Cl)c(C)cc5[nH]ncc45)c3C)C2)C1]

The title examples were prepared using a similar method to Method-2c starting from tert-butyl 6-(3-bromo-5-methyl-1H-pyrazol-1-yl)-2-azaspiro[3.3]heptane-2-carboxylate (Intermediate C3) and 3-fluoro-4-(4,4,5,5-tetramethyl-1,3,2-dioxaborolan-2-yl)phenol with an additional alkylation step introduced between step 1 and step 2 (described below to prepare tert-butyl 6-(3-(2-fluoro-4-(2-methoxyethoxy)phenyl)-5-methyl-1H-pyrazol-1-yl)-2-azaspiro[3.3]heptane-2-carboxylate). The isomers were separated by chiral SFC (C-SFC-1; mobile phase: $CO_2$/[IPA+0.1% $NEt_3$]: 70/30) to give the title compound Example 60a as the second eluting peak: $^1$H NMR (400 MHz, DMSO-$d_6$) δ 12.99 (s, 1H), 7.44 (s, 1H), 7.37 (s, 1H), 7.18 (t, 1H), 6.68-6.60 (m, 2H), 6.35-6.26 (m, 1H), 6.13-6.07 (m, 1H), 5.69-5.65 (m, 1H), 4.95-4.85 (m, 1H), 4.38 (s, 1H), 4.28 (s, 1H), 4.09 (s, 1H), 4.02-3.99 (m, 3H), 3.60-3.57 (m, 2H), 3.26 (s, 3H), 2.90-2.75 (m, 4H), 2.44 (s, 3H), 2.06 (s, 3H); UPLC-MS-3: Rt=0.97 min; MS m/z [M+H]$^+$ 564.5/566.5; C-SFC-3 (mobile phase: $CO_2$/[IPA+0.1% $NEt_3$]: 70/30): Rt=2.50 min. The other isomer Example 60b was obtained as the first eluting peak: C-SFC-3 (mobile phase: mobile phase: $CO_2$/[IPA+0.1% $NEt_3$]: 70/30): Rt=1.74 min.

Tert-butyl 6-(3-(2-fluoro-4-(2-methoxyethoxy)phenyl)-5-methyl-1H-pyrazol-1-yl)-2-azaspiro[3.3]heptane-2-carboxylate A solution of tert-butyl 6-(3-(2-fluoro-4-hydroxyphenyl)-5-methyl-1H-pyrazol-1-yl)-2-azaspiro[3.3]heptane-2-carboxylate (Step 1, 710 mg, 1.65 mmol), 1-bromo-2-methoxyethane (0.310 mL, 3.30 mmol) and cesium carbonate (1075 mg, 3.30 mmol) in DMF (5 mL) was stirred at 60° C. for 2 h. The reaction mixture was diluted with EtOAc and water, extracted with EtOAc, the organic phase washed with brine, dried (phase separator) and concentrated under reduced pressure. The crude residue was purified by normal flash column chromatography (eluent: c-hexane/EtOAc 100/0 to 70/30 within 30 min) to give the title compound. UPLC-MS-3: Rt=1.20 min; MS m/z [M+H]$^+$ 446.3.

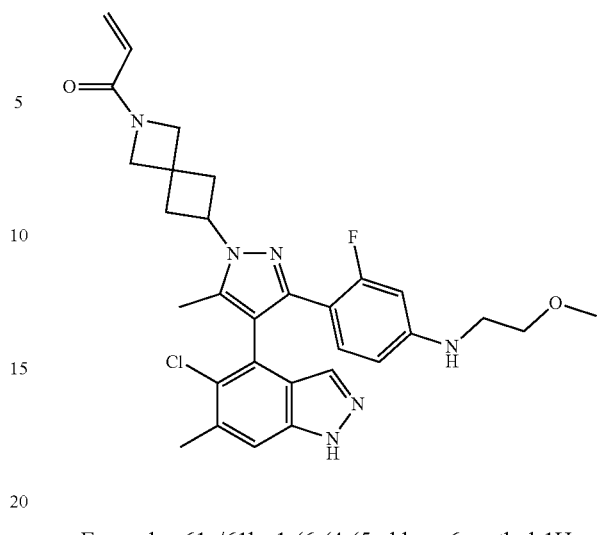

Examples 61a/61b: 1-(6-(4-(5-chloro-6-methyl-1H-indazol-4-yl)-3-(2-fluoro-4-((2-methoxyethyl)amino)phenyl)-5-methyl-1H-pyrazol-1-yl)-2-azaspiro[3.3]heptan-2-yl)prop-2-en-1-one The title examples were prepared using a similar method to Method-2c starting from tert-butyl 6-(3-bromo-5-methyl-1H-pyrazol-1-yl)-2-azaspiro[3.3]heptane-2-carboxylate (Intermediate C3) and benzyl (3-fluoro-4-(4,4,5,5-tetramethyl-1,3,2-dioxaborolan-2-yl)phenyl)carbamate with an additional alkylation step introduced between Step 1 and Step 2, and an additional hydrogenation step introduced between Step 3 and Step 4, (described below to prepare Tert-butyl 6-(3-(4-(((benzyloxy)carbonyl)(2-methoxyethyl)amino)-2-fluorophenyl)-5-methyl-1H-pyrazol-1-yl)-2-azaspiro[3.3]heptane-2-carboxylate and Tert-butyl 6-(4-(5-chloro-6-methyl-1-(tetrahydro-2H-pyran-2-yl)-1H-indazol-4-yl)-3-(2-fluoro-4-((2-methoxyethyl)amino)phenyl)-5-methyl-1H-pyrazol-1-yl)-2-azaspiro[3.3]heptane-2-carboxylate). The isomers were separated by chiral SFC (C-SFC-1; mobile phase: $CO_2$/[IPA+0.1% $NEt_3$]: 70/30) to give the title compound Example 61a as the second eluting peak: $^1$H NMR (400 MHz, DMSO-$d_6$) δ 12.96 (s, 1H), 7.42 (s, 1H), 7.34 (s, 1H), 6.94 (t, 1H), 6.35-6.25 (m, 2H), 6.15-6.07 (m, 2H), 5.86 (t, 1H), 5.69-5.64 (m, 1H), 4.91-4.81 (m, 1H), 4.37 (s, 1H), 4.28 (s, 1H), 4.09 (s, 1H), 3.99 (s, 1H), 3.41 (t, 2H), 3.24 (t, 3H), 3.09 (q, 2H), 2.88-2.76 (m, 4H), 2.44 (s, 3H), 2.04 (s, 3H); UPLC-MS-3: Rt=0.94 min; MS m/z [M+H]$^+$: 563.5/565.5; C-SFC-3 (mobile phase: $CO_2$/[IPA+0.025% $NH_3$]: 70/30): Rt=3.55 min. The other isomer Example 61b was obtained as the first eluting peak: C-SFC-3 (mobile phase: mobile phase: $CO_2$/[IPA+0.025% $NH_3$]: 70/30): Rt=2.55 min.

Tert-butyl 6-(3-(4-(((benzyloxy)carbonyl)(2-methoxyethyl)amino)-2-fluorophenyl)-5-methyl-1H-pyrazol-1-yl)-2-azaspiro[3.3]heptane-2-carboxylate To a stirred solution of tert-butyl 6-(3-(4-(((benzyloxy)carbonyl)amino)-2-fluorophenyl)-5-methyl-1H-pyrazol-1-yl)-2-azaspiro[3.3]heptane-2-carboxylate (Step 1, 1.40 g, 2.55 mmol) in DMF (20 mL) was added sodium hydride (60% in mineral oil, 0.123 g, 3.07 mmol) under an inert atmosphere. After 15 min, 1-bromo-2-methoxyethane (1.20 mL, 12.8 mmol) was added and the reaction mixture was stirred at RT overnight. The reaction mixture was quenched with water, extracted with EtOAc, the organic phase was washed with brine, dried (phase separator) and concentrated under reduced pressure. The crude residue was purified by normal phase chromatography (eluent: c-hexane/EtOAc 100/0 to 70/30 within 30 min) to give the title compound. UPLC-MS-3: Rt=1.30 min; MS m/z [M+H]$^+$: 579.4.

Tert-butyl 6-(4-(5-chloro-6-methyl-1-(tetrahydro-2H-pyran-2-yl)-1H-indazol-4-yl)-3-(2-fluoro-4-((2-methoxyethyl)amino)phenyl)-5-methyl-1H-pyrazol-1-yl)-2-azaspiro[3.3]heptane-2-carboxylate A solution of tert-butyl 6-(3-(4-(((benzyloxy)carbonyl)(2-methoxyethyl)amino)-2-fluorophenyl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (470 mg, 0.511 mmol) and palladium on carbon (5.44 mg, 0.051 mmol) in MeOH (10 mL) was stirred under a hydrogen atmosphere at RT for 0.5 h. The reaction mixture was filtered and concentrated under reduced pressure. The crude residue was purified by normal phase chromatography (eluent: c-hexane/EtOAc 100/0 to 0/100 within 30 min) to give the title compound. UPLC-MS-3: Rt=1.25 min; MS m/z [M+H]$^+$: 693.4/695.4.

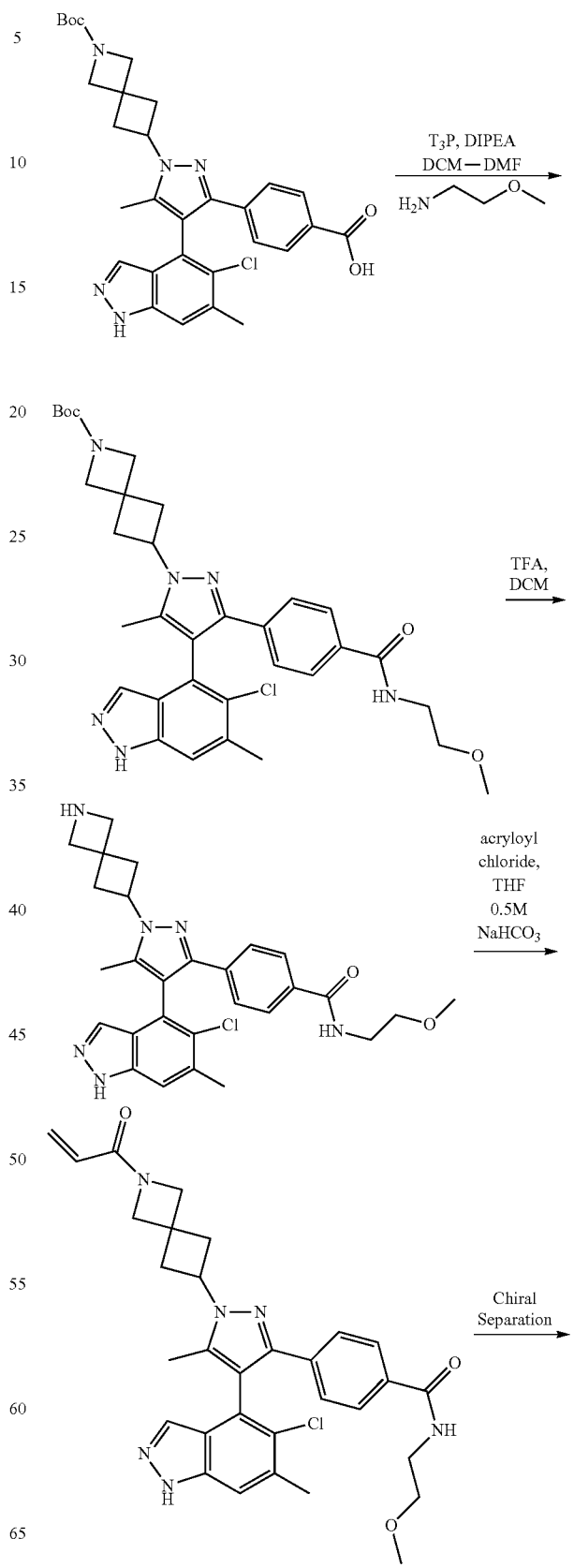

Method-3: Synthetic Scheme

-continued

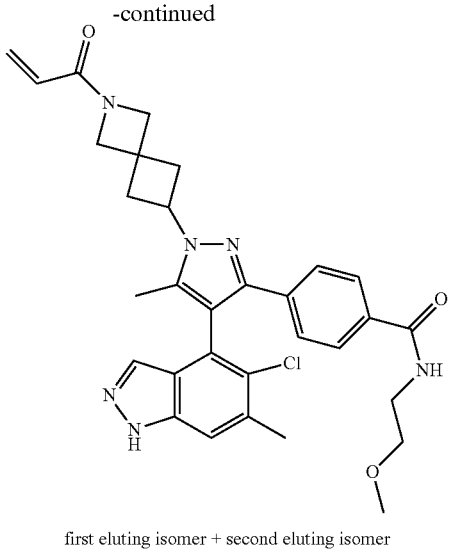

first eluting isomer + second eluting isomer

Examples 62a/62b: 4-(1-(2-acryloyl-2-azaspiro[3.3]heptan-6-yl)-4-(5-chloro-6-methyl-1H-indazol-4-yl)-5-methyl-1H-pyrazol-3-yl)-N-(2-methoxyethyl)benzamide Step 1: Tert-butyl 6-(4-(5-chloro-6-methyl-1-tosyl-1H-indazol-4-yl)-3-(4-(methoxycarbonyl)phenyl)-5-methyl-1H-pyrazol-1-yl)-2-azaspiro[3.3]heptane-2-carboxylate A solution of tert-butyl 6-(3-bromo-4-(5-chloro-6-methyl-1-tosyl-1H-indazol-4-yl)-5-methyl-1H-pyrazol-1-yl)-2-azaspiro[3.3]heptane-2-carboxylate (Intermediate C6) (1.00 g, 1.26 mmol), methyl 4-(4,4,5,5-tetramethyl-1,3,2-dioxaborolan-2-yl)benzoate (0.40 g, 1.51 mmol), RuPhos (0.06 g, 0.13 mmol), RuPhos-Pd-G3 (0.10 g, 0.13 mmol) and potassium phosphate (2N, 1.89 mL, 3.78 mmol) in dioxane (8 mL) was stirred at 80° C. for 1.5 h. The reaction mixture was cooled to RT, diluted with EtOAc and water, extracted with EtOAc, the combined organic phases washed with brine, dried (Na$_2$SO$_4$), filtered and concentrated under reduced pressure. The crude residue was purified by normal phase chromatography (eluent: c-hexane/EtOAc 100/0 to 50/50 within 30 min) to give product with some impurity. A second purification was done by normal phase chromatography (eluent: c-hexane/EtOAc 100/0 to 60/40 within 30 min) to yield the title compound (86% purity by UPLC) with some minor impurity. $^1$H NMR (600 MHz, DMSO-d$_6$) δ 8.19 (s, 1H), 7.89 (s, 1H), 7.79 (d, 2H), 7.67 (d, 2H), 7.41 (d, 2H), 7.22 (d, 2H), 4.88 (m, 1H), 4.01 (m, 2H), 3.91 (m, 2H), 3.81 (s, 3H), 2.86-2.71 (m, 4H), 2.59 (s, 3H), 2.37 (s, 3H), 2.00 (s, 3H), 1.39 (s, 9H); UPLC-MS-10: Rt=1.32 min; MS m/z [M+H]$^+$: 730.2/732.2.

Step 2: 4-(1-(2-(Tert-butoxycarbonyl)-2-azaspiro[3.3]heptan-6-yl)-4-(5-chloro-6-methyl-1H-indazol-4-yl)-5-methyl-1H-pyrazol-3-yl)benzoic acid A solution of tert-butyl 6-(4-(5-chloro-6-methyl-1-tosyl-1H-indazol-4-yl)-3-(4-(methoxycarbonyl)phenyl)-5-methyl-1H-pyrazol-1-yl)-2-azaspiro[3.3]heptane-2-carboxylate (Step 1, 100 mg, 0.14 mmol) and LiOH (2N, 0.14 mL, 0.27 mmol) in THF (2 mL) was stirred at 20° C. for 2.5 h. The mixture was warmed to 45° C. for 1.5 h, then to 70° C. for 2.5 h. After cooling to RT the reaction mixture was lyophilized and the crude product used in the next reaction without further purification. UPLC-MS-10: Rt=1.32 min; MS m/z [M+H]$^+$: 562.2/564.2.

Step 3: Tert-butyl 6-(4-(5-chloro-6-methyl-1H-indazol-4-yl)-3-(4-((2-methoxyethyl)carbamoyl)phenyl)-5-methyl-1H-pyrazol-1-yl)-2-azaspiro[3.3]heptane-2-carboxylate To a solution of 4-(1-(2-(tert-butoxycarbonyl)-2-azaspiro[3.3]heptan-6-yl)-4-(5-chloro-6-methyl-1H-indazol-4-yl)-5-methyl-1H-pyrazol-3-yl)benzoic acid (Step 2, 93 mg, 0.12 mmol) and DIPEA (0.10 mL, 0.59 mmol) in CH$_2$Cl$_2$/DMF (2.5 mL, 4/1 ratio) was added propylphosphonic anhydride (50% in EtOAc, 0.10 mL, 0.177 mmol) and the resulting solution was stirred at RT. After 10 min, 2-methoxyethan-1-amine (0.03 mL, 0.35 mmol) was added and the reaction mixture was stirred at RT for 1 h. The reaction mixture was concentrated under reduced pressure and the crude residue purified by normal phase chromatography (eluent: c-hexane/EtOAc 100/0 to 0/100 within 30 min) to give the title compound. $^1$H NMR (400 MHz, DMSO-d$_6$) δ 13.16 (s, 1H), 8.36 (t, 1H), 7.62 (d, 2H), 7.57 (s, 1H), 7.43 (s, 1H), 7.29 (d, 2H), 4.88 (m, 1H), 4.02 (brs, 2H), 3.94 (brs, 2H), 3.42-3.36 (m, 4H), 3.23 (s, 3H), 2.86-2.75 (m, 4H), 2.49 (s, 3H), 2.02 (s, 3H), 1.40 (s, 9H); UPLC-MS-10: Rt=1.09 min; MS m/z [M+H]$^+$: 619.2/621.3.

Step 4: 4-(4-(5-Chloro-6-methyl-1H-indazol-4-yl)-5-methyl-1-(2-azaspiro[3.3]heptan-6-yl)-1H-pyrazol-3-yl)-N-(2-methoxyethyl)benzamide To a solution of tert-butyl 6-(4-(5-chloro-6-methyl-1H-indazol-4-yl)-3-(4-((2-methoxyethyl)carbamoyl)phenyl)-5-methyl-1H-pyrazol-1-yl)-2-azaspiro[3.3]heptane-2-carboxylate (Step 3, 109 mg, 0.14 mmol) in THF (2 mL) was added TFA (0.33 mL, 4.28 mmol) and the reaction mixture was stirred at RT for 3 h. The reaction mixture was concentrated under reduced pressure and the oily residue was dissolved in MeOH and put on a Waters cartridge PoraPak™ Rxn Cx previously washed with MeOH. After rinsing with MeOH the resin was rinsed with NH$_3$ (7N in MeOH), the basic MeOH solution was concentrated under reduced pressure to give the title compound which was used in the next reaction without further purification. UPLC-MS-6: Rt=0.72 min; MS m/z [M+H]$^+$: 519.2/521.2.

Step 5: 4-(1-(2-Acryloyl-2-azaspiro[3.3]heptan-6-yl)-4-(5-chloro-6-methyl-1H-indazol-4-yl)-5-methyl-1H-pyrazol-3-yl)-N-(2-methoxyethyl)benzamide To a solution of 4-(4-(5-chloro-6-methyl-1H-indazol-4-yl)-5-methyl-1-(2-azaspiro[3.3]heptan-6-yl)-1H-pyrazol-3-yl)-N-(2-methoxyethyl)benzamide (Step 4, 55 mg, 0.08 mmol) in THF (3 mL) was added sodium bicarbonate (0.80 mL, 0.40 mmol) followed directly by acryloyl chloride (6.54 μl, 0.08 mmol). The reaction mixture was stirred at 0° C. for 1 h. Excess acryloyl chloride was destroyed by addition of LiOH (2N, 2 mL) and stirring at RT for 1 h. The reaction mixture was extracted with DCM, the organic phases dried (phase separator), concentrated under reduced pressure and the crude residue purified by normal phase chromatography (eluent: DCM/MeOH 100/0 to 90/10 within 30 min) to give the title compound. The isomers were separated by chiral SFC (C-SFC-2: mobile phase: CO$_2$/IPA: 65/35) to give the title compound Example 62a as the second eluting isomer (white powder): $^1$H NMR (400 MHz, DMSO-d$_6$) δ 13.15 (s, 1H), 8.35 (t, 1H), 7.63 (d, 2H), 7.57 (s, 1H), 7.44 (s, 1H), 7.31 (d, 2H), 6.37-6.30 (m, 1H), 6.15-6.09 (m, 1H), 5.71-5.67 (m, 1H), 4.98-4.88 (m, 1H), 4.40 (s, 1H), 4.34 (s, 1H), 4.11 (s, 1H), 4.04 (s, 1H), 3.35-3.32 (m, 4H), 3.22 (s, 3H), 2.94-2.78 (m, 4H), 2.04 (s, 3H); UPLC-MS-10: Rt=0.88 min; MS m/z [M+H]$^+$ 573.3/575.3; C-SFC-3: (mobile phase: CO$_2$/IPA: 65/35): Rt=2.14 min. The other isomer Example 62b was obtained as the first eluting peak: C-SFC-3: (mobile phase: CO$_2$/IPA: 65/35): Rt=1.28 min.

Method-3a: similar to Method-3 except in Step 2 NaOH 2N was used instead of LiOH 2N.

The following examples 63 to 65 in Table 3 were prepared using analogous methods to Method-3, employing the appropriate commercially available pinacol (Step 1 and amine reagents (Step 3.

TABLE 3

| Example | Structure | Method, intermediates (in step 1 and 3 and chiral separation conditions used and order of elution | Characterizing data |
|---|---|---|---|
| 63a/63b | 4-(1-(2-acryloyl-2-azaspiro[3.3]heptan-6-yl)-4-(5-chloro-6-methyl-1H-indazol-4-yl)-5-methyl-1H-pyrazol-3-yl)-2-fluoro-N-(2-methoxyethyl)benzamide | Using Method-3 with methyl 2-fluoro-4-(4,4,5,5-tetramethyl-1,3,2-dioxaborolan-2-yl)benzoate (Step 1) and C-SFC-2 (mobile phase: CO$_2$/IPA 69/31): Example 63a = 2$^{nd}$ eluting isomer, Example 63b = 1$^{st}$ eluting isomer | Example 63a: $^1$H NMR (400 MHz, DMSO-d$_6$) δ 13.20 (s, 1H), 8.17 (m, 1H), 7.60 (s, 1H), 7.49 (s, 1H), 7.42 (t, 1H), 7.12 (d, 1H), 7.02 (d, 1H), 6.37-6.29 (m, 1H), 6.15-6.09 (m, 1H), 5.71-5.67 (m, 1H), 4.99-4.89 (m, 1H), 4.40 (s, 1H), 4.34 (s, 1H), 4.11 (s, 1H), 4.04 (s, 1H), 3.43-3.31 (m, 4H), 3.24 (s, 3H), 2.94-2.78 (m, 4H), 2.03 (s, 3H); UPLC-MS-10: Rt = 0.91 min; MS m/z [M + H]$^+$: 591.2/593.2; C-SFC-3 (mobile phase: CO$_2$/IPA 69/31): Rt = 2.20 min, Example 63b: C-SFC-3 (mobile phase: CO$_2$/IPA 69/31): Rt = 1.74 min. |
| 64a/64b | 5-(1-(2-acryloyl-2-azaspiro[3.3]heptan-6-yl)-4-(5-chloro-6-methyl-1H-indazol-4-yl)-5-methyl-1H-pyrazol-3-yl)-N-(2-methoxyethyl)picolinamide | Using Method-3a with methyl 5-(4,4,5,5-tetramethyl-1,3,2-dioxaborolan-2-yl)picolinate (Step 1) and C-SFC-2 (mobile phase: CO$_2$/IPA 72/28): Example 64a = 2$^{nd}$ eluting isomer, Example 64b = 1$^{st}$ eluting isomer | Example 64a: $^1$H NMR (400 MHz, DMSO-d$_6$) δ 13.22 (s, 1H), 8.61-8.57 (m, 1H), 8.22 (dd, 1H), 8.03-7.92 (m, 2H), 7.62 (s, 1H), 7.52 (s, 1H), 6.38-6.30 (m, 1H), 6.15-6.09 (m, 1H), 5.71-5.67 (m, 1H), 5.02-4.93 (m, 1H), 4.40 (s, 1H), 4.34 (s, 1H), 4.12 (s, 1H), 4.06 (s, 1H), 3.43-3.36 (m, 4H), 3.23 (s, 3H), 2.95-2.80 (m, 4H), 2.07 (s, 3H); UPLC-MS-10; Rt = 0.90 min; MS m/z [M + H]$^+$; 574.2/576.1; C-SFC-3 (mobile phase: CO$_2$/IPA 70/30): Rt = 2.90 min, Example 64b: C-SFC-3 (mobile phase: CO$_2$/IPA 70/30): Rt = 2.32 min. |

TABLE 3-continued

| Example | Structure | Method, intermediates (in step 1 and 3 and chiral separation conditions used and order of elution | Characterizing data |
| --- | --- | --- | --- |
| 65a/65b | 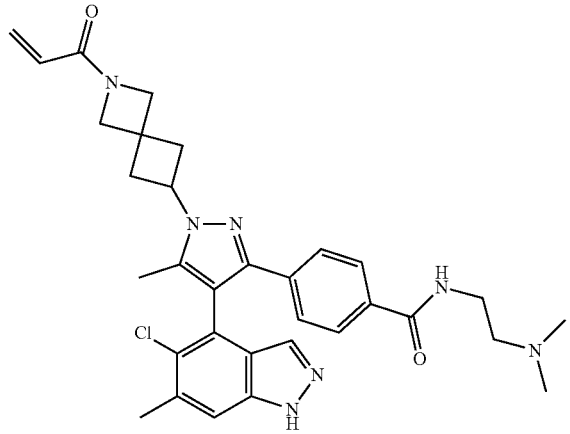

4-(1-(2-acryloyl-2-azaspiro[3.3]heptan-6-yl)-4-(5-chloro-6-methyl-1H-indazol-4-yl)-5-methyl-1H-pyrazol-3-yl)-N-(2-(dimethylamino)ethyl)benzamide | Using Method-3 with methyl 4-(4,4,5,5-tetramethyl-1,3,2-dioxaborolan-2-yl)benzoate (Step 1) and N1,N1-dimethylethane-1,2-diamine and C-SFC-1 (mobile phase: $CO_2$/[IPA + 0.1% $NEt_3$] 70/30); Example 65a = $1^{st}$ eluting isomer, Example 65b = $2^{nd}$ eluting isomer | Example 65a: $^1$H NMR (400 MHz, DMSO-$d_6$) δ 13.17 (s, 1H), 8.28 (br s, 1H), 7.65-7.61 (m, 2H), 7.58 (s, 1H), 7.44 (s, 1H), 7.37-7.30 (m, 2H), 6.38-6.30 (m, 1H), 6.15-6.09 (m, 1H), 5.71-5.67 (m, 1H), 4.98-4.88 (m, 1H), 4.40 (s, 1H), 4.34 (s, 1H), 4.11 (s, 1H), 4.04 (s, 1H), 2.94-2.78 (m, 4H), 2.46 (s, 3H), 2.24 (br s, 6H), 2.03 (s, 3H); UPLC-MS-10: Rt = 0.79 min; MS m/z [M + H]$^+$: 586.3/588.3; C-SFC-3 (mobile phase: $CO_2$/[IPA + 0.1% $NEt_3$] 70/30): Rt = 2.48 min, Example 65b: C-SFC-3 (mobile phase: $CO_2$/[IPA + 0.1% $NEt_3$] 70/30): Rt = 3.69 min. |

Method-4: Synthetic scheme

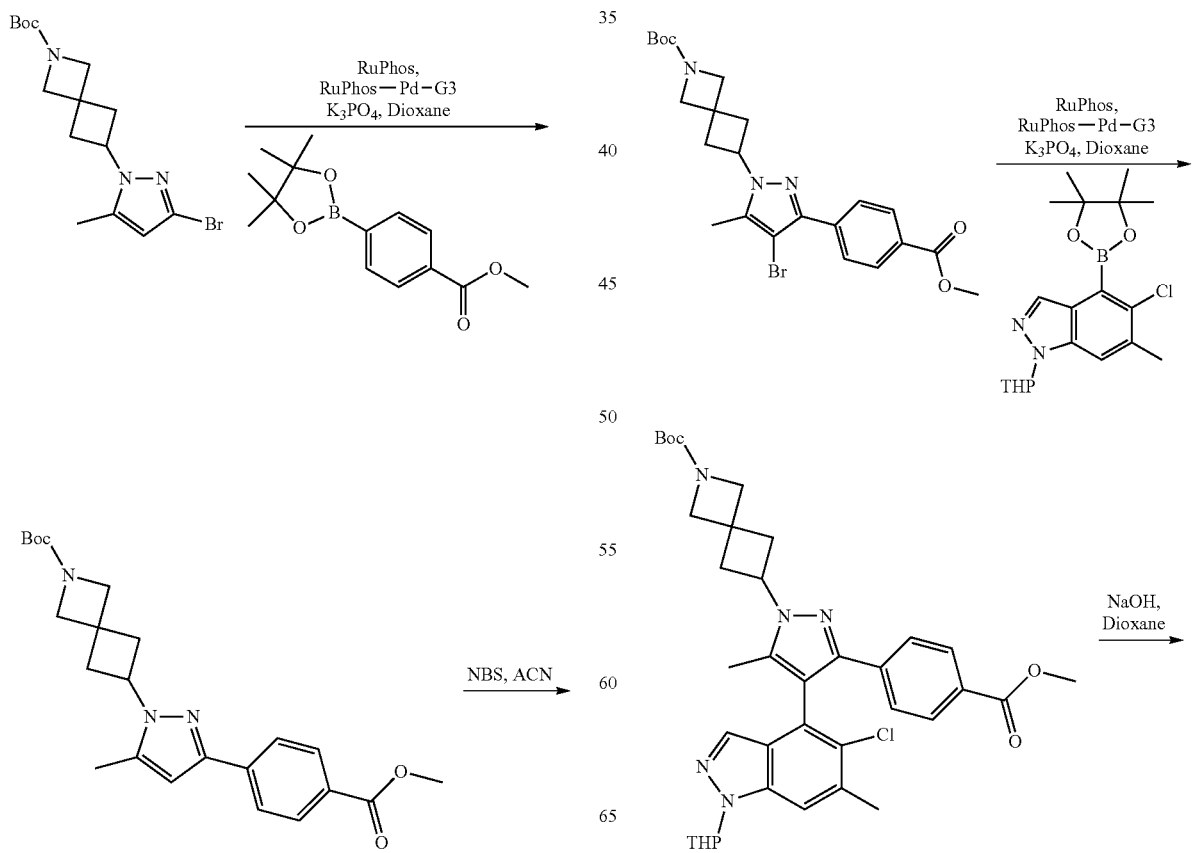

-continued

181
-continued

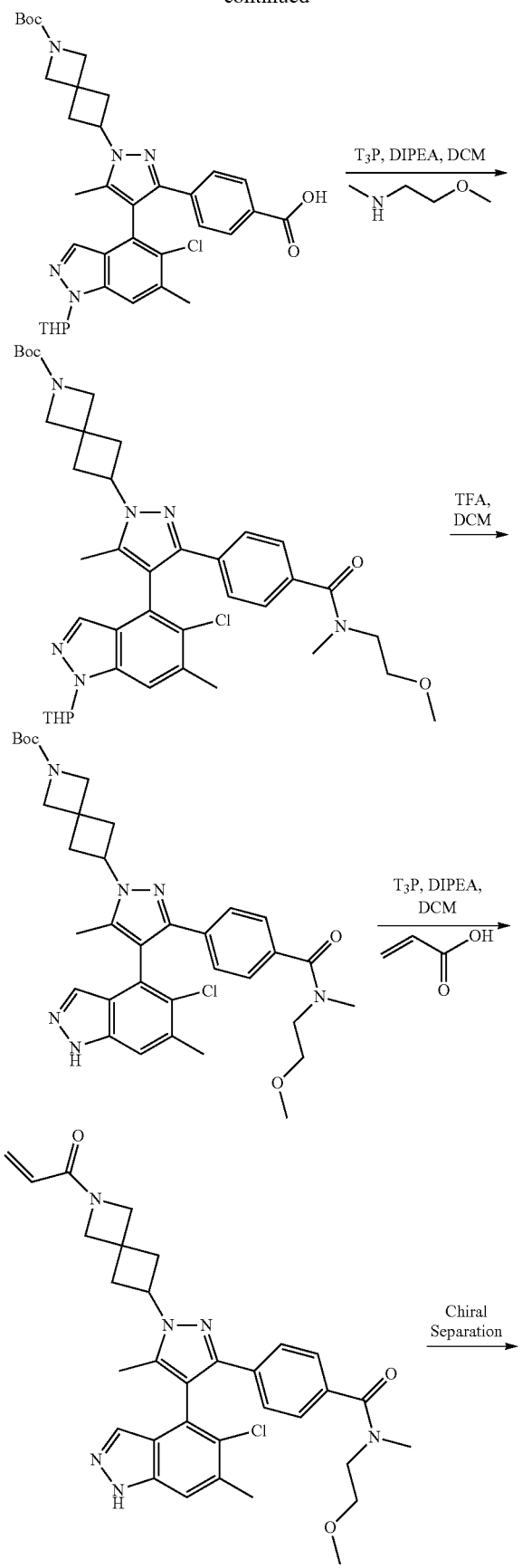

182
-continued

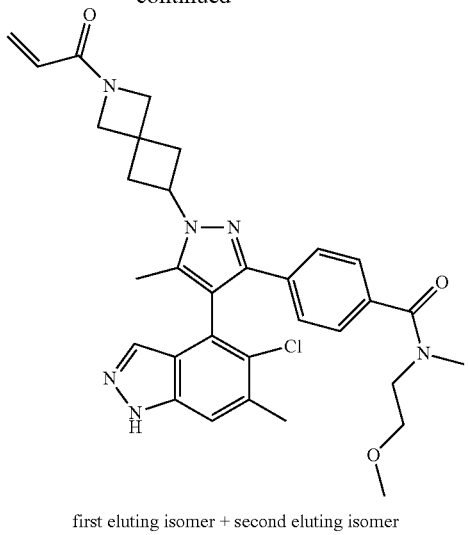

first eluting isomer + second eluting isomer

Examples 66a/66b: 4-(1-(2-acryloyl-2-azaspiro[3.3]
heptan-6-yl)-4-(5-chloro-6-methyl-1H-indazol-4-yl)-
5-methyl-1H-pyrazol-3-yl)-N-(2-methoxyethyl)-N-
methylbenzamide Step 1: Tert-butyl 6-(3-(4-(methoxycarbonyl)phenyl)-5-methyl-1H-pyrazol-1-yl)-2-azaspiro[3.3]heptane-2-carboxylate A solution of tert-butyl 6-(3-bromo-5-methyl-1H-pyrazol-1-yl)-2-azaspiro[3.3]heptane-2-carboxylate (Intermediate C3, 1.51 g, 4.24 mmol), methyl 4-(4,4,5,5-tetramethyl-1,3,2-dioxaborolan-2-yl)benzoate (1.33 g, 5.09 mmol), RuPhos (0.198 g, 0.42 mmol), RuPhos-Pd-G3 (0.355 g, 0.42 mmol) and potassium phosphate (2N, 6.36 mL, 12.7 mmol) in dioxane (20 mL) was stirred at 80° C. for 15 min. After cooling to RT the reaction mixture was added to sat. aq. NaHCO$_3$, extracted with EtOAc and the organic phase washed with brine, dried (Na$_2$SO$_4$), filtered and concentrated under reduced pressure. The crude residue was purified by normal phase chromatography (eluent: c-hexane/EtOAc 100/0 to 70/30 within 30 min) to give the title compound. $^1$H NMR (400 MHz, DMSO-d$_6$) δ 7.99 (d, 2H), 7.91 (d, 2H), 6.60 (s, 1H), 4.80-4.72 (m, 1H), 3.99 (s, 2H), 3.90 (s, 2H), 3.87 (s, 3H), 2.75-2.65 (m, 4H), 2.27 (s, 3H), 1.39 (s, 9H); UPLC-MS-6: Rt=1.23 min; MS m/z [M+H]$^+$: 412.3.

Step 2: Tert-butyl 6-(4-bromo-3-(4-(methoxycarbonyl)phenyl)-5-methyl-1H-pyrazol-1-yl)-2-azaspiro[3.3]heptane-2-carboxylate To a solution of tert-butyl 6-(3-(4-(methoxycarbonyl)phenyl)-5-methyl-1H-pyrazol-1-yl)-2-azaspiro[3.3]heptane-2-carboxylate (Step 1, 1.76 g, 4.15 mmol) in CH$_3$CN (45 mL) was added NBS (0.724 g, 4.07 mmol) and the reaction mixture was stirred at RT for 0.5 h. The reaction mixture was concentrated under reduced pressure and the crude residue was purified by normal phase chromatography (eluent: c-hexane/EtOAc 100/0 to 70/30 within 30 min) to obtain the title compound. $^1$H NMR (400 MHz, DMSO-d$_6$) δ 8.06 (d, 2H), 8.00 (d, 2H), 4.91-4.83 (m, 1H), 3.99 (s, 2H), 3.89 (s, 5H), 2.74-2.65 (m, 4H), 2.29 (s, 3H), 1.39 (s, 9H); UPLC-MS-6: Rt=1.31 min; MS m/z [M+H]$^+$: 490.1/492.1.

Step 3: Tert-butyl 6-(4-(5-chloro-6-methyl-1-(tetrahydro-2H-pyran-2-yl)-1H-indazol-4-yl)-3-(4-(methoxycarbonyl)phenyl)-5-methyl-1H-pyrazol-1-yl)-2-azaspiro[3.3]heptane-2-carboxylate A solution of tert-butyl 6-(4-bromo-3-(4-(methoxycarbonyl)phenyl)-5-methyl-1H-pyrazol-1-yl)-2-azaspiro[3.3]heptane-2-carboxylate (Step 2, 1.00 g, 2.00 mmol), 5-chloro-6-methyl-1-(tetrahydro-2H-pyran-2-yl)-4-(4,4,5,5-tetramethyl-1,3,2-dioxaborolan-2-yl)-1H-indazole (Intermediate D1, 0.98 g, 2.60 mmol), RuPhos (0.093 g, 0.20 mmol), RuPhos-Pd-G3 (0.167 g, 0.20 mmol) and potassium phosphate (2N, 3.00 mL, 6.00 mmol) in dioxane (10 mL) was stirred at 80° C. for 15 min. After cooling to RT the reaction mixture was added to sat. aq. NaHCO$_3$, extracted with EtOAc and the organic phase washed with brine, dried (Na$_2$SO$_4$) filtered and concentrated under reduced pressure. The crude residue was dissolved in THF (20 mL), SiliaMetS® Thiol (0.60 mmol, 0.84 g) was added and the mixture was vortexed at 50° C. for 0.5 h on a rotavapor. The mixture was filtered, washed with MeOH and the filtrate was concentrated under reduced pressure to give crude product which was purified by normal phase chromatography (eluent: c-hexane/EtOAc 100/0 to 60/40 within 30 min) to give the title compound as a colorless foam. UPLC-MS-6: Rt=1.31 min; MS m/z [M+H]$^+$: 660.2/662.2.

Step 4: 4-(1-(2-(Tert-butoxycarbonyl)-2-azaspiro[3.3]heptan-6-yl)-4-(5-chloro-6-methyl-1-(tetrahydro-2H-pyran-2-yl)-1H-indazol-4-yl)-5-methyl-1H-pyrazol-3-yl)benzoic acid A solution of tert-butyl 6-(4-(5-chloro-6-methyl-1-(tetrahydro-2H-pyran-2-yl)-1H-indazol-4-yl)-3-(4-(methoxycarbonyl)phenyl)-5-methyl-1H-pyrazol-1-yl)-2-azaspiro[3.3]heptane-2-carboxylate (Step 3, 1.42 g, 1.99 mmol) and NaOH (2N, 1.00 mL, 2.00 mmol) in dioxane (10 mL) was stirred at 60° C. for 15 min. More NaOH (2N, 1.00 mL, 2.00 mmol) was added and reaction mixture was stirred at RT overnight, then the reaction mixture was warmed to 60° C. for 3 h. The reaction mixture was lyophilized and the crude product used in the next step without further purification. $^1$H NMR (400 MHz, DMSO-d$_6$) δ 7.78 (br s, 1H), 7.64-7.60 (m, 2H), 7.47 (s, 0.5H), 7.45 (s, 0.5H), 7.16-7.13 (m, 2H), 5.85-5.80 (m, 1H), 4.91-4.83 (m, 1H), 4.02 (br s, 2H), 3.95-3.87 (m, 3H), 3.79-3.72 (m, 1H), 2.91-2.68 (m, 4H), 2.39-2.32 (m, 1H), 2.01-1.94 (m, 5H), 1.74-1.70 (m, 1H), 1.61-1.56 (m, 2H), 1.40 (s, 9H); UPLC-MS-6: Rt=1.23 min; MS m/z [M+H]$^+$: 646.2/648.2.

Step 5: Tert-butyl 6-(4-(5-chloro-6-methyl-1-(tetrahydro-2H-pyran-2-yl)-1H-indazol-4-yl)-3-(4-((2-methoxyethyl)(methyl)carbamoyl)phenyl)-5-methyl-1H-pyrazol-1-yl)-2-azaspiro[3.3]heptane-2-carboxylate To a solution of 4-(1-(2-(tert-butoxycarbonyl)-2-azaspiro[3.3]heptan-6-yl)-4-(5-chloro-6-methyl-1-(tetrahydro-2H-pyran-2-yl)-1H-indazol-4-yl)-5-methyl-1H-pyrazol-3-yl)benzoic acid (Step 4, 250 mg, 0.31 mmol) and 2-methoxy-N-methylethan-1-amine (0.067 ml, 0.61 mmol) in CH$_2$Cl$_2$ (3 mL) was added propylphosphonic anhydride (50% in EtOAc, 0.27 mL, 0.46 mmol). Then DIPEA (0.27 mL, 1.53 mmol) was added and the mixture stirred at RT for 5 h. The reaction mixture was concentrated under reduced pressure and the crude residue purified by normal phase chromatography (eluent: c-hexane/EtOAc 100/0 to 0/100 within 30 min) to give the title compound. $^1$H NMR (400 MHz, DMSO-d$_6$) δ 7.79 (s, 1H), 7.51 (s, 0.5H), 7.49 (s, 0.5H), 7.30-7.27 (m, 2H), 7.20-7.17 (m, 2H), 5.86-5.81 (m, 1H), 4.92-4.85 (m, 1H), 4.02 (s, 2H), 3.94-3.87 (m, 3H), 3.79-3.72 (m, 1H), 3.58-3.24 (m, 6H), 3.09 (br s, 1H), 2.93-2.74 (m, 7H), 2.03-1.96 (m, 5H), 1.73 (m, 1H), 1.62-1.55 (m, 2H), 1.40 (s, 9H); UPLC-MS-11: Rt=1.24 min; MS m/z [M+H]$^+$: 717.5/719.5.

Step 6: 4-(4-(5-Chloro-6-methyl-1H-indazol-4-yl)-5-methyl-1-(2-azaspiro[3.3]heptan-6-yl)-1H-pyrazol-3-yl)-N-(2-methoxyethyl)-N-methylbenzamide To a solution of tert-butyl 6-(4-(5-chloro-6-methyl-1-(tetrahydro-2H-pyran-2-yl)-1H-indazol-4-yl)-3-(4-((2-methoxyethyl)(methyl)carbamoyl)phenyl)-5-methyl-1H-pyrazol-1-yl)-2-azaspiro[3.3]heptane-2-carboxylate (Step 5, 168 mg, 0.23 mmol) in CH$_2$Cl$_2$ (2 mL) was added TFA (0.52 mL, 6.82 mmol) and the reaction mixture was stirred at RT for 4 h. The reaction mixture was concentrated under reduced pressure, the residue dissolved in dioxane and lyophilized to give the title compound as a trifluoroacetate salt which was used in the next reaction without further purification. UPLC-MS-6: Rt=0.73; MS m/z [M+H]$^+$: 533.3/535.3.

Step 7: 4-(1-(2-Acryloyl-2-azaspiro[3.3]heptan-6-yl)-4-(5-chloro-6-methyl-1H-indazol-4-yl)-5-methyl-1H-pyrazol-3-yl)-N-(2-methoxyethyl)-N-methylbenzamide To a solution of 4-(4-(5-Chloro-6-methyl-1H-indazol-4-yl)-5-methyl-1-(2-azaspiro[3.3]heptan-6-yl)-1H-pyrazol-3-yl)-N-(2-methoxyethyl)-N-methylbenzamide (0.23 mmol) and acrylic acid (0.016 ml, 0.23 mmol) in CH$_2$Cl$_2$ (3 mL) was added propylphosphonic anhydride (50% in EtOAc, 0.20 mL, 0.34 mmol). Then DIPEA (0.198 ml, 1.13 mmol) was added and the reaction mixture stirred at RT for 1.25 h. The reaction was quenched by addition of MeOH, the reaction mixture was concentrated under reduced pressure and the crude residue was purified by normal phase chromatography (eluent: DCM/MeOH 100/0 to 80/20 within 30 min) to give the title compound. The isomers were separated by chiral SFC (C-HPLC-11: mobile phase: n-heptane/IPA+ 0.1% NEt$_3$: 55/45) to give the title compound Example 66a as the second eluting peak: $^1$H NMR (400 MHz, DMSO-d$_6$) δ 13.15 (s, 1H), 7.57 (s, 1H), 7.45 (s, 1H), 7.30 (d, 2H), 7.18 (d, 2H), 6.37-6.30 (m, 1H), 6.15-6.09 (m, 1H), 5.71-5.67 (m, 1H), 4.98-4.88 (m, 1H), 4.40 (s, 1H), 4.33 (s, 1H), 4.11 (s, 1H), 4.04 (s, 1H), 3.55-3.46 (m, 5H), 3.09 (br s, 2H), 2.91-2.81 (m, 6H), 2.03 (s, 3H); UPLC-MS-3: Rt=0.89 min; MS m/z [M+H]$^+$: 587.3/589.3; C-HPLC-13 (mobile phase: n-heptane/[IPA+0.1% DEA]: 55/45): Rt=10.39 min. The other isomer Example 66b was obtained as the first eluting peak: C-HPLC-13 (mobile phase: n-heptane/[IPA+0.1% DEA]: 55/45): Rt=6.83 min.

The following examples 67 to 68 in Table 4 below were prepared by analogy to Method-4, employing the appropriate commercial amine (step 5) or proceeding with the acid.

TABLE 4

| Example | Structure | Method, intermediates (in step 5) and chiral separation conditions used and order of elution | Characterizing data |
|---|---|---|---|
| 67a/67b | 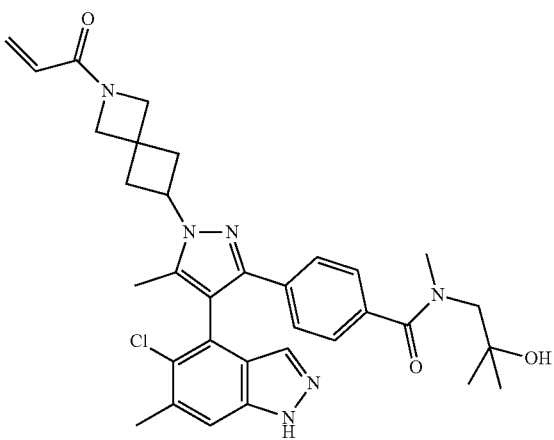<br>4-(1-(2-acryloyl-2-azaspiro[3.3]heptan-6-yl)-4-(5-chloro-6-methyl-1H-indazol-4-yl)-5-methyl-1H-pyrazol-3-yl)-N-(2-hydroxy-2-methylpropyl)-N-methylbenzamide | Using Method-4 with 2-methyl-1-(methylamino)propan-2-ol and C-HPLC-14 (mobile phase: n-heptane/[EtOH + 0.1% NEt$_3$] 60/40): Example 67a = 1$^{st}$ eluting isomer, Example 67b = 2$^{nd}$ eluting isomer | Example 67a: $^1$H NMR (400 MHz, DMSO-d$_6$) δ 13.14 (s, 1H), 7.56 (s, 1H), 7.45 (s, 1H), 7.31 (d, 2H), 7.21 (d, 2H), 6.37-6.30 (m, 1H), 6.15-6.09 (m, 1H), 5.71-5.66 (m, 1H), 4.98-4.88 (m, 1H), 4.53 (s, 1H), 4.40 (s, 1H), 4.33 (s, 1H), 4.11 (s, 1H), 4.04 (s, 1H), 3.40 (s, 2H), 3.16-2.79 (m, 7H), 2.03 (s, 3H), 1.11 (s, 6H); UPLC-MS-3: Rt = 0.88 min; MS m/z [M + H]$^+$: 601.3/603.3; C-HPLC-15 (mobile phase: n-heptane/[EtOH + 0.1% DEA] 60/40): Rt = 5.48 min, Example 67b: C-HPLC-15 (mobile phase: n-heptane/[EtOH + 0.1% DEA] 60/40): Rt = 7.51 min. |
| 68a/68b | 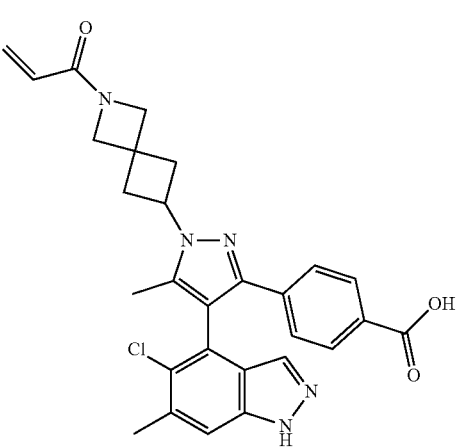<br>4-(1-(2-acryloyl-2-azaspiro[3.3]heptan-6-yl)-4-(5-chloro-6-methyl-1H-indazol-4-yl)-4-methyl-1H-pyrazol-3-yl)benzoic acid | Using Method-4 and C-HPLC-14 (mobile phase: n-heptane/[EtOH + 0.05% TFA] 60/40): Example 68a = 1$^{st}$ eluting isomer, Example 68b = 2$^{nd}$ eluting isomer | Example 68a: $^1$H NMR (400 MHz, DMSO-d$_6$) δ 13.17 (s, 1H), 7.73 (d, 2H), 7.58 (s, 1H), 7.44 (s, 1H), 7.32 (d, 2H), 6.38-6.30 (m, 1H), 6.15-6.09 (m, 1H), 5.71-5.67 (m, 1H), 4.98-4.88 (m, 1H), 4.40 (s, 1H), 4.33 (s, 1H), 4.11 (s, 1H), 4.04 (s, 1H), 2.93-2.80 (m, 4H), 2.03 (s, 3H); UPLC-MS-3: Rt = 0.90 min; MS m/z [M + H]$^+$: 516.1/518.1; C-HPLC-16 (mobile phase: n-heptane/EtOH/TFA 85/15/0.05): Rt = 32.79 min, Example 68b: C-HPLC-16 (mobile phase: n-heptane/EtOH/TFA 85/15/0.05): Rt = 37.65 min. |

Method-5: Synthetic scheme

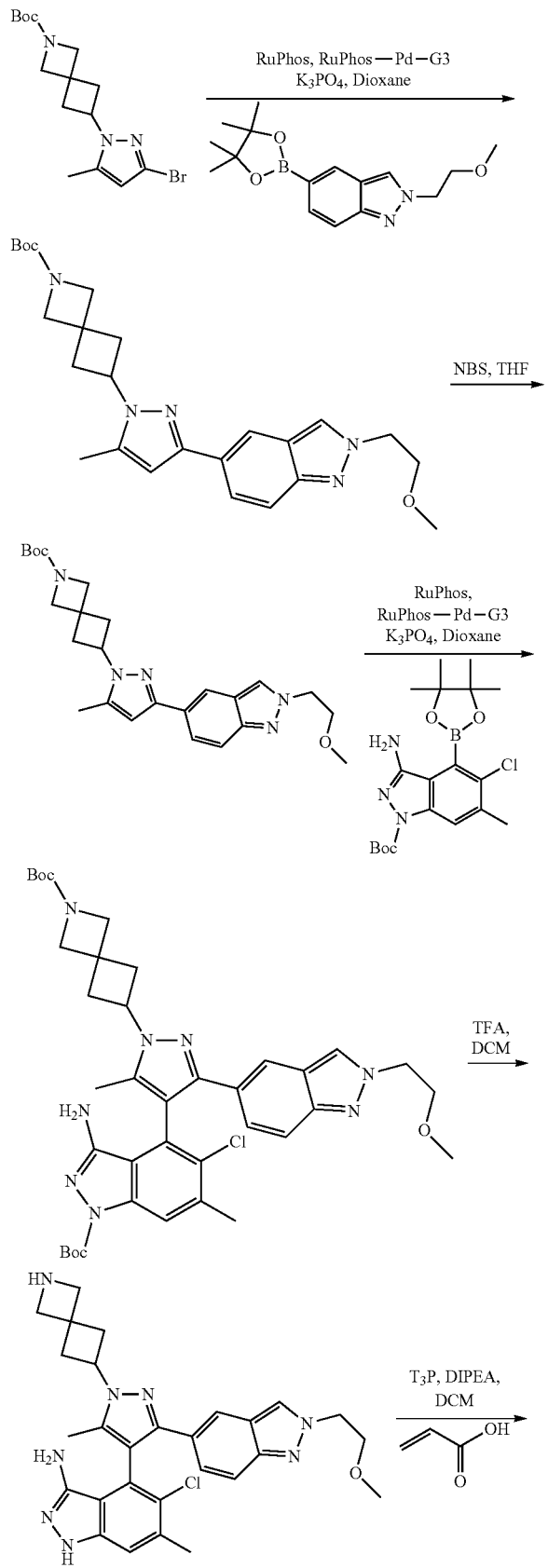

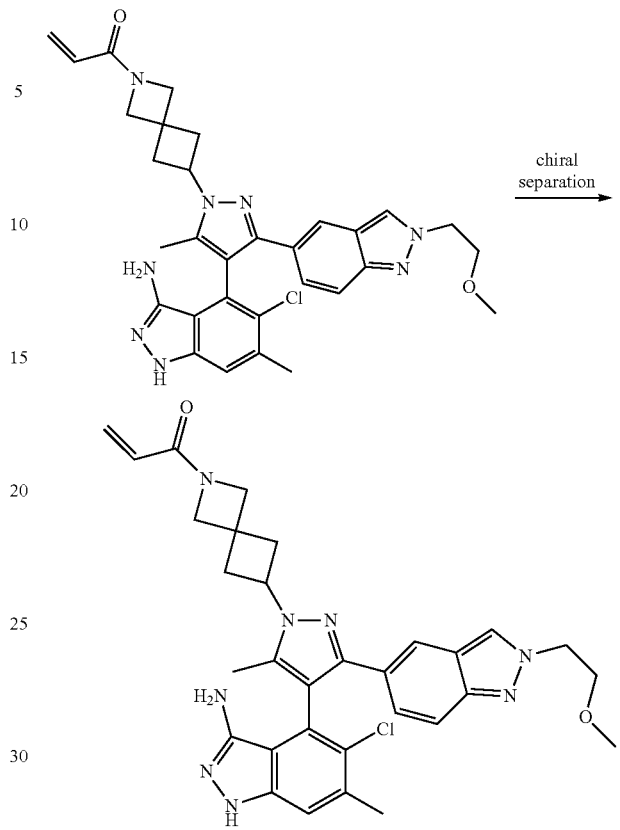

first eluting isomer + second eluting isomer

Examples 69a/69b: 1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one Step 1: Tert-butyl 6-(3-(2-(2-methoxyethyl)-2H-indazol-5-yl)-5-methyl-1H-pyrazol-1-yl)-2-azaspiro[3.3]heptane-2-carboxylate A solution of tert-butyl 6-(3-bromo-5-methyl-1H-pyrazol-1-yl)-2-azaspiro[3.3]heptane-2-carboxylate (Intermediate C3, 1.65 g, 4.63 mmol), 2-(2-methoxyethyl)-5-(4,4,5,5-tetramethyl-1,3,2-dioxaborolan-2-yl)-2H-indazole (Intermediate B22, 2.09 g, 6.95 mmol), RuPhos (0.22 g, 0.46 mmol), RuPhos-Pd-G3 (0.39 g, 0.46 mmol) and potassium phosphate (2N, 6.95 mL, 13.9 mmol) in dioxane (22 mL) was stirred at 80° C. for 15 min. After cooling to RT the reaction mixture was extracted with EtOAc, the organic phase washed with brine, dried ($Na_2SO_4$), filtered and concentrated under reduced pressure. The crude residue was purified by normal phase chromatography (eluent: c-hexane/EtOAc 100/0 to 50/50 within 30 min) to give the title compound. $^1$H NMR (400 MHz, DMSO-$d_6$) δ 8.35 (s, 1H), 8.01 (t, 1H), 7.74 (dd, 1H), 7.60 (d, 1H), 6.46 (s, 1H), 4.76-4.68 (m, 1H), 4.57 (t, 2H), 3.99 (s, 2H), 3.91 (s, 2H), 3.83 (t, 2H), 3.24 (s, 3H), 2.76-2.63 (m, 4H), 2.25 (s, 3H), 1.39 (s, 9H); UPLC-MS-3: Rt=1.07 min; MS m/z [M+H]+: 452.3.

Step 2: Tert-butyl 6-(4-bromo-3-(2-(2-methoxyethyl)-2H-indazol-5-yl)-5-methyl-1H-pyrazol-1-yl)-2-azaspiro[3.3]heptane-2-carboxylate To a solution of tert-butyl 6-(3-(2-(2-methoxyethyl)-2H-indazol-5-yl)-5-methyl-1H-pyrazol-1-yl)-2-azaspiro[3.3]heptane-2-carboxylate (Step 1, 2.02 g, 4.20 mmol) in THF (30 mL) was added NBS (0.73 g, 4.12 mmol) and the reaction mixture stirred at RT for 40 min. More NBS (75 mg, 0.42 mmol) was added and mixture was stirred at RT for 10 more min. The reaction mixture was concentrated under reduced pressure and the crude residue purified by normal phase chromatography (eluent: c-hexane/EtOAc 100/0 to 20/80 within 30 min) to give the title compound. $^1$H NMR (400 MHz, DMSO-$d_6$) δ 8.44 (s, 1H), 8.17 (s, 1H), 7.71-7.65 (m, 2H), 4.87-4.79 (m, 1H), 4.59 (t, 2H), 3.98 (s, 2H), 3.89 (s, 2H), 3.84 (t, 2H), 3.24 (s, 3H), 2.75-2.64 (m, 4H), 2.28 (s, 3H), 1.38 (s, 9H); UPLC-MS-3: Rt=1.14 min; MS m/z [M+H]$^+$: 530.2/532.2.

Step 3: Tert-butyl 3-amino-4-(1-(2-(tert-butoxycarbonyl)-2-azaspiro[3.3]heptan-6-yl)-3-(2-(2-methoxyethyl)-2H-indazol-5-yl)-5-methyl-1H-pyrazol-4-yl)-5-chloro-6-methyl-1H-indazole-1-carboxylate A solution of tert-butyl 6-(4-bromo-3-(2-(2-methoxyethyl)-2H-indazol-5-yl)-5-methyl-1H-pyrazol-1-yl)-2-azaspiro[3.3]heptane-2-carboxylate (Step 2, 0.77 g, 1.46 mmol), tert-butyl 3-amino-5-chloro-6-methyl-4-(4,4,5,5-tetramethyl-1,3,2-dioxaborolan-2-yl)-1H-indazole-1-carboxylate (Intermediate D6, 074 g, 1.82 mmol), RuPhos (0.085 g, 0.18 mmol), RuPhos-Pd-G3 (0.152 g, 0.18 mmol) and potassium phosphate (2N, 2.73 mL, 5.46 mmol) in dioxane (10 mL) was stirred at 80° C. for 2.25 h. The reaction mixture was extracted with EtOAc, the organic phase washed with sat. aq. NaHCO$_3$ and brine, dried (Na$_2$SO$_4$), filtered and concentrated under reduced pressure. The crude residue was dissolved in THF (20 mL), SiliaMetS® Thiol (0.65 mmol) was added and the mixture was swirled for 0.5 h at 50° C. The mixture was filtered, the resin washed with MeOH and the filtrate was concentrated under reduced pressure. The crude residue was purified by normal phase chromatography (eluent: c-hexane/EtOAc 100/0 to 0/100 within 30 min) to give the title compound. UPLC-MS-5: Rt=1.37 min; MS m/z [M+H]$^+$: 731.5/733.4.

Step 4: 5-Chloro-4-(3-(2-(2-methoxyethyl)-2H-indazol-5-yl)-5-methyl-1-(2-azaspiro[3.3]heptan-6-yl)-1H-pyrazol-4-yl)-6-methyl-1H-indazol-3-amine To a solution of tert-butyl 3-amino-4-(1-(2-(tert-butoxycarbonyl)-2-azaspiro[3.3]heptan-6-yl)-3-(2-(2-methoxyethyl)-2H-indazol-5-yl)-5-methyl-1H-pyrazol-4-yl)-5-chloro-6-methyl-1H-indazole-1-carboxylate (Step 1, 181 mg, 0.25 mmol) in DCM (2 mL) was added TFA (0.38 mL, 4.95 mmol) and the reaction mixture was stirred at RT for 2 h. The reaction mixture was concentrated under reduced pressure and dried under high vacuum overnight to give the title compound as a trifluoroacetate salt which was used without purification in the next step. UPLC-MS-5: Rt=0.58 min; MS m/z [M+H]$^+$: 531.3/533.3.

Step 5: 1-(6-(4-(3-Amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one To a solution of acrylic acid (0.022 mL, 0.32 mmol) and propylphosphonic anhydride (50% in EtOAc, 0.19 mL, 0.32 mmol) in CH$_2$Cl$_2$ (1.5 mL) was added DIPEA (0.21 mL, 1.22 mmol). Then, this solution was added dropwise to a solution of 5-chloro-4-(3-(2-(2-methoxyethyl)-2H-indazol-5-yl)-5-methyl-1-(2-azaspiro[3.3]heptan-6-yl)-1H-pyrazol-4-yl)-6-methyl-1H-indazol-3-amine trifluoracetic acid salt (0.24 mmol) in CH$_2$Cl$_2$ (2 mL). The reaction mixture was stirred at RT for 2.5 h. The RM was quenched with lithium hydroxide (2N, 0.61 mL, 1.22 mmol) stirred for 30 min, diluted with DCM, washed with sat. aq. NaHCO$_3$, the organic phase dried (phase separator) and concentrated under reduced pressure. The crude residue was purified by normal phase chromatography (eluent: DCM/MeOH 100/0 to 90/10 within 30 min) to give the title compound. The isomers were separated by chiral SFC (C-SFC-5: mobile phase: CO$_2$/[MeOH+0.1% NEt$_3$]: 60/40) to give the title compound Example 69a as the first eluting peak: $^1$H NMR (400 MHz, DMSO-$d_6$) δ 11.60 (s, 1H), 8.18 (s, 1H), 7.44-7.43 (m, 3H), 7.28 (d, 1H), 6.36-6.28 (m, 1H), 6.13-6.08 (m, 1H), 5.70-5.66 (m, 1H), 4.96-4.86 (m, 1H), 4.47 (t, 2H), 4.38 (s, 1H), 4.32 (s, 1H), 4.10-4.08 (m, 3H), 4.03 (s, 1H), 3.76 (t, 2H), 3.19 (s, 3H), 2.94-2.77 (m, 4H), 2.44 (s, 3H), 1.99 (s, 3H); UPLC-MS-5: Rt=0.83 min; MS m/z [M+H]$^+$: 585.4/587.4; C-SFC-6: (mobile phase: CO$_2$/[MeOH+0.1% NH$_3$]: 60/40): Rt=2.64 min. The other isomer Example 69b was obtained as the second eluting peak: C-SFC-6: (mobile phase: CO$_2$/[MeOH+0.1% NH$_3$]: 60/40): Rt=3.50 min.

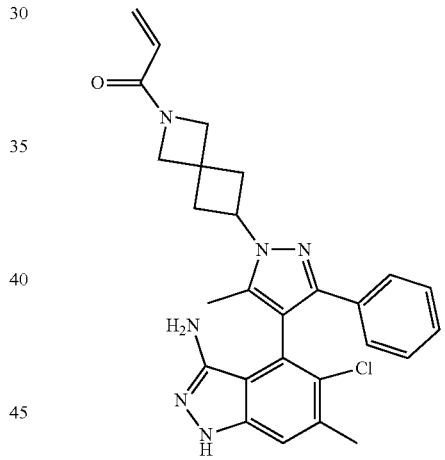

Examples 70a/70b: 1-(6-(4-(3-amino-5-chloro-6-methyl-1H-indazol-4-yl)-5-methyl-3-phenyl-1H-pyrazol-1-yl)-2-azaspiro[3.3]heptan-2-yl)prop-2-en-1-one The title examples were prepared using a similar method to Method-5 starting from phenylboronic acid instead of 2-(2-methoxyethyl)-5-(4,4,5,5-tetramethyl-1,3,2-dioxaborolan-2-yl)-2H-indazole in Step 1. The isomers were separated by chiral SFC (C-SFC-5: mobile phase: CO$_2$/IPA: 50/50) to give the title compound Example 70a as the first eluting peak: $^1$H NMR (400 MHz, DMSO-$d_6$) δ 11.61 (s, 1H), 7.35-7.32 (m, 2H), 7.27 (d, 1H), 7.21-7.14 (m, 3H), 6.36-6.28 (m, 1H), 6.13-6.07 (m, 1H), 5.70-5.65 (m, 1H), 4.96-4.86 (m, 1H), 4.38 (s, 1H), 4.31 (s, 1H), 4.08 (s, 1H), 4.02 (s, 1H), 2.92-2.76 (m, 4H), 2.43 (s, 3H), 1.98 (s, 3H); UPLC-MS-9: Rt=0.98 min; MS m/z [M+H]$^+$: 487.3/489.3; C-SFC-6: (mobile phase: CO$_2$/IPA: 50/50): Rt=1.80 min.

The other isomer Example 70b was obtained as the second eluting peak: C-SFC-6: (mobile phase: CO$_2$/IPA: 50/50): Rt=2.55 min.
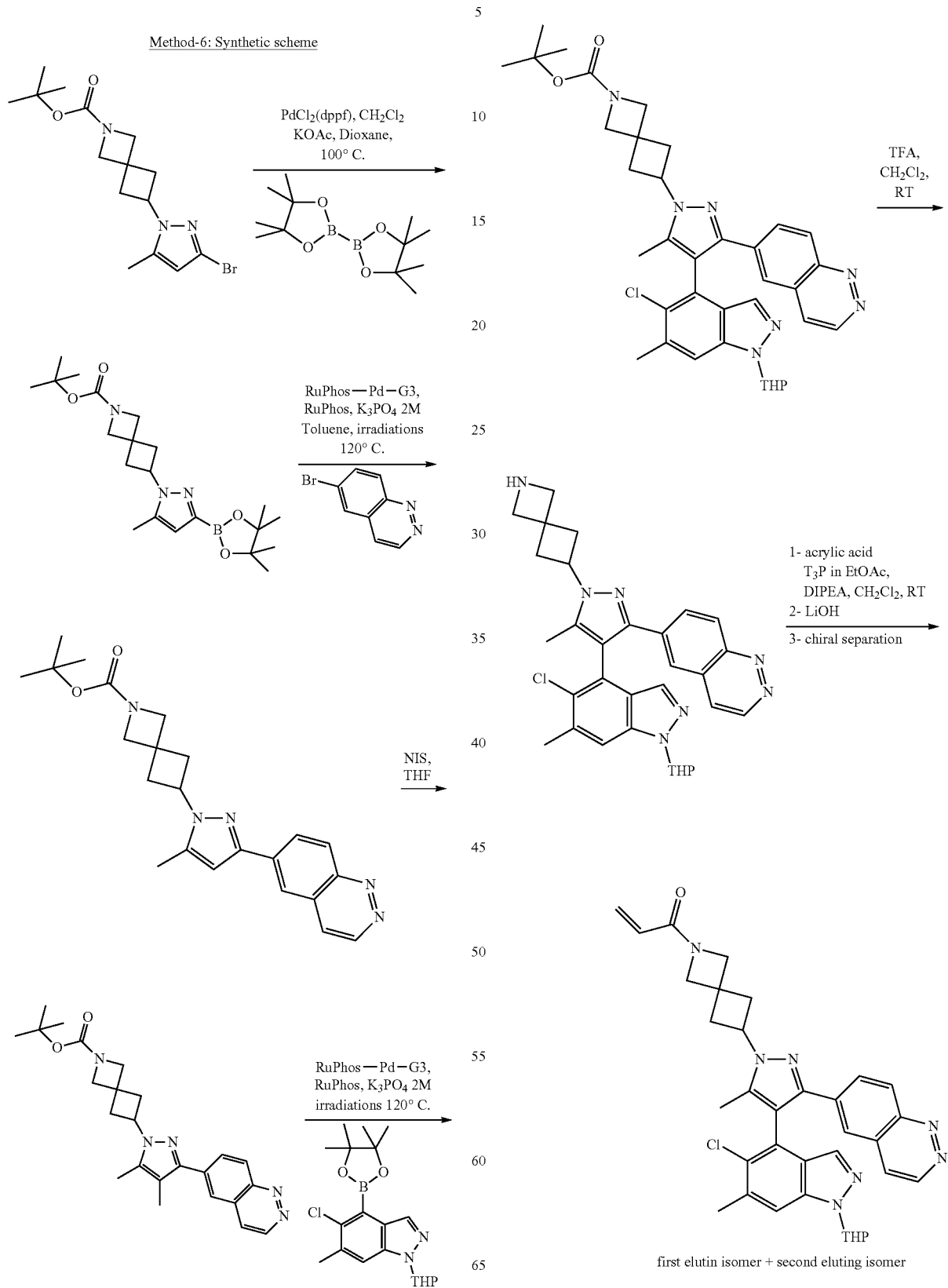

Examples 71a/71b: 1-(6-(4-(5-chloro-6-methyl-1H-indazol-4-yl)-3-(cinnolin-6-yl)-5-methyl-1H-pyrazol-1-yl)-2-azaspiro[3.3]heptan-2-yl)prop-2-en-1-one or 1-{6-[4-(5-chloro-6-methyl-1H-indazol-4-yl)-3-(cinnolin-6-yl)-5-methyl-1H-pyrazol-1-yl]-2-azaspiro[3.3]heptan-2-yl}prop-2-en-1-one Step 1: Tert-butyl 6-(5-methyl-3-(4,4,5,5-tetramethyl-1,3,2-dioxaborolan-2-yl)-1H-pyrazol-1-yl)-2-azaspiro[3.3]heptane-2-carboxylate, (1-(2-(tert-butoxycarbonyl)-2-azaspiro[3.3]heptan-6-yl)-5-methyl-1H-pyrazol-3-yl)boronic acid In an ace tube, a solution of tert-butyl 6-(3-bromo-5-methyl-1H-pyrazol-1-yl)-2-azaspiro[3.3]heptane-2-carboxylate (Intermediate C3, 5 g, 14.0 mmol), bis-(pinacolato)-diboron (5.35 g, 21.0 mmol), PdCl$_2$(dppf).CH$_2$Cl$_2$ adduct (1.15 g, 1.40 mmol) and potassium acetate (3.44 g, 35.1 mmol) in 1,4-dioxane (62.4 mL) was stirred at 100° C. overnight under a nitrogen atmosphere. The reaction mixture was poured into a sat. aq. NaHCO$_3$ solution, extracted with EtOAc (3×) and the combined organic extracts were washed with brine, dried (Na$_2$SO$_4$), filtered and evaporated to give the title compound as a dark solid which was used without purification in the next step. UPLC-MS-3: Rt=0.91 min; MS m/z [M+H]$^+$; 322.1.

Step 2: Tert-butyl 6-(3-(cinnolin-6-yl)-5-methyl-1H-pyrazol-1-yl)-2-azaspiro[3.3]heptane-2-carboxylate In a microwave vial tert-butyl 6-(5-methyl-3-(4,4,5,5-tetramethyl-1,3,2-dioxaborolan-2-yl)-1H-pyrazol-1-yl)-2-azaspiro[3.3]heptane-2-carboxylate (Step 1, 1.50 g, 1.86 mmol), 6-bromocinnoline (0.53 g, 2.42 mmol), RuPhos-Pd-G3 (0.16 g, 0.19 mmol) and RuPhos (0.087 g, 0.19 mmol) were dissolved in toluene (16.3 mL) and potassium phosphate (2 M, 2.79 mL, 5.58 mmol) was added. The reaction mixture was placed under nitrogen atmosphere and heated at 120° C. under microwave irradiations for 1 h. The reaction mixture was poured into a sat. aq. NaHCO$_3$ solution, extracted with EtOAc (×3) and the combined organic extracts were dried (phase separator) and concentrated. The crude residue was diluted in THF (6 mL), SiliaMetS® Thiol (0.8 mmol) was added and the mixture swirled for 1 h at 40° C. The mixture was filtered, the filtrate was concentrated and the crude residue was purified by normal phase chromatography (eluent: MeOH in CH$_2$Cl$_2$ from 0 to 10%), the purified fractions were again purified by normal phase chromatography (eluent: EtOAc in c-hexane from 0 to 100%) to give the title compound as brownish foam. UPLC-MS-3: Rt=1.04 min; MS m/z [M+H]$^+$; 406.3.

Step 3: Tert-butyl 6-(3-(cinnolin-6-yl)-4-iodo-5-methyl-1H-pyrazol-1-yl)-2-azaspiro[3.3]heptane-2-carboxylate To an ice-cooled solution of tert-butyl 6-(3-(cinnolin-6-yl)-5-methyl-1H-pyrazol-1-yl)-2-azaspiro[3.3]heptane-2-carboxylate (Step 2, 672 mg, 1.66 mmol) in THF (17.4 mL) was added NIS (1.49 g, 6.63 mmol) and the reaction mixture was stirred under nitrogen while allowed to slowly reach RT. After 19 h, NIS (746 mg, 3.31 mmol) was added and the reaction mixture was stirred again for 50 h. NIS (373 mg, 1.66 mmol) was added again and the reaction mixture was further stirred for 20 h. The reaction mixture was poured into a 10% Na$_2$S$_2$O$_3$ solution, extracted with CH$_2$Cl$_2$ (×2) and the combined organic extracts were washed with a sat. aq. NaHCO$_3$ solution, dried (phase separator) and concentrated. The crude residue was purified by normal phase flash chromatography (eluent: MeOH in CH$_2$Cl$_2$ from 0 to 5%) to give the title compound as a brownish foam. UPLC-MS-3: Rt=1.12 min; MS m/z [M+H]$^+$; 532.2.

Step 4: Tert-butyl 6-(4-(5-chloro-6-methyl-1-(tetrahydro-2H-pyran-2-yl)-1H-indazol-4-yl)-3-(cinnolin-6-yl)-5-methyl-1H-pyrazol-1-yl)-2-azaspiro[3.3]heptane-2-carboxylate In an Ace tube was placed under a nitrogen atmosphere, tert-butyl 6-(3-(cinnolin-6-yl)-4-iodo-5-methyl-1H-pyrazol-1-yl)-2-azaspiro[3.3]heptane-2-carboxylate (Step 3, 910 mg, 1.71 mmol), 5-chloro-6-methyl-1-(tetrahydro-2H-pyran-2-yl)-4-(4,4,5,5-tetramethyl-1,3,2-dioxaborolan-2-yl)-1H-indazole (Intermediate D1, 774 mg, 2.05 mmol), RuPhos (80 mg, 0.17 mmol), RuPhos-Pd-G3 (143 mg, 0.17 mmol) in dioxane (15 mL). K$_3$PO$_4$ (1.5 M, 3.42 mL, 5.14 mmol) was added and the reaction mixture was heated at 80° C. for 2 h. The reaction mixture was poured into a sat. aq. NaHCO$_3$ solution, extracted with EtOAc (3×) and the combined organic extracts were dried (phase separator) and concentrated. The crude residue was diluted in THF (15 mL), SiliaMetS® Thiol (0.73 mmol) was added and the mixture swirled for 1 h at 40° C. The mixture was filtered, the filtrate was concentrated and the crude residue was purified by normal phase chromatography (eluent: EtOAc in c-hexane from 0 to 100%) to give the title compound as pale yellow foam. UPLC-MS-3: Rt=1.19 min; MS m/z [M+H]$^+$; 654.3/656.3.

Step 5: 6-(4-(5-chloro-6-methyl-1H-indazol-4-yl)-5-methyl-1-(2-azaspiro[3.3]heptan-6-yl)-1H-pyrazol-3-yl)cinnoline To a solution of tert-butyl 6-(4-(5-chloro-6-methyl-1-(tetrahydro-2H-pyran-2-yl)-1H-indazol-4-yl)-3-(cinnolin-6-yl)-5-methyl-1H-pyrazol-1-yl)-2-azaspiro[3.3]heptane-2-carboxylate (Step 4, 806 mg, 1.21 mmol) in CH$_2$Cl$_2$ (9 mL) was added TFA (2.79 mL, 36.2 mmol) and the reaction mixture was stirred at RT for 16 h. The reaction mixture was concentrated to give the title compound as a trifluoroacetate salt which was used without purification in the next step. UPLC-MS-3: Rt=0.69 min; MS m/z [M+H]$^+$; 470.2/472.2.

Step 6: 1-(6-(4-(5-chloro-6-methyl-1H-indazol-4-yl)-3-(cinnolin-6-yl)-5-methyl-1H-pyrazol-1-yl)-2-azaspiro[3.3]heptan-2-yl)prop-2-en-1-one A mixture of acrylic acid (0.11 mL, 1.61 mmol), propylphosphonic anhydride (50% in EtOAc, 0.95 mL, 1.61 mmol) and DIPEA (2.81 mL, 16.1 mmol) in CH$_2$Cl$_2$ (15 mL) was stirred at RT for 15 min. This solution was added to a solution of 6-(4-(5-chloro-6-methyl-1H-indazol-4-yl)-5-methyl-1-(2-azaspiro[3.3]heptan-6-yl)-1H-pyrazol-3-yl)cinnoline trifluoroacetate (Step 5, 1.07 mmol) in $CH_2Cl_2$ (7.5 mL) and the reaction mixture was stirred at RT for 30 min. The reaction mixture was poured into a sat. aq. $NaHCO_3$ solution, extracted with $CH_2Cl_2$ (2×) and the combined organic layers were dried (phase separator) and concentrated. The crude residue was purified by normal phase chromatography (eluent: MeOH in $CH_2Cl_2$ from 0 to 10%) to give a mixture of the expected compound and a side product resulting from the addition of the acrylamide onto the indazole. The mixture was diluted in THF (15 mL) and LiOH (2 M, 5.35 mL, 10.7 mmol) was added. The solution was stirred at RT for 30 min and was poured in a sat. aq. $NaHCO_3$ solution, then was extracted with EtOAc (3×) and the combined organic extracts were dried (phase separator) and concentrated. The residue was purified by normal phase chromatography (eluent: MeOH in $CH_2Cl_2$ from 0 to 10%) to give the title compound. The isomers were separated by chiral SFC (C-SFC-1; mobile phase: $CO_2$/[EtOH+0.1% $Et_3N$]: 75/25) to give the title compound Example 71a as the second eluting peak (white powder): $^1$H NMR (600 MHz, DMSO-$d_6$) δ 13.1 (s, 1H), 9.23 (d, 1H), 8.25 (d, 1H), 7.97 (d, 1H), 7.84 (s, 1H), 7.80 (d, 1H), 6.61 (s, 1H), 7.50 (s, 1H), 6.33 (m, 1H), 6.12 (m, 1H), 5.68 (m, 1H), 4.99 (m, 1H), 4.41 (s, 1H), 4.34 (s, 1H), 4.12 (s, 1H), 4.05 (s, 1H), 2.99-2.80 (m, 4H), 2.08 (s, 3H); UPLC-MS-4: Rt=3.88 min; MS m/z [M+H]$^+$ 524.3/526.3; C-SFC-3 (mobile phase: $CO_2$/[EtOH+ 0.1% $Et_3N$]: 70/30): Rt=2.29 min. The other isomer Example 71b was obtained as the first eluting peak: C-SFC-3 (mobile phase: $CO_2$/[EtOH+0.1% $Et_3N$]: 70/30): Rt=1.91 min.

Method-6a: similar to Method-6 except that in Step 2 dioxane was used instead of toluene.

Method-6b: similar to Method-6 except that in Step 3 NBS (1.1 eq.) in acetonitrile was used instead of NIS in THF to prepare the corresponding 4-bromo-pyrazole.

Method-6c: similar to Method-6 except that Step 5 was performed using $H_2SO_4$ in dioxane as described in Method-1a Step 2.

Method-6d: similar to Method-6 except that Step 6 was performed using $NaHCO_3$, acryloyl chloride, $H_2O$ and THF as described in Method-1 b Step 3.

The following examples 72 to 77 in Table 5 below were prepared using analogous methods to Method-6 from intermediates (in Step 2) described in the intermediates synthesis section or commercially available.

TABLE 5

| Example | Structure | Method, intermediates and hciral separation conditions used and order of elution | Characterizing data |
| --- | --- | --- | --- |
| 72a/ 72b | 1-(6-(4-(5-chloro-6-methyl-1H-indazol-4-yl)-3-(2,2-dioxido-1,3-dihydrobenzo[c]thiophen-5-yl)-5-methyl-1H-pyrazol-1-yl)-2-azaspiro[3.3]heptan-2-yl)prop-2-en-1-one | Using Method-6a,b,c,d from [351005-12-4] (Step 2) and C-HPLC-2 (mobile phase: n-heptane/MTBE/MeOH/Et$_3$N 60:20:20:0.05); Example 72a = 1$^{st}$ eluting isomer, Example 72b = 2$^{nd}$ eluting isomer | Example 72a: $^1$H NMR (400 MHz, DMSO-$d_6$) δ 13.15 (s, 1H), 7.55 (s, 2H), 7.45 (s, 1H), 7.07 (m, 1H), 6.90 (m, 1H), 6.32 (m, 1H), 6.10 (m, 1H), 5.68 (m, 1H), 4.91 (m, 1H), 4.44 (s, 2H), 4.39 (s, 1H), 4.37 (s, 2H), 4.31 (s, 1H), 4.11 (s, 1H), 4.01 (s, 1H), 2.74-2.93 (m, 4H), 2.48 (m, 3H), 2.01 (s, 3H); UPLC-MS-6: Rt = 0.86 min, MS m/z [M + H]$^+$: 562.1/564.1; C-HPLC-7 (mobile phase: n-heptane/MTBE/MeOH/DEA 60:20:20:0.05): Rt = 20.58 min, Example 72b: C-HPLC-7 (mobile phase: n-heptane/MTBE/MeOH/DEA 60:20:20:0.05): Rt = 22.97 min. |

TABLE 5-continued

| Example | Structure | Method, intermediates and hciral separation conditions used and order of elution | Characterizing data |
|---|---|---|---|
| 73a/ 73b | 1-(6-(4-(5-chloro-6-methyl-1H-indazol-4-yl)-3-(8-fluoro-2,2-dimethyl-2,3-dihydroimidazo[1,2-a]pyridin-6-yl)-5-methyl-1H-pyrazol-1-yl)-2-azaspiro[3.3]heptan-2-yl)prop-2-en-1-one | Using Method 6a,d from Intermediate A9 (Step 2) and C-HPLC-1 (50:50:0.05 n-heptane/EtOH/Et$_3$N ): Example 73a = 2$^{nd}$ eluting isomer, Example 73b = 1$^{st}$ eluting isomer | Example 73a: 1H NMR (600 MHz, DMSO-d$_6$) δ 13.19 (s, 1H), 7.57 (s, 1H), 7.51 (s, 1H), 6.98 (m, 1H), 6.50 (d, 1H), 6.31 (m, 1H), 6.10 (m, 1H), 5.68 (m, 1H), 4.84 (m, 1H), 4.37 (s, 1H), 4.29 (s, 1H), 4.08 (s, 1H), 4.00 (s, 1H), 3.63 (m, 2H), 2.82 (m, 2H), 2.74 (m, 2H), 2.50 (s, 3H), 1.98 (s, 3H), 1.14 (m, 3H), 1.12 (m, 3H); UPLC-MS-7: Rt = 0.69 min, MS m/z [M + H]$^+$: 560.2/562.2; C-HPLC-4 (mobile phase: n-heptane/EtOH/DEA: 50:50:0.05): Rt = 9.20 min, Example 73b: C-HPLC-4 (mobile phase: n-heptane/EtOH/DEA: 50:50:0.05): Rt = 6.60 min. |
| 74a/ 74b | 1-(6-(4-(5-chloro-6-methyl-1H-indazol-4-yl)-3-(3,5-dimethylpyridin-4-yl)-5-methyl-1H-pyrazol-1-yl)-2-azaspiro[3.3]heptan-2-yl)prop-2-en-1-one | Using Method-6b,d from 4-bromo-3,5-dimethylpyridine (Step 2) and C-SFC-4 (mobile phase: CO$_2$/[IPA + 0.1% NEt$_3$] 75/25): Example 74a = 2$^{nd}$ eluting isomer, Example 74b = 1$^{st}$ eluting isomer | Example 74a: 1H NMR (400 MHz, DMSO-d$_6$) δ 13.07 (s, 1H), 8.13 (s, 2H), 7.46 (s, 1H), 7.43 (s, 1H), 6.36-6.27 (m, 1H), 6.14-6.07 (m, 1H), 5.70-5.65 (m, 1H), 5.01-4.91 (m, 1H), 4.39 (s, 1H), 4.28 (s, 1H), 4.10 (s, 1H), 3.98 (s, 1H), 2.85-2.77 (m, 4H), 2.41 (s, 3H), 2.13 (s, 3H), 1.99-1.96 (m, 6H); UPLC-MS-3: Rt = 0.80 min, MS m/z [M + H]$^+$: 501.2/503.2; C-SFC-3 (mobile phase: CO$_2$/[IPD + 0.1% NEt$_3$] 75/25): Rt = 3.85 min, Example 74b: C-SFC-3 (mobile phase: CO$_2$/[IPA + 0.1% NEt$_3$] 75/25): Rt = 3.43 min. |

TABLE 5-continued

| Example | Structure | Method, intermediates and hciral separation conditions used and order of elution | Characterizing data |
|---|---|---|---|
| 75a/ 75b | 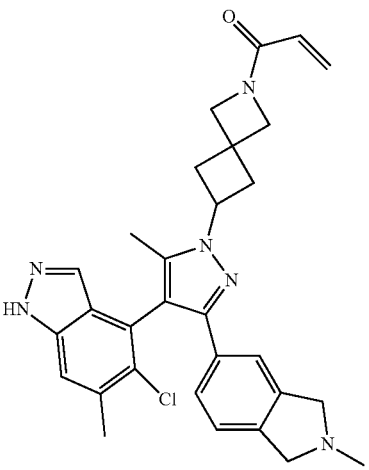<br>1-(6-(4-(5-chloro-6-methyl-1H-indazol-4-yl)-5-methyl-3-(2-methylisoindolin-5-yl)-1H-pyrazol-1-yl)-2-azaspiro[3.3]heptan-2-yl)prop-2-en-1-one | Using Method-6a,b,d from Intermediate A10 and C-HPLC-19 (mobile phase: heptane/(1:1 EtOH/MeOH)/Et₃N 80:20:0.1): Example 75a = 2$^{nd}$ eluting isomer, Example 75b = 1$^{st}$ eluting isomer | Example 75a: ¹H NMR (600 MHz, DMSO-d₆) δ 13.10 (s, 1H), 7.53 (s, 1H), 7.40 (s, 1H), 7.28 (s, 1H), 6.92 (m, 1H), 6.86 (m, 1H), 6.32 (m, 1H), 6.11 (m, 1H), 5.68 (m, 1H), 4.89 (m, 1H), 4.38 (s, 1H), 4.31 (s, 1H), 4.10 (s, 1H), 4.02 (s, 1H), 3.61-3.72 (m, 4H), 2.72-2.94 (m, 4H), 2.41 (s, 3H), 2.00 (s, 3H); UPLC-MS-12: Rt = 3.04 min, MS m/z [M + H]⁺: 527.2/529.2; C-HPLC-9 (mobile phase: heptane/(1:1 EtOH/MeOH)/DEA 80:20:0.1): Rt = 5.88 min, Example 75b: C-HPLC-9 (mobile phase: heptane/(1:1 EtOH/MeOH)/DEA 80:20:0.1): Rt = 3.52 min. |
| 76a/ 76b | 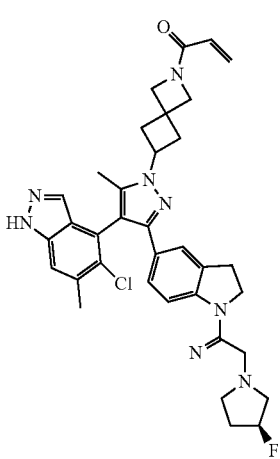<br>(S)-1-(6-(4-(5-chloro-6-methyl-1H-indazol-4-yl)-3-(1-(2-(3-fluoropyrrolidin-1-yl)acetyl)indolin-5-yl)-5-methyl-1H-pyrazol-1-yl)-2-azaspiro[3.3]heptan-2-yl)prop-2-en-1-one | Using Method-6a,b,d from Intermediate A11 and C-SFC-2 (mobile phase: CO₂/[IPA + 0.1% Et₃N] 60/40): Example 76a = 2$^{nd}$ eluting isomer, Example 76b = 1$^{st}$ eluting isomer | Example 76a: ¹H NMR (600 MHz, DMSO-d₆) δ 13.13 (s, 1H), 7.72 (m, 1H), 7.54 (s, 1H), 7.41 (s, 1H), 7.27 (m, 1H), 6.83 (m, 1H), 6.32 (m, 1H), 6.11 (m, 1H), 5.68 (m, 1H), 5.18 (m, 1H), 4.88 (m, 1H), 4.39 (s, 1H), 4.31 (s, 1H), 4.10 (s, 1H), 4.05 (t, 2H), 4.02 (s, 1H), 3.42 (d, 1H), 3.37 (d, 1H), 2.94-3.09 (m, 2H), 2.82-2.93 (m, 4H), 2.72-2.82 (m, 3H), 2.48 (s, 3H), 2.12 (m, 1H), 2.01 (s, 3H), 1.87 (m, 1H); UPLC-MS-13: Rt = 3.20 min, MS m/z [M + H]⁺: 642.2/644.1; C-SFC-3 (mobile phase: CO₂/[IPA + 0.1% Et₃N] 60/40): Rt = 2.23 min, Example 76b: C-SFC-3 (mobile phase: CO₂/[IPA + 0.1% Et₃N] 60/40): Rt = 1.39 min. |

TABLE 5-continued

| Example | Structure | Method, intermediates and hciral separation conditions used and order of elution | Characterizing data |
|---|---|---|---|
| 77 | 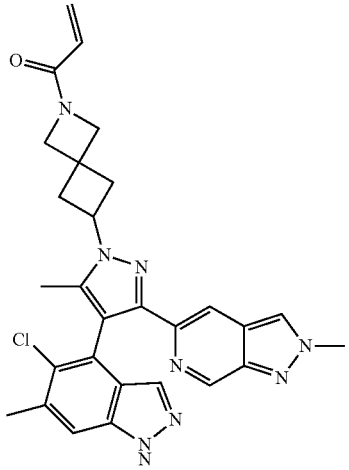

1-(6-(4-(5-chloro-6-methyl-1H-indazol-4-yl)-5-methyl-3-(2-methyl-2H-pyrazolo[3,4-c]pyridin-5-yl)-1H-pyrazol-1-yl)-2-azaspiro[3.3]heptan-2-yl)prop-2-en-1-one | Using Method-6a,b,d and 5-bromo-2-methyl-2H-pyrazolo[3,4-c]pyridine (Step 2) and normal phase chromatography (eluent: MeOH in CH$_2$Cl$_2$ from 0 to 10% MeOH). | Example 77: $^1$H NMR (600 MHz, DMSO-d$_6$) δ 12.98 (s, 1H), 8.74 (s, 1H), 8.46-8.33 (m, 1H), 7.83-7.75 (m, 1H), 7.46 (s, 1H), 7.39-7.35 (m, 1H), 6.39-6.28 (m, 1H), 6.18-6.08 (m, 1H), 5.69 (m, 1H), 4.92 (m, 1H), 4.41 (s, 1H), 4.33 (s, 1H), 4.19 (s, 3H), 4.12 (s, 1H), 4.04 (s, 1H), 2.99-2.86 (m, 2H), 2.86-2.76 (m, 2H), 2.45 (s, 3H), 2.05 (br. s, 3H); HPLC-MS-3: Rt = 0.76 min, MS m/z [M + H]$^+$; 527.2/529.3. |

Method-7: Synthetic scheme

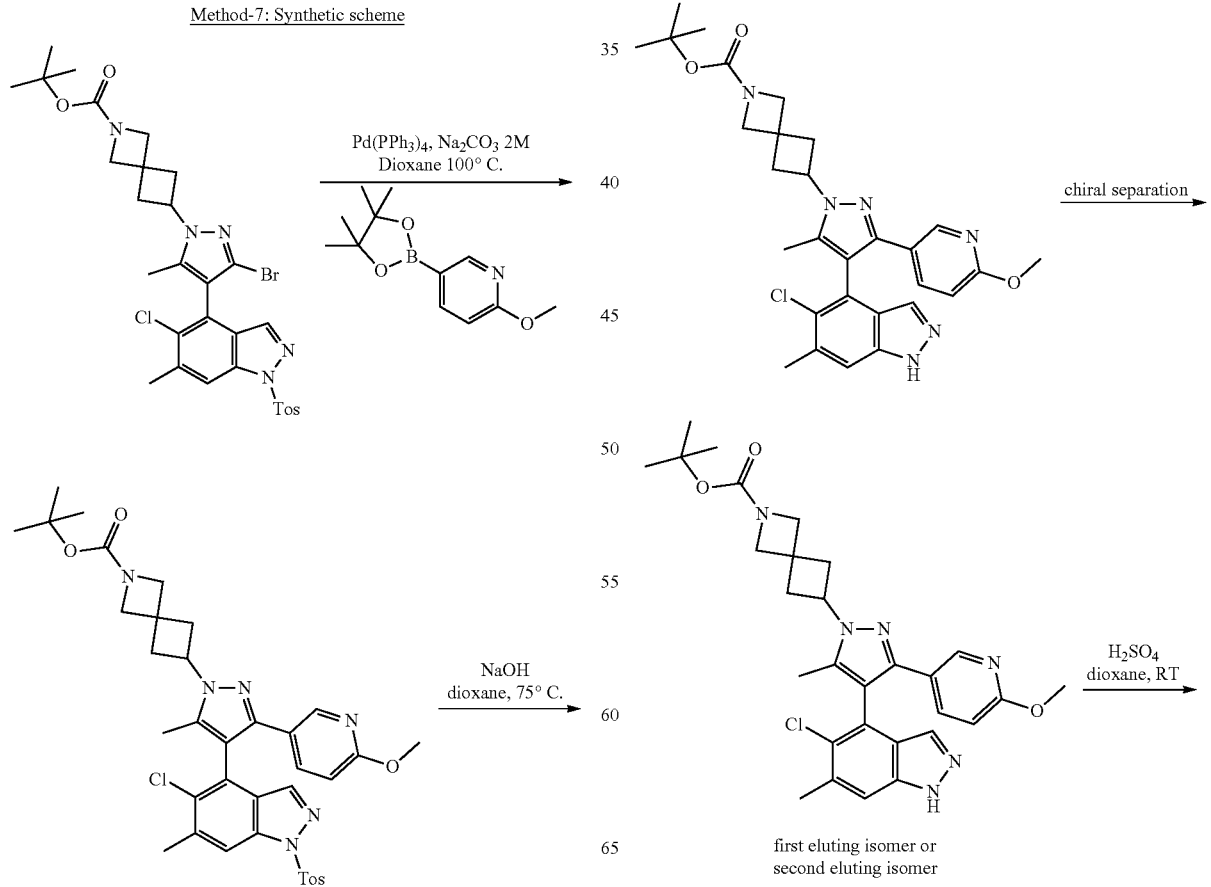

-continued

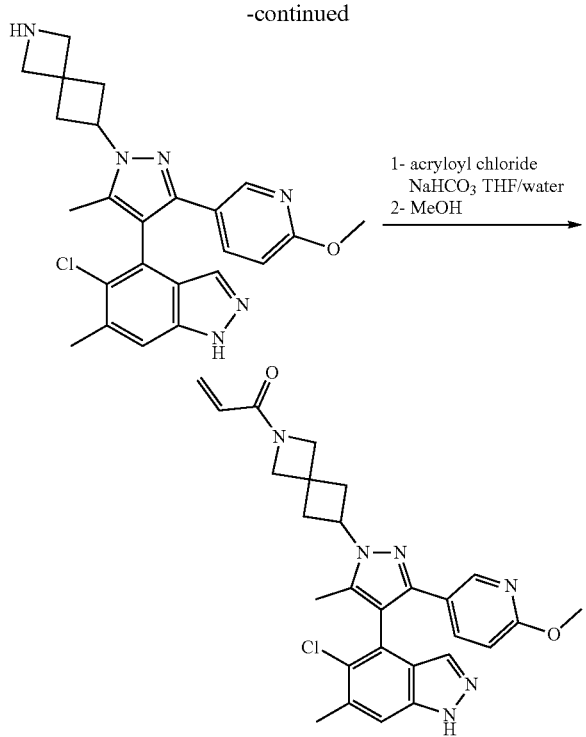

Example 78a: 1-(6-(4-(5-chloro-6-methyl-1H-indazol-4-yl)-3-(6-methoxypyridin-3-yl)-5-methyl-1H-pyrazol-1-yl)-2-azaspiro[3.3]heptan-2-yl)prop-2-en-1-one Step 1: Tert-butyl 6-(4-(5-chloro-6-methyl-1-tosyl-1H-indazol-4-yl)-3-(6-methoxypyridin-3-yl)-5-methyl-1H-pyrazol-1-yl)-2-azaspiro[3.3]heptane-2-carboxylate In an 20 mL microwave vial, was placed under an argon atmosphere, tert-butyl 6-(3-bromo-4-(5-chloro-6-methyl-1-tosyl-1H-indazol-4-yl)-5-methyl-1H-pyrazol-1-yl)-2-azaspiro[3.3]heptane-2-carboxylate (Intermediate C6, 350 mg, 0.51 mmol), 2-methoxypyridine-5-boronic acid pinacol ester (373 mg, 1.54 mmol) and Na$_2$CO$_3$ (2 M, 0.80 mL, 1.60 mmol) in 1,4-dioxane (5 mL), Pd(PPh$_3$)$_4$ (59.3 mg, 0.05 mmol) was added. The vial was sealed and the reaction mixture was heated at 100° C. for 3.5 h. 2-Methoxypyridine-5-boronic acid pinacol ester (181 mg, 0.77 mmol) and Pd(PPh$_3$)$_4$ (59.3 mg, 0.05 mmol) were added again and the RM further stirred at 100° C. for 2 h. The reaction mixture was poured into water, extracted with EtOAc (2×) and the combined organic extracts were dried (phase separator) and concentrated. The crude residue was diluted in THF, SiliaMetS® Thiol (0.91 mmol) was added and the mixture swirled for 1 h at 40° C. The mixture was filtered, the filtrate was concentrated and the crude residue was purified by normal phase chromatography (eluent: EtOAc in heptane from 0 to 60%) to give the title compound as white foam. UPLC-MS-1: Rt=1.51 min; MS m/z [M+H]$^+$: 703.2/705.2.

Step 2: Tert-butyl 6-(4-(5-chloro-6-methyl-1H-indazol-4-yl)-3-(6-methoxypyridin-3-yl)-5-methyl-1H-pyrazol-1-yl)-2-azaspiro[3.3]heptane-2-carboxylate To a solution of tert-butyl 6-(4-(5-chloro-6-methyl-1-tosyl-1H-indazol-4-yl)-3-(6-methoxypyridin-3-yl)-5-methyl-1H-pyrazol-1-yl)-2-azaspiro[3.3]heptane-2-carboxylate (Step 1, 295 mg, 0.37 mmol) in 1,4-dioxane (3.5 mL) was added NaOH (0.99 mL, 1.99 mmol) and the reaction mixture was stirred at 75° C. for 1.5 h. The RM was poured into water and extracted with EtOAc (2×). The combined organic extracts were washed with brine, dried (phase separator) and concentrated. The crude residue was purified by normal phase chromatography (eluent: (MeOH/CH$_2$Cl$_2$ (1/9)) in CH$_2$Cl$_2$ from 0 to 100%) to give the title compound as white solid. The isomers were separated by chiral HPLC (C-SFC-7; mobile phase: CO$_2$/IPA 73/27) to give tert-butyl 6-(4-(5-chloro-6-methyl-1H-indazol-4-yl)-3-(6-methoxypyridin-3-yl)-5-methyl-1H-pyrazol-1-yl)-2-azaspiro[3.3]heptane-2-carboxylate first eluting isomer (white powder); C-SFC-8 (mobile phase: CO$_2$/IPA 73/27): Rt=2.21 min and tert-butyl 6-(4-(5-chloro-6-methyl-1H-indazol-4-yl)-3-(6-methoxypyridin-3-yl)-5-methyl-1H-pyrazol-1-yl)-2-azaspiro[3.3]heptane-2-carboxylate second eluting isomer; C-SFC-8 (mobile phase: CO$_2$/IPA 73/27): Rt=3.21 min. UPLC-MS-1: Rt=1.27 min; MS m/z [M+H]$^+$; 549.2/551.2.

Step 3: 5-Chloro-4-(3-(6-methoxypyridin-3-yl)-5-methyl-1-(2-azaspiro[3.3]heptan-6-yl)-1H-pyrazol-4-yl)-6-methyl-1H-indazole A solution of tert-butyl 6-(4-(5-chloro-6-methyl-1H-indazol-4-yl)-3-(6-methoxypyridin-3-yl)-5-methyl-1H-pyrazol-1-yl)-2-azaspiro[3.3]heptane-2-carboxylate second eluting isomer (Step 2, 68 mg, 0.12 mmol) and H$_2$SO$_4$ (0.03 mL, 0.60 mmol) in dioxane (2.5 mL) was stirred at RT overnight. The RM was diluted with a sat. aq. solution of NaHCO$_3$ and was extracted with EtOAc (2×). The combined organic extracts were washed with brine, dried (phase separator) and evaporated to give the title compound as a white foam which was used without purification in the next step. UPLC-MS-7: Rt=0.71 min; MS m/z [M+H]$^+$; 449.1/451.1.

Step 4: 1-(6-(4-(5-Chloro-6-methyl-1H-indazol-4-yl)-3-(6-methoxypyridin-3-yl)-5-methyl-1H-pyrazol-1-yl)-2-azaspiro[3.3]heptan-2-yl)prop-2-en-1-one To an ice cooled solution of 5-chloro-4-(3-(6-methoxypyridin-3-yl)-5-methyl-1-(2-azaspiro[3.3]heptan-6-yl)-1H-pyrazol-4-yl)-6-methyl-1H-indazole (Step 3, 59 mg, 0.12 mmol) in THF (4.00 mL) and water (1.00 mL) were added at 0° C. under an argon atmosphere NaHCO$_3$ (30.5 mg, 0.36 mmol) and acryloyl chloride (0.015 mL, 0.18 mmol). The reaction mixture was stirred at 0-5° C. for 1.5 h. After completion of the reaction, MeOH (1 mL) was added and the mixture was stirred for 2 h at RT. The RM was diluted with EtOAc, a sat. aq. solution of NaHCO$_3$ was added and the layers were separated. The organic layer was extracted with EtOAc (2×) and the combined organic extracts were dried (phase separator) and evaporated. The crude residue was purified by normal phase chromatography (eluent: (MeOH/CH$_2$Cl$_2$ (1/4)) in CH$_2$Cl$_2$ from 0 to 30%) to give the title Example 78a as a white solid: $^1$H NMR (600 MHz, DMSO-d$_6$) δ 13.2 (s, 1H), 7.83 (m, 1H), 7.66 (m, 1H), 7.58 (s, 1H), 7.47 (s, 1H), 6.71 (m, 1H), 6.33 (m, 1H), 6.11 (m, 1H), 5.68 (m, 1H), 4.91 (m, 1H), 4.39 (s, 1H), 4.32 (s, 1H), 4.10 (s, 1H), 4.07 (s, 1H), 3.74 (s, 3H), 2.91-2.75 (m, 4H), 2.53 (s, 3H), 2.02 (s, 3H). UPLC-MS-14: Rt=0.90 min; MS m/z [M+H]$^+$; 503.1/505.1.

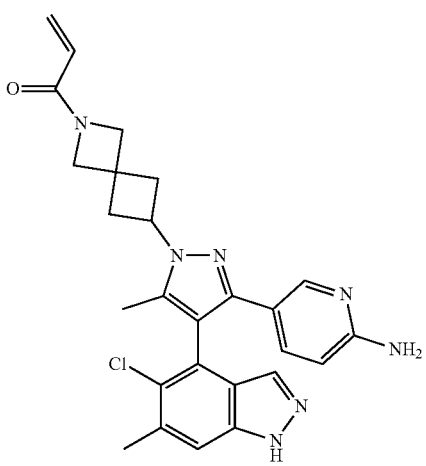 [SMILES: C=CC(=O)N1CC2(CC(n3nc(-c4ccc(N)nc4)c(-c4c(Cl)c(C)cc5[nH]ncc45)c3C)C2)C1]

Example 79a: 1-(6-(3-(6-aminopyridin-3-yl)-4-(5-chloro-6-methyl-1H-indazol-4-yl)-5-methyl-1H-pyrazol-1-yl)-2-azaspiro[3.3]heptan-2-yl)prop-2-en-1-one The title example was prepared using similar method to Method-7 Steps 3 and 4 from tert-butyl 6-(3-(6-aminopyridin-3-yl)-4-(5-chloro-6-methyl-1H-indazol-4-yl)-5-methyl-1H-pyrazol-1-yl)-2-azaspiro[3.3]heptane-2-carboxylate first eluting isomer (prepared as described below). $^1$H NMR (600 MHz, DMSO-$d_6$) δ 13.12 (s, 1H), 7.61 (m, 1H), 7.54 (s, 1H), 7.43 (s, 1H), 7.32 (m, 1H), 6.33 (m, 1H), 6.27 (m, 1H), 6.11 (m, 1H), 5.85 (br. s, 2H), 5.68 (m, 1H), 4.87 (m, 1H), 4.38 (s, 1H), 4.31 (s, 1H), 4.09 (s, 1H), 4.02 (s, 1H), 2.90-2.82 (m, 2H), 2.79-2.75 (m, 2H), 2.49 (s, 3H), 2.00 (s, 3H); UPLC-MS-14: Rt=0.67 min; MS m/z [M+H]$^+$ 488.1/490.1.

Tert-butyl 6-(3-(6-aminopyridin-3-yl)-4-(5-chloro-6-methyl-1H-indazol-4-yl)-5-methyl-1H-pyrazol-1-yl)-2-azaspiro[3.3]heptane-2-carboxylate The title compound was prepared using a similar method to Method-7 Steps 1 and 2 from (2-Aminopyridin-5-yl) boronic acid pinacol ester [CAS 827614-64-2] and tert-butyl 6-(3-bromo-4-(5-chloro-6-methyl-1-tosyl-1H-indazol-4-yl)-5-methyl-1H-pyrazol-1-yl)-2-azaspiro[3.3]heptane-2-carboxylate (Intermediate C6). The isomers were separated by chiral SFC (C-SFC-4; mobile phase: $CO_2$/[IPA+0.1% $NH_3$]: 70/30) to give tert-butyl 6-(3-(6-aminopyridin-3-yl)-4-(5-chloro-6-methyl-1H-indazol-4-yl)-5-methyl-1H-pyrazol-1-yl)-2-azaspiro[3.3]heptane-2-carboxylate first eluting isomer: C-SFC-3 (mobile phase: $CO_2$/[IPA+0.1% $NH_3$]: 70/30): Rt=2.04 min; UPLC-MS-1: Rt=0.90 min; MS m/z [M+H]$^+$; 534.2/536.2. The other isomer was obtained as the second eluting peak: C-SFC-3 (mobile phase: mobile phase: $CO_2$/[IPA+0.1% $NH_3$] 70/30): Rt=2.83 min.

Method-8: Synthetic Scheme

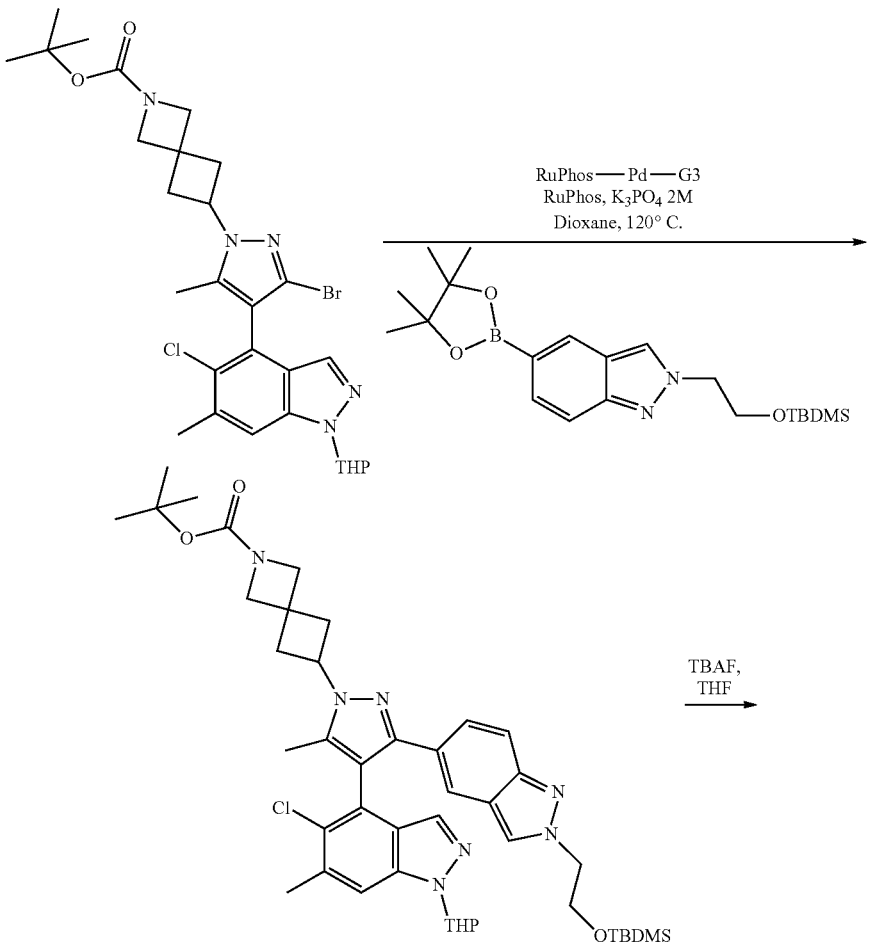

-continued
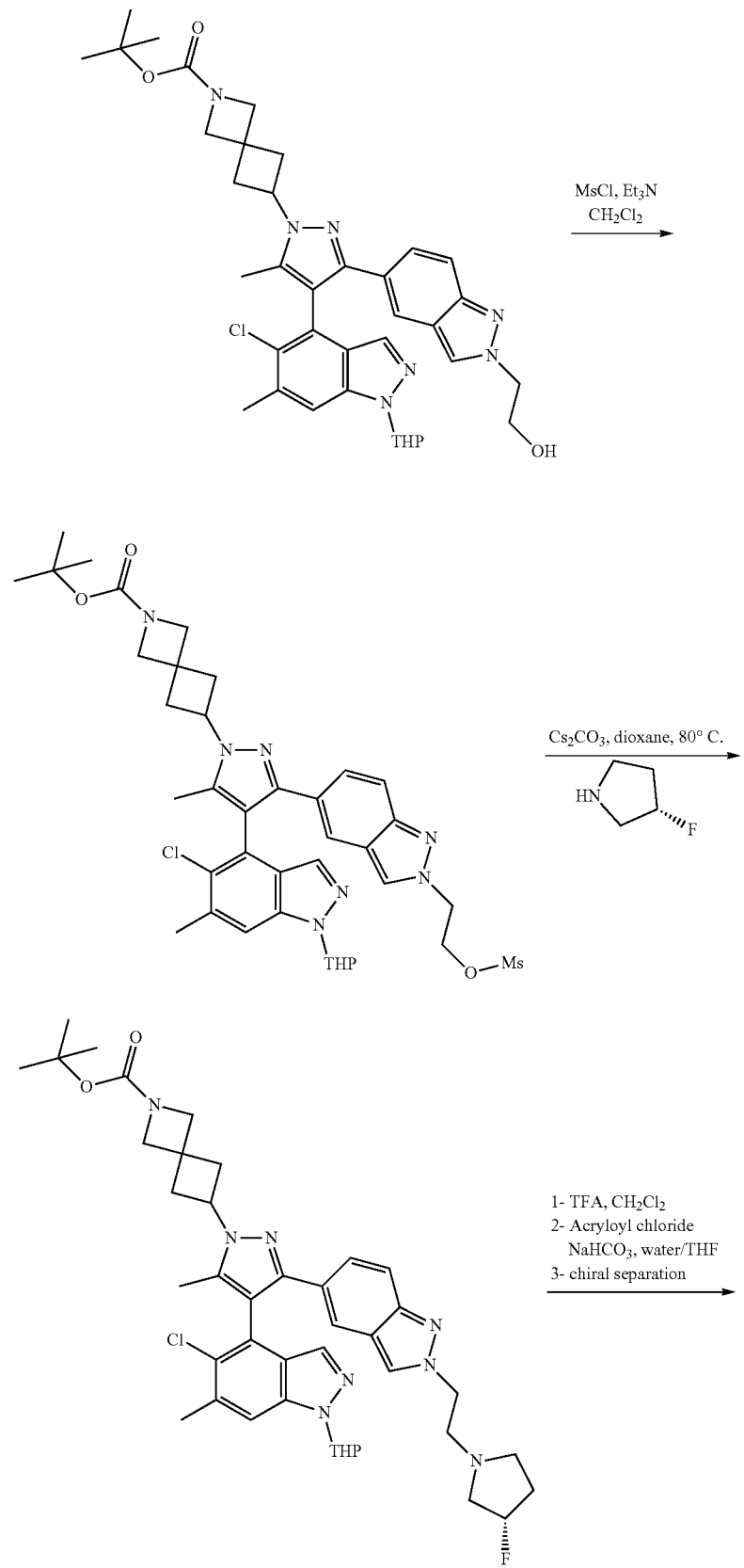

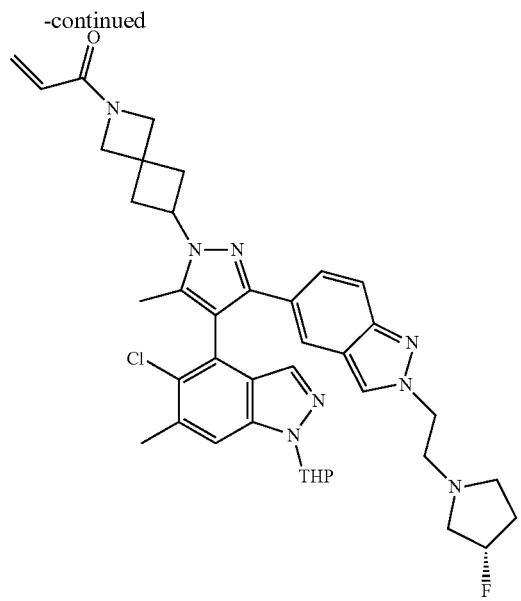

first eluting isomer + second eluting isomer

Examples 80a/80b: (S)-1-(6-(4-(5-chloro-6-methyl-1H-indazol-4-yl)-3-(2-(2-(3-fluoropyrrolidin-1-yl)ethyl)-2H-indazol-5-yl)-5-methyl-1H-pyrazol-1-yl)-2-azaspiro[3.3]heptan-2-yl)prop-2-en-1-one Step 1: Tert-butyl 6-(3-(2-(2-(((tert-butyldimethylsilyl)oxy)ethyl)-2H-indazol-5-yl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate Tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Intermediate C1, 1.50 g, 2.48 mmol), 2-(2-(((tert-butyldimethylsilyl)oxy)ethyl)-5-(4,4,5,5-tetramethyl-1,3,2-dioxaborolan-2-yl)-2H-indazole (Intermediate B19, 1.20 g, 2.99 mmol) and K$_3$PO$_4$ (1.58 g, 7.44 mmol) were dissolved in 1,4-dioxane (20 mL) and H$_2$O (10 mL). The reaction mixture was degassed with N$_2$ for 10 min. Ruphos (0.17 g, 0.37 mmol) and Ruphos-Pd-G$_3$ (0.10 g, 0.12 mmol) were added and the reaction mixture was stirred at 120° C. for 1 h. After completion of the reaction, the RM was quenched with water and extracted with EtOAc (×2). The combined organic layers were washed with brine, dried (Na$_2$SO$_4$), filtered and concentrated under vacuum to give crude residue which was purified by chromatography on neutral alumina (eluent: 0-20% EtOAc in Hexane) to obtain the desired product. LCMS-1: Rt: 2.62, 2.65 min; MS m/z [M+H]$^+$: 800.8/802.8.

Step 2: Tert-butyl 6-(4-(5-chloro-6-methyl-1-(tetrahydro-2H-pyran-2-yl)-1H-indazol-4-yl)-3-(2-(2-hydroxyethyl)-2H-indazol-5-yl)-5-methyl-1H-pyrazol-1-yl)-2-azaspiro[3.3]heptane-2-carboxylate Tert-butyl 6-(3-(2-(2-(((tert-butyldimethylsilyl)oxy)ethyl)-2H-indazol-5-yl)-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate (Step 1, 1.50 g, 1.87 mmol) was dissolved in THF (12 mL) and cooled to 0° C. under nitrogen atmosphere. TBAF (1.0 M in THF, 1.87 mL, 1.87 mmol) was added dropwise and the reaction mixture was stirred at RT for 10 min. After completion of the reaction, the reaction mixture was diluted with water and extracted with EtOAc (×2). The combined organic layers were washed with brine, dried (Na$_2$SO$_4$), filtered and concentrated under vacuum to afford a crude product which was used in the next step without further purification. LCMS-1: Rt: 1.93, 1.98 min; MS m/z [M+H]$^+$: 686.6/688.6.

Step 3: Tert-butyl 6-(4-(5-chloro-6-methyl-1-(tetrahydro-2H-pyran-2-yl)-1H-indazol-4-yl)-3-(2-(2-(mesityloxy)ethyl)-2H-indazol-5-yl)-5-methyl-1H-pyrazol-1-yl)-2-azaspiro[3.3]heptane-2-carboxylate To a solution of tert-butyl 6-(4-(5-chloro-6-methyl-1-(tetrahydro-2H-pyran-2-yl)-1H-indazol-4-yl)-3-(2-(2-hydroxyethyl)-2H-indazol-5-yl)-5-methyl-1H-pyrazol-1-yl)-2-azaspiro[3.3]heptane-2-carboxylate (1.40 g, 2.04 mmol) and triethylamine (Step 2, 1.22 mL, 8.16 mmol) in CH$_2$Cl$_2$ (15.5 mL) at 0° C. under nitrogen atmosphere was added mesyl chloride (0.24 mL, 3.06 mmol) and the reaction mixture was stirred at RT for 30 min. After completion of the reaction, the RM was quenched with water and extracted with EtOAc (×2). The combined organic layers were washed with brine, dried (Na$_2$SO$_4$), filtered and concentrated under vacuum. The crude residue was purified by trituration in pentane and diethyl ether to obtain the desired product. LCMS-1: Rt: 2.04, 2.09 min; MS m/z [M+H]$^+$: 764.5/766.5.

Step 4: Tert-butyl 6-(4-(5-chloro-6-methyl-1-(tetrahydro-2H-pyran-2-yl)-1H-indazol-4-yl)-3-(2-(2-((S)-3-fluoropyrrolidin-1-yl)ethyl)-2H-indazol-5-yl)-5-methyl-1H-pyrazol-1-yl)-2-azaspiro[3.3]heptane-2-carboxylate A solution of tert-butyl 6-(4-(5-chloro-6-methyl-1-(tetrahydro-2H-pyran-2-yl)-1H-indazol-4-yl)-3-(2-(2-(mesityloxy)ethyl)-2H-indazol-5-yl)-5-methyl-1H-pyrazol-1-yl)-2-azaspiro[3.3]heptane-2-carboxylate (Step 3, 0.75 g, 0.98 mmol), (S)-3-fluoropyrrolidine.HCl (0.31 g, 2.45 mmol) and Cs₂CO₃ (1.44 g, 4.41 mmol) in 1,4-dioxane (9 mL) was stirred at 80° C. overnight. After completion of the reaction, the reaction mixture was diluted with water and extracted with EtOAc (×2). The combined organic layers were washed with brine, dried (Na₂SO₄), filtered and concentrated under vacuum. The crude crude residue was purified by normal phase chromatography (eluent: 4% MeOH in CH₂Cl₂) to obtain the desired product. LCMS-1: Rt: 1.77, 1.80 min; MS m/z [M+H]⁺: 757.7/759.7.

Step 5: (S)-5-chloro-4-(3-(2-(2-(3-fluoropyrrolidin-1-yl)ethyl)-2H-indazol-5-yl)-5-methyl-1-(2-azaspiro[3.3]heptan-6-yl)-1H-pyrazol-4-yl)-6-methyl-1H-indazole To a solution of tert-butyl 6-(4-(5-chloro-6-methyl-1-(tetrahydro-2H-pyran-2-yl)-1H-indazol-4-yl)-3-(2-(2-((S)-3-fluoropyrrolidin-1-yl)ethyl)-2H-indazol-5-yl)-5-methyl-1H-pyrazol-1-yl)-2-azaspiro[3.3]heptane-2-carboxylate (Step 4, 0.48 g, 0.63 mmol) in CH₂Cl₂ (10 mL) at 0° C. was added TFA (5 mL) and the reaction mixture was stirred at RT for 2 h. The RM was concentrated under vacuum to afford a crude residue which was purified by reverse phase chromatography on C18 silica gel (15 micron) (eluent: 0-53% CH₃CN in H₂O containing 0.025% NH₃) to obtain the desired product. LCMS-1: Rt: 1.28 min; MS m/z [M+H]⁺: 573.5/575.5.

Step 6: (S)-1-(6-(4-(5-chloro-6-methyl-1H-indazol-4-yl)-3-(2-(2-(3-fluoropyrrolidin-1-yl)ethyl)-2H-indazol-5-yl)-5-methyl-1H-pyrazol-1-yl)-2-azaspiro[3.3]heptan-2-yl)prop-2-en-1-one To a solution of (S)-5-chloro-4-(3-(2-(2-(3-fluoropyrrolidin-1-yl)ethyl)-2H-indazol-5-yl)-5-methyl-1-(2-azaspiro[3.3]heptan-6-yl)-1H-pyrazol-4-yl)-6-methyl-1H-indazole (Step 5, 0.25 g, 0.44 mmol) in THF (2 mL) was added NaHCO₃ (0.33 g, 3.93 mmol) in solution in H₂O (3 mL) followed by acroyl chloride (0.05 g, 0.52 mmol) as a solution in THF (1 mL) at 0° C. The reaction mixture was stirred at 0° C. for 10 min, then was poured into water and extracted with EtOAc. The combined organic layers were washed with a sat. aq. NaHCO₃ solution, brine, dried (Na₂SO₄), filtered and concentrated under vacuum. The crude residue which was purified by reverse phase chromatography on C18 silica gel (15 micron) (eluent: 0-53% CH₃CN in H₂O containing 0.1% NH₃) to give the title compound. The isomers were separated by chiral SFC (C-SFC-17; mobile phase: CO₂/MeOH/CH₃CN 65:18:7; UV: 242 nM) to give the title compound Example 80a as the second eluting peak: ¹H NMR (400 MHz, CD₃OD) δ 8.00 (s, 1H), 7.51 (m, 2H), 7.43 (m, 3H), 6.38 (m, 1H), 6.29 (m, 1H), 5.78 (m, 1H), 5.18-5.03 (m, 1H), 4.84 (m, 2H), 4.52 (m, 2H), 4.44 (s, 1H), 4.26 (s, 1H), 4.20 (s, 1H), 3.24-3.07 (m, 4H), 2.89-2.67 (m, 5H), 2.56 (s, 3H), 2.46 (m, 1H), 2.17 (s, 3H), 2.08-2.00 (m, 2H); LCMS-1: Rt: 1.49 min; MS m/z [M+H]⁺: 627.6/629.6; C-SFC-18 (mobile phase: CO₂/MeOH 60/40; UV: 242 nM): Rt: 14.37 min. The other isomer Example 80b was obtained as the first eluting: C-SFC-18 (mobile phase: CO₂/MeOH 60/40: UV: 242 nM): Rt: 7.31 min.

The following examples 81 to 82 in Table 6 below were prepared using analogous methods to Method-8 from intermediates (in Step 1) described in the intermediate synthesis section or commercially available.

TABLE 6

| Example | Structure | Method, intermediates (Step 1) and chiral separation conditions used and order of elution | Characterizing data |
|---|---|---|---|
| 81a/ 81b | 1-(6-(4-(5-chloro-6-methyl-1H-indazol-4-yl)-3-(1-(2-(3-methoxyazetidin-1-yl)ethyl)-1H-indazol-5-yl)-5-methyl-1H-pyrazol-1-yl)-2-azaspiro[3.3]heptan-2-yl)prop-2-en-1-one | Using Method-8 from 3-methoxyazetidine hydrochloride (Step 4) and C-HPLC-23: (mobile phase: Hexane/IPA/CH₃CN 60/2020; flow rate; 20 mL/min; UV: 242 nM); Example 81a = 2ⁿᵈ eluting isomer, Example 81b = 1ˢᵗ eluting isomer | Example 81a: ¹H NMR (400 MHz, CD₃OD) δ 7.88 (s, 1H), 7.65 (s, 1H), 7.50 (s, 1H), 7.43 (m, 3H), 6.38 (m, 1H), 6.28 (m, 1H), 5.77 (m, 1H), 4.49 (s, 1H), 4.43 (s, 1H), 4.36 (m, 2H), 4.26 (s, 1H), 4.21 (s, 1H), 3.90 (m, 1H), 3.16 (s, 3H), 3.08 (m, 2H), 2.99 (m, 2H), 2.85 (m, 4H), 2.55 (s, 3H), 2.12 (s, 3H); LCMS-1: Rt - 1.42 min; MS m/z [M + H]⁺: 625.4/627.4; C-HPLC-24 (mobile phase: [Hexane + 0.1% Et₂NH]/IPA/CH₃CN gradient), Rt = 12.1 min, Example 81b: C-HPLC-24 (mobile phase: [Hexane + 0.1% Et₂NH]/IPA/CH₃CN gradient), Rt = 10.7 min. |

TABLE 6-continued

| Example | Structure | Method, intermediates (Step 1) and chiral separation conditions used and order of elution | Characterizing data |
|---|---|---|---|
| 82a/ 82b | 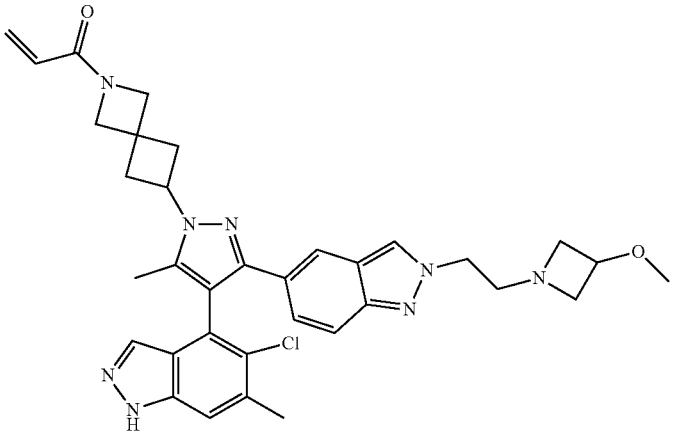<br>1-(6-(4-(5-chloro-6-methyl-1H-indazol-4-yl)-3-(2-(2-(3-methoxyazetidin-1-yl)ethyl)-2H-indazol-5-yl)-5-methyl-1H-pyrazol-1-yl)-2-azaspiro[3.3]heptan-2-yl)prop-2-en-1-one | Using Method-8 from 1-(2-((tert-butyldimethylsilyl)oxy)ethyl)-5-(4,4,5,5-tetramethyl-1,3,2-dioxaborolan-2-yl)-1H-indazole (Intermediate B20) (Step 1) and 3-methoxyazetidine hydrochloride (Step 4) and C-HPLC-23: (mobile phase: Hexane/IPA/CH$_3$CN 60/20/20; flow rate: 20 mL/min; UV: 242 nM); Example 82a = 2$^{nd}$ eluting isomer, Example 82b = 1$^{st}$ eluting isomer | Example 82a: $^1$H NMR (400 MHz, CD$_3$OD) δ 8.04 (s, 1H), 7.51-7.43 (m, 5H), 6.42 (m, 1H), 6.38 (d, 1H), 5.78 (d, 1H), 4.50 (s, 1H), 4.44 (s, 1H), 4.38 (m, 2H), 4.26 (s, 1H), 4.22 (s, 1H), 3.95 (m, 1H), 3.45 (m, 2H), 3.19 (s, 3H), 3.05 (m, 4H), 2.91 (m, 4H), 2.56 (s, 3H), 2.12 (s, 3H); LCMS-4; Rt = 2.60 min; MS m/z [M + H]$^+$ = 625.3/ 627.3; C-SFC-18 (mobile phase: CO$_2$/[MeOH-ACN + 0.1% Et$_2$NH] 60/20/20, UV: 242 nM): Rt = 7.69 min; Example 82b: C-SFC-18 (mobile phase: CO$_2$/[MeOH-ACN + 0.1% Et$_2$NH] 60/20/20, UV: 242 nM): Rt = 5.44 min. |

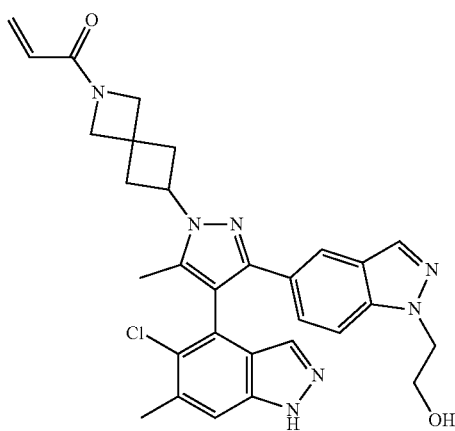 [SMILES: C=CC(=O)N1CC2(CC(n3nc(-c4ccc5c(cnn5CCO)c4)c(-c4c(Cl)c(C)cc5[nH]ncc45)c3C)C2)C1]

Examples 83a/83b: 1-(6-(4-(5-chloro-6-methyl-1H-indazol-4-yl)-3-(1-(2-hydroxyethyl)-1H-indazol-5-yl)-5-methyl-1H-pyrazol-1-yl)-2-azaspiro[3.3]heptan-2-yl)prop-2-en-1-one The title examples were prepared using similar method to Method-8 Steps 4 and 5 from tert-butyl 6-(4-(5-chloro-6-methyl-1-(tetrahydro-2H-pyran-2-yl)-1H-indazol-4-yl)-3-(2-(2-hydroxyethyl)-2H-indazol-5-yl)-5-methyl-1H-pyrazol-1-yl)-2-azaspiro[3.3]heptane-2-carboxylate (Intermediate prepared in Step 2 Method-8). The isomers were separated by chiral SFC (C-SFC-2; mobile phase: CO$_2$/IPA: 72/28) to give the title compound Example 83a as the second eluting peak: $^1$H NMR (400 MHz, DMSO-d$_6$) δ 13.14 (s, 1H), 7.89 (s, 1H), 7.55 (m, 2H), 7.45 (m, 2H), 7.31 (m, 1H), 6.35 (m, 1H), 6.13 (m, 1H), 5.69 (m, 1H), 4.93-4.82 (m, 2H), 4.39 (s, 1H), 4.32 (m, 2H), 4.10 (s, 1H), 4.03 (s, 1H), 3.74 (m, 2H), 2.90-2.78 (m, 4H), 2.04 (s, 3H); LCMS-5: Rt=19.3 min; MS m/z [M+H]$^+$: 556.2/558.2; C-SFC-18 (mobile phase: MeOH, UV: 242 nM): Rt=7.52 min. The other isomer Example 83b was obtained as the first eluting peak: C-SFC-18 (mobile phase: mobile phase: MeOH; UV: 242 nM): Rt=6.85 min.

Method-9: Synthetic scheme

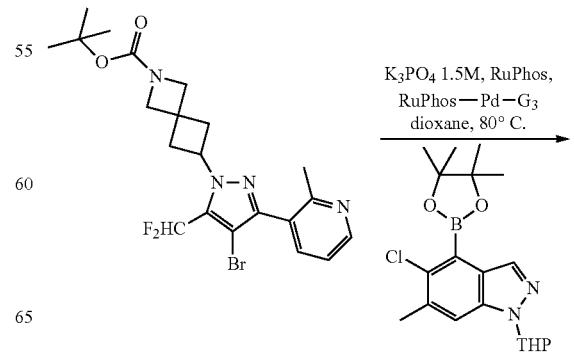

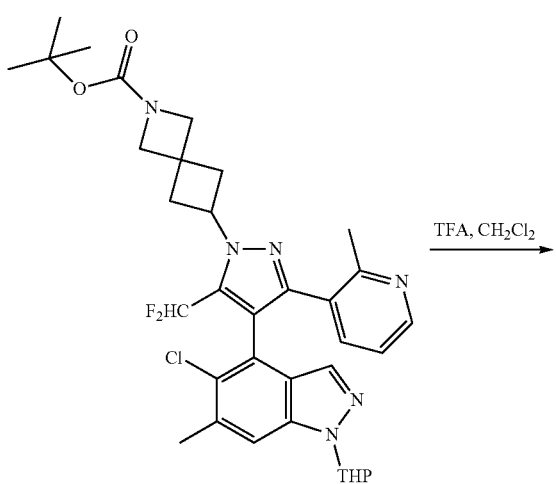

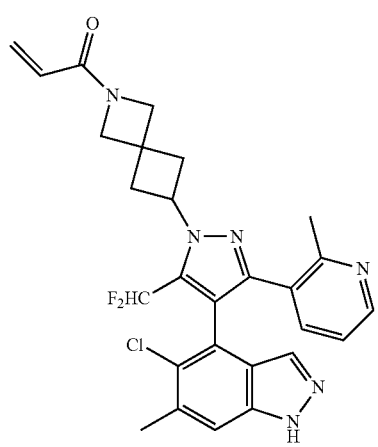

first eluting isomer + second eluting isomer

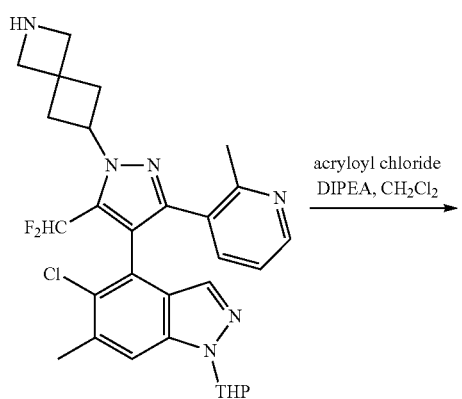

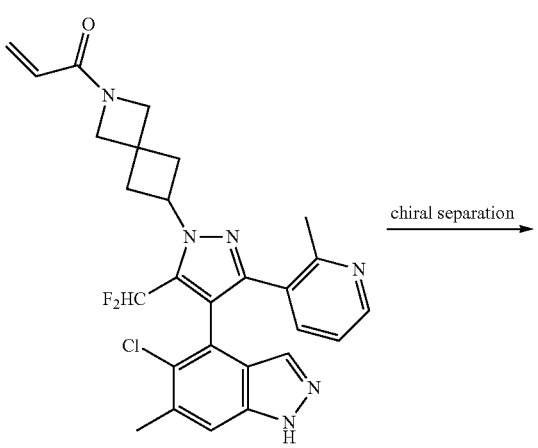

Examples 84a/84b: 1-(6-(4-(5-Chloro-6-methyl-1H-indazol-4-yl)-5-(difluoromethyl)-3-(2-methylpyridin-3-yl)-1H-pyrazol-1-yl)-2-azaspiro[3.3]heptan-2-yl)prop-2-en-1-one Step 1: Tert-butyl 6-(4-(5-chloro-6-methyl-1-(tetrahydro-2H-pyran-2-yl)-1H-indazol-4-yl)-5-(difluoromethyl)-3-(2-methylpyridin-3-yl)-1H-pyrazol-1-yl)-2-azaspiro[3.3]heptane-2-carboxylate To a solution of tert-butyl 6-(5-(difluoromethyl)-4-iodo-3-(2-methylpyridin-3-yl)-1H-pyrazol-1-yl)-2-azaspiro[3.3]heptane-2-carboxylate (Intermediate C9, 135 mg, 0.25 mmol) in dioxane (2 mL) were added 5-chloro-6-methyl-1-(tetrahydro-2H-pyran-2-yl)-4-(4,4,5,5-tetramethyl-1,3,2-dioxaborolan-2-yl)-1H-indazole (Intermediate D1, 125 mg, 0.33 mmol), RuPhos (17.8 mg, 0.04 mmol), RuPhos-Pd-G3 (31.9 mg, 0.04 mmol) and $K_3PO_4$ (1.5 M, 0.51 mL, 0.77 mmol). The vial was flushed with argon sealed and heated at 80° C. for 1 h. The RM was poured into a sat. aq. $NaHCO_3$ solution and extracted with EtOAc (2×). The combined organic extracts were washed with brine, dried ($Na_2SO_4$) and filtered. SiliaMetS® Thiol (0.16 mmol) was added and the mixture swirled for 1 h at 40° C., filtered and concentrated. The crude was purified by normal phase chromatography (eluent: tBME in c-hexane from 1 to 100%) to give the title compound. UPLC-MS-1: Rt=1.40 min; MS m/z [M+H]$^+$: 653.7/655.7.

Step 2: 5-chloro-4-(5-(Difluoromethyl)-3-(2-methylpyridin-3-yl)-1-(2-azaspiro[3.3]heptan-6-yl)-1H-pyrazol-4-yl)-6-methyl-1H-indazole trifluoroactetate To a solution of tert-butyl 6-(4-(5-chloro-6-methyl-1-(tetrahydro-2H-pyran-2-yl)-1H-indazol-4-yl)-5-(difluoromethyl)-3-(2-methylpyridin-3-yl)-1H-pyrazol-1-yl)-2-azaspiro[3.3]heptane-2-carboxylate (Step 1, 119 mg, 0.18 mmol) in $CH_2Cl_2$ (2 mL) was added at 0° C. TFA (0.35 mL, 4.55 mmol) and the reaction mixture was stirred at RT until completion. Volatils were removed by evaporation to give the title compound as a trifluoroacetate salt which was used without purification in the next step. UPLC-MS-1: Rt=0.63 min; MS m/z [M+H]+: 469.5/471.5.

Step 3: 1-(6-(4-(5-Chloro-6-methyl-1H-indazol-4-yl)-5-(difluoromethyl)-3-(2-methylpyridin-3-yl)-1H-pyrazol-1-yl)-2-azaspiro[3.3]heptan-2-yl)prop-2-en-1-one To a solution of 5-chloro-4-(5-(difluoromethyl)-3-(2-methylpyridin-3-yl)-1-(2-azaspiro[3.3]heptan-6-yl)-1H-pyrazol-4-yl)-6-methyl-1H-indazole trifluoroactetate salt (Step 2, 0.18 mmol) in $CH_2Cl_2$ (5 mL) at 0° C. under argon atmosphere were added DIPEA (0.47 mL, 2.69 mmol) and acryloyl chloride (0.022 mL, 0.27 mmol). The reaction mixture was stirred at 0° C. for 1.5 h. MeOH (10 mL) was added and the RM was stirred for 15 min while allowed to reach RT. The RM was poured into a sat. aq. $NaHCO_3$ solution and extracted with $CH_2Cl_2$ (2×). The combined organic extracts were dried (phase separator), filtered and evaporated. The crude residue was purified by normal phase chromatography (eluent: MeOH/$CH_2Cl_2$ (10/90)) to give the title compound. The isomers were separated by chiral SFC (C-SFC-7; mobile phase: $CO_2$/IPA 63/37) to give the title compound Example 84a as the second eluting peak (white powder): $^1$H NMR (600 MHz, DMSO-$d_6$) δ 13.1 (s, 1H), 8.30 (d, 1H), 7.52 (d, 2H), 7.28 (m, 1H), 7.04-6.86 (m, 2H), 6.30 (m, 1H), 6.10 (m, 1H), 5.67 (m, 1H), 5.11 (m, 1H), 4.39 (s, 1H), 4.30 (s, 1H), 4.10 (s, 1H), 4.00 (s, 1H), 2.95-2.84 (m, 4H), 2.41 (s, 3H), 2.36 (s, 1.5H), 2.35 (s, 1.5H); UPLC-MS-1: Rt=0.89 min; MS m/z [M+H]+: 523.3/525.3; C-SFC-8 (mobile phase: $CO_2$/IPA 63/37): Rt=2.66 min. The other isomer Example 84b was obtained as the first eluting peak: C-SFC-8 (mobile phase: $CO_2$/IPA 63/37): Rt=1.61 min.

Method-9a: similar to Method-9 except that Step 2 was performed using $H_2SO_4$ in dioxane as described in Method-1a Step 2.

Method-9b: similar to Method-9 except Step 3 was performed using acryloyl chloride and $NaHCO_3$ followed by a treatment with LiOH as described in Method-1 b Step 3.

Method-9c: similar to Method-9 except Step 3 was performed using acrylic acid, DIPEA and HATU in DMF.

The following examples 85 to 93 in Table 7 below were prepared using analogous methods to Method-9 from intermediates (in Step 1) described in the intermediates synthesis section or commercially available.

TABLE 7

| Example | Structure | Method, intermediates and chiral separation conditions used and order of elution | Characterizing data |
|---|---|---|---|
| 85a/85b | 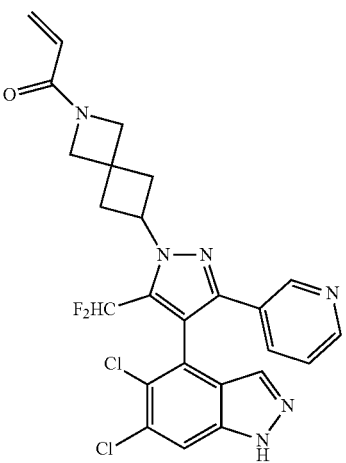<br>1-(6-(4-(5,6-dichloro-1H-indazol-4-yl)-5-(difluoromethyl)-3-(pyridin-3-yl)-1H-pyrazol-1-yl)-2-azaspiro[3.3]heptan-2-yl)prop-2-en-1-one | Using Method-9 from Intermediate C11 and Intermediate D3 (Step 1) and C-HPLC-8 (mobile phase: n-heptane/IPA/Et$_3$N 80:20:0.05); Example 85a = 1$^{st}$ eluting isomer, Example 85b = 2$^{nd}$ eluting isomer | Example 85a: $^1$H NMR (400 MHz, DMSO-$d_6$) δ 13.54 (br s, 1H), 8.43 (m, 1H), 8.37 (m, 1H), 7.99 (m, 1H), 7.68 (s, 1H), 7.61 (m, 1H), 7.30 (m, 1H), 7.04 (m, 1H), 6.32 (m, 1H), 6.10 (m, 1H), 5.68 (m, 1H), 5.10 (m, 1H), 4.39 (s, 1H), 4.34 (s, 1H), 4.10 (s, 1H), 4.05 (s, 1H), 2.81-3.02 (m, 4H); UPLC-MS-7: Rt = 0.98 min, MS m/z [M + H]+: 529.1/531.1/533.2; C-HPLC-9 (mobile phase n-heptane/IPA/DEA 80:20:0.05): Rt - 4.72 min, Example 85b: C-HPLC-9 (mobile phase: n-heptane/IPA/DEA 80:20:0.05): Rt = 5.74 min. |

TABLE 7-continued

| Example | Structure | Method, intermediates and chiral separation conditions used and order of elution | Characterizing data |
|---|---|---|---|
| 86a/86b | 1-(6-(4-(5,6-dichloro-1H-indazol-4-yl)-5-(difluoromethyl)-3-(pyrimidin-5-yl)-1H-pyrazol-1-yl)-2-azaspiro[3.3]heptan-2-yl)prop-2-en-1-one | Using Method-9 from Intermediate C10 and Intermediate D3 (Step 1) and C-SFC-5 (mobile phase: IPA/$CO_2$ 35:65): Example 86a = 1$^{st}$ eluting isomer, Example 86b = 2$^{nd}$ eluting isomer | Example 86a: $^1$H NMR (400 MHz, DMSO-$d_6$) δ 13.57 (br s, 1H), 9.07 (s, 1H), 8.57 (s, 2H), 8.00 (s, 1H), 7.72 (s, 1H), 7.09 (m, 1H), 6.32 (m, 1H), 6.10 (m, 1H), 5.67 (m, 1H), 5.13 (m, 1H), 4.39 (s, 1H), 4.35 (s, 1H), 4.10 (s, 1H), 4.06 (s, 1H), 2.81-3.04 (m, 4H); UPLC-MS-1: Rt = 0.94 min, MS m/z [M + H]$^+$: 530.2/532.3; C-SFC-6 (mobile phase: IPA/$CO_2$ 35:65): Rt = 1.67 min, Example 86b: C-SFC-6 (mobile phase: IPA/$CO_2$ 35:65): Rt = 2.24 min. |
| 87a/87b | 1-(6-(4-(5-chloro-6-methyl-1H-indazol-4-yl)-5-(difluoromethyl)-3-(pyridin-3-yl)-1H-pyrazol-1-yl)-2-azaspiro[3.3]heptan-2-yl)prop-2-en-1-one | Using method 9a,b from Intermediate C11 and Intermediate D1 (Step 1) and C-SFC-5 (Mobile phase: IPA/$CO_2$ 30:70); Example 87a = 1$^{st}$ eluting isomer, Example 87b = 2$^{nd}$ eluting isomer | Example 87a: $^1$H NMR (400 MHz, DMSO-$d_6$) δ 13.27 (s, 1H), 8.41 (m, 1H), 8.35 (m, 1H), 7.63 (s, 1H), 7.62 (m, 1H), 7.53 (s, 1H), 7.28 (m, 1H), 6.92 (m, 1H), 6.32 (m, 1H), 6.10 (m, 1H), 5.68 (m, 1H), 5.10 (m, 1H), 4.39 (s, 1H), 4.34 (s, 1H), 4.10 (s, 1H), 4.05 (s, 1H), 3.02-2.93 (m, 2H) 2.89-2.83 (m, 2H), 2.458 (m, 3H); UPLC-MS-6: Rt = 1.00 min, MS m/z [M + H]$^+$ 509.1/511.1; C-SFC-6 (mobile phase: IPA/$CO_2$ 30:70): Rt = 3.21 min, Example 87a: C-HPLC-6 (mobile phase: IPA/$CO_2$ 30:70): Rt = 3.77 min. |

TABLE 7-continued

| Example | Structure | Method, intermediates and chiral separation conditions used and order of elution | Characterizing data |
|---|---|---|---|
| 88 | 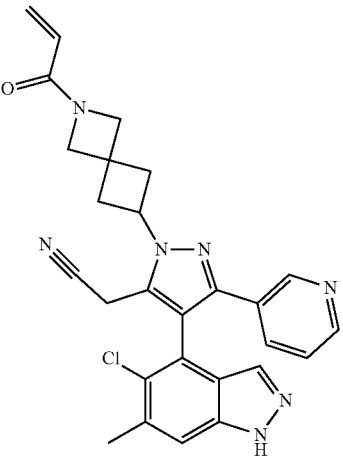<br>2-(1-(2-acryloyl-2-azaspiro[3.3]heptan-6-yl)-4-(5-chloro-6-methyl-1H-indazol-4-yl)-3-(pyridin-3-yl)-1H-pyrazol-5-yl)acetonitrile | Using Method-9a,c from Intermediate C12 and Intermediate D1 (Step 1) | Exmple 88: $^1$H NMR (600 MHz, DMSO-$d_6$) δ 13.24 (s, 1H), 8.33-8.40 (m, 2H), 7.62 (s, 2H), 7.48 (s, 1H), 7.26 (m, 1H), 6.33 (m, 1H), 6.11 (m, 1H), 5.68 (m, 1H), 5.07 (m, 1H), 4.40 (s, 1H), 4.35 (s, 1H), 4.11 (s, 1H), 4.06 (s, 1H), 3.95 (m, 2H), 2.80-3.00 (m, 4H); UPLC-MS-7: Rt = 0.76 min, MS m/z [M + H]$^+$ : 498.3/500.3. |
| 89a/89b | 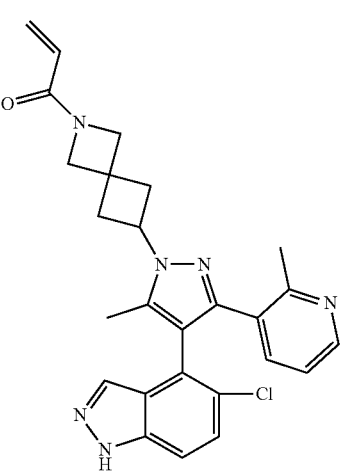<br>1-(6-(4-(5-chloro-1H-indazol-4-yl)-5-methyl-3-(2-methylpyridin-3-yl)-1H-pyrazol-1-yl)-2-azaspiro[3.3]heptan-2-yl)prop-2-en-1-one | Using Method-9 from Intermediate C13 and Intermediate D4 (Step 1) and C-HPLC-23 (mobile phase: Hexane/IPA/MeOH 75/12.5/12.5; flow rate: 18 mL/min, UV: 296 nM):<br>Example 89a = 1$^{st}$ eluting isomer,<br>Example 89b = 2$^{nd}$ eluting isomer | Example 89a: $^1$H NMR (400 MHz, DMSO-$d_6$) δ 13.24 (s, 1H), 8.27 (s, 1H), 7.56-7.46 (m, 2H), 7.39 (m, 1H), 7.29 (m, 1H), 7.02 (m, 1H), 6.36 (m, 1H), 6.12 (m, 1H), 5.67 (m, 1H), 4.95 (m, 1H), 4.39 (s, 1H), 4.29 (s, 1H), 4.10 (s, 1H), 3.99 (s, 1H), 2.90-2.80 (m, 4H), 2.31 (s, 3H), 2.13 (s, 3H); LCMS-1: Rt = 1.38 min, MS m/z [M + H]$^+$: 473.7/475.7; C-HPLC-29 (mobile phase: [Hexane + 0.1% NH$_3$]/IPA/MeOH 35/32.5/32.5), Rt = 5.78 min,<br>Example 89b: C-HPLC-29 (mobile phase: [Hexane + 0.1% NH$_3$[/IPA/MeOH 35/32.5/32.5), Rt = 6.99 min. |

TABLE 7-continued

| Example | Structure | Method, intermediates and chiral separation conditions used and order of elution | Characterizing data |
|---|---|---|---|
| 90a/90b | 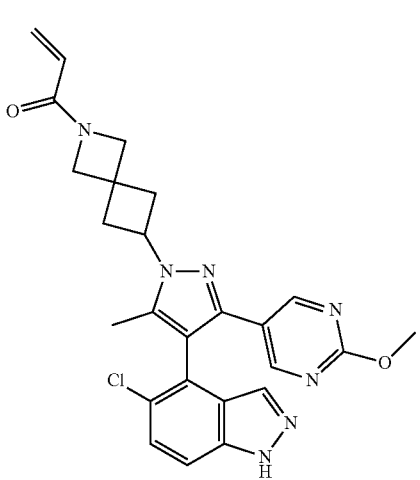<br>1-(6-(4-(5-chloro-1H-indazol-4-yl)-3-(2-methoxypyrimidin-5-yl)-5-methyl-1H-pyrazol-1-yl)-2-azaspiro[3.3]heptan-2-yl)prop-2-en-1-one | Using Method-9 from Intermediate C14 and Intermediate D4 (Step 1) and C-SFC-4 (mobile phase: IPA/CO$_2$ 35/65); Example 90a = 1$^{st}$ eluting isomer, Example 90b = 2$^{nd}$ eluting isomer | Example 90a: $^1$H NMR (600 MHz, DMSO-d$_6$) δ 13.38 (br s, 1H), 8.33 (s, 2H), 7.61 (m, 2H), 7.49 (m, 1H), 6.32 (m, 1H), 6.10 (m, 1H), 5.68 (m, 1H), 4.93 (m, 1H), 4.38 (s, 1H), 4.32 (s, 1H), 4.09 (s, 1H), 4.03 (s, 1H), 3.83 (s, 3H), 2.77-2.93 (m, 4H), 2.07 (s, 3H). UPLC-MS-1: Rt = 0.87 min, MS m/z [M + H]$^+$ = 490.5/492.5; C-SFC-3 (mobile phase: IPA/CO$_2$ 35/65): Rt = 1.23 min, Example 90b: C-SFC-3 (mobile phase: IPA/CO$_2$ 35.65): Rt = 2.18 min. |
| 91a/91b | 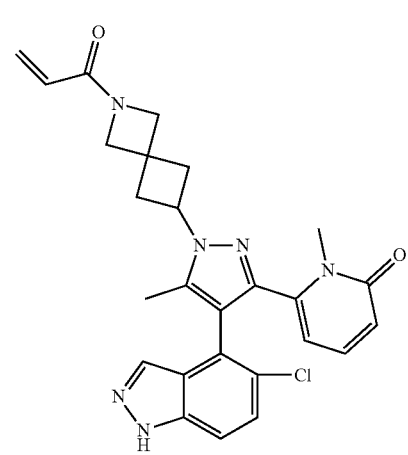<br>6-(1-(2-acryloyl-2-azaspiro[3.3]heptan-6-yl)-4-(5-chloro-1H-indazol-4-yl)-5-methyl-1H-pyrazol-3-yl)-1-methylpyridin-2(1H)-one | Using Method-9 from Intermediate C15 and Intermediate D4 and C-HPLC-28 (mobile phase: Hexane/IPA/ACN 75/17.5/7.5; UV: 306 nM): Example 91a = 1$^{st}$ eluting isomer, Example 91b = 2$^{nd}$ eluting isomer | Example 91a: $^1$H NMR (400 MHz, DMSO-d$_6$) δ 13.34 (s, 1H), 7.70 (s, 1H), 7.55 (m, 1H), 7.44 (m, 1H), 7.21 (m, 1H), 6.37 (m, 1H), 6.25 (m, 1H), 6.13 (m, 1H), 5.86 (m, 1H), 5.70 (m, 1H), 4.99 (m, 1H), 4.38 (s, 1H), 4.29 (s, 1H), 4.09 (s, 1H), 3.99 (s, 1H), 3.32 (s, 3H), 2.89-2.79 (m, 4H), 2.12 (s, 3H); LCMS-1: Rt = 1.425 min, MS m/z [M + H]$^+$ 489.7/491.7; C-HPLC-29 (mobile phase: Hexane/IPA-ACN gradient; UV: 306 nM): Rt = 16.58 min, Example 91b: C-HPLC-29 (mobile phase: Hexane/IPA-ACN gradient; UV: 306 nM): Rt = 17.65 min. |

TABLE 7-continued

| Example | Structure | Method, intermediates and chiral separation conditions used and order of elution | Characterizing data |
|---|---|---|---|
| 92a/92b | 1-(6-(4-(5-chloro-6-methyl-1H-indaozl-4-yl)-2'-(2-(dimethylamino)ethyl)-5,5'-dimethyl-1H,2'H-[3,3'-bipyrazol]-1-yl)-2-azaspiro[3.3]heptan-2-yl)prop-2-en-1-one | Using Method-9 from tert-butyl 6-(4-bromo-2'-(2-(dimethylamino)ethyl)-5,5'-dimethyl-1H,2'H-[3,3'-bipyrazol]-1-yl)-2-azaspiro[3.3]heptane-2-carboxylate (Intermediate C16) and Inttermediate D1 (Step 1) and C-SFC-4 (mobile phase: $CO_2$/[IPA + 0.1% $Et_3N$] 60/40) Example 92a = $2^{nd}$ eluting isomer, Example 92b = $1^{st}$ eluting isomer | Example 92a: $^1$H NMR (600 MHz, DMSO-$d_6$) δ 13.16 (s, 1H), 7.55 (s, 1H), 7.49 (s, 1H), 6.32 (m, 1H), 6.11 (m, 1H), 5.68 (m, 1H), 5.23 (s, 1H), 4.95 (m, 1H), 4.48-4.42 (m, 1H), 4.41-4.36 (m, 1H), 4.39 (s, 1H), 4.27 (s, 1H), 4.10 (s, 1H), 3.97 (s, 1H), 2.88-2.78 (m, 4H), 2.65-2.58 (m, 1H), 2.57-2.51 (m, 1H), 2.48 (s, 3H), 2.18 (s, 6H), 2.03 (s, 3H), 1.89 (s, 3H); HPLC-MS-1: Rt = 0.78 min; MS m/z [M + H]$^+$ 547.4/549.4; C-SFC-3 (mobile phase: $CO_2$/[IPA + 0.1% $Et_3N$] 60/40): Rt = 2.13 min, Example 92b: C-SFC-3 (mobile phase: $CO_2$/[IPA + 0.1% $Et_3N$] 60/40): Rt = 0.85 min. |
| 93a/93b | 1-(6-(4-(5-chloro-6-methyl-1H-indazol-4-yl)-1'-(2-(dimethylamino)ethyl)-5,5'-dimethyl-1H,1'H,1'H-[3,3'-bipyrazol]-1-yl)-2-azaspiro[3.3]heptan-2-yl)prop-2-en-1-one | Using Method from tert-butyl 6-(4-bromo-1'-(2-(dimethylamino)ethyl)-5,5'-dimethyl-1H,1'H-[3,3'-bipyrazol]-1-yl)-2-azaspiro[3.3]heptane-2-carboxylate (Intermediate C17) (Step 1) and C-SFC-7 (mobile phase: $CO_2$/[MeOH + 0.1% $Et_3N$] 45.55) Example 93a = $1^{st}$ eluting isomer, Example 93b = $2^{nd}$ eluting isomer | Example 93a: $^1$H NMR (600 MHz, DMSO-$d_6$) δ 13.10 (s, 1H), 7.49 (s, 1H), 7.38 (s, 1H), 6.33 (m, 1H), 6.11 (m, 1H), 5.74 (s, 1H), 5.68 (m, 1H), 4.86 (m, 1H), 4.39 (s, 1H), 4.31 (s, 1H), 4.10 (s, 1H), 4.02 (s, 1H), 3.82 (m, 2H), 2.88-2.81 (m, 2H), 2.78-2.74 (m, 2H), 2.48 (s, 3H), 2.25 (m, 2H), 2.11 (s, 3H), 2.04 (s, 6H), 2.00 (s, 3H); UPLC-MS-1: Rt = 0.75 min; MS m/z [M + H]$^+$ 547.4/549.4; C-SFC-8 (mobile phase: $CO_2$/[MeOH + 0.1% $Et_3N$] 45.55): Rt = 1.13 min, Example 93b: C-SFC-8 (mobile phase: $CO_2$/[MeOH + 0.1% $Et_3N$] 45.55): Rt = 2.70 min. |

Method-10: Synthetic scheme

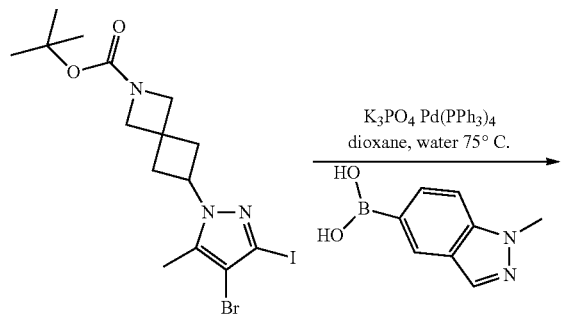

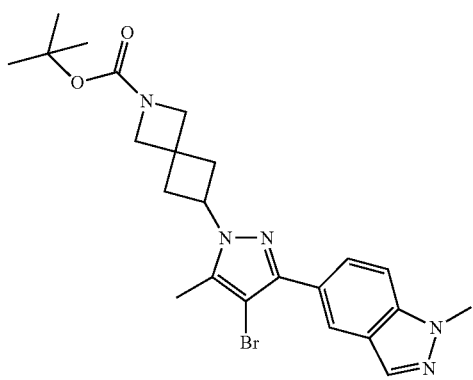

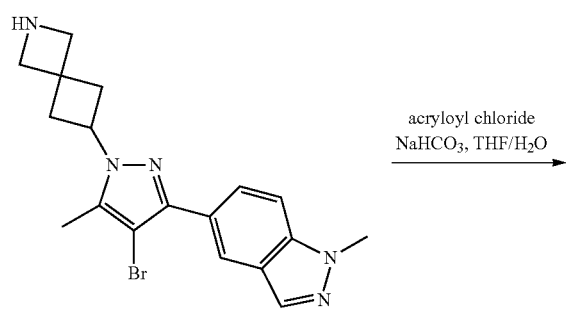

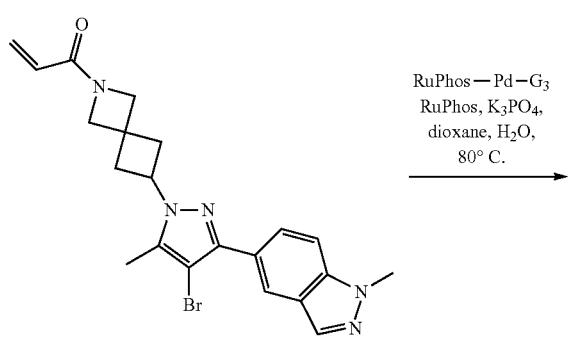

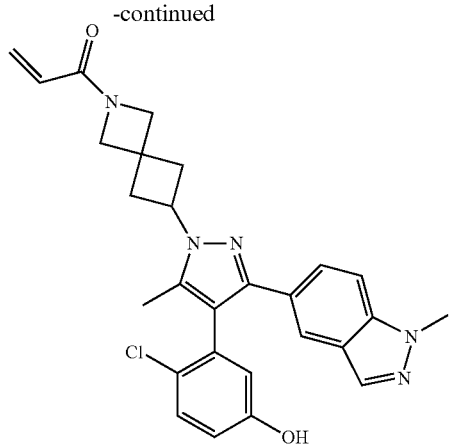

Example 94: 1-(6-(4-(2-chloro-5-hydroxyphenyl)-5-methyl-3-(1-methyl-1H-indazol-5-yl)-1H-pyrazol-1-yl)-2-azaspiro[3.3]heptan-2-yl)prop-2-en-1-one

Step 1: Tert-butyl 6-(4-bromo-5-methyl-3-(1-methyl-1H-indazol-5-yl)-1H-pyrazol-1-yl)-2-azaspiro[3.3]heptane-2-carboxylate To a suspension of (Intermediate C7, 3.00 g, 6.22 mmol), (1-methyl-1H-indazol-5-yl)boronic acid (1.09 g, 6.22 mmol), $K_3PO_4$ (3.96 g, 18.7 mmol) in 1,4-dioxane (20 mL) and Water (5.00 mL), degassed with Argon were added tetrakis(triphenylphosphine)palladium (0.72 g, 0.62 mmol) and $K_3PO_4$ (3.96 g, 18.7 mmol). The reaction mixture was stirred at 75° C. for 8 h. The RM was quenched by addition of sat. aq. solution of $NaHCO_3$. EtOAc was added and the layer were separated. The aqueous layer was extracted with EtOAc and the combined organic extracts were washed with brine, dried ($MgSO_4$), filtered and evaporated. The crude residue was purified by normal phase chromatography (eluent: EtOAc in n-heptane from 0 to 30%) to give the title compound. UPLC-MS-3: Rt=1.20 min; MS m/z [M+H]$^+$: 486.1/488.1.

Step 2: 5-(4-Bromo-5-methyl-1-(2-azaspiro[3.3]heptan-6-yl)-1H-pyrazol-3-yl)-1-methyl-1H-indazole To a stirred solution of tert-butyl 6-(4-bromo-5-methyl-3-(1-methyl-1H-indazol-5-yl)-1H-pyrazol-1-yl)-2-azaspiro[3.3]heptane-2-carboxylate (Step 1, 460 mg, 0.95 mmol) in 1,4-dioxane (5 mL) was added $H_2SO_4$ (0.15 mL, 2.84 mmol) and the solution was stirred at RT for 8 h. The RM was quenched by addition of sat. aq. solution of $NaHCO_3$. The mixture was extracted with DCM (×2) and the combined organic extracts were washed with brine, dried ($MgSO_4$), filtered and evaporated to dryness. UPLC-MS-3: Rt=0.74 min; MS m/z [M+H]$^+$: 387.2/389.2.

Step 3: 1-(6-(4-Bromo-5-methyl-3-(1-methyl-1H-indazol-5-yl)-1H-pyrazol-1-yl)-2-azaspiro[3.3]heptan-2-yl)prop-2-en-1-one To a solution of 5-(4-bromo-5-methyl-1-(2-azaspiro[3.3]heptan-6-yl)-1H-pyrazol-3-yl)-1-methyl-1H-indazole (Step 2, 350 mg, 0.91 mmol) in THF (15 mL) at 0° C. were added a solution of $NaHCO_3$ (0.5 M, 5.44 mL, 2.72 mmol) and acryloyl chloride (0.08 mL, 0.99 mmol). The reaction mixture was stirred at 0° C. and allowed to reach RT in 1 h. A sat. aq. solution of NaHCO$_3$ and DCM were added. The layer were separated and the organic layer was washed with brine, dried (MgSO$_4$), filtered and evaporated. The crude residue was purified by normal phase chromatography (eluent: ((MeOH/DCM 10/90) in DCM) from 0 to 100%) the purified again by normal phase chromatography (eluent: EtOAc in n-heptane from 0 to 100% then (MeOH/DCM 10/90) in DCM from 0 to 100%) to give the title compound. UPLC-MS-3: Rt=0.95 min; MS m/z [M+H]$^+$: 440.2/442.2.

Step 4: 1-(6-(4-(2-chloro-5-hydroxyphenyl)-5-methyl-3-(1-methyl-1H-indazol-5-yl)-1H-pyrazol-1-yl)-2-azaspiro[3.3]heptan-2-yl)prop-2-en-1-one To a suspension of 1-(6-(4-Bromo-5-methyl-3-(1-methyl-1H-indazol-5-yl)-1H-pyrazol-1-yl)-2-azaspiro[3.3]heptan-2-yl)prop-2-en-1-one (Step 3, 220 mg, 0.50 mmol), (2-chloro-5-hydroxyphenyl)boronic acid (86 mg, 0.50 mmol), K$_3$PO$_4$ (318 mg, 1.50 mmol) in 1,4-dioxane (2 mL) and Water (0.50 mL), degassed with Argon were added RuPhos (23.3 mg, 0.05 mmol) and RuPhos-Pd-G3 (41.8 mg, 0.05 mmol). The reaction mixture was stirred at 80° C. for 1 h. The RM was quenched by addition of a sat. aq. solution of NaHCO$_3$, extracted with EtOAc and the organic layer was washed with brine, dried (MgSO$_4$), filtered and evaporated. The crude residue was purified by normal phase chromatography (eluent: (MeOH/DCM (10-90) in DCM) from 0 to 100%) to give the title Example 94. $^1$H NMR (600 MHz, DMSO-d$_6$) δ 9.69 (s, 1H), 7.97 (s, 1H), 7.64 (s, 1H), 7.53 (d, 1H), 7.40 (d, 1H), 7.33 (d, 1H), 6.79 (dd, 1H), 6.60 (d, 1H), 6.33 (m, 1H), 6.11 (m, 1H), 5.68 (m, 1H), 4.86 (m, 1H), 4.38 (s, 1H), 4.31 (s, 1H), 4.10 (s, 1H), 4.02 (s, 1H), 4.01 (s, 3H), 2.89-2.82 (m, 2H), 2.79-2.73 (m, 2H), 2.09 (s, 3H); UPLC-MS-3: Rt=0.92 min; MS m/z [M+H]$^+$: 488.1/490.1.

Example 95: Crystalline Isopropyl Alcohol (IPA) Solvate of Compound X and Crystalline Hydrate (Modification HA) Form of Compound X 25 mg of Compound X (Example 1a) was added to 0.1 mL of 2-propanol. The resulting clear solution was stirred at 25° C. for 3 days, after which crystalline solid precipitated out. The solid was collected by centrifuge filtration and dried at ambient condition overnight. The wet cake was characterized as crystalline isopropyl (IPA) solvate of Compound X. Drying of the wet cake at ambient condition overnight provided crystalline hydrate (Modification HA) form.

Crystalline hydrate (Modification HA) form of Compound X was analysed by XRPD and the most characteristic peaks are shown in the Table below (see also FIG. 1).

In particular, the most characteristic peaks of the XRPD pattern of the crystalline hydrate (Modification HA) form may be selected from one, two, three or four peaks having an angle of refraction 2θ values (CuKα λ=1.5418 Å) selected from the group consisting of 8.2°, 11.6°, 12.9° and 18.8°.

| Index | Two-Theta | d value | Relative intensity | Intensity |
| --- | --- | --- | --- | --- |
| 1 | 8.2° | 10.72 Å | 100% | Strong |
| 2 | 11.6° | 7.60 Å | 11% | Weak |
| 3 | 12.1° | 7.30 Å | 10% | Weak |
| 4 | 12.9° | 6.87 Å | 14% | Medium |
| 5 | 14.6° | 6.05 Å | 21% | Medium |
| 6 | 16.2° | 5.47 Å | 15% | Medium |
| 7 | 18.8° | 4.73 Å | 28% | Medium |
| 8 | 20.4° | 4.34 Å | 18% | Medium |
| 9 | 24.1° | 3.69 Å | 29% | Medium |

Figure 2:
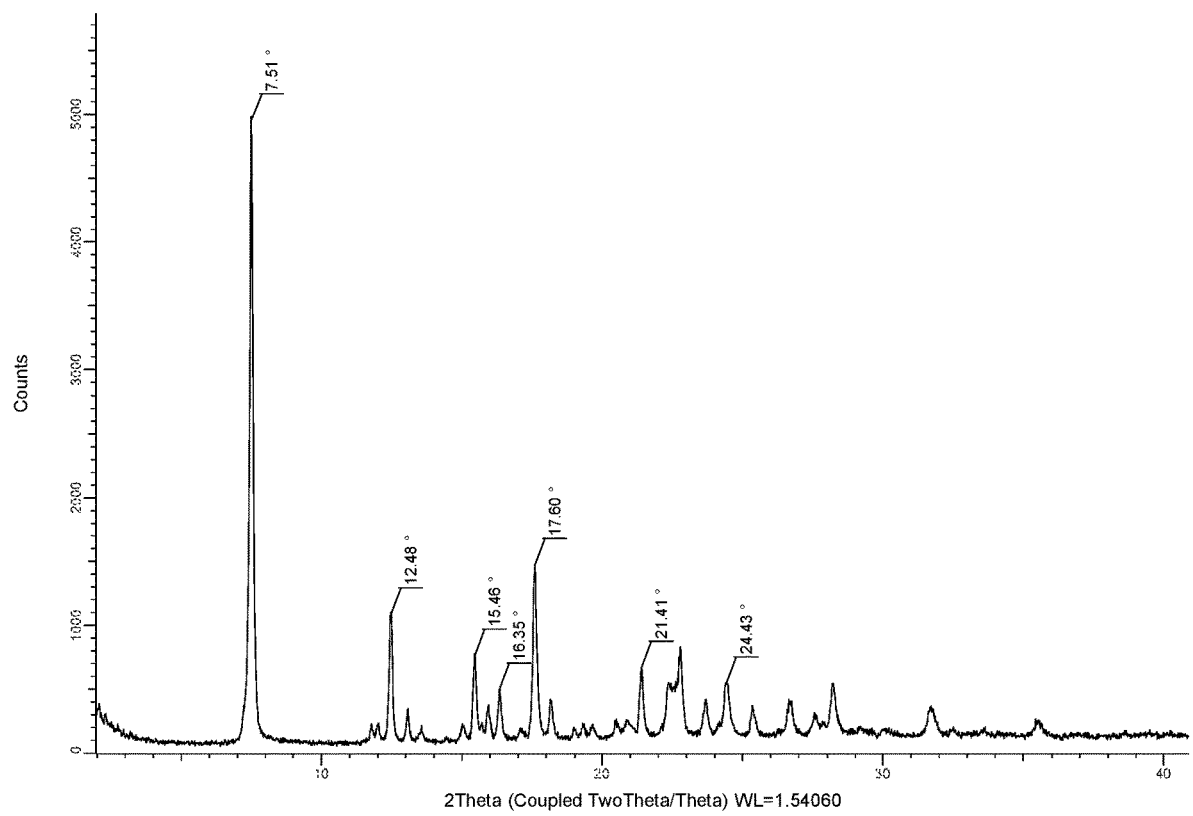
FIG. 2. illustrates the x-ray powder diffraction pattern of the isopropyl alcohol (IPA) solvate of a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Compound X).
Figure 3:
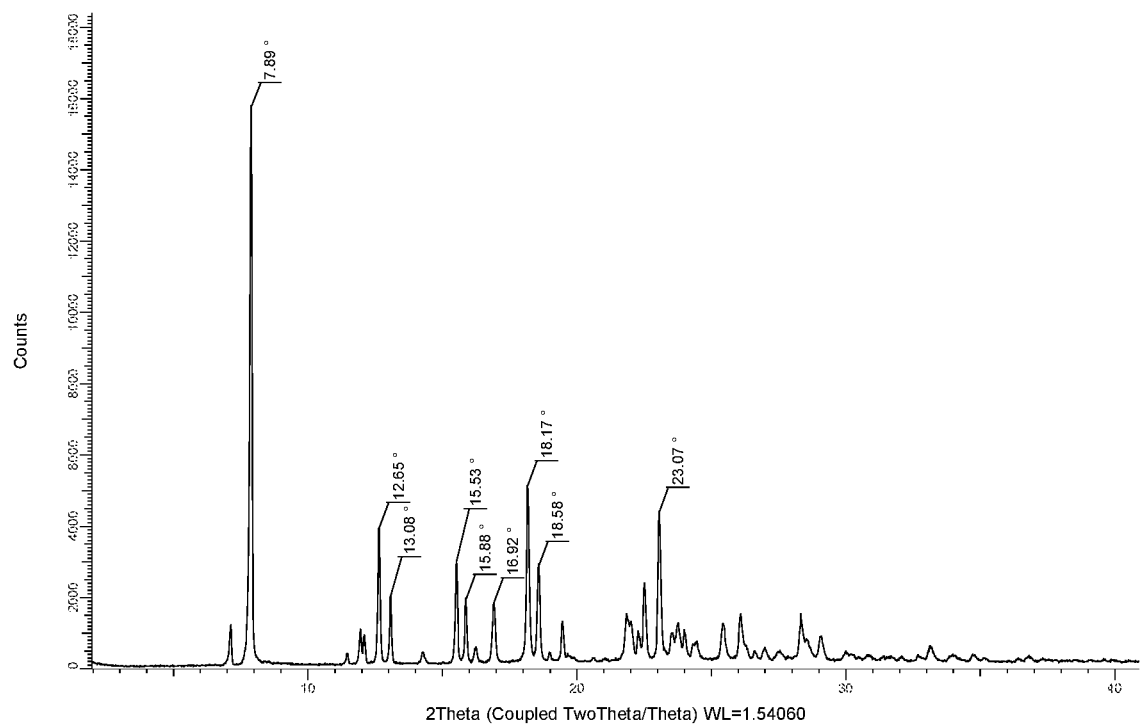
FIG. 3. illustrates the x-ray powder diffraction pattern of the ethanol (EtOH) solvate of a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Compound X).

Crystalline IPA solvate form of Compound X was analysed by XRPD and the most characteristic peaks are shown in the Table below (see also FIG. 2).

In particular, the most characteristic peaks of the XRPD pattern of the crystalline IPA solvate form may be selected from one, two, or three peaks having an angle of refraction 2θ values (CuKα λ=1.5418 Å) selected from the group consisting of 7.5°, 12.5° and 17.6°.

| Index | Two-Theta | d value | Relative intensity | Intensity |
| --- | --- | --- | --- | --- |
| 1 | 7.5° | 11.77 | 100% | Strong |
| 2 | 12.5° | 7.08 Å | 20% | Medium |
| 3 | 15.5° | 5.73 Å | 14% | Low |
| 4 | 16.4° | 5.42 Å | 8% | Low |
| 5 | 17.6° | 5.04 Å | 28% | Medium |
| 6 | 21.4° | 4.15 Å | 11% | Low |
| 7 | 24.4° | 3.64 Å | 8% | Low |

Example 96: Crystalline Ethanol (EtOH) Solvate of Compound X and Crystalline Hydrate (Modification HA) Form of Compound X 25 mg of Compound X (Example 1a) was added to 0.1 mL of ethanol. The resulting clear solution was stirred at 25° C. for 3 days. Crystalline hydrate (Modification HA) form of Compound X obtained in example 1a was added as seeds to the resulting solution. The resulting suspension was equilibrated for another 1 day, after which a solid precipitated out. The solid was collected by centrifuge filtration and dried at ambient condition overnight. The wet cake was characterized as crystalline ethanol solvate, which after drying at ambient condition overnight, produced crystalline hydrate (Modification HA).

Alternatively, 3.1 g of Compound X was added to 20 mL of ethanol, the resulting clear solution was stirred at 25° C. for 20 mins. Approximately 50 mg crystalline hydrate (Modification HA) (obtained above) was added as seeds, and the resulting mixture was equilibrated at 25° C. for 6 hours. The resulting suspension was filtrated and the wet cake was characterized as crystalline ethanol solvate. The solid was then dried at ambient condition (25° C. 60-70% Relative Humidity) for 3 days, 2.8 g of Compound X hydrate Modification HA was obtained with a yield of 90%. Crystalline ethanol solvate form of Compound X was analysed by XRPD and the most characteristic peaks are shown in the Table below (see also FIG. 3).

In particular, the most characteristic peaks of the XRPD pattern of the crystalline ethanol solvate form may be selected from one, two, or three or four peaks having an angle of refraction 2θ values (CuKα λ=1.5418 Å) selected from the group consisting of 7.9°, 12.7°, 18.2° and 23.1°.

| Index | Two-Theta | d value | Relative intensity | Intensity |
| --- | --- | --- | --- | --- |
| 1 | 7.9° | 11.20 Å | 100% | Strong |
| 2 | 12.7° | 6.99 Å | 24% | Medium |
| 3 | 13.1° | 6.76 Å | 12% | weak |
| 4 | 15.5° | 5.70 Å | 18% | weak |

| Index | Two-Theta | d value | Relative intensity | Intensity |
|---|---|---|---|---|
| 5 | 15.9° | 5.58 Å | 11% | weak |
| 6 | 16.9° | 5.24 Å | 11% | weak |
| 7 | 18.2° | 4.88 Å | 32% | medium |
| 8 | 18.6° | 4.77 Å | 17% | weak |
| 9 | 23.1° | 3.85 Å | 26% | Medium |

Example 97: Alternative Preparation of Crystalline Hydrate (Modification HA) Preparation 25 mg of Compound X (Example 1a) was added to 0.1 mL of methanol. The resulting clear solution was stirred at 25° C. for 3 days. Crystalline hydrate (Modification HA) obtained in example 1A was added as seeds to the resulting solution. The resulting suspension was equilibrated for another 1 day, after which a solid precipitated out. The solid was collected by centrifuge filtration and dried at ambient condition overnight. After drying at ambient condition overnight, the wet cake produced crystalline hydrate (Modification HA).

Example 98: Crystalline Propylene Glycol Solvate Preparation and Hydrate (Modification HA) Preparation 25 mg of Compound X (Example 1a) was added to 0.1 mL of propylene glycol. The resulting suspension was stirred at 50° C. for 1 week. The solid was collected by centrifuge filtration. The wet cake obtained after filtration was characterized as crystalline propylene glycol solvate. After drying of the cake at ambient condition for 1 week, crystalline hydrate (Modification HA) was obtained.

Figure 4:
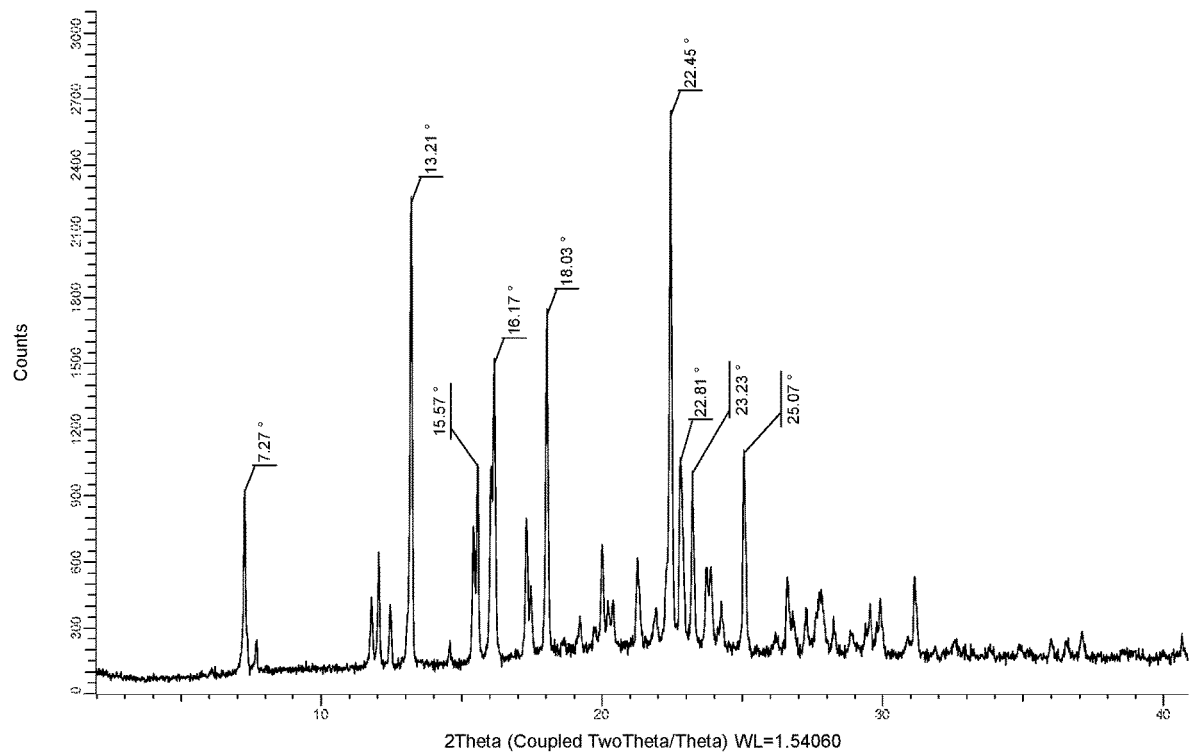
FIG. 4. illustrates the x-ray powder diffraction pattern of the propylene glycol solvate of a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one (Compound X).

Crystalline propylene glycol solvate form of Compound X was analysed by XRPD and the most characteristic peaks are shown in the Table below (see also FIG. 4).

In particular, the most characteristic peaks of the XRPD pattern of the crystalline propylene glycol solvate form may be selected from one, two, or three or four peaks having an angle of refraction 2θ values (CuKα λ=1.5418 Å) selected from the group consisting of 7.3°, 13.2°, 18.0° and 25.5°.

| Index | Two-Theta | d value | Relative intensity | Intensity |
|---|---|---|---|---|
| 1 | 7.3° | 12.15 Å | 34% | weak |
| 2 | 13.2° | 6.70 Å | 87% | Strong |
| 3 | 15.6° | 5.69 Å | 37% | weak |
| 4 | 16.2° | 5.48 Å | 56% | Medium |
| 5 | 18.0° | 4.92 Å | 64% | Medium |
| 6 | 22.5° | 3.96 Å | 100% | Strong |
| 7 | 22.8° | 3.90 Å | 35% | weak |
| 8 | 23.2° | 3.83 Å | 33% | weak |
| 9 | 25.1° | 3.55 Å | 37% | weak |

Synthesis of Intermediates

Aryl Bromide Intermediates: Intermediates A

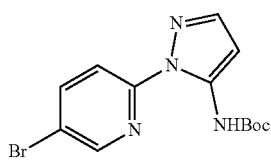

Intermediate A1: tert-butyl (1-(5-bromopyridin-2-yl)-1H-pyrazol-5-yl)carbamate 1-(5-bromopyridin-2-yl)-1H-pyrazol-5-amine (0.80 g, 3.35 mmol) was dissolved in dry THF (7 mL) and cooled to −78° C. under nitrogen atmosphere. NaHMDS (1M in THF, 6.70 mL, 6.69 mmol) was added dropwise and stirred for 10 min. Boc anhydride (0.73 g, 3.35 mmol) in THF (1 mL) was added dropwise at −78° C. and stirred at RT for 30 min. After completion of the reaction, the RM was diluted with water and extracted with EtOAc (×2). The combined organic extracts were washed with brine, dried ($Na_2SO_4$), filtered and concentrated under vacuum. The crude residue was purified by normal phase chromatography (eluent: EtOAc in hexane from 5 to 7%) to obtain the title product as pale white solid. LCMS-1: Rt=2.10 min; MS m/z $[M+H]^+$=339.1/341.1.

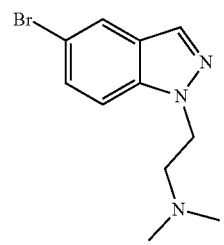

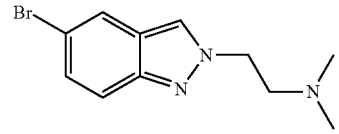

Intermediate A2 and A3: 2-(5-bromo-1H-indazol-1-yl)-N,N-dimethylethan-1-amine (A2) and 2-(5-bromo-2H-indazol-2-yl)-N,N-dimethylethan-1-amine (A3)

In a microwave vial, a solution of 5-bromoindazole (1 g, 5.02 mmol), dimethylamino ethyl chloride hydrochloride (0.40 g, and 2.64 mmol) and potassium carbonate (3.47 g, 25.1 mmol) in DMF (10 mL) was heated at 80° C. for 18 h. Dimethylamino ethyl chloride hydrochloride (0.33 g, and 2.2 mmol) was added and the reaction mixture was further stirred at 80° C. for 6 h. Dimethylamino ethyl chloride hydrochloride (0.40 g, and 2.64 mmol) was again added and the RM was further heated for 15 h. The RM was poured into water and extracted with EtOAc (×2). The combined organic extracts were washed with brine, dried ($Na_2SO_4$), filtered and evaporated. The crude residue was purified by normal phase chromatography (eluent: MeOH in $CH_2Cl_2$ from 0 to 8%) to give a mixture of both regioisomers. The regioisomers were separated by SFC-1 (mobile phase: MeOH in $CO_2$ from 2 to 6%) to give 2-(5-bromo-1H-indazol-1-yl)-N,N-dimethylethan-1-amine as the first eluting isomer: UPLC-MS-1: Rt=0.58 min; MS m/z $[M+H]^+$ 268.1/270.1 and -(5-bromo-2H-indazol-2-yl)-N,N-dimethylethan-1-amine as the second eluting isomer: UPLC-MS-1: Rt=0.57 min; MS m/z $[M+H]^+$ 268.1/270.1.

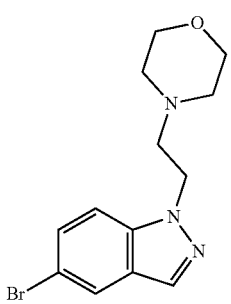 [SMILES: Brc1ccc2c(cnn2CCN2CCOCC2)c1]

Intermediate A4: 4-(2-(5-bromo-1H-indazol-1-yl)ethyl)morpholine

Step 1: ethyl 2-(5-bromo-1H-indazol-1-yl)acetate

To a solution of 5-bromoindazole ([53857-57-1], 6 g, 30.1 mmol) and cesium carbonate (19.65 g, 6.3 mmol) in DMF (80 mL) under Argon was added ethyl chloroacetate (4.60 g, 36.8 mmol) and the reaction mixture was stirred at 60° C. for 2 h. The RM was poured into water and extracted with EtOAc (×2). The combined organic extracts were washed with brine, dried ($Na_2SO_4$), filtered and evaporated. The crude residue was purified by normal phase chromatography (eluent: AcOEt in heptane from 0 to 30%) to give the title compound. UPLC-MS-10: Rt=1.02 min; MS m/z [M+H]$^+$ 283.0/285.0.

Step 2: 2-(5-bromo-1H-indazol-1-yl)ethan-1-ol

To a solution of ethyl 2-(5-bromo-1H-indazol-1-yl)acetate (4.86 g, 16.5 mmol) in THF (100 mL) was added under Ar at 0° C. DIBAL-H (25% in toluene, 54.9 mL, 82 mmol). The reaction mixture was stirred at 0° C. for 30 min, then at RT for 2 days. The reaction mixture was cooled to 0° C., carefully poured into water and extracted with EtOAc (×2). The combined organic extracts were washed with brine, dried ($Na_2SO_4$), filtered and evaporated to give the title compound as an oil. UPLC-MS-10: Rt=0.88 min; MS m/z [M+H]$^+$ 241.0/243.0.

Step 3: 2-(5-bromo-1H-indazol-1-yl)ethyl methanesulfonate

To a solution of 2-(5-bromo-1H-indazol-1-yl)ethan-1-ol (4.10 g, 15.3 mmol) in $CH_2Cl_2$ (50 mL) cooled at 0° C. was added under Argon $Et_3N$ (4.50 mL, 32.3 mmol) followed by methanesulfonyl chloride (1.45 mL, 18.4 mmol). The reaction mixture was stirred at 0° C. for 2.5 h. Then the RM was poured into a sat. aq. solution of $NaHCO_3$ and extracted with EtOAc (×2). The combined organic extracts were washed with brine, dried ($Na_2SO_4$), filtered and evaporated to give the title compound as a yellow solid which was used without further purification in the next step. UPLC-MS-10: Rt=0.88 min; MS m/z [M+H]$^+$ 319.0/321.0.

Step 4: 4-(2-(5-bromo-1H-indazol-1-yl)ethyl)morpholine

A solution of 2-(5-bromo-1H-indazol-1-yl)ethyl methanesulfonate (1.50 g, 4.23 mmol) and morpholine (5 mL, 56.8 mmol) in THF (20 mL) was heated at 60° C. under an argon atmosphere for 18 h. The mixture was diluted with a sat. aq. solution of $NaHCO_3$ and extracted with EtOAc (×2). The combined organic extracts were washed with brine, dried ($Na_2SO_4$), filtered and evaporated. The crude residue was purified by normal phase chromatography (eluent: MeOH in $CH_2Cl_2$ from 0 to 5%) to give the title compound. UPLC-MS-6: Rt=0.73 min; MS m/z [M+H]$^+$ 310.0/312.0.

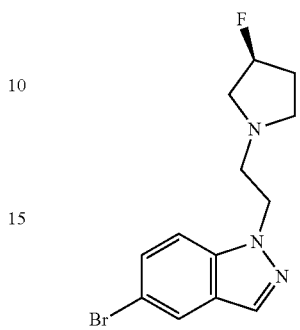

Intermediate A5: (S)-5-bromo-1-(2-(3-fluoropyrrolidin-1-yl)ethyl)-1H-indazole

The title compound was prepared using similar method as described for the synthesis of 4-(2-(5-bromo-1H-indazol-1-yl)ethyl)morpholine (Intermediate A4). UPLC-MS-3: Rt=0.65 min; MS m/z [M+H]$^+$ 312.0/314.0.

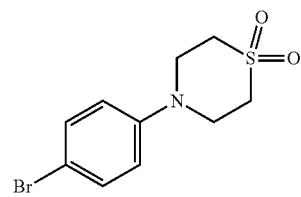

Intermediate A6: 4-(4-bromophenyl)thiomorpholine 1,1-dioxide

Thiomorpholine dioxide (5.00 g, 37 mmol), 1,4-dibromobenzene (4.61, 40.7 mmol) and $Cs_2CO_3$ (36.2 g, 111 mmol) were suspended in dry 1,4-dioxane (150 mL) and the reaction mixture was degassed with nitrogen for 10 min. $Pd(OAc)_2$ (0.83 g, 3.70 mmol) and BINAP (2.31 g, 3.70 mmol) were added and the reaction mixture was heated to 120° C. in a sealed tube for 12 h. The RM was filtered through a celite pad and washed with EtOAc. The filtrate was poured into water and extracted with EtOAc (×2). The combined organic extracts were washed with brine, dried ($Na_2SO_4$) and concentrated under vacuum. The crude residue was purified by normal phase chromatography (eluent: 0-50% EtOAc in Hexane) to obtain the desired product. LCMS-1: Rt=1.57 min; MS m/z [M+H]$^+$=290.1/292.0.

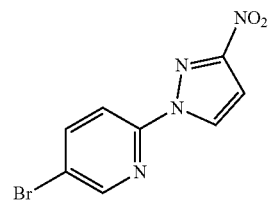 [SMILES: O=[N+]([O-])c1ccn(-c2ccc(Br)cn2)n1]

Intermediate A7: 5-Bromo-2-(3-nitro-1H-pyrazol-1-yl)pyridine

5-Nitro-1H-pyrazole (0.50 g, 0.44 mmol), 2,5-dibromopyridine (1.05 g, 0.44 mmol) and $Cs_2CO_3$ (1.44 g, 0.44 mmol) were suspended in NMP (15 mL) and degassed with nitrogen for 5 min. CuI (0.084 g, 0.04 equiv) was added and the reaction mixture was stirred at 120° C. for 1 h. After completion of the reaction, the reaction mixture was diluted with EtOAc and filtered through a pad of celite. The filtrate was washed with cold water, brine, dried ($Na_2SO_4$), filtered and concentrated under vacuum. The crude residue was purified by normal phase chromatography (eluent: 0-7% EtOAc in Hexane) to obtain the desired product. $^1$H NMR (400 MHz, DMSO-$d_6$) δ 8.85 (d, 1H), 8.79 (s, 1H), 8.36 (d, 1H), 7.97 (d, 1H), 7.36 (d, 1H).

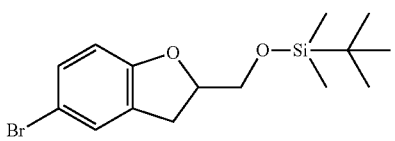 [SMILES: CC(C)(C)[Si](C)(C)OCC1Cc2cc(Br)ccc2O1]

Intermediate A8: ((5-bromo-2,3-dihydrobenzofuran-2-yl)methoxy)(tert-butyl)dimethylsilane To a solution of (5-bromo-2,3-dihydrobenzofuran-2-yl)methanol (1.00 g, 4.15 mmol) in DCM (20 mL) was added 1H-imidazole (0.90 g, 13.3 mmol) and the reaction mixture was stirred for 5 min. Then tert-butylchlorodimethylsilane (1.97 g, 12.4 mmol) was added and the RM was stirred for 2 h at RT. The reaction mixture was diluted with EtOAc (40 mL) and washed with a sat. aq. $NaHCO_3$ solution. The organic layer was washed with water, dried ($Na_2SO_4$), filtered and evaporated to dryness. UPLC-MS-3: Rt=1.55 min; MS m/z [M+H]$^+$: 343.1/345.0.

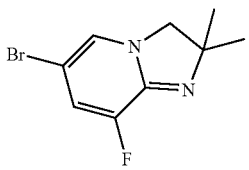

Intermediate A9: 6-bromo-8-fluoro-2,2-dimethyl-2,3-dihydroimidazo[1,2-a]pyridine

Step 1: 2-((5-bromo-3-fluoropyridin-2-yl)amino)-2-methylpropan-1-ol

A mixture of 5-bromo-2,3-difluoropyridine [89402-44-8] (6.93 g, 35.0 mmol) and 2-amino-2-methylpropan-1-ol [124-68-5] (7.43 mL, 70.0 mmol) was stirred at 100° C. After 22 h, the cooled reaction mixture was diluted with sat. aq. $NaHCO_3$ and extracted with EtOAc (2×). The combined organic layers were washed with brine, dried ($Na_2SO_4$) and concentrated. The crude residue was purified by normal phase chromatography (eluent: heptane/(20:1 EtOAc/MeOH) from 0 to 90%) to give the title compound as a colorless oil. UPLC-MS-1: Rt=1.00 min; MS m/z [M+H]$^+$; 263.0/265.0.

Step 2: 6-bromo-8-fluoro-2,2-dimethyl-2,3-dihydroimidazo[1,2-a]pyridine

Thionyl chloride (5.55 mL, 76.0 mmol) was added dropwise to a solution of 2-((5-bromo-3-fluoropyridin-2-yl)amino)-2-methylpropan-1-ol (5.05 g, 19.0 mmol) in xylene (38 mL) at RT. After stirring for 15 min, the mixture was warmed to 100° C. After 15 h, the cooled reaction mixture was diluted with sat. aq. $NaHCO_3$ and extracted with EtOAc (2×). The combined aqueous layers were re-extracted with DCM (4×). The combined organic layers were dried ($Na_2SO_4$) and concentrated to give the title compound which was used without purification in the next step. NMR (400 MHz, DMSO-$d_6$) δ 7.48 (s, 1H), 6.98 (dd, 1H), 3.73 (s, 2H), 1.18 (s, 6H). UPLC-MS-1: Rt=0.34 min; MS m/z [M+H]$^+$; 245.0/247.0.

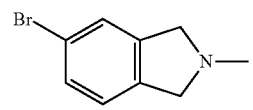

Intermediate A10: 5-bromo-2-methylisoindoline

To a solution of 5-bromoisoindoline [127168-84-7] (0.50 g, 2.52 mmol) in MeOH (31.9 mL)/$H_2O$ (3.19 mL) at RT was added $CH_3COOH$ to reach pH 5. To the reaction mixture was added formaldehyde (37% in water, 0.376 ml, 5.05 mmol) followed after 15 min by $NaCNBH_3$ (0.24 g, 3.79 mmol). The reaction mixture was stirred at RT for 16 h under a nitrogen atmosphere. The RM was concentrated, diluted with EtOAc and washed with NaOH (1N) and brine. The organic layer was dried ($Na_2SO_4$), filtered and evaporated to give the title compound which was used without purification in the next step. UPLC-MS-1: Rt=0.39 min; MS m/z [M+H]$^+$: 212/214.

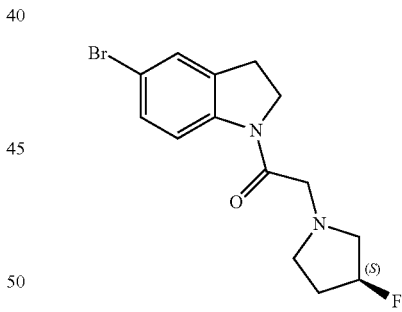

Intermediate A11: (S)-1-(5-bromoindolin-1-yl)-2-(3-fluoropyrrolidin-1-yl)ethan-1-one

Step 1: 1-(5-bromoindolin-1-yl)-2-chloroethan-1-one

To a solution of 5-bromoindoline [22190-33-6] (2.00 g, 10.1 mmol) in DCM (101 mL) at 0° C. under inert atmosphere were added dropwise $Et_3N$ (3.52 mL, 25.2 mmol) followed by a solution of 2-chloroacetyl chloride (1.71 g, 15.15 mmol) in DCM (100 uL). The reaction mixture was stirred at RT for 2 h. Then, the RM was washed with HCl (1N) and a sat. aq. solution of $NaHCO_3$. The organic layer was dried ($Na_2SO_4$), filtered and evaporated to give the title compound which was used without purification in the next step. UPLC-MS-1: Rt=0.99 min; MS m/z [M+H]⁺: 274/276/278.

Step 2: (S)-1-(5-bromoindolin-1-yl)-2-(3-fluoropyrrolidin-1-yl)ethan-1-one

To a solution of 1-(5-bromoindolin-1-yl)-2-chloroethan-1-one (0.50 g, 1.82 mmol) in acetonitrile (11.3 mL)/H₂O (0.81 mL) were added K₂CO₃ (0.75 g, 5.46 mmol) and (S)-3-fluoropyrrolidine (0.46 g, 3.64 mmol). The reaction mixture was stirred at 60° C. for 1 h. The RM diluted with CH₂Cl₂ and washed with water. The organic layer was dried (Na₂SO₄), filtered and concentrated under reduced pressure. The crude residue was purified by normal phase chromatography (eluent: 0-5% MeOH in CH₂Cl₂) to give the title compound. UPLC-MS-7: Rt=0.61 min; MS m/z [M+H]⁺: 327/329.

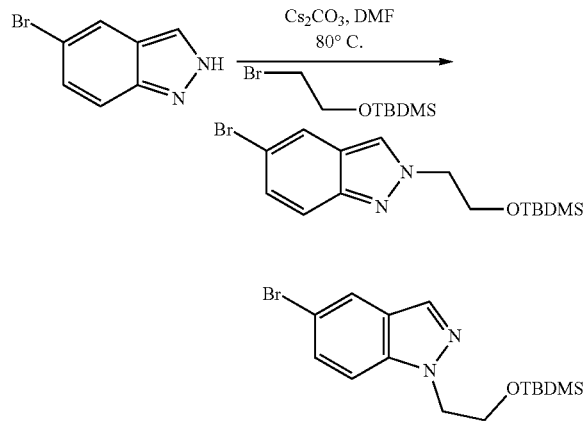

Intermediate A12 and A13: 5-Bromo-2-(2-((tert-butyldimethylsilyl)oxy)ethyl)-2H-indazole and 5-bromo-1-(2-((tert-butyldimethylsilyl)oxy)ethyl)-1H-indazole and 5-bromo-1-(2-((tert-butyldimethylsilyl)oxy)ethyl)-1H-indazole (2-Bromoethoxy)(tert-butyl)dimethylsilane (4.85 g, 20.3 mmol) was added dropwise at 0° C. to a suspension of 5-bromo-1H-indazole (2.0 g, 10.2 mmol) and Cs₂CO₃ (9.93 g, 30.5 mmol) in DMF (30 mL) and then reaction mixture was stirred at 60° C. for 5 h in sealed tube. The RM was filtered through a pad of celite and washed with EtOAc. The filtrate was poured to ice-cold water and extracted with EtOAc (×2). The combined organic layer were washed with cold water, brine, dried (Na₂SO₄), filtered and concentrated under vacuum. The crude residue was purified by chromatography on neutral alumina (eluent: 0-1% EtOAc in Hexane) to give 5-bromo-1-(2-((tert-butyldimethylsilyl)oxy)ethyl)-1H-indazole A13 as a pale orange liquid as the first eluting isomer: ¹H NMR (400 MHz, CDCl₃) δ 7.96 (s, 1H), 7.86 (s, 1H), 7.45 (m, 2H), 4.50 (t, 2H), 4.05 (t, 2H), 0.75 (s, 9H), 0.19 (s, 6H); LCMS-1: Rt=2.27 min; MS m/z [M+H]⁺: 355.3/357.2 and 5-bromo-2-(2-((tert-butyldimethylsilyl)oxy)ethyl)-2H-indazole A12 as a pale orange liquid as the second eluting isomer; ¹H NMR (400 MHz, CDCl₃) δ 7.96 (s, 1H), 7.83 (s, 1H), 7.60 (d, 1H), 7.36 (d, 1H), 4.53 (t, 2H), 4.10 (t, 2H), 0.85 (s, 9H), −0.12 (s, 6H); LCMS-1: Rt=2.33 min; MS m/z [M+H]⁺; 355.4/357.4.

Boronic Ester/Acid Intermediates: Intermediates B

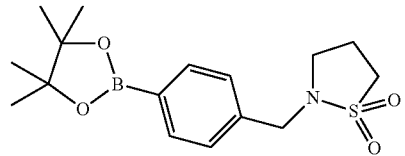 [SMILES: CC1(C)OB(c2ccc(CN3CCCS3(=O)=O)cc2)OC1(C)C]

Intermediate B1: 2-(4-(4,4,5,5-tetramethyl-1,3,2-dioxaborolan-2-yl)benzyl)isothiazolidine 1,1-dioxide To a solution of 1,3-propanesultam (1.00 g, 8.25 mmol) in DMF (20 mL) at 0° C. under nitrogen atmosphere was added NaH (60% in paraffin, 0.26 g, 10.7 mmol) and mixture was stirred at 0° C. for 15 min. 2-(4-(Bromomethyl)phenyl)-4,4,5,5-tetramethyl-1,3,2-dioxaborolane (1.96 g, 6.60 mmol) was added and the reaction mixture was stirred at RT for 16 h. The RM was quenched with cold water, extracted with EtOAc (×2). The combined organic layers were washed with brine, dried over sodium sulfate and concentrated under vacuum to afford the desired product which was directly used in the next step without further purification. ¹H NMR (400 MHz, DMSO-d₆) δ 7.96 (d, 2H), 7.37 (d, 2H), 4.11 (s, 2H), 3.28 (m, 2H), 2.08 (m, 2H), 2.25 (m, 2H), 1.33 (s, 12H).

Method-B1: Synthesis of Intermediate B2:

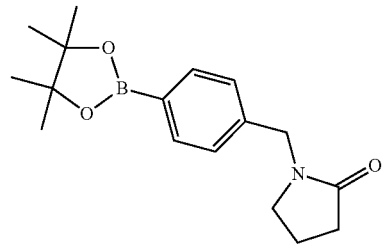 [SMILES: CC1(C)OB(c2ccc(CN3CCCC3=O)cc2)OC1(C)C]

Intermediate B2: 1-(4-(4,4,5,5-tetramethyl-1,3,2-dioxaborolan-2-yl)benzyl)pyrrolidin-2-one 1-[(4-Bromophenyl)methyl]-2-pyrrolidinone (400 mg, 1.57 mmol), bis(pinacolato)diboron (480 mg, 1.89 mmol), KOAc (340 mg, 3.46 mmol) and PdCl₂(dppf).CH₂Cl₂ (70.7 mg, 0.087 mmol) were suspended in dioxane (6.05 mL) under argon in a 20 mL microwave vial. The suspension was submitted to microwave irradiations for 30 min at 120° C. UPLC-MS after 30 min indicated completion of the reaction. The RM was concentrated in vacuo and diluted with CH₂Cl₂ (40 mL), washed with water (2×15 mL), dried (MgSO₄), filtered and concentrated in vacuo to give the title compound which was used without purification in the next step. UPLC-MS-3: Rt=1.04 min; MS m/z [M+H]⁺ 302.3.

Method-B1a: similar to Method-B1 except that the reaction mixture was heated at 100° C. instead of 120° C.

The following intermediates B3 to B20 were prepared using analogous methods to Method-B1 from the corresponding intermediates A or commercially available reagents.

| Intermediate | Structure | Method, intermediates and chiral separation conditions used and order of elution | Characterizing data |
|---|---|---|---|
| B3 | tert-butyl (1-(5-(4,4,5,5-tetramethyl-1,3,2-dioxaborolan-2-yl)pyridin-2-yl)-1H-pyrazol-5-yl)carbamate | Using Method-B1 form tert-butyl (1-(4-bromopyridin-2-yl)-1H-pyrazol-5-yl)carbamate A1 | LCMS-1: Rt = 2.45 min; MS m/z [M + H]+ 387.6. |
| B4 | 1-methyl-3-(4-(4,4,5,5-tetramethyl-1,3,2-dioxaborolan-2-yl)phenyl)imidazolidin-2-one | Using Method-B1a from [530080-95-6] | UPLC-MS-6: Rt = 1.02 min; MS m/z [M + H]$^+$ 303.2. |
| B5 | N,N-dimethyl-2-(5-(4,4,5,5-tetramethyl-1,3,2-dioxaborolan-2-yl)-1H-indazol-1-yl)ethan-1-amine | Using Method-B1a from 2-(5-bromo-1H-indazol-1-yl)-N,N-dimethylethan-1-amine (Intermediate A2) | UPLC-MS-1: Rt = 0.73 min; MS m/z [M + H]$^+$ 316.3. |
| B6 | N,N-dimethyl-2-(5-(4,4,5,5-tetramethyl-1,3,2-dioxaborolan-2-yl)-2H-indazol-2-yl)ethan-1-amine | Using Method-B1a from 2-(5-bromo-2H-indazol-2-yl)-N,N-dimethylethan-1-amine (Intermediate A3) | UPLC-MS-1: Rt = 0.72 min; MS m/z [M + H]$^+$ 316.3. |

| Intermediate | Structure | Method, intermediates and chiral separation conditions used and order of elution | Characterizing data |
| --- | --- | --- | --- |
| B7 | 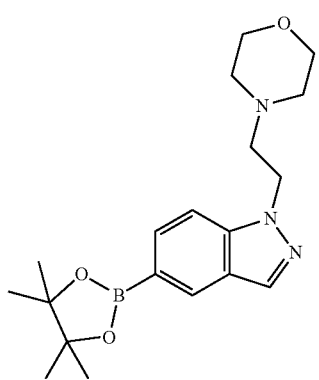<br>4-(2-(5-(4,4,5,5-tetramethyl-1,3,2-dioxaborolan-2-yl)-1H-indazol-1-yl)ethyl)morpholine | Using Method-B1a from 4-(2-(5-bromo-1H-indazol-1-yl)ethyl)morpholine (Intermediate A4) | UPLC-MS-1: Rt = 0.86 min; MS m/z [M + H]$^+$ 358.3. |
| B8 | 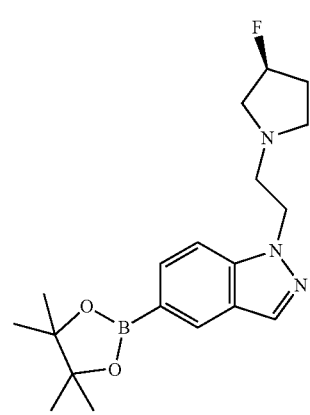<br>(S)-1-(2-(3-fluoropyrrolidin-1-yl)ethyl)-5-(4,4,5,5-tetramethyl-1,3,2-dioxaborolan-2-yl)-1H-indazole | Using Method-B1a from (S)-5-bromo-1-(2-(3-fluoropyrrolidin-1-yl)ethyl)-1H-indazole (Intermediate A5) | UPLC-MS-3: Rt = 0.79 min; MS m/z [M + H]$^+$ 360.3. |
| B9 | 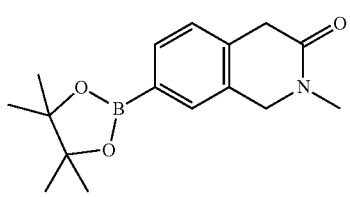<br>2-methyl-7-(4,4,5,5-tetramethyl-1,3,2-dioxaborolan-2-yl)-1,4-dihydroisoquinolin-3(2H)-one | Using Method-B1 from [877265-10-6] | HPLC-MS-1: Rt = 0.96 min; MS m/z [M + H]$^+$ 288.2. |

-continued

| Intermediate | Structure | Method, intermediates and chiral separation conditions used and order of elution | Characterizing data |
|---|---|---|---|
| B10 | 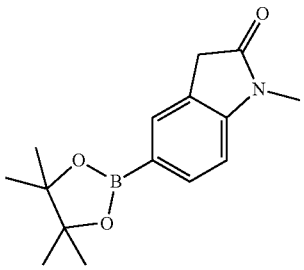<br>1-methyl-5-(4,4,5,5-tetramethyl-1,3,2-dioxaborolan-2-yl)indolin-2-one | Using Method-B1 from 5-bromo-1-methylindolin-2-one [20870-90-0] | UPLC-MS-1: Rt = 1.01 min; MS m/z [M + H]+ 274. |
| B11 | 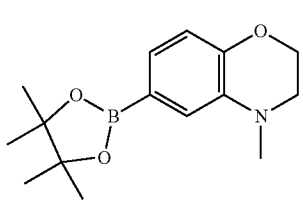<br>4-methyl-6-(4,4,5,5-tetramethyl-1,3,2-dioxaborolan-2-yl)-3,4-dihydro-2H-benzo[b][1,4]oxazine | Using Method-B1 from 6-bromo-4-methyl-3,4-dihydro-2H-benzo[b][1,4]oxazine | UPLC-MS-1: Rt = 1.17 min; MS m/z [M + H]+ 275.0. |
| B12 | 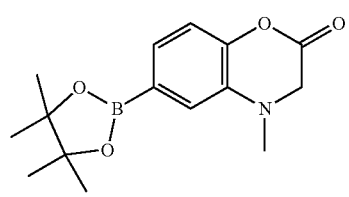<br>4-methyl-6-(4,4,5,5-tetramethyl-1,3,2-dioxaborolan-2-yl)-3,4-dihydro-2H-benzo[b][1,4]oxazin-2-one | Using Method-B1a from 6-bromo-4-methyl-3,4-dihydro-2H-benzo[b][1,4]oxazin-2-one | UPLC-MS-1: Rt = 1.07 min; MS m/z [M + H]+ 290.0. |
| B13 | 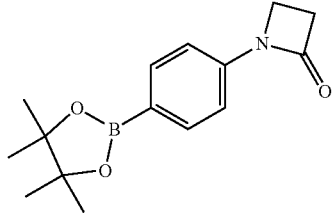<br>1-(4-(4,4,5,5-tetramethyl-1,3,2-dioxaborolan-2-yl)phenyl)azetidin-2-one | Using Method-B1 from 1-(4-bromophenyl)azetidin-2-one | UPLC-MS-6: Rt = 1.04 min; MS m/z [M + H]+ 274.1. |

-continued

| Intermediate | Structure | Method, intermediates and chiral separation conditions used and order of elution | Characterizing data |
|---|---|---|---|
| B14 | 3-methyl-6-(4,4,5,5-tetramethyl-1,3,2-dioxaborolan-2-yl)-3H-imidazo[4,5-b]pyridine | Using Method-B1 from 5-bromo-1-methyl-1H-pyrazolo[3,4-b]pyridine | UPLC-MS-1: Rt = 1.02 min; MS m/z [M + H]$^+$ 260.4. |
| B15 | 4-(4-(4,4,5,5-tetramethyl-1,3,2-dioxaborolan-2-yl)phenyl)thiomorpholine 1,1-dioxide | Using Method-B1 from 4-(4-bromophenyl)thiomorpholine 1,1-dioxide (Intermediate A6) | LCMS-1: Rt = 1.64 min; MS m/z [M + H]$^+$ 338.2. |
| B16 | 2-(3-nitro-1H-pyrazol-1-yl)-5-(4,4,5,5-tetramethyl-1,3,2-dioxaborolan-2-yl)pyridine | Using Method-B1 from 5-bromo-2-(3-nitro-1H-pyrazol-1-yl)pyridine (Intermediate A7) | 1H NMR (400 MHz, DMSO-d$_6$) δ 8.81 (d, 1H), 8.74 (s, 1H), 8.30 (d, 1H), 8.11 (d, 1H), 7.11 (d, 1H), 1.4 (s, 12H). |
| B17 | 6-(4,4,5,5-tetramethyl-1,3,2-dioxaborolan-2-yl)isobenzofuran-1(3H)-one | Using Method-B1a from [862081, 2 or 38-7] | UPLC-MS-1: Rt = 1.05 min; MS m/z [M + H]$^+$ 261.4. |

| Intermediate | Structure | Method, intermediates and chiral separation conditions used and order of elution | Characterizing data |
|---|---|---|---|
| B18 | 3-tert-butyldimethyl((5-(4,4,5,5-tetramethyl-1,3,2-dioxaborolan-2-yl)-2,3-dihydrobenzofuran-2-yl)methoxy)silane | Using Method-B1 from ((5-bromo-2,3-dihydrobenzofuran-2-yl)methoxy)(tert-butyl)dimethylsilane (Intermediate A8) | UPLC-MS-3: Rt = 1.52 min; MS m/z [M + H]⁺ 391.2. |
| B19 | 2-(2-((tert-butyldimethylsilyl)oxy)ethyl)-5-(4,4,5,5-tetramethyl-1,3,2-dioxaborolan-2-yl)-2H-indazole | Using Method-B1 from 5-bromo-2-(2-((tert-butyldimethylsilyl)oxy)ethyl)-2H-indazole (Intermediate A12) | LCMS-1: Rt = 2.37 min; MS m/z [M + H]⁺ 402.5/404.5 |
| B20 | 1-(2-((tert-butyldimethylsilyl)oxy)ethyl)-5-(4,4,5,5-tetramethyl-1,3,2-dioxaborolan-2-yl)-1H-indazole | Using Method-B1 from 5-bromo-1-(2-((tert-butyldimethylsilyl)oxy)ethyl)-1H-indazole (Intermediate A13) | LCMS-1: Rt = 2.48 min; MS m/z [M + H]⁺ 402.5/404.5. |

Intermediate B21: (1-(tetrahydro-2H-pyran-2-yl)-1H-indazol-6-yl)boronic acid

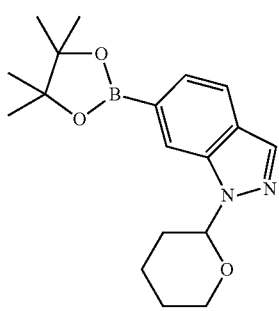 [SMILES: CC1(C)OB(c2ccc3cnn(C4CCCCO4)c3c2)OC1(C)C]

A solution of indazole-6-boronic acid pinacol ester (0.5 g, 1.95 mmol), p-toluenesulfonic acid monohydrate (37 mg, 0.195 mmol) and 3,4-dihydro-2H-pyran (0.45 mL, 4.46 mmol) in $CH_2Cl_2$ (10 mL) was stirred at RT overnight under an argon atmosphere. The reaction mixture was poured into a sat. aq. solution of $NaHCO_3$ and extracted with EtOAc. The combined organic extracts were was washed with brine, dried ($Na_2SO_4$), filtered and evaporated. The crude residue was purified by normal phase chromatography (EtOAc in heptane from 0 to 25%) to give the title compound. UPLC-MS-1: Rt=1.28 min; MS m/z [M+H]⁺: 329.3.

Method-B2: Synthesis of Intermediate B22:

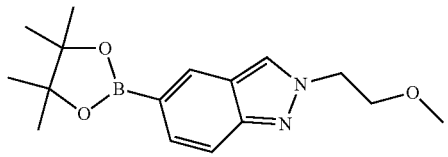

Intermediate B22: 2-(2-methoxyethyl)-5-(4,4,5,5-tetramethyl-1,3,2-dioxaborolan-2-yl)-2H-indazole Step 1: 5-bromo-2-(2-methoxyethyl)-2H-indazole To a solution of 5-bromo-2-nitrobenzaldehyde (5.18 g, 22.5 mmol) in MeOH (55 mL) was added 2-methoxyethan-1-amine (1.98 mL, 22.75 mmol) and the reaction mixture was stirred at 70° C. for 1.15 h. Then the reaction mixture was concentrated and dried under high vacuum. The residual white solid was dissolved with triethyl phosphite (39.4 mL, 225 mmol) and the solution was stirred at 140° C. overnight. After cooling to RT the excess of triethyl phosphite was evaporated under high vacuum (rotavap) and the crude residue purified by normal phase chromatography (eluent: c-hexane/EtOAc 100/0 to 70/30 within 30 min) to give the title compound. $^1$H NMR (400 MHz, DMSO-d$_6$) δ 8.36 (d, 1H), 7.97 (dd, 1H), 7.59 (dt, 1H), 7.31 (dd, 1H), 4.59 (t, 2H), 3.82 (t, 2H), 3.22 (s, 3H); UPLC-MS-3: Rt=0.97 min; MS m/z [M+H]$^+$: 255.1/257.1.

Step 2: 2-(2-methoxyethyl)-5-(4,4,5,5-tetramethyl-1,3,2-dioxaborolan-2-yl)-2H-indazole In a sealed tube, a solution of 5-bromo-2-(2-methoxyethyl)-2H-indazole (6.12 g, 17.75 mmol), bis-(pinacolato)-diboron (9.02 g, 35.5 mmol), PdCl$_2$(dppf) (1.30 g, 1.77 mmol) and potassium acetate (4.36 g, 44.4 mmol) in dioxane (60 mL) was stirred at 90° C. for 1.5 h. The reaction mixture was cooled to RT diluted with water, extracted with EtOAc, the organic phase washed with brine, dried with a phase separator and concentrated under reduced pressure. The crude residue was purified by normal phase chromatography (eluent: c-hexane/EtOAc 100/0 to 40/60 within 30 min) to give the title compound. $^1$H NMR (400 MHz, DMSO-d$_6$) δ 8.42 (d, 1H), 8.15 (s, 1H), 7.55 (dt, 1H), 7.45 (dd, 1H), 4.59 (t, 2H), 3.83 (t, 2H), 3.22 (s, 3H), 1.31 (s, 12H); UPLC-MS-3: Rt=1.02 min; MS m/z [M+H]$^+$: 303.3.

The following intermediates B23 to B24 were prepared using analogous methods to Method-B2 from commercially available building blocks.

| Example | Structure | Precursor | Characterizing data |
|---|---|---|---|
| B23 | 2-methyl-1-(5-(4,4,5,5-tetramethyl-1,3,2-dioxaborolan-2-yl)-2H-indazol-2-yl)propan-2-ol | using 1-amino-2-methylpropan-2-ol (Step 1) | $^1$H NMR (400 MHz, DMSO-d$_6$) δ 8.37 (s, 1H), 8.18 (s, 1H), 7.56 (d, 1H), 7.44 (dd, 1H), 4.86 (s, 1H), 4.34 (s, 2H), 1.31 (s, 12H), 1.07 (s, 6H); UPLC-MS-5: Rt = 0.97 min; MS m/z [M + H]$^+$: 317.3. |
| B24 | 2-(2-(2-methoxyethoxy)ethyl)-5-(4,4,5,5-tetramethyl-1,3,2-dioxaborolan-2-yl)-2H-indazole | using 2-(2-methoxyethoxy)ethan-1-amine (Step 1) | $^1$H NMR (400 MHz, DMSO-d$_6$) δ 8.43 (s, 1H), 8.15 (s, 1H), 7.56 (d, 1H), 7.45 (dd, 1H), 4.58 (t, 2H), 3.91 (t, 2H), 3.50 (dd, 2H), 3.37 (dd, 2H), 3.18 (s, 3H), 1.31 (s, 12H); UPLC-MS-3: Rt = 1.00 min; MS m/z [M + H]$^+$: 347.3. |

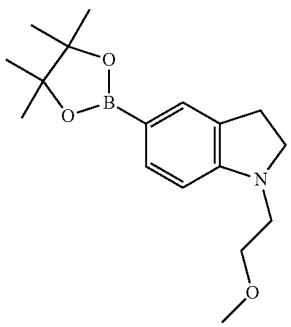 [SMILES: COCCN1CCc2cc(B3OC(C)(C)C(C)(C)O3)ccc21]

Intermediate B25: 1-(2-methoxyethyl)-5-(4,4,5,5-tetramethyl-1,3,2-dioxaborolan-2-yl)indoline Step 1: 5-bromo-1-(2-methoxyethyl)indoline A solution of 5-bromoindoline (1 g, 5.05 mmol), 1-bromo-2-methoxyethane (0.95 mL, 10.1 mmol) and cesium carbonate (3.29 g, 10.1 mmol) in DMF (15 mL) was stirred at 60° C. for 5 h, then more 1-bromo-2-methoxyethane (0.95 mL, 10.1 mmol) was added and the reaction mixture was stirred at 60° C. overnight. After cooling to RT, the reaction mixture was diluted with EtOAc and water, extracted with EtOAc, the organic phase washed with brine, dried with a phase separator and concentrated under reduced pressure. The crude residue was purified by normal phase chromatography (eluent: c-hexane/EtOAc 100/0 to 70/30 within 30 min) to give the title compound. $^1$H NMR (400 MHz, DMSO-d$_6$) δ 7.14 (dd, 1H), 7.09 (dd, 1H), 6.43 (d, 1H), 3.51 (t, 2H), 3.40 (t, 2H), 3.27 (s, 3H), 3.20 (t, 2H), 2.89 (t, 2H); UPLC-MS-3: Rt=1.17 min; MS m/z [M+H]$^+$: 256.1/258.1.

Step 2: 1-(2-methoxyethyl)-5-(4,4,5,5-tetramethyl-1,3,2-dioxaborolan-2-yl)indoline In a sealed tube, a solution of 5-bromo-1-(2-methoxyethyl)indoline (650 mg, 2.11 mmol), bis-(pinacolato)-diboron (1070 mg, 4.21 mmol), PdCl$_2$(dppf) (154 mg, 0.21 mmol) and potassium acetate (517 mg, 5.27 mmol) in dioxane (8 mL) was stirred at 90° C. for 30 min. After cooling to RT, the reaction mixture was diluted with EtOAc and water, extracted with EtOAc, the organic phase washed with brine, dried with a phase separator and concentrated under reduced pressure. The crude residue was purified by normal phase chromatography (eluent: c-hexane/EtOAc 100/0 to 70/30 within 30 min) to give the title compound. $^1$H NMR (400 MHz, DMSO-d$_6$) δ 7.33 (dd, 1H), 7.28 (d, 1H), 6.44 (d, 1H), 3.52 (t, 2H), 3.44 (t, 2H), 3.28-3.25 (m, 5H), 2.88 (t, 2H), 1.25 (s, 12H); UPLC-MS-3: Rt=1.18 min; MS m/z [M+H]$^+$: 304.2.

Pyrazoles Intermediates: Intermediates C

Intermediate C1: tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate

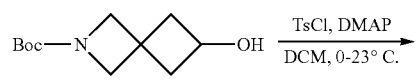

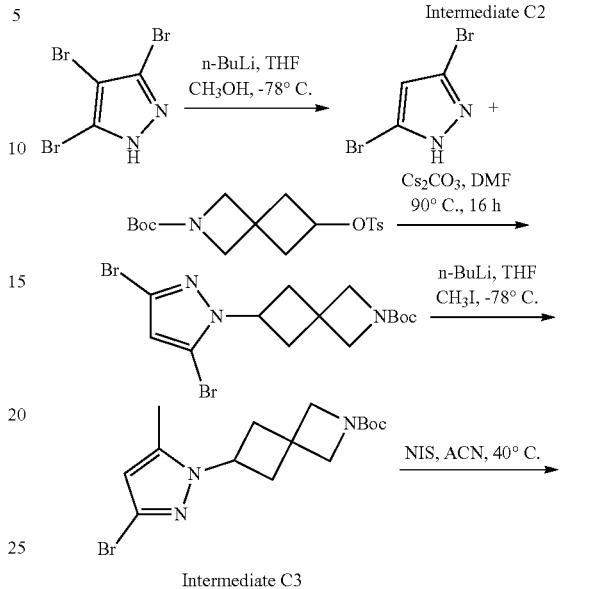

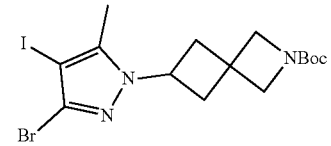

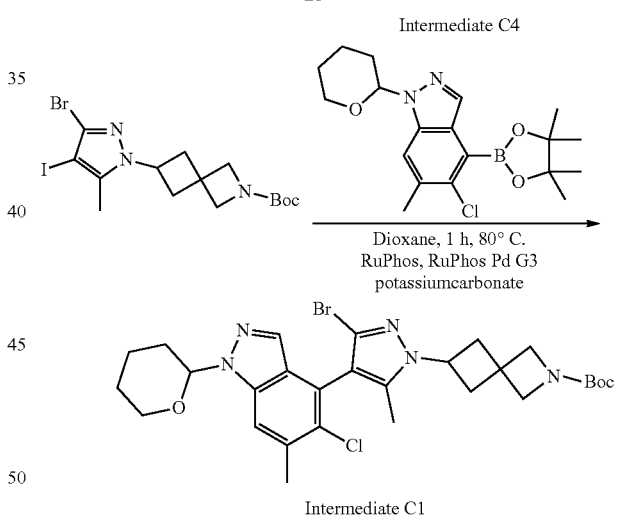

Step 1: Intermediate C2: tert-butyl 6-(tosyloxy)-2-azaspiro[3.3]heptane-2-carboxylate To a solution of tert-butyl 6-hydroxy-2-azaspiro[3.3]heptane-2-carboxylate [1147557-97-8] (2.92 kg, 12.94 mmol) in DCM (16.5 L) were added DMAP (316.12 g, 2.59 mol) and TsCl (2.96 kg, 15.52 mol) at 20° C.-25° C. To the reaction mixture was added dropwise Et$_3$N (2.62 kg, 25.88 mol) at 10° C.-20° C. The reaction mixture was stirred 0.5 h at 5° C.-15° C. and then was stirred 1.5 h at 18° C.-28° C. After completion of the reaction, the reaction mixture was concentrated under vacuum. To the residue was added NaCl (5% in water, 23 L) followed by extraction with EtOAc (23

L). The combined aqueous layers were extracted with EtOAc (10 L×2). The combined organic layers were washed with NaHCO$_3$ (3% in water, 10 L×2)) and concentrated under vacuum to give the title compound. $^1$H NMR (400 MHz, DMSO-d$_6$) δ 7.81-7.70 (m, 2H), 7.53-7.36 (m, 2H), 4.79-4.62 (m, 1H), 3.84-3.68 (m, 4H), 2.46-2.38 (m, 5H), 2.26-2.16 (m, 2H), 1.33 (s, 9H). UPLC-MS-1: Rt=1.18 min; MS m/z [M+H]$^+$: 368.2.

Step 2: 3,5-dibromo-1H-pyrazole

To a solution of 3,4,5-tribromo-1H-pyrazole [17635-44-8] (55.0 g, 182.2 mmol) in anhydrous THF (550 mL) was added at −78° C. n-BuLi (145.8 mL, 364.5 mmol) dropwise over 20 min maintaining the internal temperature at −78° C./−60° C. The RM was stirred at this temperature for 45 min. Then the reaction mixture was carefully quenched with MeOH (109 mL) at −78° C. and stirred at this temperature for 30 min. The mixture was allowed to reach to 0° C. and stirred for 1 h. Then, the mixture was diluted with EtOAc (750 mL) and HCl (0.5 N, 300 mL) was added. The layers were concentrated under vacuum. The crude residue was dissolved in DCM (100 mL), cooled to −50° C. and petroleum ether (400 mL) was added. The precipitated solid was filtered and washed with n-hexane (250 mL×2) and dried under vacuum to give the title compound. $^1$H NMR (400 MHz, DMSO-d$_6$) δ 13.5 (br s, 1H), 6.58 (s, 1H).

Step 3: tert-butyl 6-(3,5-dibromo-1H-pyrazol-1-yl)-2-azaspiro[3.3]heptane-2-carboxylate To a solution of tert-butyl 6-(tosyloxy)-2-azaspiro[3.3]heptane-2-carboxylate (Step 1, 900 g, 2.40 mol) in DMF (10.8 L) was added Cs$_2$CO$_3$ (1988 g, 6.10 mol) and 3,5-dibromo-1H-pyrazole (Step 2, 606 g, 2.68 mol) at 15° C. The reaction mixture was stirred at 90° C. for 16 h. The reaction mixture was poured into ice-water/brine (80 L) and extracted with EtOAc (20 L). The aqueous layer was re-extracted with EtOAc (10 L×2). The combined organic layers were washed with brine (10 L), dried (Na$_2$SO$_4$), filtered, and concentrated under vacuum. The residue was triturated with dioxane (1.8 L) and dissolved at 60° C. To the light yellow solution was slowly added water (2.2 L), and recrystallization started after addition of 900 mL of water. The resulting suspension was cooled down to 0° C., filtered, and washed with cold water. The filtered cake was triturated with n-heptane, filtered, then dried under vacuum at 40° C. to give the title compound. $^1$H NMR (400 MHz, DMSO-d$_6$) δ 6.66 (s, 1H), 4.86-4.82 (m, 1H), 3.96-3.85 (m, 4H), 2.69-2.62 (m, 4H), 1.37 (s, 9H); UPLC-MS-3: Rt=1.19 min; MS m/z [M+H]$^+$: 420.0/422.0/424.0.

Step 4: Intermediate C3: tert-butyl 6-(3-bromo-5-methyl-1H-pyrazol-1-yl)-2-azaspiro[3.3]heptane-2-carboxylate To a solution of tert-butyl 6-(3,5-dibromo-1H-pyrazol-1-yl)-2-azaspiro[3.3]heptane-2-carboxylate (Step 3, 960 g, 2.3 mol) in THF (9.6 L) was added n-BuLi (1.2 L, 2.5 mol) dropwise at −80° C. under an inert atmosphere. The reaction mixture was stirred 10 min at −80° C. To the reaction mixture was then added dropwise iodomethane (1633 g, 11.5 mol) at −80° C. After stirring for 5 min at −80° C., the reaction mixture was allowed to warm up to 18° C. The reaction mixture was poured into sat. aq. NH$_4$Cl solution (4 L) and extracted with DCM (10 L). The separated aqueous layer was re-extracted with DCM (5 L) and the combined organic layers were concentrated under vacuum. The crude product was dissolved in 1,4-dioxane (4.8 L) at 60° C., then water (8.00 L) was added dropwise slowly. The resulting suspension was cooled to 17° C. and stirred for 30 min. The solid was filtered, washed with water, and dried under vacuum to give the title compound. $^1$H NMR (400 MHz, DMSO-d$_6$) δ 6.14 (s, 1H), 4.74-4.66 (m, 1H), 3.95-3.84 (m, 4H), 2.61-2.58 (m, 4H), 2.20 (s, 3H), 1.37 (s, 9H); UPLC-MS-1: Rt=1.18 min; MS m/z [M+H]$^+$: 356.1/358.1.

Step 5: Intermediate C4: tert-butyl 6-(3-bromo-4-iodo-5-methyl-1H-pyrazol-1-yl)-2-azaspiro[3.3]heptane-2-carboxylate To a solution of tert-butyl 6-(3-bromo-5-methyl-1H-pyrazol-1-yl)-2-azaspiro[3.3]heptane-2-carboxylate (Step 4, 350 g, 0.980 mol) in acetonitrile (3.5 L) was added NIS (332 g, 1.47 mol) at 15° C. The reaction mixture was stirred at 40° C. for 6 h. After completion of the reaction, the reaction mixture was diluted with EtOAc (3 L) and washed with water (5 L×2). The organic layer was washed with Na$_2$SO$_3$ (10% in water, 2 L), with brine (2 L), was dried (Na$_2$SO$_4$), filtered, and concentrated under vacuum to give the title compound. $^1$H NMR (400 MHz, DMSO-d$_6$) δ 4.81-4.77 (m, 1H), 3.94-3.83 (m, 4H), 2.61-5.59 (m, 4H), 2.26 (s, 3H), 1.37 (s, 9H); UPLC-MS-1: Rt=1.31 min; MS m/z [M+H]$^+$: 482.0/484.0.

Step 6: tert-butyl 6-(3-bromo-4-(5-chloro-6-methyl-1-(tetrahydro-2H-pyran-2-yl)-1H-indazol-4-yl)-5-methyl-1H-pyrazol-1-yl)-2-azaspiro[3.3]heptane-2-carboxylate To a stirred suspension of tert-butyl 6-(3-bromo-4-iodo-5-methyl-1H-pyrazol-1-yl)-2-azaspiro[3.3]heptane-2-carboxylate (Step 5, 136 g, 282 mmol) and 5-chloro-6-methyl-1-(tetrahydro-2H-pyran-2-yl)-4-(4,4,5,5-tetramethyl-1,3,2-dioxaborolan-2-yl)-1H-indazole (Intermediate D1, 116 g, 310 mmol) in 1,4-dioxane (680 mL) was added aqueous K$_3$PO$_4$ (2M, 467 mL, 934 mmol) followed by RuPhos (13.1 g, 28.2 mmol) and RuPhos-Pd-G3 (14.1 g, 16.9 mmol). The reaction mixture was stirred at 80° C. for 1 h under inert atmosphere. After completion of the reaction, the reaction mixture was poured into 1M aqueous NaHCO$_3$ solution (1 L) and extracted with EtOAc (1 L×3). The combined organic layers were washed with brine (1 L×3), dried (Na$_2$SO$_4$), filtered, and concentrated under vacuum. The crude residue was purified by normal phase chromatography (eluent: Petroleum ether/EtOAc from 1/0 to 0/1) to give a yellow oil. The oil was dissolved in petroleum ether (1 L) and MTBE (500 mL), then concentrated in vacuo to give the title compound. $^1$H NMR (400 MHz, DMSO-d$_6$) δ 7.81 (s, 1H), 7.66 (s, 1H), 5.94-5.81 (m, 1H), 4.90-4.78 (m, 1H), 3.99 (br s, 2H), 3.93-3.84 (m, 3H), 3.81-3.70 (m, 1H), 2.81-2.64 (m, 4H), 2.52 (s, 3H), 2.46-2.31 (m, 1H), 2.11-1.92 (m, 5H), 1.82-1.67 (m, 1H), 1.64-1.52 (m, 2H), 1.38 (s, 9H); UPLC-MS-3: Rt=1.30 min; MS m/z [M+H]$^+$: 604.1/606.1.

The following intermediates C5 and C6 were prepared using analogous methods to the method used in the preparation of Intermediate C1 from intermediates described in the intermediates synthesis section or commercially available (in Step 7).

| Intermediate | Structure | Precursor | Characterizing data |
|---|---|---|---|
| C5 | tert-butyl 6-(3-bromo-4-(5-chloro-1-(tetrahydro-2H-pyran-2-yl)-1H-indazol-4-yl)-5-methyl-1H-pyrazol-1-yl)-2-azaspiro[3.3]heptane-2-carboxylate | from Intermediate D4 (Step 6) | UPLC-MS-1: Rt = 1.42 min; MS m/z [M + H]⁺; 590.2/592.2. |
| C6 | tert-butyl 6-(3-bromo-4-(5-chloro-6-methyl-1-tosyl-1H-indazol-4-yl)-5-methyl-1H-pyrazol-1-yl)-2-azaspiro[3.3]heptane-2-carboxylate | from Intermediate D2 (Step 6) | $^1$H NMR (400 MHz, DMSO-d$_6$) δ 8.49-8.09 (m, 2H), 7.98-7.84 (m, 2H), 7.53-7.37 (m, 2H), 4.93-4.77 (m, 1H), 4.04-3.94 (m, 2H), 3.93-3.84 (m, 2H), 2.78-2.64 (m, 4H), 2.61 (s, 3H), 2.35 (s, 3H), 2.03 (s, 3H), 1.40 (s, 9H); UPLC-MS-1: Rt = 1.47 min; MS m/z [M + H]⁺; 674.2/676.1/678.2. |

Intermediate C7: tert-butyl 6-(4-bromo-3-iodo-5-methyl-1H-pyrazol-1-yl)-2-azaspiro[3.3]heptane-2-carboxylate

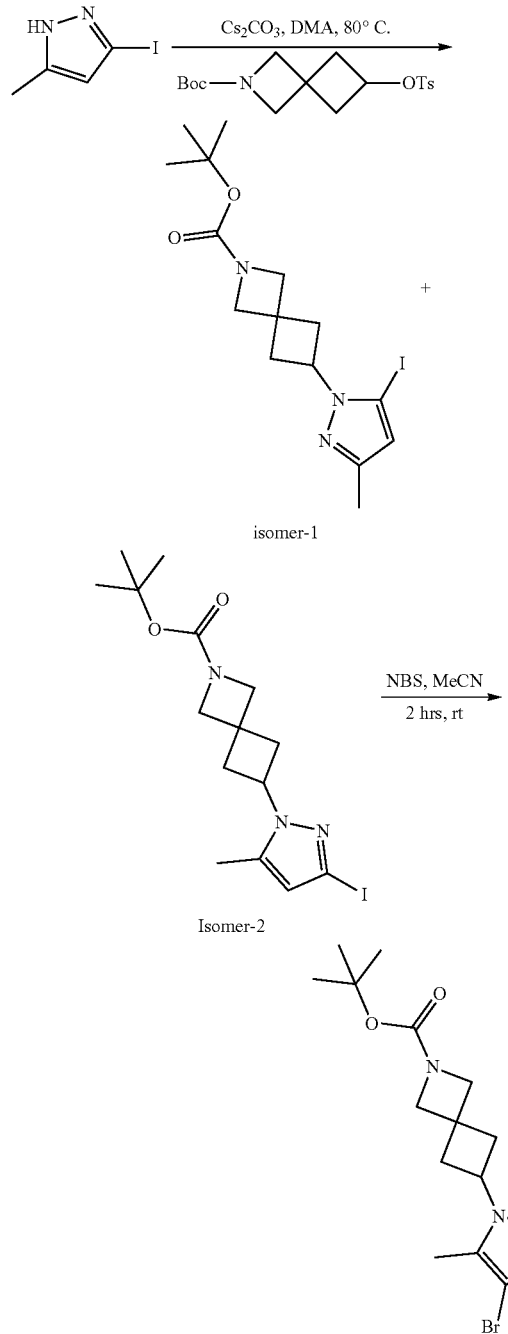

Step 1: tert-butyl 6-(3-iodo-5-methyl-1H-pyrazol-1-yl)-2-azaspiro[3.3]heptane-2-carboxylate To a solution of 3-iodo-5-methyl-1H-pyrazole (340 g, 925 mmol) in DMA (3.4 L) was added $Cs_2CO_3$ (754 g, 2.31 mol) followed by tert-butyl 6-(tosyloxy)-2-azaspiro[3.3]heptane-2-carboxylate (Intermediate C2, 193 g, 925 mmol). The reaction mixture was stirred at 80° C. for 16 h. The reaction mixture was poured into water (3000 mL) and extracted with EtOAc (1000 mL×3). The combined organic layers were washed with brine (1 L×3), dried ($Na_2SO_4$), filtered and concentrated under vacuum to give a crude product as mixture of 2 regioisomers. The regioisomers were separated by normal phase chromatography (eluent: heptane/EtOAc from 8/1 to 5/1) to give isomer-1 as a white solid: UPLC-MS-1: Rt=1.23 min; MS m/z [M+H]$^+$: 404.1, and the title compound isomer-2 as a white solid. $^1$H NMR (400 MHz, DMSO-$d_6$) δ 6.24-6.22 (m, 1H), 4.82-4.60 (m, 1H), 4.01-3.92 (m, 2H), 3.88-3.81 (m, 2H), 2.66-2.57 (m, 4H), 2.18 (s, 3H), 1.37 (s, 9H). UPLC-MS-1: Rt=1.20 min; MS m/z [M+H]$^+$: 404.1.

Step 2: tert-butyl 6-(4-bromo-3-iodo-5-methyl-1H-pyrazol-1-yl)-2-azaspiro[3.3]heptane-2-carboxylate To a solution of tert-butyl 6-(3-iodo-5-methyl-1H-pyrazol-1-yl)-2-azaspiro[3.3]heptane-2-carboxylate (Step 1, 100 g, 248 mmol) in acetonitrile (1 L) was added NBS (53 g, 298 mmol) and the reaction mixture was stirred at RT for 3 h. The reaction mixture was diluted with EtOAc (1.5 L), washed with a sat. aq. $NaHCO_3$ solution (1 L×3) then with brine (1 L), dried ($Na_2SO_4$), filtered and concentrated under vacuum. The residue was triturated with MTBE (200 ml), the solid was filtered, and dried under vacuum to give the title compound as a white solid. $^1$H NMR (400 MHz, $CDCl_3$) δ 4.83-4.73 (m, 1H), 4.01-3.91 (m, 2H), 3.90-3.80 (m, 2H), 2.87-2.82 (m, 2H), 2.66-2.57 (m, 2H), 2.27 (s, 3H), 1.44 (s, 9H). UPLC-MS-1: Rt=1.31 min; MS m/z [M+H]$^+$: 482.1/484.1.

Intermediate C8: Tert-butyl 6-(4-bromo-3-(2-(((tert-butyldimethylsilyl)oxy)methyl)-2,3-dihydrobenzofuran-5-yl)-5-methyl-1H-pyrazol-1-yl)-2-azaspiro[3.3]heptane-2-carboxylate

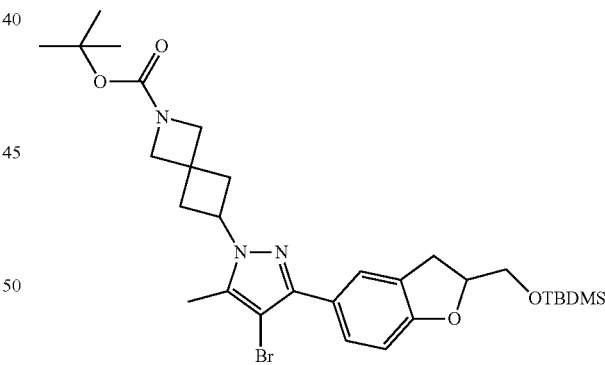

To a stirred solution of tert-butyl 6-(4-bromo-3-iodo-5-methyl-1H-pyrazol-1-yl)-2-azaspiro[3.3]heptane-2-carboxylate (Intermediate C7, 800 mg, 1.66 mmol), 3-tert-butyldimethyl((5-(4,4,5,5-tetramethyl-1,3,2-dioxaborolan-2-yl)-2,3-dihydrobenzofuran-2-yl)methoxy)silane (Intermediate B18) (777 mg, 1.99 mmol) and potassium phosphate (2 M aq. solution; 2.50 mL, 5.00 mmol) in 1,4-dioxane (10 mL) was added tetrakis(triphenylphosphine)palladium (192 mg, 0.16 mmol) and the reaction mixture was stirred at 90° C. for 14 h. The reaction mixture was allowed to cool to RT, was diluted with water (10 mL) and extracted with EtOAc (×2). The combined organic extracts were washed with water, dried and concentrated.

The crude residue was purified by normal phase chromatography (eluent: MeOH in CH₂Cl₂ from 0 to to 10%) to give the title compound as a racemic mixture. The enantiomers were separated by chiral SFC separation using method C-SFC-20 (mobile phase: CO₂/[IPA/0.025% NH₃] 85/15) to give the 2$^{nd}$ eluting isomer: $^1$H NMR (400 MHz, CDCl₃) δ 7.60 (d, 1H), 7.53 (dd, 1H), 6.80 (d, 1H), 4.92-4.86 (m, 1H), 4.84-4.73 (m, 1H), 3.98 (br s, 2H), 3.88 (bs. s, 2H), 3.79 (ddd, 2H), 3.28 (dd, 1H), 3.03 (dd, 1H), 2.72-2.62 (m, 4H), 2.26 (s, 3H), 1.39 (s, 9H), 0.83 (s, 9H), 0.08 (s, 3H), 0.03 (s, 3H); UPLC-MS-3: Rt=1.57 min; MS m/z [M+H]⁺; 618.3/620.3; C-SFC-11 (mobile phase: CO₂/[IPA/0.025% NH₃] 85/15); 2$^{nd}$ eluting isomer: Rt=3.90 min. The other enantiomer was obtained as first eluting isomer; C-SFC-11 (mobile phase: CO₂/[IPA/0.025% NH₃] 85/15): 1$^{st}$ eluting isomer: Rt=3.14 min.

Intermediate C9: Tert-butyl 6-(5-(difluoromethyl)-4-iodo-3-(2-methylpyridin-3-yl)-1H-pyrazol-1-yl)-2-azaspiro[3.3]heptane-2-carboxylate

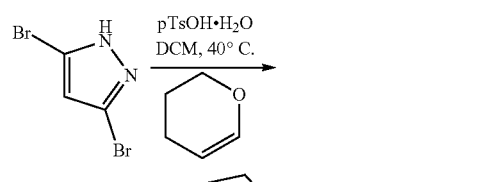

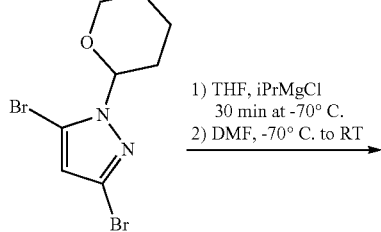

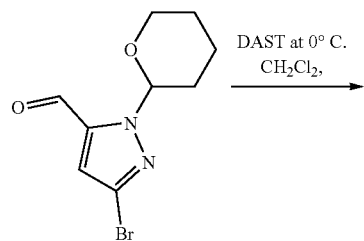

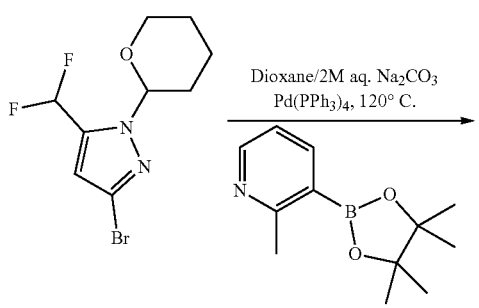

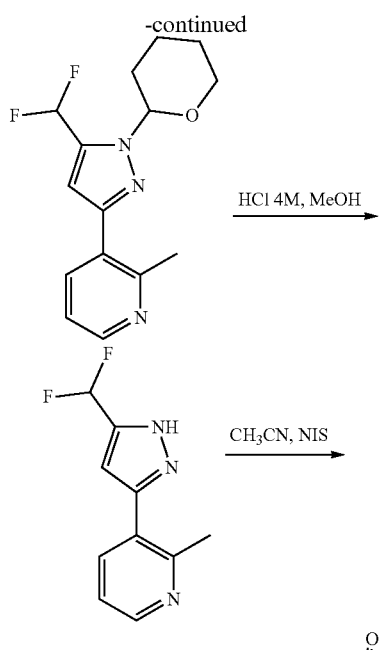

Step 1: 3,5-Dibromo-1-(tetrahydro-2H-pyran-2-yl)-1H-pyrazole

To a solution of 3,5-dibromo-1H-pyrazole (Intermediate C1, Step 2, 5.12 g, 20.4 mmol) in DCM (100 ml) were added 3,4-dihydro-2H-pyran (3.45 mL, 36.7 mmol) and PTSA (241 mg, 1.27 mmol) and the reaction mixture was stirred at room temperature overnight. The reaction was quenched with sat. aq. NaHCO₃ solution and extracted with DCM. The combined organic layers were dried (phase separator), and concentrated under vacuum. The residue was purified by normal phase chromatography (eluent: TBME in n-heptane 0 to 50%) to give the title compound as a white solid. UPLC-MS-1: Rt=1.11 min; MS m/z [M+H]⁺: 309.0/311.0/312.9.

Step 2: 3-Bromo-1-(tetrahydro-2H-pyran-2-yl)-1H-pyrazole-5-carbaldehyde

To a solution of 3,5-dibromo-1-(tetrahydro-2H-pyran-2-yl)-1H-pyrazole (Step 1, 2.50 g, 7.98 mmol) in THF (80.0 mL) was added a solution of iPrMgCl (2M in THF, 5.19 mL, 10.38 mmol) dropwise with stirring at −70° C. under inert atmosphere. During the addition, the temperature was kept below −60° C. The reaction mixture was stirred at −70° C./−60° C. for 1 h. Then to the reaction mixture was added DMF (6.18 mL, 80 mmol) dropwise with stirring, keeping the temperature below −60° C. The reaction mixture was stirred for 5 min at the same temperature then slowly warmed up to room temperature over 1 h. The reaction mixture was stirred overnight at room temperature. The RM was quenched with sat. aq. NH$_4$Cl solution and extracted with a mixture of tBME and EtOAc. The combined organic layers were washed with brine, dried (phase separator) and concentrated under vacuum to give the title compound as a yellow oil which was used without purification in the next step. UPLC-MS-1: Rt=0.96 min; MS m/z [M+H]$^+$: 259.2/261.1.

Step 3: 3-Bromo-5-(difluoromethyl)-1-(tetrahydro-2H-pyran-2-yl)-1H-pyrazole

To a solution of 3-bromo-1-(tetrahydro-2H-pyran-2-yl)-1H-pyrazole-5-carbaldehyde (Step 2, 508 mg, 1.51 mmol) in DCM (15.0 mL) was added DAST (0.60 mL, 4.53 mmol) dropwise with stirring at 0° C. under inert atmosphere. The reaction mixture was stirred and allowed to warm to RT overnight. The reaction mixture was quenched with crushed ice then sat. aq. NaHCO$_3$ solution and was extracted with DCM (×2). The combined organic layers were washed with brine, dried (phase separator) and concentrated under vacuum to give the title compound as a yellow oil which was used without purification in the next step. $^1$H NMR (400 MHz, DMSO-d$_6$) δ 7.30 (t, 1H), 6.87 (t, 1H), 5.60-5.48 (m, 1H), 3.90-3.78 (m, 1H), 3.68-3.60 (m, 1H), 2.20-2.07 (m, 1H), 1.96-1.89 (m, 2H), 1.69-1.59 (m, 1H), 1.55-1.50 (m, 2H).

Step 4: 3-(5-(Difluoromethyl)-1-(tetrahydro-2H-pyran-2-yl)-1H-pyrazol-3-yl)-2-methylpyridine To a solution of 3-bromo-5-(difluoromethyl)-1-(tetrahydro-2H-pyran-2-yl)-1H-pyrazole (Step 3, 950 mg, 1.69 mmol) in 1,4-dioxane (10.0 mL) under inert atmosphere were added 2-methyl-3-(4,4,5,5-tetramethyl-1,3,2-dioxaborolan-2-yl)pyridine (1.11 g, 5.07 mmol), Pd(PPh$_3$)$_4$ (195 mg, 0.17 mmol), and 2M aqueous Na$_2$CO$_3$ solution. The reaction mixture was stirred at 120° C. for 15 min. The reaction mixture was diluted with EtOAc and the aqueous layer was separated. The organic layer was washed with sat. aq. NaHCO$_3$ solution and the combined aqueous layers were extracted with EtOAc. The combined organic layers were washed with brine, dried (phase separator) and concentrated under vacuum. The crude residue was purified by normal phase chromatography (eluent: [tBME/MeOH 9/1] in tBME from 0 to 40%) to give the title compound as a white solid. UPLC-MS-1: Rt=0.85 min; MS m/z [M+H]$^+$: 294.2.

Step 5: 3-(5-(Difluoromethyl)-1H-pyrazol-3-yl)-2-methylpyridine

To a solution of 3-(5-(difluoromethyl)-1-(tetrahydro-2H-pyran-2-yl)-1H-pyrazol-3-yl)-2-methylpyridine (Step 4, 420 mg, 1.35 mmol) in MeOH (10 mL) was added an aqueous solution of HCl (4M, 3.36 mL, 13.5 mmol) and the reaction mixture was stirred for 1 h at RT. The reaction mixture was quenched with a sat. aq. NaHCO$_3$ solution and extracted with DCM (×3). The combined organic layers were dried (phase separator) and concentrated under vacuum to give the title compound which was used without further purification in the next step. UPLC-MS-1: Rt=0.54 min; MS m/z [M+H]$^+$: 210.2.

Step 6: 3-(5-(Difluoromethyl)-4-iodo-1H-pyrazol-3-yl)-2-methylpyridine

To a solution of 3-(5-(difluoromethyl)-1H-pyrazol-3-yl)-2-methylpyridine (Step 5, 280 mg, 1.03 mmol) in acetonitrile (7 mL) was added NIS (348 mg, 1.55 mmol) and the reaction mixture was stirred overnight at RT. The RM was quenched by addition of a sat. aq. Na$_2$S$_2$O$_3$ solution and extracted with EtOAc. The organic layer was washed with brine, then dried (phase separator) and concentrated under vacuum. The residue was purified by normal phase chromatography (eluent: [TBME/MeOH 9/1] in TBME from 0 to 100%) to give the title compound as a white solid. UPLC-MS-1: Rt=0.77 min; MS m/z [M+H]$^+$; 336.1.

Step 7: Tert-butyl 6-(5-(difluoromethyl)-4-iodo-3-(2-methylpyridin-3-yl)-1H-pyrazol-1-yl)-2-azaspiro[3.3]heptane-2-carboxylate To a clear yellow solution of 3-(5-(difluoromethyl)-4-iodo-1H-pyrazol-3-yl)-2-methylpyridine (Step 6, 25 mg, 0.75 mmol) in dry DMF (5 mL) was added Cs$_2$CO$_3$ (736 mg, 2.26 mmol) and tert-butyl 6-(tosyloxy)-2-azaspiro[3.3]heptane-2-carboxylate (Intermediate C2, 305 mg, 0.83 mmol). The reaction mixture was stirred at 120° C. under inert atmosphere for 1.5 h. More tert-butyl 6-(tosyloxy)-2-azaspiro[3.3]heptane-2-carboxylate (Intermediate C2, 83 mg, 0.23 mmol) was added and the reaction mixture was stirred at 120° C. for another 1 h. The reaction mixture was poured into water/tBME mixture then extracted twice with tBME. The combined organic layers were washed with brine, dried (phase separator) and concentrated under vacuum. The crude residue was purified by normal phase chromatography (eluent: tBME in heptane from 0 to 90%) to give the desired isomer tert-butyl 6-(5-(difluoromethyl)-4-iodo-3-(2-methylpyridin-3-yl)-1H-pyrazol-1-yl)-2-azaspiro[3.3]heptane-2-carboxylate as a white solid. $^1$H NMR (400 MHz, DMSO-d$_6$) δ 8.59-8.49 (m, 1H), 7.74-7.62 (m, 1H), 7.41-7.28 (m, 1H), 7.24 (t, 1H), 5.13-4.95 (m, 1H), 4.02-3.91 (m, 2H), 3.89-3.79 (m, 2H), 2.81-2.65 (m, 4H) 2.37 (s, 3H), 1.37 (s, 9H); UPLC-MS-1: Rt=1.22 min; MS m/z [M+H]$^+$: 531.5.

The following intermediate C10 was prepared using analogous methods to the method used in the preparation of Intermediate C9 from intermediates commercially available (in Step 1).

| Intermediate | Structure | Precursor | Characterizing data |
|---|---|---|---|
| C10 | tert-butyl 6-(5-(difluoromethyl)-4-iodo-3-(pyrimidin-5-yl)-1H-pyrazol-1-yl)-2-azaspiro[3.3]heptane-2-carboxylate | from pyrimidin-5-ylboronic acid (Step 5) | $^1$H NMR (600 MHz, DMSO-d$_6$) δ 9.27 (s, 1H), 9.18 (s, 2H), 7.28 (t, 1H), 5.14-5.02 (m, 1H), 4.03-3.92 (m, 2H), 3.91-3.84 (m, 2H), 2.86-2.68 (m, 4H), 1.37 (s, 9H); HPLC-MS-1: Rt = 1.19 min; MS m/z [M + H]$^+$: 518.2. |

Intermediate C11: Tert-butyl 6-(5-(difluoromethyl)-4-iodo-3-(pyridin-3-yl)-1H-pyrazol-1-yl)-2-azaspiro[3.3]heptane-2-carboxylate

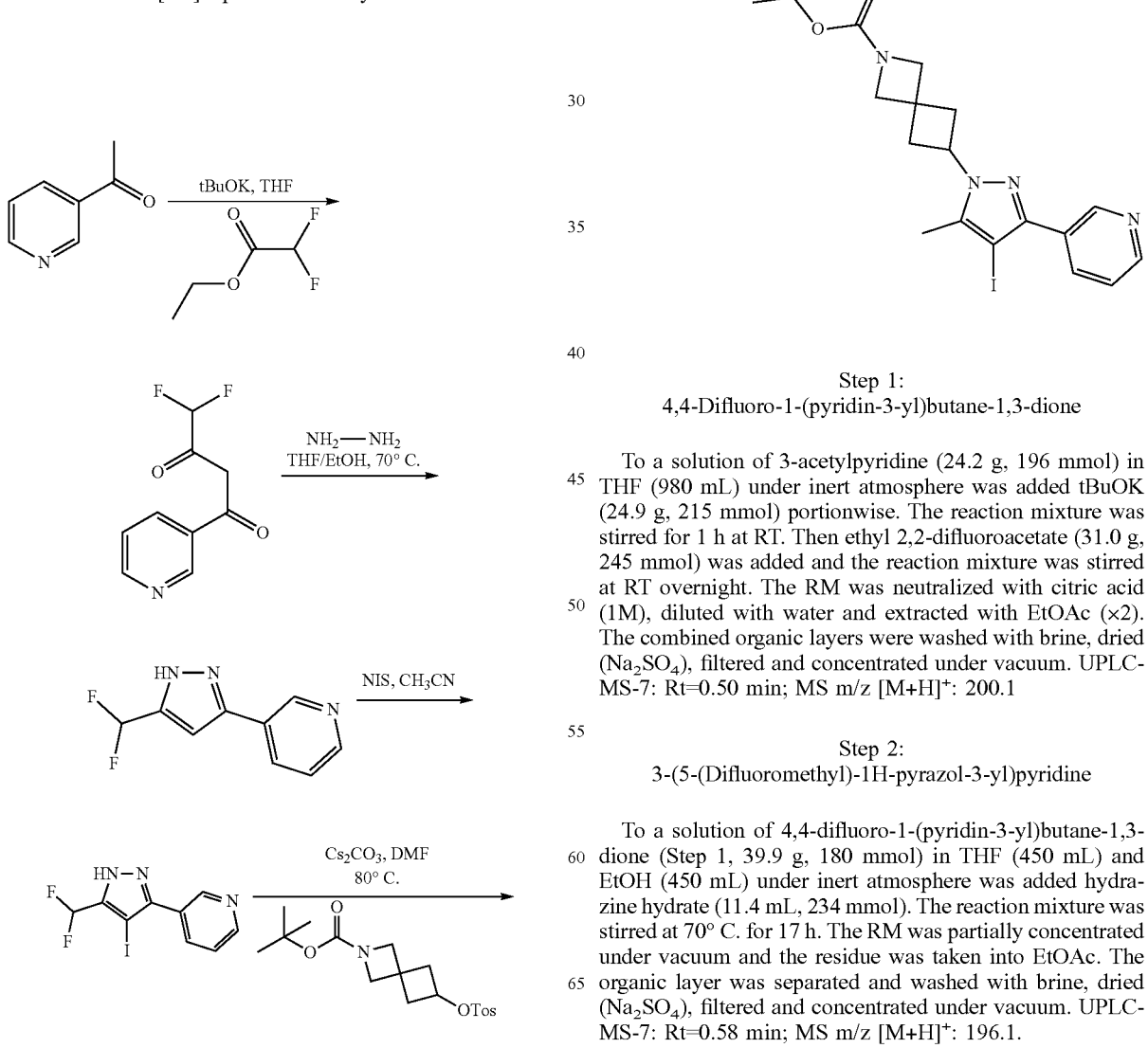

Step 1: 4,4-Difluoro-1-(pyridin-3-yl)butane-1,3-dione

To a solution of 3-acetylpyridine (24.2 g, 196 mmol) in THF (980 mL) under inert atmosphere was added tBuOK (24.9 g, 215 mmol) portionwise. The reaction mixture was stirred for 1 h at RT. Then ethyl 2,2-difluoroacetate (31.0 g, 245 mmol) was added and the reaction mixture was stirred at RT overnight. The RM was neutralized with citric acid (1M), diluted with water and extracted with EtOAc (×2). The combined organic layers were washed with brine, dried (Na$_2$SO$_4$), filtered and concentrated under vacuum. UPLC-MS-7: Rt=0.50 min; MS m/z [M+H]$^+$: 200.1

Step 2: 3-(5-(Difluoromethyl)-1H-pyrazol-3-yl)pyridine

To a solution of 4,4-difluoro-1-(pyridin-3-yl)butane-1,3-dione (Step 1, 39.9 g, 180 mmol) in THF (450 mL) and EtOH (450 mL) under inert atmosphere was added hydrazine hydrate (11.4 mL, 234 mmol). The reaction mixture was stirred at 70° C. for 17 h. The RM was partially concentrated under vacuum and the residue was taken into EtOAc. The organic layer was separated and washed with brine, dried (Na$_2$SO$_4$), filtered and concentrated under vacuum. UPLC-MS-7: Rt=0.58 min; MS m/z [M+H]$^+$: 196.1.

Step 3: 3-(5-(difluoromethyl)-4-iodo-1H-pyrazol-3-yl)pyridine

To a solution of 3-(5-(difluoromethyl)-1H-pyrazol-3-yl)pyridine (Step 2, 35.0 g, 126 mmol) in acetonitrile (630 mL) was added NIS (36.7 g, 163 mmol) and the reaction mixture was stirred at RT for 17 h. More NIS (8.50 g, 37.7 mmol) was added and the RM which was stirred at RT for an additional 6 h. The RM was quenched by addition of sodium thiosulfate (1M, 500 mL). The solvent was removed under vacuum and the solution was extracted twice with EtOAc. The organic layer was washed with water, brine, dried ($Na_2SO_4$), filtered and evaporated. The crude product was purified by normal phase chromatography (eluent: [$CH_2Cl_2$/MeOH/$NH_4$OH; 100/10/1] in $CH_2Cl_2$ from 0 to 80%) to give the title compound. UPLC-MS-7: Rt=0.79 min; MS m/z [M+H]$^+$: 322.0.

Step 4: Tert-butyl 6-(5-(difluoromethyl)-4-iodo-3-(pyridin-3-yl)-1H-pyrazol-1-yl)-2-azaspiro[3.3]heptane-2-carboxylate To a stirred solution of 3-(5-(difluoromethyl)-4-iodo-1H-pyrazol-3-yl)pyridine (Step 3, 5.20 g, 16.2 mmol) and tert-butyl 6-(tosyloxy)-2-azaspiro[3.3]heptane-2-carboxylate (Intermediate C2, 8.93 g, 24.3 mmol) in DMF (81 mL) was added $Cs_2CO_3$ (13.2 g, 40.5 mmol) and the mixture was stirred at 80° C. overnight. The RM was poured into $NaHCO_3$ (1M, 25 mL) and extracted with EtOAc (×2). The combined organic layers were washed with brine, dried ($Na_2SO_4$), filtered and concentrated under vacuum. The crude product was purified by normal phase chromatography (eluent: [EtOAc/MeOH; 20/1] in n-heptane from 0 to 100%) and re-purified by normal phase chromatography (eluent: tBME in n-heptane from 0 to 100%) to give the desired regioisomer tert-butyl 6-(5-(difluoromethyl)-4-iodo-3-(pyridin-3-yl)-1H-pyrazol-1-yl)-2-azaspiro[3.3]heptane-2-carboxylate: $^1$H NMR (400 MHz, DMSO-d$_6$) δ 9.00-8.87 (m, 1H), 8.68-8.50 (m, 1H), 8.19-8.06 (m, 1H), 7.61-7.47 (m, 1H), 7.24 (t, 1H), 5.13-4.93 (m, 1H), 4.04-3.90 (m, 2H), 3.92-3.79 (m, 2H), 2.85-2.60 (m, 4H), 1.37 (s, 9H); UPLC-MS-6: Rt=1.17 min; MS m/z [M+H]$^+$; 517.2. The other regioisomer tert-butyl 6-(4-iodo-3-methyl-5-(pyridin-3-yl)-1H-pyrazol-1-yl)-2-azaspiro[3.3]heptane-2-carboxylate was isolated as well: UPLC-MS-6: Rt=1.14 min; MS m/z [M+H]$^+$; 517.2.

Intermediate C12: Tert-butyl 6-(5-(bromomethyl)-4-iodo-3-(pyridin-3-yl)-1H-pyrazol-1-yl)-2-azaspiro[3.3]heptane-2-carboxylate

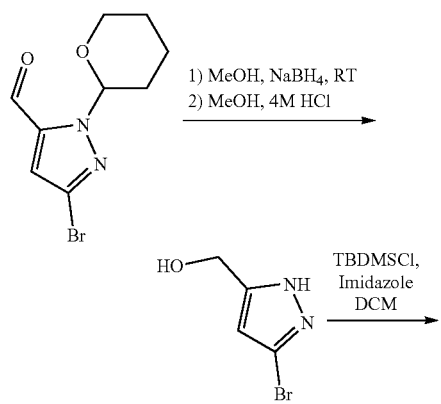

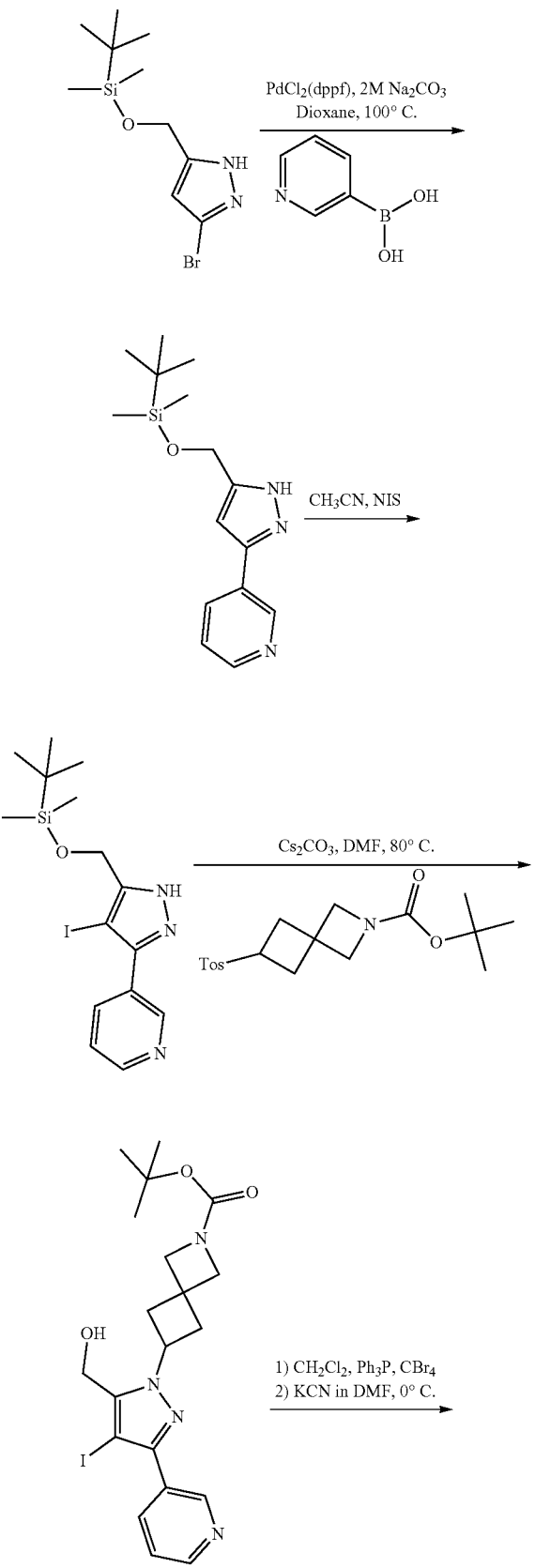

-continued

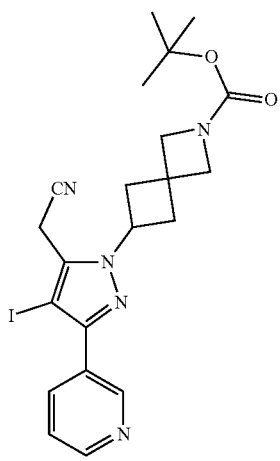

Step 1: (3-Bromo-1H-pyrazol-5-yl)methanol

To a solution of 3-bromo-1-(tetrahydro-2H-pyran-2-yl)-1H-pyrazole-5-carbaldehyde (Intermediate C9, step 2) (980 mg, 3.78 mmol) in MeOH (20 mL) was added NaBH$_4$ (572 mg, 15.1 mmol). The reaction mixture was stirred at RT overnight. After completion of the reduction, HCl (4M in dioxane, 9.46 mL, 37.8 mmol) was added and the reaction mixture was stirred for 1 h at RT. The reaction mixture was neutralized with a sat. aq. NaHCO$_3$ solution and extracted with EtOAc (×2). The combined organic layers were dried (phase separator) and concentrated under reduced pressure to give the title compound which was used without purification in the next step. UPLC-MS-1: Rt=0.42 min; MS m/z [M–H]$^-$: 175.0/177.0.

Step 2: 3-Bromo-5-(((tert-butyldimethylsilyl)oxy)methyl)-1H-pyrazole

To a solution of (3-bromo-1H-pyrazol-5-yl)methanol (Step 1, 1.00 g, 4.24 mmol) in DCM (20 mL) under inert atmosphere were added imidazole (822 mg, 12.1 mmol) and TBDMSCl (1.59 g, 10.6 mmol) and the reaction mixture was stirred overnight under inert atmosphere. The reaction mixture was quenched with sat. aq. NaHCO$_3$ and extracted with EtOAc (×3). The combined organic extracts were concentrated under reduced pressure. The crude residue was purified by normal phase chromatography (eluent: EtOAc in n-heptane from 0 to 100%) to give the title compound. UPLC-MS-1: Rt=1.24 min; MS m/z [M+H]$^+$: 289.2/291.1.

Step 3: 3-(5-(((Tert-butyldimethylsilyl)oxy)methyl)-1H-pyrazol-3-yl)pyridine

To a mixture of 3-bromo-5-(((tert-butyldimethylsilyl)oxy)methyl)-1H-pyrazole (Step 2, 800 mg, 2.06 mmol) and pyridin-3-ylboronic acid (506 mg, 4.12 mmol) in 1,4-dioxane (15 mL) under inert atmosphere were added PdCl$_2$(dppf) (106 mg, 0.144 mmol) and Na$_2$CO$_3$ (2M, 4.12 mL, 8.24 mmol). The reaction mixture was stirred at 100° C. for 1 h. Then the RM was partitioned between EtOAc and water. The organic layer was extracted with EtOAc (×2). The combined organic extracts were washed with water, brine, dried (MgSO$_4$), filtered and concentrated in vacuo. The crude residue was purified by normal phase chromatography (eluent: [tBME/iPrOH 8/2] in tBME from 0 to 25%) to give the title compound. UPLC-MS-1: Rt=1.10 min; MS m/z [M+H]$^+$: 290.3.

Step 4: 3-(5-(((Tert-butyldimethylsilyl)oxy)methyl)-4-iodo-1H-pyrazol-3-yl)pyridine To a solution of 3-(5-(((tert-butyldimethylsilyl)oxy)methyl)-1H-pyrazol-3-yl)pyridine (Step 3, 440 mg, 1.44 mmol) in acetonitrile (10 mL) under inert atmosphere was added NIS (406 mg, 1.80 mmol) and the reaction mixture was stirred overnight at RT. The RM was quenched by addition of Na$_2$S$_2$O$_3$ (10% in water), extracted with EtOAc (×2). The combined organic extracts were washed with a sat. aq. solution of NaHCO$_3$, brine, dried (MgSO$_4$), filtered and evaporated. The crude residue was purified by normal phase chromatography (eluent: EtOAc in n-heptane from 0 to 100%) to give the title compound. UPLC-MS-1: Rt=1.26 min; MS m/z [M+H]$^+$: 416.2.

Step 5: Tert-butyl 6-(5-(hydroxymethyl)-4-iodo-3-(pyridin-3-yl)-1H-pyrazol-1-yl)-2-azaspiro[3.3]heptane-2-carboxylate To a solution of 3-(5-(((tert-butyldimethylsilyl)oxy)methyl)-4-iodo-1H-pyrazol-3-yl)pyridine (Step 4, 576 mg, 1.39 mmol) in DMF (15 mL) was added Cs$_2$CO$_3$ (1356 mg, 4.16 mmol) and tert-butyl 6-(tosyloxy)-2-azaspiro[3.3]heptane-2-carboxylate (Intermediate C2, 561 mg, 1.52 mmol). The reaction mixture was stirred under inert atmosphere at 80° C. for 16 h. The reaction mixture was partitioned between EtOAc and water. The organic layer was extracted with EtOAc (×2). The combined organic extracts were washed with water, brine, dried (MgSO$_4$), filtered and concentrated in vacuo. The crude residue was purified by normal phase chromatography (eluent: EtOAc in n-heptane from 0 to 100%) to give the title compound as the desired isomer. UPLC-MS-1: Rt=1.01 min; MS m/z [M+H]$^+$: 497.5.

Step 6: Tert-butyl 6-(5-(cyanomethyl)-4-iodo-3-(pyridin-3-yl)-1H-pyrazol-1-yl)-2-azaspiro[3.3]heptane-2-carboxylate To an ice-cooled solution of tert-butyl 6-(5-(hydroxymethyl)-4-iodo-3-(pyridin-3-yl)-1H-pyrazol-1-yl)-2-azaspiro[3.3]heptane-2-carboxylate (Step 5, 170 mg, 0.31 mmol) in CH$_2$Cl$_2$ (5 mL) were added under inert atmosphere Ph$_3$P (170 mg, 0.65 mmol) and CBr$_4$ (215 mg, 0.65 mmol). The reaction mixture was stirred for 60 min at 0-5° C. The formation of the bromo intermediate was confirmed UPLC-MS. UPLC-MS-1: Rt=1.27 min; MS m/z [M+H]$^+$: 559/561. The above reaction mixture was slowly added under inert atmosphere to an ice-cooled solution of KCN (301 mg, 4.62 mmol) in DMF (5 mL). The reaction mixture was stirred overnight letting the temperature to slowly rise to RT. The reaction mixture was partitioned between tBME and water. The organic layer was extracted twice with tBME. The combined organic extracts were washed with brine, dried (MgSO₄), filtered and concentrated in vacuo. The crude residue was purified by normal phase chromatography (eluent: [tBME/CH₃OH 9/1] in n-heptane from 0 to 100%) to give the title compound. ¹H NMR (400 MHz, DMSO-d₆) δ 9.00-8.95 (m, 1H), 8.65-8.61 (m, 1H), 8.16-8.13 (m, 1H), 7.57-7.51 (m, 1H), 5.12-5.01 (m, 1H), 4.27 (s, 2H), 4.02-3.86 (m, 4H), 2.77-2.71 (m, 4H), 1.39 (s, 9H); UPLC-MS-1: Rt=1.11 min; MS m/z [M+H]⁺: 506.1.

Intermediate C13: Tert-butyl 6-(4-bromo-5-methyl-3-(2-methylpyridin-3-yl)-1H-pyrazol-1-yl)-2-azaspiro[3.3]heptane-2-carboxylate

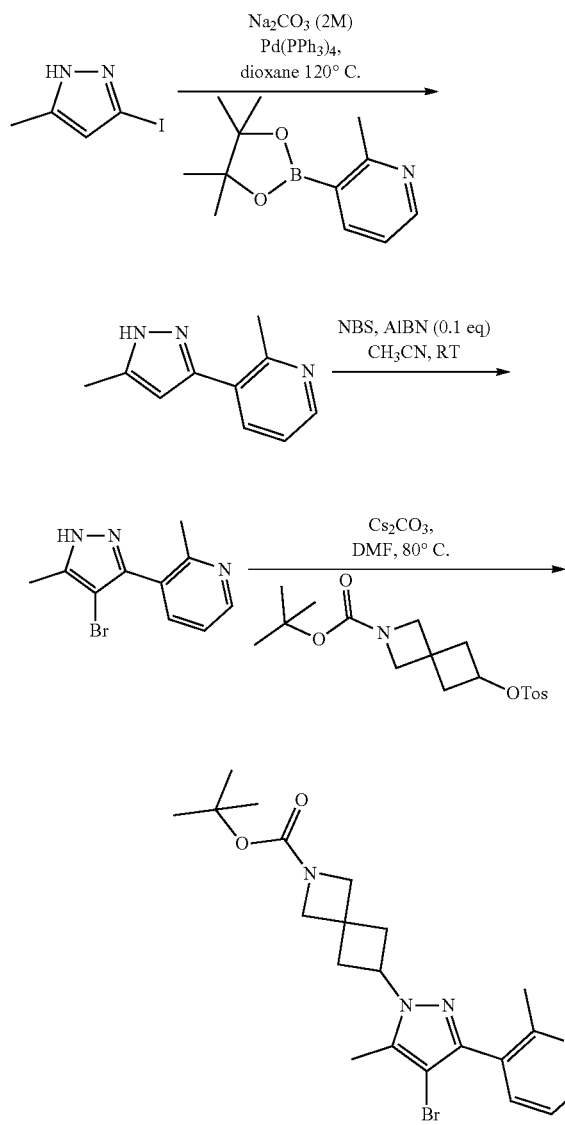

Step 1: 2-Methyl-3-(5-methyl-1H-pyrazol-3-yl)pyridine

3-Iodo-5-methyl-1H-pyrazole (1.50 g, 7.21 mmol), 2-methyl-3-(4,4,5,5-tetramethyl-1,3,2-dioxaborolan-2-yl)pyridine (2.05 g, 9.30 mmol) and Na₂CO₃ (2.0 M in water, 10.8 mL, 21.6 mmol) were added in 1,4-dioxane (60 mL) and the reaction mixture was degassed for 5 min. Pd(PPh₃)₄ (0.42 g, 0.36 mmol) was added and the reaction mixture was stirred at 120° C. for 15 h. The reaction mixture was quenched with ice-cold water and extracted with EtOAc (×2). The combined organic layers were washed with brine, dried (Na₂SO₄), filtered and concentrated under vacuum. The crude residue was purified by normal phase chromatography (eluent: 0-1.5% MeOH in CH₂Cl₂) to obtain the desired product. LCMS-1: Rt=1.19 min, MS m/z [M+H]⁺: 174.31.

Step 2: 3-(4-Bromo-5-methyl-1H-pyrazol-3-yl)-2-methylpyridine

To a solution of 2-methyl-3-(5-methyl-1H-pyrazol-3-yl)pyridine (Step 1, 0.50 g, 2.89 mmol) in CH₃CN at 0° C. was added AIBN (0.047 g, 0.28 mmol). The mixture was stirred for 5 min, N-bromosuccinimide (0.62 g, 3.47 mmol) was added portion wise and the RM was stirred at RT for 2 h. After completion of the reaction, the RM was poured into ice-cold water, extracted with EtOAc (×2). The combined organic layers were washed with a sat. aq. NaHCO₃ solution, brine, dried (Na₂SO₄), filtered and concentrated under vacuum to afford a desired product which was directly used in the next step without further purification. LCMS-1: Rt=1.26 min, MS m/z [M+H]⁺: 252/254.

Step 3: Tert-butyl 6-(4-bromo-5-methyl-3-(2-methylpyridin-3-yl)-1H-pyrazol-1-yl)-2-azaspiro[3.3]heptane-2-carboxylate Cs₂CO₃ (1.93 g, 5.95 mmol) was added to a solution of 3-(4-bromo-5-methyl-1H-pyrazol-3-yl)-2-methylpyridine (Step 2, 0.60 g, 2.38 mmol) in DMF (6 mL) and stirred for 10 min. Tert-butyl 6-(tosyloxy)-2-azaspiro[3.3]heptane-2-carboxylate (Intermediate C2, 0.87 g, 2.38 mmol) was added and reaction mixture was stirred at 80° C. for 15 h. After completion of the reaction, the reaction mixture was poured into ice-cold water and extracted with EtOAc (×2). The combined organic layers were washed with water, brine, dried (Na₂SO₄), filtered and concentrated under vacuum. The crude residue was purified by normal phase chromatography (eluent: 0-20% EtOAc in Hexane) to give the desired product tert-butyl 6-(4-bromo-5-methyl-3-(2-methylpyridin-3-yl)-1H-pyrazol-1-yl)-2-azaspiro[3.3]heptane-2-carboxylate: ¹H NMR (400 MHz, CDCl₃) δ 8.62 (m, 1H), 7.91 (m, 1H), 7.40 (m, 1H), 4.69 (m, 1H), 4.10 (s, 2H), 3.99 (s, 2H), 2.93 (m, 2H), 2.88-2.76 (m, 5H), 2.36 (s, 3H), 1.48 (s, 9H); LCMS-1: Rt=1.62 min, MS m/z [M+H]⁺: 447.3/449.3 and tert-butyl 6-(4-bromo-3-methyl-5-(2-methylpyridin-3-yl)-1H-pyrazol-1-yl)-2-azaspiro[3.3]heptane-2-carboxylate: LCMS-1: Rt=1.83 min, MS m/z [M+H]⁺: 447.3/449.3.

The following intermediate C14 was prepared using analogous methods to the method used in the preparation of Intermediate C13 from commercially available building blocks.

| Intermediate | Structure | Precursor | Characterizing data |
|---|---|---|---|
| C14 | tert-butyl 6-(4-bromo-3-(2-methoxypyrimidin-5-yl)-5-methyl-1H-pyrazol-1-yl)-2-azaspiro[3.3]heptane-2-carboxylate | From (2-methoxypyrimidin-5-yl)boronic acid (Step 1) | LCMS-1: Rt = 1.91 min, MS m/z [M + H]⁺: 464.3/466.3. |

Intermediate C15: Tert-butyl 6-(4-bromo-5-methyl-3-(1-methyl-6-oxo-1,6-dihydropyridin-2-yl)-1H-pyrazol-1-yl)-2-azaspiro[3.3]heptane-2-carboxylate

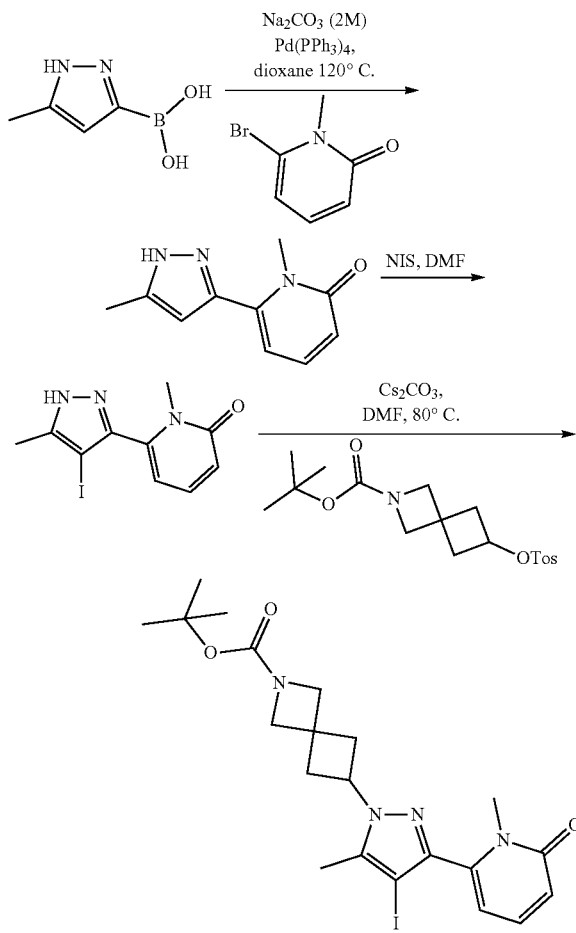

Step 1: 1-Methyl-6-(5-methyl-1H-pyrazol-3-yl)pyridin-2(1H)-one

3-Methyl-1H-pyrazole-5-boronic acid (1.00 g, 8.00 mmol), 6-bromo-1-methylpyridin-2(1H)-one (1.24 g, 6.60 mmol), Na$_2$CO$_3$ (2.0 M in water, 9.90 mL, 19.7 mmol) were placed in 1,4-dioxane (30 mL) and the reaction mixture was degassed for 10 min. Pd(PPh$_3$)$_4$ (0.27 g, 0.24 mmol) was added and the reaction mixture was stirred at 110° C. for 20 h. The RM was diluted with ice-cold water and extracted with EtOAc (×2). The combined organic layers were washed with brine, dried (Na$_2$SO$_4$), filtered and concentrated under vacuum. The crude residue was purified by normal phase chromatography (eluent: 0-8% MeOH in CH$_2$Cl$_2$) to give the desired product. $^1$H NMR (400 MHz, CDCl$_3$) δ 11.0 (br, 1H), 7.40 (t, 1H), 6.67 (d, 1H), 6.39 (d, 1H), 6.24 (s, 1H), 3.64 (s, 3H), 2.41 (s, 3H).

Step 2: 6-(4-Iodo-5-methyl-1H-pyrazol-3-yl)-1-methylpyridin-2(1H)-one

To a solution of 1-methyl-6-(5-methyl-1H-pyrazol-3-yl)pyridin-2(1H)-one (Step 1, 0.48 g, 2.52 mmol) in dry DMF (25 mL) cooled down to −20° C. was added N-iodosuccinimide (0.57 g, 2.52 mmol) portion wise and the reaction mixture was stirred for 4 h. The reaction mixture was poured into ice-cold water, extracted with EtOAc (×2). The combined organic layers were washed with a sat. aq. solution of Na$_2$S$_2$O$_3$, brine, dried (Na$_2$SO$_4$), filtered and concentrated under vacuum to afford the desired product which was directly used in the next step without further purification. LCMS-1: Rt=1.36 min, MS m/z [M+H]⁺: 316.1.

Step 3: Tert-butyl 6-(4-iodo-5-methyl-3-(1-methyl-6-oxo-1,6-dihydropyridin-2-yl)-1H-pyrazol-1-yl)-2-azaspiro[3.3]heptane-2-carboxylate To a solution of 6-(4-iodo-5-methyl-1H-pyrazol-3-yl)-1-methylpyridin-2(1H)-one (Step 2, 0.53 g, 1.68 mmol) and tert-butyl 6-(tosyloxy)-2-azaspiro[3.3]heptane-2-carboxylate (Intermediate C2, 0.68 g, 1.85 mmol) in CH$_3$CN (35 mL) was added Cs$_2$CO$_3$ (0.60 g, 1.85 mmol) and the reaction mixture was stirred at 70-75° C. for 16 h. The reaction mixture was poured into water and extracted with EtOAc (×2). The combined organic layers were washed with water, brine, dried (Na$_2$SO$_4$), filtered and concentrated under vacuum. The crude residue was purified by normal phase chromatography (eluent: 0-7% MeOH in CH$_2$Cl$_2$) to give the desired product: $^1$H NMR (400 MHz, CDCl$_3$) δ 7.41 (m, 1H), 6.70 (d, 1H), 6.26 (d, 1H), 4.72 (m, 1H), 4.09 (s, 2H), 3.98 (s, 2H), 3.43 (s, 3H), 2.9 (m 2H), 2.75 (m, 2H), 2.35 (s, 3H), 1.48 (s, 9H). LCMS-1: Rt=1.71 min, MS m/z [M+H]$^+$: 511.3. The other regioisomer tert-butyl 6-(4-bromo-3-methyl-5-(1-methyl-6-oxo-1,6-dihydropyridin-2-yl)-1H-pyrazol-1-yl)-2-azaspiro[3.3]heptane-2-carboxylate was isolated as well; LCMS-Pir-1:Rt=1.78 min, MS m/z [M+H]$^+$: =511.8.

Intermediate C16 and C$_{17}$: tert-butyl 6-(4-bromo-2'-(2-(dimethylamino)ethyl)-5,5'-dimethyl-1H,2'H-[3,3'-bipyrazol]-1-yl)-2-azaspiro[3.3]heptane-2-carboxylate (C$_{16}$) and tert-butyl 6-(4-bromo-1'-(2-(dimethylamino)ethyl)-5,5'-dimethyl-1H,1'H-[3,3'-bipyrazol]-1-yl)-2-azaspiro[3.3]heptane-2-carboxylate (C17)

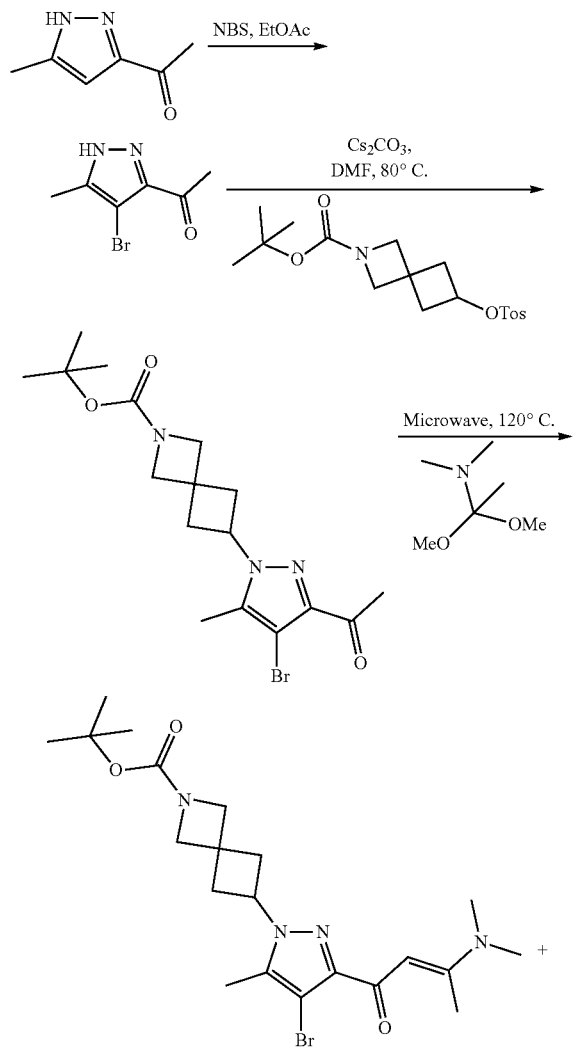

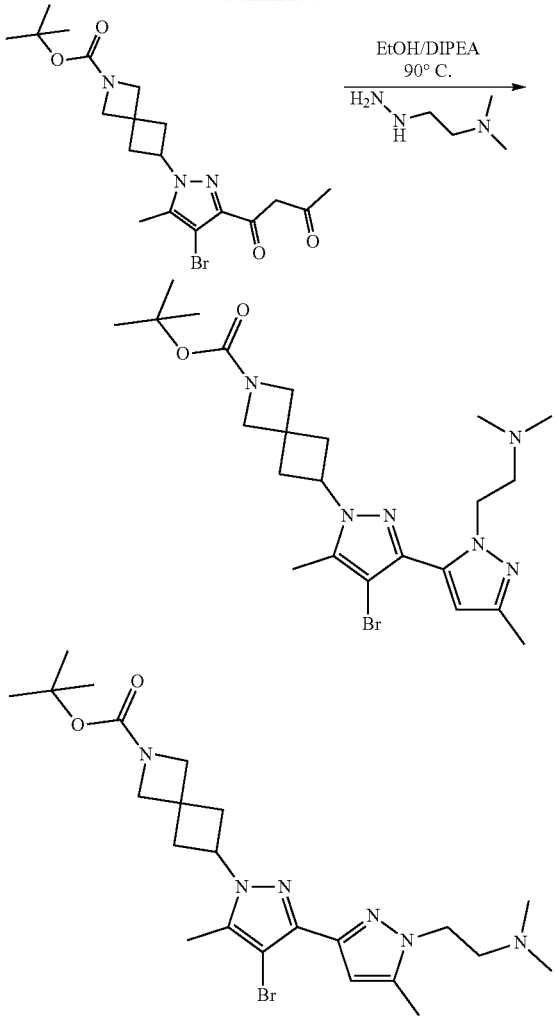

Step 1: 1-(4-Bromo-5-methyl-1H-pyrazol-3-yl)ethan-1-one

A solution of 1-(5-methyl-1H-pyrazol-3-yl) ethanone ([17357-74-3], 963 mg, 7.45 mmol) and N-bromosuccinimide (2.38 g, 13.4 mmol) in EtOAc (30 mL) was stirred at RT overnight under Argon. The reaction mixture was poured into a 10% aqueous solution of sodium thiosulfate and extracted with EtOAc (×2). The combined organic extracts were washed with brine, dried (Na$_2$SO$_4$), filtered and evaporated to give the title compound as a white solid. UPLC-MS-1: Rt=0.64 min; MS m/z [M+H]$^+$: 201.0/203.0.

Step 2: Tert-butyl 6-(3-acetyl-4-bromo-5-methyl-1H-pyrazol-1-yl)-2-azaspiro[3.3]heptane-2-carboxylate To a solution of 1-(4-bromo-5-methyl-1H-pyrazol-3-yl)ethan-1-one (Step 1, 1.63 g, 7.79 mmol) in DMF (30 mL) was added cesium carbonate (6.34 g, 19.5 mmol), tert-butyl 6-(tosyloxy)-2-azaspiro[3.3]heptane-2-carboxylate (Intermediate C2, 3.72 g, 10.1 mmol) and the reaction mixture was stirred at 80° C. under Argon for 16 h. The RM was poured into water and extracted with EtOAc (×2), the combined organic extracts were washed with brine, dried (Na$_2$SO$_4$), filtered and evaporated. The crude residue was purified by normal phase chromatography (eluent: EtOAc in n-heptane from 0 to 30%) to give the title compound as a white solid. UPLC-MS-1: Rt=1.17 min; MS m/z [M+H]$^+$: 398.2/400.2.

Step 3: Tert-butyl-6-(4-bromo-3-(3-(dimethylamino) but-2-enoyl)-5-methyl-1H-pyrazol-1-yl)-2-azaspiro [3.3]heptane-2-carboxylate and tert-butyl 6-(4-bromo-5-methyl-3-(3-oxobutanoyl)-1H-pyrazol-1-yl)-2-azaspiro[3.3]heptane-2-carboxylate A solution of tert-butyl 6-(3-acetyl-4-bromo-5-methyl-1H-pyrazol-1-yl)-2-azaspiro[3.3]heptane-2-carboxylate (Step 2, 700 mg, 1.71 mmol) in n,n-dimethylacetamide dimethyl acetal (84 mL, 24.6 mmol) was flushed with Argon and stirred at 120° C. under microwave irradiations for 1 h. The reaction mixture was concentrated and the crude residue was purified by normal phase chromatography (eluent: MeOH in CH$_2$Cl$_2$ from 0 to 4%) to give a mixture of the title compounds. UPLC-MS-1: Rt=1.06 and 1.14 min; MS m/z [M+H]$^+$; 467.3/469.3 and 440.2/442.2.

Step 4: Intermediate C16: tert-butyl 6-(4-bromo-2'-(2-(dimethylamino)ethyl)-5,5'-dimethyl-1H,2'H-[3, 3'-bipyrazol]-1-yl)-2-azaspiro[3.3]heptane-2-carboxylate and Intermediate C17: tert-butyl 6-(4-bromo-1'-(2-(dimethylamino)ethyl)-5,5'-dimethyl-1H,1'H-[3,3'-bipyrazol]-1-yl)-2-azaspiro[3.3] heptane-2-carboxylate A mixture of tert-butyl-6-(4-bromo-3-(3-(dimethylamino) but-2-enoyl)-5-methyl-1H-pyrazol-1-yl)-2-azaspiro[3.3] heptane-2-carboxylate and tert-butyl 6-(4-bromo-5-methyl-3-(3-oxobutanoyl)-1H-pyrazol-1-yl)-2-azaspiro[3.3] heptane-2-carboxylate (Step 3, 2.50 mmol), 2-(dimethylamino)ethylhydrazine dihydrochloride (330 mg, 1.87 mmol) and DIPEA (0.65 mL, 3.75 mmol) in EtOH (8 mL) was stirred at 80° C. for 45 min. The reaction mixture was poured into a sat. aq. solution of NaHCO$_3$ and extracted with EtOAc (×2). The combined organic extracts were washed with brine, dried (Na$_2$SO$_4$), filtered and evaporated. The crude residue was purified by normal phase chromatography (eluent: MeOH in CH$_2$Cl$_2$ from 0 to 10%) to give the tert-butyl 6-(4-bromo-2'-(2-(dimethylamino)ethyl)-5,5'-dimethyl-1H,2'H-[3,3'-bipyrazol]-1-yl)-2-azaspiro[3.3]heptane-2-carboxylate as the first eluting isomer: UPLC-MS-1: Rt=0.98 min; MS m/z [M+H]$^+$; 507.3/509.3. The column was further eluted to give a mixture of the title compounds which was further purified by SFC (SFC-1; mobile phase: 0 to 15% MeOH in CO$_2$) to give tert-butyl 6-(4-bromo-1'-(2-(dimethylamino)ethyl)-5,5'-dimethyl-1H,1'H-[3,3'-bipyrazol]-1-yl)-2-azaspiro[3.3]heptane-2-carboxylate: UPLC-MS-1: Rt=0.93 min; MS m/z [M+H]$^+$; 507.3/509.3.

Indazoles Intermediates: Intermediates D

Intermediate D1: 5-chloro-6-methyl-1-(tetrahydro-2H-pyran-2-yl)-4-(4,4,5,5-tetramethyl-1,3,2-dioxaborolan-2-yl)-1H-indazole

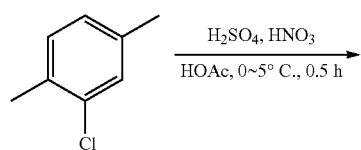

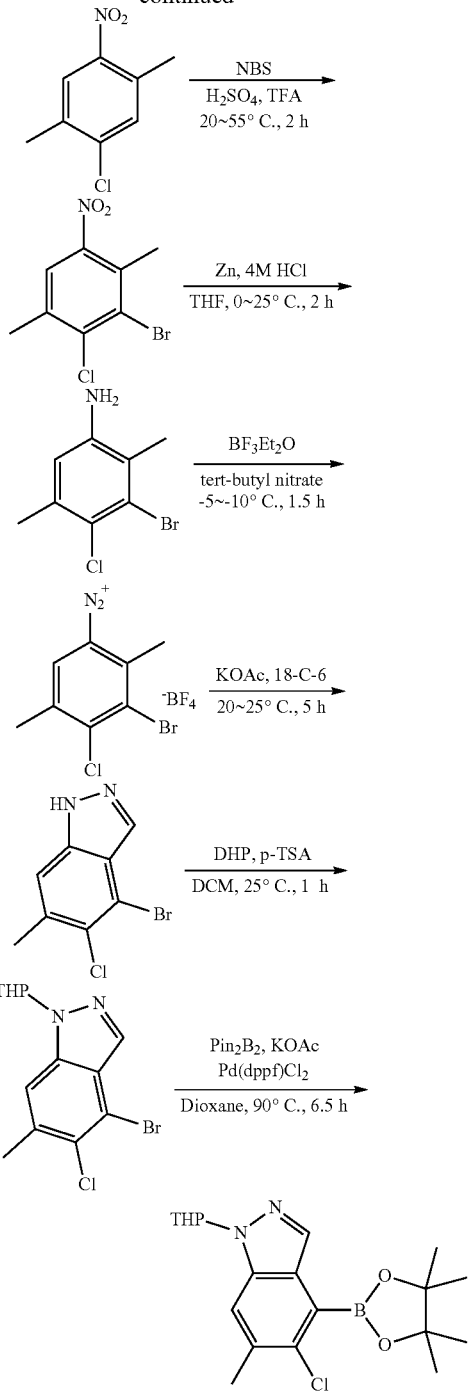

Step 1: 1-chloro-2,5-dimethyl-4-nitrobenzene

To an ice-cooled solution of 2-chloro-1,4-dimethylbenzene (3.40 kg, 24.2 mol) in AcOH (20.0 L) was added H$_2$SO$_4$ (4.74 kg, 48.4. mol, 2.58 L) followed by a dropwise addition (dropping funnel) of a cold solution of HNO$_3$ (3.41 kg, 36.3 mol, 2.44 L, 67.0% purity) in H$_2$SO$_4$ (19.0 kg, 193. mol, 10.3 L). The reaction mixture was then allowed to stir at 0-5° C. for 0.5 h. The reaction mixture was poured slowly into crushed ice (35.0 L) and the yellow solid precipitated out. The suspension was filtered and the cake was washed with water (5.00 L×5) to give a yellow solid which was suspended in MTBE (2.00 L) for 1 h, filtered, and dried to give the title compound as a yellow solid. $^1$H NMR (400 MHz, CDCl$_3$) δ 7.90 (s, 1H), 7.34 (s, 1H), 2.57 (s, 3H), 2.42 (s, 3H).

Step 2:
3-bromo-2-chloro-1,4-dimethyl-5-nitrobenzene

To a cooled solution of 1-chloro-2,5-dimethyl-4-nitrobenzene (Step 1, 2.00 kg, 10.8 mol) in TFA (10.5 L) was slowly added concentrated H$_2$SO$_4$ (4.23 kg, 43.1 mol, 2.30 L) and the reaction mixture was stirred at 20° C. NBS (1.92 kg, 10.8 mol) was added in small portions and the reaction mixture was heated at 55° C. for 2 h. The reaction mixture was cooled to 25° C., then poured into crushed ice solution to obtain a pale white precipitate which was filtered through vacuum, washed with cold water and dried under vacuum to give the title compound as a yellow solid which was used without further purification in the next step. $^1$H NMR (400 MHz, CDCl$_3$) δ 7.65 (s, 1H), 2.60 (s, 3H), 2.49 (s, 3H).

Step 3: 3-bromo-4-chloro-2,5-dimethylaniline

To a ice-cooled solution of 3-bromo-2-chloro-1,4-dimethyl-5-nitrobenzene (Step 2, 2.75 kg, 10.4 mol) in THF (27.5 L) was added HCl (4M, 15.6 L) then Zn (2.72 kg, 41.6 mol) in small portions. The reaction mixture was allowed to stir at 25° C. for 2 h. The reaction mixture was basified by addition of a sat. aq. NaHCO$_3$ solution (until pH=8). The mixture was diluted with EtOAc (2.50 L) and stirred vigorously for 10 min and then filtered through a pad of celite. The organic layer was separated and the aqueous layer was re-extracted with EtOAc (3.00 L×4). The combined organic layers were washed with brine (10.0 L), dried (Na$_2$SO$_4$), filtered and concentrated under vacuum to give the title compound as a yellow solid which was used without further purification in the next step. $^1$H NMR (400 MHz, DMSO-d$_6$) δ 6.59 (s, 1H), 5.23 (s, 2H), 2.22 (s, 3H), 2.18 (s, 3H).

Step 4:
3-bromo-4-chloro-2,5-dimethylbenzenediazonium tetrafluoroborate

BF$_3$.Et$_2$O (2.00 kg, 14.1 mol, 1.74 L) was dissolved in DCM (20.0 L) and cooled to −5 to −10° C. under nitrogen atmosphere. A solution of 3-bromo-4-chloro-2,5-dimethylaniline (Step 3, 2.20 kg, 9.38 mol) in DCM (5.00 L) was added to above reaction mixture and stirred for 0.5 h. Tert-butyl nitrite (1.16 kg, 11.3 mol, 1.34 L) was added dropwise and the reaction mixture was stirred at the same temperature for 1.5 h. TLC (petroleum ether:EtOAc=5:1) showed that starting material (R$_f$=0.45) was consumed completely. MTBE (3.00 L) was added to the reaction mixture to give a yellow precipitate, which was filtered through vacuum and washed with cold MTBE (1.50 L×2) to give the title compound as a yellow solid which was used without further purification in the next step.

Step 5: 4-bromo-5-chloro-6-methyl-1H-indazole

To 18-Crown-6 ether (744 g, 2.82 mol) in chloroform (20.0 L) was added KOAc (1.29 kg, 13.2 mol) and the reaction mixture was cooled to 20° C. Then 3-bromo-4-chloro-2,5-dimethylbenzenediazonium tetrafluoroborate (Step 4, 3.13 kg, 9.39 mol) was added slowly. The reaction mixture was then allowed to stir at 25° C. for 5 h. After completion of the reaction, the reaction mixture was poured into ice cold water (10.0 L), and the aqueous layer was extracted with DCM (5.00 L×3). The combined organic layers were washed with a sat. aq. NaHCO$_3$ solution (5.00 L), brine (5.00 L), dried (Na$_2$SO$_4$), filtered and concentrated under vacuum to give the title compound as a yellow solid. $^1$H NMR (600 MHz, CDCl$_3$) δ 10.42 (br s, 1H), 8.04 (s, 1H), 7.35 (s, 1H), 2.58 (s, 3H). UPLC-MS-1: Rt=1.02 min; MS m/z [M+H]$^+$; 243/245/247.

Step 6: 4-bromo-5-chloro-6-methyl-1-(tetrahydro-2H-pyran-2-yl)-1H-indazole

To a solution of PTSA (89.8 g, 521 mmol) and 4-bromo-5-chloro-6-methyl-1H-indazole (Step 5, 1.28 kg, 5.21 mol) in DCM (12.0 L) was added DHP (658 g, 7.82 mol, 715 mL) dropwise at 25° C. The mixture was stirred at 25° C. for 1 h. After completion the reaction, the reaction mixture was diluted with water (5.00 L) and the organic layer was separated. The aqueous layer was re-extracted with DCM (2.00 L). The combined organic layers were washed with a sat. aq. NaHCO$_3$ solution (1.50 L), brine (1.50 L), dried over Na$_2$SO$_4$, filtered and concentrated under vacuum. The crude residue was purified by normal phase chromatography (eluent: Petroleum ether/EtOAc from 100/1 to 10/1) to give the title compound as a yellow solid. $^1$H NMR (600 MHz, DMSO-d$_6$) δ 8.04 (s, 1H), 7.81 (s, 1H), 5.88-5.79 (m, 1H), 3.92-3.83 (m, 1H), 3.80-3.68 (m, 1H), 2.53 (s, 3H), 2.40-2.32 (m, 1H), 2.06-1.99 (m, 1H), 1.99-1.93 (m, 1H), 1.77-1.69 (m, 1H), 1.60-1.56 (m, 2H). UPLC-MS-6: Rt=1.32 min; MS m/z [M+H]$^+$; 329.0/331.0/333.0

Step 7: 5-chloro-6-methyl-1-(tetrahydro-2H-pyran-2-yl)-4-(4,4,5,5-tetramethyl-1,3,2-dioxaborolan-2-yl)-1H-indazole A suspension of 4-bromo-5-chloro-6-methyl-1-(tetrahydro-2H-pyran-2-yl)-1H-indazole (Step 6, 450 g, 1.37 mol), KOAc (401 g, 4.10 mol) and B$_2$Pin$_2$ (520 g, 2.05 mol) in 1,4-dioxane (3.60 L) was degassed with nitrogen for 0.5 h. Pd(dppf)Cl$_2$.CH$_2$Cl$_2$ (55.7 g, 68.3 mmol) was added and the reaction mixture was stirred at 90° C. for 6 h. The reaction mixture was filtered through diatomite and the filter cake was washed with EtOAc (1.50 L×3). The mixture was concentrated under vacuum to give a black oil which was purified by normal phase chromatography (eluent: Petroleum ether/EtOAc from 100/1 to 10/1) to give the desired product as brown oil. The residue was suspended in petroleum ether (250 mL) for 1 h to obtain a white precipitate. The suspension was filtered, dried under vacuum to give the title compound as a white solid. $^1$H NMR (400 MHz, CDCl$_3$) δ 8.17 (d, 1H), 7.52 (s, 1H), 5.69-5.66 (m, 1H), 3.99-3.96 (m, 1H), 3.75-3.70 (m, 1H), 2.51 (d, 4H), 2.21-2.10 (m, 1H), 2.09-1.99 (m, 1H), 1.84-1.61 (m, 3H), 1.44 (s, 12H); UPLC-MS-6: Rt=1.29 min; MS m/z [M+H]$^+$; 377.1/379.

Intermediate D2: 5-chloro-6-methyl-4-(4,4,5,5-tetramethyl-1,3,2-dioxaborolan-2-yl)-1-tosyl-1H-indazole

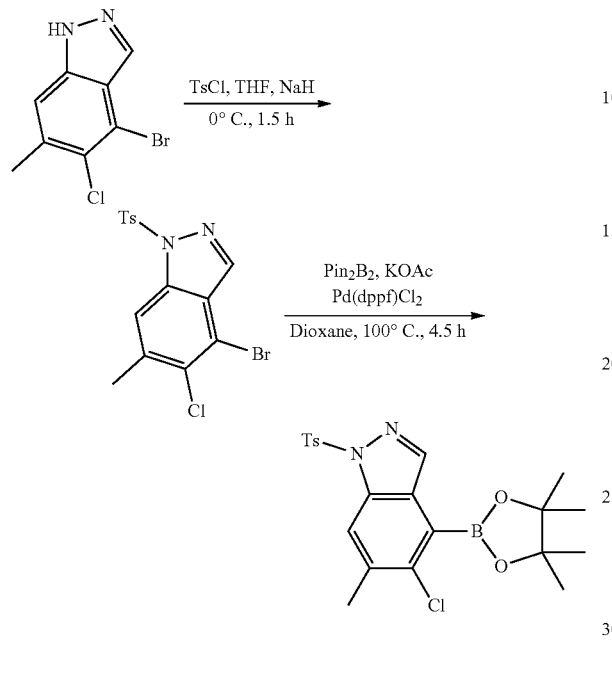

Step 1:
4-bromo-5-chloro-6-methyl-1-tosyl-1H-indazole

A stirred solution of 4-bromo-5-chloro-6-methyl-1H-indazole (Intermediate D1 Step 5, 240 g, 977 mmol) in THF (2.40 L) was treated with NaH (43.0 g, 1.08 mol, 60.0% purity) under nitrogen atmosphere and the reaction mixture was stirred at 0° C. for 30 min. Then the reaction mixture was treated with TsCl (195 g, 1.03 mol) and stirred at 0° C. for 1 h. The reaction was quenched with water (1.00 L), diluted and extracted with EtOAc (1.00 L×3). The combined organic layers were washed with water, brine, dried (MgSO$_4$), filtered and concentrated under vacuum. The residue was suspended in MTBE (200 mL) for 20 min to give the title compound an off-white solid. $^1$H NMR (400 MHz, DMSO-d$_6$) δ 8.49 (s, 1H), 8.16 (s, 1H), 7.91-7.83 (m, 2H), 7.47-7.37 (m, 2H), 2.61 (s, 3H), 2.35 (s, 3H). UPLC-MS-1: Rt=1.42 min; MS m/z [M+H]$^+$; 399.1/401.1/403.1

Step 2: 5-chloro-6-methyl-4-(4,4,5,5-tetramethyl-1,3,2-dioxaborolan-2-yl)-1-tosyl-1H-indazole A suspension of 4-bromo-5-chloro-6-methyl-1-tosyl-1H-indazole (Step 1, 370 g, 925 mmol), KOAc (272 g, 2.78 mol) and B$_2$Pin$_2$ (470 g, 1.85 mol) in 1,4-dioxane (3.00 L) was degassed with nitrogen for 30 min. Pd(dppf)Cl$_2$.CH$_2$Cl$_2$ (75.6 g, 92.6 mmol) was added and the reaction mixture was stirred at 100° C. for 4 h. The reaction mixture was filtered through diatomite and the filtered cake was washed with EtOAc (1.50 L). The filtrate was concentrated under vacuum to give a black oil which was filtered through silica gel and then the residue was suspended in EtOAc (500 mL) at 60° C. for 1 h. The mixture was cooled to 25° C. and the solid was precipitated out. The solid was filtered and concentrated under vacuum to give the title compound as a light yellow solid. $^1$H NMR (400 MHz, CDCl$_3$) δ 8.36 (d, 1H), 8.15 (s, 1H), 7.83 (d, 2H), 7.24 (d, 2H), 2.56 (s, 3H), 2.36 (s, 3H), 1.41 (s, 12H); UPLC-MS-7: Rt=1.27 min; MS m/z [M+H]$^+$: 447.1/449.2.

Intermediate D3: 5,6-dichloro-1-(tetrahydro-2H-pyran-2-yl)-4-(4,4,5,5-tetramethyl-1,3,2-dioxaborolan-2-yl)-1H-indazole

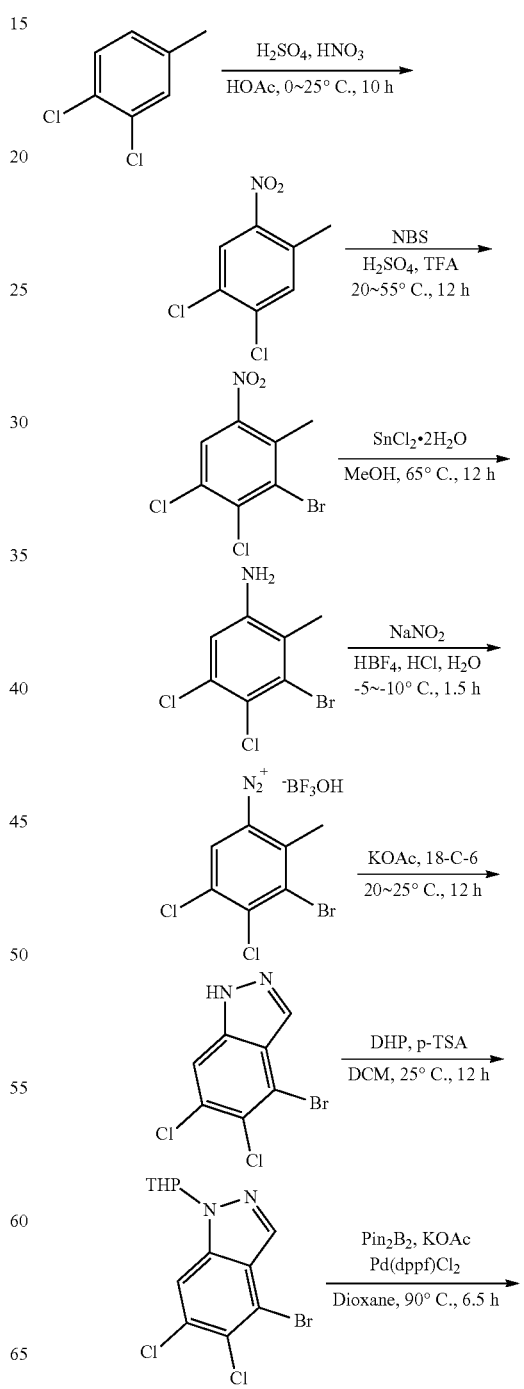

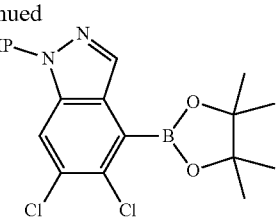

Step 1: 1,2-dichloro-4-methyl-5-nitrobenzene

The title compound was prepared by a method similar to Step 1 in the synthesis of Intermediate D1 by replacing 2-chloro-1,4-dimethylbenzene with 1,2-dichloro-4-methylbenzene. $^1$H NMR (400 MHz, CDCl$_3$) δ 8.08 (s, 1H), 7.43 (s, 1H), 2.56 (s, 3H).

Step 2: 3-bromo-1,2-dichloro-4-methyl-5-nitrobenzene

The title compound was prepared by a method similar to Step 2 in the synthesis of Intermediate D1 by replacing 1-chloro-2,5-dimethyl-4-nitrobenzene with 1,2-dichloro-4-methyl-5-nitrobenzene. $^1$H NMR (400 MHz, CDCl$_3$) δ 7.90 (s, 1H), 2.62 (s, 3H).

Step 3: 3-bromo-4,5-dichloro-2-methylaniline

To a solution of 3-bromo-1,2-dichloro-4-methyl-5-nitrobenzene (Step 2, 3.45 kg, 12.1 mol) in MeOH (27.0 L) was added SnCl$_2$.2H$_2$O (8.20 kg, 36.3 mol) and the reaction mixture was stirred at 65° C. for 10 h. TLC (petroleum ether:EtOAc=5:1 (R$_f$ (starting material)=0.49, R$_f$ (product) =0.22) showed that the starting material was consumed completely and a new main spot was formed. The pH of the mixture was adjusted to pH=8 with 20.0% (w/w) aqueous NaOH solution (10.0 L) at 0-10° C. and the mixture was extracted with EtOAc (5.00 L×8). The combined organic layers were washed with brine (5.00 L×2), dried (Na$_2$SO$_4$), filtered and concentrated under vacuum. The crude residue was triturated with petroleum ether (2.00 L) at 25° C. for 12 h to give the title compound as a yellow solid. $^1$H NMR (400 MHz, CDCl$_3$) δ 6.77 (s, 1H), 3.61-3.89 (m, 2H), 2.30 (s, 3H).

Step 4: 3-bromo-4,5-dichloro-2-methylbenzenediazonium trifluoro(hydroxy)borate To an ice-cooled solution of 3-bromo-4,5-dichloro-2-methylaniline (Step 3, 1.70 kg, 6.67 mol) in HCl (6M, 17.4 L, 105 mmol) stirred for 30 min was added dropwise an ice-cooled solution of NaNO$_2$ (506 g, 7.34 mol) in H$_2$O (1.20 L) while maintaining a temperature of 0° C. The resulting mixture was stirred for 1 h. HBF$_4$ (9.22 kg, 42.0 mol, 6.54 L, 40.0% purity) was added dropwise and the reaction mixture was stirred at 0° C. for 30 min. TLC (petroleum ether:EtOAc=5:1) showed that the starting material (R$_f$=0.39) was consumed completely, and a new spot (R$_f$=0.00) was formed. The resulting precipitate was filtered through vacuum, washed with cold water (2.00 L) and MTBE (2.00 L) and then dried under vacuum to obtain a pale yellow solid of diazonium salt. The crude product was triturated with MTBE (1000 mL) at 25° C. for 30 min to give the title compound as a yellow solid which was used without further purification in the next step.

Step 5: 4-bromo-5,6-dichloro-1H-indazole

The title compound was prepared by a method similar to that of Intermediate D1, Step 5 by replacing 3-bromo-4-chloro-2,5-dimethylbenzenediazonium tetrafluoroborate with 3-bromo-4,5-dichloro-2-methylbenzenediazonium trifluoro(hydroxy)borate. $^1$H NMR (400 MHz, DMSO-d$_6$) δ 13.71 (br s, 1H), 8.10 (d, 1H), 7.94 (d, 1H); UPLC-MS-9: Rt=1.18 min; MS m/z [M+H]$^-$: 262.9/264.9/266.8/268.8.

Step 6: 4-bromo-5,6-dichloro-1-(tetrahydro-2H-pyran-2-yl)-1H-indazole

The title compound was prepared by a method similar to Step 6 in the synthesis of Intermediate D1 by replacing 4-bromo-5-chloro-6-methyl-1H-indazole with 4-bromo-5,6-dichloro-1H-indazole. $^1$H NMR (400 MHz, DMSO-d$_6$) δ 8.22 (s, 1H), 8.13 (s, 1H), 5.91-5.88 (m, 1H), 3.90-3.83 (m, 1H), 3.81-3.72 (m, 1H), 2.40-2.27 (m, 1H), 2.07-1.92 (m, 2H), 1.78-1.65 (m, 1H), 1.62-1.52 (m, 2H); UPLC-MS-9: Rt=1.55 min; MS m/z [M+H]$^+$: 349.1/351.0/353.0.

Step 7: 5,6-dichloro-1-(tetrahydro-2H-pyran-2-yl)-4-(4,4,5,5-tetramethyl-1,3,2-dioxaborolan-2-yl)-1H-indazole The title compound was prepared by a method similar to Step 7 in the synthesis of Intermediate D1, Step 7 by replacing 4-bromo-5-chloro-6-methyl-1-(tetrahydro-2H-pyran-2-yl)-1H-indazole with 4-bromo-5,6-dichloro-1-(tetrahydro-2H-pyran-2-yl)-1H-indazole. $^1$H NMR (400 MHz, DMSO-d$_6$) δ 8.23 (s, 1H), 8.16 (s, 1H), 5.90-5.87 (m, 1H), 3.89-3.71 (m, 2H), 2.41-2.28 (m, 1H), 2.07-1.90 (m, 2H), 1.78-1.65 (m, 1H), 1.62-1.52 (m, 2H), 1.38 (s, 12H); UPLC-MS-9: Rt=1.53 min; MS m/z [M+H]$^+$: 395.3/397.3/399.3.

Intermediate D4: 5-chloro-1-(tetrahydro-2H-pyran-2-yl)-4-(4,4,5,5-tetramethyl-1,3,2-dioxaborolan-2-yl)-1H-indazole

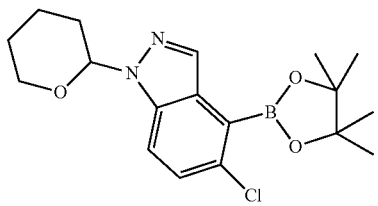 [SMILES: CC1(C)OB(c2c(Cl)ccc3c2cnn3C2CCCCO2)OC1(C)C]

Step 1: 4-bromo-5-chloro-1-(tetrahydro-2H-pyran-2-yl)-1H-indazole

To a solution of 4-bromo-5-chloro-1H-indazole (250 g, 1.08 mol, 1.00 eq) in DCM (2.50 L) were added p-TSA (9.30 g, 54.0 mmol, 0.05 eq) followed by DHP (273 g, 3.24 mol, 296 mL, 3.00 eq). The resulting reaction mixture was stirred at 25° C. for 1 h. The mixture was poured into a sat. aq. NaHCO$_3$ solution (1 L), washed with brine and dried (Na$_2$SO$_4$), filtered and concentrated in vacuum. The crude product was triturated in Petroleum ether (500 mL) and collected by filtration to give the title product. UPLC-MS-1: Rt=1.28 min; MS m/z [M+H]⁺; 315/317/319.

Step 2: 5-chloro-1-(tetrahydro-2H-pyran-2-yl)-4-(4,4,5,5-tetramethyl-1,3,2-dioxaborolan-2-yl)-1H-indazole A solution of 4-bromo-5-chloro-1-(tetrahydro-2H-pyran-2-yl)-1H-indazole (step 1) (320 g, 1.01 mol, 1.00 eq), $B_2Pin_2$ (283 g, 1.12 mol, 1.10 eq) and KOAc (299 g, 3.04 mol, 3.00 eq) in dioxane (1.39 L) was degassed with N2. Then Pd(dppf)Cl$_2$.CH$_2$Cl$_2$ (24.8 g, 30.4 mmol, 0.03 eq) was added and the reaction mixture was stirred at 110° C. for 18 h. The mixture was filtered, the cake was washed with EtOAc (10 L) and the filtrate was concentrated in vacuum. The crude product was purified by normal phase chromatography (eluent: EtOAc in petroleum ether from 0 to 50%) to give the title compound. UPLC-MS-1: Rt=1.35 min; MS m/z [M+H]⁺: 363/365.

Intermediate D5: 5-methyl-4-(4,4,5,5-tetramethyl-1,3,2-dioxaborolan-2-yl)-1-tosyl-1H-indazole

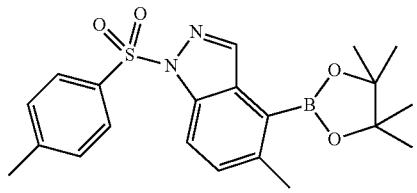

Step 1: 4-bromo-5-methyl-1-tosyl-1H-indazole

To an ice-cooled solution of 4-bromo-5-methyl-1H-indazole (5 g, 23.7 mmol) in THF (50 mL) under inert atmosphere was added NaH (1.90 g, 47.4 mmol), followed by toluene-4-sulfonyl chloride (4.97 g, 26.1 mmol) and the reaction mixture was stirred at RT for 1 h. The reaction mixture was quenched carefully at 0° C. with water and extracted with CH$_2$Cl$_2$. The organic phase was dried over Na$_2$SO$_4$, filtered and evaporated. The crude residue was triturated with Et$_2$O and the white precipitate was filtered, washed with cold Et$_2$O and dried under high vacuum to give the title compound as a white solid. UPLC-MS-1: Rt=1.34 min; MS m/z [M+H]⁺: 365/367.

Step 2: 5-methyl-4-(4,4,5,5-tetramethyl-1,3,2-dioxaborolan-2-yl)-1-tosyl-1H-indazole To a solution of 4-bromo-5-methyl-1-tosyl-1H-indazole (step 1) (7.94 g, 21.7 mmol) in 1,4-dioxane (80 mL) under inert atmosphere were added BISPIN (11.04 g, 43.5 mmol), PdCl$_2$(dppf).CH$_2$Cl$_2$ adduct (0.89 g, 1.09 mmol) and KOAc (6.40 g, 65.2 mmol). The reaction mixture was degassed then stirred at 100° C. for 16 h. The reaction mixture was quenched with water and extracted with CH$_2$Cl$_2$. The organic phase was washed with brine, then dried over Na$_2$SO$_4$, filtered and evaporated. The crude residue was triturated with Et$_2$O, the white precipitate was filtered, washed with cold Et$_2$O and dried under high vacuum. The crude product was purified by normal phase chromatography (eluent: EtOAc in c-hexane from 0 to 40%) to give the title compound. UPLC-MS-1: Rt=1.48 min; MS m/z [M+H]⁺: 413.

Intermediate D6: Tert-butyl 3-amino-5-chloro-6-methyl-4-(4,4,5,5-tetramethyl-1,3,2-dioxaborolan-2-yl)-1H-indazole-1-carboxylate

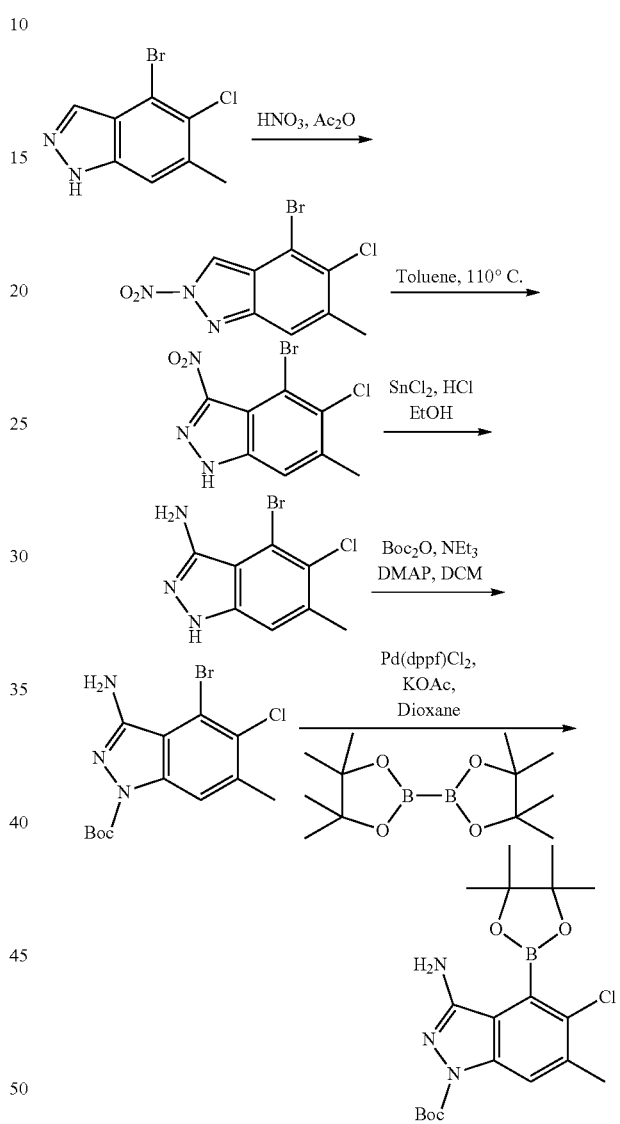

Step 1: 4-Bromo-5-chloro-6-methyl-2-nitro-2H-indazole

To a solution of fuming nitric acid (3.64 mL, 81 mmol) in acetic anhydride (100 mL) was added at 0° C. 4-bromo-5-chloro-6-methyl-1H-indazole (Intermediate D1. step 5, 5 g, 20.4 mmol) and the reaction mixture was stirred at 0° C. for 30 min. The reaction mixture was poured into a mix of ice/water and the precipitate was filtered off, washed with water and dried under reduced pressure to give the title compound. ¹H NMR (400 MHz, DMSO-d$_6$) δ 9.35 (s, 1H), 7.78 (s, 1H); UPLC-MS-5: Rt=1.36 min; MS m/z [M−H]⁻: 288.0/290.0.

Step 2:
4-Bromo-5-chloro-6-methyl-3-nitro-1H-indazole

A solution of 4-bromo-5-chloro-6-methyl-2-nitro-2H-indazole (Step 1, 5.55 g, 17.4 mmol) in toluene (100 mL) was warmed to 120° C. and stirred for 1 h. The reaction mixture was cooled to RT and the solid was filtered off, washed with toluene and dried under reduced pressure to give the title compound. $^1$H NMR (400 MHz, DMSO-$d_6$) δ 14.58 (br s, 1H), 7.79 (s, 1H), 2.57 (s, 3H); UPLC-MS-5: Rt=1.13 min; MS m/z [M−H]$^-$: 288.0/290.0.

Step 3:
4-Bromo-5-chloro-6-methyl-1H-indazol-3-amine

To a suspension of 4-bromo-5-chloro-6-methyl-3-nitro-1H-indazole (Step 2, 4.19 g, 14.3 mmol) in EtOH (160 mL) and hydrochloric acid (10.55N, 27.1 mL, 286 mmol) was added tin(II) chloride (13.5 g, 71.4 mmol) and the reaction mixture was stirred at RT for 2 h. The reaction mixture was concentrated under reduced pressure, the white residue was diluted with DCM (150 mL) and water (200 mL), cooled to 0° C. and basified with solid NaOH until pH 9. Clowdy mixture was extracted with DCM (3×500 mL), the organic phase dried (phase separator) and concentrated under reduced pressure to give the title compound as a light pink cotton. $^1$H NMR (400 MHz, DMSO-$d_6$) δ 11.86 (s, 1H), 7.26 (s, 1H), 5.19 (s, 2H), 2.44 (s, 3H); UPLC-MS-5: Rt=0.88 min; MS m/z [M+H]$^+$: 260.1/262.0.

Step 4: Tert-butyl 3-amino-4-bromo-5-chloro-6-methyl-1H-indazole-1-carboxylate To a suspension of 4-bromo-5-chloro-6-methyl-1H-indazol-3-amine (Step 3, 3.25 g, 12.5 mmol), triethylamine (3.48 mL, 24.95 mmol) and DMAP (0.38 g, 3.12 mmol) in DCM (70 mL) was added Boc-anhydride (3.13 g, 14.35 mmol) and the reaction mixture was stirred at RT for 2.33 and a precipitate formed. The reaction mixture was filtered to give tert-butyl 3-amino-4-bromo-5-chloro-6-methyl-1H-indazole-1-carboxylate as the major product: $^1$H NMR (400 MHz, DMSO-$d_6$) δ 8.03 (s, 1H), 6.10 (s, 2H), 2.52 (s, 3H), 1.59 (s, 9H); UPLC-MS-5: Rt=1.30 min; MS m/z [M+H]$^+$: 360.0/362.0. The filtrate was concentrated under reduced pressure, the residue dissolved in EtOAc, washed with sat. aq. NaHCO$_3$ and brine, the organic phase dried with a phase separator and concentrated under reduced pressure. The crude residue was purified by normal phase chromatography (eluent: c-hexane/EtOAc 100/0 to 70/30 within 30 min) to give tert-butyl 3-amino-4-bromo-5-chloro-6-methyl-2H-indazole-2-carboxylate: $^1$H NMR (400 MHz, DMSO-$d_6$) δ 7.21 (s, 1H), 7.03 (s, 2H), 2.36 (s, 3H), 1.60 (s, 9H); UPLC-MS-5: Rt=1.31 min; MS m/z [M+H]$^+$: 360.1/362.1.

Step 5: Tert-butyl 3-amino-5-chloro-6-methyl-4-(4,4,5,5-tetramethyl-1,3,2-dioxaborolan-2-yl)-1H-indazole-1-carboxylate In a sealed tube, a solution of tert-butyl 3-amino-4-bromo-5-chloro-6-methyl-1H-indazole-1-carboxylate (Step 4, 1.00 g, 2.77 mmol), bis-(pinacolato)-diboron (2.82 g, 11.1 mmol), PdCl$_2$(dppf) (0.20 g, 0.28 mmol) and potassium acetate (0.68 g, 6.93 mmol) in 1,4-dioxane (24 mL) was stirred at 80° C. for 16 h. More bis-(pinacolato)-diboron (2.82 g, 11.1 mmol) and PdCl$_2$(dppf) (0.20 g, 0.28 mmol) was added and the reaction mixture was stirred for additional 13.5 h. The reaction mixture was filtered, the filtrate concentrated under reduced pressure and the crude residue purified by normal phase chromatography (eluent: c-hexane/EtOAc 100/0 to 40/60 within 30 min) to give the title compound. 1H NMR (400 MHz, DMSO-$d_6$) δ 7.92 (s, 2H), 6.35 (s, 1H), 2.45 (s, 3H), 1.59 (s, 9H), 1.40 (s, 12H); UPLC-MS-5: Rt=1.43 min; MS m/z [M+H]$^+$: 408.3/410.3.

Biological Assays and Biological Data

The activity of a compound according to the present invention can be assessed by the following in vitro methods.

Purification of Human KRasG12C 1-169, Biotinylated on the N-Terminus

Human KRASG12C (UniProtKB: P01116) amino acids M1-K169 were expressed from plasmid pCZ239 (SEQ ID NO: 1) in E. coli BL21 (DE3) in the presence of a plasmid encoding biotin-[acetyl-CoA-carboxylase] ligase BirA (NCBI Reference Sequence: NP_418404.1, aa 1-321, full length) in Luria-Bertani (LB) medium-supplemented with 25 µg/ml kanamycin, 34 µg/ml chloramphenicol, 135 µM biotin and 1 mM isopropyl (3-D-1-thiogalactopyranoside overnight at 18° C. Cells were harvested by centrifugation and frozen at −80° C. until further processing. Cells were thawed and resuspended in Buffer A (20 mM Tris-HCl pH8, 500 mM NaCl, 5 mM imidazole, 2 mM TCEP, 10% glycerol) supplemented with 1 tablet protease inhibitor/50 ml buffer (Complete EDTA free, Roche) and 15 µl Turbonuclease (90% purity, 50KUN, ≥200,000 units/mL, Sigma) and incubated for 20 min at 4° C. The cells were lysed by 4 passages through an Avestin Emulsiflex at about 20000 psi and insoluble debris removed by centrifugation and filtered through a 0.45 µm Durapore membrane (Millipore). Immobilized metal affinity chromatography was performed with a HisTrap HP 5 mL column (GE) with Buffer A and eluted with a linear gradient over 10 column volumes of Buffer A substituted with 200 mM imidazole. Eluted protein fractions were analyzed by Novex NuPage 4-12% PAGE. The affinity tag was removed by HRV3C protease cleavage (HRV3C protease produced in-house but also available commercially) during dialysis against Buffer A for 18 h at 4° C. and capturing by a reverse IMAC purification on a HisTrap HP 5 mL column. The protein in the flow through was subjected to a final polishing step on a HiLoad 16/60 Superdex 200 prep grade size-exclusion column pre-equilibrated with SEC-buffer (20 mM HEPES pH 7.4, 150 mM NaCl, 5 mM MgCl$_2$, 1 µM GDP). Positive fractions were determined by PAGE (Novex NuPage 4-12% BisTris) analysis. The correct mass was determined by RP (Reverse Phase) LC-MS, and indicated complete biotinylation of the protein.

DNA sequence of plasmid pCZ239, coding sequence underlined

SEQ ID No: 1

ATGCGTCCGGCGTAGAGGATCGAGATCGATCTCGATCCCGCGAAATTAATA

CGACTCACTATAGGGGAATTGTGAGCGGATAACAATTCCCCTCTAGAAATA

ATTTTGTTTAACTTTAAGAAGGAGATATACAT<u>ATGAAAACACATCATCATC</u>

<u>ATCATCATGGTGGCGGCAGTGGCGGTGGCTCAGGCGGTGGTTCTCTCGAGG</u>

<u>TTCTGTTCCAGGGTCCGGGTTTGAACGACATCTTCGAAGCTCAGAAGATCG</u>

<u>AATGGCACGAGGGTGGCGGTAGTGGTGGTGGCTCTATGACTGAATACAAGC</u>

<u>TGGTTGTTGTTGGTGCTTGTGGCGTTGGTAAGAGCGCACTGACCATCCAGC</u>

<u>TCATTCAGAATCACTTCGTGGACGAGTACGACCCGACCATCGAAGATTCTT</u>

<u>ACCGTAAACAGGTGGTTATTGATGGCGAAACCTGTCTGCTGGATATTCTGG</u>

-continued

<u>ACACTGCTGGTCAGGAAGAGTACTCCGCTATGCGTGATCAGTACATGCGTA</u>
<u>CTGGTGAAGGTTTCCTCTGCGTGTTCGCTATCAACAACACCAAGTCCTTCG</u>
<u>AAGATATCCACCATTACCGTGAACAGATCAAACGTGTGAAGGACAGCGAAG</u>
<u>ACGTGCCAATGGTTCTGGTGGGCAACAAATGTGATCTCCCGAGCCGTACCG</u>
<u>TTGACACCAAACAGGCACAAGACCTGGCACGTTCCTACGGCATCCCATTCA</u>
<u>TTGAAACTAGCGCGAAGACTCGTCAGGGTGTGGACGACGCATTCTACACTC</u>
<u>TGGTGCGTGAAATTCGCAAGCACAAAGAGAAATAATGGTACCGAATTCGCG</u>
GCCGCCTGCAGCCTAGGCTGCTAAACAAAGCCCGAAAGGAAGCTGAGTTGG
CTGCTGCCACCGCTGAGCAATAACTAGCATAACCCCTTGGGGCCTCTAAAC
GGGTCTTGAGGGGTTTTTGCTGAAAGGAGGAACTATATCCGGATTGGCGA
ATGGGACGCGCCCTGTAGCGGCGCATTAAGTGCAGCGTCAAAAGGGCGACA
CAAAATTTATTCTAAATGCATAATAAATACTGATAACATCTTATAGTTTGT
ATTATATTTTGTATTATCGTTGACATGTATAATTTTGATATCAAAAACTGA
TTTTCCCTTTATTATTTTCGAGATTTATTTTCTTAATTCTCTTTAACAAAC
TAGAAATATTGTATATACAAAAAATCATAAATAATAGATGAATAGTTTAAT
TATAGGTGTTCATCAATCGAAAAGCAACGTATCTTATTTAAAGTGCGTTG
CTTTTTTCTCATTTATAAGGTTAAATAATTCTCATATATCAAGCAAAGTGA
CAGGCGCCCTTAAATATTCTGACAAATGCTCTTTCCCTAAACTCCCCCCAT
AAAAAAACCCGCCGAAGCGGGTTTTTACGTTATTTGCGGATTAACGATTAC
TCGTTATCAGAACCGCCCAGGGGGCCCGAGCTTAAGACTGGCCGTCGTTTT
ACAACACAGAAAGAGTTTGTAGAAACGCAAAAAGGCCATCCGTCAGGGGCC
TTCTGCTTAGTTTGATGCCTGGCAGTTCCCTACTCTCGCCTTCCGCTTCCT
CGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGC
CACTGGCAGCAGCCACTGGTAACAGGATTAGCAGAGCGAGGTATGTAGGCG
GTGCTACAGAGTTCTTGAAGTGGTGGGCTAACTACGGCTACACTAGAAGAA
CAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTT
TTGTTTGCAAGCAGCAGATTACGCGCAGAAAAAAGGATCTCAAGAAGATC
CTTTGATCTTTTCTACGGGGTCTGACGCTCAGTGGAACGACGCGCGTAA
CTCACGTTAAGGGATTTTGGTCATGAGCTTGCGCCGTCCCGTCAAGTCAGC
GTAATGCTCTGCTTTTAGAAAAACTCATCGAGCATCAAATGAAACTGCAAT
TTATTCATATCAGGATTATCAATACCATATTTTTGAAAAAGCCGTTTCTGT

-continued

AATGAAGGAGAAAACTCACCGAGGCAGTTCCATAGGATGGCAAGATCCTGG
TATCGGTCTGCGATTCCGACTCGTCCAACATCAATACAACCTATTAATTTC
CCCTCGTCAAAAATAAGGTTATCAAGTGAGAAATCACCATGAGTGACGACT
GAATCCGGTGAGAATGGCAAAAGTTTATGCATTTCTTTCCAGACTTGTTCA
ACAGGCCAGCCATTACGCTCGTCATCAAAATCACTCGCATCAACCAAACCG
TTATTCATTCGTGATTGCGCCTGAGCGAGGCGAAATACGCGATCGCTGTTA
AAAGGACAATTACAAACAGGAATCGAGTGCAACCGGCGCAGGAACACTGCC
AGCGCATCAACAATATTTTCACCTGAATCAGGATATTCTTCTAATACCTGG
AACGCTGTTTTTCCGGGGATCGCAGTGGTGAGTAACCATGCATCATCAGGA
GTACGGATAAAATGCTTGATGGTCGGAAGTGGCATAAATTCCGTCAGCCAG
TTTAGTCTGACCATCTCATCTGTAACATCATTGGCAACGCTACCTTTGCCA
TGTTTCAGAAACAACTCTGGCGCATCGGGCTTCCCATACAAGCGATAGATT
GTCGCACCTGATTGCCCGACATTATCGCGAGCCCATTTATACCCATATAAA
TCAGCATCCATGTTGGAATTTAATCGCGGCCTCGACGTTTCCCGTTGAATA
TGGCTCATATTCTTCCTTTTTCAATATTATTGAAGCATTTATCAGGGTTAT
TGTCTCATGAGCGGATACATATTTGAATGTATTTAGAAAAATAAACAAATA
GGGGTCAGTGTTACAACCAATTAACCAATTCTGAACATTATCGCGAGCCCA
TTTATACCTGAATATGGCTCATAACACCCCTTGTTTGCCTGGCGGCAGTAG
CGCGGTGGTCCCACCTGACCCCATGCCGAACTCAGAAGTGAAACGCCGTAG
CGCCGATGGTAGTGTGGGGACTCCCCATGCGAGAGTAGGGAACTGCCAGGC
ATCAAATAAAACGAAAGGCTCAGTCGAAAGACTGGGCCTTTCGCCCGGGCT
AATTAGGGGGTGTCGCCCTTCGCTGAAGAATTGATCCCGGTGCCTAATGAG
TGAGCTAACTTACATTAATTGCGTTGCGCTCACTGCCCGCTTTCCAGTCGG
GAAACCTGTCGTGCCAGCTGCATTAATGAATCGGCCAACGCGCGGGGAGAG
GCGGTTTGCGTATTGGGCGCCAGGGTGGTTTTTCTTTTCACCAGTGACACG
GGCAACAGCTGATTGCCCTTCACCGCCTGGCCCTGAGAGAGTTGCAGCAAG
CGGTCCACGCTGGTTTGCCCCAGCAGGCGAAAATCCTGTTTGATGGTGGTT
AACGGCGGGATATAACATGAGCTGTCTTCGGTATCGTCGTATCCCACTACC
GAGATGTCCGCACCAACGCGCAGCCCGGACTCGGTAATGGCGCGCATTGCG
CCCAGCGCCATCTGATCGTTGGCAACCAGCATCGCAGTGGGAACGATGCCC
TCATTCAGCATTTGCATGGTTTGTTGAAAACCGGACATGGCACTCCAGTCG
CCTTCCCGTTCCGCTATCGGCTGAATTTGATTGCGAGTGAGATATTTATGC
CAGCCAGCCAGACGCAGACGCGCCGAGACAGAACTTAATGGGCCCGCTAAC
AGCGCGATTTGCTGGTGACCCAATGCGACCAGATGCTCCACGCCCAGTCGC
GTACCGTCTTCATGGGAGAAAATAATACTGTTGATGGGTGTCTGGTCAGAG
ACATCAAGAAATAACGCCGGAACATTAGTGCAGGCAGCTTCCACAGCAATG
GCATCCTGGTCATCCAGCGGATAGTTAATGATCAGCCCACTGACGCGTTGC
GCGAGAAGATTGTGCACCGCCGCTTTACAGGCTTCGACGCCGCTTCGTTCT
ACCATCGACACCACCACGCTGGCACCCAGTTGATCGGCGCGAGATTTAATC
GCCGCGACAATTTGCGACGGCGCGTGCAGGGCCAGACTGGAGGTGGCAACG

```
CCAATCAGCAACGACTGTTTGCCCGCCAGTTGTTGTGCCACGCGGTTGGGA

ATGTAATTCAGCTCCGCCATCGCCGCTTCCACTTTTTCCCGCGTTTTCGCA

GAAACGTGGCTGGCCTGGTTCACCACGCGGGAAACGGTCTGATAAGAGACA

CCGGCATACTCTGCGACATCGTATAACGTTACTGGTTTCACATTCACCACC

CTGAATTGACTCTCTTCCGGGCGCTATCATGCCATACCGCGAAAGGTTTTG

CGCCATTCGATGGTGTCCGGGATCTCGACGCTCTCCCTTATGCGACTCCTG

CATTAGGAAGCAGCCCAGTAGTAGGTTGAGGCCGTTGAGCACCGCCGCCGC

AAGGAATGGTGCATGCAAGGAGATGGCGCCCAACAGTCCCCGGCCACGGG

GCCTGCCACCATACCCACGCCGAAACAAGCGCTCATGAGCCCGAAGTGGCG

AGCCCGATCTTCCCCATCGGTGATGTCGGCGATATAGGCGCCAGCAACCGC

ACCTGTGGCGCCGGTGATGCCGGCCACG
```

Preparation of: N-(3-fluoro-4-(2-methyl-3-(5-methyl-1H-indazol-4-yl)-1H-pyrrolo[2,3-b]pyridin-1-yl)phenyl)acrylamide (Compound A)

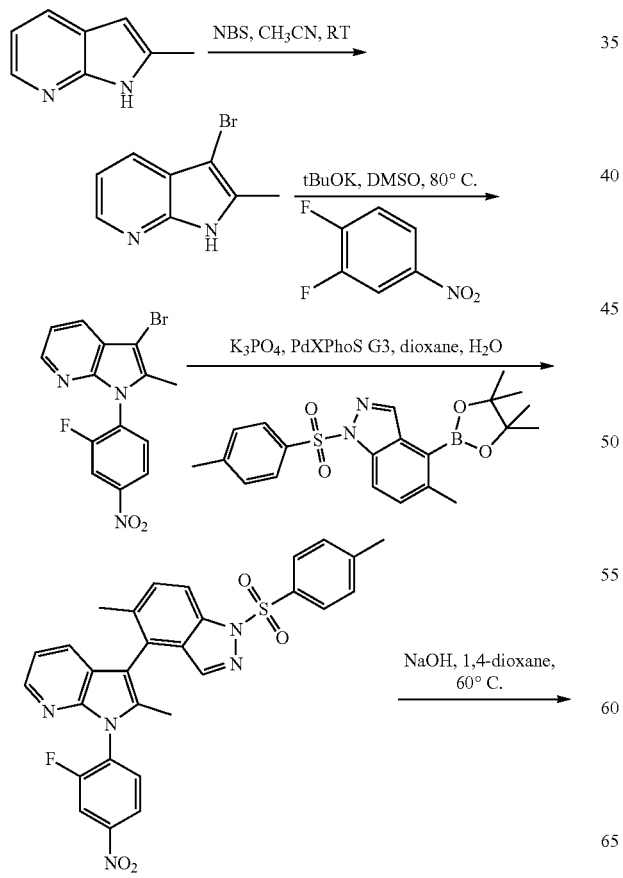

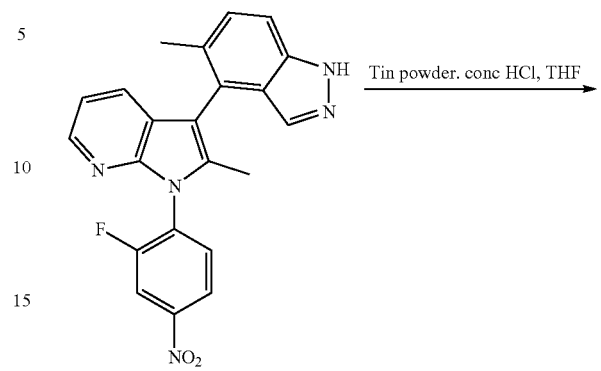

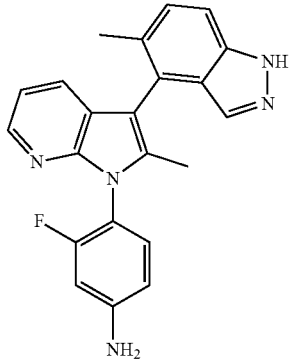

: second eluting peak

-continued

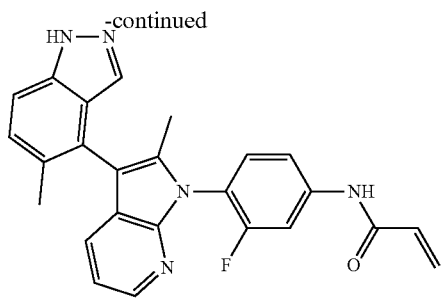

Step 1: 3-bromo-2-methyl-1H-pyrrolo[2,3-b]pyridine

To a solution of 2-methyl-1H-pyrrolo[2,3-b]pyridine (1.63 g, 12.3 mmol) in acetonitrile (50 mL) was added NBS (2.19 g, 12.33 mmol) at RT. The reaction mixture was stirred at RT for 1 h. The reaction was quenched by addition of a 10% solution of sodium thiosulfate (10 mL). The solution was then extracted with EtOAc (20 mL). The organic phase was washed with water (3×), brine, then dried (MgSO$_4$), filtered and evaporated. UPLC-MS-1: Rt=0.88 min; MS m/z [M+H]$^+$; 211/213.

Step 2: 3-bromo-1-(2-fluoro-4-nitrophenyl)-2-methyl-1H-pyrrolo[2,3-b]pyridine To a solution of 3-bromo-2-methyl-1H-pyrrolo[2,3-b]pyridine (Step 1, 2.4 g, 11.37 mmol) in dry DMSO (20 mL) was added under inert atmosphere potassium tert-butoxide (1.40 g, 12.5 mmol) and 1,2-difluoro-4-nitrobenzene (1.81 g, 11.4 mmol). The reaction mixture was stirred at 80° C. for 2 h. The reaction was quenched by addition of water. The solution was then extracted with EtOAc (3×). The organic phase was washed with brine, then dried (MgSO$_4$), filtered and evaporated. The crude product was purified by normal phase chromatography (eluent: EtOAc in Heptane 0 to 30%) to give the title compound. UPLC-MS-1: Rt=1.24 min; MS m/z [M+H]$^+$; 350.0/352.1.

Step 3: 4-(1-(2-fluoro-4-nitrophenyl)-2-methyl-1H-pyrrolo[2,3-b]pyridin-3-yl)-5-methyl-1-tosyl-1H-indazole To a solution of 3-bromo-1-(2-fluoro-4-nitrophenyl)-2-methyl-1H-pyrrolo[2,3-b]pyridine (Step 2, 1.00 g, 2.86 mmol) in 1,4-Dioxane (10 mL)/water (2.8 mL) was added under inert atmosphere 5-methyl-4-(4,4,5,5-tetramethyl-1,3,2-dioxaborolan-2-yl)-1-tosyl-1H-indazole (Intermediate D5) (1.41 g, 3.43 mmol) followed by K$_3$PO$_4$ (1.21 g, 5.71 mmol) and then Pd-XPhos-G3 (0.24 g, 0.29 mmol). The reaction mixture was stirred 3 h at 80° C. The reaction was quenched by addition of saturated solution of NaHCO$_3$. The solution was then extracted with EtOAc. The organic phase was washed with brine, then dried (MgSO$_4$) and evaporated. The crude product was purified by normal phase chromatography (eluent: EtOAc in n-heptane 0 to 50%) to give the title compound. UPLC-MS-1: Rt=1.38 min; MS m/z [M+H]$^+$; 556.2.

Step 4: 4-(1-(2-fluoro-4-nitrophenyl)-2-methyl-1H-pyrrolo[2,3-b]pyridin-3-yl)-5-methyl-1H-indazole To a stirred solution of 4-(1-(2-fluoro-4-nitrophenyl)-2-methyl-1H-pyrrolo[2,3-b]pyridin-3-yl)-5-methyl-1-tosyl-1H-indazole (Step 3, 1.34 g, 2.41 mmol) in 1,4-Dioxane (12 mL) was added NaOH (6.03 mL, 12.1 mmol) at RT. The mixture was stirred at 60° C. for 3 h. The reaction was quenched by addition of water. The solution was then extracted with EtOAc. The organic phase was washed with brine, then dried over MgSO$_4$, filtered and evaporated. The crude product was purified by normal phase chromatography (eluent: EtOAc in Heptane 0 to 100%) to give the title compound. UPLC-MS-1: Rt=1.11 min; MS m/z [M+H]$^+$; 402.2.

Step 5: 3-fluoro-4-(2-methyl-3-(5-methyl-1H-indazol-4-yl)-1H-pyrrolo[2,3-b]pyridin-1-yl)aniline To a solution of 4-(1-(2-fluoro-4-nitrophenyl)-2-methyl-1H-pyrrolo[2,3-b]pyridin-3-yl)-5-methyl-1H-indazole (Step 4, 780 mg, 1.94 mmol) in THF (10 mL) were added Tin powder (807 mg, 6.80 mmol) and HCl conc (0.59 mL, 19.43 mmol). The solution was stirred at 70° C. for 4 h. The reaction was quenched by addition of sodium hydroxide and water. The solution was then extracted with EtOAc. The organic phase was washed with brine, then dried over MgSO$_4$, filtered and evaporated to give the title compound. UPLC-MS-1: Rt=0.93 min; MS m/z [M+H]$^+$; 372.4.

Step 6: 3-fluoro-4-(2-methyl-3-(5-methyl-1H-indazol-4-yl)-1H-pyrrolo[2,3-b]pyridin-1-yl)aniline 3-fluoro-4-(2-methyl-3-(5-methyl-1H-indazol-4-yl)-1H-pyrrolo[2,3-b]pyridin-1-yl)aniline as mixture of isomers (454 mg) in IPA (30 mg/mL) were separated by chiral SFC (column: Lux IC 5 μm; 250×21.2 mm; mobile phase: CO$_2$/IPA 55/45; flow rate: 50 mL/min; column temperature: 40° C.; back pressure: 105 bars) to give 3-fluoro-4-(2-methyl-3-(5-methyl-1H-indazol-4-yl)-1H-pyrrolo[2,3-b]pyridin-1-yl)aniline as first eluting isomer (analytical chiral SFC; column: Chiralpak AD-H 5 μm; 250×4.6 mm; mobile phase: CO$_2$/[IPA+1% isopropylamine]: 50/50; flow rate: 3 mL/min; column temperature: 40° C.; back pressure: 120 bars): Rt=2.99 min and 3-fluoro-4-(2-methyl-3-(5-methyl-1H-indazol-4-yl)-1H-pyrrolo[2,3-b]pyridin-1-yl)aniline as the second eluting isomer (analytical chiral SFC; column: Chiralpak AD-H 5 μm; 250×4.6 mm; mobile phase: CO$_2$/[IPA+1% isopropylamine]: 50/50; flow rate: 3 mL/min; column temperature: 40° C.; back pressure: 120 bars): Rt=5.79 min. UPLC-MS-1: Rt=0.92 min; MS m/z [M+H]$^+$; 372.2.

Step 7: N-(3-fluoro-4-(2-methyl-3-(5-methyl-1H-indazol-4-yl)-1H-pyrrolo[2,3-b]pyridin-1-yl)phenyl)acrylamide To a solution of 3-fluoro-4-(2-methyl-3-(5-methyl-1H-indazol-4-yl)-1H-pyrrolo[2,3-b]pyridin-1-yl)aniline (Step 6, second eluting peak, 19 mg, 0.05 mmol) in CH$_2$Cl$_2$ (1.5 mL) were added DIPEA (0.03 mL, 0.15 mmol) and acryloyl chloride (4.57 μl, 0.06 mmol) at 0° C. The reaction mixture was stirred at 0° C. for 4 h. MeOH was added to the mixture and evaporated to dryness. The reaction was quenched by addition of saturated solution of NaHCO$_3$. The solution was then extracted with CH$_2$Cl$_2$. The organic phase was washed with brine, then dried over MgSO$_4$, filtered and evaporated. The crude product was purified by normal phase chromatography (eluent: EtOAc in n-heptane 0 to 100%) to give the title compound. $^1$H NMR (600 MHz, DMSO-d$_6$) δ 13.12-13.03 (m, 1H), 10.63 (s, 1H), 8.21-8.16 (m, 1H), 8.03-7.96 (m, 1H), 7.79-7.45 (m, 5H), 7.43-7.37 (m, 1H), 7.18-7.10

(m, 1H), 6.54-6.45 (m, 1H), 6.40-6.32 (m, 1H), 5.90-5.83 (m, 1H), 2.29-2.22 (m, 3H), 2.09 (s, 3H); UPLC-MS-1: Rt=0.98 min; MS m/z [M+H]⁺; 426.4.

Preparation of [acrylamide-2.3-³H₂]—N-(3-fluoro-4-(2-methyl-3-(5-methyl-1H-indazol-4-yl)-1H-pyrrolo[2,3-b]pyridin-1-yl)phenyl)acrylamide (Compound B)

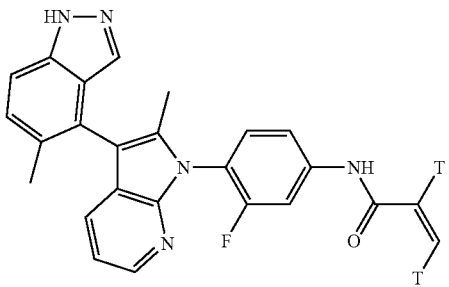

Step 1: N-(3-fluoro-4-(2-methyl-3-(5-methyl-1H-indazol-4-yl)-1H-pyrrolo[2,3-b]pyridin-1-yl)phenyl) propiolamide To an ice-cooled solution of 3-fluoro-4-(2-methyl-3-(5-methyl-1H-indazol-4-yl)-1H-pyrrolo[2,3-b]pyridin-1-yl) aniline (Compound A, step 6 second eluting peak) (50 mg, 0.14 mmol) in DMF (1.5 mL) was added a mixture of DIPEA (0.09 mL, 0.54 mmol), propiolic acid (9.43 mg, 0.14 mmol) and propylphosphonic anhydride (50% in DMF, 0.16 mL, 0.27 mmol). The reaction mixture was stirred at RT under nitrogen for 15 min. The reaction mixture was poured into a sat. aq. NaHCO₃ solution and extracted with EtOAc (×3). The combined organic layers were dried over MgSO₄, and concentrated. The crude product was purified by achiral SFC (column: Princeton PPU 5 μm; 250×30 mm; mobile phase: CO₂/MeOH: gradient with 24-29% MeOH in CO₂ over 9.8 minutes; flow rate: 30 mL/min; column temperature: 36° C.; back pressure: 120 bars) and re-purified by achiral SFC (column: Princeton PPU 5 μm; 250×30 mm; mobile phase: CO₂/MeOH: gradient with 20-26% MeOH in CO₂ over 9.8 minutes; flow rate: 30 mL/min; column temperature: 36° C.; back pressure: 120 bars) to give the title compound. UPLC-MS-1: Rt=0.97 min; MS m/z [M+H]⁺; 424.4.

Step 2: [acrylamide-2,3-³H₂]—N-(3-fluoro-4-(2-methyl-3-(5-methyl-1H-indazol-4-yl)-1H-pyrrolo[2,3-b]pyridin-1-yl)phenyl)acrylamide N-(3-fluoro-4-(2-methyl-3-(5-methyl-1H-indazol-4-yl)-1H-pyrrolo[2,3-b]pyridin-1-yl)phenyl)propiolamide (step 1) (3.20 mg, 7.56 μmol), Lindlar catalyst (6.57 mg), quinoline (11.8 μL, 12.90 mg, 99.6 μmol) were suspended in DMF (0.60 mL). The suspension was degassed three times at the high vacuum manifold and stirred under an atmosphere of tritium gas (355 GBq, 508 mbar initial pressure) for 80 mins at room temperature (end pressure was 505 mbar, no more tritium gas consumption was observed). The solvent was removed in vacuo, and labile tritium was exchanged by adding methanol (0.70 mL), stirring the solution, and removing the solvent again under vacuo. This process was repeated two times. Finally, the well dried solid was extracted with 5 mL of ethanol and the suspension was filtered through a 0.2 μm nylon membrane obtaining a clear and colourless solution. The radiochemical purity was determined to 86% by HPLC (Waters Sunfire HPLC with UV detector; column: C18 5 μm; 250×4.6 mm; mobile phase: A: water/B: acetonitrile, 0 min 10% B, 10 min 95% B, 14.5 min 95% B, 15 min 10% B; flow rate: 1 mL/min; column temperature: 30° C.). Purification of the crude product was carried out by reverse phase HPLC (Waters Sunfire; column: C18 5 μm; 250×10 mm; detection UV 254 nM; mobile phase: A: water/B: MeOH, isocratic 62% B; flow rate: 4.7 mL/min; column temperature: 25° C.). The target compound eluted at 19.1 min. The combined HPLC fractions were partially reduced at the rotary evaporator at 40° C. Then, the product was extracted with a Phenomenex StrataX cartridge (33 μm Polymeric Reversed Phase, 100 mg, 3 mL; 8B-S100-EB) which was eluted with 5 mL of ethanol. The extracted product contained the title compound with an activity of 2.61 GBq and a radiochemical purity of >99%. The molar activity was determined to be 2.12 TBq/mmol.

In Vitro Biochemical Quantification of Covalent Modification of KRASG12C

A scintillation proximity assay (SPA) was used to determine the potency of the compounds. This assay measures the ability of the test compound to compete with the radiolabeled covalent probe for binding to and covalently modify KRASG12C.

The signal to be measured is generated by binding of an isotopic dilution of the covalent radio-ligand [[acrylamide-2,3-³H₂]—N-(3-fluoro-4-(2-methyl-3-(5-methyl-1H-indazol-4-yl)-1H-pyrrolo[2,3-b]pyridin-1-yl)phenyl)acrylamide (Compound B) (2.12 TBq/mmol) and its non-labeled analog [N-(3-fluoro-4-(2-methyl-3-(5-methyl-1H-indazol-4-yl)-1H-pyrrolo[2,3-b]pyridin-1-yl)phenyl)acrylamide (Compound A) to KRasG12C (M1-K169, biotinylated on the N-terminus) which is bound to SPA beads via biotin-streptavidin coupling, (see below for synthesis of Compound A and Compound B). A serial dilution of the compounds to be tested is mixed with a fixed concentration of the radiolabeled covalent probe before incubation with KRASG12C:GDP as described below. KRASG12C can either be bound by the radiolabeled covalent probe (Compound B), resulting in light being emitted from the beads, or bound by covalent test compound preventing signal generation.

Assays were run using 384-well plates (781207/Greiner) in which one column was designated as the high signal (no inhibition) control, and contained DMSO with no test compound, and another column was designated as the low signal control (maximal inhibition), and contained no protein. Serial dilutions of compounds to be tested were added to the assay plate (resulting in duplicate 11-point dose response with semi-log compound dilutions from 50 μM to 0.5 nM or from 5 μM to 0.05 nM for the most potent compounds). A 1/20 isotopic dilution of labeled (Compound B) and non-labeled covalent (Compound A) probe was prepared and added to all wells on the plate. The reaction was started by addition of KRasG12C (M1-K169, biotinylated on the N-terminus) to the compounds and incubated for 2 hours with continuous agitation allowing for full modification of KRasG12C with probe or test compounds. Final concentrations in an assay volume of 40 μL were 10 nM KRASG12C, 25 nM radio-ligand and 475 nM unlabelled ligand. The assay buffer contained 20 mM Tris-HCl pH 7.5 (Invitrogen), 150 mM NaCl (Sigma Aldrich), 0.1 mM MgCl₂ (Sigma Aldrich), and 0.01% Tween-20 (Sigma Aldrich). Following addition of 50 μL of a 400 μg/ml. suspension of streptavidin-coated YSi beads (Perkin Elmer), plates were incubated for a further 30 min with continuous agitation before reading the plates on a scintillation counter (Topcount NXT 384 (Packard).

Evaluation was carried out using assay data analysis software (such as the standard Novartis in-house Helios software application, Novartis Institutes for BioMedical Research, unpublished) using the methods described in Formenko et al., *Robust Regression for high-throughput screening. Computer Methods and Programs in Biomedicine,* 2006, 82, 31-37. Following normalization of activity values for the wells to % inhibition (% inhibition=[(high control−sample)/(high control−low control)]×100), $IC_{50}$ fitting was carried out from the duplicate determinations present on each plate according to Formenko et al., 2006.

Evaluation can also be carried out using commercially available software which is designed to derive $IC_{50}$ values using 4-parameter fits (e.g. GraphPad Prism, XL fit).

Titration of the non-labelled version of the probe, Compound A, in this assay resulted in an $IC_{50}$ of 0.5 µM. $IC_{50}$ values for examples 1 to 94 are tabulated in Table 2.

Note: Endpoint $IC_{50}$ values generated in this way could in principle be used to derive second order rate constants for the covalent binders in agreement with a method described by Miyahisa et al. 2015, *Rapid Determination of the Specificity Constant of Irreversible Inhibitors (kinact/KI) by Means of an Endpoint Competition Assay, Angew. Chem, Int, Ed. Engl,* 2015 Nov. 16; 54(47); 14099-14102).

Following this, rate constants can be derived applying the equation (kinact/KI)inhibitor=(kinact/KI)probe×[probe]/IC50 using 0.5 uM as [probe], "$(k_{inact}/K_I)$probe" the second order rate constant for modification of KRasG12C by this probe had was internally determined to ~5,000 M-1*s-1 for the non-labeled ligand [N-(3-fluoro-4-(2-methyl-3-(5-methyl-1H-indazol-4-yl)-1H-pyrrolo[2,3-b]pyridin-1-yl)phenyl)acrylamide (Compound A) using an MS-based assay (assessing % modification for a range of compound concentrations and time points).

TABLE 2

Tabulated in vitro KRASG12C activities

| Example | Covalent Competition Assay IC50 (µM) |
|---|---|
| 1a | 0.017 |
| 1b | 0.444 |
| 2a | 0.093 |
| 2b | >50 |
| 3a | 0.465 |
| 3b | 1.2 |
| 4a | 0.240 |
| 4b | 45.0 |
| 5a | 0.043 |
| 5b | 15.0 |
| 6a | 1.2 |
| 6b | >50 |
| 7a | 0.162 |
| 7b | >5 |
| 8a | 0.066 |
| 8b | 2.9 |
| 9a | 0.743 |
| 9b | >50 |
| 10a | 1.2 |
| 10b | >50 |
| 11a | 0.973 |
| 11b | >50 |
| 12a | 0.024 |
| 12b | 6.1 |
| 13a | 0.018 |
| 13b | 14.8 |
| 14 | 0.310 |

TABLE 2-continued

Tabulated in vitro KRASG12C activities

| Example | Covalent Competition Assay IC50 (µM) |
|---|---|
| 15a | 0.016 |
| 15b | 4.8 |
| 16a | 0.011 |
| 16b | 23.4 |
| 17a | 0.013 |
| 17b | 14.6 |
| 18a | 0.014 |
| 18b | >50 |
| 19a | 1.9 |
| 19b | >50 |
| 20a | 0.148 |
| 20b | 12.5 |
| 21a | 0.060 |
| 21b | 15.0 |
| 22a | 0.023 |
| 22b | >50 |
| 23a | 0.564 |
| 23b | 13.9 |
| 24a | 0.071 |
| 24b | >50 |
| 25a | 0.041 |
| 25b | 7.8 |
| 26a | 0.043 |
| 26b | 45.6 |
| 27a | 0.251 |
| 27b | 19.9 |
| 28a | 1.281 |
| 28b | >50 |
| 29a | 0.220 |
| 29b | 15.0 |
| 30a | 0.103 |
| 30b | >50 |
| 31a | 13.9 |
| 31b | 0.374 |
| 32a | 0.871 |
| 32b | >50 |
| 33a | 0.253 |
| 33b | >50 |
| 34a | 0.827 |
| 34b | >50 |
| 35a | 0.027 |
| 35b | 15.0 |
| 36a | 0.516 |
| 36b | >50 |
| 37a | 0.112 |
| 37b | >50 |
| 38a | 0.487 |
| 38b | >50 |
| 39a | 0.032 |
| 39b | >5 |
| 40a | 0.099 |
| 40b | >50 |
| 41a | 0.011 |
| 41b | 0.941 |
| 42a | 0.012 |
| 42b | 1.2 |
| 43a | 0.010 |
| 43b | 2.9 |
| 44a | 0.019 |
| 44b | >5 |
| 45a | 0.235 |
| 45b | >50 |
| 46a | 0.423 |
| 46b | >50 |
| 47a | 0.043 |
| 47b | 23.4 |
| 48 | 0.049 |
| 49a | 0.227 |
| 49b | 5.384 |
| 50a | 0.035 |
| 50b | 4.240 |
| 51a | 0.465 |
| 51b | 36.1 |
| 52a | 0.026 |
| 52b | 2.810 |

TABLE 2-continued

Tabulated in vitro KRASG12C activities

| Example | Covalent Competition Assay IC50 (μM) |
|---|---|
| 53 | 0.320 |
| 54a | 0.360 |
| 54b | >50 |
| 55a | 1.6 |
| 55b | >50 |
| 56a | 0.038 |
| 56b | >50 |
| 57a | 0.033 |
| 57b | 3.2 |
| 58a | 0.064 |
| 58b | >5 |
| 59a | 0.173 |
| 59b | >50 |
| 60a | 0.051 |
| 60b | >5 |
| 61a | 0.027 |
| 61b | >5 |
| 62a | 0.045 |
| 62b | 19.3 |
| 63a | 0.088 |
| 63b | 33.8 |
| 64a | 0.055 |
| 64b | 24.5 |
| 65a | 0.046 |
| 65b | 17.4 |
| 66a | 0.240 |
| 66b | 4.297 |
| 67a | 0.202 |
| 67b | 12.1 |
| 68a | 0.059 |
| 68b | 1.9 |
| 69a | 0.009 |
| 69b | 0.840 |
| 70a | 0.030 |
| 70b | 2.1 |
| 71a | 0.101 |
| 71b | >5 |
| 72a | 0.306 |
| 72b | 23.954 |
| 73a | 5.306 |
| 73b | >50 |
| 74a | 1.554 |
| 74b | >50 |
| 75a | 0.251 |
| 75b | >50 |
| 76a | 0.015 |
| 76b | 13.3 |

TABLE 2-continued

Tabulated in vitro KRASG12C activities

| Example | Covalent Competition Assay IC50 (μM) |
|---|---|
| 77 | 0.195 |
| 78a | 0.216 |
| 79a | 0.092 |
| 80a | 1.3 |
| 80b | 0.008 |
| 81a | 0.110 |
| 81b | 2.6 |
| 82a | 0.012 |
| 82b | 0.712 |
| 83a | 0.018 |
| 83b | 4.0 |
| 84a | 0.536 |
| 84b | >50 |
| 85a | 0.335 |
| 85b | 21.6 |
| 86a | 1.3 |
| 86b | >50 |
| 87a | 0.806 |
| 87b | >50 |
| 88 | 13.5 |
| 89a | 2.3 |
| 89b | 25.5 |
| 90a | 3.5 |
| 90b | >50 |
| 91a | 5.3 |
| 91b | 25.3 |
| 92a | 1.4 |
| 92b | 43 |
| 93a | 2.1 |
| 93b | 9.5 |
| 94 | 2.3 |
| 86b | >50 |
| 87a | 0.806 |
| 87b | >50 |
| 88 | 13.5 |
| 89a | 2.3 |
| 89b | 25.5 |
| 90a | 3.5 |
| 90b | >50 |
| 91a | 5.3 |
| 91b | 25.3 |
| 92a | 1.4 |
| 92b | 43 |
| 93a | 2.1 |
| 93b | 9.5 |
| 94 | 2.3 |

The invention claimed is:

1. A compound of formula (Ia)

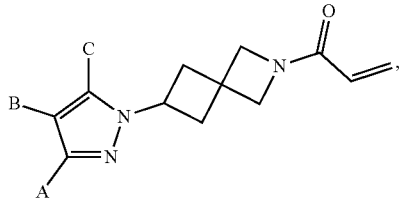

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof, wherein A is 8-10 membered heteroaryl ring containing 1 to 3 heteroatoms independently selected from nitrogen, oxygen and sulfur, or an 8-10 membered partially saturated hetero-bicyclic ring containing 1 to 3 heteroatoms or heteroatom groups independently selected from 0-3 nitrogen atoms, 0-2 oxygen atoms, 0-1 sulfur atom and 0-1 S(=O)$_2$ group in the hetero-bicyclic ring, wherein said heteroaryl ring or hetero-bicyclic ring is unsubstituted or substituted on a carbon atom with 1, 2, 3, 4 or 5 $R^{A4}$, and wherein the hetero-bicyclic ring is further optionally substituted on a carbon atom by oxo and wherein a nitrogen atom, when present, is unsubstituted or substituted with a substituent which is —(CO)—$C_1$-$C_4$-alkyl or $C_1$-$C_4$-alkyl, and wherein said $C_1$-$C_4$-alkyl is optionally substituted with 1 or 2 substituents independently selected from cyano, hydroxy, oxo, fluoro, $C_1$-$C_4$-alkoxy, $C_1$-$C_4$-alkoxy-$C_1$-$C_4$-alkyl-oxy, Het$^b$ and NR$^9$R$^{10}$;

wherein A is attached to the rest of the compound of Formula (Ia) by a carbon atom on A;

B is selected from the group consisting of $B^1$ and $B^2$, wherein $B^1$ is $C_{6-10}$ aryl which is unsubstituted or substituted with 1, 2, 3 or 4 $R^{Ba}$; and $B^2$ is a 6-13 membered heteroaryl which comprises 1, 2 or 3 nitrogen atoms, wherein $B^2$ is unsubstituted or substituted with 1, 2, 3 or 4 $R^{Bb}$;

C is selected from the group consisting of hydrogen, $C_1$-$C_3$ alkyl, $C_3$-$C_5$ cycloalkyl, fluoro-$C_1$-$C_3$ alkyl, cyano, —CH$_2$—CN, —CH(CN)—CH$_3$, —CH$_2$—OH, —CH(OH)—CH$_3$ and halo;

each $R^{A4}$ is independently selected from the group consisting of cyano, CO$_2$H, halo, $C_1$-$C_4$-alkyl, fluoro-$C_1$-$C_4$-alkyl, hydroxy, hydroxy-$C_1$-$C_4$-alkyl, hydroxy-$C_1$-$C_4$-alkyl-oxy, $C_1$-$C_4$-alkoxy, $C_1$-$C_4$-alkoxy-$C_1$-$C_4$-alkyl, $C_1$-$C_4$-alkoxy-$C_1$-$C_4$-alkyl-oxy, NR$^9$R$^{10}$, (N(R$^9$)(R$^{10}$)—$C_1$-$C_4$-alkyl, (N(R$^9$)(R$^{10}$)—$C_1$-$C_4$-alkyl-oxy, —(CO)—$C_1$-$C_4$-alkyl, and R$^9$R$^{10}$N—$C_1$-$C_4$-alkyl-oxy-(CO)—$C_1$-$C_4$-alkyl;

$R^9$ is selected from hydrogen and $C_1$-$C_4$-alkyl;

$R^{10}$ is selected from the group consisting of hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl;

Het$^b$ is a 4- or 5- or 6-membered heterocyclic ring comprising 1 or 2 heteroatoms or groups independently selected from N, O, S, SO and SO$_2$, wherein said Het$^b$ is unsubstituted or substituted on a carbon atom with one or two substituents independently selected from $C_1$-$C_4$-alkyl, hydroxy, cyano, fluoro, $C_1$-$C_4$-alkoxy-hydroxy-$C_1$-$C_4$-alkyl, hydroxy-$C_1$-$C_4$-alkyl, $C_1$-$C_4$-alkoxy, fluoro-$C_1$-$C_4$-alkoxy and fluoro-$C_1$-$C_4$-alkyl, and wherein said Het$^b$ is further optionally substituted on a carbon atom by oxo, and wherein the nitrogen atom when present in Het$^b$ is optionally further substituted with $C_1$-$C_4$-alkyl which is optionally substituted with 1 to 3 substituents independently selected from fluoro, hydroxy and $C_1$-$C_4$-alkoxy;

each $R^{Ba}$ is independently selected from the group consisting of hydroxy, NH$_2$, $C_1$-$C_4$-alkyl and halo; and each $R^{Bb}$ is independently selected from the group consisting of $C_1$-$C_4$-alkyl, cyclopropyl, fluoro-$C_1$-$C_3$-alkyl, cyano, halo, NH$_2$ and $C_1$-$C_3$-alkoxy.

2. The compound of claim 1, wherein A is selected from the group consisting of:

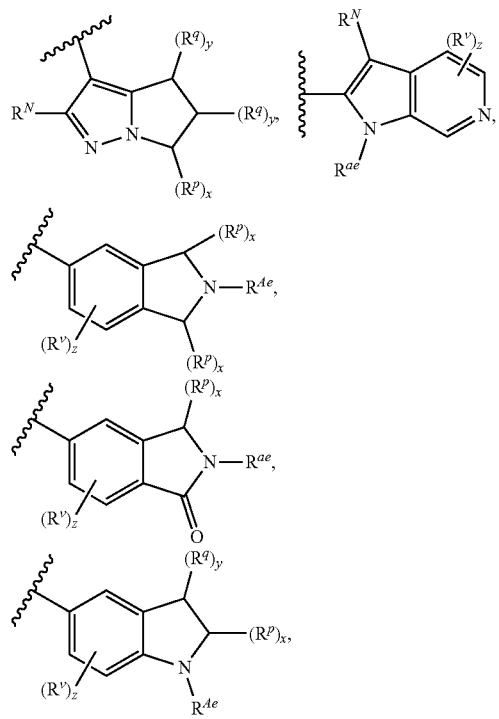

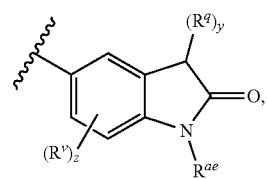
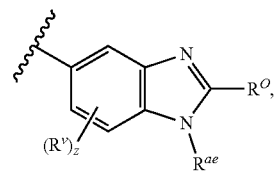
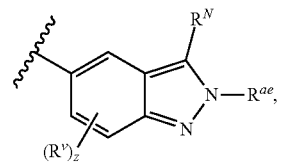
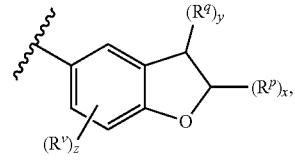
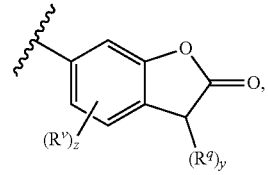
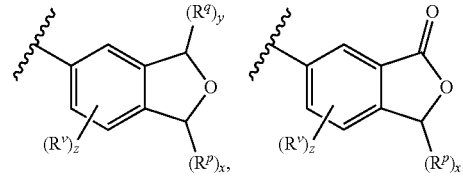
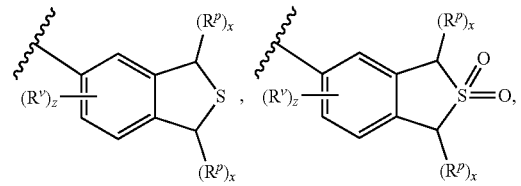
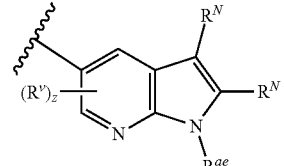
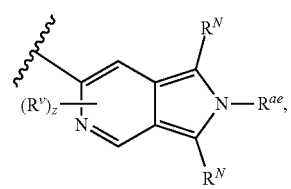
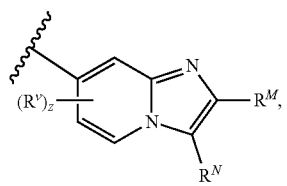
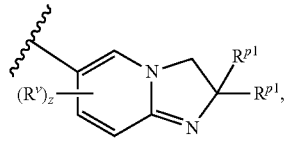
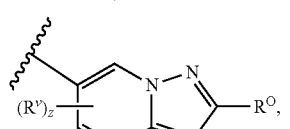
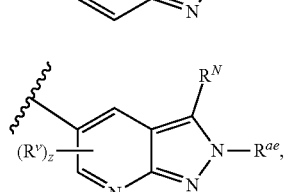
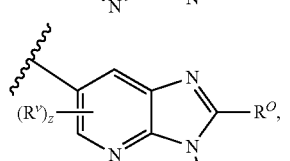
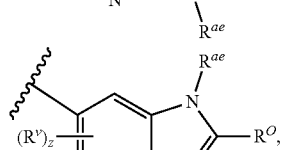
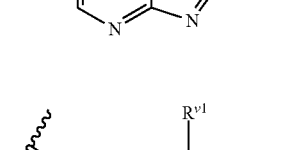
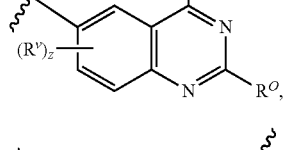
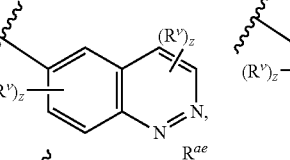
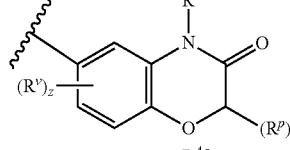
and
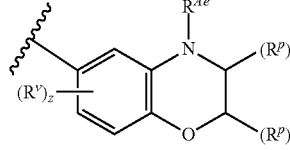

wherein y is 0, 1 or 2;

x is 0, 1 or 2;

z is 0, 1 or 2;

$R^O$ is selected from the group consisting of hydrogen, $NR^9R^{10}$, $R^9R^{10}N$—$C_1$-$C_4$-alkyl-oxy, $C_1$-$C_4$-alkoxy-$C_1$-$C_4$-alkyl-oxy, hydroxy-$C_1$-$C_4$-alkyl-oxy and $C_1$-$C_4$-alkyl;

$R^M$ is hydrogen, halo or $C_1$-$C_4$-alkyl, wherein said alkyl is optionally substituted by OH, $C_1$-$C_4$-alkoxy or $NR^9R^{10}$;

$R^N$ is hydrogen, $C_1$-$C_4$-alkyl, halo or fluoro-$C_1$-$C_4$-alkyl;

$R^q$ is independently selected from the group consisting of $C_1$-$C_4$-alkyl, hydroxy, $C_1$-$C_4$-alkoxy and $NR^9R^{10}$;

$R^p$ is $C_1$-$C_4$-alkyl;

each $R^{v1}$ is independently selected from hydrogen and $C_1$-$C_4$-alkyl;

$R^v$ is independently selected from halogen, $C_1$-$C_4$-alkyl and fluoro-$C_1$-$C_4$-alkyl;

$R^{ae}$ is selected from the group consisting of hydrogen and $C_1$-$C_4$-alkyl, wherein said alkyl is optionally substituted with 1 or 2 substituents selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$;

$R^{Ae}$ is selected from the group consisting of hydrogen, —(CO)—$C_1$-$C_4$-alkyl and $C_1$-$C_4$-alkyl wherein the $C_1$-$C_4$alkyl in each instance is optionally substituted with 1 or 2 substituents selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$; wherein $R^9$ is selected from hydrogen and $C_1$-$C_4$-alkyl;

$R^{10}$ is selected from hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl; and $Het^b$ is a 4- or 5- or 6-membered heterocyclic ring comprising 1 or 2 heteroatoms or groups independently selected from N, O, S, SO and $SO_2$, wherein said heterocyclic ring $Het^b$ is unsubstituted or substituted on a carbon atom with one or two substituents independently selected from $C_1$-$C_4$-alkyl, hydroxy, cyano, fluoro, hydroxy-$C_1$-$C_4$-alkyl, $C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is optionally further substituted with $C_1$-$C_4$-alkyl which is optionally substituted with 1 to 3 substituents independently selected from fluoro, hydroxy and $C_1$-$C_4$-alkoxy;

or an atropisomer thereof, or a pharmaceutically acceptable salt thereof, or a pharmaceutically acceptable salt of a stereoisomer thereof, or a pharmaceutically acceptable salt of an atropisomer thereof.

3. The compound of claim 1, wherein A is selected from the group consisting of:

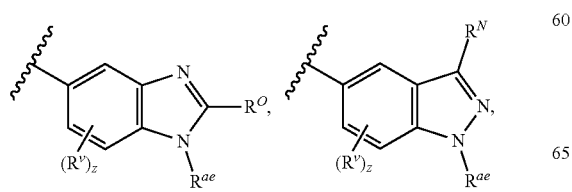

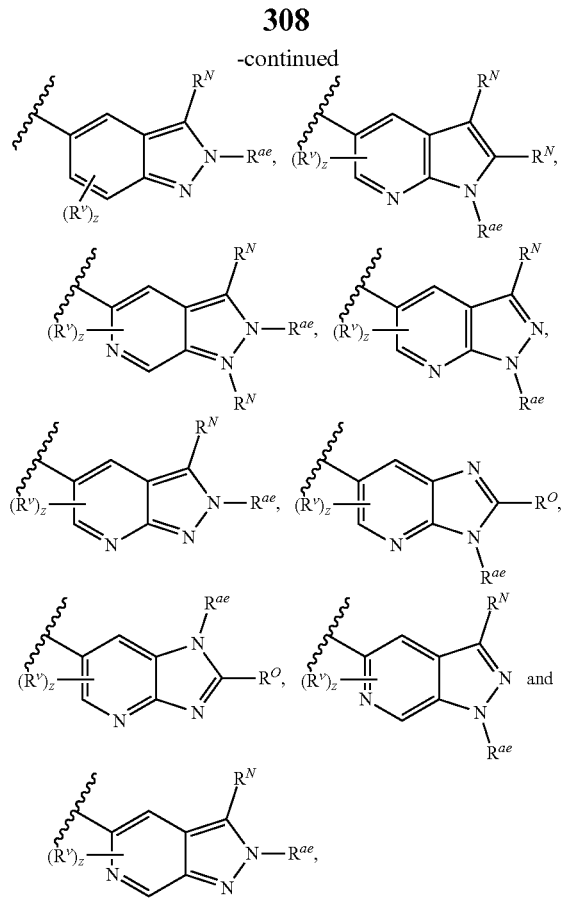

wherein z is 0, 1 or 2;

$R^v$ is independently selected from halogen, $C_1$-$C_4$-alkyl and fluoro-$C_1$-$C_4$-alkyl;

$R^N$ is hydrogen, $C_1$-$C_4$-alkyl, halo or fluoro-$C_1$-$C_4$-alkyl;

$R^O$ is selected from the group consisting of hydrogen, $NR^9R^{10}$, $N(R^9)(R^{10})$—$C_1$-$C_4$-alkyl-oxy, $C_1$-$C_4$-alkoxy-$C_1$-$C_4$-alkyl-oxy, hydroxy-$C_1$-$C_4$-alkyl-oxy and $C_1$-$C_4$-alkyl;

$R^{ae}$ is selected from the group consisting of hydrogen and $C_1$-$C_4$-alkyl, wherein said alkyl is optionally substituted with 1 or 2 substituents selected from cyano, hydroxy, fluoro, $C_1$-$C_4$-alkoxy, $C_1$-$C_4$-alkoxy-$C_1$-$C_4$-alkyl-oxy, $Het^b$ and $NR^9R^{10}$;

$R^9$ is selected from hydrogen and $C_1$-$C_4$-alkyl;

$R^{10}$ is selected from hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl; and wherein $Het^b$ is a 4- or 5- or 6-membered heterocyclic ring comprising 1 or 2 heteroatoms or groups independently selected from N, O, S, SO and $SO_2$, wherein said heterocyclic ring $Het^b$ is unsubstituted or substituted on a carbon atom with one or two substituents independently selected from $C_1$-$C_4$-alkyl, hydroxy, cyano, fluoro, hydroxy-$C_1$-$C_4$-alkyl, $C_1$-$C_4$-alkoxy and fluoro-$C_1$-$C_4$-alkyl, and wherein said heterocyclic ring $Het^b$ is further optionally substituted on a carbon atom by oxo, and wherein the nitrogen atom when present in $Het^b$ is further optionally substituted with $C_1$-$C_4$-alkyl which is optionally substituted with 1 to 3 substituents independently selected from fluoro, hydroxy and $C_1$-$C_4$-alkoxy;

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

4. The compound of claim 3, wherein A is selected from the group consisting of:

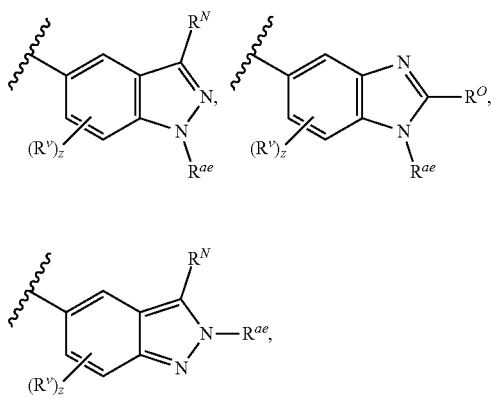

or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

5. The compound of claim 4, wherein
$R^N$ is hydrogen or $C_1$-$C_4$-alkyl;
$R^O$ is hydrogen or $NR^9R^{10}$;
$R^v$ is independently selected from fluoro, chloro and $C_1$-$C_4$-alkyl; and
z is 0 or 1;
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

6. The compound of claim 2, wherein $R^{ae}$ is selected from the group consisting of hydrogen, $C_1$-$C_4$-alkyl, —$(CH_2)_2$-$Het^b$, —$CH_2$—CN, —$(CH_2)_2$—O—$C_1$-$C_4$-alkyl, hydroxy-$C_1$-$C_4$-alkyl, —$(CH_2)_2$—O—$(CH_2)_2$—O—$C_1$-$C_4$-alkyl and —$(CH_2)_2$-di$C_1$-$C_4$-alkylamino, or wherein $R^{Ae}$ is selected from the group consisting of hydrogen, fluoro-$C_1$-$C_4$-alkyl and $C_1$-$C_4$-alkyl; and
$Het^b$ is a 4-, 5- or 6-membered heterocyclic ring comprising 1 nitrogen atom and 1 oxygen atom, or 1-2 nitrogen atoms, wherein said heterocyclic ring is unsubstituted or substituted on a carbon atom by one or two substituents independently selected from $C_1$-$C_4$-alkyl, hydroxy-$C_1$-$C_4$-alkyl, $C_1$-$C_4$-alkoxy and fluoro, and wherein the nitrogen atom when present in the heterocycle is optionally further substituted with $C_1$-$C_4$-alkyl,
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

7. The compound of claim 2, wherein $R^{ae}$ is selected from the group consisting of hydrogen, methyl, —$CH_2$—CN, —$(CH_2)_2$—OH, —$(CH_2)_2$—$OCH_3$, —$(CH_2)$—$C(CH_3)_2$—OH, —$(CH_2)_2$—O—$(CH_2)_2$—$OCH_3$, —$(CH_2)_2$—$N(CH_3)_2$, and —$(CH_2)_2$-$Het^b$; and
$Het^b$ is a 4-, 5- or 6-membered heterocyclic ring comprising 1 nitrogen atom and 1 oxygen atom, or 1-2 nitrogen atoms, wherein said heterocyclic ring is unsubstituted or substituted on a carbon atom by one or two substituents independently selected from $C_1$-$C_4$-alkyl, hydroxy-$C_1$-$C_4$-alkyl, $C_1$-$C_4$-alkoxy and fluoro, and wherein the nitrogen atom when present in the heterocycle is optionally further substituted with $C_1$-$C_4$-alkyl,
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

8. The compound of claim 2, wherein $R^{ae}$ is selected from the group consisting of hydrogen, methyl, —$CH_2$—CN, —$(CH_2)_2$—OH, —$(CH_2)_2$—$OCH_3$, —$(CH_2)$—$C(CH_3)_2$—OH, —$(CH_2)_2$—O—$(CH_2)_2$—$OCH_3$, —$(CH_2)_2$—$N(CH_3)_2$, and —$(CH_2)_2$-$Het^b$, wherein $Het^b$ is selected from the group consisting of azetidin-1-yl, pyrrolidin-1-yl, pyrrolidin-3-yl and morpholin-1-yl, each of which is optionally further substituted with one or two substituents independently selected from methyl, hydroxy-methyl, methoxy and fluoro,
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

9. The compound of claim 2, wherein $R^{ae}$ is selected from the group consisting of hydrogen, fluoro-$C_1$-$C_4$-alkyl, $C_1$-$C_4$-alkyl, —$(CH_2)_2$-$Het^b$, —$(CH_2)_2$—OH, —$(CH_2)_2$—O—$C_1$-$C_4$-alkyl, hydroxy-$C_1$-$C_4$-alkyl, —$(CH_2)_2$—O—$(CH_2)_2$—O—$C_1$-$C_4$-alkyl and —$(CH_2)_2$-di$C_1$-$C_4$-alkylamino, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

10. The compound of claim 1, wherein the compound of formula (Ia) is a compound of formula (Ib*),

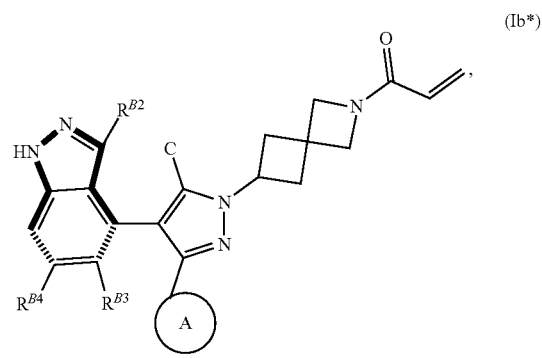

(Ib*)

or a pharmaceutically acceptable salt thereof, wherein
$R^{B2}$ is selected from hydrogen, halo, $C_1$-$C_4$-alkyl, cyclopropyl and $NH_2$;
$R^{B3}$ is selected from hydrogen, halo, cyclopropyl and $C_1$-$C_4$-alkyl; and
$R^{B4}$ is selected from hydrogen, halo and $C_1$-$C_4$-alkyl.

11. The compound of claim 1, wherein the compound of formula (Ia) is a compound of formula (Id*),

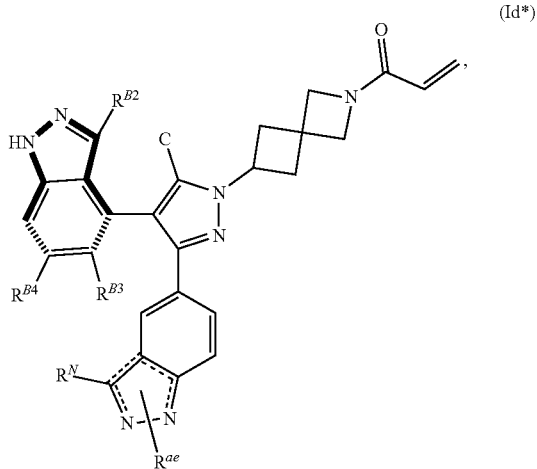

(Id*)

wherein
$R^{B2}$ is selected from hydrogen, halo, $C_1$-$C_4$-alkyl, cyclopropyl and $NH_2$;
$R^{B3}$ is selected from hydrogen, halo, cyclopropyl and $C_1$-$C_4$-alkyl; and
$R^{B4}$ is selected from hydrogen, halo and $C_1$-$C_4$-alkyl;
$R^N$ is hydrogen, $C_1$-$C_4$-alkyl, halo or fluoro-$C_1$-$C_4$-alkyl;
$R^{ae}$ is selected from the group consisting of hydrogen and $C_1$-$C_4$-alkyl, wherein said alkyl is optionally substituted with 1 or 2 substituents selected from cyano, hydroxy, fluoro, $C_1$-$C_4$-alkoxy, $C_1$-$C_4$-alkoxy-$C_1$-$C_4$-alkyl-oxy, Het$^b$ and $NR^9R^{10}$;
$R^9$ is selected from hydrogen and $C_1$-$C_4$-alkyl;
$R^{10}$ is selected from hydrogen, $C_1$-$C_4$-alkyl, hydroxy-$C_1$-$C_4$-alkyl, $C_1$-$C_4$-alkoxy-$C_1$-$C_4$-alkyl and di-$C_1$-$C_4$-alkyl-amino-$C_1$-$C_4$-alkyl;
Het$^b$ is a 4- or 5- or 6-membered heterocyclic ring comprising 1 or 2 heteroatoms or groups independently selected from N, O, S, SO and $SO_2$, wherein said heterocyclic ring Het$^b$ is unsubstituted or substituted on a carbon atom with one or two substituents independently selected from $C_1$-$C_4$-alkyl, hydroxy, cyano, fluoro, hydroxy-$C_1$-$C_4$-alkyl, $C_1$-$C_4$-alkoxy and fluoro-$C_1$-$C_4$-alkyl, and wherein said heterocyclic ring Het$^b$ is further optionally substituted on a carbon atom by oxo, and wherein the nitrogen atom when present in Het$^b$ is optionally further substituted with $C_1$-$C_4$-alkyl which is optionally substituted with 1 to 3 substituents independently selected from fluoro, hydroxy and $C_1$-$C_4$-alkoxy; and
the ---- lines indicate a single bond or a double bond.

12. The compound of claim 1, which is selected from:
a(R)-1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one,
a(R)(S)-1-(6-(4-(5-chloro-6-methyl-1H-indazol-4-yl)-3-(1-(2-(3-fluoropyrrolidin-1-yl)ethyl)-1H-indazol-5-yl)-5-methyl-1H-pyrazol-1-yl)-2-azaspiro[3.3]heptan-2-yl)prop-2-en-1-one,
a(R)1-(6-(4-(5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one,
a(R)1-(6-(4-(5-chloro-6-methyl-1H-indazol-4-yl)-3-(2-(2-hydroxy-2-methylpropyl)-2H-indazol-5-yl)-5-methyl-1H-pyrazol-1-yl)-2-azaspiro[3.3]heptan-2-yl)prop-2-en-1-one,
a(R)1-(6-(4-(5-chloro-6-methyl-1H-indazol-4-yl)-3-(2-(2-(2-methoxyethoxy)ethyl)-2H-indazol-5-yl)-5-methyl-1H-pyrazol-1-yl)-2-azaspiro[3.3]heptan-2-yl)prop-2-en-1-one, and
a(R)1-(6-(4-(3-amino-5-chloro-6-methyl-1H-indazol-4-yl)-3-(2-(2-methoxyethyl)-2H-indazol-5-yl)-5-methyl-1H-pyrazol-1-yl)-2-azaspiro[3.3]heptan-2-yl)prop-2-en-1-one,
or a pharmaceutically acceptable salt thereof.

13. A compound which is selected from:
1-{6-[(4M)-4-(5-Chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one,
1-{6-[(4M)-4-(5-Chloro-6-methyl-1H-indazol-4-yl)-3-(1-{2-[(3S)-3-fluoropyrrolidin-1-yl]ethyl}-1H-indazol-5-yl)-5-methyl-1H-pyrazol-1-yl]-2-azaspiro[3.3]heptan-2-yl}prop-2-en-1-one,
1-(6-{(4M)-4-(5-Chloro-6-methyl-1H-indazol-4-yl)-3-[2-(2-methoxyethyl)-2H-indazol-5-yl]-5-methyl-1H-pyrazol-1-yl}-2-azaspiro[3.3]heptan-2-yl)prop-2-en-1-one,
1-(6-{(4M)-4-(5-Chloro-6-methyl-1H-indazol-4-yl)-3-[2-(2-hydroxy-2-methylpropyl)-2H-indazol-5-yl]-5-methyl-1H-pyrazol-1-yl}-2-azaspiro[3.3]heptan-2-yl)prop-2-en-1-one,
1-{6-[(4M)-4-(5-Chloro-6-methyl-1H-indazol-4-yl)-3-{2-[2-(2-methoxyethoxy)ethyl]-2H-indazol-5-yl}-5-methyl-1H-pyrazol-1-yl]-2-azaspiro[3.3]heptan-2-yl}prop-2-en-1-one,
1-(6-{(4M)-4-(3-Amino-5-chloro-6-methyl-1H-indazol-4-yl)-3-[2-(2-methoxyethyl)-2H-indazol-5-yl]-5-methyl-1H-pyrazol-1-yl}-2-azaspiro[3.3]heptan-2-yl)prop-2-en-1-one,
1-(6-(4-(5-chloro-6-methyl-1H-indazol-4-yl)-5-methyl-3-(1-methyl-1H-pyrrolo[2,3-b]pyridin-5-yl)-1H-pyrazol-1-yl)-2-azaspiro[3.3]heptan-2-yl)prop-2-en-1-one;
1-(6-(4-(5-chloro-6-methyl-1H-indazol-4-yl)-3-(1H-indazol-5-yl)-5-methyl-1H-pyrazol-1-yl)-2-azaspiro[3.3]heptan-2-yl)prop-2-en-1-one;
1-(6-(4-(5-chloro-6-methyl-1H-indazol-4-yl)-3-(1H-indazol-6-yl)-5-methyl-1H-pyrazol-1-yl)-2-azaspiro[3.3]heptan-2-yl)prop-2-en-1-one;
1-(6-(4-(5-chloro-6-methyl-1H-indazol-4-yl)-3-(1-(2-(dimethylamino)ethyl)-1H-indazol-5-yl)-5-methyl-1H-pyrazol-1-yl)-2-azaspiro[3.3]heptan-2-yl)prop-2-en-1-one;
1-(6-(4-(5-chloro-6-methyl-1H-indazol-4-yl)-3-(2-(2-(dimethylamino)ethyl)-2H-indazol-5-yl)-5-methyl-1H-pyrazol-1-yl)-2-azaspiro[3.3]heptan-2-yl)prop-2-en-1-one;
1-(6-(4-(5-chloro-6-methyl-1H-indazol-4-yl)-5-methyl-3-(1-(2-morpholinoethyl)-1H-indazol-5-yl)-1H-pyrazol-1-yl)-2-azaspiro[3.3]heptan-2-yl)prop-2-en-1-one;
1-(6-(3-([1,2,4]triazolo[1,5-a]pyridin-6-yl)-4-(5-chloro-6-methyl-1H-indazol-4-yl)-5-methyl-1H-pyrazol-1-yl)-2-azaspiro[3.3]heptan-2-yl)prop-2-en-1-one;
1-(6-(4-(5-chloro-6-methyl-1H-indazol-4-yl)-3-(isoquinolin-6-yl)-5-methyl-1H-pyrazol-1-yl)-2-azaspiro[3.3]heptan-2-yl)prop-2-en-1-one;

1-(6-(4-(5-chloro-6-methyl-1H-indazol-4-yl)-5-methyl-3-(1-methyl-1H-indazol-4-yl)-1H-pyrazol-1-yl)-2-azaspiro[3.3]heptan-2-yl)prop-2-en-1-one;

1-(6-(4-(5-chloro-6-methyl-1H-indazol-4-yl)-5-methyl-3-(1-methyl-1H-benzo[d]imidazol-5-yl)-1H-pyrazol-1-yl)-2-azaspiro[3.3]heptan-2-yl)prop-2-en-1-one;

1-(6-(4-(5-chloro-6-methyl-1H-indazol-4-yl)-3-(imidazo[1,2-a]pyridin-7-yl)-5-methyl-1H-pyrazol-1-yl)-2-azaspiro[3.3]heptan-2-yl)prop-2-en-1-one;

1-(6-(4-(5-chloro-6-methyl-1H-indazol-4-yl)-5-methyl-3-(1-methyl-1H-pyrazolo[3,4-b]pyridin-5-yl)-1H-pyrazol-1-yl)-2-azaspiro[3.3]heptan-2-yl)prop-2-en-1-one;

1-(6-(4-(5-chloro-6-methyl-1H-indazol-4-yl)-5-methyl-3-(3-methyl-3H-imidazo[4,5-b]pyridin-6-yl)-1H-pyrazol-1-yl)-2-azaspiro[3.3]heptan-2-yl)prop-2-en-1-one; and 1-(6-(4-(5-chloro-6-methyl-1H-indazol-4-yl)-5-methyl-3-(2-(methylamino)quinazolin-6-yl)-1H-pyrazol-1-yl)-2-azaspiro[3.3]heptan-2-yl)prop-2-en-1-one;

or a pharmaceutically acceptable salt thereof.

14. A method of treating a cancer characterized by one or more mutations of KRAS in a patient in need thereof, comprising administering to the patient a therapeutically effective amount of a compound of claim 1, or a stereoisomer thereof, or an atropisomer thereof, or a pharmaceutically acceptable salt thereof, or a crystalline form thereof, or a pharmaceutically acceptable salt of a stereoisomer thereof, or a pharmaceutically acceptable salt of an atropisomer thereof.

15. A pharmaceutical composition comprising a compound according to claim 1, or a stereoisomer thereof, or an atropisomer thereof, or a pharmaceutically acceptable salt thereof, or a crystalline form thereof, or a pharmaceutically acceptable salt of a stereoisomer thereof, or a pharmaceutically acceptable salt of an atropisomer thereof, and at least one pharmaceutically acceptable excipient.

16. The compound of claim 10, wherein C is $C_1$-$C_3$ alkyl.

17. The compound of claim 11, wherein C is $C_1$-$C_3$ alkyl.

18. The compound of claim 1, wherein
A is 8-10 membered heteroaryl ring containing 1 to 3 heteroatoms independently selected from nitrogen, oxygen and sulfur, wherein a nitrogen atom, when present, is unsubstituted or substituted with $C_1$-$C_4$-alkyl;
B is 6-13 membered heteroaryl which comprises 1, 2 or 3 nitrogen atoms, wherein $B^2$ is unsubstituted or substituted with 1, 2, 3 or 4 $R^{Bb}$;
C is $C_1$-$C_3$ alkyl; and
each $R^{Bb}$ is independently selected from the group consisting of $C_1$-$C_4$-alkyl and halo.

19. The compound of claim 1, wherein the compound of formula (Ia) is 1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one,
or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

20. A compound, which is

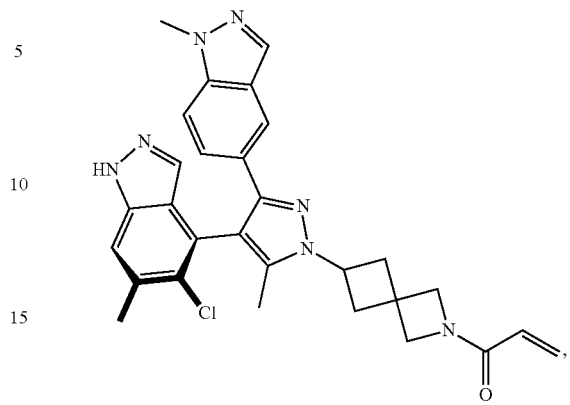

or a pharmaceutically acceptable salt thereof.

21. A compound, which is

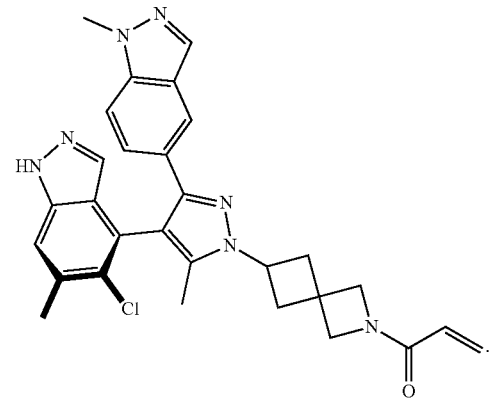

22. A pharmaceutical composition comprising a compound according to claim 20, or a pharmaceutically acceptable salt thereof, and at least one pharmaceutically acceptable excipient.

23. A method of treating a cancer characterized by one or more mutations of KRAS in a patient in need thereof, comprising administering to the patient a therapeutically effective amount of a compound of claim 20, or a pharmaceutically acceptable salt thereof.

24. The method of claim 23, wherein the cancer is lung cancer, colorectal cancer, pancreatic cancer, uterine cancer, or rectal cancer.

25. The method of claim 23, wherein the cancer is a solid tumor.

26. The method of claim 24, wherein the lung cancer is non-small cell lung cancer.

27. The method of claim 26, wherein the non-small cell lung cancer is characterized by a G12C mutation of KRAS.

28. The method of claim 24, wherein the colorectal cancer is characterized by a G12C mutation of KRAS.

29. A method of treating a cancer characterized by a G12C mutation of KRAS in a patient in need thereof, comprising administering to the patient a therapeutically effective amount of a compound that is 1-(6-(4-(5-chloro-6-methyl-1H-indazol-4-yl)-5-methyl-3-(1-methyl-1H-indazol-5-yl)-1H-pyrazol-1-yl)-2-azaspiro[3.3]heptan-2-yl)prop-2-en-1-one, or a stereoisomer thereof, or an atropisomer thereof, or a pharmaceutically acceptable salt thereof, or a pharmaceutically acceptable salt of a stereoisomer thereof, or a pharmaceutically acceptable salt of an atropisomer thereof.

30. The method of claim 29, wherein the compound is 1-{6-[(4M)-4-(5-Chloro-6-methyl-1H-indazol-4-yl)-5-methyl-3-(1-methyl-1H-indazol-5-yl)-1H-pyrazol-1-yl]-2-azaspiro[3.3]heptan-2-yl}prop-2-en-1-one, or a pharmaceutically acceptable salt thereof.

31. The method of claim 29, wherein the cancer is non-small cell lung cancer.

32. The method of claim 29, wherein the cancer is colorectal cancer.

33. The method of claim 30, wherein the cancer is non-small cell lung cancer.

34. The method of claim 30, wherein the cancer is colorectal cancer.

* * * * *